US012435116B2

(12) United States Patent
Hurt et al.

(10) Patent No.: US 12,435,116 B2

(45) Date of Patent: Oct. 7, 2025

(54) COMPOUNDS, COMPOSITIONS, METHODS, AND USES FOR TREATING INSULIN RESISTANCE, TYPE 2 DIABETES AND METABOLIC SYNDROME

(71) Applicants: Clarence Hurt, Los Altos, CA (US); Luis Soares, Ormond Beach, FL (US)

(72) Inventors: Clarence Hurt, Los Altos, CA (US); Luis Soares, Ormond Beach, FL (US)

( * ) Notice: Subject to any disclaimer, the term of this patent is extended or adjusted under 35 U.S.C. 154(b) by 241 days.

(21) Appl. No.: 17/073,138

(22) Filed: Oct. 16, 2020

(65) Prior Publication Data

US 2022/0064249 A1 Mar. 3, 2022

Related U.S. Application Data

(60) Provisional application No. 62/915,680, filed on Oct. 16, 2019.

(51) Int. Cl.

*C07K 14/62* (2006.01)
*A61K 31/519* (2006.01)
*A61K 38/00* (2006.01)
*A61K 47/64* (2017.01)

(52) U.S. Cl.

CPC ............ *C07K 14/62* (2013.01); *A61K 31/519* (2013.01); *A61K 47/64* (2017.08); *A61K 38/00* (2013.01); *C07K 2319/00* (2013.01)

(58) Field of Classification Search

None

See application file for complete search history.

(56) References Cited

U.S. PATENT DOCUMENTS

| | | | | |
|---|---|---|---|---|
| 1,017,556 | A | 2/1912 | Keighley | |
| 6,841,361 | B1 | 1/2005 | Oka et al. | |
| 7,879,588 | B2 | 2/2011 | Vetter et al. | |
| 8,088,387 | B2 | 1/2012 | Steeves et al. | |
| 8,568,728 | B2 * | 10/2013 | Jeffrey .................. | C07H 17/08 424/179.1 |
| 9,265,723 | B2 | 2/2016 | Sprogoe et al. | |
| 9,457,066 | B2 | 10/2016 | Cleemann et al. | |
| 9,505,823 | B2 | 11/2016 | Bell et al. | |
| 9,593,156 | B2 | 3/2017 | Dimarchi et al. | |
| 10,251,957 | B2 | 4/2019 | Jang et al. | |
| 10,696,726 | B2 | 6/2020 | Dimarchi et al. | |
| 2014/0364362 | A1 | 12/2014 | Jowett | |

FOREIGN PATENT DOCUMENTS

| | | | |
|---|---|---|---|
| WO | 2011012718 | 2/2011 | |
| WO | 2013121175 | 8/2013 | |
| WO | WO-2019227764 A1 * | 12/2019 | .......... A61K 31/519 |

OTHER PUBLICATIONS

He et al. "Peptide Conjugates with Small Molecules Designed to Enhance Efficacy and Safety," Molecules 2019, 24, 1855, pp. 1-34 (Year: 2019).*

Liu et al. "Synthesis and Characterization of the Tumor Targeting Mitoxantrone-Insulin Conjugate" Arch Pharm Res vol. 26, No. 11, 892-897, 2003 (Year: 2003).*

Tong et al. ("MLN4924 (Pevonedistat), a protein neddylation inhibitor, suppresses proliferation and migration of human clear cell renal cell carcinoma," Nature, 7: 5599) (Year: 2017).*

Supplemental Materials for Wang et al. Glucose transporter inhibitor-conjugated insulin mitigates hypoglycemia. PNAS vol. 116, No. 22, 10744-10748, May 28, 2019 (Year: 2019).*

Wang et al. Glucose transporter inhibitor-conjugated insulin mitigates hypoglycemia. PNAS vol. 116, No. 22, 10744-10748, May 28, 2019 (Year: 2019).*

Deepak K. Sharma, Jyotsana Pandey, Akhilesh K. Tamrakar, Debaraj Mukherjee, Synthesis of heteroaryl/aryl kojic acid conjugates as stimulators of glucose uptake by GLUT4 translocation, European Journal of Medicinal Chemistry, vol. 85, 2014, pp. 727-736, ISSN 0223-5234, https://doi.org/10.1016/j.ejmech.2014.08.041.

Zhi Y, Gao LX, Jin Y, Tang CL, Li JY, Li J, Long YQ. 4-Quinolone-3-carboxylic acids as cell-permeable inhibitors of protein tyrosine phosphatase 1B. Bioorg Med Chem. Jul. 15, 2014;22(14):3670-83. doi: 10.1016/j.bmc.2014.05.028. Epub May 20, 2014. Erratum in: Bioorg Med Chem. Aug. 1, 2014;22(15):4347. PMID: 24906513.

Ahn S, Lee IH, Lee E, Kim H, Kim YC, Jon S. Oral delivery of an anti-diabetic peptide drug via conjugation and complexation with low molecular weight chitosan. J Control Release. Sep. 10, 2013;170(2):226-32. doi: 10.1016/j.jconrel.2013.05.031. Epub Jun. 4, 2013. PMID: 23747732.

Patil NA, Tailhades J, Karas JA, Separovic F, Wade JD, Hossain MA. A One-Pot Chemically Cleavable Bis-Linker Tether Strategy for the Synthesis of Heterodimeric Peptides. Angew Chem Int Ed Engl. Nov. 14, 2016;55(47):14552-14556. doi: 10.1002/anie.201604733. Epub Aug. 16, 2016. PMID: 27529162.

Irwin N, Patterson S, de Kort M, Moffett RC, Wisse JA, Dokter WH, Bos ES, Miltenburg AM, Flatt PR. Synthesis and Evaluation of a Series of Long-Acting Glucagon-Like Peptide-1 (GLP-1) Pentasaccharide Conjugates for the Treatment of Type 2 Diabetes. ChemMedChem. Aug. 2015; 10(8):1424-34. doi: 10.1002/cmdc.201500140. Epub Jun. 9, 2015. PMID: 26059252.

(Continued)

*Primary Examiner* — Christina Bradley

(74) *Attorney, Agent, or Firm* — Gary P Katz; Katz Law Group, LLC

(57) ABSTRACT

Novel insulin, insulin-fusion proteins and insulin homologs protein-small molecule drug conjugates, where conjugation takes place through the use of cleavable and non-cleavable linkers are disclosed. The small molecules chemically linked to the protein carrier are imported into the specific insulin-responsive target tissue or cell through receptor-mediated endocytosis and released from the carrier protein through enzymatic cleavage of the linker-drug moiety or through lysosomal degradation of the carrier protein. Free drug can then act to modify insulin receptor-triggered biochemical pathways that are altered in conditions of insulin-resistance. Drug will correct altered pathway allowing re-sensitization of receptor signaling. This will greatly aid in the resolution of pathologies either initiated at the onset of insulin resistance or exacerbated by it.

9 Claims, 9 Drawing Sheets

Specification includes a Sequence Listing.

(56) References Cited

OTHER PUBLICATIONS

Kishore B. Chalasani, G.J. Russell-Jones, Sarath K. Yandrapu, Prakash V. Diwan, Sanjay K. Jain, A novel vitamin B12-nanosphere conjugate carrier system for peroral delivery of insulin, Journal of Controlled Release, vol. 117, Issue 3, 2007, pp. 421-429, ISSN 0168-3659, https://doi.org/10.1016/j.jconrel.2006.12.003.
Wancewicz, Edward V., et al., Peptide Nucleic Acids Conjugated to Short Basic Peptides Show Improved Pharmacokinetics and Antisense Activity in Adipose Tissue, J. Med. Chem. 2010, 53, 10, 3919-3926 Publication Date:Apr. 26, 2010 https://doi.org/10.1021/jm901489k.
Huining He, Jianyong Sheng, Allan E. David, Young Min Kwon, Jian Zhang, Yongzhuo Huang, Jianxin Wang, Victor C. Yang, The use of low molecular weight protamine chemical chimera to enhance monomeric insulin intestinal absorption, Biomaterials, vol. 34, Issue 31, 2013, pp. 7733-7743, ISSN 0142-9612, https://doi.org/10.1016/j. biomaterials.2013.06.047. (http://www.sciencedirect.com/science/article/pii/S014296121300762X).

* cited by examiner

Maleimidocaproyl (MC)

Maleimidocaproyl like (MC)

Maleimidocaproyl
Cyclohexane-1-Carboxylate (MC)

Hydrazine Linker

Dipeptide Bioconjugation 1

Dipeptide Bioconjugation 2

Dipeptide Bioconjugation 3

Dipeptide Bioconjugation 4

Glucuronide Bioconjugation 1

Glucuronide Bioconjugation 2

Glucuronide Bioconjugation 3

Glucuronide Bioconjugation 4

COMPOUNDS, COMPOSITIONS, METHODS, AND USES FOR TREATING INSULIN RESISTANCE, TYPE 2 DIABETES AND METABOLIC SYNDROME

CROSS REFERENCE TO RELATED APPLICATIONS

This Non-Provisional patent application claims priority to the U.S. patent provisional application Ser. No. 62/915,680, filed Oct. 16, 2019, which is incorporated in its entirety by reference.

TECHNICAL FIELD

The present disclosure relates generally to chemical compounds. More particularly, embodiments relate to pharmaceuticals. Even more particularly, embodiments relate to insulin-based drug conjugates.

BACKGROUND

The prevalence of conditions associated with insulin resistance, including metabolic syndrome and type 2 diabetes, has been increasing over the past few decades. Insulin resistance is identified as an impaired biologic response to insulin stimulation of target tissues, primarily the liver, muscle, and adipose tissue. The consequences of insulin resistance can result in hyperglycemia, hypertension, dyslipidemia, visceral adiposity, hyperuricemia, elevated inflammatory markers, endothelial dysfunction, and a prothrombic state. Ultimately, insulin resistance can lead to metabolic syndrome, nonalcoholic fatty liver disease (NAFLD), and type 2 diabetes mellitus. With nearly 500 million adults (20-79 years) worldwide currently living with diabetes (and the number is expected to increase to 700 million by 2045), the burden on the health care system will be enormous.

Current treatments for insulin resistance, type 2 diabetes and metabolic syndrome focus on stimulation of insulin secretion ((sulfonylureas, meglitinides, incretin mimetics) and insulin sensitivity (thiazolidinediones (or TZDs) and metformin) as well as concentrated high doses of insulin called Humulin 500. In addition, TZDs can have serious side effects, including weight gain, swelling, and an increase risk of heart failure and fractures. Over time, all these therapies eventually lead to a decrease in insulin sensitivity and a progressive disease state. Accordingly, there is a worldwide need for cost effective therapies to treat insulin resistance, metabolic syndrome and type 2 diabetes. The embodiments disclosed herein, address this need.

BRIEF SUMMARY OF THE INVENTION

In a first embodiment a compound is disclosed. The compound has a structure of Formula (I):

$$X1\text{-}[X2\text{-}(X3)m]n \qquad (I)$$

or a pharmaceutically acceptable salt, solvate, hydrate, isomer, or tautomer thereof: wherein:

m is 1, 2, 3, 4, 5, 6, 7, 8, 9, or 10;

n is 1, 2, 3, 4, 5, 6, 7, 8, 9, 10 or 11;

X1 is a biologically active polypeptide or hormone;

X2 is a linker; and

X3 is a therapeutic compound.

In a second embodiment, the compound, or a pharmaceutically acceptable salt, solvate, hydrate, isomer, or tautomer of the first embodiment is closed. In this embodiment, the therapeutic compound is an agent to treat insulin resistance, type 2 diabetes and metabolic syndrome.

The summary above is not intended to summarize each potential embodiment or every aspect of the present disclosure.

BRIEF DESCRIPTION OF THE DRAWINGS

The foregoing is intended to give a general idea of the invention and is not intended to fully define nor limit the invention. The invention will be more fully understood and better appreciated by reference to the following description and drawings.

FIG. 2 is a schematic showing Cys-specific hIns polypeptide is a table showing Cys-specific Insulin polypeptide-Linker-therapeutic compound conjugations in accordance with some embodiments of the disclosure. R groups =H, glycol ether, or an additional glycol linker alkyl, aryl, and arylalkyl, alkynes, alkenes, substituted phenyl groups, aromatic heterocycles, glycol ether, or an additional glycol linker and the like.

FIG. 3 is a table showing various di-Cys-specific Insulin polypeptide-Linker-therapeutic compound conjugations (which resulted from reduction of protein disulfides and rebridging to linker allowing di-substitution) in accordance with some embodiments of the disclosure. R groups =H, glycol ether, or an additional glycol linker alkyl, aryl, and arylalkyl, alkynes, alkenes, substituted phenyl groups, aromatic heterocycles, glycol ether, or an additional glycol linker and the like.

FIG. 4 is a table showing Lys-specific hIns polypeptide-Linker-therapeutic compound conjugations in accordance with some embodiments of the disclosure. R groups =H, glycol ether, or an additional glycol linker alkyl, aryl, and arylalkyl, alkynes, alkenes, substituted phenyl groups, aromatic heterocycles, glycol ether, or an additional glycol linker and the like.

DETAILED DESCRIPTION OF THE DISCLOSURE

Figure 1:
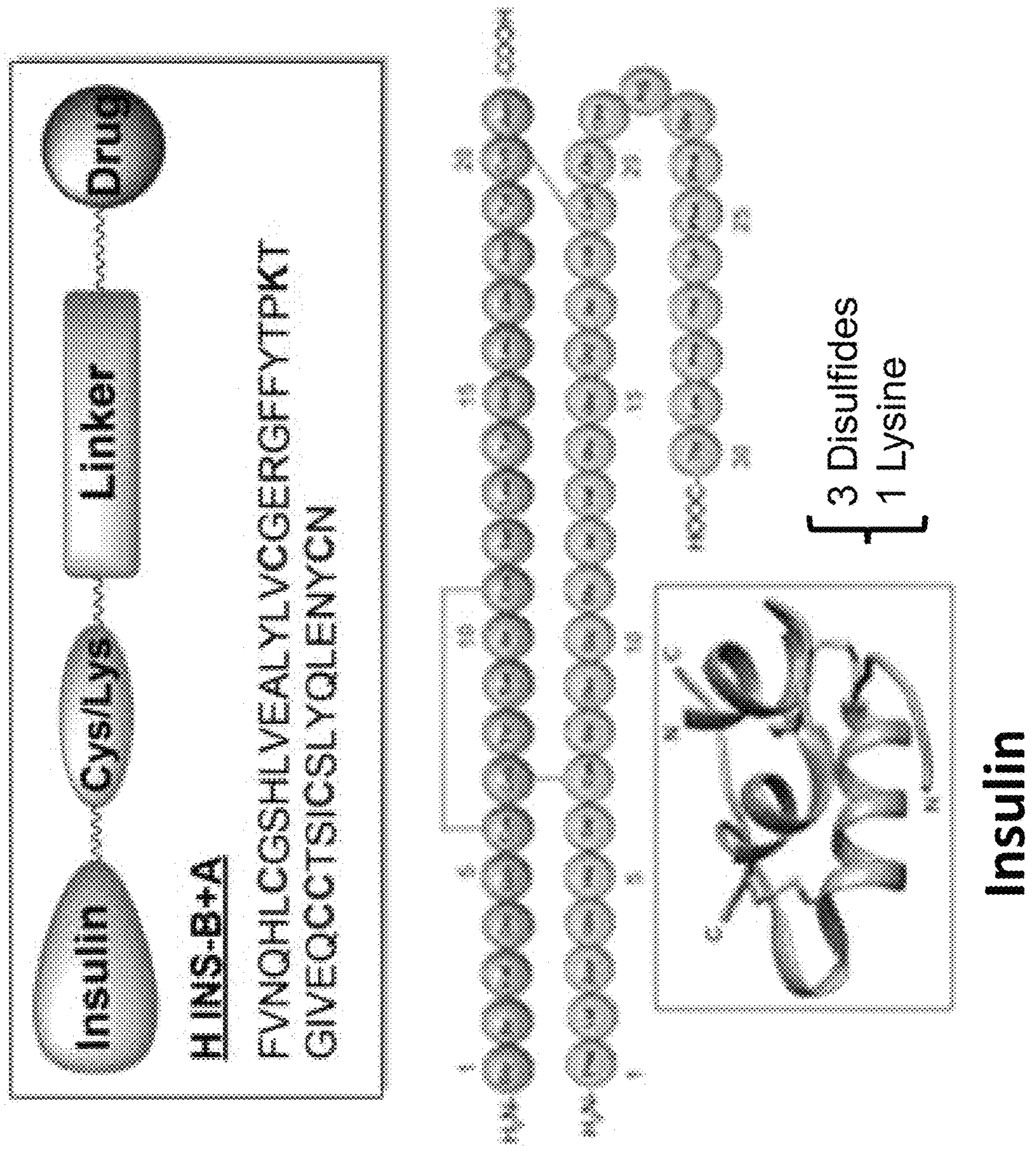
FIG. 1 is a schematic showing sequence-specific human Insulin (hIns) polypeptide-Linker-therapeutic compound conjugations in accordance with some embodiments of the disclosure.

Before describing selected embodiments of the present disclosure in detail, it is to be understood that the present invention is not limited to the embodiments described herein. The disclosure and description herein are illustrative and explanatory of one or more presently preferred embodiments and variations thereof, and it will be appreciated by those skilled in the art that various changes in the design, organization, means of operation, structures and location, methodology, and use of mechanical equivalents may be made without departing from the spirit of the invention.

As well, it should be understood that the drawings are intended to illustrate and disclose presently preferred embodiments to one of skill in the art, but are not intended to be manufacturing level drawings or renditions of final products and may include simplified conceptual views to facilitate understanding or explanation. As well, the relative size and arrangement of the components may differ from that shown and still operate within the spirit of the invention.

Moreover, it will be understood that various directions such as "upper", "lower", "bottom", "top", "left", "right", "first", "second" and so forth are made only concerning explanation in conjunction with the drawings, and that components may be oriented differently, for instance, during transportation and manufacturing as well as operation. Because many varying and different embodiments may be made within the scope of the concept(s) herein taught, and because many modifications may be made in the embodiments described herein, it is to be understood that the details herein are to be interpreted as illustrative and non-limiting.

The present disclosure provides a particular bioactive polypeptide hormones of the insulin family and it's homologs as drug-conjugates that are effective therapeutics for metabolic disorders, including, but not limited to, Type 2 diabetes, Insulin resistance, metabolic syndrome and type 1 diabetes. Again without wishing to be bound to any particular theory of action, Insulin signals by binding to its insulin receptor (IR) on the surface of responding cells. The IR receptor relies on the insulin receptor substrate proteins 1 and 2 adaptors or organizing and coordinating its signal transduction which culminates among other things on the translocation of glucose transporters to the cell surface for the import of glucose from the blood into cells for metabolic consumption and storage. Like many other receptors signal transduction from the insulin receptor involves many proteins that transect several other signaling pathways and it is thus, affected by crosstalk from other cellular responses. In particular, pro-inflammatory pathways triggered by cytokines such as interleukin 6 and interferon induce their own negative feedback responses in order to self-limit their own actions. Thus, under chronic pro-inflammatory conditions such as those taking place in obese subjects or those suffering from metabolic syndrome and other related conditions [2] cytokine-induced SOCS activation causes inhibition of the insulin receptor signaling capability first by competing with receptor signaling intermediates for IRS1/2 binding and secondly by inducing CRL-mediated ubiquitination and degradation of IRS1/2. The elevated SOCS activity and concomitant decrease in the IRS1/2 protein levels impair insulin receptor signaling consequently establishing the insulin-resistance pathology. The present invention relates to novel insulin, insulin-fusion proteins and insulin homologs protein-small molecule drug conjugates, where conjugation takes place through the use of cleavable and non-cleavable linkers. The small molecules chemically linked to the protein carrier are imported into the specific insulin-responsive target tissue or cell through receptor-mediated endocytosis and released from the carrier protein through enzymatic cleavage of the linker-drug moiety or through lysosomal degradation of the carrier protein. Free drug then act to modify insulin receptor-triggered biochemical pathways that are altered in conditions of insulin-resistance such as SOCS-mediated CRL-dependent IRS-1/2 degradation. Drug will correct altered pathway allowing resensitization of receptor signaling. This will greatly aid in the resolution of pathologies either initiated at the onset of insulin resistance or exacerbated by it.

Some exemplary embodiments of the present disclosure include a compound having the structure of Formula (I):

$$X_{2a}—(X_3)_m \quad (I),$$

and pharmaceutically acceptable salts, solvates, hydrates, isomers, or tautomers thereof, wherein:

m is 1, 2, 3, 4, 5, 6, 7, 8, 9, or 10;

$X_{2a}$ is a linker; and $X_3$ is a therapeutic compound.

In some embodiments of the compound of Formula (I), m is 1. In some embodiments of the compound of Formula (I), m is 2, 3, 4, 5, 6, 7, or 8. In some embodiments of the compound of Formula (I), m is 1, 2, or 3. In some embodiments of the compound of Formula (I), m is 2, 3, 4, or 5.

In some embodiments of the compound of Formula (I), $X_{2a}$ is a cleavable linker. In some embodiments of the compound of Formula (I), $X_{2a}$ is a non-cleavable linker. In some embodiments of the compound of Formula (I), $X_{2a}$ is selected from the group consisting of L-1, L-2, L-3, L-4, L-5, L-6, L-7, L-8, L-9, L-10, L-11, L-12, L-13, L-14, L-15, L-16, L-17, L-18, L-19, L-20, L-21, L-22, L-23 and L-24, as disclosed herein, wherein, R is H, alkyl, aryl, arylalkyl, a glycol ether, or a glycol linker. In some embodiments of the compound of Formula (I), $X_{2a}$ is selected from the group consisting of L-2 and L-4. In some embodiments of the compound of Formula (I), $X_{2a}$ is selected from the group consisting of L-4 and L-6. In some embodiments of the compound of Formula (I), $X_{2a}$ is selected from the group consisting of L-8 and L-10. In some embodiments of the compound of Formula (I), $X_{2a}$ is selected from the group consisting of L-10 and L-12. In some embodiments of the compound of Formula (I), $X_{2a}$ is selected from the group consisting of L-14 and L-16. In some embodiments of the compound of Formula (I), $X_{2a}$ is selected from the group consisting of L-16 and L-18. In some embodiments of the compound of Formula (I), $X_{2a}$ is selected from the group consisting of L-19, L-20, L-21, L-22, L-23 and L-24, as disclosed herein. In some embodiments of the compound of Formula (I), $X_3$ is an immunomodulating agent. In some embodiments of the compound of Formula (I), $X_3$ is selected from the group consisting of JNK (c-Jun N-terminal kinase) inhibitors, PKR-like endoplasmic reticulum kinase (PERK) inhibitor, PERK (PKR-like endoplasmic reticulum kinase), PTP1B (protein-tyrosine phosphatase 1B), AKT (Protein Kinase B) an antidiabetic, a neddylation inhibitor, a ubiquitin-activating enzyme inhibitor, a ubiquitin-activating enzyme E1 inhibitor, and a proteasome inhibitor. In some embodiments of the compound of Formula (I), $X_3$ is selected from the group consisting of: MLN4924 (pevonedistat or ((1R,2R,4S)-4-(4-(((R)-2,3-dihydro-1H-inden-1-yl)amino)-7H-pyrrolo[2,3-d]pyrimidin-7-yl)-2-hydroxycyclopentyl) methyl sulfamate); TAS4464 (((2S,3S,4R,5R)-5-(4-amino-5-((4,7-dimethyl-3,4-dihydro-2H-benzo[b][1,4]oxazin-8-yl) ethynyl)-7H-pyrrolo[2,3-d]pyrimidin-7-yl)-3,4-dihydroxytetrahydrofuran-2-yl)methyl sulfamate); ABP1 (((2S,3R,4S,5S)-5-(6-((3-ethynylphenyl)amino)-9H-purin-9-yl)-3,4-dihydroxytetrahydrofuran-2-yl)methyl sulfamate); GSK2-606414 (1-(5-(4-amino-7-methyl-7H-pyrrolo[2,3-d]pyrimidin-5-yl)indolin-1-yl)-2-(3-(trifluoromethyl)phenyl)ethan-1-one); AMG PERK 44 (4-(2-amino-4-methyl-3-(2-methylquinolin-6-yl)benzoyl)-1-methyl-2,5-diphenyl-1,2-dihydro-3H-pyrazol-3-one hydrochloride); FK866 HCl ((E)-N-(4-(1-benzoylpiperidin-4-yl)butyl)-3-(pyridin-3-yl)acrylamide hydrochloride); CHS 828 (2-[6-(4-chlorophenoxy) hexyl]-1-cyano-3-pyridin-4-ylguanidine); STF 118804 (4-(5-methyl-4-(tosylmethyl)oxazol-2-yl)-N-(pyridin-3-ylmethyl)benzamide); GPP 78 (N-([1,1'-biphenyl]-2-yl)-8-(4-

(pyridin-3-yl)-1H-1,2,3-triazol-1-yl)octanamide); GNE 617 (N-(4-((3,5-difluorophenyl)sulfonyl)benzyl)imidazo[1,2-a] pyridine-6-carboxamide); CB30865 (4-(((7-bromo-2-methyl-4-oxo-3,4-dihydroquinazolin-6-yl)methyl)(prop-2-yn-1-yl)amino)-N-(pyridin-3-ylmethyl)benzamide); TCS 401 (2-(carboxyformamido)-4,5,6,7-tetrahydrothieno[2,3-c] pyridine-3-carboxylic acid); CX08005 (2-((2-(tetradecyloxy)phenyl)carbamoyl)benzoic acid); methyl 5-((N-(4-(N-(2-methoxy-2-oxoethyl)methylsulfonamido)benzyl)-1-phenylmethyl)sulfonamido)-2-((4-methylbenzyl)oxy) benzoate; ((3-bromo-7-cyanonaphthalen-2-yl)difluoromethyl)phosphonic acid; BVT 948 (4-hydroxy-3,3-dimethyl-2H-benzo[g]indole-2,5(3H)-dione); SC79 (ethyl 2-amino-6-chloro-4-(1-cyano-2-ethoxy-2-oxoethyl)-4H-chromene-3-carboxylate); SP600125 (dibenzo[cd,g]indazol-6 (2H)-one; CC 401 (3-(3-(2-(piperidin-1-yl)ethoxy)phenyl)-5-(1H-1,2,4-triazol-5-yl)-1H-indazole hydrochloride); TCS JNK 60 (N-(4-amino-5-cyano-6-ethoxypyridin-2-yl)-2-(2,5-dimethoxyphenyl)acetamide); TCS JNK 5a (N-(3-cyano-4,5,6,7-tetrahydrobenzo[b]thiophen-2-yl)-1-naphthamide); JNK-IN-7 ((E)-3-(4-(dimethylamino)but-2-enamido)-N-(4-((4-(pyridin-3-yl)pyrimidin-2-yl)amino)phenyl)benzamide); JNK-IN-8 ((E)-3-(4-(dimethylamino)but-2-enamido)-N-(2-methyl-4-((4-(pyridin-3-yl)pyrimidin-2-yl)amino)phenyl) benzamide; JNK-IN-11 ((E)-3-(4-(dimethylamino)but-2-enamido)-N-(4-((4-(2-phenylpyrazolo[1,5-a]pyridin-3-yl) pyrimidin-2-yl)amino)phenyl)benzamide; Fostriecin (sodium (1E,3R,4R,6R,7Z,9Z,11E)-3,6,13-trihydroxy-3-methyl-1-((R)-6-oxo-3,6-dihydro-2H-pyran-2-yl)trideca-1,7,9,11-tetraen-4-yl hydrogen phosphate; Endothall (3-(4-methylpiperazine-1-carbonyl)-7-oxabicyclo[2.2.1]heptane-2-carboxylic acid); Rubratoxin A ((E)-3-(4-(dimethylamino) but-2-enamido)-N-(4-((4-(2-phenylpyrazolo[1,5-a]pyridin-3-yl)pyrimidin-2-yl)amino)phenyl)benzamide); Okadaic Acid ((2R)-2-hydroxy-3-((2S,3S,6R)-3-hydroxy-8-((2R,E)-4-((2R,5R,6'S,8'R)-8'-hydroxy-6'-((1S,3S)-1-hydroxy-3-((2S,3R,6S)-3-methyl-1,7-dioxaspiro[5.5]undecan-2-yl) butyl)-7'-methyleneoctahydro-3H,3'H-spiro[furan-2,2'-pyrano[3,2-b] pyran]-5-yl)but-3-en-2-yl)-10-methyl-1,7-dioxaspiro[5.5]undec-10-en-2-yl)-2-methylpropanoic acid). In some embodiments, $X_3$ is Pevonedistat.

In some embodiments of the compound of Formula (I), the compound of Formula (I) is selected from the group consisting of: A-1, A-2, A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-32, A-33, A-34, A-35, A-36, A-37, A-38, A-39, A-40, A-41, A-42, A-43, A-44, A-45, A-46, A-47, A-48, A-49, A-50, A-51, A-52, A-53, A-54, A-55, A-56, A-57, A-58, A-59, A-60, A-61, A-62, A-63, A-64, A-65, A-66, A-67, A-68, A-69, A-70, A-71, A-72, A-73, A-74, A-75, A-76, A-77, A-78, A-79, A-80, A-81, A-82, A-83, A-84, A-85, A-86, A-87, A-88, A-89, A-90, A-91, A-92, A-93, A-94, A-95, A-96, A-97, A-98, A-99, A-100, A-101, A-102, A-103, A-104, A-105, A-106, A-107 and A-108 as disclosed herein, wherein R is H, alkyl, aryl, arylalkyl, a glycol ether, or a glycol linker and p is 1, 2, 3, 4, 5, or 6. In some embodiments of the compound of Formula (I), the compound of Formula (I) is selected from the group consisting of A-1, A-2, A-3, A-4, A-19, A-20, A-21, A-22, A-37, A-38, A-39, A-40, A-55, A-56, A-57, A-58, A-73, A-74, A-75, A-76, A-91, A-92, A-93, A-94. In some embodiments of the compound of Formula (I), the compound of Formula (I) is selected from the group consisting of A-13, A-31, A-49, A-67, A-67, A-85, A-103. In some embodiments of the compound of Formula (I), the compound of Formula (I) is selected from the group consisting of A-5, A-6, A-23, A-24, A-41, A-42, A-59, A-60, A-77, A-78, A-95, A-96. In some embodiments of the compound of Formula (I), the compound of Formula (I) is selected from the group consisting of A-14, A-15, A-16, A-32, A-33, A-34, A-50, A-51, A-52, A-68, A-69, A-70, A-86, A-87, A-88, A-104, A-105, A-106. In some embodiments of the compound of Formula (I), the compound of Formula (I) is selected from the group consisting of A-12, A-30, A-48, A-66, A-84, A-102. In some embodiments of the compound of Formula (I), the compound of Formula (I) is selected from the group consisting of A-7, A-8, A-9, A-10, A-11, A-25, A-26, A-27, A-28, A-29, A-43, A-44, A-45, A-46, A-47, A-61, A-62, A-63, A-64, A-65, A-79, A-80, A-81, A-82, A-83, A-97, A-98, A-99, A-100, A-101 In some embodiments of the compound of Formula (I), the compound of Formula (I) is selected from the group consisting of A-17, A-18, A-35, A-36, A-53, A-54, A-71, A-72, A-89, A-90, A-107, A-108

Some exemplary embodiments of the present disclosure include a compound having the structure of Formula (II):

$$X_1—[X_2—(X_3)_m]_n \quad \text{(II)},$$

and pharmaceutically acceptable salts, solvates, hydrates, isomers, or tautomers thereof, wherein:

m is 1, 2, 3, 4, 5, 6, 7, 8, 9, or 10;

n is 1, 2, 3, 4, 5, 6, 7, 8, 9, 10, or 11;

$X_1$ is a biologically active polypeptide or hormone;

$X_2$ is a linker; and $X_3$ is a therapeutic compound.

Some exemplary embodiments of the present disclosure include a compound having the structure of Formula (III):

$$X_1—[X_2—(X_3)_m]_n \quad \text{(III)},$$

and pharmaceutically acceptable salts, solvates, hydrates, isomers, or tautomers thereof, wherein:

m is 1, 2, 3, 4, 5, 6, 7, 8, 9, or 10;

n is 1, 2, 3, 4, 5, 6, 7, 8, 9, 10, or 11;

$X_1$ is an Insulin polypeptide or a bio-active homolog polypeptide thereof;

$X_2$ is a linker; and $X_3$ is a therapeutic compound.

In some embodiments of the compound of Formula (II) or Formula (III), $X_3$ is a drug to treat insulin resistance, type 2 diabetes and metabolic syndrome.

In some embodiments of the compound of Formula (II) or Formula (III), $X_2$ is a cleavable linker. In some embodiments of the compound of Formula (II) or Formula (III), $X_2$ is a non-cleavable linker.

In some embodiments of the compound of Formula (II) or Formula (III), $X_2$ is bound to $X_1$ at a Cys residue thereof. Among these are embodiments in which $X_3$ is a drug to treat insulin resistance, type 2 diabetes and metabolic syndrome. Among these embodiments are those in which $X_2$ is a cleavable linker, and those in which $X_2$ is a non-cleavable linker.

In some embodiments of the compound of Formula (II) or Formula (III), $X_2$ is bound to $X_1$ at a Lys residue thereof. Among these are embodiments in which $X_3$ is a drug to treat insulin resistance, type 2 diabetes and metabolic syndrome. Among these embodiments are those in which $X_2$ is a cleavable linker, and those in which $X_2$ is a non-cleavable linker.

In some embodiments of the compound of Formula (II) or Formula (III), n is 2, 3, 4, 5, 6, 7, 8, or 9. In some embodiments of the compound of Formula (II) or Formula (III), n is 3, 4, 5, 6, 7, or 8. In some embodiments of the compound of Formula (II) or Formula (III), n is 4, 5, 6, or 7. In some embodiments of the compound of Formula (II) or Formula (III), n is 5 or 6. In some embodiments of the compound of Formula (II) or Formula (III), m=n. In some embodiments of the compound of Formula (II) or Formula (III), n is greater than m. In some embodiments of the compound of Formula (II) or Formula (III), m is 1 and n is 1, 2, 3, 4, 5, 6, 7, 8, 9, 10, or 11. In some embodiments of the compound of Formula (II) or Formula (III), m is 2 and n is 1, 2, 3, 4, 5, 6, 7, 8, 9, 10, or 11. In some embodiments of the compound of Formula (II) or Formula (III), n is an integer between 2 and 9, an integer between 3 and 8, an integer between 4 and 7, or n can be 5 or 6. In some embodiments of the compound of Formula (II) or Formula (III), n is an integer between 1 and 11. In some embodiments of the compound of Formula (II) or Formula (III), m is an integer between 1 and 10. In some embodiments of the compound of Formula (II) or Formula (III), m is 1. In some embodiments of the compound of Formula (II) or Formula (III), m is 2, 3, 4, 5, 6, 7, or 8. In some embodiments of the compound of Formula (II) or Formula (III), m is 1, 2, or 3. In some embodiments of the compound of Formula (II) or Formula (III), m is 2, 3, 4, or 5.

In another aspect, the present disclosure provides a method of treating a disorder in a subject, comprising administering to said subject a therapeutically effective amount of a compound of the disclosure, or a pharmaceutically acceptable salt, hydrate, solvate, isomer, or tautomer thereof, in a pharmaceutically acceptable carrier.

In some embodiments of the compound of Formula (II) or Formula (III), the Insulin polypeptide or the bio-active homolog polypeptide thereof comprises an amino acid sequence set forth in Table 4. In some embodiments of the compound of Formula (II) or Formula (III), the Insulin polypeptide or the bio-active homolog polypeptide thereof comprises an amino acid sequence set forth in SEQ ID NO: 1 or SEQ ID NO:2.

In some embodiments of the compound of Formula (II) or Formula (III), $X_2$ is a cleavable linker. In some embodiments of the compound of Formula (II) or Formula (III), $X_2$ is a non-cleavable linker. In some embodiments of the compound of Formula (II) or Formula (III), $X_2$ is selected from the group consisting of: K-1, K-2, K-3, K-4, K-5, K-6, K-7, K-8, K-9, K-10, K-11, K-12, K-13, K-14, K-15, K-16, K-19, K-20, K-21, K-22, K-23 and K-24, as disclosed herein, wherein the left side of $X_2$, as drawn, is bound to $X_1$, and the right side of $X_2$, as drawn, is bound to $X_3$ and wherein R is H, alkyl, aryl, arylalkyl, a glycol ether, or a glycol linker. In some embodiments of the compound of Formula (II) or Formula (III), $X_2$ is selected from the group consisting of K-14 and K-18. In some embodiments of the compound of Formula (II) or Formula (III), $X_2$ is selected from the group consisting of K-16 and K-18, wherein the left side of $X_2$, as drawn, is bound to $X_1$, and the right side of $X_2$, as drawn, is bound to $X_3$. In some embodiments of the compound of Formula (II) or Formula (III), $X_2$ is bound to $X_1$ at a Cys residue thereof. In some embodiments of the compound of Formula (II) or Formula (III), $X_2$ is bound to $X_1$ at a Lys residue thereof. In some embodiments of the compound of Formula (II) or Formula (III), $X_2$ is bound to $X_1$ at two different sites on $X_1$. In some embodiments of the compound of Formula (II) or Formula (III), $X_2$ is bound to $X_1$ at two different Cys residues on $X_1$. In some embodiments of the compound of Formula (II) or Formula (III), $X_2$ is bound to $X_1$ at two different Lys residues on $X_1$. In some embodiments of the compound of Formula (II) or Formula (III), $X_2$ is a mixture of $X_{2b}$ and $X_{2c}$, wherein $X_{2b}$ is a linker that is bound to one Cys residue on $X_1$ and $X_{2c}$ is a linker that is bound to two Cys residues on $X_1$, wherein n is a combination of n1 and n2, wherein n1 corresponds to the number of $X_{2b}$ moieties bound to $X_1$ and n2 corresponds to the number of $X_{2c}$ moieties bound to $X_1$ and wherein the sum of n1 and n2 is 2, 3, 4, 5, 6, 7, 8, 9, 10, or 11. In certain such embodiments, $X_{2b}$ is K-2 and $X_{2c}$ is K-4. In some embodiments, $X_{2b}$ is selected from the group consisting of K-1, K-2, K-7, K-8, K-13, K-14, K-19, K-20 and $X_{2c}$ is K-3, K-4, K-9, K-10, K-15, K-16, K-21 and K-22. In some embodiments, each $X_2$ bound to $X_1$ is an $X_{2b}$ moiety. In some embodiments, each $X_2$ bound to $X_1$ is an $X_{2c}$ moiety.

The description of n as used in the disclosure is inclusive of n1, n2, or the combination of n1 and n2, with the sum of n1 and n2 being between 2 and 11. In some embodiments of the compound of Formula (II) or Formula (III), n1 is 2 or 3 and n2 is 1. In some embodiments of the compound of Formula (II) or Formula (III), n1 is 2 and n2 is 1. In some embodiments of the compound of Formula (II) or Formula (III), n1 is 3 and n2 is 1. In some embodiments of the compound of Formula (II) or Formula (III), n1 is 1, 2, 3, 4, or 5 and n2 is 1, 2 or 3.

In some embodiments of the compound of Formula (II) or Formula (III), $X_3$ is an immunomodulating agent. In some embodiments of the compound of Formula (II) or Formula (III), $X_3$ of JNK (c-Jun N-terminal kinase) inhibitors, PKR-like endoplasmic reticulum kinase (PERK) inhibitor, PERK (PKR-like endoplasmic reticulum kinase), PTP1B (protein-tyrosine phosphatase 1B), AKT (Protein Kinase B) an antidiabetic, a neddylation inhibitor, a ubiquitin-activating enzyme inhibitor, a ubiquitin-activating enzyme E1 inhibitor, and a proteasome inhibitor. In some embodiments of the compound of Formula (II) or Formula (III), $X_3$ is selected from the group consisting of: MLN4924 (pevonedistat or ((1R,2R,4S)-4-(4-(((R)-2,3-dihydro-1H-inden-1-yl)amino)-7H-pyrrolo[2,3-d]pyrimidin-7-yl)-2-hydroxycyclopentyl) methyl sulfamate); TAS4464 (((2S,3S,4R,5R)-5-(4-amino-5-((4,7-dimethyl-3,4-dihydro-2H-benzo[b][1,4]oxazin-8-yl) ethynyl)-7H-pyrrolo[2,3-d]pyrimidin-7-yl)-3,4-dihydroxy-tetrahydrofuran-2-yl)methyl sulfamate); ABP1 (((2S,3R,4S,5S)-5-(6-((3-ethynylphenyl)amino)-9H-purin-9-yl)-3,4-dihydroxytetrahydrofuran-2-yl)methyl sulfamate); GSK-2606414 (1-(5-(4-amino-7-methyl-7H-pyrrolo[2,3-d]pyrimidin-5-yl)indolin-1-yl)-2-(3-(trifluoromethyl)phenyl) ethan-1-one); AMG PERK 44 (4-(2-amino-4-methyl-3-(2-methylquinolin-6-yl)benzoyl)-1-methyl-2,5-diphenyl-1,2-dihydro-3H-pyrazol-3-one hydrochloride); FK866 HCl ((E)-N-(4-(1-benzoylpiperidin-4-yl)butyl)-3-(pyridin-3-yl) acrylamide hydrochloride); CHS 828 (2-[6-(4-chlorophenoxy)hexyl]-1-cyano-3-pyridin-4-ylguanidine); STF 118804 (4-(5-methyl-4-(tosylmethyl)oxazol-2-yl)-N-(pyridin-3-ylmethyl)benzamide); GPP 78 (N-([1,1'-biphenyl]-2-yl)-8-(4-(pyridin-3-yl)-1H-1,2,3-triazol-1-yl)octanamide); GNE 617 (N-(4-((3,5-difluorophenyl)sulfonyl)benzyl)imidazo[1,2-a]pyridine-6-carboxamide); CB30865 (4-(((7-bromo-2-methyl-4-oxo-3,4-dihydroquinazolin-6-yl)methyl) (prop-2-yn-1-yl)amino)-N-(pyridin-3-ylmethyl) benzamide); TCS 401 (2-(carboxyformamido)-4,5,6,7-tetrahydrothieno[2,3-c]pyridine-3-carboxylic acid); CX08005 (2-((2-(tetradecyloxy)phenyl)carbamoyl)benzoic acid); methyl 5-((N-(4-(N-(2-methoxy-2-oxoethyl)methylsulfonamido)benzyl)-1-phenylmethyl)sulfonamido)-2-((4-methylbenzyl)oxy)benzoate; ((3-bromo-7-cyanonaphthalen-2-yl)difluoromethyl)phosphonic acid; BVT 948 (4-hydroxy-3,3-dimethyl-2H-benzo[g] indole-2,5 (3H)-dione); SC79 (ethyl 2-amino-6-chloro-4-(1-cyano-2-ethoxy-2-oxoethyl)-4H-chromene-3-carboxylate); SP600125 (dibenzo[cd,g] indazol-6 (2H)-one; CC 401 (3-(3-(2-(piperidin-1-yl)ethoxy)phenyl)-5-(1H-1,2,4-triazol-5-yl)-1H-indazole hydrochloride); TCS JNK 60 (N-(4-amino-5-cyano-6-ethoxypyridin-2-yl)-2-(2,5-dimethoxyphenyl)acetamide); TCS JNK 5a (N-(3-cyano-4,5,6,7-tetrahydrobenzo[b]thiophen-2-yl)-1-naphthamide); JNK-IN-7 ((E)-3-(4-(dimethylamino)but-2-enamido)-N-(4-((4-(pyridin-3-yl)pyrimidin-2-yl)amino)phenyl)benzamide); JNK-IN-8 ((E)-3-(4-(dimethylamino)but-2-enamido)-N-(2-methyl-4-((4-(pyridin-3-yl)pyrimidin-2-yl)amino)phenyl)benzamide; JNK-IN-11 ((E)-3-(4-(dimethylamino)but-2-enamido)-N-(4-((4-(2-phenylpyrazolo[1,5-a]pyridin-3-yl)pyrimidin-2-yl)amino)phenyl)benzamide; Fostriecin (sodium (1E,3R,4R,6R,7Z,9Z,11E)-3,6,13-trihydroxy-3-methyl-1-((R)-6-oxo-3,6-dihydro-2H-pyran-2-yl)trideca-1,7,9,11-tetraen-4-yl hydrogen phosphate; Endothall (3-(4-methylpiperazine-1-carbonyl)-7-oxabicyclo[2.2.1]heptane-2-carboxylic acid); Rubratoxin A ((E)-3-(4-(dimethylamino)but-2-enamido)-N-(4-((4-(2-phenylpyrazolo[1,5-a]pyridin-3-yl)pyrimidin-2-yl)amino)phenyl)benzamide); Okadaic Acid ((2R)-2-hydroxy-3-((2S,3S,6R)-3-hydroxy-8-((2R,E)-4-((2R,5R,6'S,8'R)-8'-hydroxy-6'-((1S,3S)-1-hydroxy-3-((2S,3R,6S)-3-methyl-1,7-dioxaspiro[5.5]undecan-2-yl)butyl)-7'-methyleneoctahydro-3H,3'H-spiro[furan-2,2'-pyrano[3,2-b]pyran]-5-yl)but-3-en-2-yl)-10-methyl-1,7-dioxaspiro[5.5]undec-10-en-2-yl)-2-methylpropanoic acid). In some embodiments, $X_3$ is Pevonedistat.

In some embodiments of the compound of Formula (II) or Formula (III), the compound of Formula (II) or Formula (III) is selected from the group consisting of: B-1, B-2, B-3, B-4, B-5, B-6, B-7, B-8, B-9, B-10, B-11, B-12, B-13, B-14, B-15, B-16, B-17, B-18, B-19, B-20, B-21, B-22, B-23, B-24, B-25, B-26, B-27, B-28, B-29, B-30, B-31, B-32, B-33, B-34, B-35, B-36, B-37, B-38, B-39, B-40, B-41, B-42, B-43, B-44, B-45, B-46, B-47, B-48, B-49, B-50, B-51, B-52, B-53, B-54, B-55, B-56, B-57, B-58, B-59, B-60, B-61, B-62, B-63, B-64, B-65, B-66, B-67, B-68, B-69, B-70, B-71, B-72, B-73, B-74, B-75, B-76, B-77, B-78, B-79, B-80, B-81, B-82, B-83, B-84, B-85, B-86, B-87, B-88, B-89, B-90, B-91, B-92, B-93, B-94, B-95, B-96, B-97, B-98, B-99, B-100, B-101, B-102, B-103, B-104, B-105, B-106, B-107 and B-108, wherein R is H, alkyl, aryl, arylalkyl, a glycol ether, or a glycol linker and q is 1, 2, 3, or 4. In some embodiments of the compound of Formula (II) or Formula (III), the compound of Formula (II) or Formula (III) is selected from the group consisting of B-1, B-2, B-3, B-4, B-19, B-20, B-21, B-22, B-37, B-38, B-39, B-40, B-55, B-56, B-57, B-58, B-73, B-74, B-75, B-76, B-91, B-92, B-93, B-94. In some embodiments of the compound of Formula (II) or Formula (III), the compound of Formula (II) or Formula (III) is selected from the group consisting of B-13, B-31, B-49, B-67, B-67, B-85, B-103. In some embodiments of the compound of Formula (II) or Formula (III), the compound of Formula (II) or Formula (III) is selected from the group consisting of B-5, B-6, B-23, B-24, B-41, B-42, B-59, B-60, B-77, B-78, B-95, B-96. In some embodiments of the compound of Formula (II) or Formula (III), the compound of Formula (II) or Formula (III) is selected from the group consisting of B-14, B-15, B-16, B-32, B-33, B-34, B-50, B-51, B-52, B-68, B-69, B-70, B-86, B-87, B-88, B-104, B-105, B-106. In some embodiments of the compound of Formula (II) or Formula (III), the compound of Formula (II) or Formula (III) is selected from the group consisting of B-12, B-30, B-48, B-66, B-84, B-102. In some embodiments of the compound of Formula (II) or Formula (III), the compound of Formula (II) or Formula (III) is selected from the group consisting of B-7, B-8, B-9, B-10, B-11, B-25, B-26, B-27, B-28, B-29, B-43, B-44, B-45, B-46, B-47, B-61, B-62, B-63, B-64, B-65, B-79, B-80, B-81, B-82, B-83, B-97, B-98, B-99, B-100, B-101 In some embodiments of the compound of Formula (II) or Formula (III), the compound of Formula (II) or Formula (III) is selected from the group consisting of B-17, B-18, B-35, B-36, B-53, B-54, B-71, B-72, B-89, B-90, B-107, B-108.

In some embodiments of the compound of Formula (II) or Formula (III), the compound of Formula (II) or Formula (III) is selected from the group consisting of B-1, B-2, B-3, B-4, B-19, B-20, B-21, B-22, B-37, B-38, B-39, B-40, B-55, B-56, B-57, B-58, B-73, B-74, B-75, B-76, B-91, B-92, B-93, B-94, wherein n is 1, 2, 3, 4, 5, or 6, and wherein $X_1$ is an Insulin polypeptide or a bio-active homolog polypeptide thereof comprising an amino acid sequence set forth in SEQ ID NO: 1 or SEQ ID NO:2.

In some embodiments of the compound of Formula (II) or Formula (III), the compound of Formula (II) or Formula (III) is selected from the group consisting of B-13, B-31, B-49, B-67, B-67, B-85, B-103, wherein n is 1, 2, 3, 4, 5, or 6, and wherein $X_1$ is an Insulin polypeptide or a bio-active homolog polypeptide thereof comprising an amino acid sequence set forth in SEQ ID NO: 1 or SEQ ID NO:2.

In some embodiments of the compound of Formula (II) or Formula (III), the compound of Formula (II) or Formula (III) is selected from the group consisting of B-5, B-6, B-23, B-24, B-41, B-42, B-59, B-60, B-77, B-78, B-95, B-96, wherein n is 1, 2, 3, 4, 5, or 6, and wherein $X_1$ is an Insulin polypeptide or a bio-active homolog polypeptide thereof comprising an amino acid sequence set forth in SEQ ID NO:1 or SEQ ID NO:2.

In some embodiments of the compound of Formula (II) or Formula (III), the compound of Formula (II) or Formula (III) is selected from the group consisting of B-14, B-15, B-16, B-32, B-33, B-34, B-50, B-51, B-52, B-68, B-69, B-70, B-86, B-87, B-88, B-104, B-105, B-106, wherein n is 1, 2, 3, 4, 5, or 6, and wherein $X_1$ is an Insulin polypeptide or a bio-active homolog polypeptide thereof comprising an amino acid sequence set forth in SEQ ID NO:1 or SEQ ID NO:2.

In some embodiments of the compound of Formula (II) or Formula (III), the compound of Formula (II) or Formula (III) is selected from the group consisting of B-12, B-30, B-48, B-66, B-84, B-102, wherein n is 1, 2, 3, 4, 5, or 6, and wherein $X_1$ is an Insulin polypeptide or a bio-active homolog polypeptide thereof comprising an amino acid sequence set forth in SEQ ID NO:1 or SEQ ID NO: 2.

In some embodiments of the compound of Formula (II) or Formula (III), the compound of Formula (II) or Formula (III) is selected from the group consisting of B-7, B-8, B-9, B-10, B-11, B-25, B-26, B-27, B-28, B-29, B-43, B-44, B-45, B-46, B-47, B-61, B-62, B-63, B-64, B-65, B-79, B-80, B-81, B-82, B-83, B-97, B-98, B-99, B-100, B-101, wherein n is 1, 2, 3, 4, 5, or 6, and wherein $X_1$ is an Insulin polypeptide or a bio-active homolog polypeptide thereof comprising an amino acid sequence set forth in SEQ ID NO:1 or SEQ ID NO:2.

In some embodiments of the compound of Formula (II) or Formula (III), the compound of Formula (II) or Formula (III) is selected from the group consisting of B-17, B-18, B-35, B-36, B-53, B-54, B-71, B-72, B-89, B-90, B-107, B-108, wherein n is 1, 2, 3, 4, 5, or 6, and wherein $X_1$ is an Insulin polypeptide or a bio-active homolog polypeptide thereof comprising an amino acid sequence set forth in SEQ ID NO:1 or SEQ ID NO:2.

In some embodiments of the compound of Formula (II) or Formula (III), $X_2$ is a mixture of $X_{2b}$ and $X_{2c}$, wherein $X_{2b}$ is a linker that is bound to one Cys residue on $X_1$ and $X_{2c}$ is a linker that is bound to two Cys residues on $X_1$, wherein n is a combination of n1 and n2, n is 1, 2, 3, 4, 5, or 6 and $X_1$ is an Insulin polypeptide or a bio-active homolog polypeptide thereof comprising an amino acid sequence set forth in SEQ ID NO: 1 or SEQ ID NO:2.

In some embodiments of the compound of Formula (II) or Formula (III), the compound of Formula (II) or Formula (III) is B-49, wherein $X_1$ is an Insulin polypeptide or a bio-active homolog polypeptide thereof comprising an amino acid sequence set forth in SEQ ID NO:1 or SEQ ID NO: 2, and n1 is 2 or 3 and n2 is 1. In some embodiments of the compound of Formula (II) or Formula (III), the Insulin polypeptide or the bio-active homolog polypeptide thereof comprises the amino acid sequence set forth in SEQ ID NO:2. An aspect of the disclosure relates to a pharmaceutical composition comprising a compound of Formula (II) or Formula (III), or a pharmaceutically acceptable salt, solvate, hydrate, or tautomer thereof, and a pharmaceutically acceptable carrier.

Another aspect of the disclosure relates to a method for treating a disorder in a subject, comprising administering to a subject in need thereof a therapeutically effective amount of a compound of Formula (II) or Formula (III), or a pharmaceutically acceptable salt, solvate, hydrate, or tautomer thereof, wherein the disorder is insulin resistance, type 2 diabetes and metabolic syndrome.

One aspect of the disclosure relates to a method for treating a disorder in a subject, comprising administering to a subject in need thereof a therapeutically effective amount of a pharmaceutical composition comprising a compound of Formula (II) or Formula (III), or a pharmaceutically acceptable salt, solvate, hydrate, or tautomer thereof, wherein the disorder is insulin resistance, type 2 diabetes and metabolic syndrome.

An aspect of the disclosure relates to use of a compound of Formula (II) or Formula (III), or a pharmaceutically acceptable salt, solvate, hydrate, or tautomer thereof, in the manufacture of a medicament for treating a disorder in a subject in need thereof, wherein the disorder is insulin resistance, type 2 diabetes and metabolic syndrome.

Another aspect of the disclosure relates to use of a pharmaceutical composition comprising a compound of Formula (II) or Formula (III), or a pharmaceutically acceptable salt, solvate, hydrate, or tautomer thereof, in the manufacture of a medicament for treating a disorder in a subject in need thereof, wherein the disorder is insulin resistance, type 2 diabetes and metabolic syndrome.

One aspect of the disclosure relates to use of a compound of Formula (II) or Formula (III), or a pharmaceutically acceptable salt, solvate, hydrate, or tautomer thereof, for treating a disorder in a subject in need thereof.

An aspect of the disclosure relates to use of a pharmaceutical composition comprising a compound of Formula (II) or Formula (III), or a pharmaceutically acceptable salt, solvate, hydrate, or tautomer thereof, for treating a disorder in a subject in need thereof.

Another aspect of the disclosure relates to use of a compound of Formula (II) or Formula (III), or a pharmaceutically acceptable salt, solvate, hydrate, or tautomer thereof, for treating a disorder in a subject in need thereof, wherein the disorder is insulin resistance, type 2 diabetes and metabolic syndrome.

One aspect of the disclosure relates to use of a pharmaceutical composition comprising a compound of Formula (II) or Formula (III), or a pharmaceutically acceptable salt, solvate, hydrate, or tautomer thereof, for treating a disorder in a subject in need thereof, wherein the disorder is insulin resistance, type 2 diabetes and metabolic syndrome.

An aspect of the disclosure relates to a compound of Formula (II) or Formula (III), or a pharmaceutically acceptable salt, solvate, hydrate, or tautomer thereof, for use in a method of treating a disorder in a subject in need thereof, wherein the disorder is insulin resistance, type 2 diabetes and metabolic syndrome. Another aspect of the disclosure relates to a pharmaceutical composition comprising a compound of Formula (II) or Formula (III), or a pharmaceutically acceptable salt, solvate, hydrate, or tautomer thereof, for use in a method of treating a disorder in a subject in need thereof, wherein the disorder is insulin resistance, type 2 diabetes and metabolic syndrome.

In some embodiments of the methods, uses, medicaments, compounds for use or pharmaceutical compositions for use of the disclosure, the disorder is a metabolic disorder. In some embodiments of the methods, uses, medicaments, compounds for use or pharmaceutical compositions for use of the disclosure wherein the disorder is insulin resistance, type 2 diabetes and metabolic syndrome.

One aspect of the disclosure relates to an Insulin polypeptide or a bio-active homolog polypeptide thereof comprising an amino acid sequence set forth in Table 4.

An aspect of the disclosure relates to an Insulin polypeptide or a bio-active homolog polypeptide thereof comprising an amino acid sequence set forth in SEQ ID NO: 1 or SEQ ID NO:2.

In one embodiment, the present disclosure provides compounds (e.g., compounds of formula II or III), or pharmaceutically acceptable salts, hydrates, solvates, isomers, or tautomers thereof, useful for the treatment of disorders, such as insulin resistance, type 2 diabetes and metabolic syndrome. The compounds of the disclosure, or pharmaceutically acceptable salts, hydrates, solvates, isomers, or tautomers thereof, may comprise biologically active polypeptides or hormones modified to include the attachment of therapeutic compounds using linkers. Further, the present disclosure provides pharmaceutical compositions comprising compounds of the disclosure, or pharmaceutically acceptable salts, hydrates, solvates, isomers, or tautomers thereof, as well as methods, uses, compounds for use, medicaments, and including pharmaceutical compositions for use comprising said compounds. The present disclosure also provides compounds comprising therapeutic compounds and a linker, useful for the preparation of the compounds comprising biologically active polypeptides or hormones modified to include the attachment of therapeutic compounds using linkers (e.g., compounds of Formula I, or pharmaceutically acceptable salts, hydrates, solvates, isomers, or tautomers thereof). The present disclosure also provides bio-active homolog polypeptides of human insulin.

The compounds of the disclosure, or pharmaceutically acceptable salts, hydrates, solvates, isomers, or tautomers thereof, comprising biologically active polypeptides or hormones modified to include the attachment of therapeutic compounds using linkers provide a highly targeted therapy useful in the treatment of insulin resistance, type 2 diabetes and metabolic syndrome. The biologically active polypeptide or hormone selectively interacts with its cell surface receptor and it taken up by the cell through receptor mediated endocytosis. The compound of the disclosure is then degraded by the cell, releasing the therapeutic compound within the cell. Treatment of insulin resistance, type 2 diabetes and metabolic syndrome with the compounds of the disclosure, or pharmaceutically acceptable salts, hydrates, solvates, isomers, or tautomers thereof, comprising biologically active polypeptides or hormones modified to include the attachment of therapeutic compounds using linkers is specific, potentially reducing off-target effects compared to standard therapies, and may exhibit high affinity for target cells, resulting in low immunogenicity. The compounds of the disclosure, or pharmaceutically acceptable salts, hydrates, solvates, isomers, or tautomers thereof, comprising biologically active polypeptides or hormones modified to include the attachment of therapeutic compounds using linkers may be very potent in the treatment of insulin resistance, type 2 diabetes and metabolic syndrome and are may be stable at physiological pH, in circulation, and in storage.

Due to the specificity of the compounds of the disclosure, or pharmaceutically acceptable salts, hydrates, solvates, isomers, or tautomers thereof, comprising biologically active polypeptides or hormones modified to include the attachment of therapeutic compounds using linkers for their targeted cells and receptors, a lower therapeutic dose of therapeutic compound may be required, reducing side effects and potentially providing a wider therapeutic window. For example, the therapeutic compounds TAS4464 and pevonedistat, both neddylation inhibitors detailed herein, show promise for the treatment of cancer. But these compounds have apparently struggled in clinical trials due to issues with toxicity. Using the compounds of the disclosure, or pharmaceutically acceptable salts, hydrates, solvates, isomers, or tautomers thereof, reduced amounts of therapeutic compound should be required to exhibit a therapeutic effect, likely only picomolar therapeutic compound concentration doses instead of nanomolar or micromolar concentration doses of therapeutic compound, possibly reducing the therapeutic compound's toxicity. Remarkably, these dose concentrations are consistent with the dose concentrations typically utilized in human insulin polypeptide therapy, wherein the human insulin plasma levels peaks at 1500 pmol/L 2 hours after subcutaneous injection [1] of some forms of recombinant Insulin.

The present disclosure provides in particular bioactive polypeptide hormones of the insulin family and it's homologs as drug-conjugates that are effective therapeutics for metabolic disorders, including, but not limited to, Type 2 diabetes, Insulin resistance, metabolic syndrome and type 1 diabetes. Again without wishing to be bound to any particular theory of action, Insulin signals by binding to its insulin receptor (IR) on the surface of responding cells. The IR receptor relies on the insulin receptor substrate proteins 1 and 2 adaptors for organizing and coordinating its signal transduction which culminates among other things on the translocation of glucose transporters to the cell surface for the import of glucose from the blood into cells for metabolic consumption and storage. Like many other receptors signal transduction from the insulin receptor involves many proteins that transect several other signaling pathways and it is thus, affected by crosstalk from other cellular responses. In particular, pro-inflammatory pathways triggered by cytokines such as interleukin 6 and interferon induce their own negative feedback responses in order to self-limit their own actions. Thus, under chronic pro-inflammatory conditions such as those taking place in obese subjects or those suffering from metabolic syndrome and other related conditions [2] cytokine-induced SOCS activation causes inhibition of the insulin receptor signaling capability first by competing with receptor signaling intermediates for IRS1/2 binding and secondly by inducing CRL-mediated ubiquitination and degradation of IRS1/2. The magnified signaling activity under those chronic inflammatory conditions also causes overt negative interference on the insulin receptor signaling by the actions of protein tyrosine phosphatases such as PTP1B [3] and the serine/threonine phosphatases PHLPP [4] and PP2A [5]. This overall inability of the IR to transduce signal despite normal binding of insulin is characterized biochemically as insulin resistance. Thus, chronic systemic inflammatory states indirectly results in inhibition of insulin receptor signaling as a result of the biochemical crosstalk between these pathways due to the utilization of common signaling intermediates. SOCS3 specifically is part of a multi-component cullin ring ligase (CRL) protein complex with elongin, Cullin5, RBX, and ubiquitin transferase (E2). The CRL complex requires neddylation of Cullin5 by NEDD8 to function as an E3 ligase. Inhibiting neddylation of Cullin5 prevents it from mediating the ubiquitination of IRS1 and therefore preserving insulin receptor signaling capability [6].

The present disclosure thus provides a platform strategy for the integration of diverse forms of insulin, insulin-like proteins and distinct small molecules as single compounds to specifically target the insulin receptor. Targeting of major insulin-responsive cells and tissues with the compounds of the disclosure, or pharmaceutically acceptable salts, hydrates, solvates, isomers, or tautomers thereof, restores insulin sensitivity and function in order to treat conditions were insulin resistance occurs. In some embodiments, the compound of the disclosure, or pharmaceutically acceptable salts, hydrates, solvates, isomers, or tautomers thereof, comprises a neddylation inhibitor, preventing neddylation of Cullin5, thus, maintaining IRS-1 function. Also, IRS-1 has been shown to be ubiquitinated by a distinct CRL complex composed of Cullin7, ROC1 and SKP1-FBXW8 resulting in it's degradation. This is part of a negative feedback loop initiated by insulin receptor signaling and intermediated by the activity of the mTORC1 pathway and serves to limit PI3K and AKT activation [7]. Thus, this pathway can also be restored by the use of the insulin-nedd8 inhibitor single drug platform.

Utilizing insulin and insulin-like proteins and homologs covalently bound to drugs other than nedd8 inhibitors, such as PTPIB inhibitors, PP2A inhibitors, PHLPP inhibitors and AKT activators [8] the present disclosure also provides new treatments for treating insulin resistance caused by biochemical events other than IRS-1 degradation.

In some embodiments, the compounds of the disclosure, or pharmaceutically acceptable salts, hydrates, solvates, isomers, or tautomers thereof, comprises a neddylation (NEDD8) inhibitor, preventing neddylation of Cullin5, thus, maintaining JAK function.

In some embodiments, the compounds of the disclosure, or pharmaceutically acceptable salts, hydrates, solvates, isomers, or tautomers thereof, comprises a Nicotinamide phosphoribosyltransferase (NAMPT) inhibitor, which reduces the levels of circulating NAMPT levels that has been directly associated with insulin resistance.

In some embodiments, the compounds of the disclosure, or pharmaceutically acceptable salts, hydrates, solvates, isomers, or tautomers thereof, comprises Protein Phosphatase 2A (PP2A) inhibitor, preventing negative regulation of the insulin metabolic signaling pathway by inhibiting Protein Kinase B activity in 3T3-L1 adipocytes.

In some embodiments, the compounds of the disclosure, or pharmaceutically acceptable salts, hydrates, solvates, isomers, or tautomers thereof, comprises Protein Tyrosine Phosphatase 1B (PTP1B) inhibitors, preventing dephosphorylation of the insulin receptor substrate and improving regulation of the insulin receptor.

In some embodiments, the compounds of the disclosure, or pharmaceutically acceptable salts, hydrates, solvates, isomers, or tautomers thereof, comprises c-Jun N-terminal Kinases 1 and 2 (JNK1/2) inhibitors, preventing inhibitory phosphorylation of Insulin Receptor Substrate 1 and Insulin Receptor Substrate 2.

In some embodiments, the compounds of the disclosure, or pharmaceutically acceptable salts, hydrates, solvates, isomers, or tautomers thereof, comprises Protein Kinase B (AKT or PKB) activators, preventing dephosphorylation of protein side chains on insulin receptor substrates and the loss of insulin receptor substrates from cell surface membranes.

In some embodiments, the compounds of the disclosure, or pharmaceutically acceptable salts, hydrates, solvates, isomers, or tautomers thereof, comprises PKR-like kinase (PERK) inhibitors, resulting in enhanced glucose stimulated insulin secretion and sensitivity.

Other targets in addition to Insulin receptor, such as receptors for cytokines, growth factors, or hormones, can also be targeted using cytokine polypeptides, growth factor polypeptides, or hormones conjugated to therapeutic small molecules disclosed herein.

General Information

The articles "a" and "an" are used in this disclosure and may refer to one or more than one (e.g., to at least one) of the grammatical object of the article. By way of example, "an element" may mean one element or more than one element.

The term "and/or" is used in this disclosure and may mean either "and" or "or" unless indicated otherwise.

Unless specifically stated, as used herein, the term "about" may refer to a range of values ±10% of a specified value. For example, the phrase "about 200" may include ±10% of 200, or from 180 to 220. When stated otherwise, the term about may refer to a range of values that include ±20%, ±10%, or ±5%, etc.

An "Insulin-like protein and homologs" may refer to a non-wild-type insulin polypeptide which can include coded and non-coded amino acids, chemically or biochemically modified or derivatized amino acids, variants of a wild-type insulin polypeptide, a fusion insulin polypeptide, or an insulin polypeptide having modified peptide backbones. The insulin-like proteins and homologs polypeptides disclosed herein may also be variants differing from a wild-type insulin polypeptide by amino acid insertions, deletions, mutations, and/or substitutions. The insulin-like proteins and homologs disclosed herein may be a fusion of an insulin polypeptide with another non-insulin polypeptide (e.g, same species ferritin heavy chain or thioredoxin). For examples, the insulin-like proteins and homologs disclosed herein may be a fusion of a non-wild-type insulin polypeptide, which may include coded and non-coded amino acids, chemically or biochemically modified or derivatized amino acids, a variants of a wild-type insulin polypeptide, or an insulin polypeptide having modified peptide backbones with another non-insulin polypeptide (e.g., ferritin heavy chain and thioredoxin).

The terms "peptide," "polypeptide," and "protein" may be used interchangeably herein, and may refer to a polymeric form of amino acids of any length, which can include coded and non-coded amino acids, chemically or biochemically modified or derivatized amino acids, full-length polypeptides, fragments of polypeptides, variants of polypeptides, truncated polypeptides, fusion polypeptides, or polypeptides having modified peptide backbones. The polypeptides disclosed herein may also be variants differing from a specifically recited "reference" polypeptide (e.g., a wild-type polypeptide) by amino acid insertions, deletions, mutations, and/or substitutions.

In some embodiments, conservative substitutions may be made in the amino acid sequence of a polypeptide without disrupting the three-dimensional structure or function of the polypeptide. Conservative substitutions may be accomplished by the skilled artisan by substituting amino acids with similar hydrophobicity, polarity, and R-chain length for one another. Additionally, by comparing aligned sequences of homologous proteins from different species, conservative substitutions may be identified by locating amino acid residues that have been mutated between species without altering the basic functions of the encoded proteins. The term "conservative amino acid substitution" may refer to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polypeptide has a certain percent "sequence identity" to another polypeptide, meaning that, when aligned, that percentage of bases or amino acids are the same, and in the same relative position, when comparing the two sequences. Sequence identity can be determined in a number of different manners. To determine sequence identity, sequences can be aligned using various methods and computer programs (e.g., BLAST, T-COFFEE, MUSCLE, MAFFT, etc.), available over the world wide web at sites including ncbi.nlm.nili.gov/BLAST,ebi.ac.uk/Tools/msa/tcoffee/ebi.ac.uk/Tools/msa/muscle/mafft.cbrc.jp/alignment/software/. See, e.g., Altschul et al. (1990), J. Mol. Biol. 215:403-10.

"Optionally substituted" may refer to the replacement of hydrogen with a monovalent or divalent radical. Suitable substitution groups include, for example, hydroxyl, nitro, amino, imino, cyano, halo, thio, thioamido, amidino, oxo, oxamidino, methoxamidino, imidino, guanidino, sulfonamido, carboxyl, formyl, lower alkyl, halo lower alkyl, lower alkoxy, halo lower alkoxy, lower alkoxyalkyl, alkylcarbonyl, arylcarbonyl, aralkylcarbonyl, heteroarylcarbonyl, heteroaralkylcarbonyl, alkylthio, aminoalkyl, cyanoalkyl, and the like as defined herein. The substitution group can itself be substituted. The group substituted onto the substitution group can be, for example, carboxyl, halo; nitro, amino, cyano, hydroxyl, lower alkyl, lower alkoxy, aminocarbonyl, —SR, thioamido, —$SO_3H$, —$SO_2R$ or cycloalkyl, where R is typically hydrogen, hydroxyl or lower alkyl. When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substitutents can be straight chain, branched or cyclic arrangements of covalently bonded carbon or heteroatoms.

"Lower alkyl" as used herein may refer to branched or straight chain alkyl groups comprising one to ten carbon atoms that independently are unsubstituted or substituted, e.g., with one or more halogen, hydroxyl or other groups. Examples of lower alkyl groups include, but are not limited to, methyl, ethyl, propyl, isopropyl, n-butyl, t-butyl, n-hexyl, neopentyl, trifluoromethyl, pentafluoroethyl, and the like.

"Alkylenyl" may refer to a divalent straight chain or branched chain saturated aliphatic radical having from 1 to 20 carbon atoms. Typical alkylenyl groups employed in compounds of the present disclosure are lower alkylenyl groups that have from 1 to about 6 carbon atoms in their backbone.

"Alkenyl" may refer herein to straight chain, branched, or cyclic radicals having one or more double bonds and from 2 to 20 carbon atoms.

"Alkynyl" may refer herein to straight chain, branched, or cyclic radicals having one or more triple bonds and from 2 to 20 carbon atoms.

"Halo lower alkyl" may refer to a lower alkyl radical substituted with one or more halogen atoms.

"Lower alkoxy" as used herein may refer to RO— wherein R is lower alkyl.

Representative examples of lower alkoxy groups include methoxy, ethoxy, t-butoxy, trifluoromethoxy and the like.

"Lower alkythio" as used herein may refer to RS— wherein R is lower alkyl.

"Alkoxyalkyl" refers to the group -$alk_1$-O-$alk_2$, where $alk_1$ is alkylenyl or alkenyl, and $alk_2$ is alkyl or alkenyl.

"Lower alkoxyalkyl" refers to an alkoxyalkyl as defined herein, where $alk_1$ is lower alkylenyl or lower alkenyl, and $alk_2$ is lower alkyl or lower alkenyl.

"Aryloxyalkyl" refers to the group alkylenyl-O-aryl.

"Aralkoxyalkyl" refers to the group alkylenyl-O-aralkyl, where aralkyl is a lower aralkyl.

"Cycloalkyl" refers to a monoor polycyclic, lower alkyl substituent. Typical cycloalkyl substituents have from 3 to 8 backbone (i.e., ring) atoms in which each backbone atom is optionally substituted carbon. When used in context with cycloalkyl substituents, the term polycyclic refers herein to fused, nonfused cyclic carbon structures and spirocycles. Examples of cycloalkyl groups include, but are not limited to, cyclopropyl, cyclobutyl, cyclopentyl, cyclohexyl, adamantyl, bornyl, norbornyl, and the like.

"Cycloheteroalkyl" refers herein to cycloalkyl substituents that have from 1 to 5, and more typically from 1 to 4 heteroatoms (i.e., non-carbon atoms such as nitrogen, sulfur, and oxygen) in the ring structure, with the balance of atoms in the ring being optionally substituted carbon. Representative heterocycloalkyl moieties include, for example, morpholino, piperazinyl, piperidinyl, pyrrolidinyl, methylpryolidinyl, pyrrolidinone-yl, and the like.

"(Cycloalkyl)alkyl" and "(cycloheteroalkyl)alkyl" refer to alkyl chains substituted with cycloalkyl and cycloheteroalkyl groups respectively.

"Haloalkoxy" refers to an alkoxy radical substituted with one or more halogen atoms. The term "halo lower alkoxy" refers to a lower alkoxy radical substituted with one or more halogen atoms.

"Halo" refers herein to a halogen radical, such as fluorine, chlorine, bromine, or iodine.

"Aryl" refers to monocyclic and polycyclic aromatic groups, or fused ring systems having at least one aromatic ring, having from 3 to 14 backbone carbon atoms. Examples of aryl groups include without limitation phenyl, naphthyl, dihydronaphtyl, tetrahydronaphthyl, and the like.

"Aralkyl" refers to an alkyl group substituted with an aryl group. Typically, aralkyl groups employed in compounds of the present disclosure have from 1 to 6 carbon atoms incorporated within the alkyl portion of the aralkyl group. Suitable aralkyl groups employed in compounds of the present disclosure include, for example, benzyl, picolyl, and the like.

"Heteroaryl" refers herein to aryl groups having from one to four heteroatoms as ring atoms in an aromatic ring with the remainder of the ring atoms being aromatic or non-aromatic carbon atoms. When used in connection with aryl substituents, the term polycyclic refers herein to fused and non-fused cyclic structures in which at least one cyclic structure is aromatic, such as, for example, benzodioxozolo, naphthyl, and the like. Exemplary heteroaryl moieties employed as substituents in compounds of the present disclosure include pyridyl, pyrimidinyl, thiazolyl, indolyl, imidazolyl, oxadiazolyl, tetrazolyl, pyrazinyl, triazolyl, thiophenyl, furanyl, quinolinyl, purinyl, benzothiazolyl, benzopyridyl, and benzimidazolyl, and the like.

"Amino" refers herein to the group —$NH_2$. The term "lower alkylamino" refers herein to the group —$NRR^I$ where R and $R^I$ are each independently selected from hydrogen or lower alkyl. The term "arylamino" refers herein to the group —$NRR^I$ where R is aryl and $R^I$ is hydrogen, lower alkyl, aryl, or aralkyl. The term "aralkylamino" refers herein to the group —$NRR^I$ where R is aralkyl and $R^I$ is hydrogen, lower alkyl, aryl, or aralkyl. The terms "heteroarylamino" and "heteroaralkylamino" are defined by analogy to arylamino and aralkylamino.

"Aminocarbonyl" refers herein to the group —C(O)$NH_2$. The terms "lower alkylaminocarbonyl," "arylaminocarbonyl," "aralkylaminocarbonyl," "heteroarylaminocarbonyl," and "heteroaralkylaminocarbonyl" refer to —C(O)$NRR^I$ where R and $R^I$ independently are hydrogen and optionally substituted lower alkyl, aryl, aralkyl, heteroaryl, and heteroaralkyl respectively by analogy to the corresponding terms herein.

"Thio" refers to —SH. The terms lower alkylthio, arylthio, heteroarylthio, cycloalkylthio, cycloheteroalkylthio, aralkylthio, heteroaralkylthio, (cycloalkyl)alkylthio, and (cycloheteroalkyl)alkylthio refer to —SR, where R is optionally substituted lower alkyl, aryl, heteroaryl, cycloalkyl, cycloheteroalkyl, aralkyl, heteroaralkyl, (cycloalkyl) alkyl, and (cycloheteroalkyl)alkyl respectively.

"Sulfonyl" refers herein to the group —$SO_2$—. The terms lower alkylsulfonyl, arylsulfonyl, textitheteroarylsulfonyl, cycloalkylsulfonyl, cycloheteroalkylsulfonyl, aralkylsulfonyl, heteroaralkylsulfonyl, (cycloalkyl)alkylsulfonyl, and (cycloheteroalkyl)alkylsulfonyl refer to —$SO_2$R where R is optionally substituted lower alkyl, aryl, heteroaryl, cycloalkyl, cycloheteroalkyl, aralkyl, heteroaralkyl, (cycloalkyl) alkyl, and (cycloheteroalkyl)alkyl respectively.

"Sulfinyl" refers herein to the group —SO—. The terms lower alkylsulfinyl, arylsulfinyl, heteroarylsulfinyl, cycloalkylsulfinyl, cycloheteroalkylsulfinyl, aralkylsulfinyl, heteroaralkylsulfinyl, (cycloalkyl)alkylsulfinyl, and (cycloheteroalkyl)alkylsulfinyl refer to —SOR where R is optionally substituted lower alkyl, aryl, heteroaryl, cycloalkyl, cycloheteroalkyl, aralkyl, heteroaralkyl, (cycloalkyl)alkyl, and (cycloheteroalkyl)alkyl respectively.

"Nitrilo" refers to —CN.

"Formyl" refers to —C(O)H.

"Carboxyl" refers to —C(O)OH.

"Carbonyl" refers to the divalent group —C(O)—. The terms lower alkylcarbonyl, arylcarbonyl, heteroarylcarbonyl, cycloalkylcarbonyl, cycloheteroalkylcarbonyl, aralkycarbonyl, heteroaralkylcarbonyl, (cycloalkyl)alkylcarbonyl, and (cycloheteroalkyl)alkylcarbonyl refer to —C(OR)—, where R is optionally substituted lower alkyl, aryl, heteroaryl, cycloalkyl, cycloheteroalkyl, aralkyl, heteroaralkyl, (cycloalkyl)alkyl, and (cycloheteroalkyl)alkyl respectively.

"Thiocarbonyl" refers to the group —C(S)—. The terms lower alkylthiocarbonyl, arylthiocarbonyl, heteroarylthiocarbonyl, cycloalkylthiocarbonyl, cycloheteroalkylthiocarbonyl, aralkylthiocarbonyloxlthiocarbonyl, heteroaralkylthiocarbonyl, (cycloalkyl)alkylthiocarbonyl, and (cycloheteroalkyl)alkylthiocarbonyl refer to —C(S)R—, where R is optionally substituted lower alkyl, aryl, heteroaryl, cycloalkyl, cycloheteroalkyl, aralkyl, heteroaralkyl, (cycloalkyl)alkyl, and (cycloheteroalkyl)alkyl respectively.

"Carbonyloxy" refers generally to the group —C(O)O—. The terms lower alkylcarbonyloxy, arylcarbonyloxy, heteroarylcarbonyloxy, cycloalkylcarbonyloxy, aralkylcarbonyloxy, heteroaralkylcarbonyloxy, cycloheteroalkylcarbonyloxy, (cycloalkyl)alkylcarbonyloxy, (cycloheteroalkyl) alkylcarbonyloxy refer to —C(O)OR, where R is optionally substituted lower alkyl, aryl, heteroaryl, cycloalkyl, cycloheteroalkyl, aralkyl, heteroaralkyl, (cycloalkyl)alkyl, and (cycloheteroalkyl)alkyl respectively.

"Oxycarbonyl" refers to the group —OC(O)—. The terms lower alkyloxycarbonyl, aryloxycarbonyl, heteroaryloxycarbonyl, cycloalkyloxycarbonyl, cycloheteroalkyloxycarbonyl, aralkyloxycarbonyloxycarbonyl, heteroaralkyloxycarbonyl, (cycloalkyl)alkyloxycarbonyl, (cycloheteroalkyl) alkyloxycarbonyl refer to —OC(O)R, where R is optionally substituted lower alkyl, aryl, heteroaryl, cycloalkyl, cycloheteroalkyl, aralkyl, heteroaralkyl, (cycloalkyl)alkyl, and (cycloheteroalkyl)alkylrespectively.

"Carbonylamino" refers to the group —NHC(O)—. The terms lower alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, and (cycloheteroalkyl)alkylcarbonylamino refer to —NHC(O)R—, where R is optionally substituted lower alkyl, aryl, heteroaryl, cycloalkyl, cycloheteroalkyl, aralkyl, heteroaralkyl, (cycloalkyl)alkyl, or (cycloheteroalkyl)alkyl respectively. In addition, the present disclosure includes n-substituted carbonylamino (—$NR^I$C(O)R), where $R^I$ is optionally substituted lower alkyl, aryl, heteroaryl, aralkyl, or heteroaralkyl and R retains the previous definition.

"Carbonylthio" refers to the group —C(O)S—. The terms lower alkylcarbonylthio, arylcarbonylthio, heteroarylcarbonylthio, cycloalkylcarbonylthio, cycloheteroalkylcarbonylthio, aralkylcarbonylthio, heteroaralkylcarbonylthio, (cycloalkyl)alkylcarbonylthio, (cycloheteroalkyl) alkylcarbonylthio refer to —C(O)SR, where R is optionally substituted lower alkyl, aryl, heteroaryl, cycloalkyl, cycloheteroalkyl, aralkyl, heteroaralkyl, (cycloalkyl)alkyl, and (cycloheteroalkyl)alkyl respectively.

"Guanidino" or "Guanidyl" refers to moieties derived from guanidine, $H_2N$—C(═NH)—$NH_2$. Such moieties include those bonded at the nitrogen atom carrying the formal double bond (the 2-position of the guanidine, e.g., diaminomethyleneamino, ($(H_2N)_2$—C═NH—) and those bonded at either of the nitrogen atoms carrying a formal single bond (the 1 or 3-positions of the guanidine, e.g., $H_2$NC(═NH)—NH—). The hydrogen atoms at either nitrogen can be replaced with a suitable substituent, such as lower alkyl, aryl, or lower aralkyl.

"Amidino" refers to the moieties R—C(═N)—$NR^I$— (the radical being at the $N^1$ nitrogen) and R—($NR^I$)CN— (the radical being at the $N^2$ nitrogen), where R and $R^I$ can be hydrogen, lower alkyl, aryl, or lower aralkyl.

"Imino" refers to the group —C(═NR)—, where R can be hydrogen or optionally substituted lower alkyl, aryl, heteroaryl, or heteroaralkyl respectively. The terms "imino lower alkyl," "iminocycloalkyl," "iminocycloheteroalkyl," "iminoaralkyl," "iminoheteroaralkyl," "(cycloalkyl)iminoalkyl," "(cycloiminoalkyl)alkyl," "(cycloiminoheteroalkyl) alkyl," and "(cycloheteroalkyl)iminoalkyl" refer to optionally substituted lower alkyl, cycloalkyl, cycloheteroalkyl, aralkyl, heteroaralkyl, (cycloalkyl)alkyl, and (cycloheteroalkyl)alkyl groups that include an imino group, respectively.

"Oximino" refers to the group —C(═NOR)—, where R can be hydrogen ("hydroximino") or optionally substituted lower alkyl, aryl, heteroaryl, or heteroaralkyl respectively. The terms "oximino lower alkyl," "oximinocycloalkyl," "oximinocycloheteroalkyl," "oximinoaralkyl," "oximinoheteroaralkyl," "(cycloalkyl)oximinoalkyl," "(cyclooximinoalkyl)alkyl," "(cyclooximinoheteroalkyl)alkyl," and "(cycloheteroalkyl)oximinoalkyl" refer to optionally substituted lower alkyl, cycloalkyl, cycloheteroalkyl, aralkyl, heteroaralkyl, (cycloalkyl)alkyl, and (cycloheteroalkyl)alkyl groups that include an oximino group, respectively.

"Methylene" as used herein refers to an unsubstituted, monosubstituted, or disubstituted carbon atom having a formal $sp^3$ hybridization (i.e., —$CRR^I$—, where R and $R^I$ are hydrogen or independent substituents).

"Methine" as used herein refers to an unsubstituted or substituted carbon atom having a formal $sp^2$ hybridization (i.e., CR═ or ═CR—, where R is hydrogen or a substituent).

Compounds of the Disclosure

The present disclosure relates to compounds (e.g., Formulae II and III), or pharmaceutically acceptable salts, hydrates, solvates, isomers, or tautomers thereof, useful for the treatment of disorders, such as insulin resistance, type 2 diabetes and metabolic syndrome. More particularly, the compounds of the disclosure (e.g., Formulae II and III), or pharmaceutically acceptable salts, hydrates, solvates, isomers, or tautomers thereof, may comprise biologically active polypeptides or hormones modified to include the attachment of therapeutic compounds using linkers. The compounds of the disclosure, or pharmaceutically acceptable salts, hydrates, solvates, isomers, or tautomers thereof, also comprise therapeutic compounds connected to linkers.

In an aspect, the present disclosure provides compounds having the structure of Formula (I):

$$X_{2a}\text{—}(X_3)_m \quad \text{(I),}$$

and pharmaceutically acceptable salts, solvates, hydrates, isomers, or tautomers thereof, wherein:

m is 1, 2, 3, 4, 5, 6, 7, 8, 9, or 10;

$X_{2a}$ is a linker; and $X_3$ is a therapeutic compound.

As shown in Formula (I), multiple $X_3$ moieties, the number defined by m, may be attached to $X_{2a}$.

In some embodiments of the compound of Formula (I), m is 1. In some embodiments of the compound of Formula (I), m is 2, 3, 4, 5, 6, 7, or 8. In some embodiments of the compound of Formula (I), m is 1, 2, or 3. In some embodiments of the compound of Formula (I), m is 2, 3, 4, or 5. In some embodiments of the compound of Formula (I), m is 2. In some embodiments of the compound of Formula (I), m is 3. In some embodiments of the compound of Formula (I), m is 4. In some embodiments of the compound of Formula (I), m is 5. In some embodiments of the compound of Formula (I), m is 6. In some embodiments of the compound of Formula (I), m is 7. In some embodiments of the compound of Formula (I), m is 8. In some embodiments of the compound of Formula (I), m is 9. In some embodiments of the compound of Formula (I), m is 10. In some embodiments, m is an integer between 1 and 10.

$X_{2a}$ is a linker, which can take many forms as shown herein. In some embodiments of the compound of Formula (I), $X_{2a}$ is a linker which has not yet been reacted with a biologically active polypeptide or hormone. In some embodiments of the compound of Formula (I), $X_{2a}$ is a cleavable linker. In some embodiments of the compound of Formula (I), $X_{2a}$ is a non-cleavable linker. As used herein, a "cleavable linker" may refer to a linker comprising a lysosomal and/or endosomal-specific enzyme cleavage site, such as a β-glucuronidase site, a β-galactosidase site, or a cathepsin site. With a cleavable linker, the therapeutic compound may be liberated only after internalization of the conjugate by the cell, in proximity to the therapeutic compound's intracellular target. This targeted liberation may enable use of toxic, potent therapeutic compounds for treatment of disorders. "Non-cleavable linkers" may refer to linkers conjugated to therapeutic compounds that will act directly absent release.

In some embodiments of the compound of Formula (I), $X_{2a}$ is a linker listed in Table 1, wherein the right side of $X_{2a}$, as drawn, is bound to $X_3$. In Table 1, R groups =H, glycol ether, or an additional glycol linker alkyl, aryl, and arylalkyl, alkynes, alkenes, substituted phenyl groups, aromatic heterocycles, glycol ether, or an additional glycol linker attaching to the therapeutic compound.

TABLE 1

Exemplary $X_{2a}$ Linker Linkers

| Compound Number | Structure |
| --- | --- |
| L-1 Cleavable Linker | 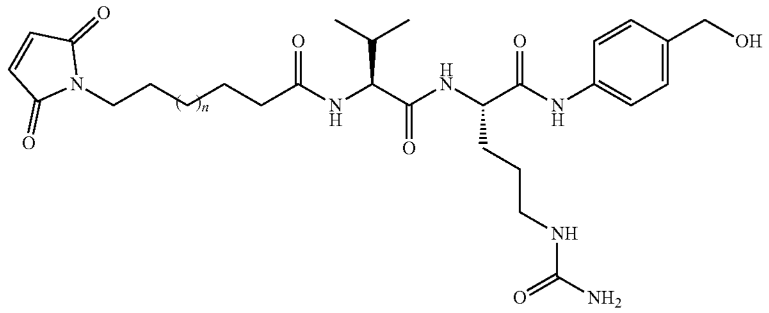 |
| L-2 Cleavable Linker | 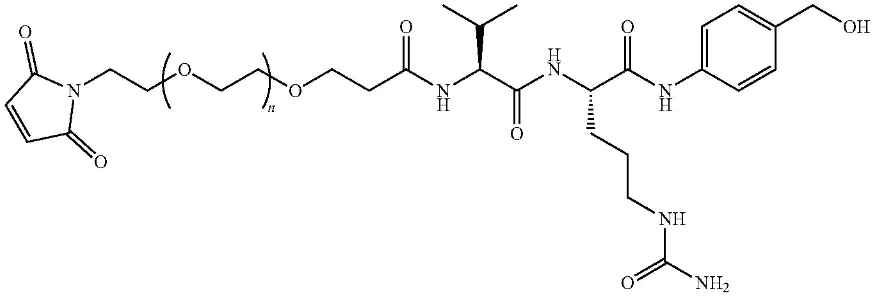 |
| L-3 Cleavable Linker | 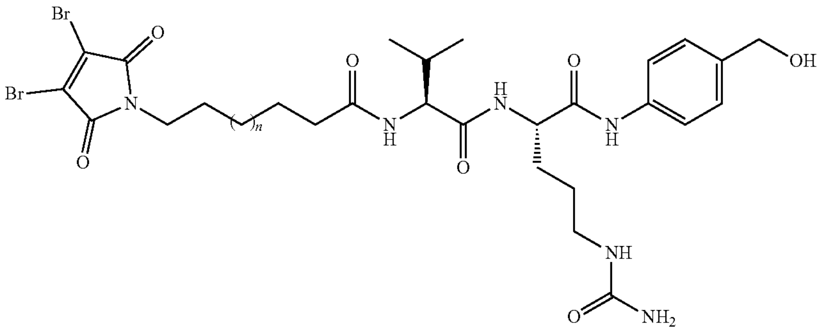 |

TABLE 1-continued
| Exemplary $X_{2a}$ Linker Linkers | |
|---|---|
| Compound Number | Structure |
| L-4 Cleavable Linker | 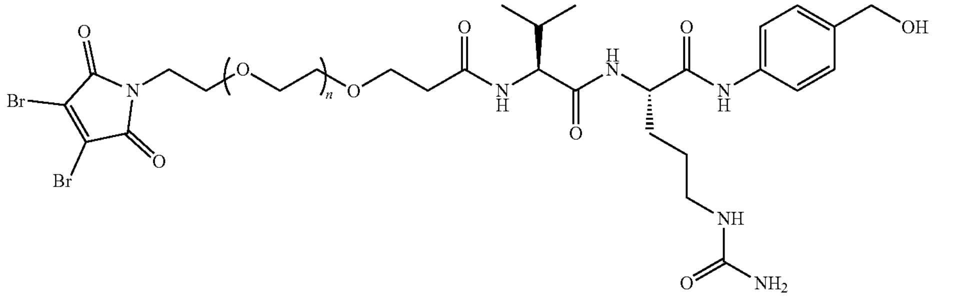 |
| L-5 Cleavable Linker | 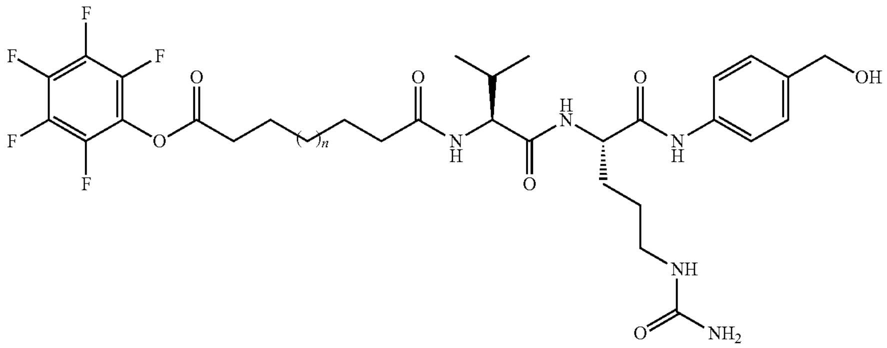 |
| L-6 Cleavable Linker | 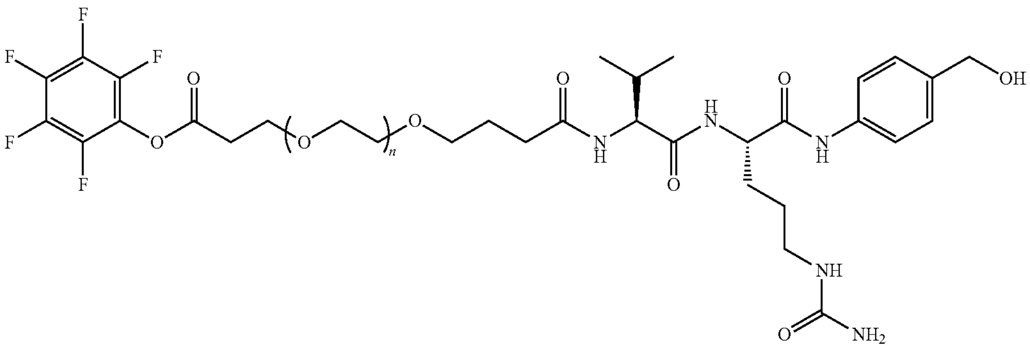 |
| L-7 Cleavable Linker | 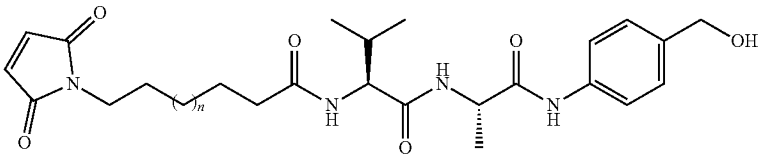 |
| L-8 Cleavable Linker | 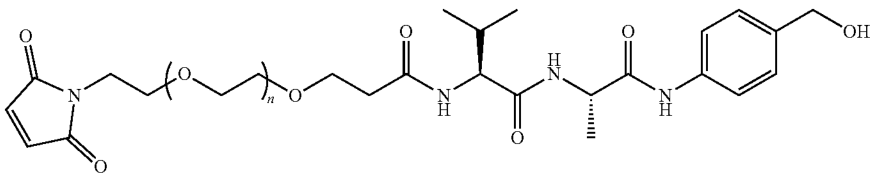 |
| L-9 Cleavable Linker | 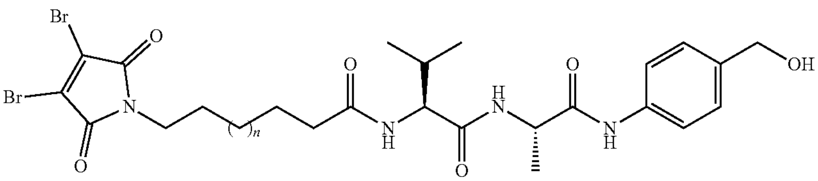 |

TABLE 1-continued
| Exemplary $X_{2a}$ Linker Linkers | |
|---|---|
| Compound Number | Structure |
| L-10 Cleavable Linker | 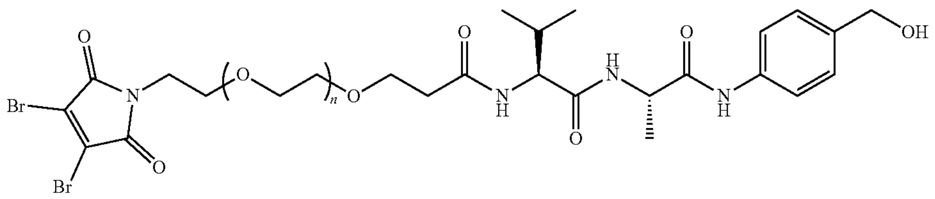 |
| L-11 Cleavable Linker | 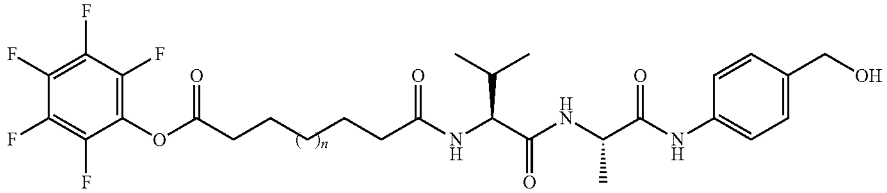 |
| L-12 Cleavable Linker | 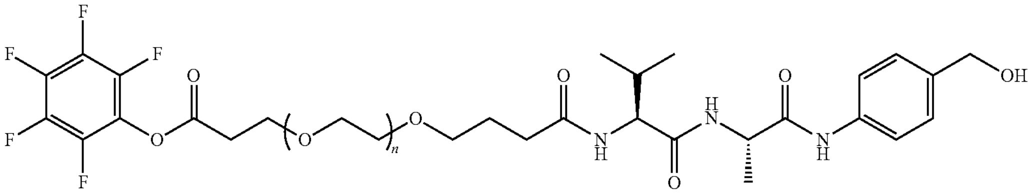 |
| L-13 Cleavable Linker | 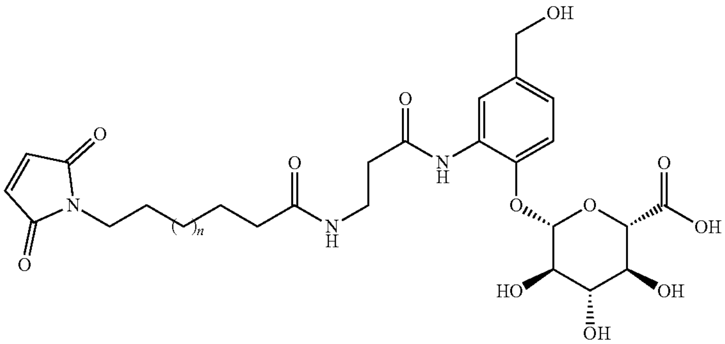 |
| L-14 Cleavable Linker | 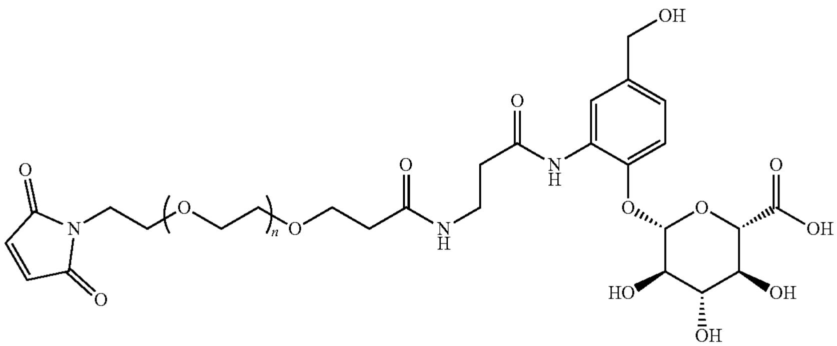 |

TABLE 1-continued
| Exemplary $X_{2a}$ Linker Linkers | |
|---|---|
| Compound Number | Structure |
| L-15 Cleavable Linker | 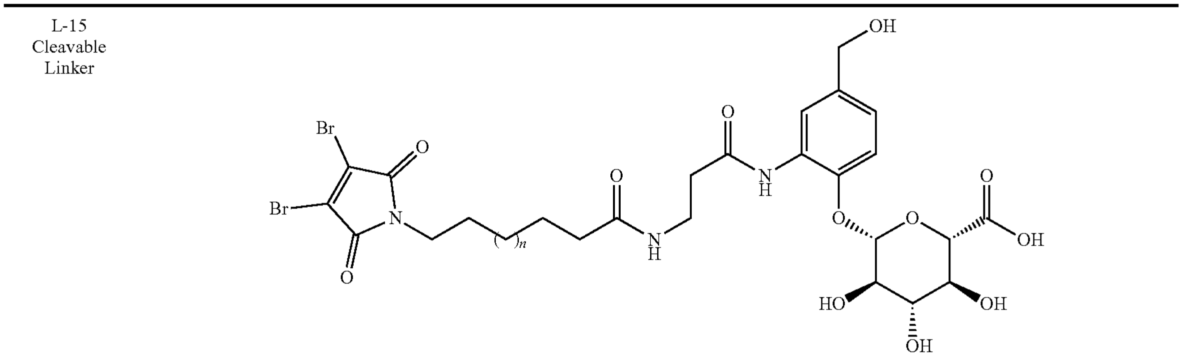 |
| L-16 Cleavable Linker | 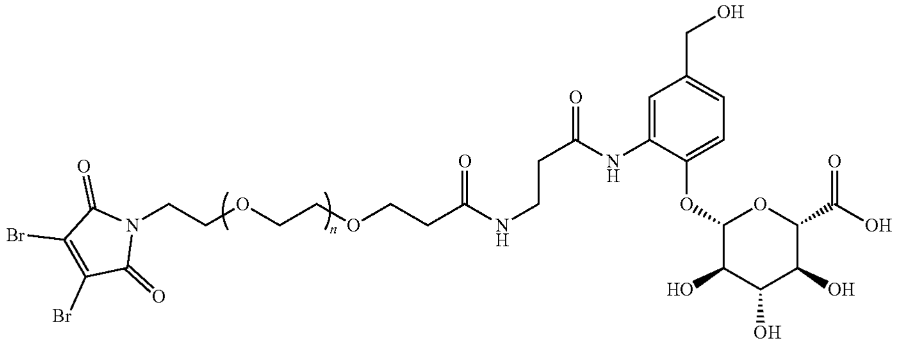 |
| L-17 Cleavable Linker | 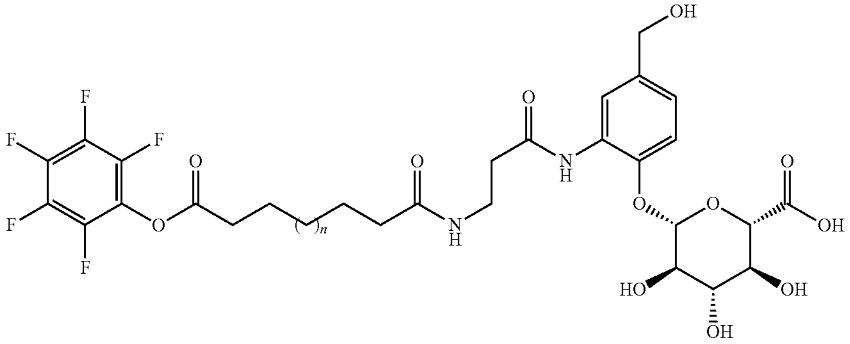 |
| L-18 Cleavable Linker | 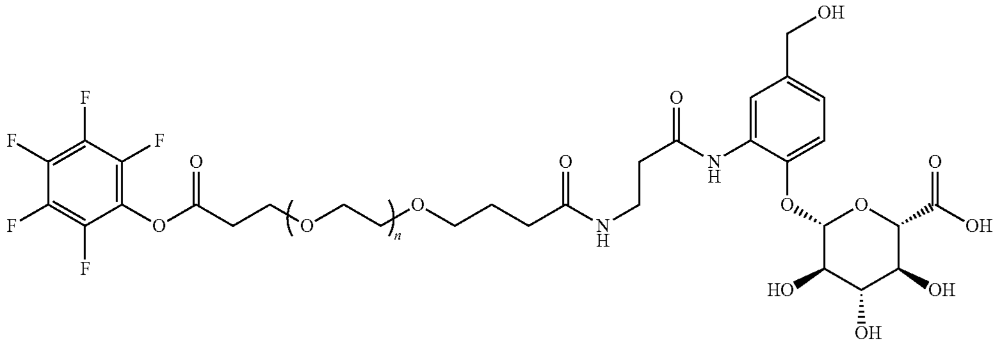 |
| L-19 Non-Cleavable Linker | 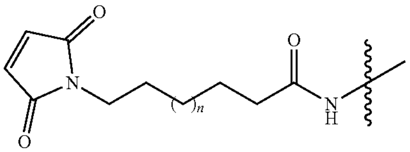 |

TABLE 1-continued

| Exemplary $X_{2a}$ Linker Linkers | |
|---|---|
| Compound Number | Structure |
| L-20 Non-Cleavable Linker | 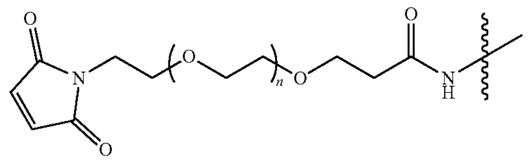 |
| L-21 Non-Cleavable Linker | 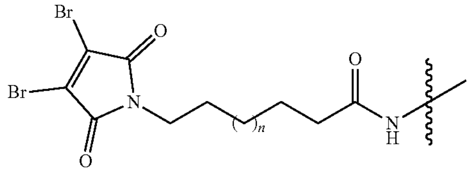 |
| L-22 Non-Cleavable Linker | 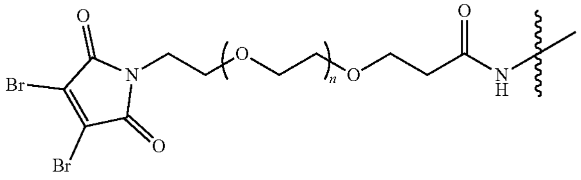 |
| L-23 Non-Cleavable Linker | 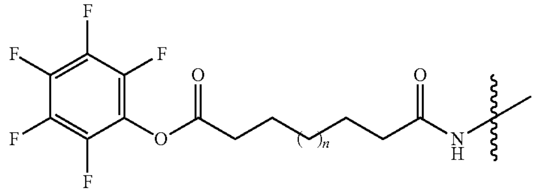 |
| L-24 Non-Cleavable Linker | 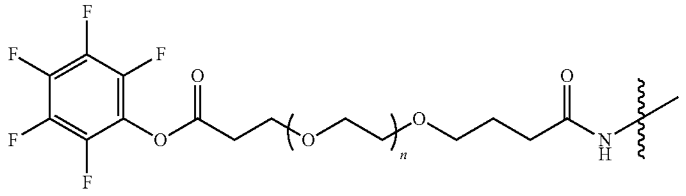 |

In some embodiments of the compound of Formula (I), $X_{2a}$ is a cleavable linker selected from the group consisting of L-1, L-2, L-3, L-4, L-5, L-6, L-7, L-8, L-9, L-10, L-11, L-12, L-13, L-14, L-15, L-16, L-17 and L-18.

In some embodiments of the compound of Formula (I), $X_{2a}$ is a non-cleavable linker selected from the group consisting of L-19, L-20, L-21, L-22, L-23 and L-24.

Figure 5A:
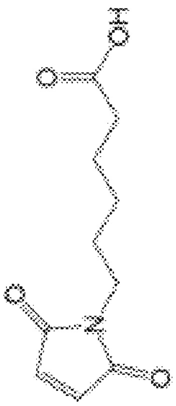
FIGS. 5A and 5B are schematics showing some non-cleavable linkers (FIG. 5A) and several protein drug conjugates with non-cleavable linkers (FIG. 5B) in accordance with some embodiments of the disclosure.
Figure 5A:
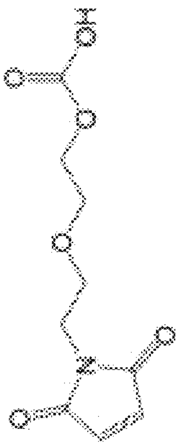
Figure 5A:
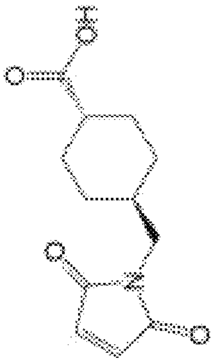
Figure 5A:
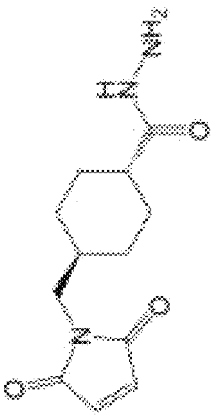
Figure 5B:
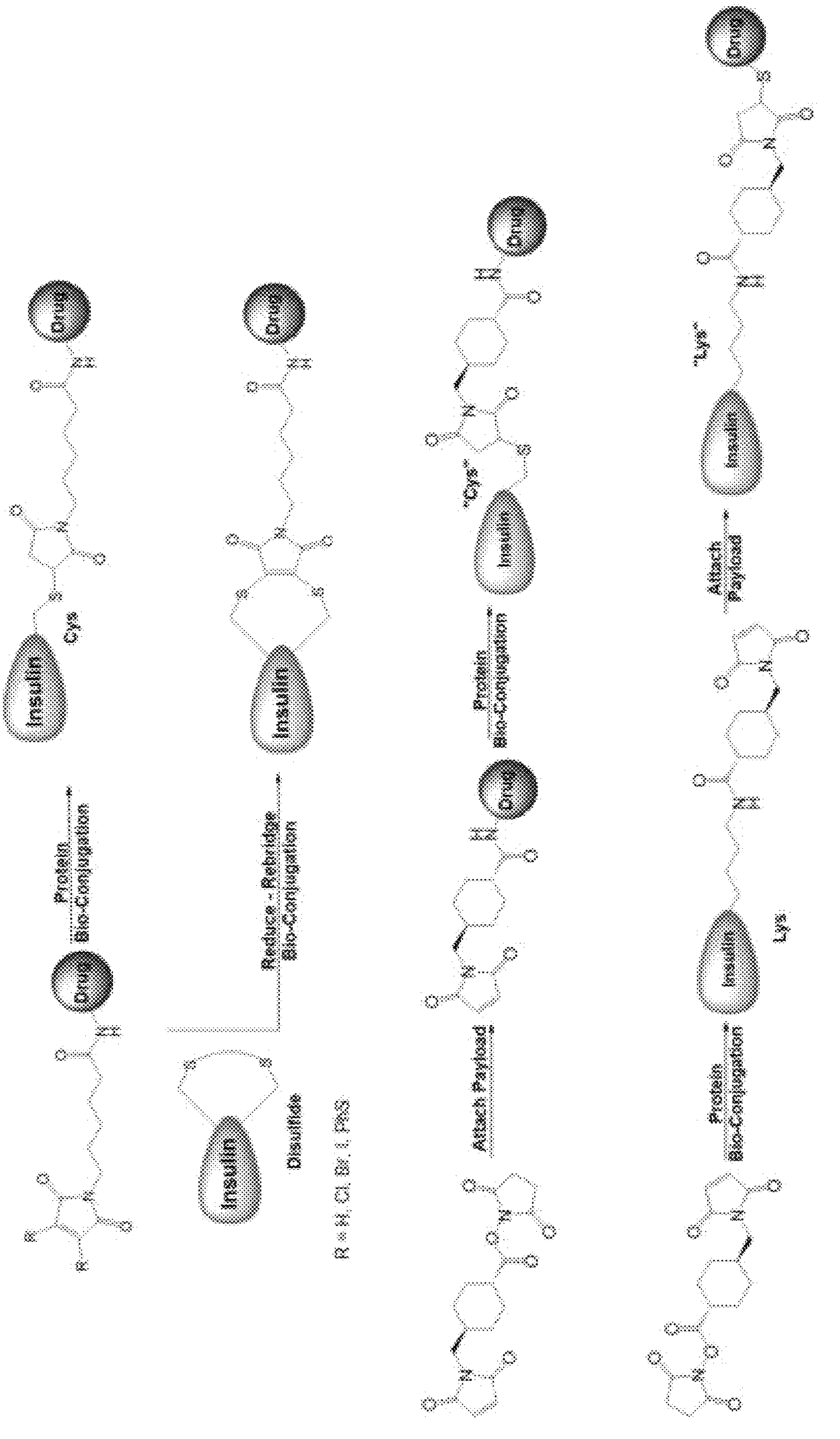
Figure 6A:
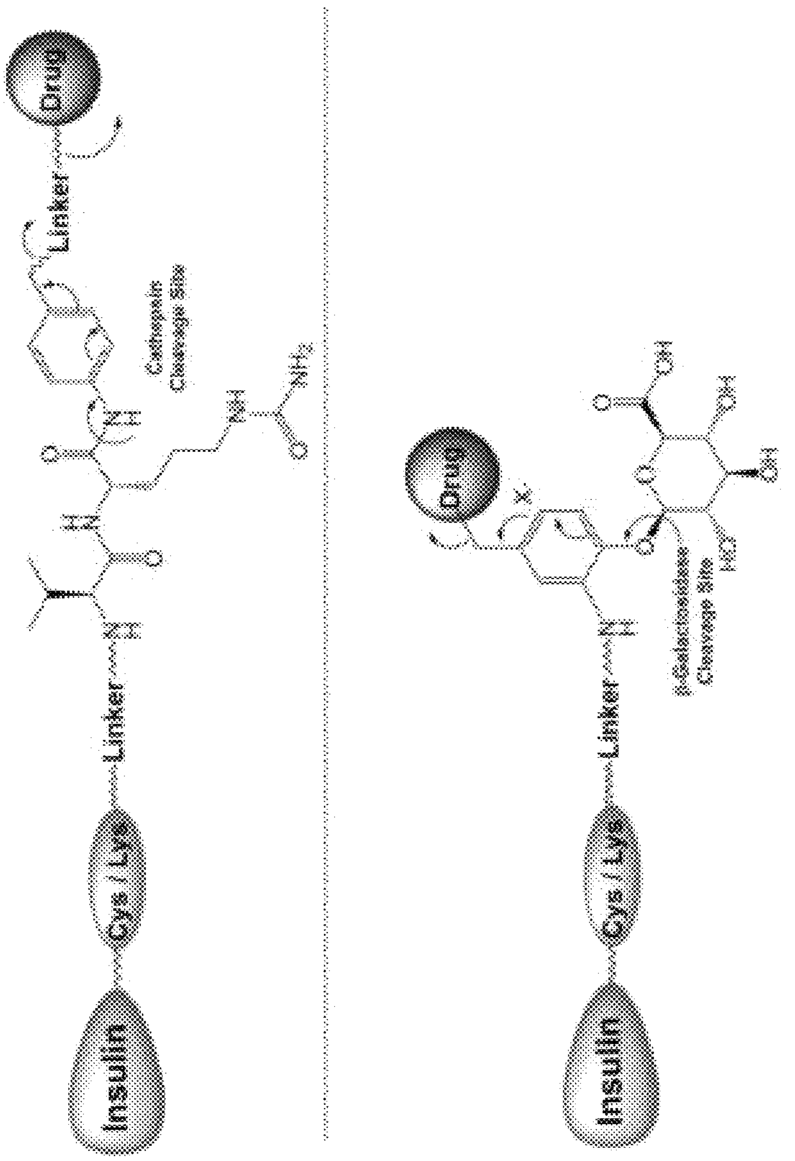
FIGS. 6A, 6B and 6C are schematics showing two classes of cleavable linkers (Dipeptides and Glucuronides, FIG. 6A), along with various protein drug conjugates with dipeptide linkers (FIG. 6B) and various protein drug conjugates with glucuronide linkers (FIG. 6C) in accordance with some embodiments of the disclosure.
Figure 6B:
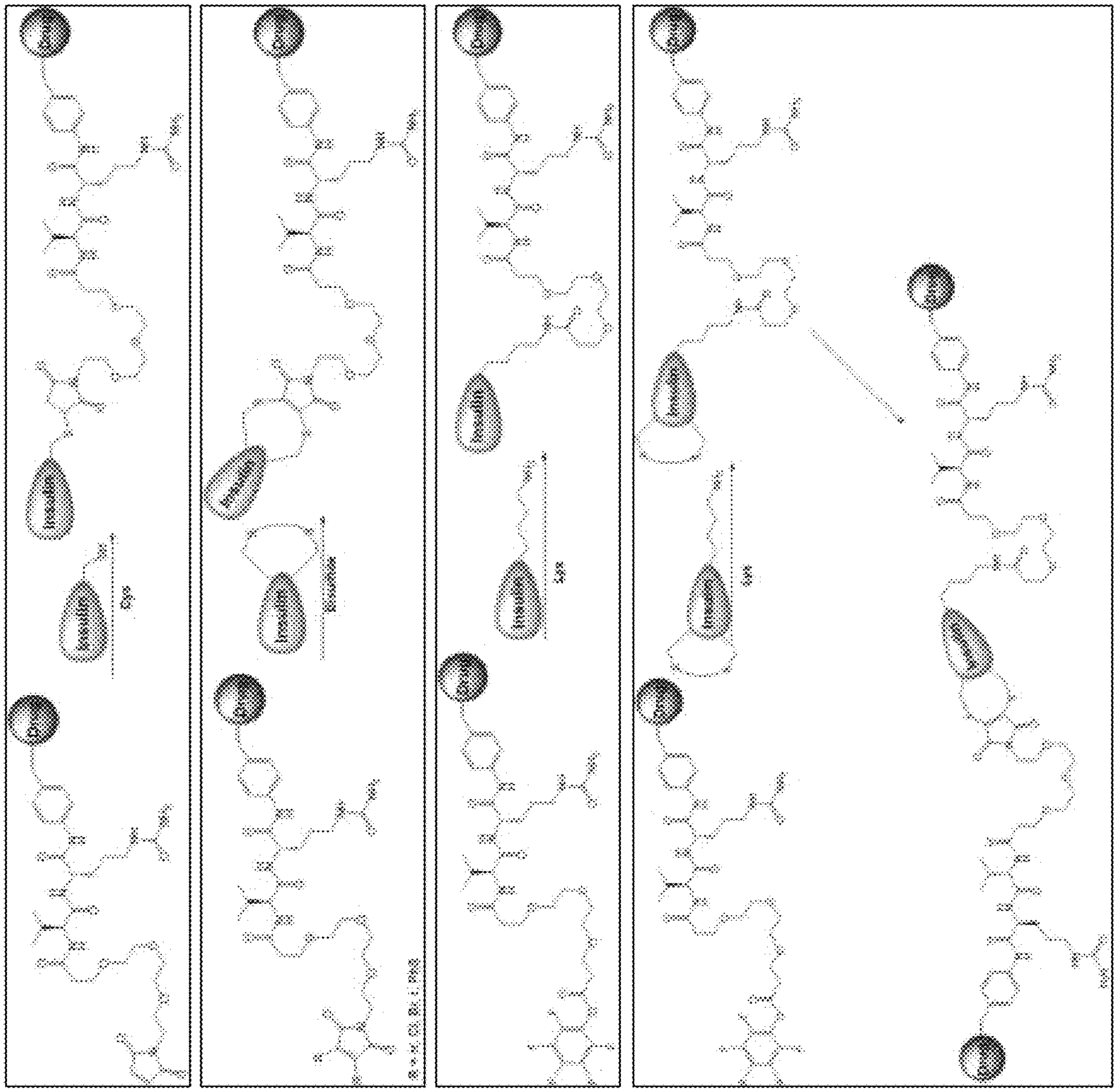
Figure 6C:
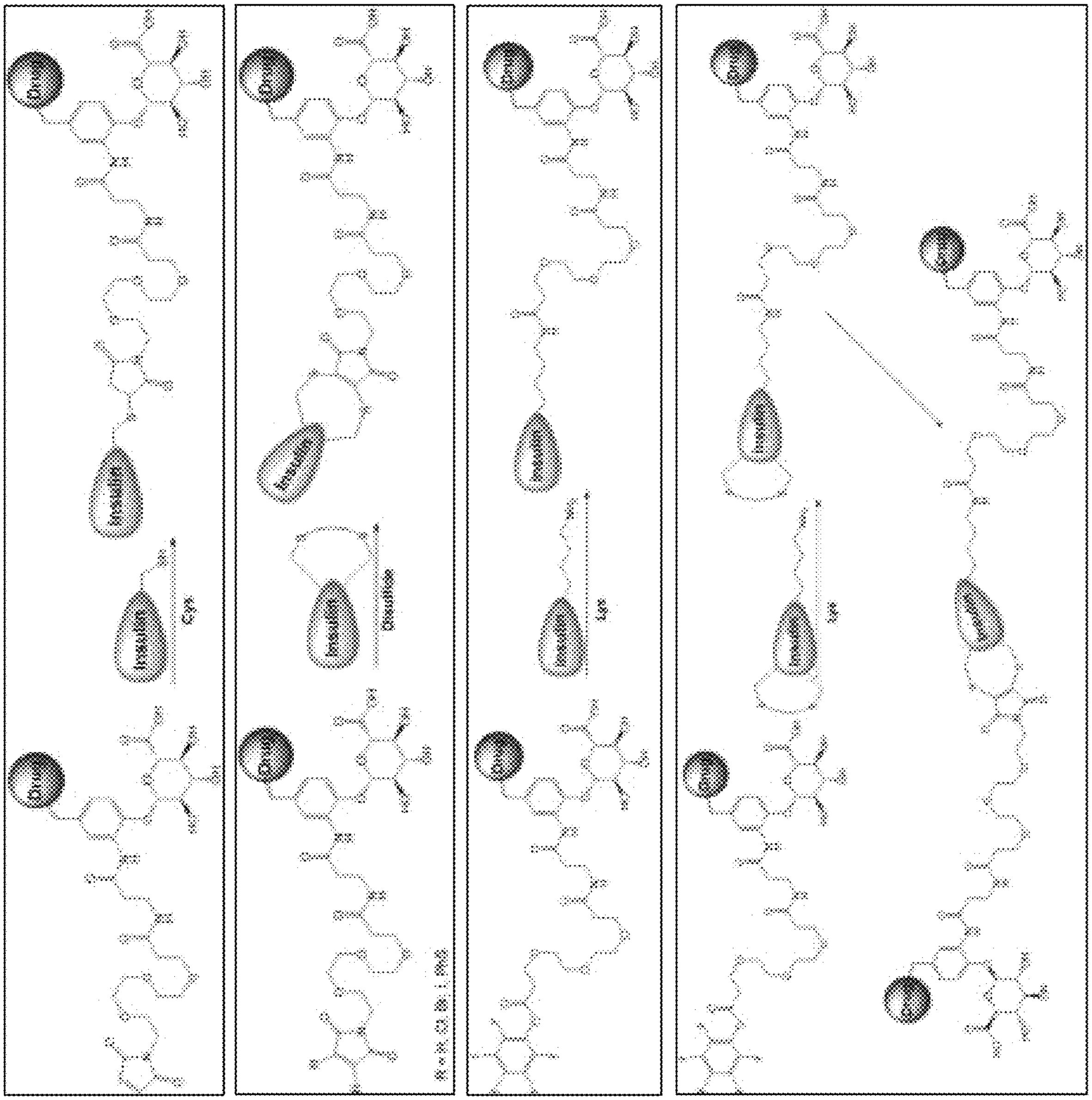

FIGS. 5A and 6A show exemplary cleavable and non-cleavable linkers, which are discussed in more detail herein.

The therapeutic compound $X_3$ can be any suitable therapeutic compound for the desired therapeutic application. Examples of therapeutic compounds useful for the treatment of metabolic disorders (e.g., diabetes, Insulin resistance, fatty liver disease, obesity, etc.) include, but are not limited to, the following classes of metabolic disorder treatments: JNK (c-Jun N-terminal kinase) inhibitors, PKR-like endoplasmic reticulum kinase (PERK) inhibitor, PTP1B (protein-tyrosine phosphatase 1B), AKT (Protein Kinase B) an antidiabetic, a neddylation inhibitor, a ubiquitin-activating enzyme inhibitor, a ubiquitin-activating enzyme E1 inhibitor, and a proteasome inhibitor. Examples of such therapeutic compounds include, but are not limited to: MLN4924 (pevonedistat or ((1R,2R,4S)-4-(4-(((R)-2,3-dihydro-1H-inden-1-yl)amino)-7H-pyrrolo[2,3-d]pyrimidin-7-yl)-2-hydroxycyclopentyl)methyl sulfamate); TAS4464 (((2S,3S,4R,5R)-5-(4-amino-5-((4,7-dimethyl-3,4-dihydro-2H-benzo[b][1,4]oxazin-8-yl)ethynyl)-7H-pyrrolo[2,3-d]pyrimidin-7-yl)-3,4-dihydroxytetrahydrofuran-2-yl)methyl sulfamate); ABP1 (((2S,3R,4S,5S)-5-(6-((3-ethynylphenyl)amino)-9H-purin-9-yl)-3,4-dihydroxytetrahydrofuran-2-yl)methyl sulfamate); GSK2606414 (1-(5-(4-amino-7-methyl-7H-pyrrolo[2,3-d]pyrimidin-5-yl)indolin-1-yl)-2-(3-(trifluoromethyl)phenyl)ethan-1-one); AMG PERK 44 (4-(2-amino-4-methyl-3-(2-methylquinolin-6-yl)benzoyl)-1-methyl-2,5-diphenyl-1,2-dihydro-3H-pyrazol-3-one hydrochloride); FK866 HCl ((E)-N-(4-(1-benzoylpiperidin-4-yl)butyl)-3-(pyridin-3-yl)acrylamide hydrochloride); CHS 828 (2-[6-(4-chlorophenoxy)hexyl]-1-cyano-3-pyridin-4-ylguanidine); STF 118804 (4-(5-methyl-4-(tosylmethyl)oxazol-2-yl)-N-(pyridin-3-ylmethyl)benzamide); GPP 78 (N-([1,1'-biphenyl]-2-yl)-8-(4-(pyridin-3-yl)-1H-1,2,3-triazol-1-yl)octanamide); GNE 617 (N-(4-((3,5-difluorophenyl)sulfonyl)benzyl)imidazo[1,2-a]pyridine-6-carboxamide); CB30865 (4-(((7-bromo-2-methyl-4-oxo-3,4-dihydroquinazolin-6-yl)methyl)(prop-2-yn-1-yl)amino)-N-(pyridin-3-ylmethyl)benzamide); TCS 401 (2-

(carboxyformamido)-4,5,6,7-tetrahydrothieno[2,3-c] pyridine-3-carboxylic acid); CX08005 (2-((2-(tetradecyloxy)phenyl)carbamoyl)benzoic acid); methyl 5-((N-(4-(N-(2-methoxy-2-oxoethyl)methylsulfonamido) benzyl)-1-phenylmethyl)sulfonamido)-2-((4-methylbenzyl) oxy)benzoate; ((3-bromo-7-cyanonaphthalen-2-yl)difluoromethyl)phosphonic acid; BVT 948 (4-hydroxy-3,3-dimethyl-2H-benzo[g] indole-2,5 (3H)-dione); SC79 (ethyl 2-amino-6-chloro-4-(1-cyano-2-ethoxy-2-oxoethyl)-4H-chromene-3-carboxylate); SP600125 (dibenzo[cd,g] indazol-6 (2H)-one; CC 401 (3-(3-(2-(piperidin-1-yl)ethoxy) phenyl)-5-(1H-1,2,4-triazol-5-yl)-1H-indazole hydrochloride); TCS JNK 60 (N-(4-amino-5-cyano-6-ethoxypyridin-2-yl)-2-(2,5-dimethoxyphenyl)acetamide); TCS JNK 5a (N-(3-cyano-4,5,6,7-tetrahydrobenzo[b]thiophen-2-yl)-1-naphthamide); JNK-IN-7 ((E)-3-(4-(dimethylamino)but-2-enamido)-N-(4-((4-(pyridin-3-yl)pyrimidin-2-yl)amino)phenyl)benzamide); JNK-IN-8 ((E)-3-(4-(dimethylamino)but-2-enamido)-N-(2-methyl-4-((4-(pyridin-3-yl)pyrimidin-2-yl)amino)phenyl)benzamide; JNK-IN-11 ((E)-3-(4-(dimethylamino)but-2-enamido)-N-(4-((4-(2-phenylpyrazolo[1,5-a]pyridin-3-yl)pyrimidin-2-yl)amino)phenyl)benzamide; Fostriecin (sodium (1E,3R, 4R,6R,7Z,9Z,11E)-3,6,13-trihydroxy-3-methyl-1-((R)-6-oxo-3,6-dihydro-2H-pyran-2-yl)trideca-1,7,9,11-tetraen-4-yl hydrogen phosphate; Endothall (3-(4-methylpiperazine-1-carbonyl)-7-oxabicyclo[2.2.1]heptane-2-carboxylic acid); Rubratoxin A ((E)-3-(4-(dimethylamino)but-2-enamido)-N-(4-((4-(2-phenylpyrazolo[1,5-a]pyridin-3-yl)pyrimidin-2-yl)amino)phenyl)benzamide); Okadaic Acid ((2R)-2-hydroxy-3-((2S,3S,6R)-3-hydroxy-8-((2R,E)-4-((2R,5R,6'S, 8'R)-8'-hydroxy-6'-((1S,3S)-1-hydroxy-3-((2S,3R,6S)-3-methyl-1,7-dioxaspiro[5.5]undecan-2-yl)butyl)-7'-methyleneoctahydro-3H,3'H-spiro[furan-2,2'-pyrano[3,2-b] pyran]-5-yl)but-3-en-2-yl)-10-methyl-1,7-dioxaspiro[5.5] undec-10-en-2-yl)-2-methylpropanoic acid). In some embodiments, the immunomodulatory agent is Pevonedistat.

In some embodiments, $X_3$ can be any suitable therapeutic compound for the desired therapeutic application. Examples of therapeutic compounds useful for the treatment of metabolic disorders (e.g., diabetes, Insulin resistance, fatty liver disease, obesity, etc.) include, but are not limited to, the following classes of metabolic disorder treatments: JNK (c-Jun N-terminal kinase) inhibitors, PKR-like endoplasmic reticulum kinase (PERK) inhibitor, PERK (PKR-like endoplasmic reticulum kinase), PTP1B (protein-tyrosine phosphatase 1B), AKT (Protein Kinase B) an antidiabetic, a neddylation inhibitor, a ubiquitin-activating enzyme inhibitor, a ubiquitin-activating enzyme E1 inhibitor, and a proteasome inhibitor.

Examples of therapeutic compounds, or pharmaceutically acceptable salts, solvates, hydrates, isomers, or tautomers thereof, useful in the disclosure are detailed in Table 2. In Table 2, $R_1$=H, alkyl, aryl, arylalkyl, arylalkyne, arylalkene, heterocyclic, heteroaryl, substituted phenyl groups, aromatic heterocycles, glycol ether, or an additional glycol linker. $R_2$ groups =H, alkyl, aryl, and arylalkyl, alkynes, alkenes, substituted phenyl groups, aromatic heterocycles, glycol ether, or an additional glycol linker and the like.

TABLE 2

Exemplary Therapeutic Compounds for $X_3$

| Compound Name | Drug ID | Structure | Activity |
|---|---|---|---|
| ((1R,2R,4S)-4-(4-(((R)-2,3-dihydro-1H-inden-1-yl)amino)-7H-pyrrolo[2,3-d]pyrimidin-7-yl)-2-hydroxycyclopentyl) methyl sulfamate | MNL4924 | 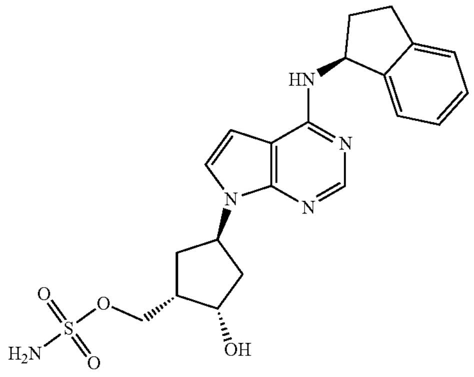 [SMILES: NS(=O)(=O)OC[C@@H]1C[C@@H](n2ccc3c(N[C@H]4CCc5ccccc54)ncnc32)C[C@@H]1O] | NEED8 Inhibitor |
| 4-Amino-7-[(1R,4R,5S)-4,5-dihydroxy-3-[sulfamoylamino) methyl]cyclopent-2-en-1-yl]-5-[2-(2-ethoxy-6-fluoro-phenyl) ethynyl]pyrrolo[2,3-d]pyrimidine | TAS4464 | 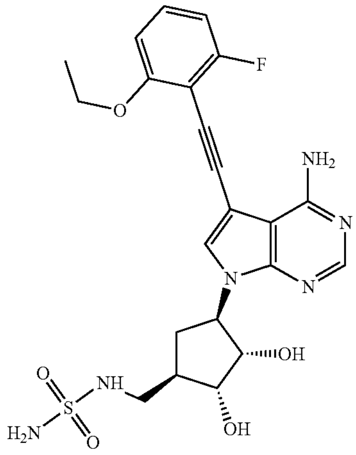 [SMILES: CCOc1cccc(F)c1C#Cc1cn([C@@H]2C[C@H](CNS(N)(=O)=O)[C@@H](O)[C@H]2O)c2ncnc(N)c12] | NEED8 Inhibitor |

TABLE 2-continued

| Exemplary Therapeutic Compounds for $X_3$ | | | |
|---|---|---|---|
| Compound Name | Drug ID | Structure | Activity |
| ((2S,3R,4S,5S)-5-(6-((3-ethynylphenyl)amino)-9H-purin-9-yl)-3,4-dihydroxytetrahydrfuran-2-yl)methyl sulfamate | ABP1 | 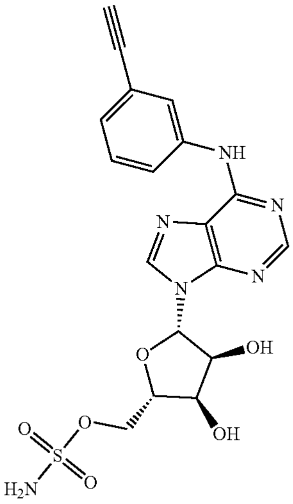 [SMILES: C#Cc1cccc(Nc2ncnc3c2ncn3[C@H]2O[C@@H](COS(N)(=O)=O)[C@H](O)[C@@H]2O)c1] | NEED8 Inhibitor |
| ((1R,2R,3S,4R)-2,3-dihydroxy-4-((2-(3-(trifluoromethyl) phenyl)pyrazolo [1,5-a]pyrimidin-7-yl) amino)cyclopentyl) methyl sulfamate | MLN7243 (TAK-243) | 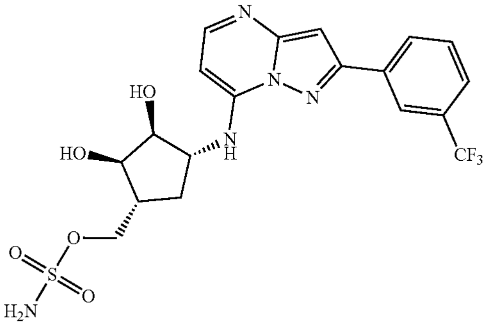 [SMILES: NS(=O)(=O)OC[C@H]1C[C@@H](Nc2ccnc3cc(-c4cccc(C(F)(F)F)c4)nn23)[C@H](O)[C@@H]1O] | NEED8 Inhibitor |
| 1-(5-(4-amino-7-methyl-4H-pyrrolo [2,3-d]pyrimidin-5-yl) indolin-1-yl)-2-(3-(trifluoromethyl)phenyl) ethan-1-one | GSK2606414 | 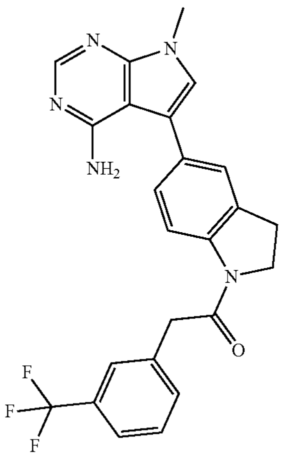 [SMILES: Cn1cc(-c2ccc3c(c2)CCN3C(=O)Cc2cccc(C(F)(F)F)c2)c2c(N)ncnc21] | PERK Inhibitors |

TABLE 2-continued

| Exemplary Therapeutic Compounds for $X_3$ | | | |
|---|---|---|---|
| Compound Name | Drug ID | Structure | Activity |
| 4-(2-amino-4-methyl-3-(2-methylquinolin-6-yl) benzoyl)-1-methyl-2,5-diphenyl-1,2-dihydro-3H-pyrazol-3-one hydrochloride | AMG PERK 44 | 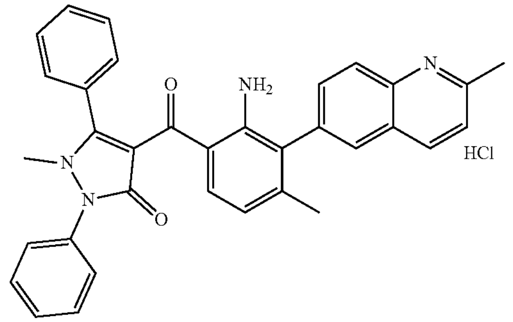 [SMILES: Cc1ccc2cc(-c3c(C)ccc(C(=O)c4c(-c5ccccc5)n(C)n(-c5ccccc5)c4=O)c3N)ccc2n1 ; Cl] | PERK Inhibitors |
| (E)-N-(4-(1-benzoylpiperidin-4-yl)butyl)-3-(pyridin-3-yl)acrylamide hydrochloride | FK866 HCl | 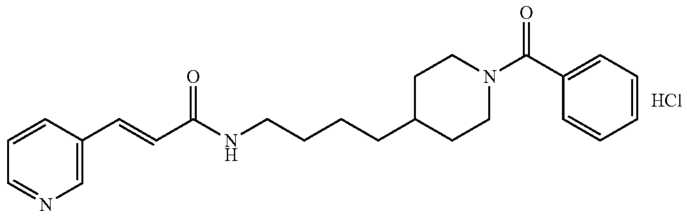 [SMILES: O=C(/C=C/c1cccnc1)NCCCCC1CCN(C(=O)c2ccccc2)CC1 ; Cl] | NAMPT Inhibitor |
| 2-[6-(4-chlorophenoxy) hexyl]-1-cyano-3-pyridin-4-ylguanidine | CHS 828 | 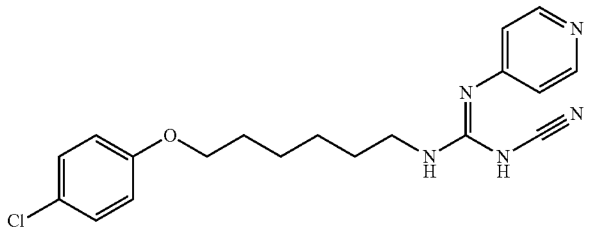 [SMILES: N#CN/C(=N\c1ccncc1)NCCCCCCOc1ccc(Cl)cc1] | NAMPT Inhibitor |
| 4-(5-methyl-4-(tosylmethyl) oxazol-2-yl)-N-(pyridin-3-ylmethyl) benzamide | STF 118804 | 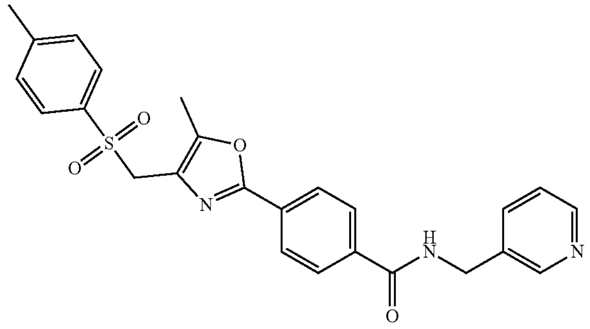 [SMILES: Cc1ccc(S(=O)(=O)Cc2nc(-c3ccc(C(=O)NCc4cccnc4)cc3)oc2C)cc1] | NAMPT Inhibitor |
| N-([1,1'-biphenyl]-2-yl)-8-(4-(pyridin-3-yl)-1H-1,2,3-triazol-1-yl)octanamide | GPP 78 | 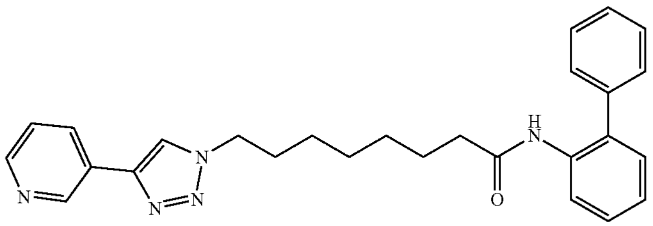 [SMILES: O=C(CCCCCCCn1cc(-c2cccnc2)nn1)Nc1ccccc1-c1ccccc1] | NAMPT Inhibitor |

TABLE 2-continued

| Exemplary Therapeutic Compounds for $X_3$ | | | |
|---|---|---|---|
| Compound Name | Drug ID | Structure | Activity |
| N-(4-((3,5-difluorophenyl)sulfonyl) benzyl) imidazo[1,2-a]pyridine-6-carboxamide | GNE 617 | 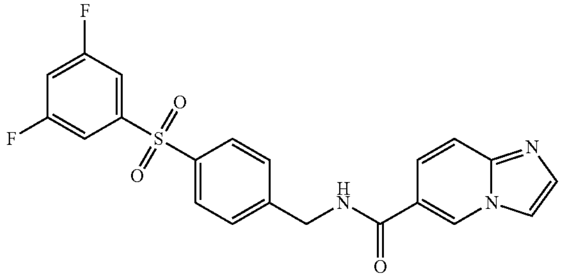 [SMILES: O=C(NCc1ccc(S(=O)(=O)c2cc(F)cc(F)c2)cc1)c1ccc2nccn2c1] | NAMPT Inhibitor |
| 4-(((7-bromo-2-methyl-4-oxo-3,4-dihydroquinazolin-6-yl) methyl)(prop-2-yn-1-yl)amino)-N-(pyridin-3-ylmethyl)benzamide | CB30865 (or ZM 242421) | 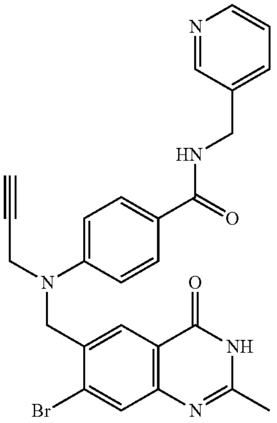 [SMILES: C#CCN(Cc1cc2c(=O)[nH]c(C)nc2cc1Br)c1ccc(C(=O)NCc2cccnc2)cc1] | NAMPT Inhibitor |
| 2-(carboxyformamido)-4,5,6,7-tetrahydrothieno [2,3-c]pyridine-3-carboxylic acid | TCS 401 | 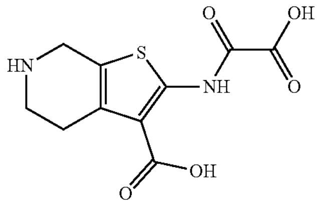 [SMILES: O=C(O)C(=O)Nc1sc2c(c1C(=O)O)CCNC2] | PTP1B Inhibitor |
| 2-((2-(tetradecyloxy) phenyl)carbamoyl) benzoic acid | CX08005 | 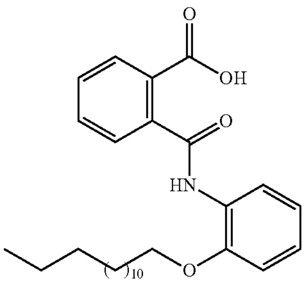 | PTP1B Inhibitor |

TABLE 2-continued

| Exemplary Therapeutic Compounds for $X_3$ | | | |
|---|---|---|---|
| Compound Name | Drug ID | Structure | Activity |
| methyl 5-((N-(4-(N-(2-methoxy-2-oxoethyl) methylsulfonamido) benzyl)-1-phenylmethyl) sulfonamido)-2-((4-methylbenzyl)oxy) benzoate | PTP1B-IN-2 | 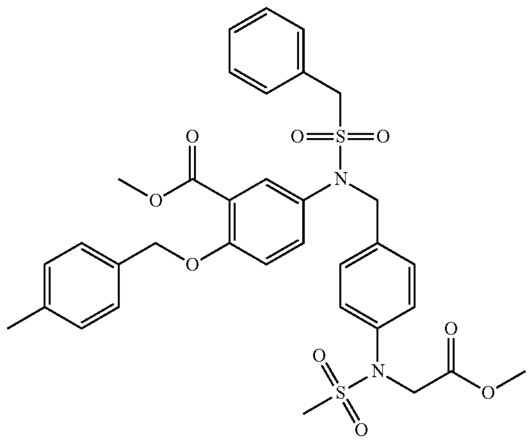 | PTP1B Inhibitor |
| ((3-bromo-7-cyanonaphthalen-2-yl)difluoromethyl) phosphonic acid | PTP1B-IN-3 | 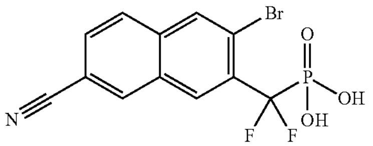 [SMILES: N#Cc1ccc2cc(Br)c(C(F)(F)P(=O)(O)O)cc2c1] | PTP1B Inhibitor |
| 4-hydroxy-3,3-dimethyl-2H-benzo [g]indole-2,5(3H)-dione | BVT948 | 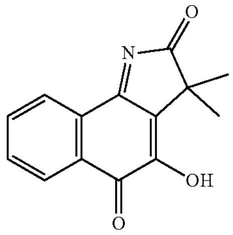 [SMILES: CC1(C)C(=O)N=C2C1=C(O)C(=O)c1ccccc12] | PTP1B Inhibitor |
| ethyl 2-amino-6-chloro-4-(1-cyano-2-ethoxy-2-oxoethyl)-4H-chromene-3-carboxylate | SC79 | 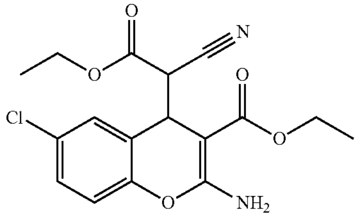 [SMILES: CCOC(=O)C1=C(N)Oc2ccc(Cl)cc2C1C(C#N)C(=O)OCC] | AKT Activator |
| dibenzo[cd,g]indazol-6(2H)-one | SP600125 | 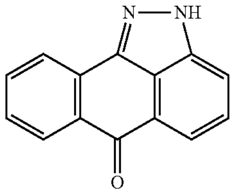 [SMILES: O=C1c2ccccc2-c2n[nH]c3cccc1c23] | JNK Inhibitor |
| 3-(3-(2-(piperidin-1-yl)ethoxy)phenyl)-5-(1H-1,2,4-triazol-5-yl)-1H-indazole hydrochloride | CC 401 | 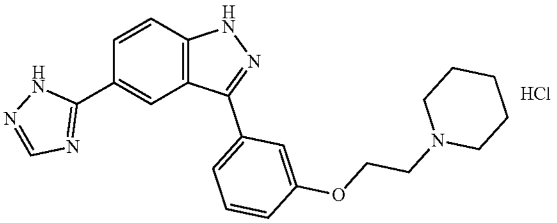 [SMILES: c1cc(OCCN2CCCCC2)cc(-c2n[nH]c3ccc(-c4ncn[nH]4)cc23)c1 ; Cl] | JNK Inhibitor |

TABLE 2-continued

| Exemplary Therapeutic Compounds for $X_3$ | | | |
|---|---|---|---|
| Compound Name | Drug ID | Structure | Activity |
| N-(4-amino-5-cyano-6-ethoxypyridin-2-yl)-2-(2,5-dimethoxyphenyl) acetamide | TCS JNK 6o | 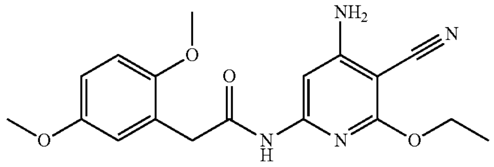 [SMILES: CCOc1nc(NC(=O)Cc2cc(OC)ccc2OC)cc(N)c1C#N] | JNK Inhibitor |
| N-(3-cyano-4,5,6,7-tetrahydrobenzo[b] thiophen-2-yl)-1-naphthamide | TCS JNK 5a | 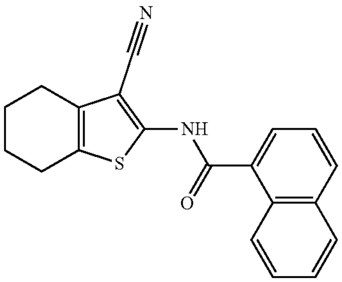 [SMILES: N#Cc1c(NC(=O)c2cccc3ccccc23)sc2c1CCCC2] | JNK Inhibitor |
| (E)-3-(4-(dimethylamino)but-2-enamido)-N-(4-((4-(pyridin-3-yl)pyrimidin-2-yl) amino)phenyl) benzamide | JNK-IN-7 | 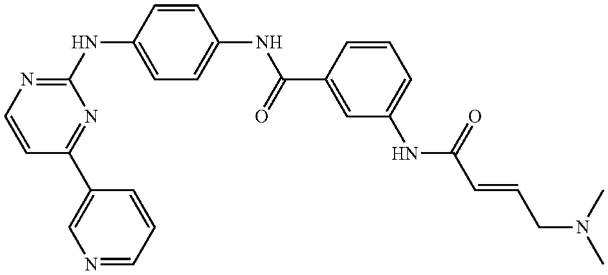 [SMILES: CN(C)C/C=C/C(=O)Nc1cccc(C(=O)Nc2ccc(Nc3nccc(-c4cccnc4)n3)cc2)c1] | JNK Inhibitor |
| (E)-3-(4-(dimethylamino) but-2-enamido)-N-(2-methyl-4-((4-(pyridin-3-yl)pyrimidin-2-yl)amino)phenyl) benzamide | JNK-IN-8 | 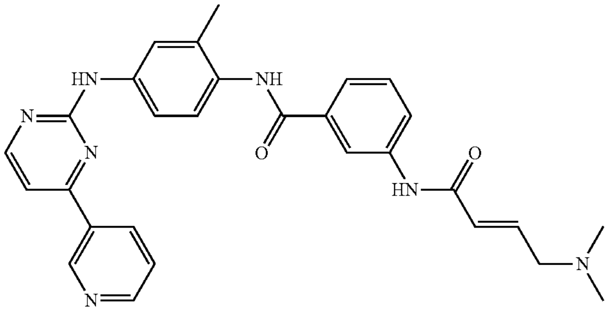 [SMILES: Cc1cc(Nc2nccc(-c3cccnc3)n2)ccc1NC(=O)c1cccc(NC(=O)/C=C/CN(C)C)c1] | JNK Inhibitor |
| (E)-3-(4-(dimethylamino)but-2-enamido)-N-(4-((4-(2-phenylpyrazolo[1,5-a] pyridin-3-yl) pyrimidin-2-yl)amino) phenyl)benzamide | JNK-IN-11 | 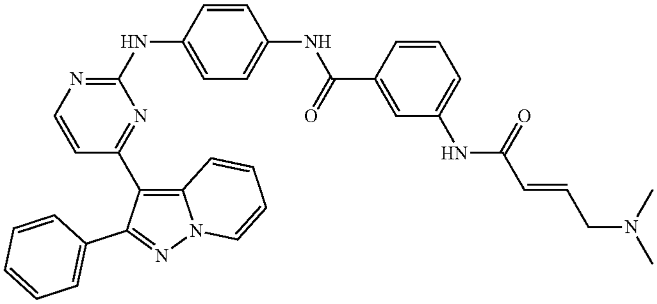 [SMILES: CN(C)C/C=C/C(=O)Nc1cccc(C(=O)Nc2ccc(Nc3nccc(-c4c(-c5ccccc5)nn5ccccc45)n3)cc2)c1] | JNK Inhibitor |

TABLE 2-continued

| Exemplary Therapeutic Compounds for $X_3$ | | | |
|---|---|---|---|
| Compound Name | Drug ID | Structure | Activity |
| sodium (1E,3R,4R,6R, 7Z,9Z,11E)- 3,6,13-trihydroxy-3- methyl-1-((R)-6-oxo- 3,6-dihydro-2H-pyran- 2-yl)trideca-1,7,9,11- tetraen-4-yl hydrogen phosphate | Fostriecin | 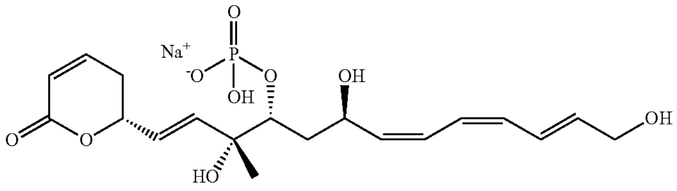 | PP2A Inhibitor |
| 3-(4- methylpiperazine- 1-carbonyl)-7- oxabicyclo[2.2.1] heptane- 2-carboxylic acid | Endothall | 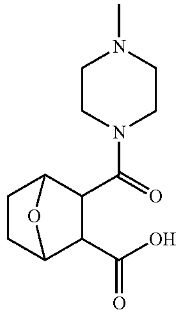 [SMILES: CN1CCN(C(=O)C2C3CCC(O3)C2C(=O)O)CC1] | PP2A Inhibitor |
| (E)-3-(4- (dimethylamino)but-2- enamido)-N-(4-((4-(2- phenylpyrazolo [1,5-a]pyridin-3- yl)pyrimidin-2-yl) amino)phenyl) benzamide | Rubratoxin A | 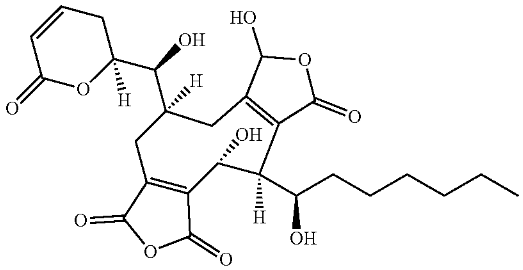 [SMILES: CCCCCC[C@@H](O)[C@@H]1C2=C(C[C@H]([C@H](O)[C@@H]3CC=CC(=O)O3)CC3=C(C(=O)OC3=O)[C@@H]1O)C(O)OC2=O] | PP2A Inhibitor |
| (2R)-2-hydroxy-3- ((2S,3S,6R)-3- hydroxy-8-((2R,E)-4- ((2R,5R,6'S,8'R)-8'- hydroxy-6'-((1S,3S)-1- hydroxy-3-((2S,3R,6S)- 3-methyl-1,7-dioxaspiro [5.5]undecan-2-yl)butyl)- 7'-methyleneoctahydro- 3H,3'H-spiro[furan-2,2'- pyrano[3,2-b]pyran]- 5-yl)but-3-en-2-yl)-10- methyl-1,7-dioxaspiro [5.5]undec-10-en-2-yl)- 2-methylpropanoic acid | Okadaic Acid | 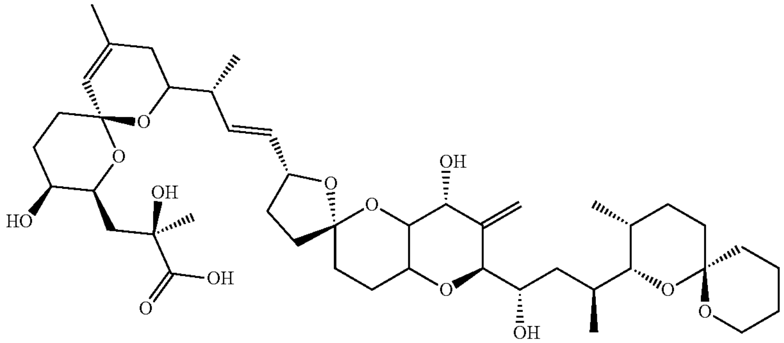 | PP2A Inhibitor |

In some embodiments, the compound of Formula (I) is a compound listed in Table 3, or a pharmaceutically acceptable salt, solvate, hydrate, isomer, or tautomer thereof. In Table 3, R groups ═H, alkyl, aryl, and arylalkyl, alkynes, alkenes, substituted phenyl groups, aromatic heterocycles, glycol ether, or an additional glycol linker attaching to the therapeutic compound; and p is 1, 2, 3, 4, 5, or 6.

TABLE 3
| Exemplary Compounds of Formula (I) | |
|---|---|
| Compound | Structure |
| A-1 | 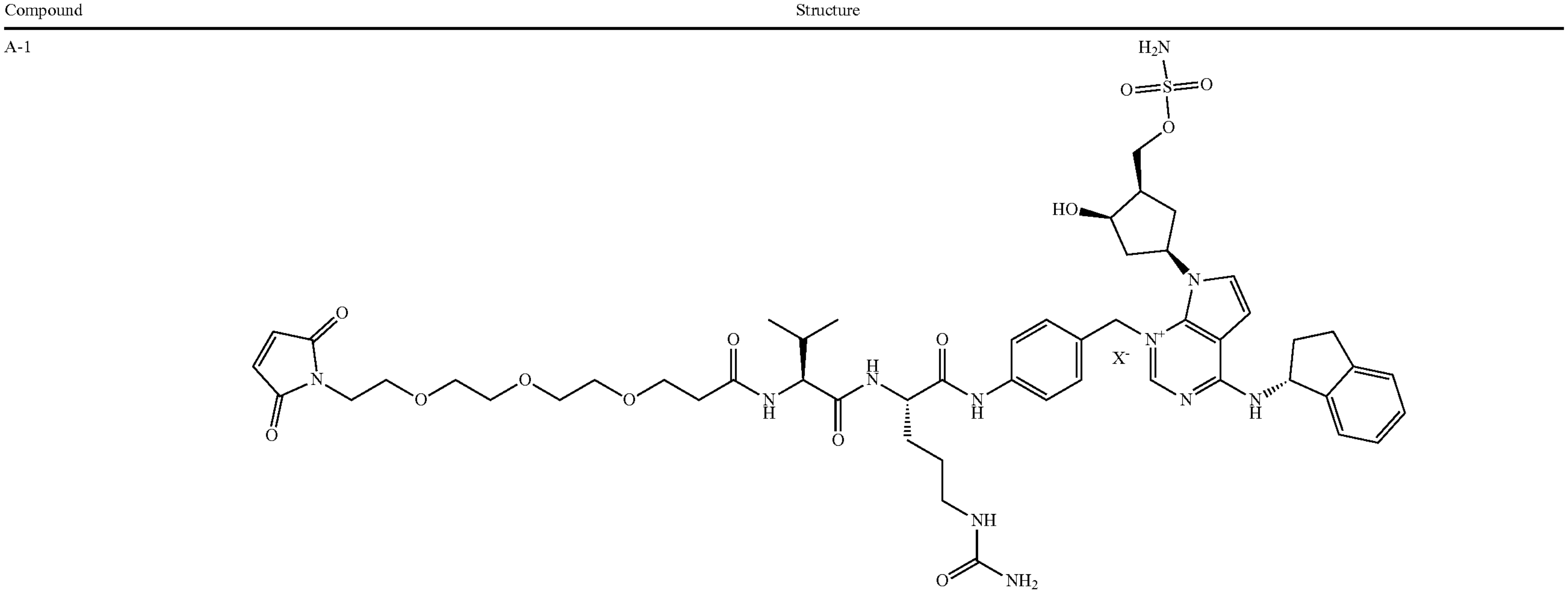 |

TABLE 3-continued
| Exemplary Compounds of Formula (I) | |
|---|---|
| Compound | Structure |
| A-2 | 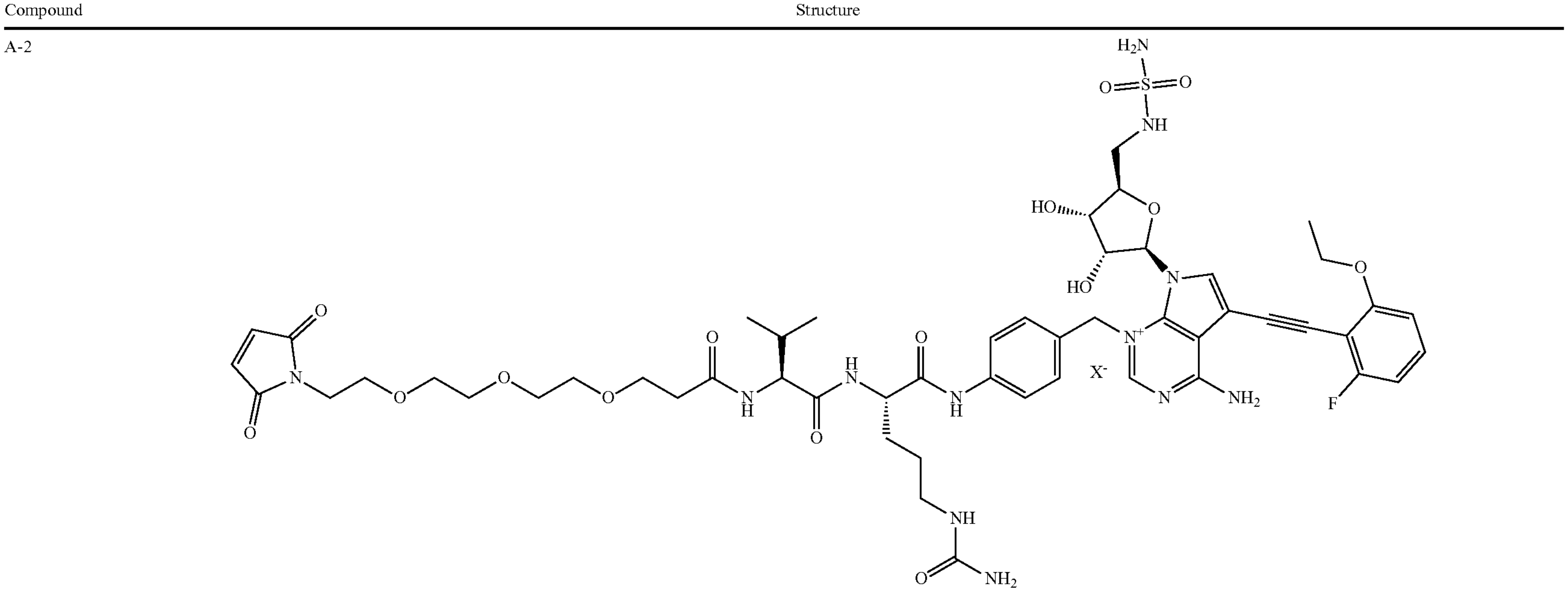 |

TABLE 3-continued
| Exemplary Compounds of Formula (I) | |
|---|---|
| Compound | Structure |
| A-3 | 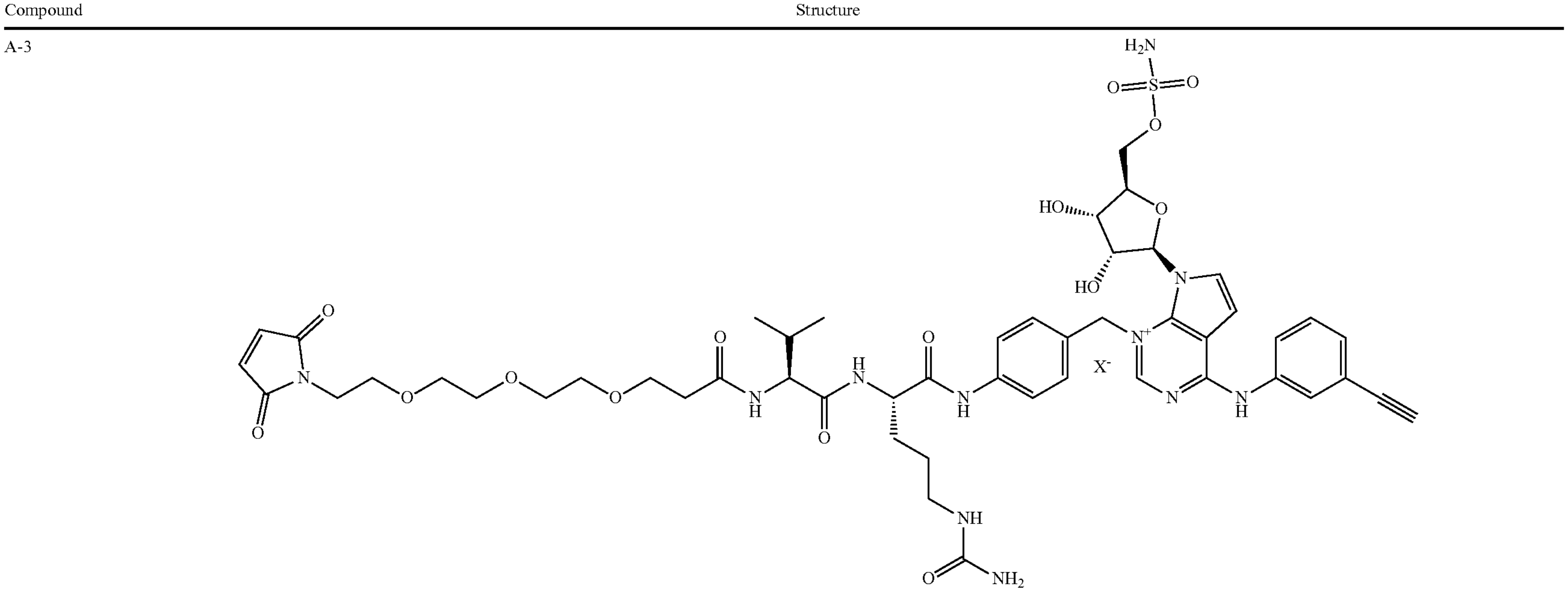 |
| A-4 | 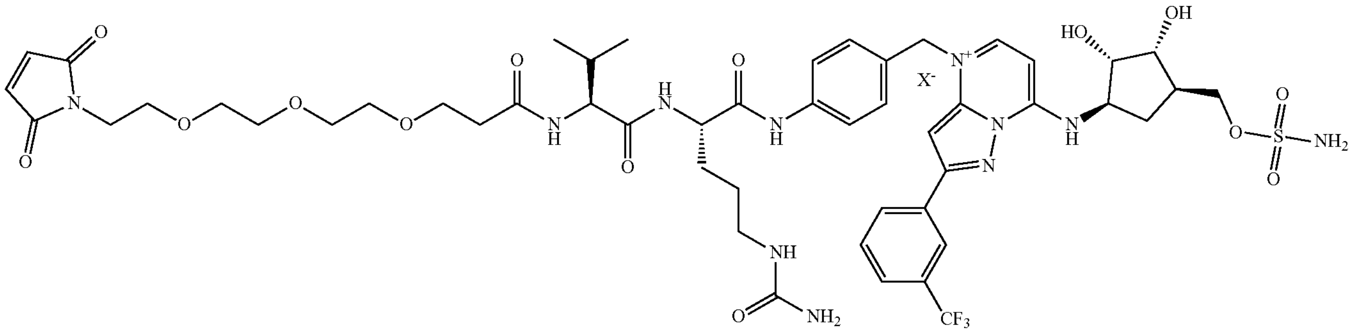 |

TABLE 3-continued
| Exemplary Compounds of Formula (I) | |
|---|---|
| Compound | Structure |
| A-5 | 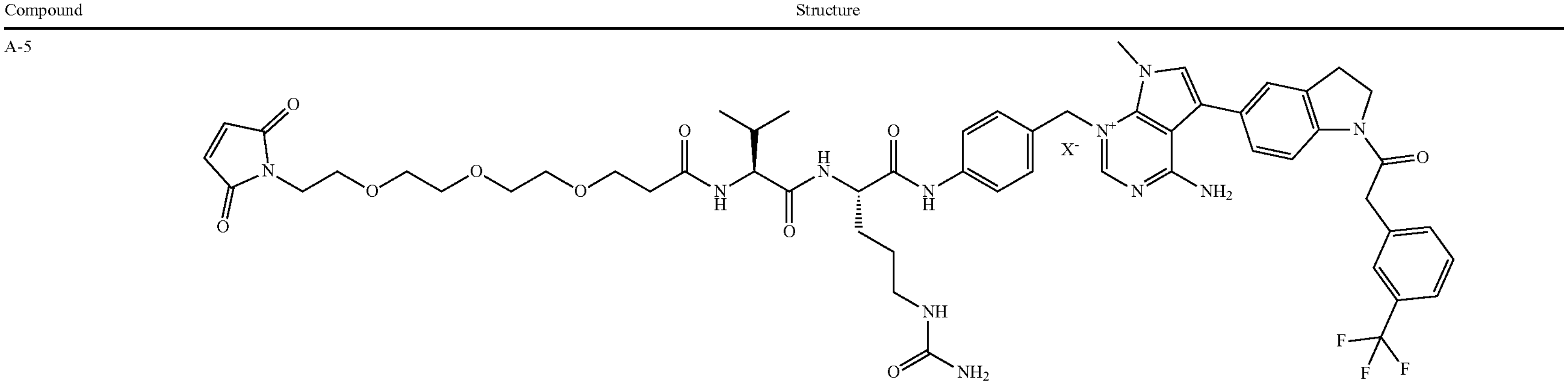 |
| A-6 | 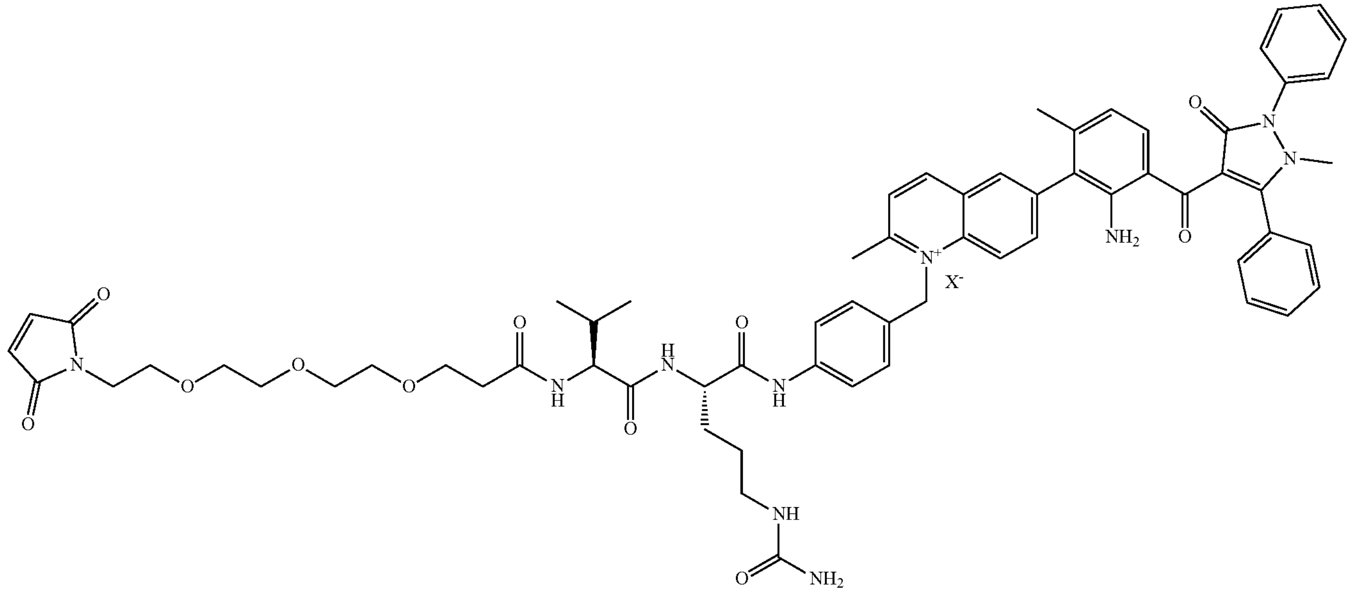 |

TABLE 3-continued
| Exemplary Compounds of Formula (I) | |
|---|---|
| Compound | Structure |
| A-7 | 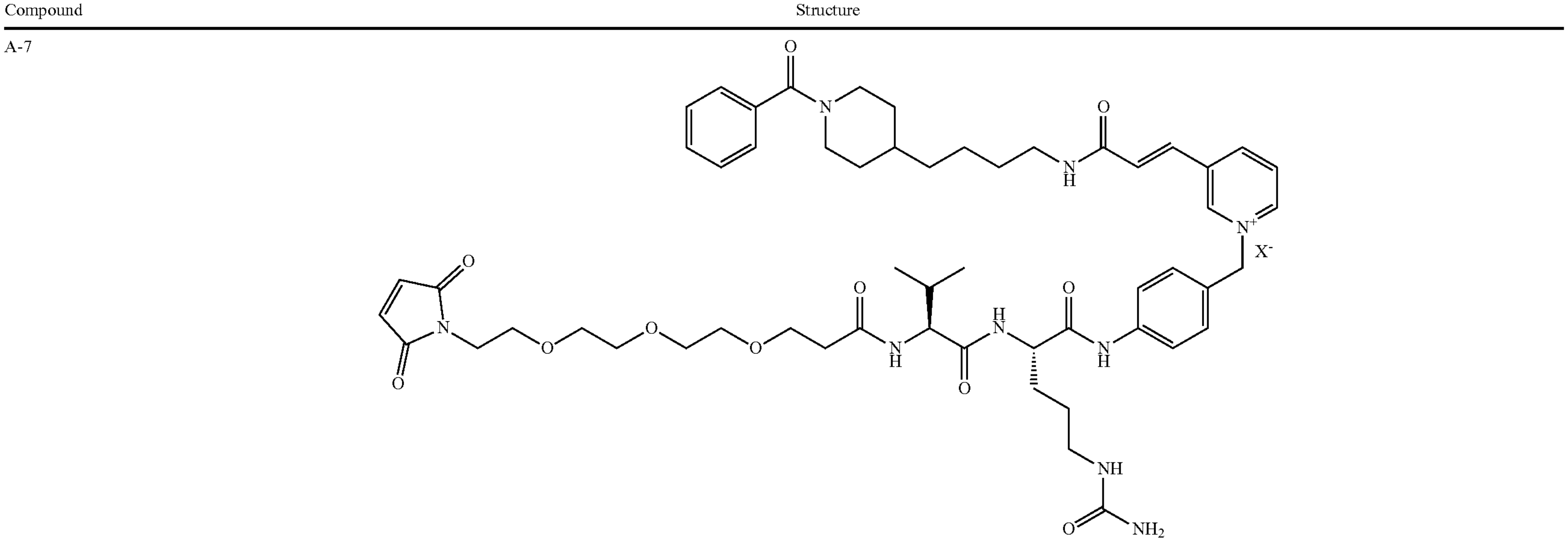 |

TABLE 3-continued
| Exemplary Compounds of Formula (I) | |
|---|---|
| Compound | Structure |
| A-8 | 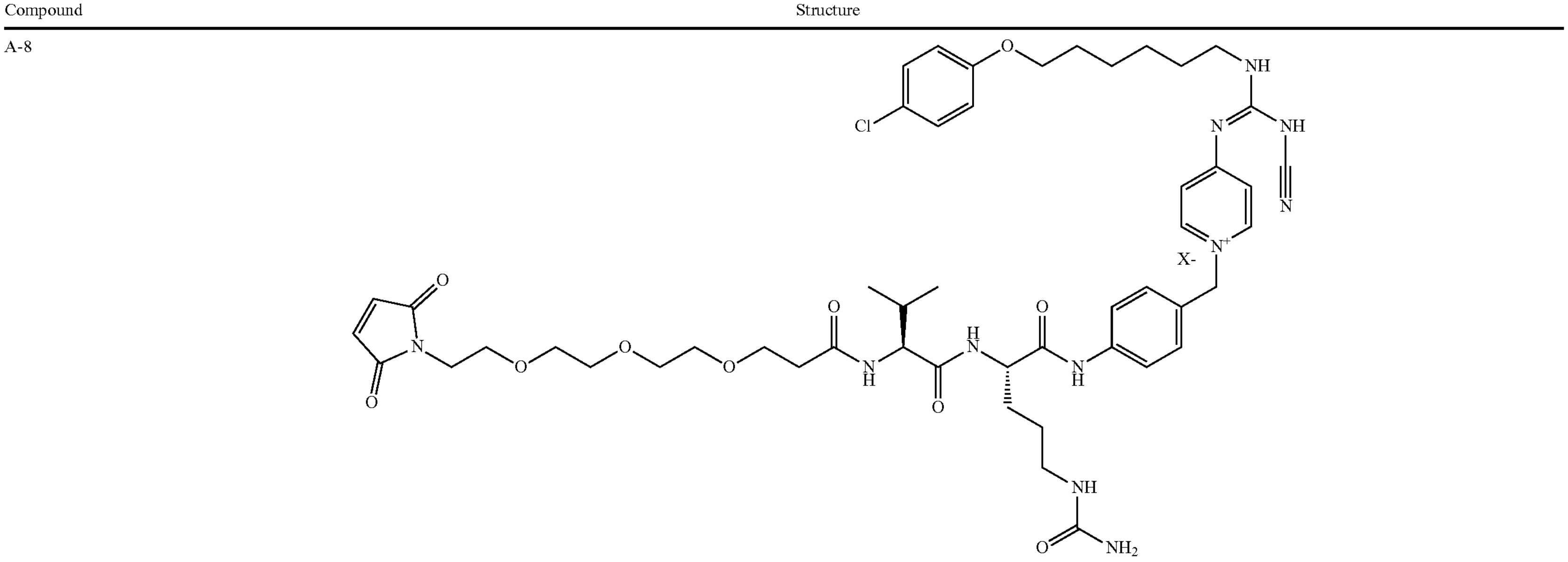 |
| A-9 | 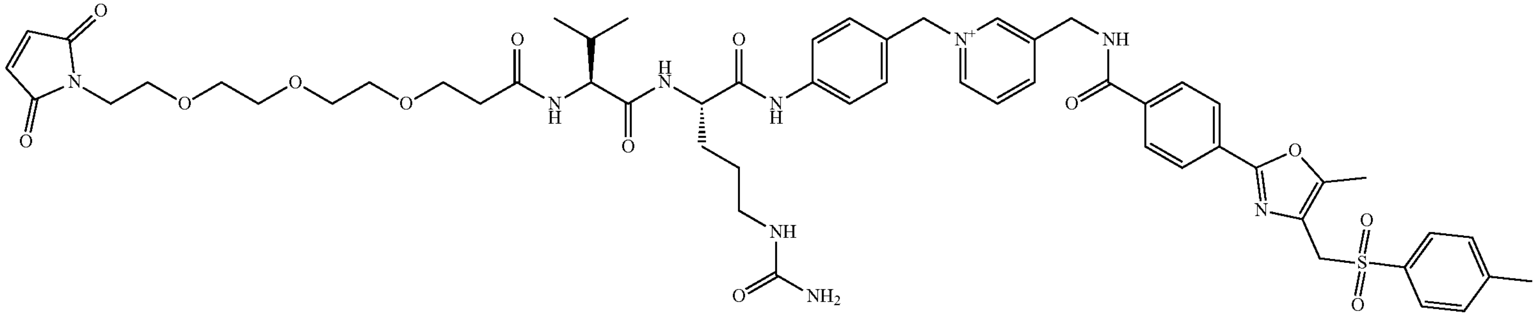 [SMILES: Cc1ccc(S(=O)(=O)Cc2nc(-c3ccc(C(=O)NCc4ccc[n+](Cc5ccc(NC(=O)[C@H](CCCNC(N)=O)NC(=O)[C@@H](NC(=O)CCOCCOCCOCCN6C(=O)C=CC6=O)C(C)C)cc5)c4)cc3)oc2C)cc1] |

TABLE 3-continued
| Exemplary Compounds of Formula (I) | |
|---|---|
| Compound | Structure |
| A-10 | 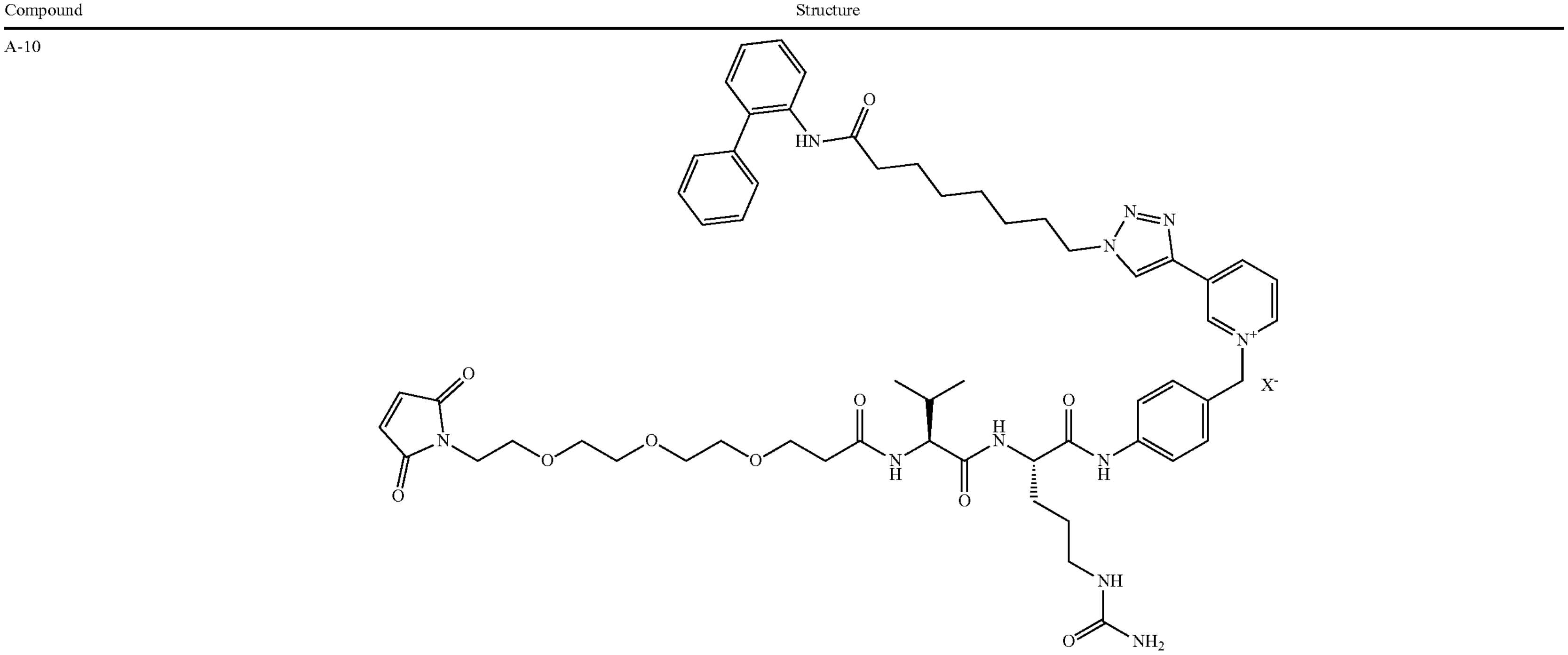 |

TABLE 3-continued
| Exemplary Compounds of Formula (I) | |
|---|---|
| Compound | Structure |
| A-11 | 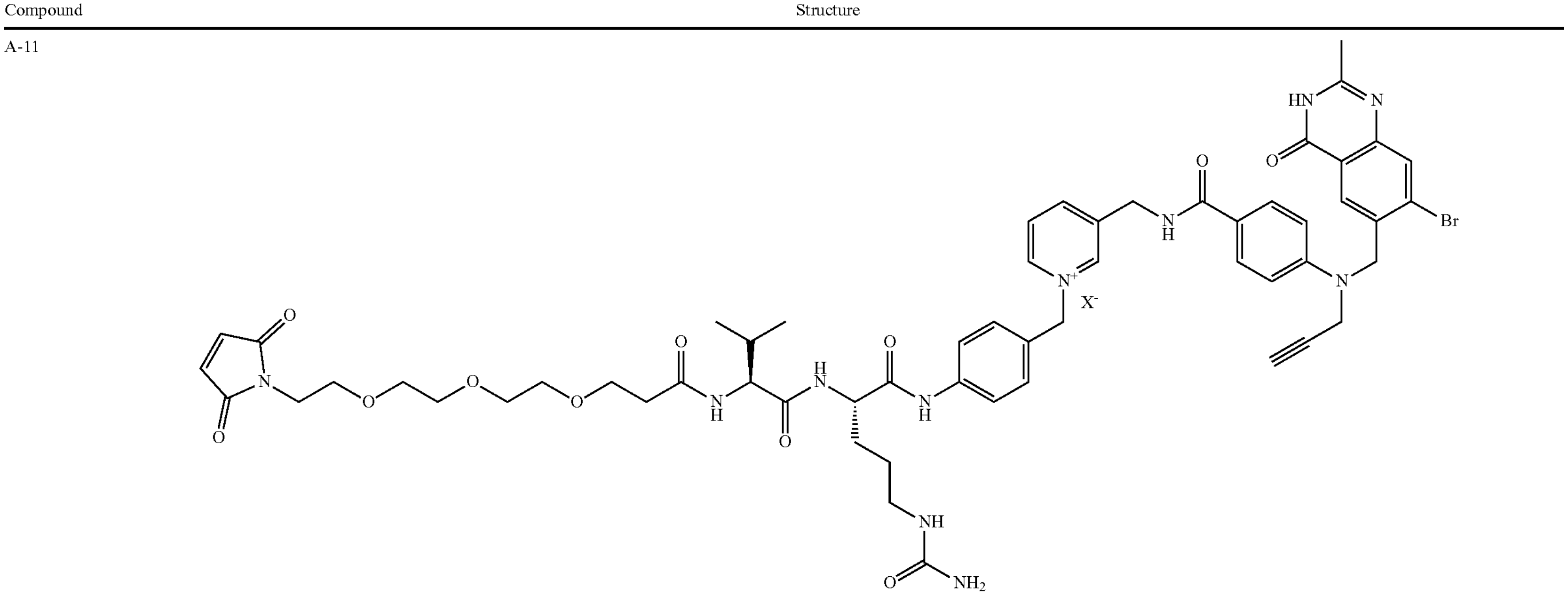 |
| A-12 | 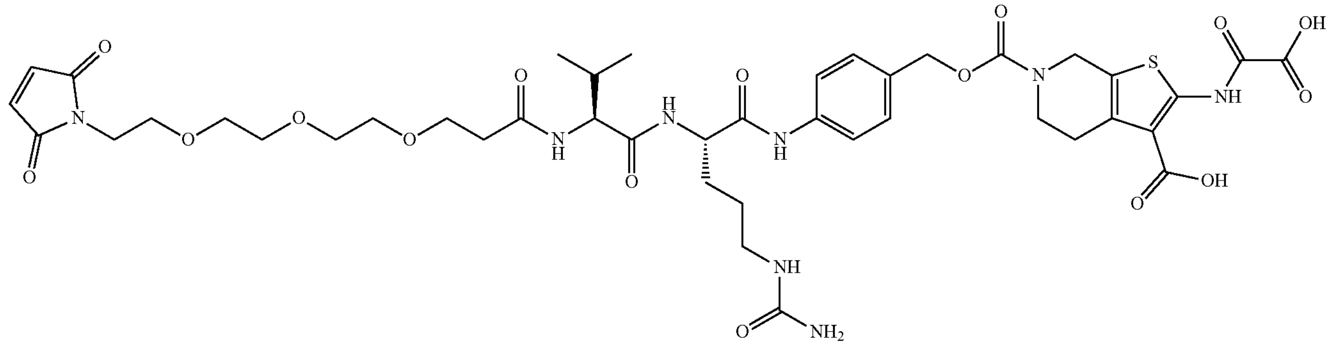 [SMILES: CC(C)[C@H](NC(=O)CCOCCOCCOCCN1C(=O)C=CC1=O)C(=O)N[C@@H](CCCNC(N)=O)C(=O)Nc1ccc(COC(=O)N2CCc3c(sc(NC(=O)C(=O)O)c3C(=O)O)C2)cc1] |

TABLE 3-continued
Exemplary Compounds of Formula (I)
| Compound | Structure |
| --- | --- |
| A-13 | 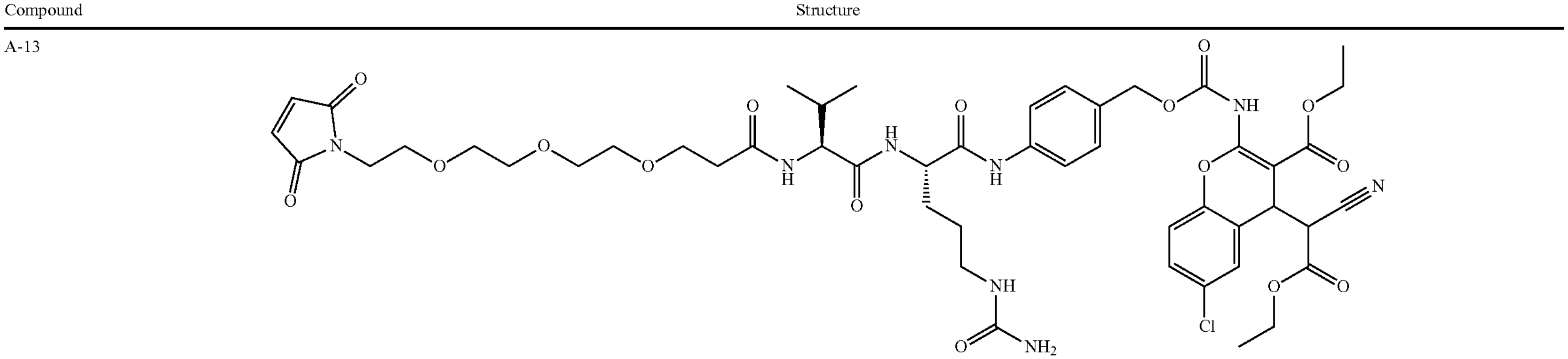 |
| A-14 | 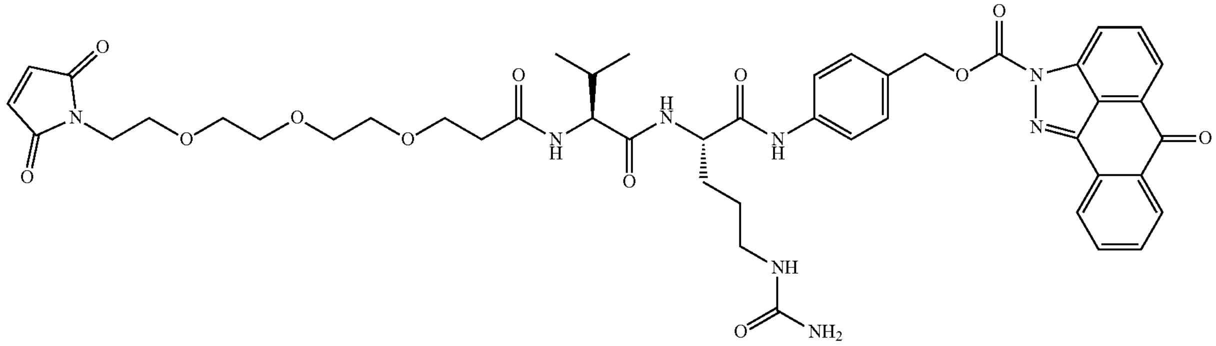 [SMILES: CC(C)[C@H](NC(=O)CCOCCOCCOCCN1C(=O)C=CC1=O)C(=O)N[C@@H](CCCNC(N)=O)C(=O)Nc1ccc(COC(=O)n2nc3c4c(cccc42)C(=O)c2ccccc2-3)cc1] |

TABLE 3-continued
| Exemplary Compounds of Formula (I) | |
|---|---|
| Compound | Structure |
| A-15 | 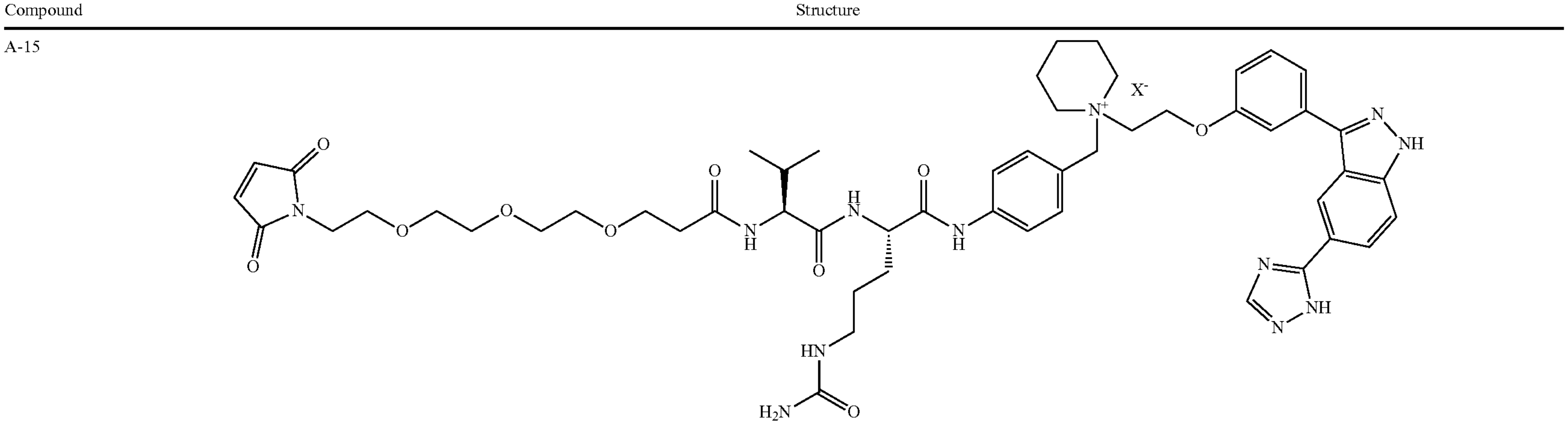 |
| A-16 | 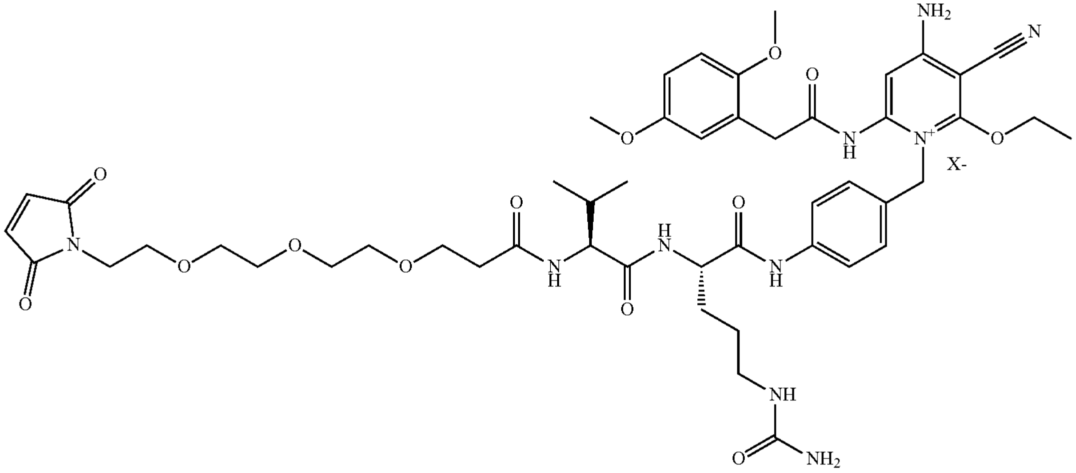 |

TABLE 3-continued
| Exemplary Compounds of Formula (I) | |
|---|---|
| Compound | Structure |
| A-17 | 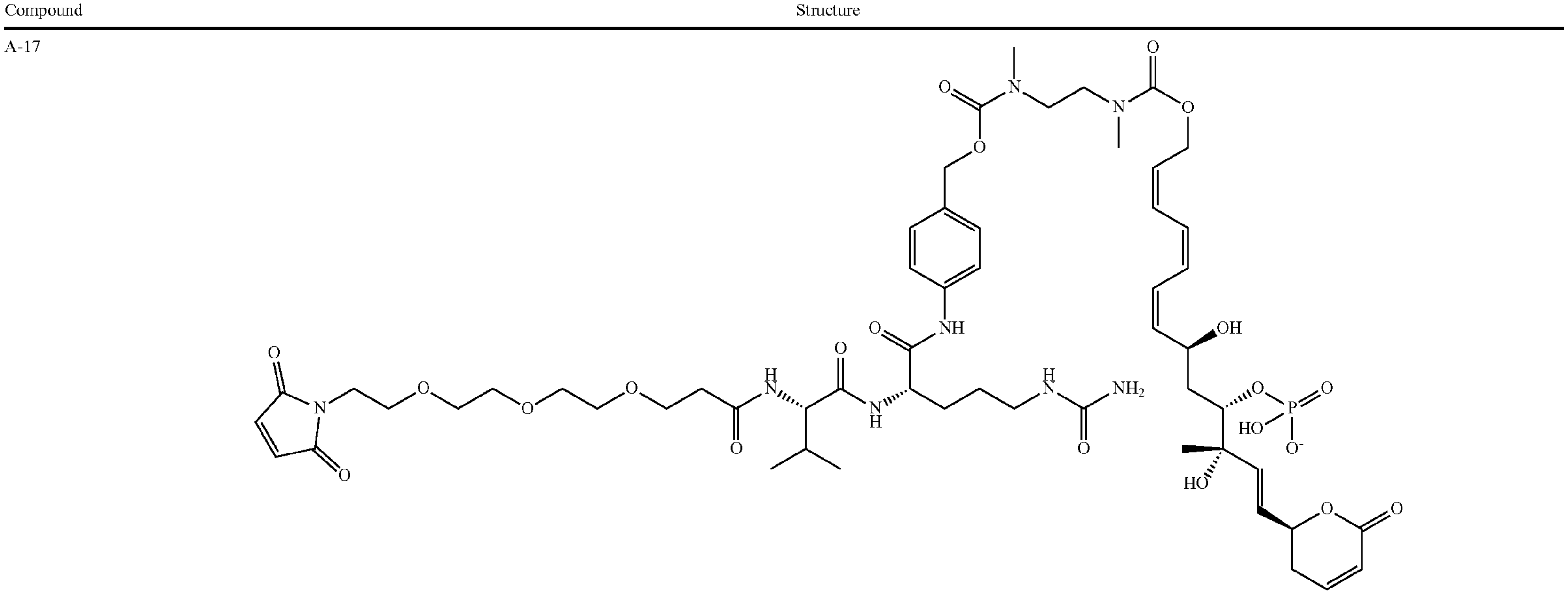 |

TABLE 3-continued
| Exemplary Compounds of Formula (I) | |
|---|---|
| Compound | Structure |
| A-18 | 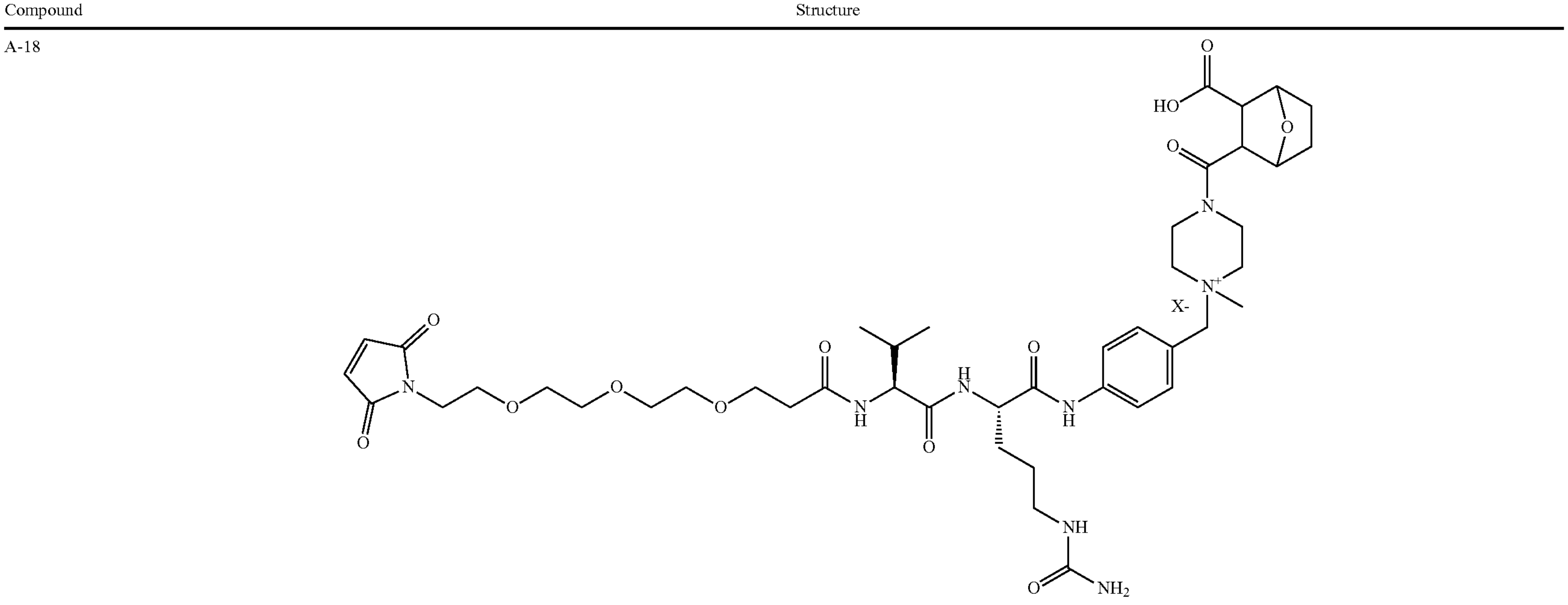 |

TABLE 3-continued
| Exemplary Compounds of Formula (I) | |
|---|---|
| Compound | Structure |
| A-19 | 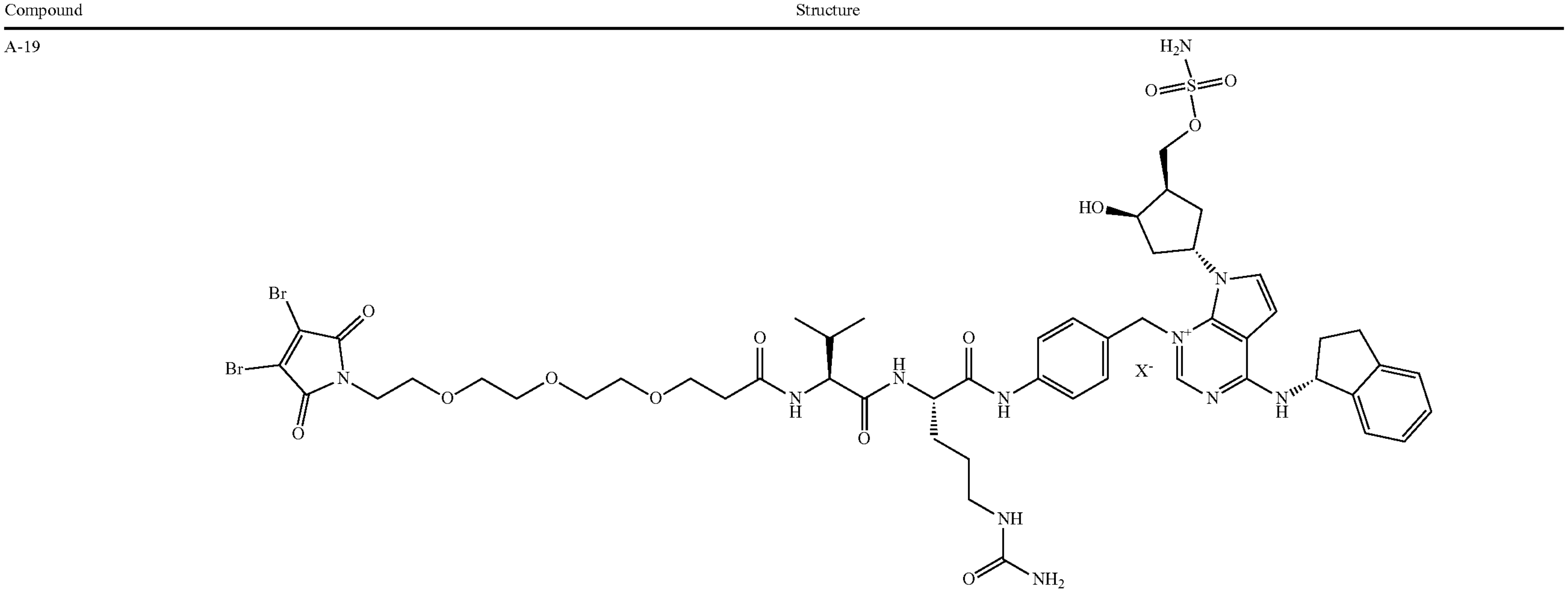 |

TABLE 3-continued
| Exemplary Compounds of Formula (I) | |
| --- | --- |
| Compound | Structure |
| A-20 | 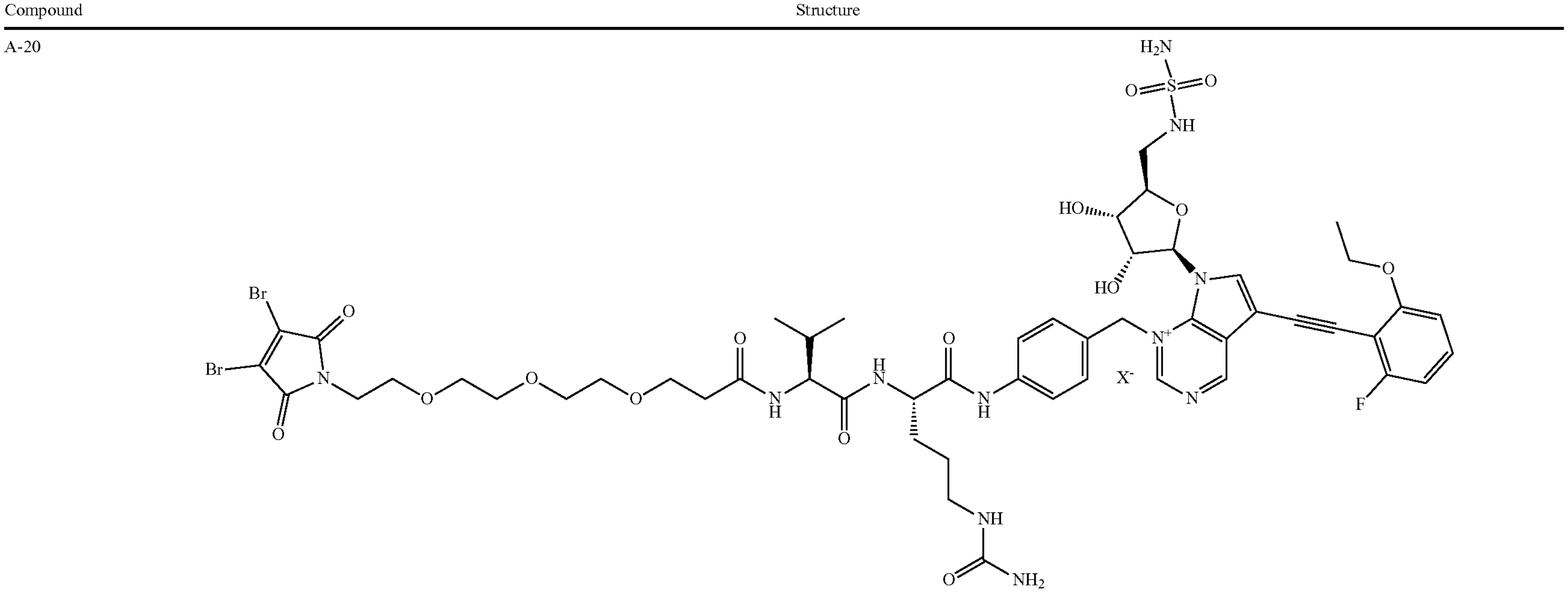 |

TABLE 3-continued
| Exemplary Compounds of Formula (I) | |
|---|---|
| Compound | Structure |
| A-21 | 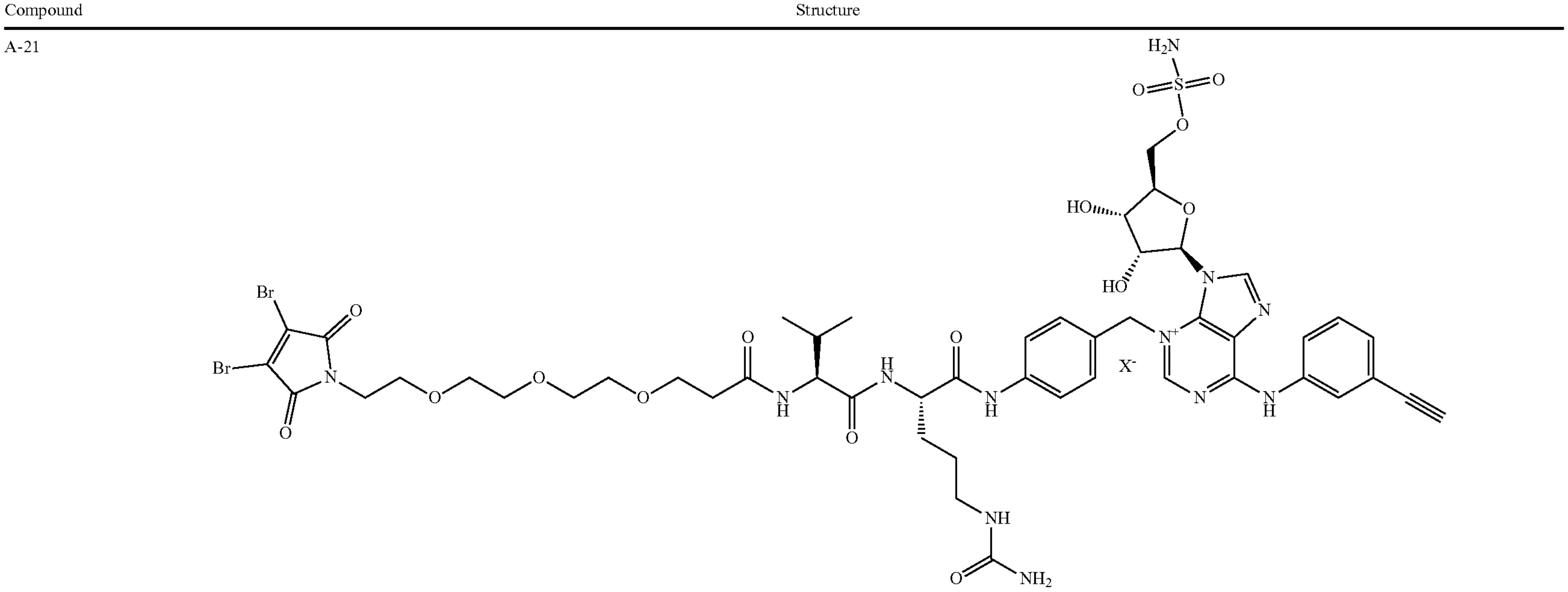 |
| A-22 | 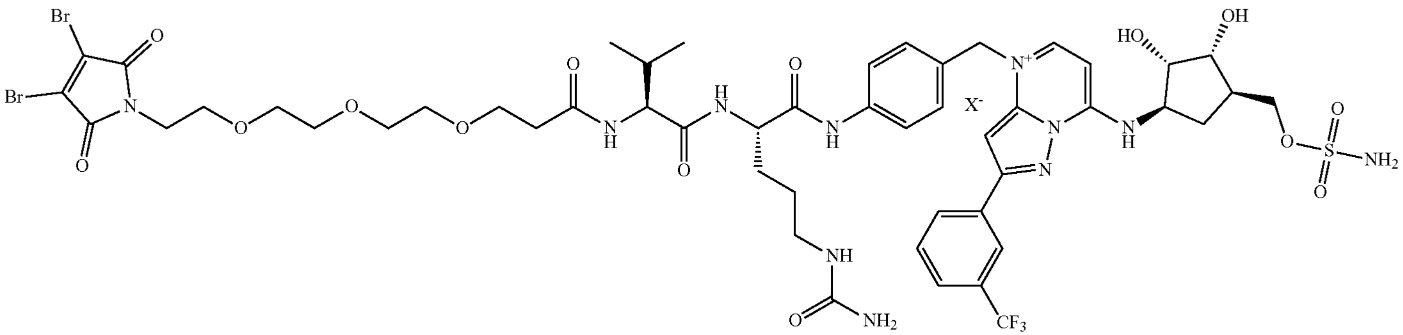 |

TABLE 3-continued
| Exemplary Compounds of Formula (I) | |
|---|---|
| Compound | Structure |
| A-23 | 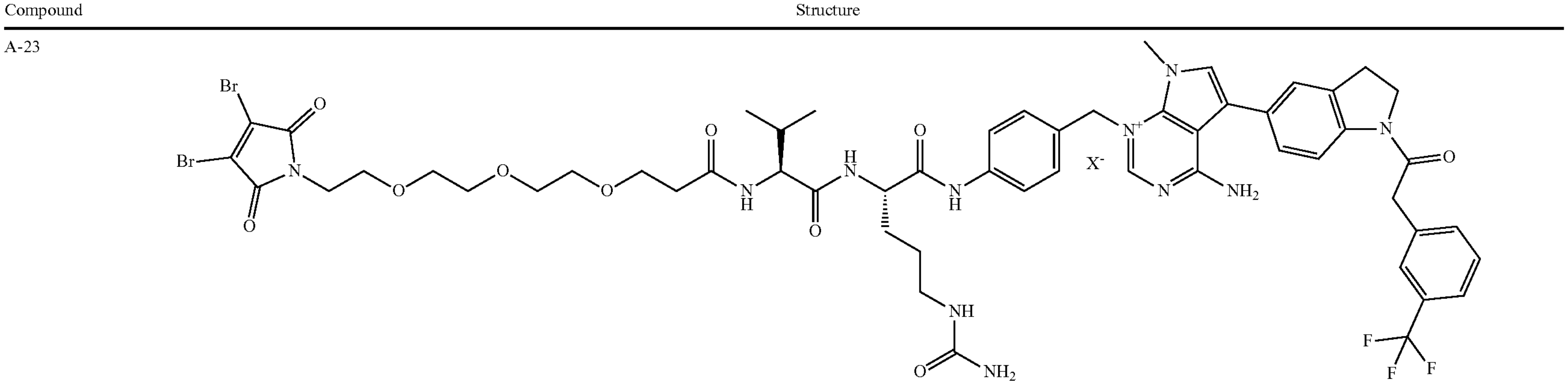 |
| A-24 | 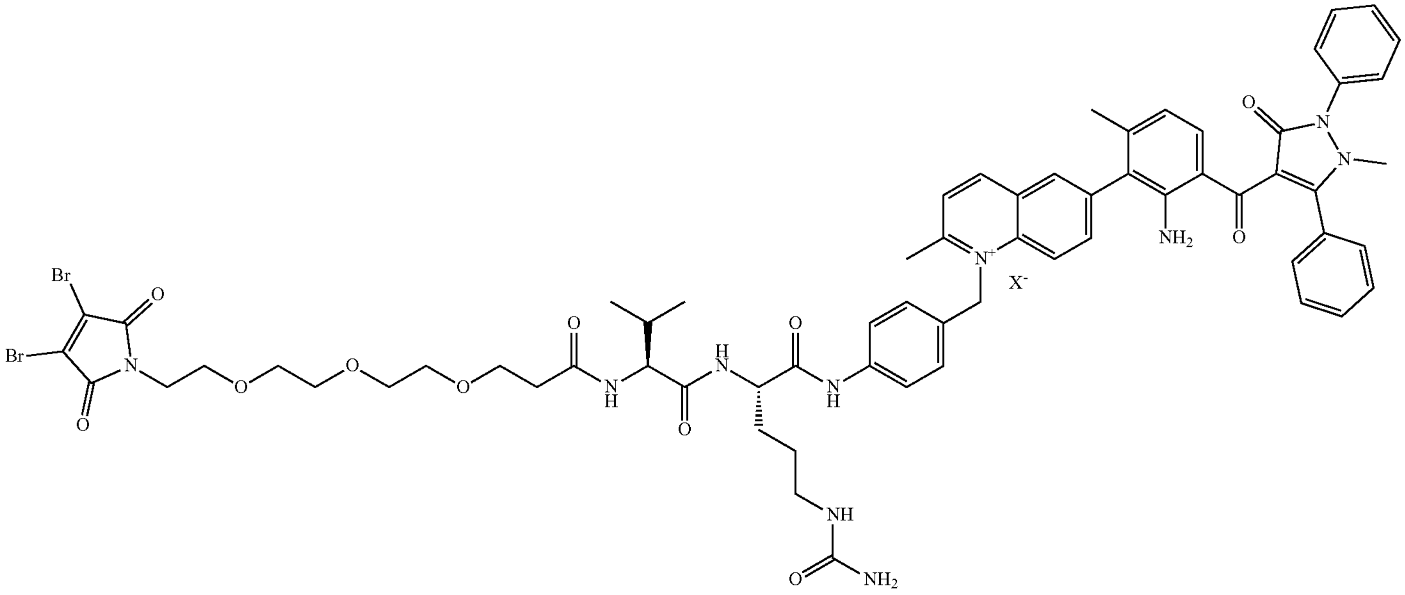 |

TABLE 3-continued
| Exemplary Compounds of Formula (I) | |
|---|---|
| Compound | Structure |
| A-25 | 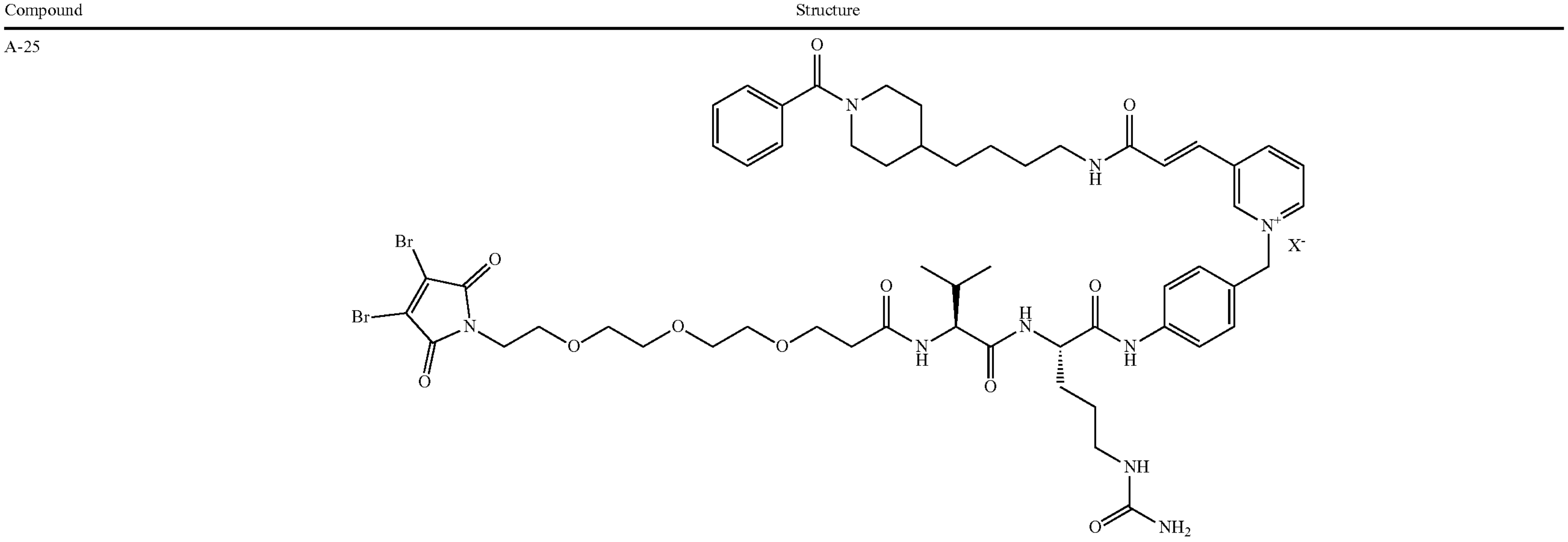 |

TABLE 3-continued
| Exemplary Compounds of Formula (I) | |
|---|---|
| Compound | Structure |
| A-26 | 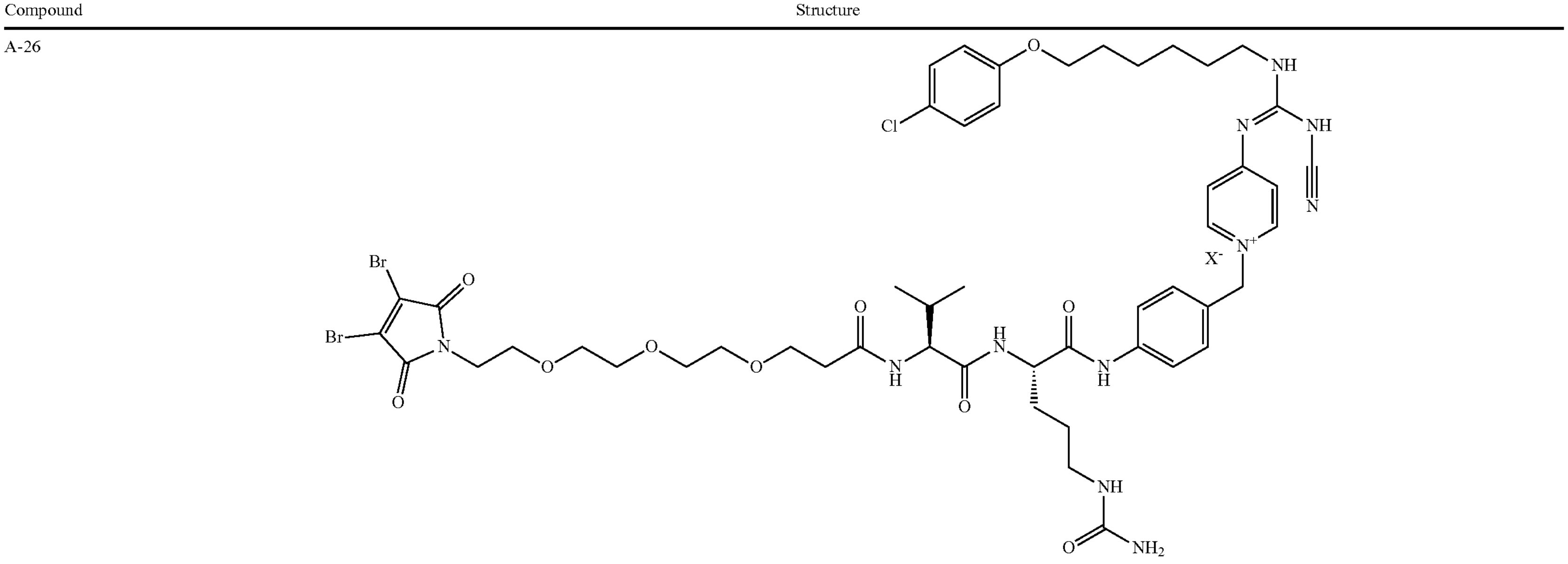 |
| A-27 | 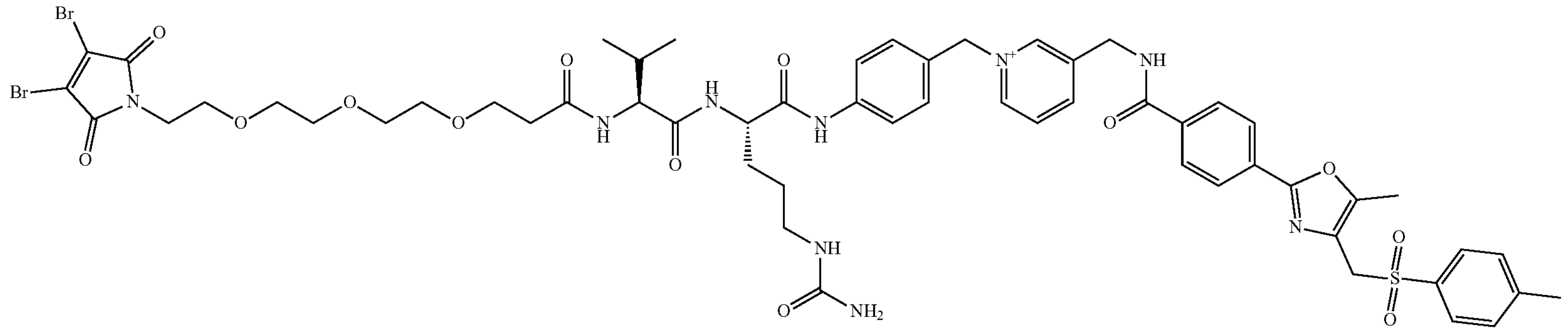 [SMILES: Cc1ccc(S(=O)(=O)Cc2nc(-c3ccc(C(=O)NCc4ccc[n+](Cc5ccc(NC(=O)[C@H](CCCNC(N)=O)NC(=O)[C@@H](NC(=O)CCOCCOCCOCCN6C(=O)C(Br)=C(Br)C6=O)C(C)C)cc5)c4)cc3)oc2C)cc1] |

TABLE 3-continued
| Exemplary Compounds of Formula (I) | |
|---|---|
| Compound | Structure |
| A-28 | 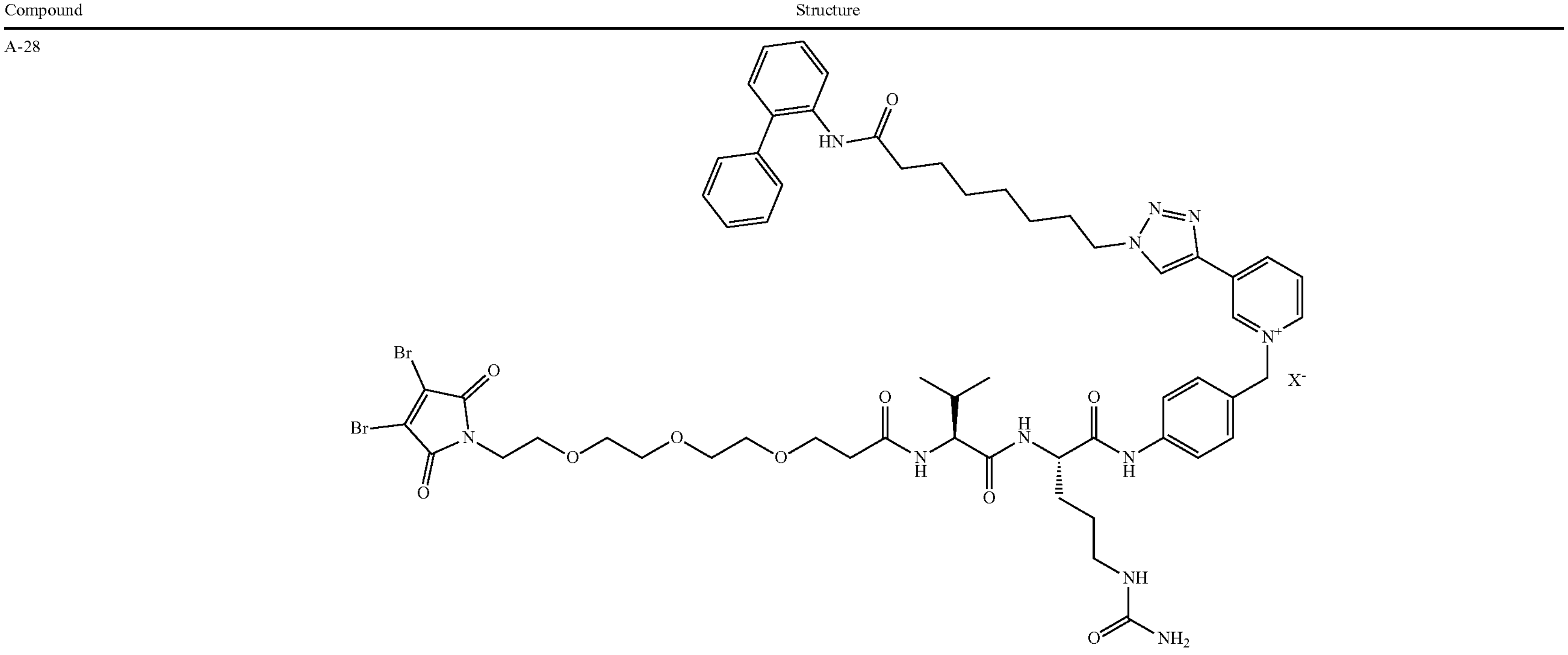 |

TABLE 3-continued
| Exemplary Compounds of Formula (I) | |
|---|---|
| Compound | Structure |
| A-29 | 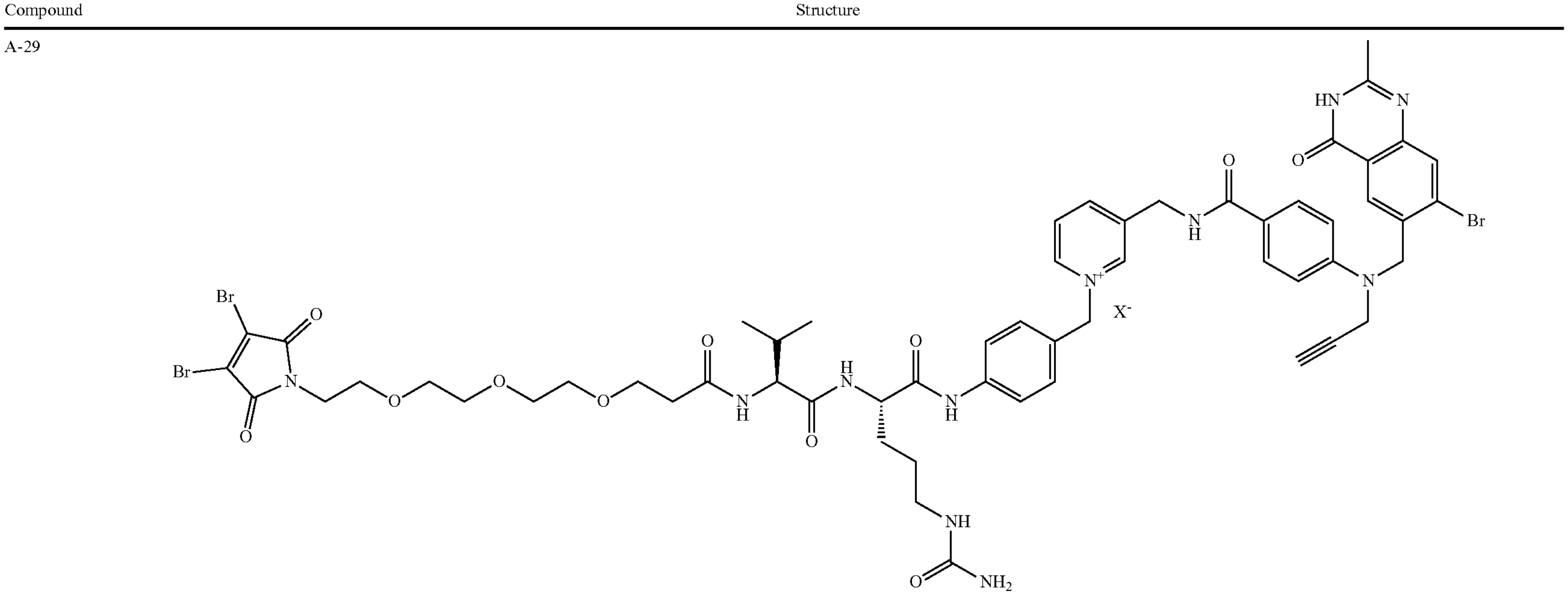 |

TABLE 3-continued
| Exemplary Compounds of Formula (I) | |
|---|---|
| Compound | Structure |
| A-30 | 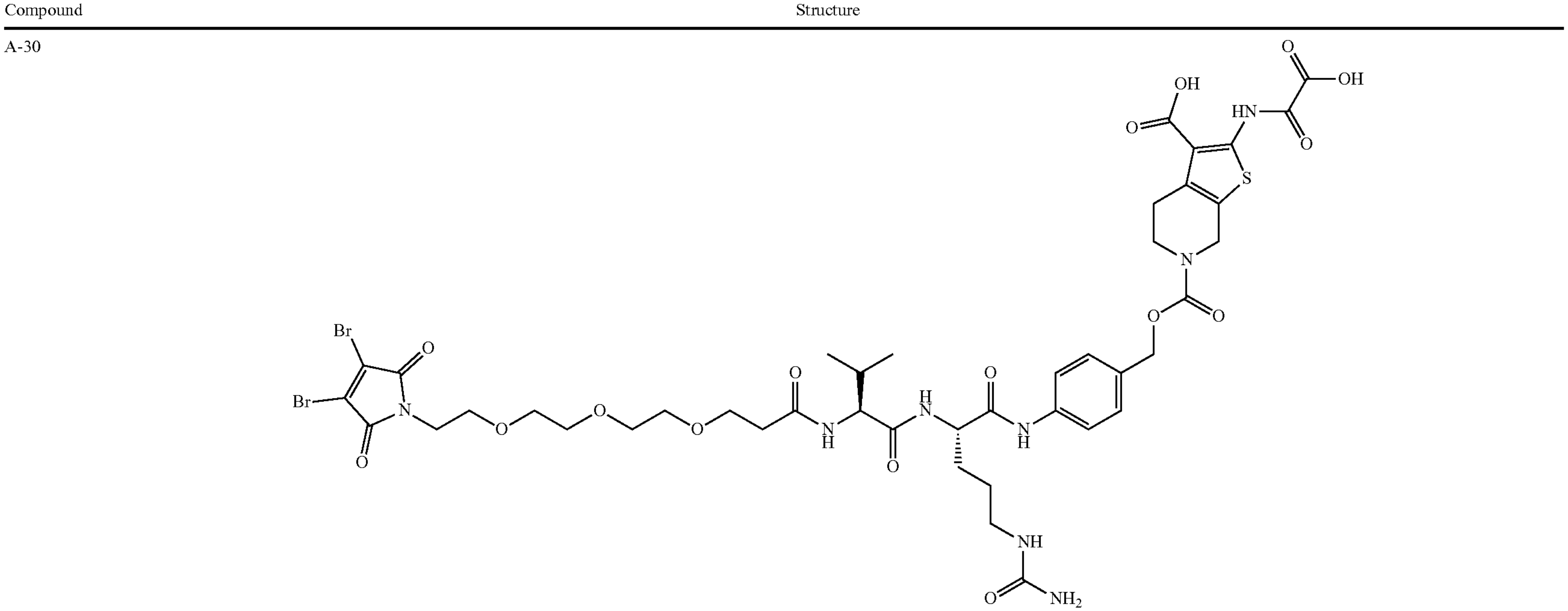 |
| A-31 | 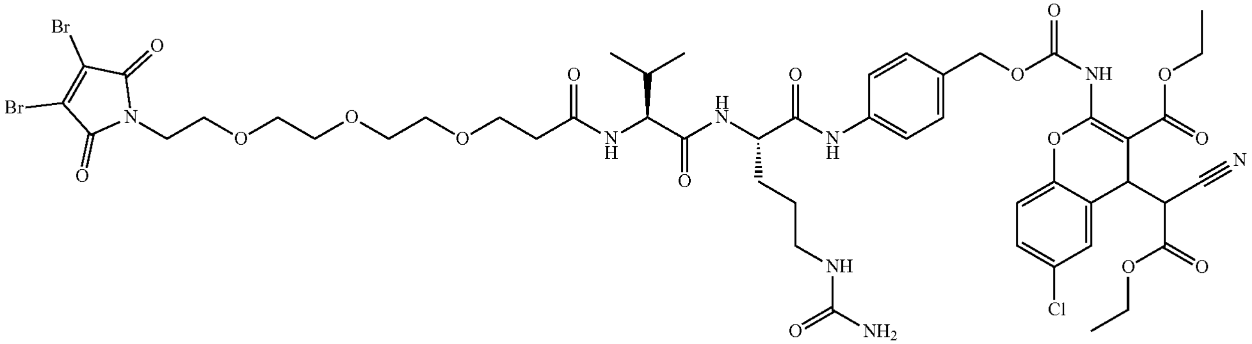 [SMILES: CCOC(=O)C1=C(NC(=O)OCc2ccc(NC(=O)[C@H](CCCNC(N)=O)NC(=O)[C@@H](NC(=O)CCOCCOCCOCCN3C(=O)C(Br)=C(Br)C3=O)C(C)C)cc2)Oc2ccc(Cl)cc2C1C(C#N)C(=O)OCC] |

TABLE 3-continued
| Exemplary Compounds of Formula (I) | |
|---|---|
| Compound | Structure |
| A-32 | 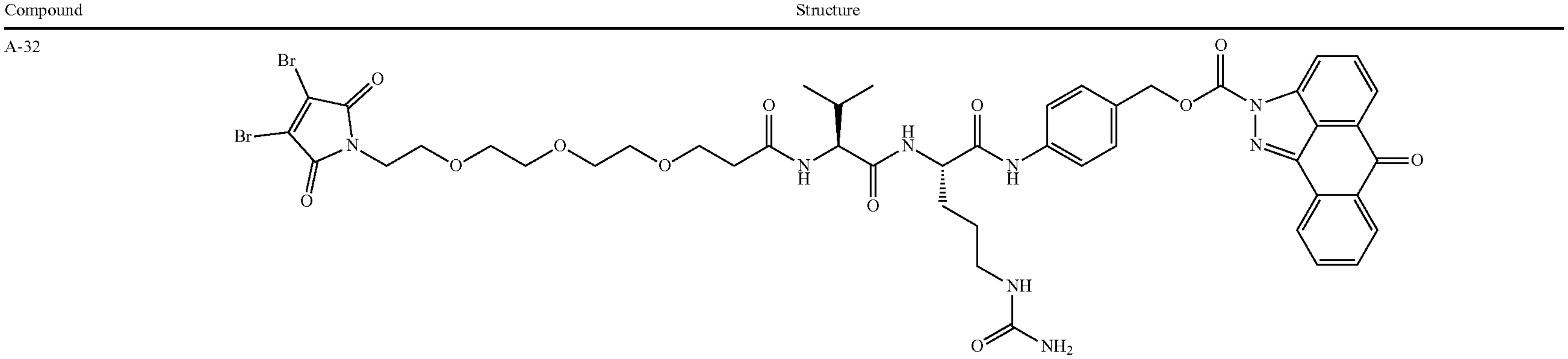 |
| A-33 | 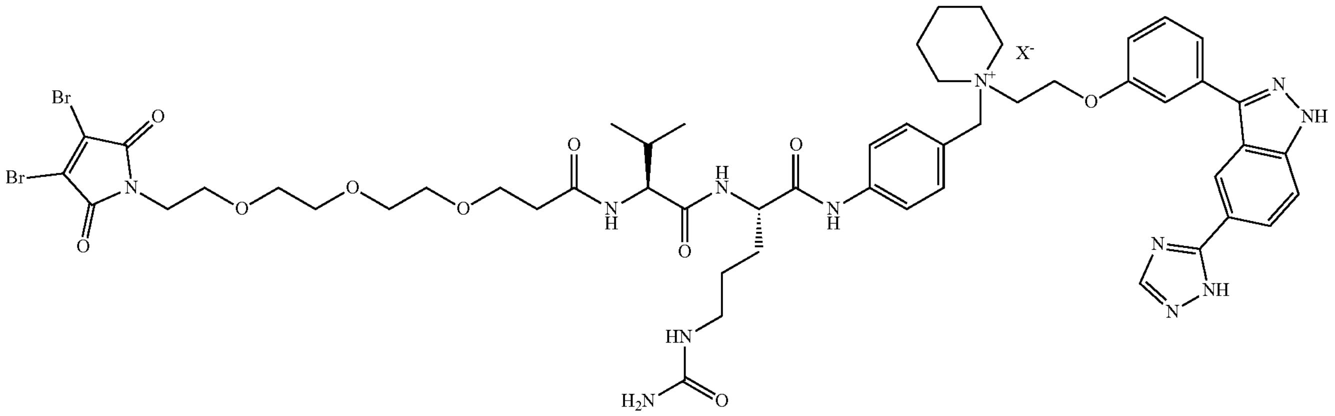 |

TABLE 3-continued
| Exemplary Compounds of Formula (I) | |
|---|---|
| Compound | Structure |
| A-34 | 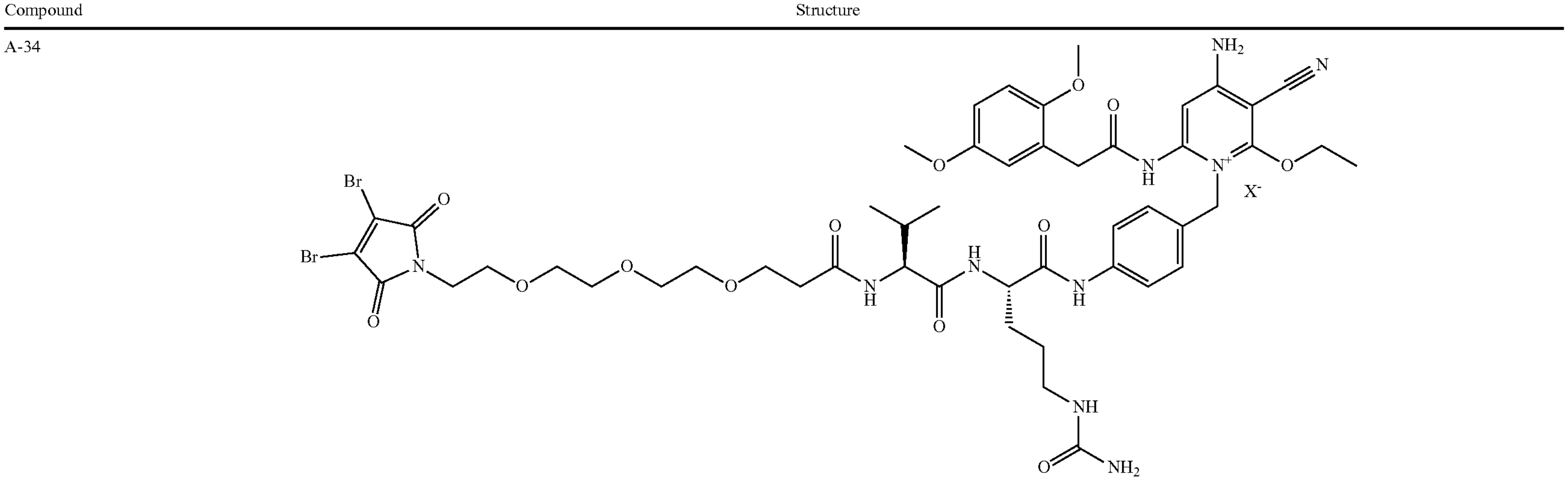 |
| A-35 | 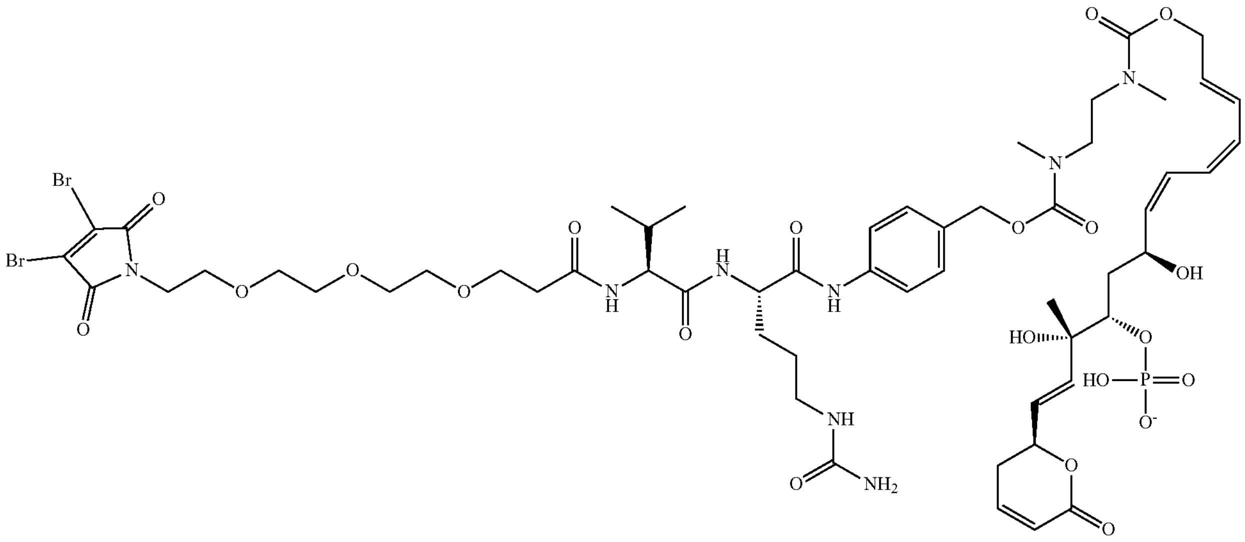 [SMILES: CC(C)[C@H](NC(=O)CCOCCOCCOCCN1C(=O)C(Br)=C(Br)C1=O)C(=O)N[C@@H](CCCNC(N)=O)C(=O)Nc1ccc(COC(=O)N(C)CCN(C)C(=O)OC/C=C/C=C\C=C/[C@@H](O)C[C@H](OP(=O)([O-])O)[C@@](C)(O)/C=C/[C@@H]2CC=CC(=O)O2)cc1] |

TABLE 3-continued
| Exemplary Compounds of Formula (I) | |
|---|---|
| Compound | Structure |
| A-36 | 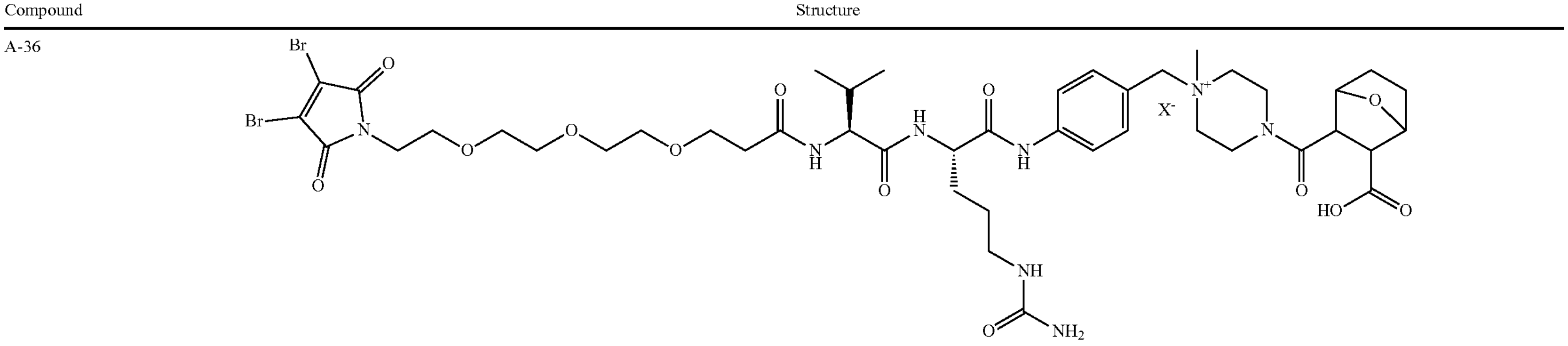 |
| A-37 | 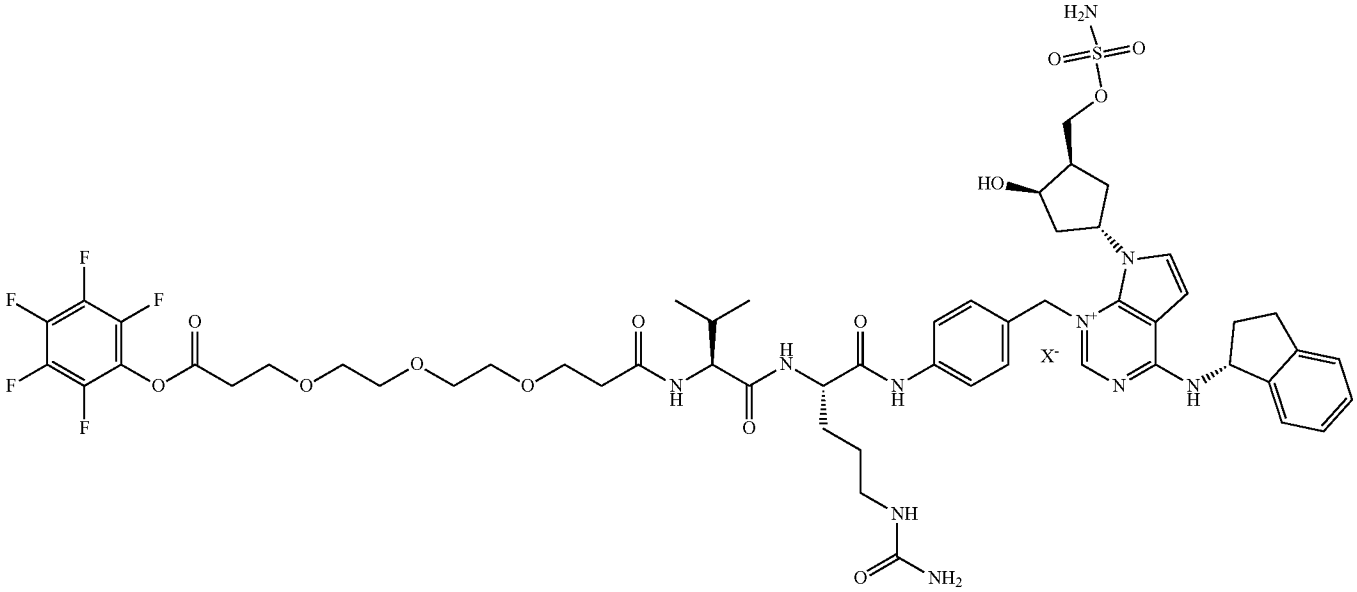 |

TABLE 3-continued
| Exemplary Compounds of Formula (I) | |
|---|---|
| Compound | Structure |
| A-38 | 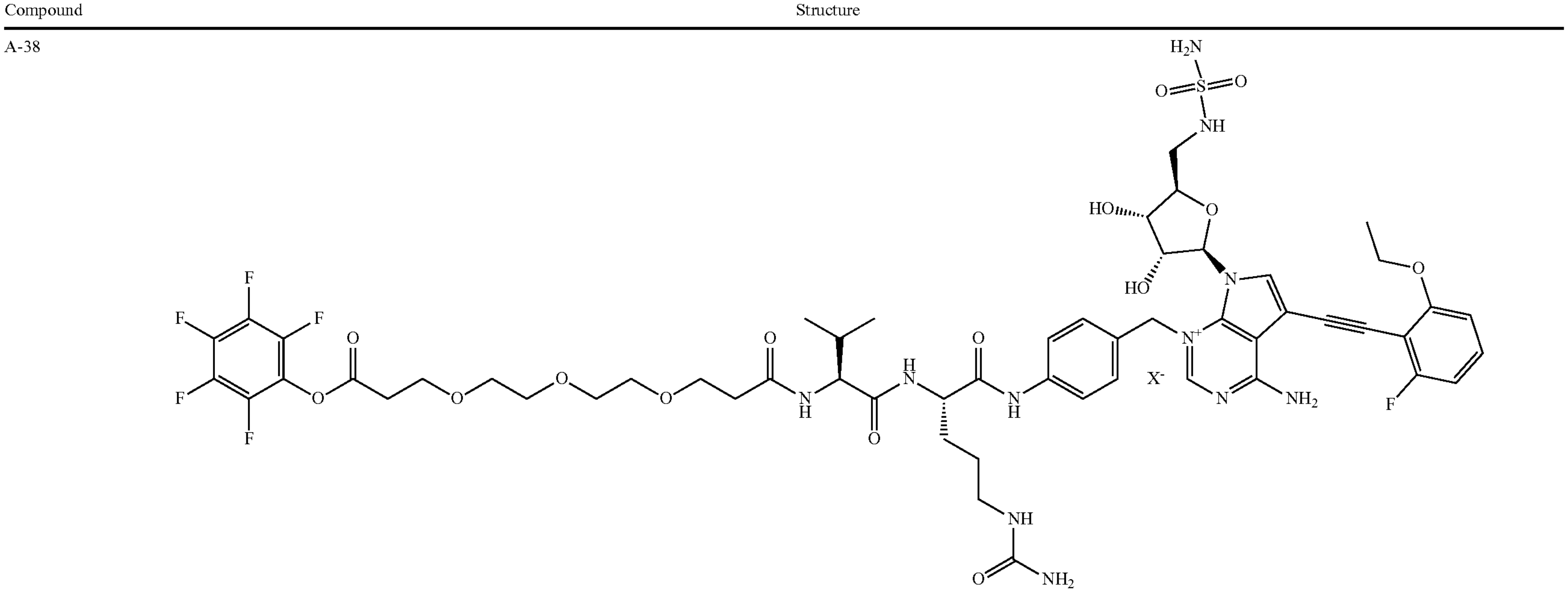 |

TABLE 3-continued
| Exemplary Compounds of Formula (I) | |
|---|---|
| Compound | Structure |
| A-39 | 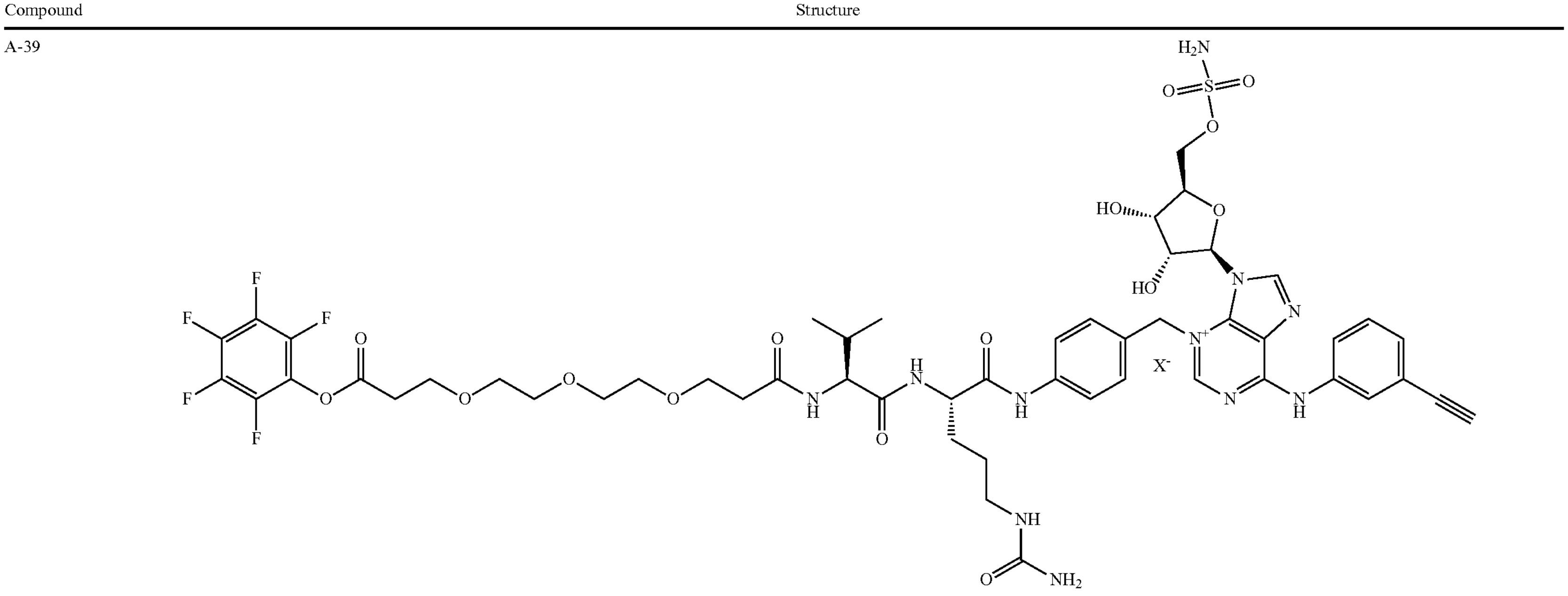 |
| A-40 | 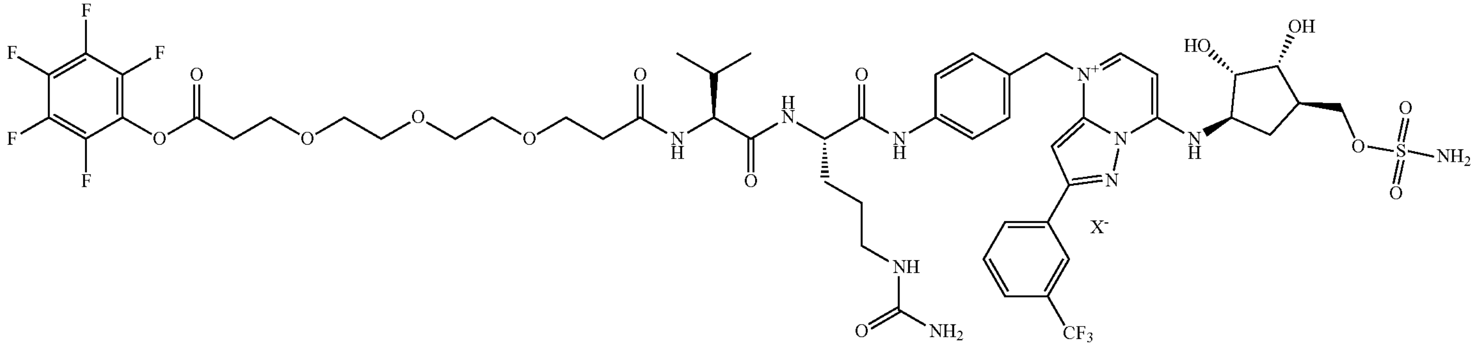 |

TABLE 3-continued
| Exemplary Compounds of Formula (I) | |
| --- | --- |
| Compound | Structure |
| A-41 | 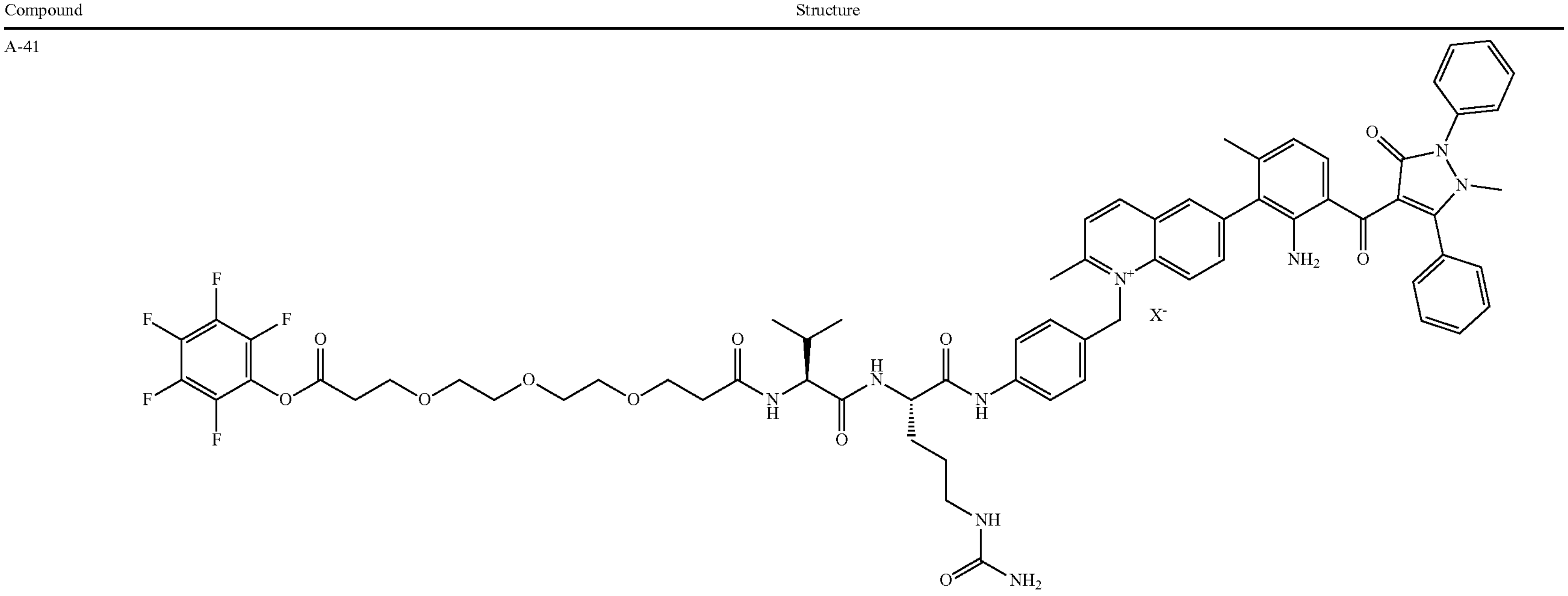 |
| A-42 | 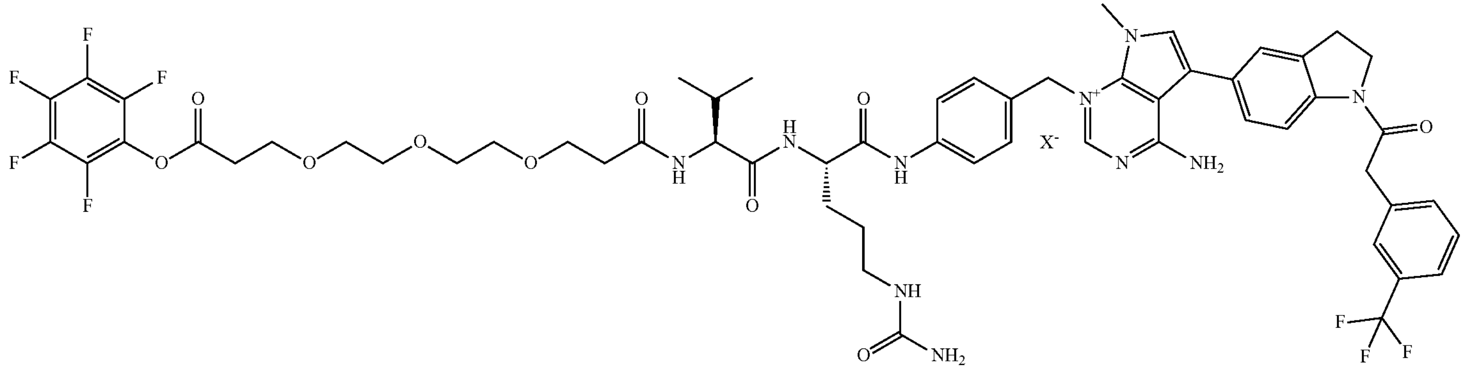 |

TABLE 3-continued
| Exemplary Compounds of Formula (I) | |
|---|---|
| Compound | Structure |
| A-43 | 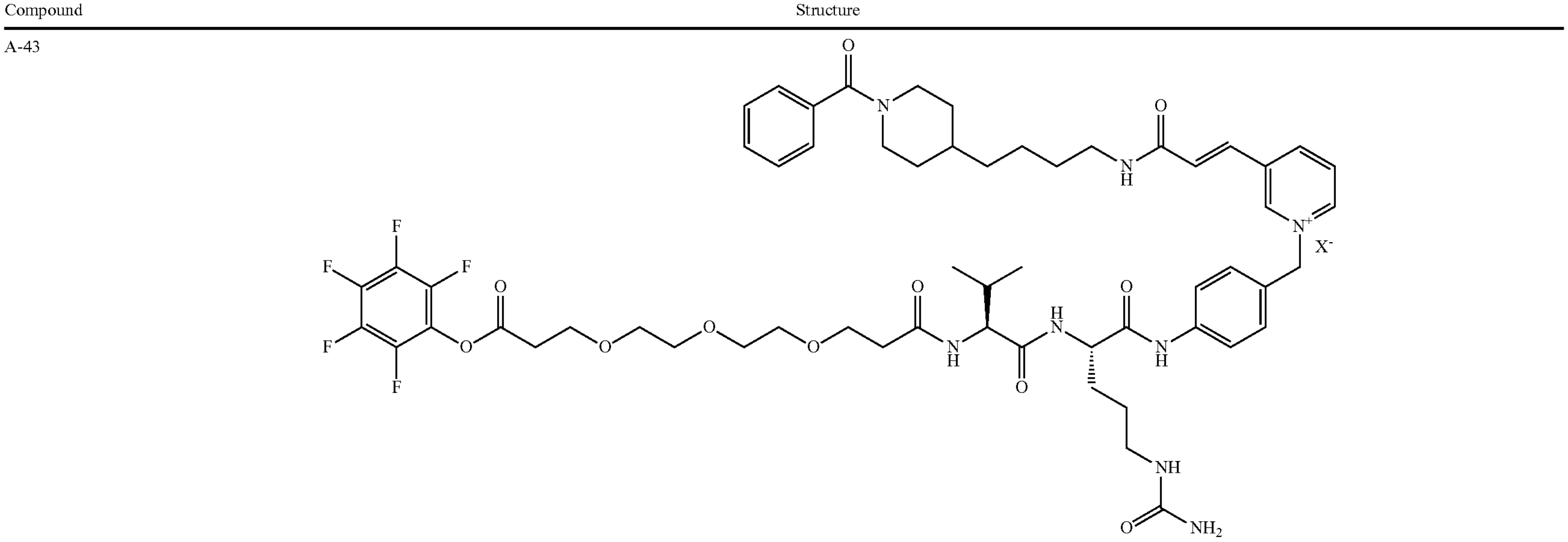 |

TABLE 3-continued
| Exemplary Compounds of Formula (I) | |
|---|---|
| Compound | Structure |
| A-44 | 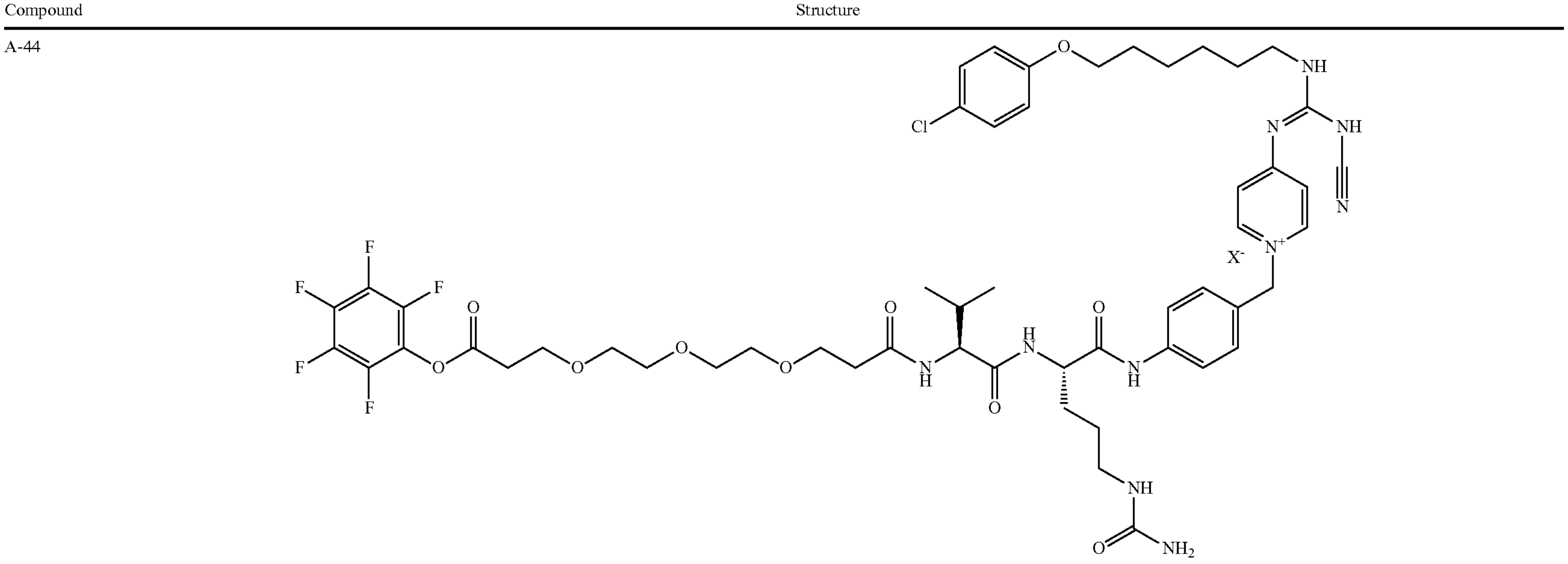 |
| A-45 | 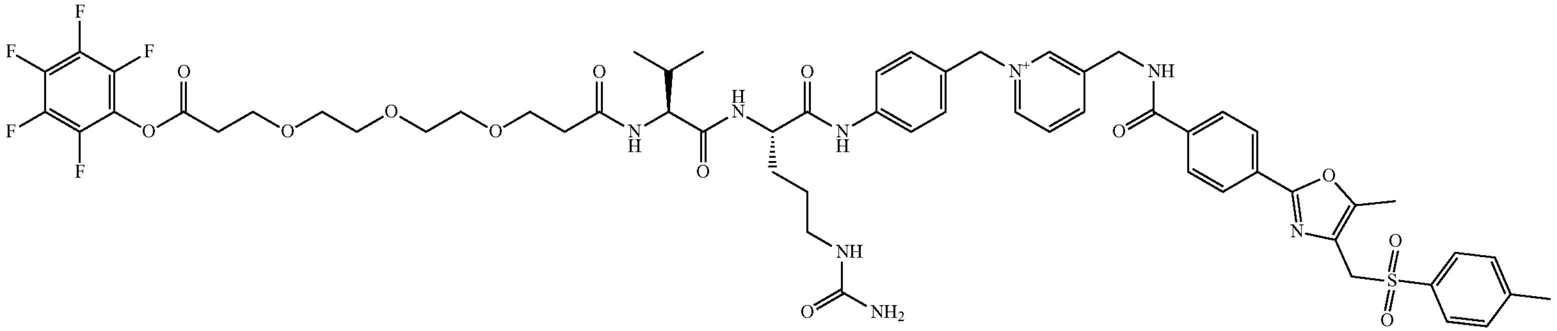 [SMILES: Cc1ccc(S(=O)(=O)Cc2nc(-c3ccc(C(=O)NCc4ccc[n+](Cc5ccc(NC(=O)[C@H](CCCNC(N)=O)NC(=O)[C@@H](NC(=O)CCOCCOCCOCCC(=O)Oc6c(F)c(F)c(F)c(F)c6F)C(C)C)cc5)c4)cc3)oc2C)cc1] |

TABLE 3-continued
| Exemplary Compounds of Formula (I) | |
|---|---|
| Compound | Structure |
| A-46 | 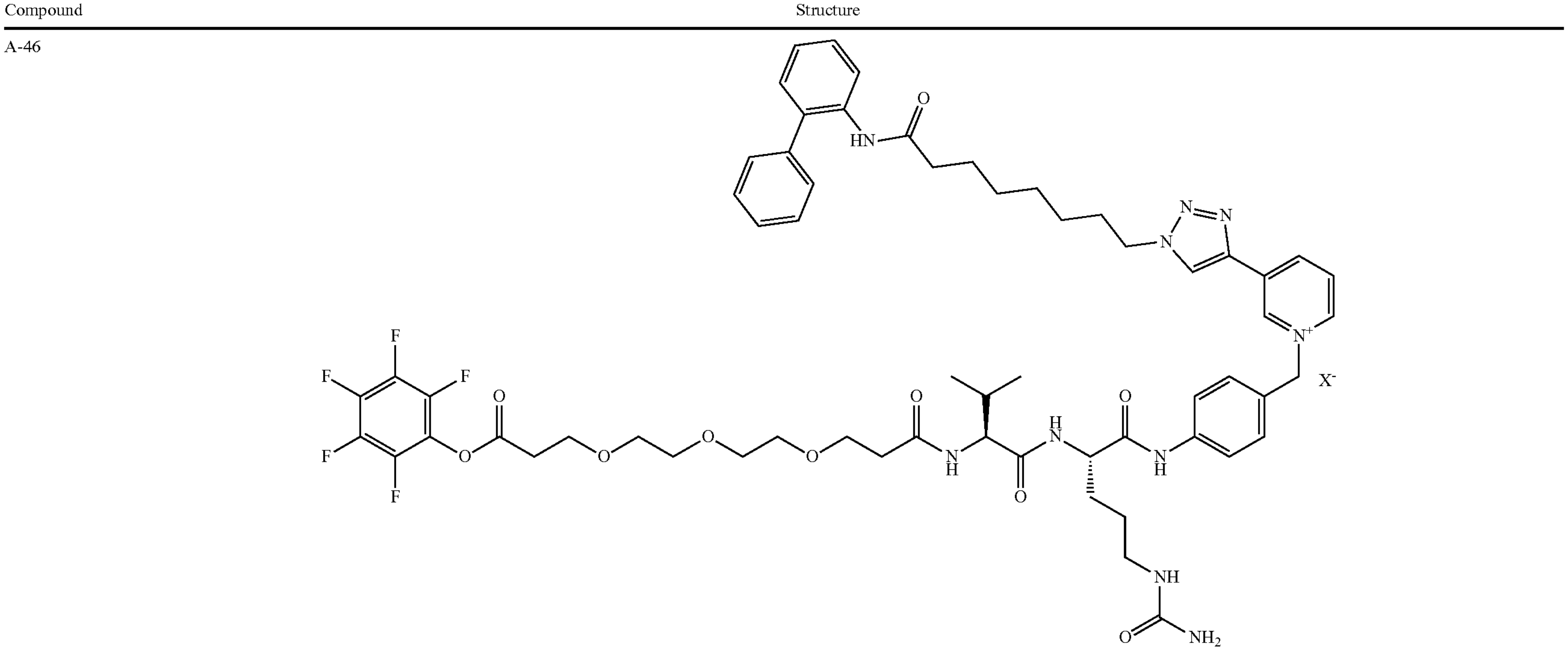 |

TABLE 3-continued
| Exemplary Compounds of Formula (I) | |
|---|---|
| Compound | Structure |
| A-47 | 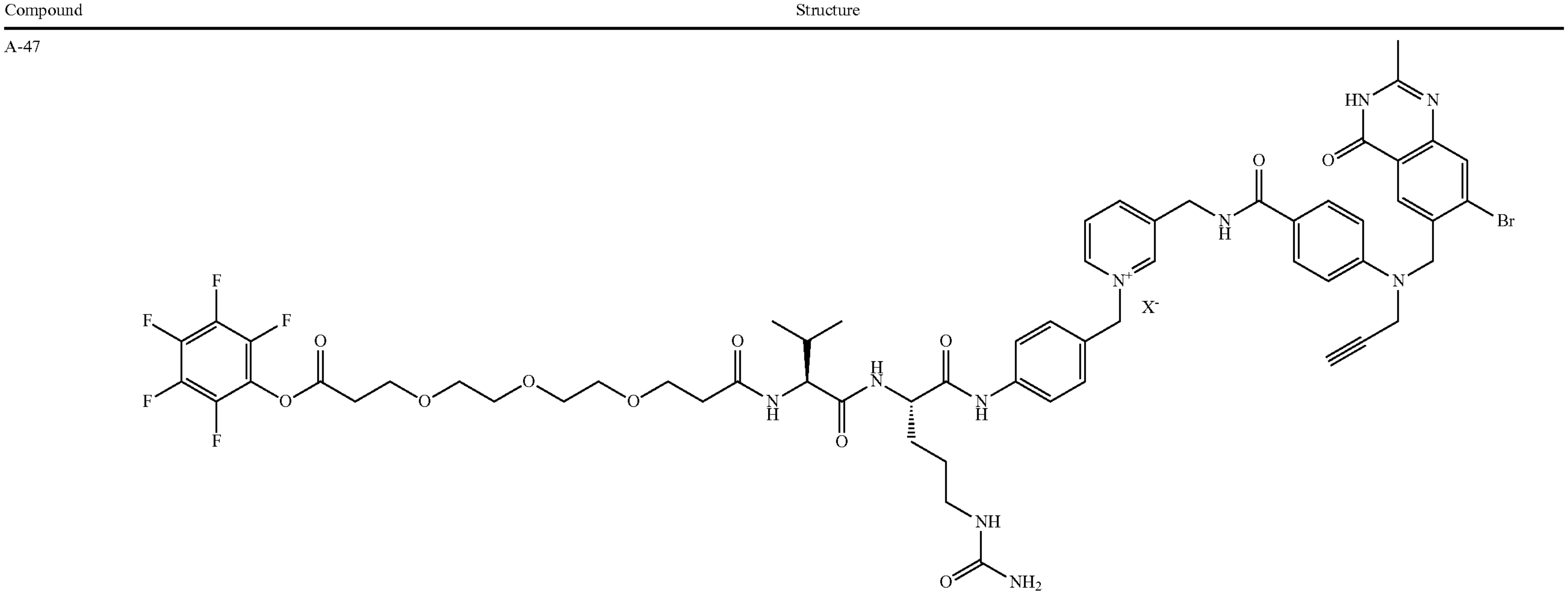 |

TABLE 3-continued
| Exemplary Compounds of Formula (I) | |
|---|---|
| Compound | Structure |
| A-48 | 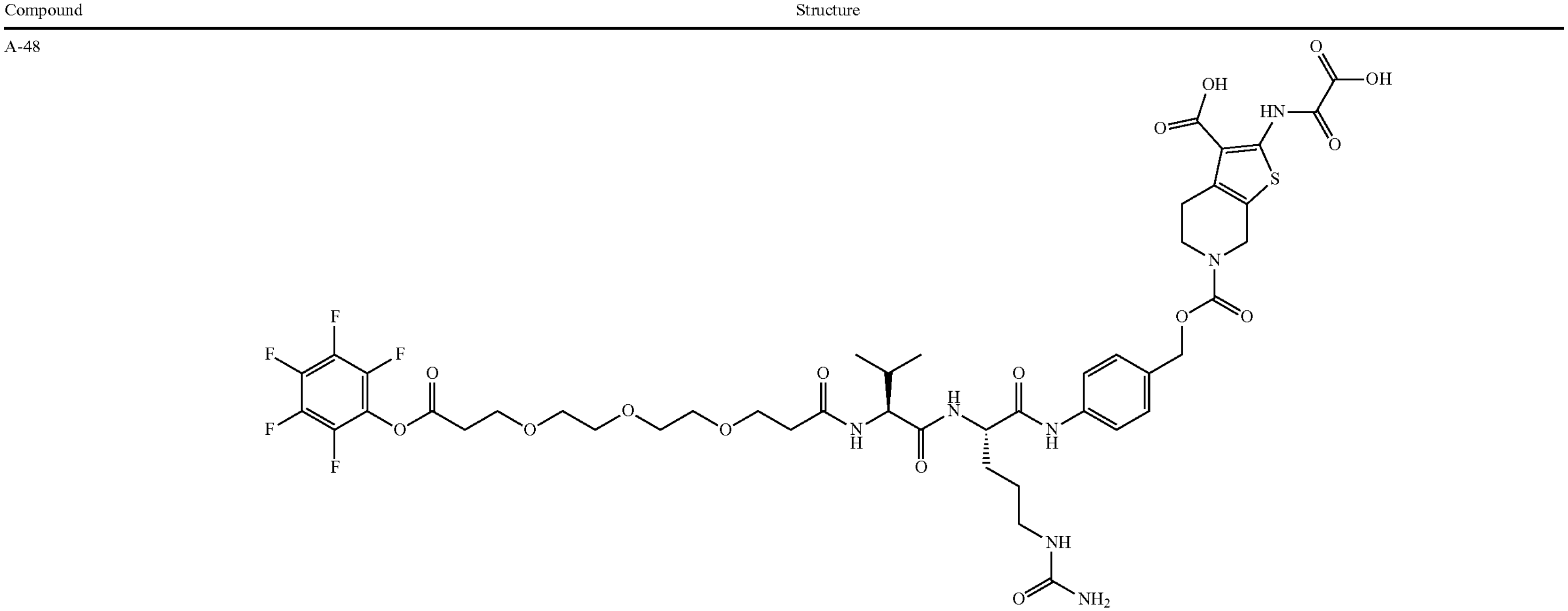 |
| A-49 | 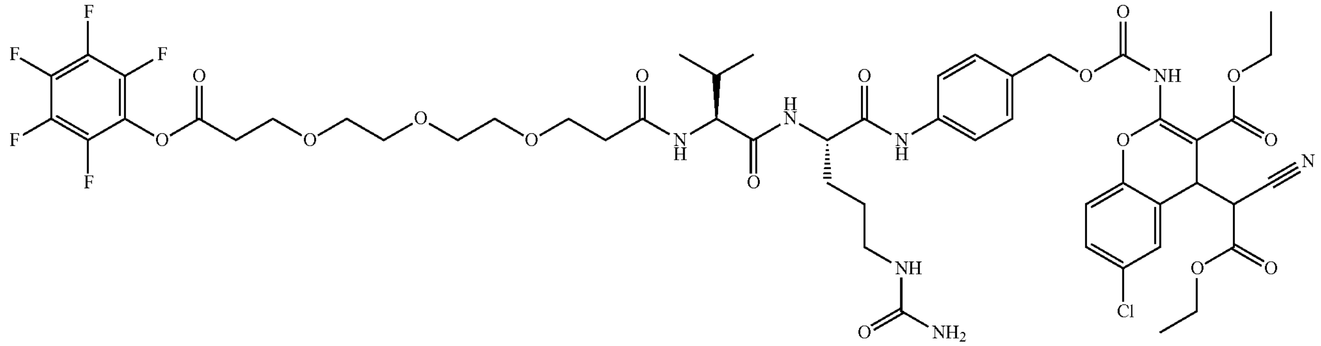 [SMILES: CCOC(=O)C1=C(NC(=O)OCc2ccc(NC(=O)[C@H](CCCNC(N)=O)NC(=O)[C@@H](NC(=O)CCOCCOCCOCCC(=O)Oc3c(F)c(F)c(F)c(F)c3F)C(C)C)cc2)Oc2ccc(Cl)cc2C1C(C#N)C(=O)OCC] |

TABLE 3-continued
| Exemplary Compounds of Formula (I) | |
|---|---|
| Compound | Structure |
| A-50 | 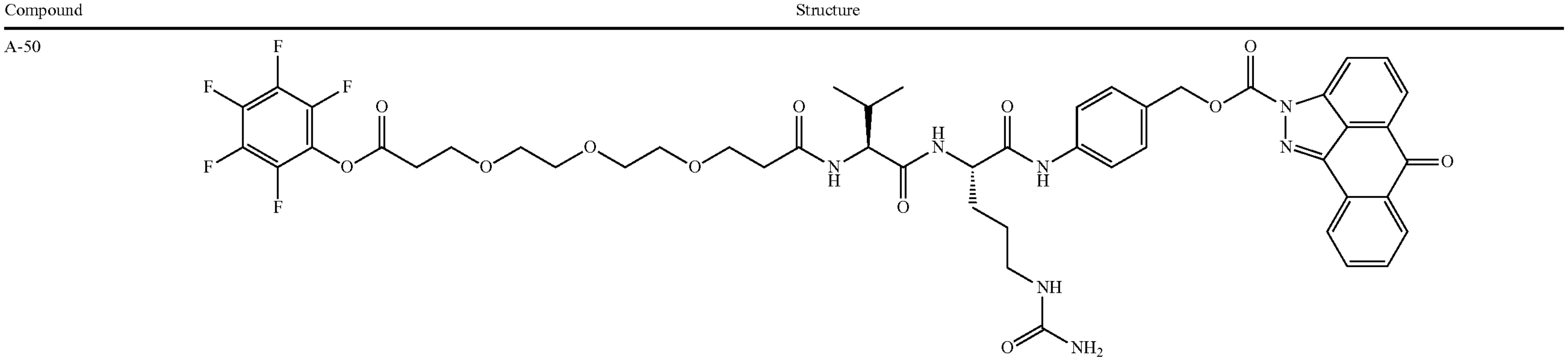 |
| A-51 | 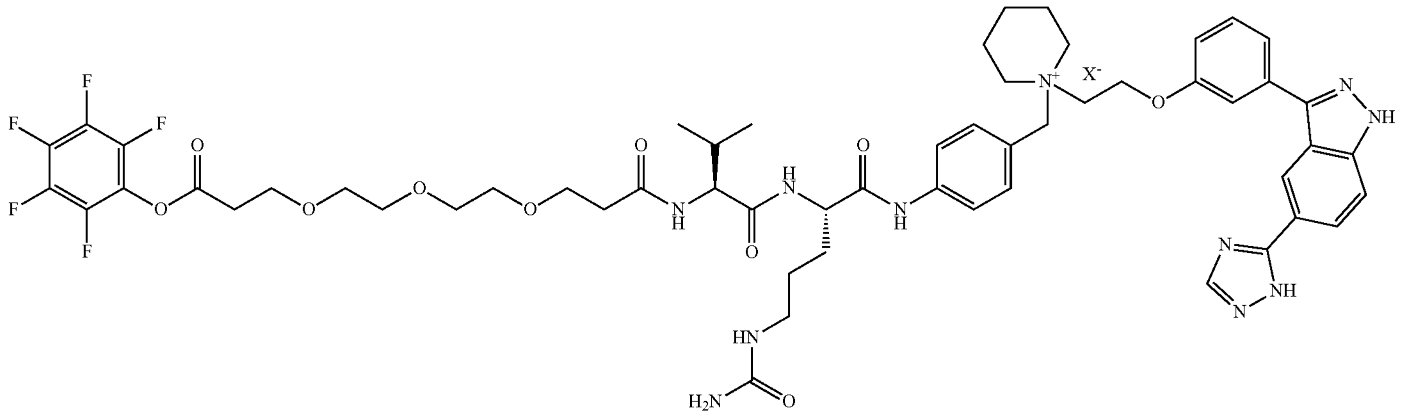 |

TABLE 3-continued
| Exemplary Compounds of Formula (I) | |
|---|---|
| Compound | Structure |
| A-52 | 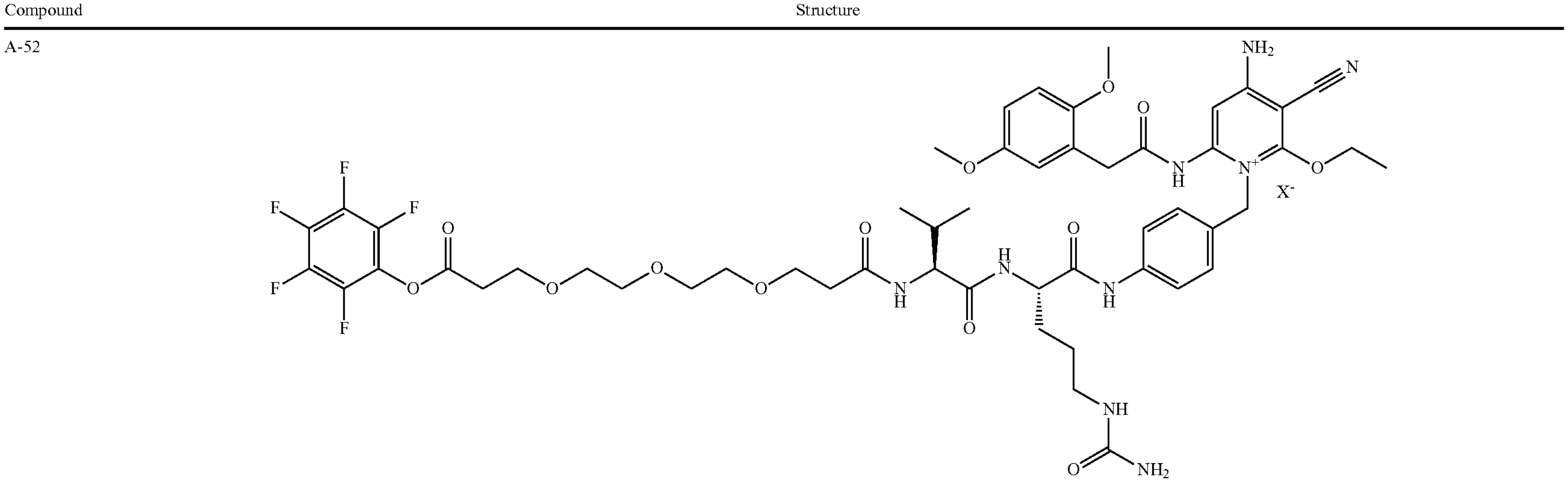 |

TABLE 3-continued
| Exemplary Compounds of Formula (I) | |
|---|---|
| Compound | Structure |
| A-53 | 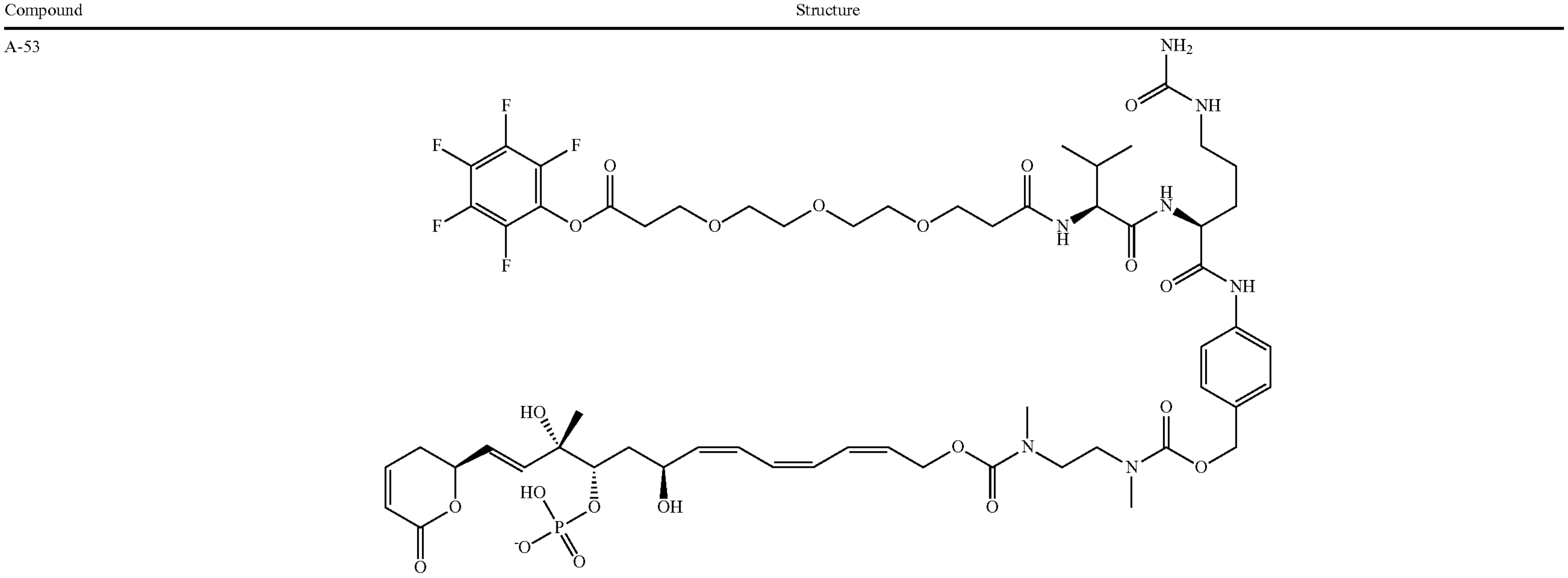 |
| A-54 | 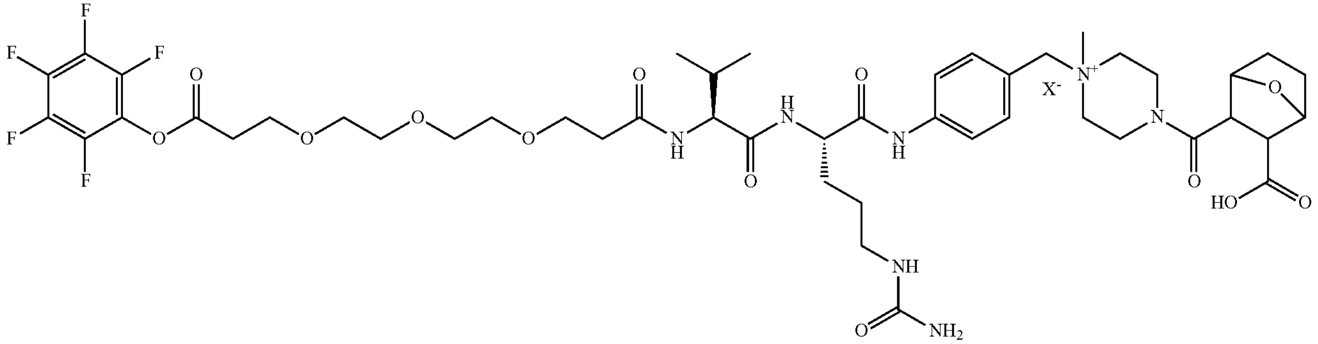 |

TABLE 3-continued
| Exemplary Compounds of Formula (I) | |
|---|---|
| Compound | Structure |
| A-55 | 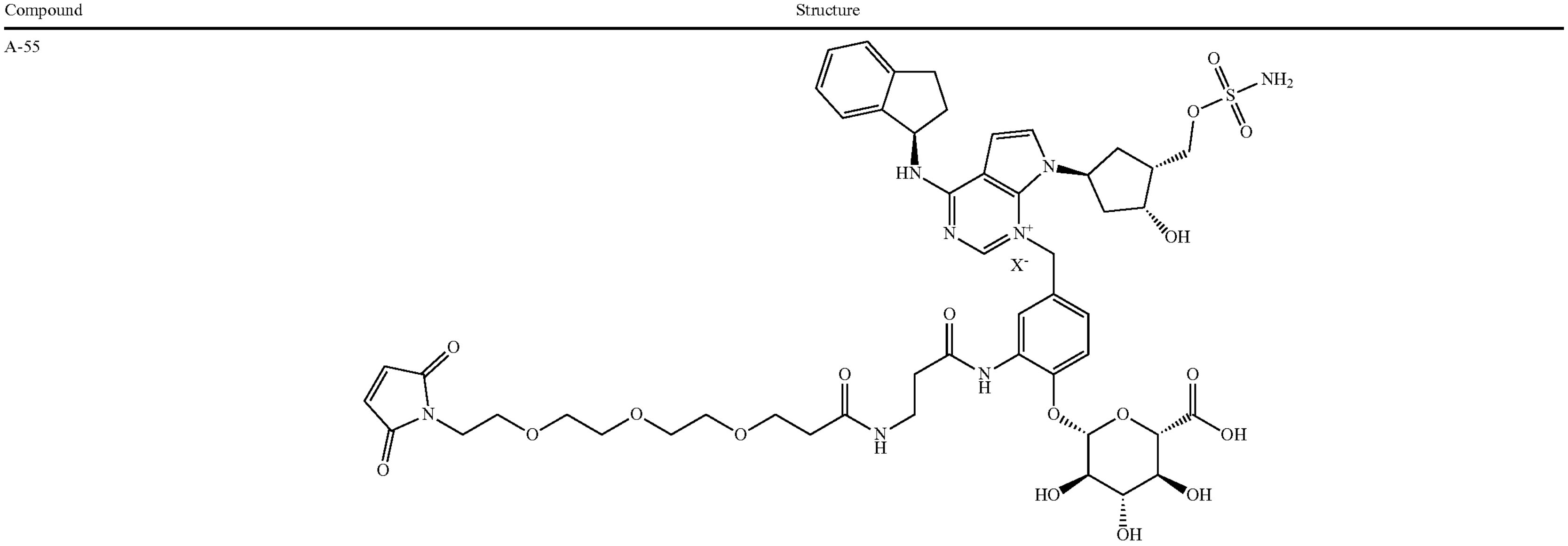 |

TABLE 3-continued
| Exemplary Compounds of Formula (I) | |
|---|---|
| Compound | Structure |
| A-56 | 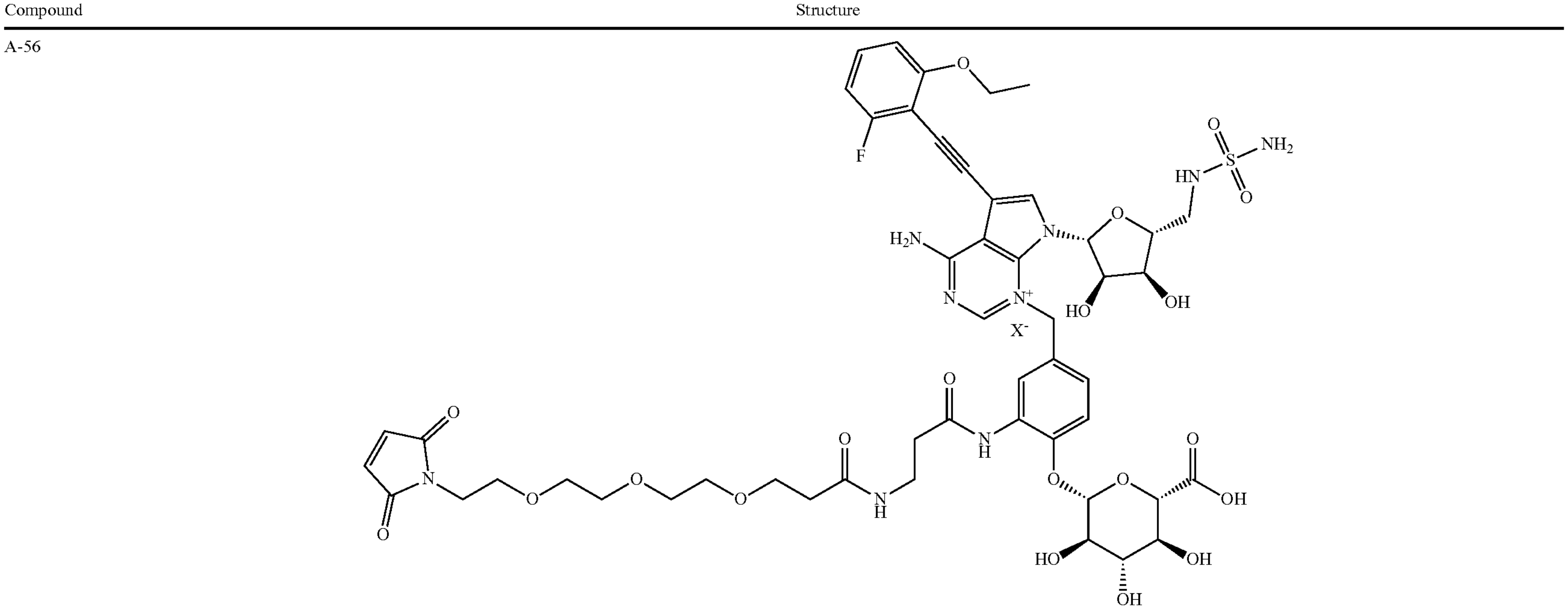 |

TABLE 3-continued
| Exemplary Compounds of Formula (I) | |
|---|---|
| Compound | Structure |
| A-57 | 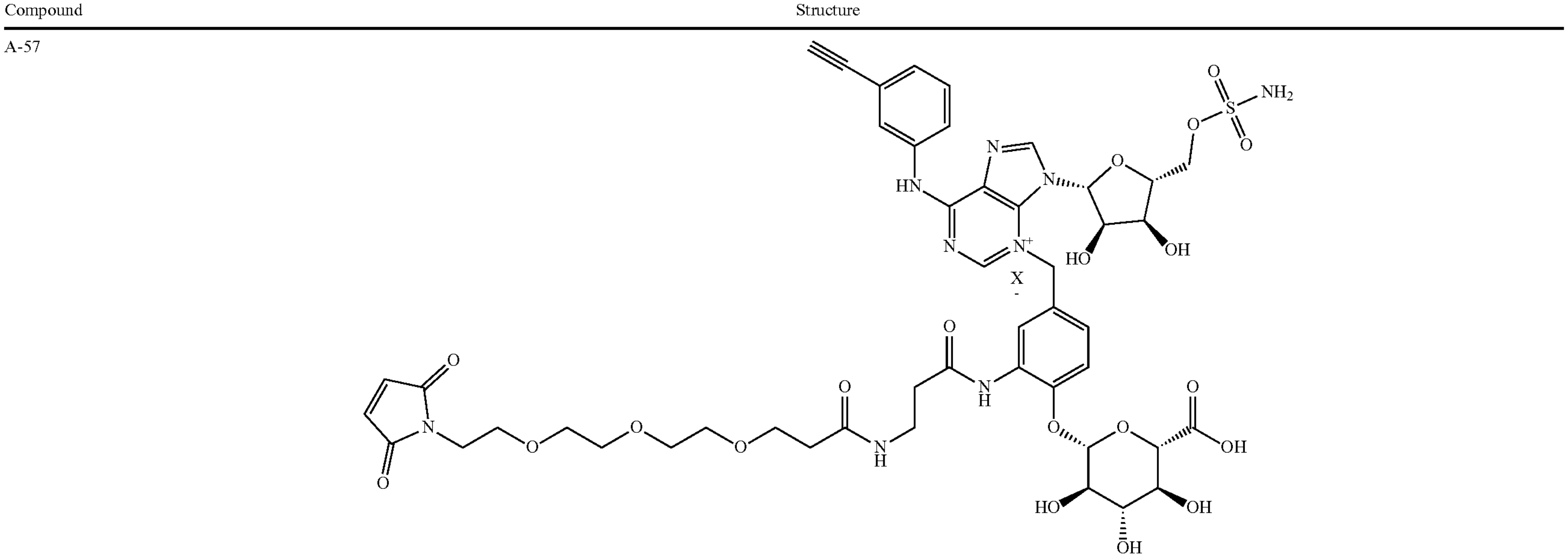 |

TABLE 3-continued
| Exemplary Compounds of Formula (I) | |
|---|---|
| Compound | Structure |
| A-58 | 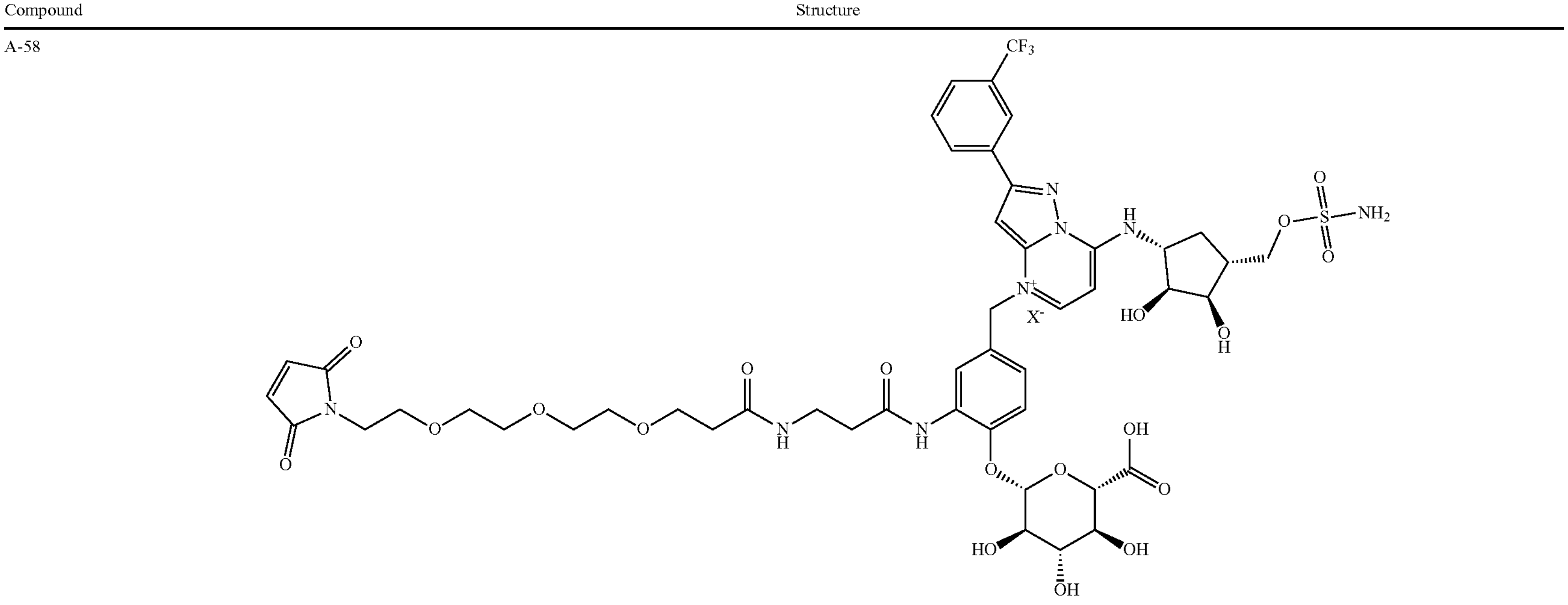 |
| A-59 | 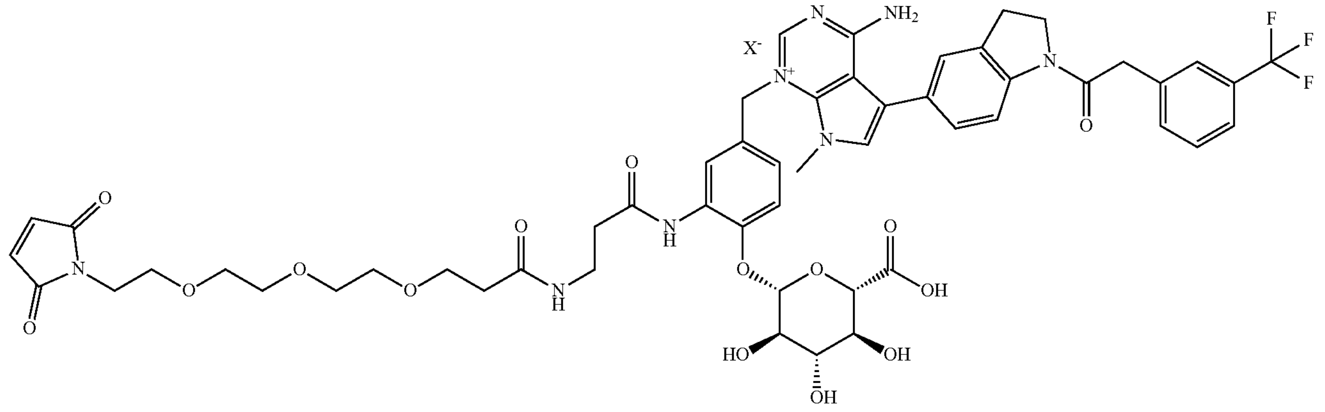 |

TABLE 3-continued
| Exemplary Compounds of Formula (I) | |
|---|---|
| Compound | Structure |
| A-60 | 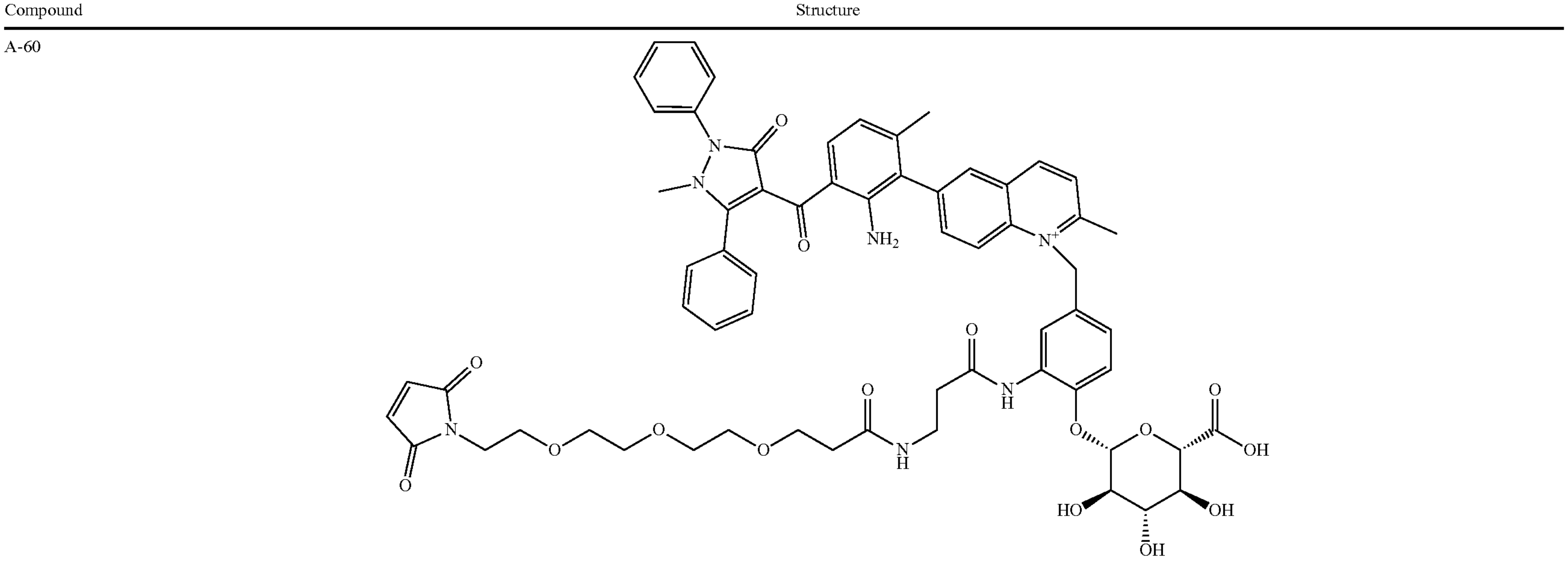 |

TABLE 3-continued
| Exemplary Compounds of Formula (I) | |
|---|---|
| Compound | Structure |
| A-61 | 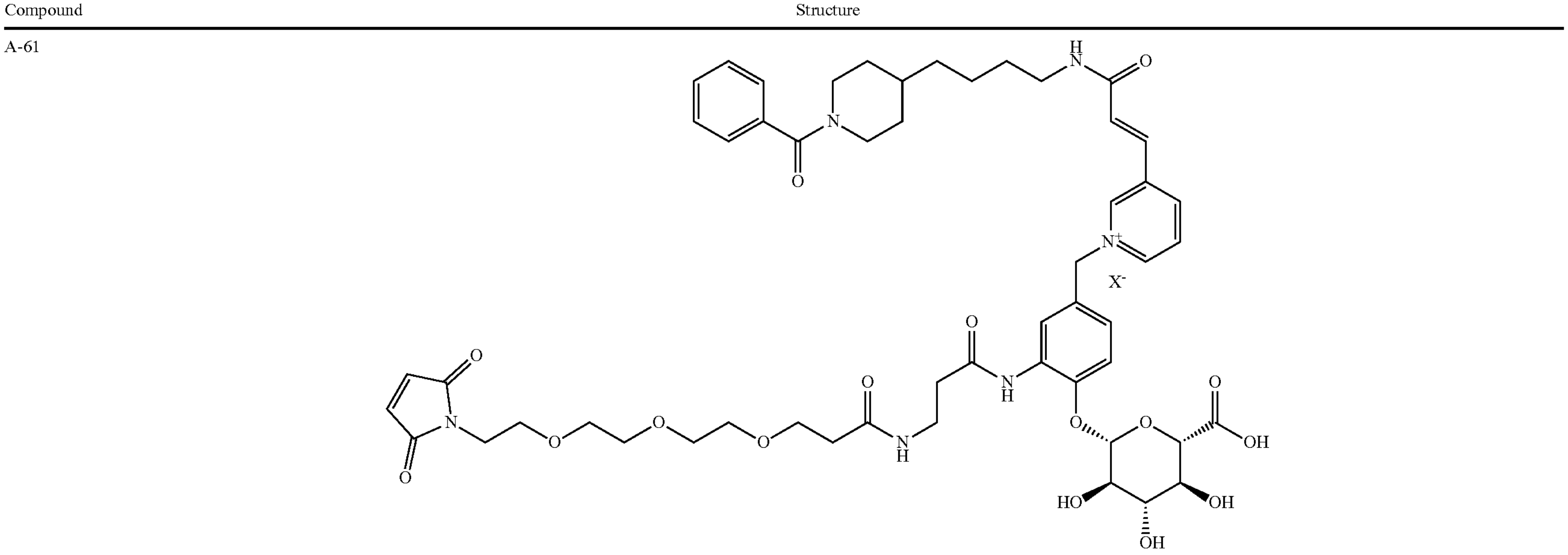 |

TABLE 3-continued
| Exemplary Compounds of Formula (I) | |
|---|---|
| Compound | Structure |
| A-62 | 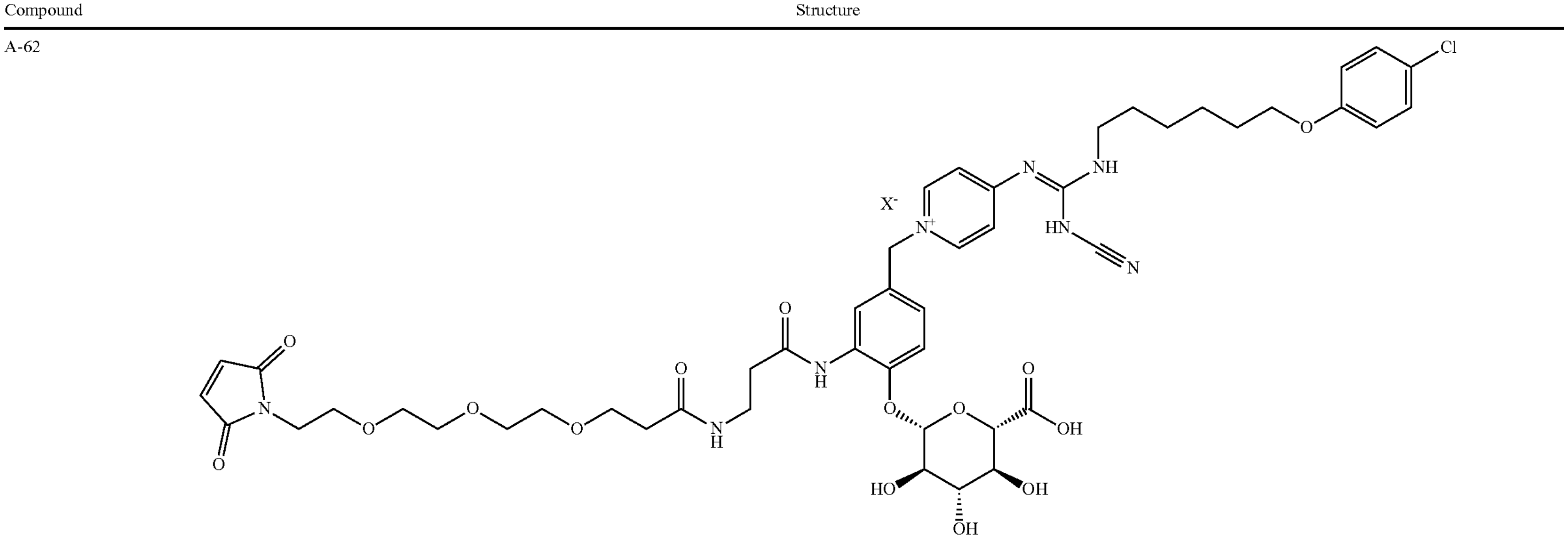 |
| A-63 | 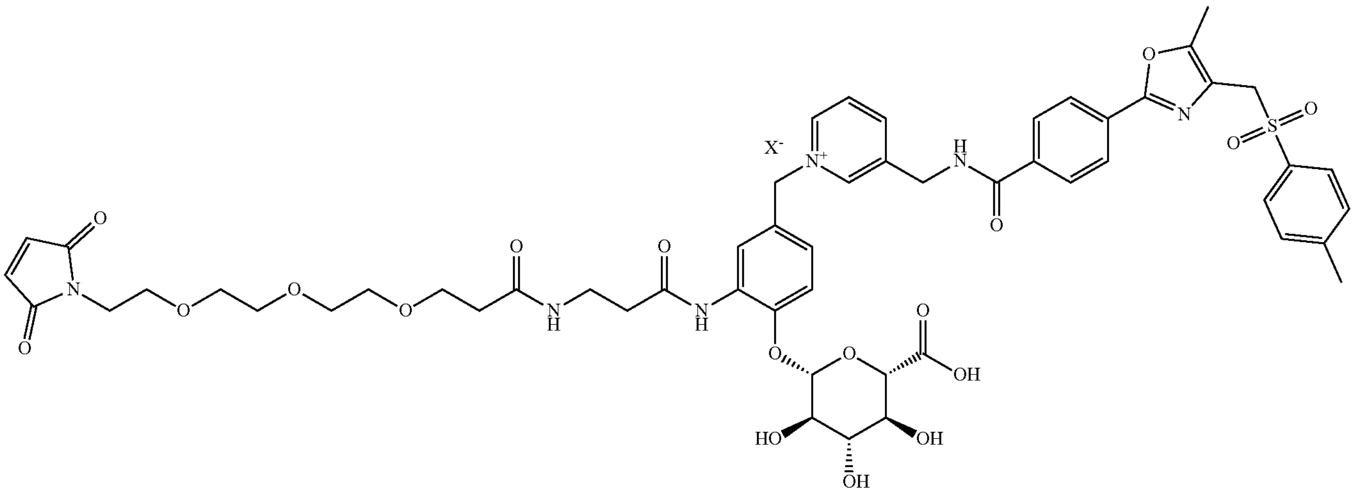 |

TABLE 3-continued
| Exemplary Compounds of Formula (I) | |
|---|---|
| Compound | Structure |
| A 64 | 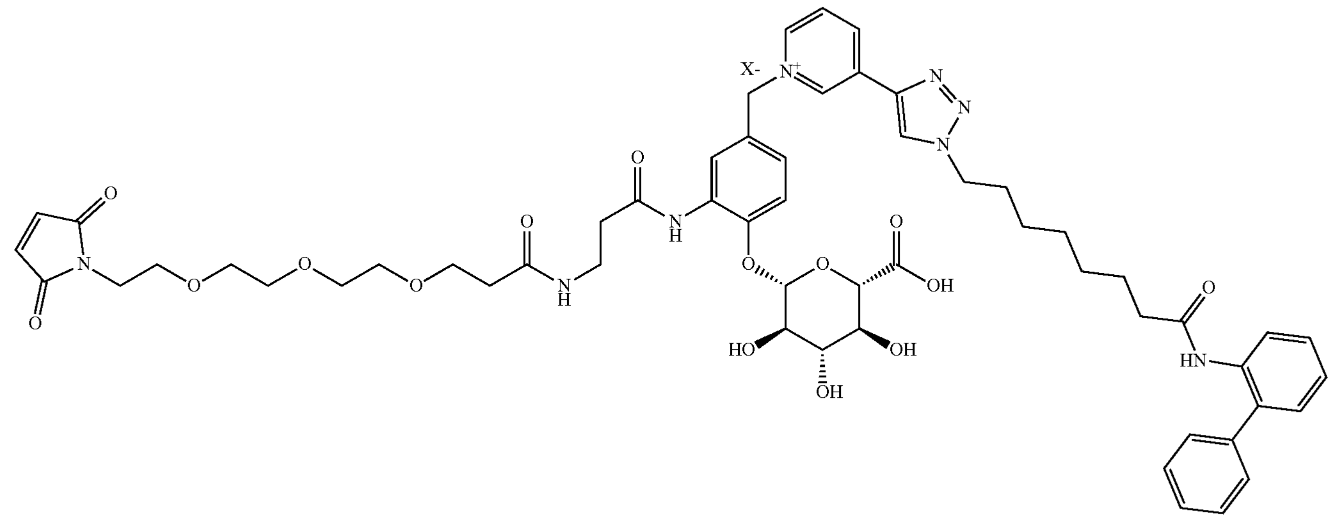 |
| A-65 | 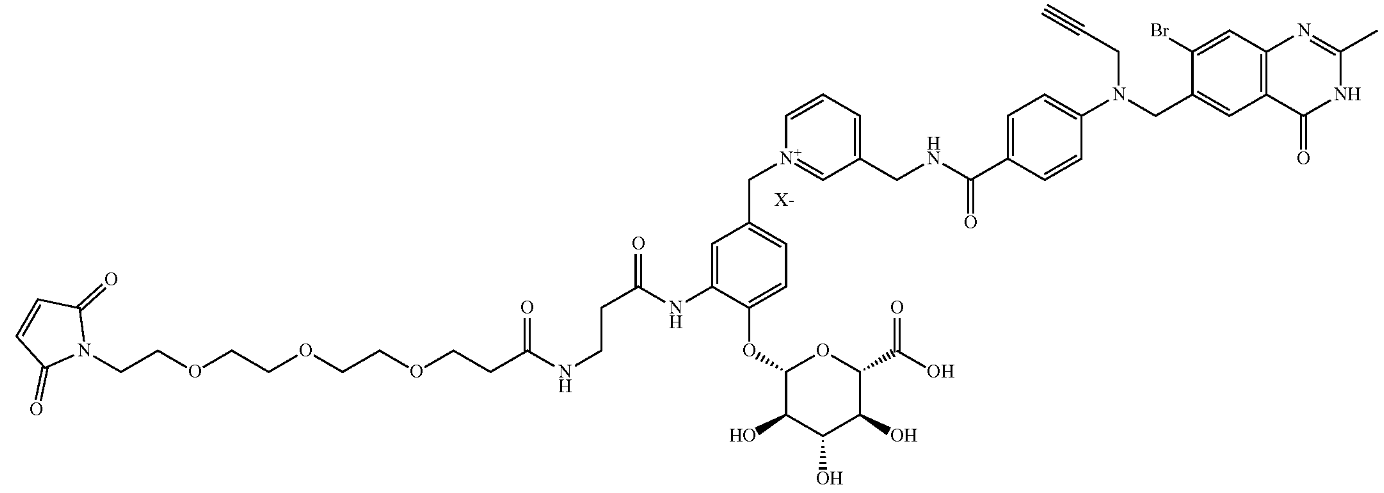 |

TABLE 3-continued
| Exemplary Compounds of Formula (I) | |
|---|---|
| Compound | Structure |
| A-66 | 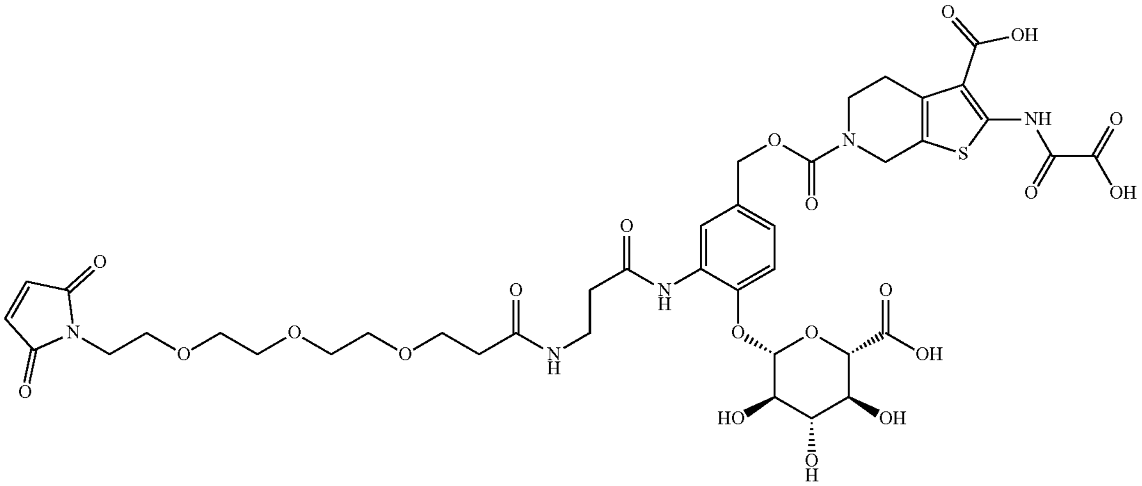 [SMILES: O=C(CCOCCOCCOCCN1C(=O)C=CC1=O)NCCC(=O)Nc1cc(COC(=O)N2CCc3c(sc(NC(=O)C(=O)O)c3C(=O)O)C2)ccc1O[C@@H]1O[C@H](C(=O)O)[C@@H](O)[C@H](O)[C@H]1O] |
| A-67 | 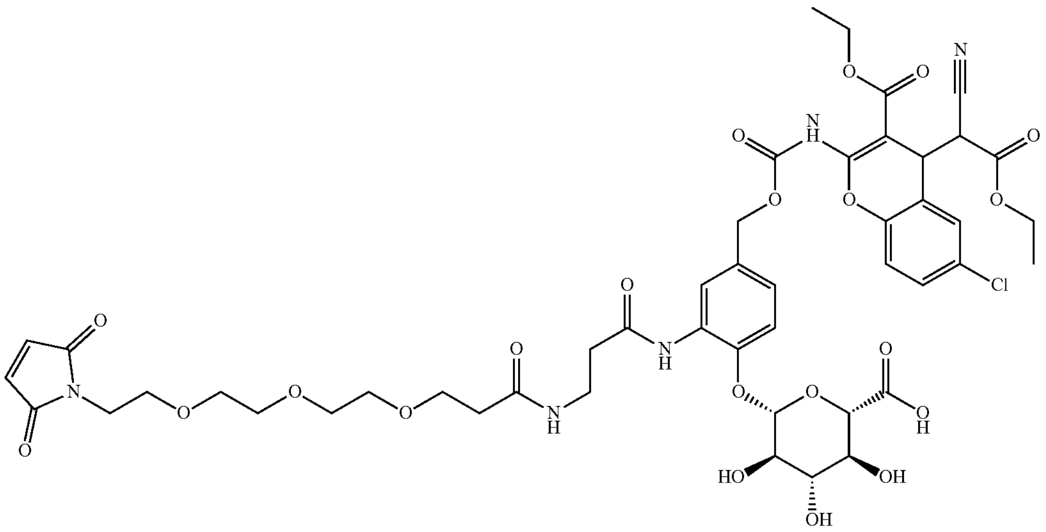 [SMILES: CCOC(=O)C1=C(NC(=O)OCc2ccc(O[C@@H]3O[C@H](C(=O)O)[C@@H](O)[C@H](O)[C@H]3O)c(NC(=O)CCNC(=O)CCOCCOCCOCCN3C(=O)C=CC3=O)c2)Oc2ccc(Cl)cc2C1C(C#N)C(=O)OCC] |

TABLE 3-continued
| Exemplary Compounds of Formula (I) | |
|---|---|
| Compound | Structure |
| A-68 | 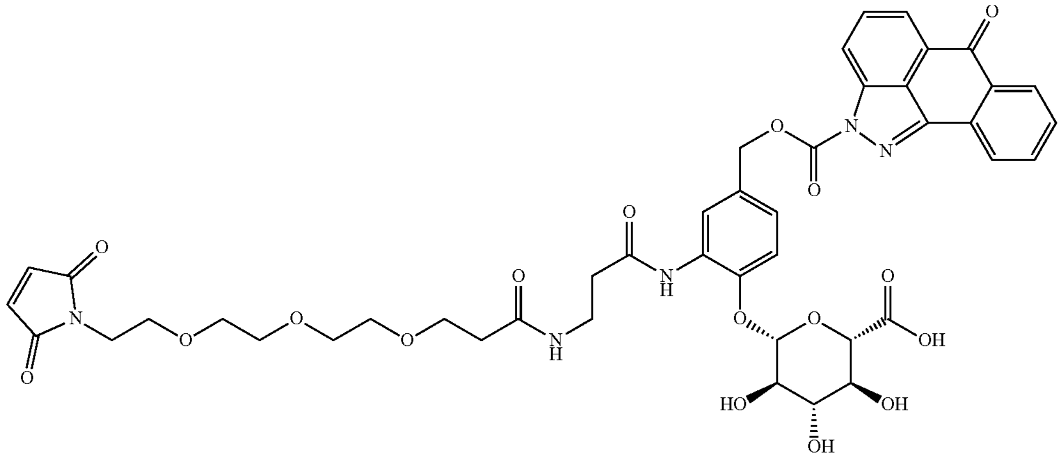 [SMILES: O=C(CCOCCOCCOCCN1C(=O)C=CC1=O)NCCC(=O)Nc1cc(COC(=O)n2nc3c4c(cccc42)C(=O)c2ccccc2-3)ccc1O[C@@H]1O[C@H](C(=O)O)[C@@H](O)[C@H](O)[C@H]1O] |
| A-69 | 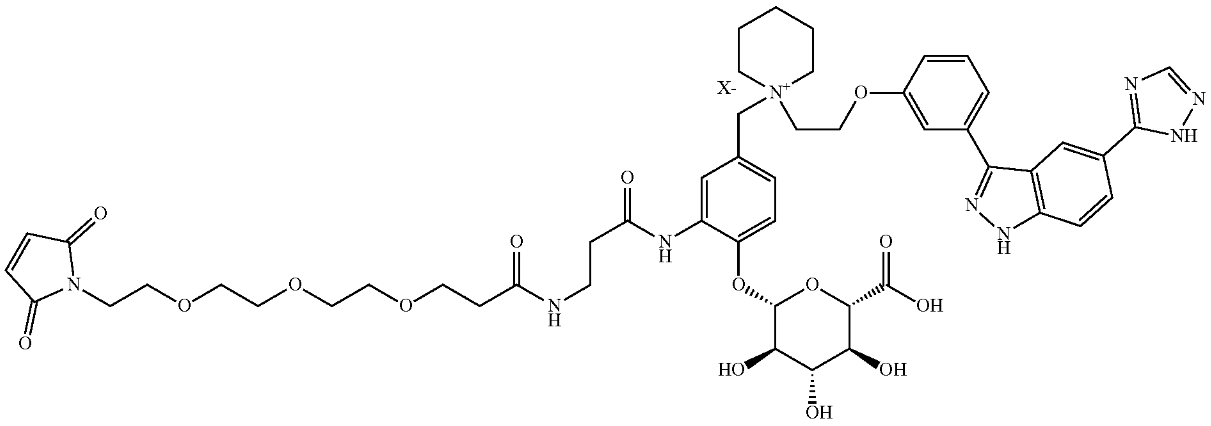 |

TABLE 3-continued
| Exemplary Compounds of Formula (I) | |
|---|---|
| Compound | Structure |
| A 70 | 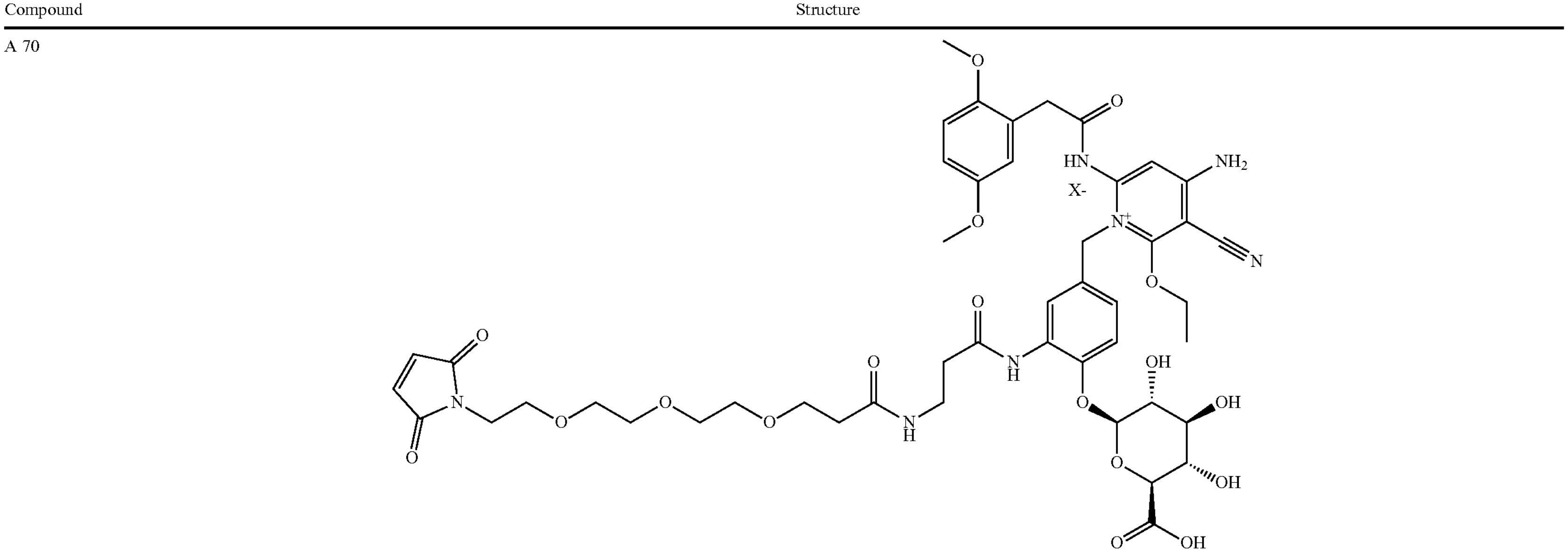 |
| A-71 | 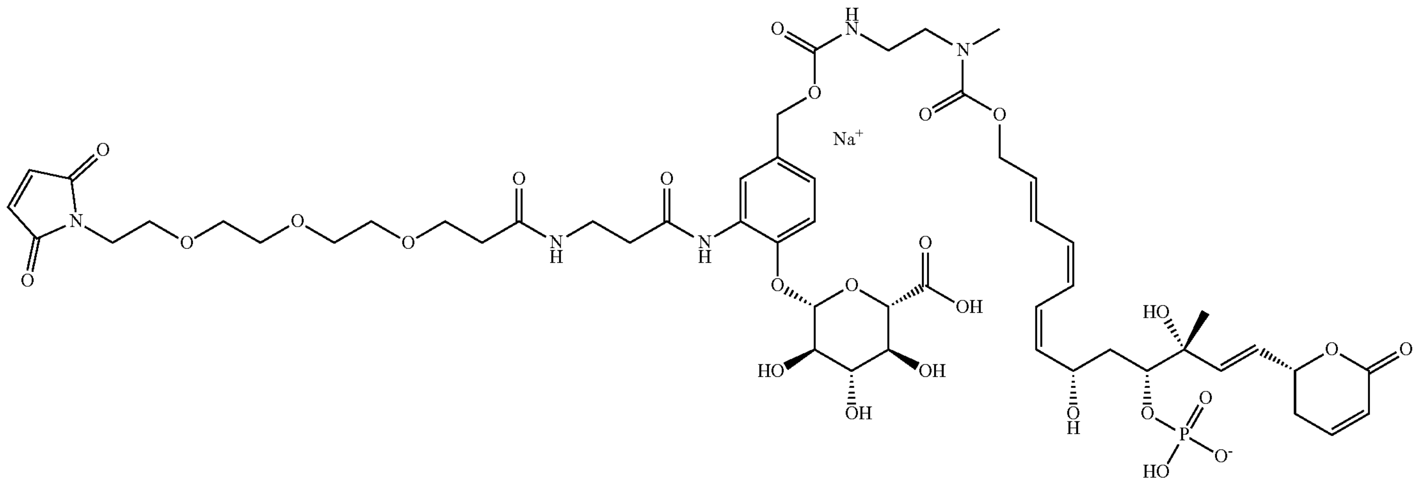 [SMILES: CN(CCNC(=O)OCc1ccc(O[C@@H]2O[C@H](C(=O)O)[C@@H](O)[C@H](O)[C@H]2O)c(NC(=O)CCNC(=O)CCOCCOCCOCCN2C(=O)C=CC2=O)c1)C(=O)OC/C=C/C=C\C=C/[C@@H](O)C[C@@H](OP(=O)([O-])O)[C@](C)(O)/C=C/[C@H]1CC=CC(=O)O1 ; [Na+]] |

TABLE 3-continued
| Exemplary Compounds of Formula (I) | |
|---|---|
| Compound | Structure |
| A-72 | 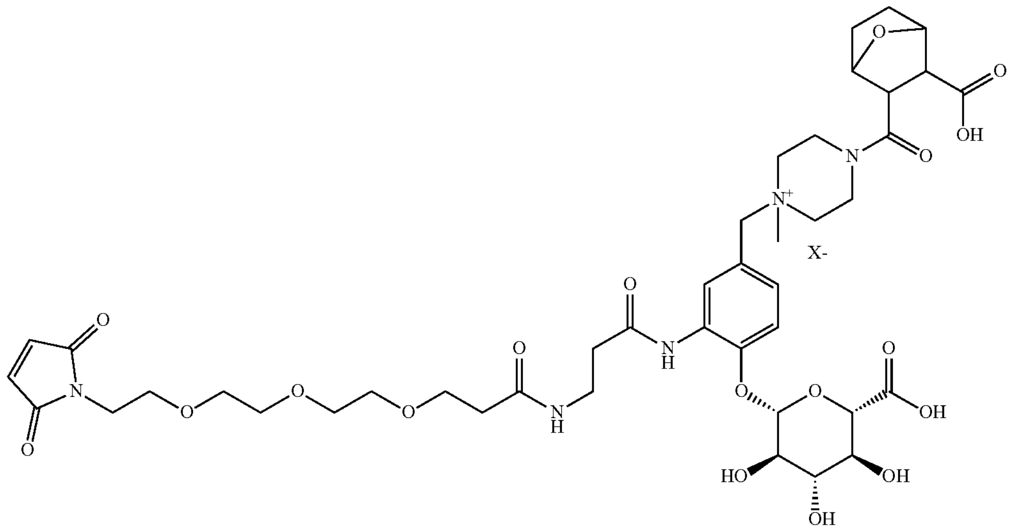 |

TABLE 3-continued
| Exemplary Compounds of Formula (I) | |
|---|---|
| Compound | Structure |
| A-73 | 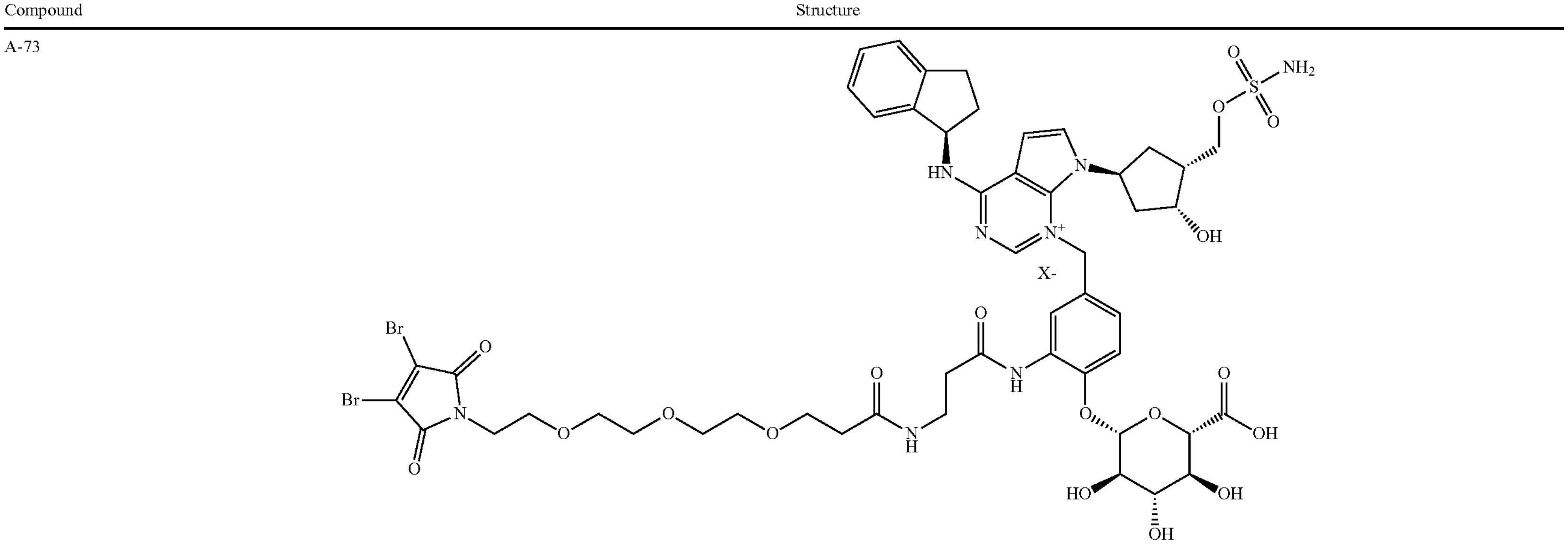 |

TABLE 3-continued
| Exemplary Compounds of Formula (I) | |
|---|---|
| Compound | Structure |
| A-74 | 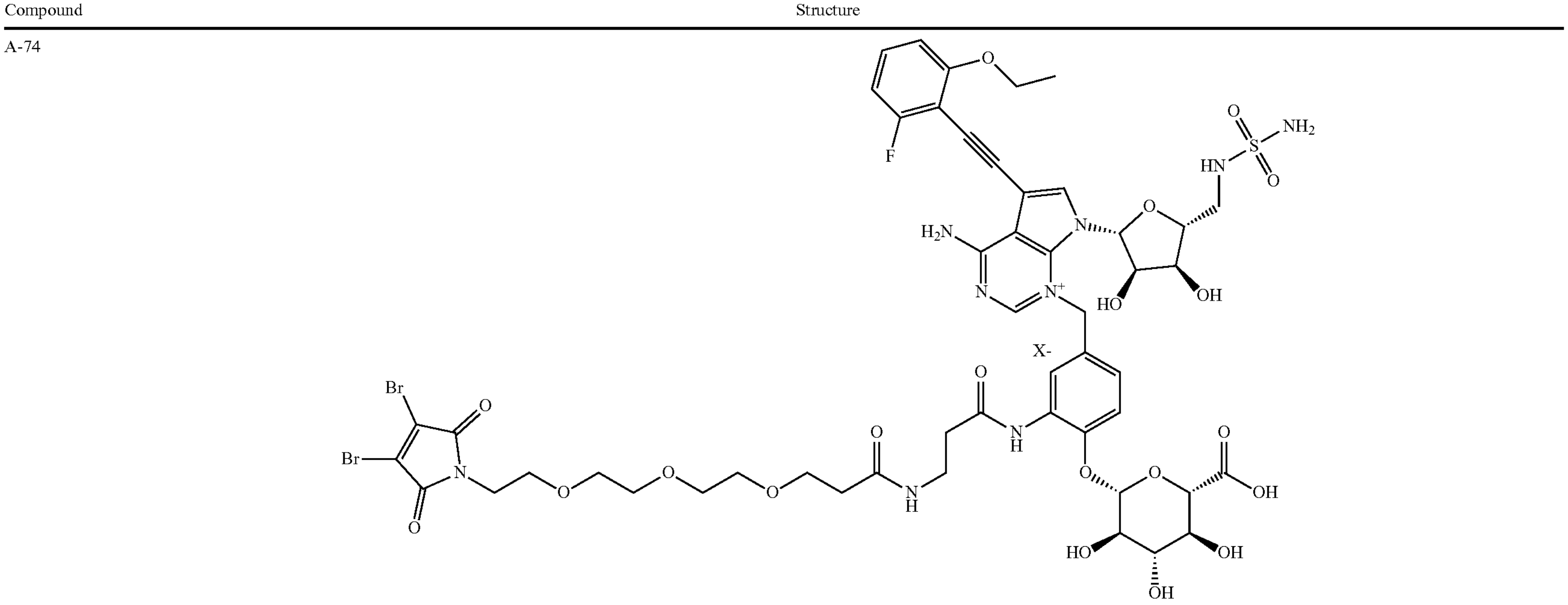 |

TABLE 3-continued
| Exemplary Compounds of Formula (I) | |
|---|---|
| Compound | Structure |
| A-75 | 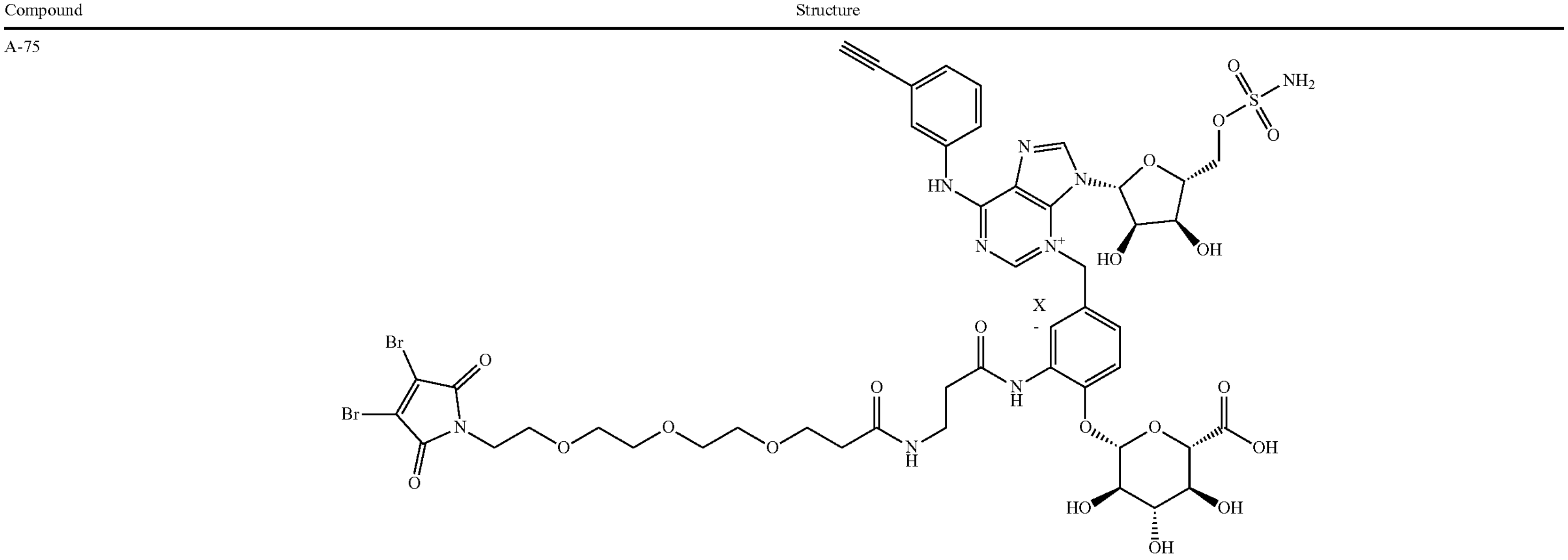 |

TABLE 3-continued
| Exemplary Compounds of Formula (I) | |
|---|---|
| Compound | Structure |
| A-76 | 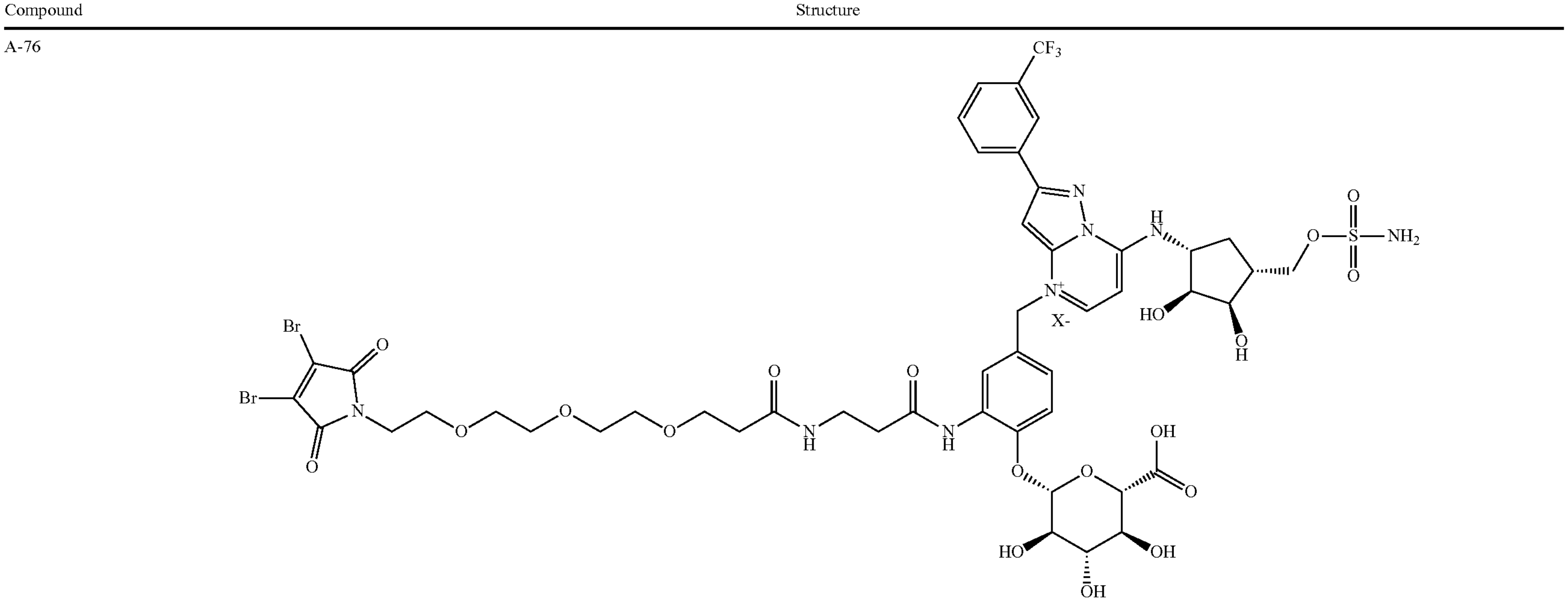 |
| A-77 | 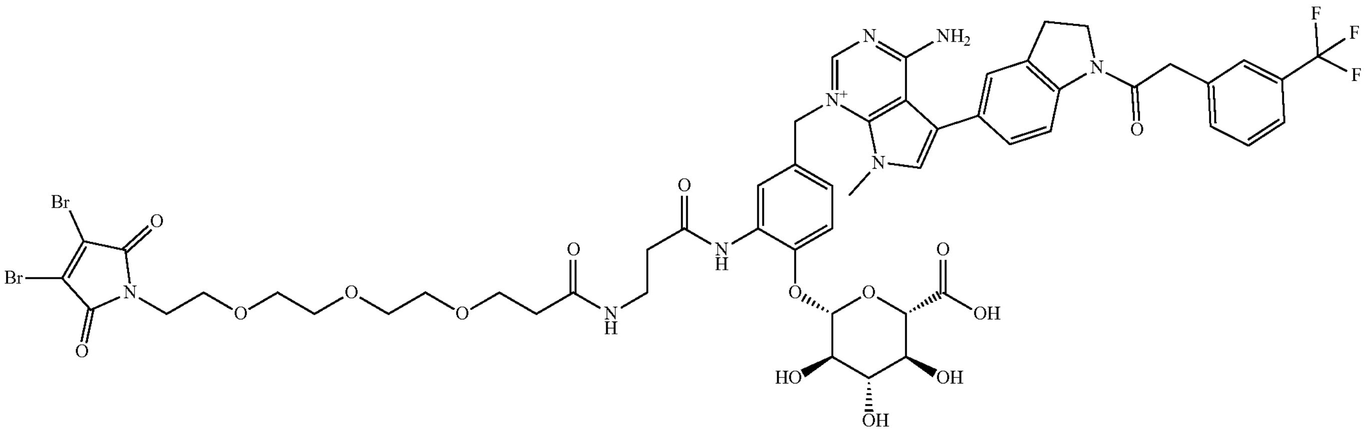 [SMILES: Cn1cc(-c2ccc3c(c2)CCN3C(=O)Cc2cccc(C(F)(F)F)c2)c2c(N)nc[n+](Cc3ccc(O[C@@H]4O[C@H](C(=O)O)[C@@H](O)[C@H](O)[C@H]4O)c(NC(=O)CCNC(=O)CCOCCOCCOCCN4C(=O)C(Br)=C(Br)C4=O)c3)c21] |

TABLE 3-continued
| Exemplary Compounds of Formula (I) | |
|---|---|
| Compound | Structure |
| A-78 | 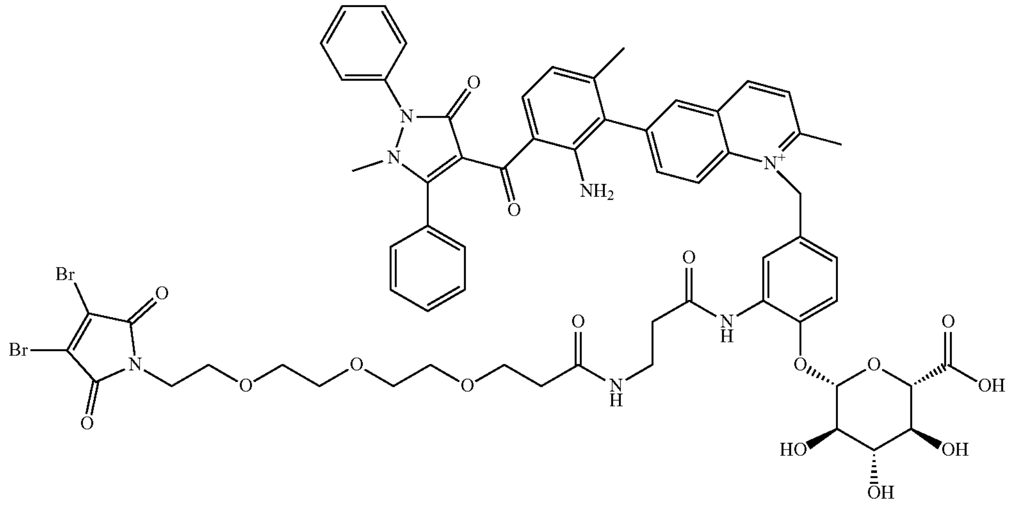 [SMILES: Cc1ccc(C(=O)c2c(-c3ccccc3)n(C)n(-c3ccccc3)c2=O)c(N)c1-c1ccc2c(ccc(C)[n+]2Cc2ccc(O[C@@H]3O[C@H](C(=O)O)[C@@H](O)[C@H](O)[C@H]3O)c(NC(=O)CCNC(=O)CCOCCOCCOCCN3C(=O)C(Br)=C(Br)C3=O)c2)c1] |

TABLE 3-continued
| Exemplary Compounds of Formula (I) | |
|---|---|
| Compound | Structure |
| A-79 | 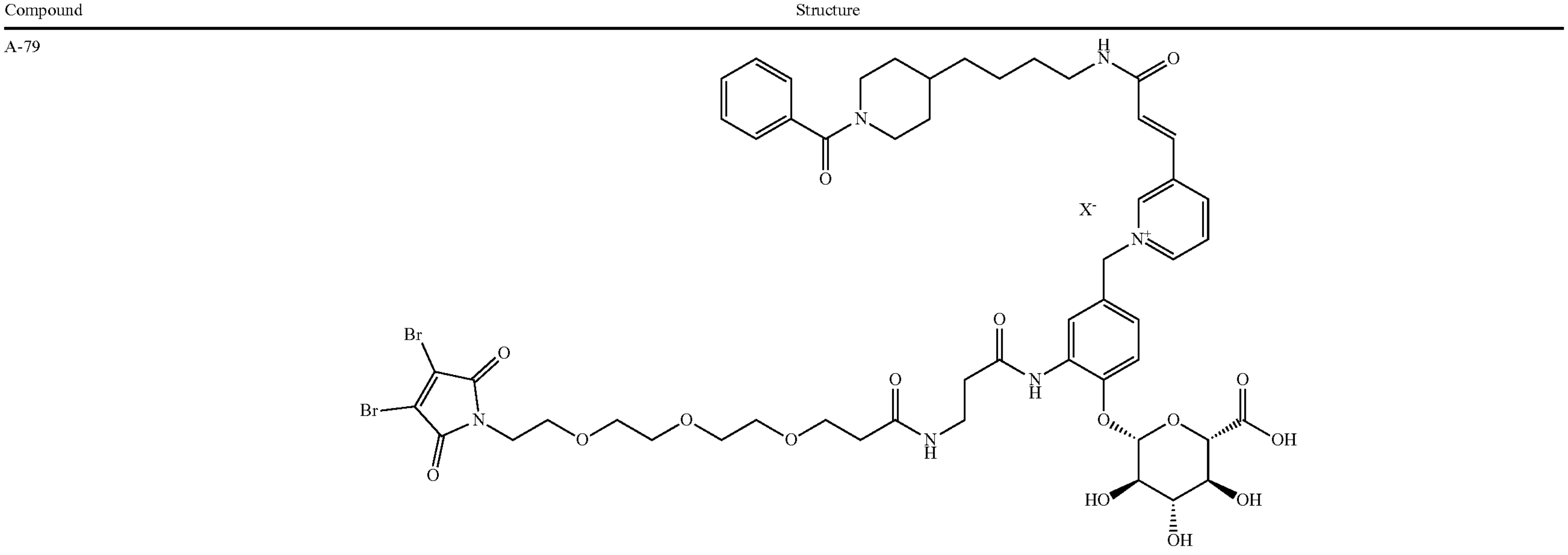 |

TABLE 3-continued
| Exemplary Compounds of Formula (I) | |
|---|---|
| Compound | Structure |
| A-80 | 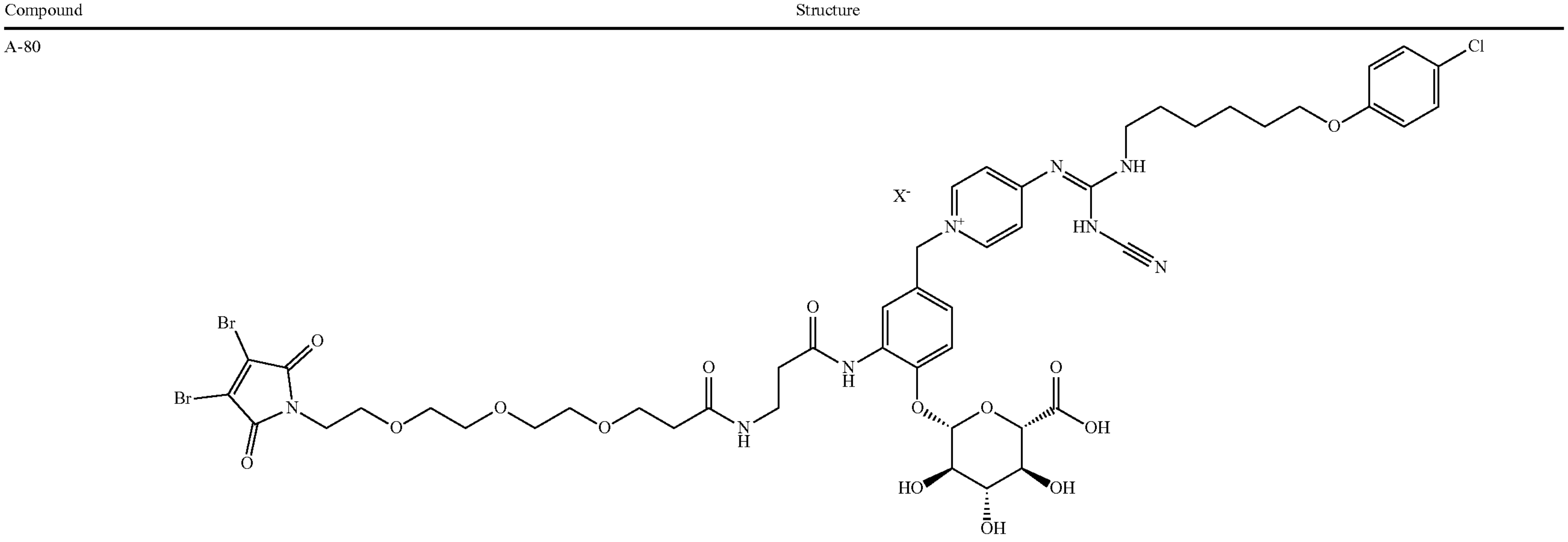 |
| A-81 | 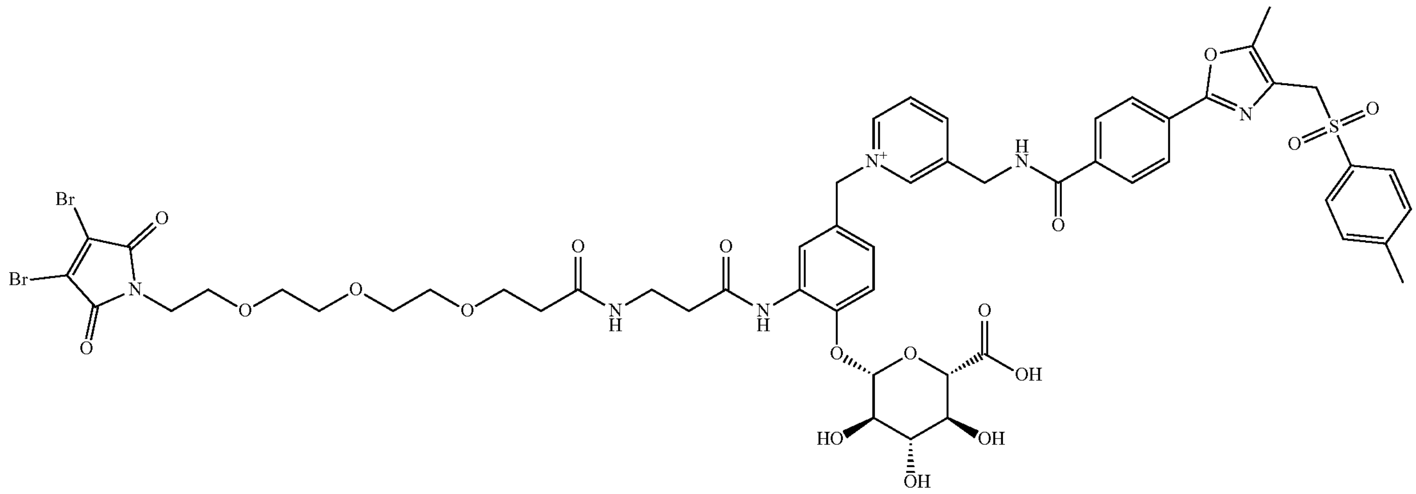 [SMILES: Cc1ccc(S(=O)(=O)Cc2nc(-c3ccc(C(=O)NCc4ccc[n+](Cc5ccc(O[C@@H]6O[C@H](C(=O)O)[C@@H](O)[C@H](O)[C@H]6O)c(NC(=O)CCNC(=O)CCOCCOCCOCCN6C(=O)C(Br)=C(Br)C6=O)c5)c4)cc3)oc2C)cc1] |

TABLE 3-continued
| Exemplary Compounds of Formula (I) | |
|---|---|
| Compound | Structure |
| A-82 | 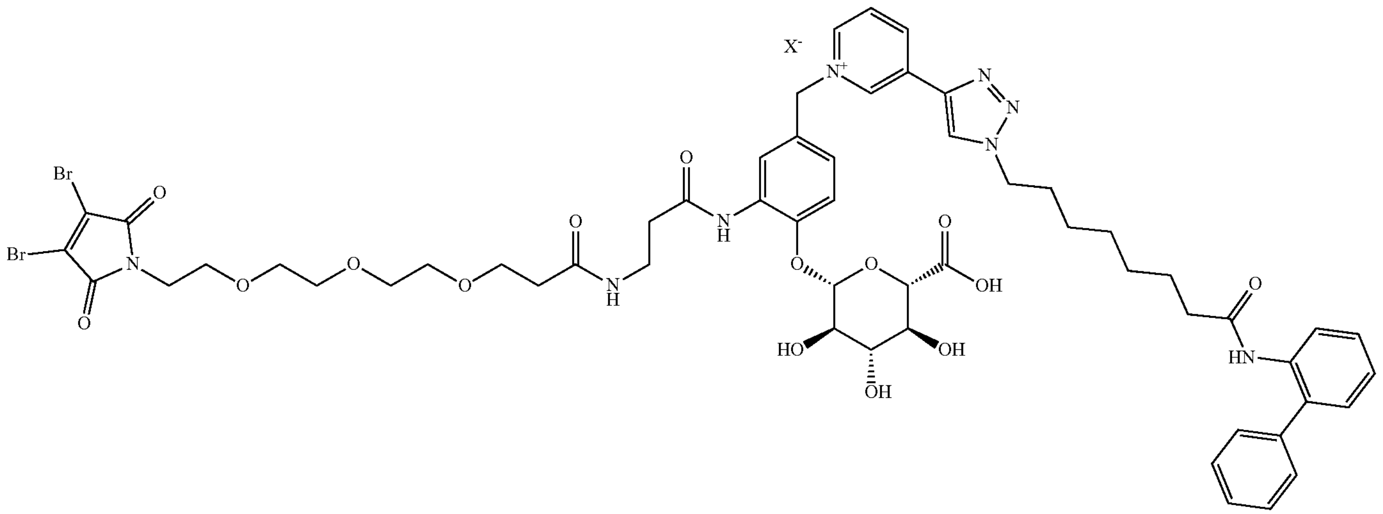 |
| A-83 | 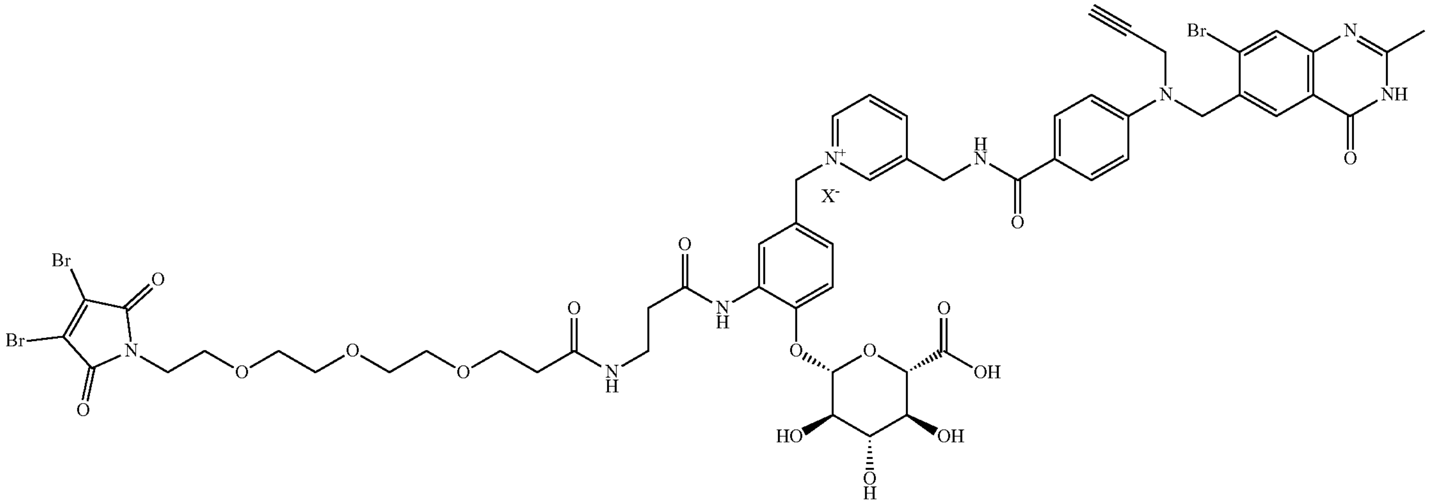 |

TABLE 3-continued
| Exemplary Compounds of Formula (I) | |
|---|---|
| Compound | Structure |
| A-84 | 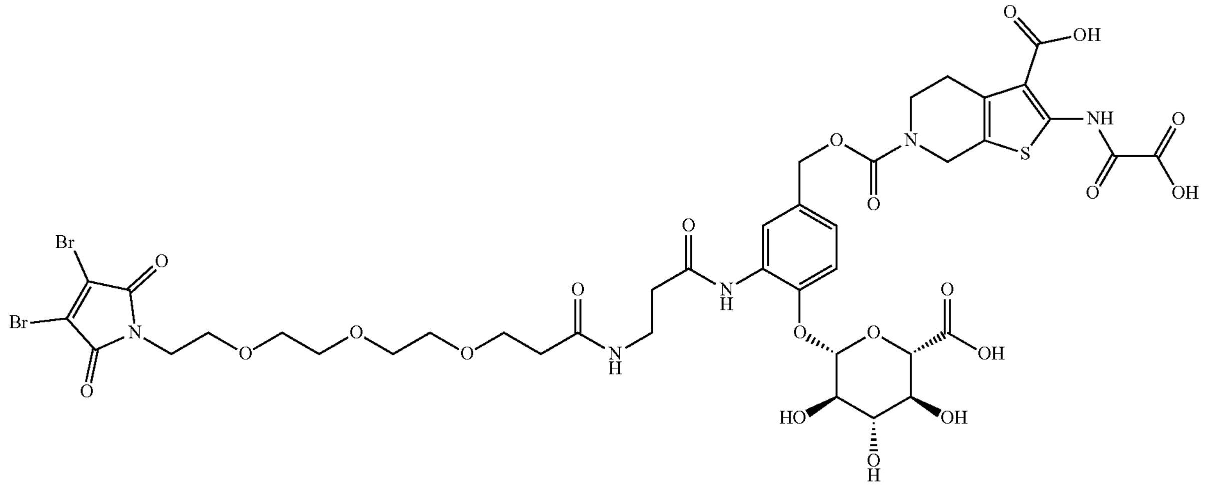 [SMILES: O=C(CCOCCOCCOCCN1C(=O)C(Br)=C(Br)C1=O)NCCC(=O)Nc1cc(COC(=O)N2CCc3c(sc(NC(=O)C(=O)O)c3C(=O)O)C2)ccc1O[C@@H]1O[C@H](C(=O)O)[C@@H](O)[C@H](O)[C@H]1O] |
| A-85 | 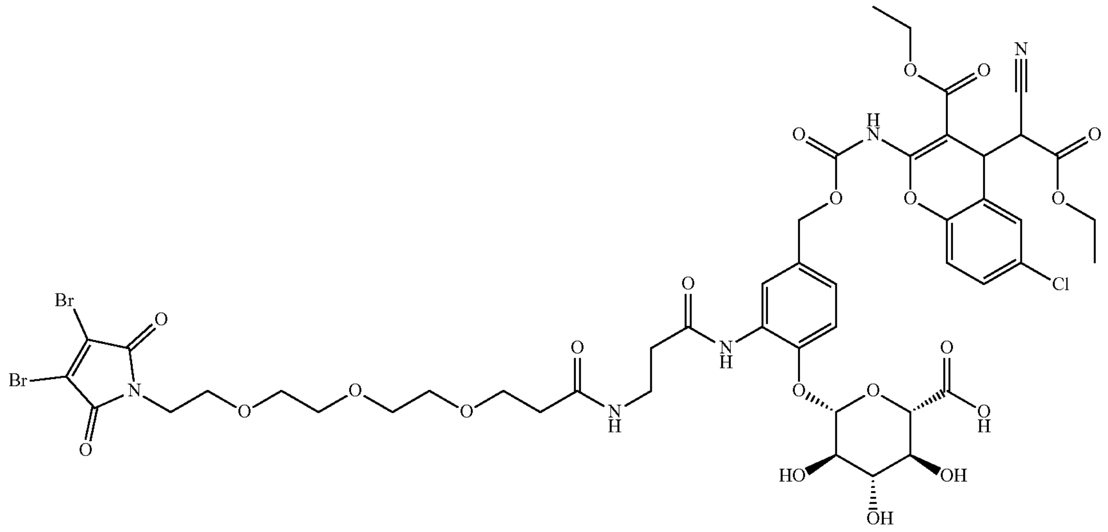 [SMILES: CCOC(=O)C1=C(NC(=O)OCc2ccc(O[C@@H]3O[C@H](C(=O)O)[C@@H](O)[C@H](O)[C@H]3O)c(NC(=O)CCNC(=O)CCOCCOCCOCCN3C(=O)C(Br)=C(Br)C3=O)c2)Oc2ccc(Cl)cc2C1C(C#N)C(=O)OCC] |

TABLE 3-continued
| Exemplary Compounds of Formula (I) | |
|---|---|
| Compound | Structure |
| A-86 | 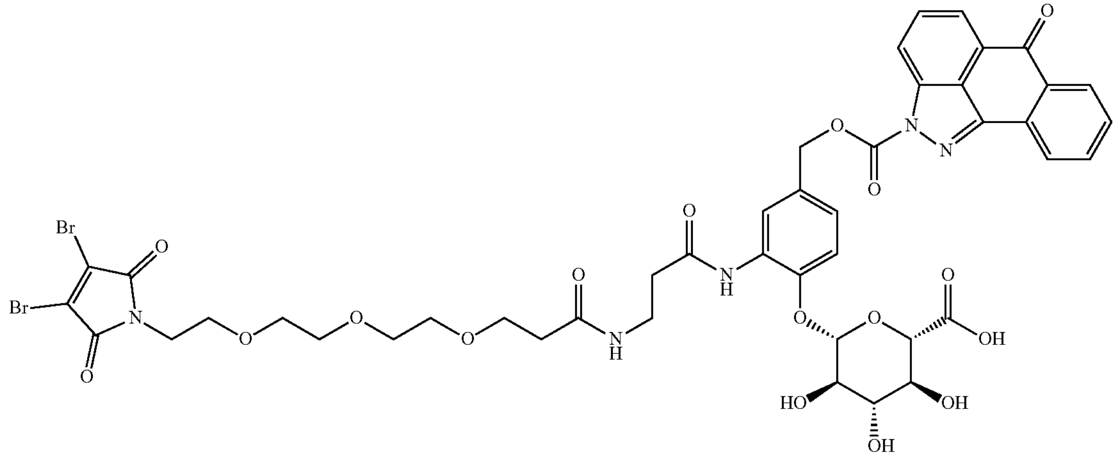 [SMILES: O=C(CCOCCOCCOCCN1C(=O)C(Br)=C(Br)C1=O)NCCC(=O)Nc1cc(COC(=O)n2nc3c4c(cccc42)C(=O)c2ccccc2-3)ccc1O[C@@H]1O[C@H](C(=O)O)[C@@H](O)[C@H](O)[C@H]1O] |
| A-87 | 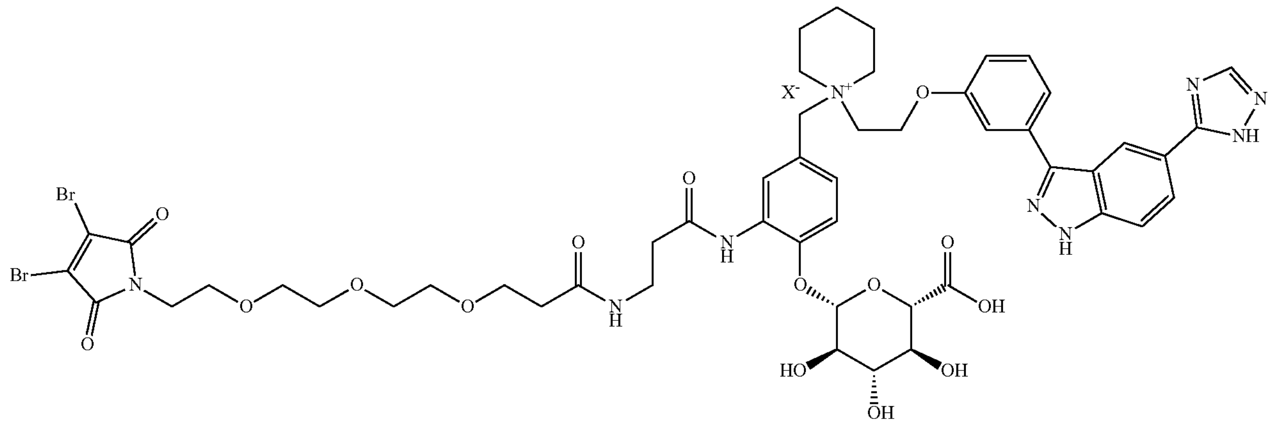 |

TABLE 3-continued
| Exemplary Compounds of Formula (I) | |
|---|---|
| Compound | Structure |
| A-88 | 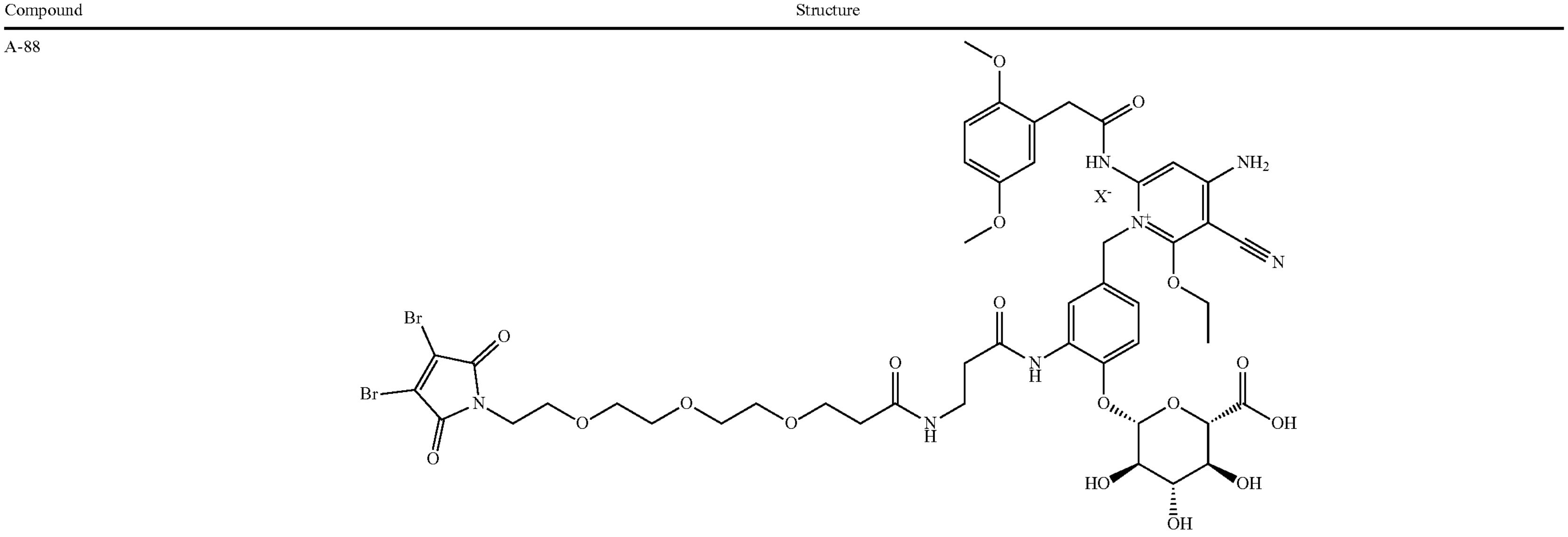 |
| A-89 | 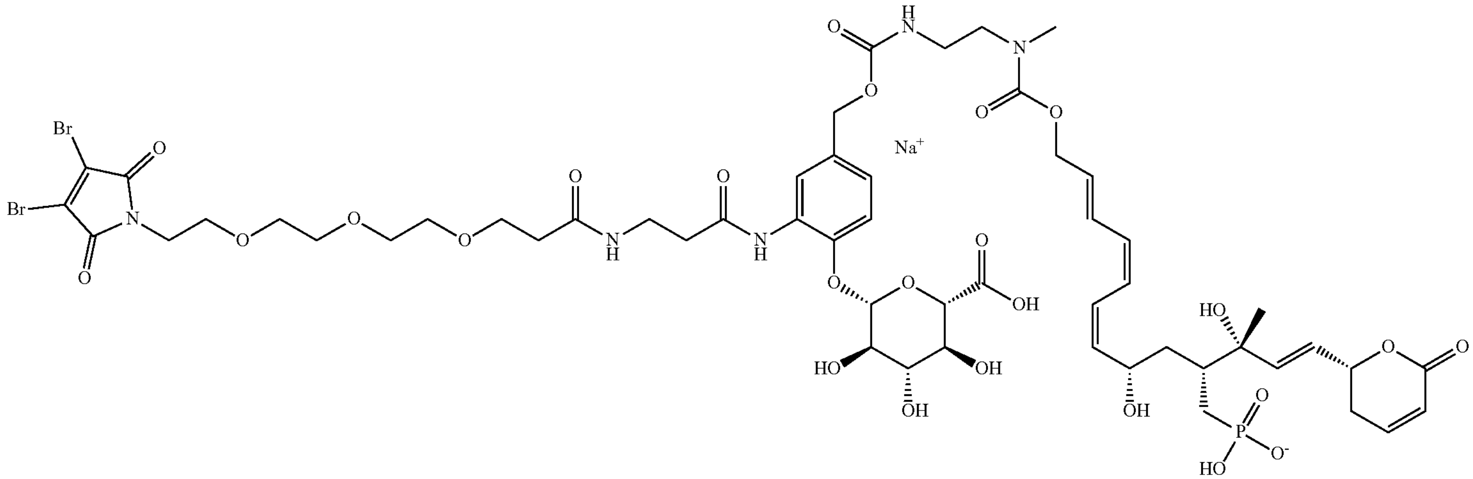 [SMILES: CN(CCNC(=O)OCc1ccc(O[C@@H]2O[C@H](C(=O)O)[C@@H](O)[C@H](O)[C@H]2O)c(NC(=O)CCNC(=O)CCOCCOCCOCCN2C(=O)C(Br)=C(Br)C2=O)c1)C(=O)OC/C=C/C=C\C=C/[C@@H](O)C[C@@H](CP(=O)([O-])O)[C@](C)(O)/C=C/[C@H]1CC=CC(=O)O1 ; [Na+]] |

TABLE 3-continued
| Exemplary Compounds of Formula (I) | |
|---|---|
| Compound | Structure |
| A-90 | 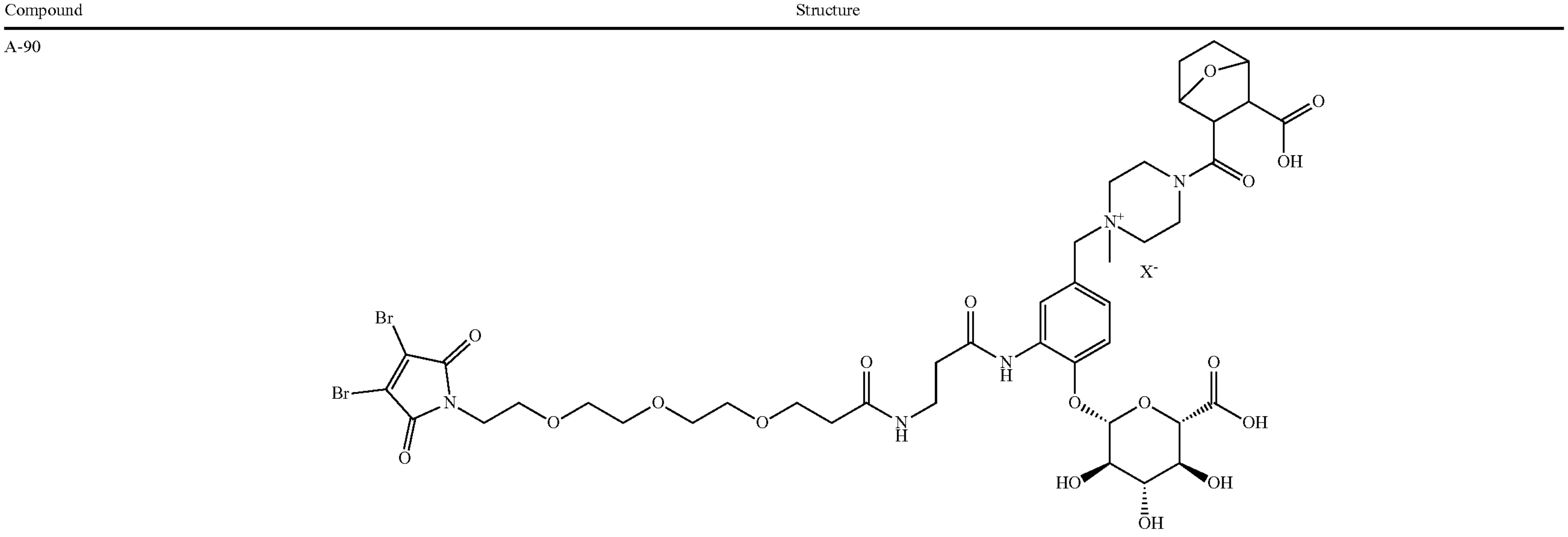 |
| A-91 | 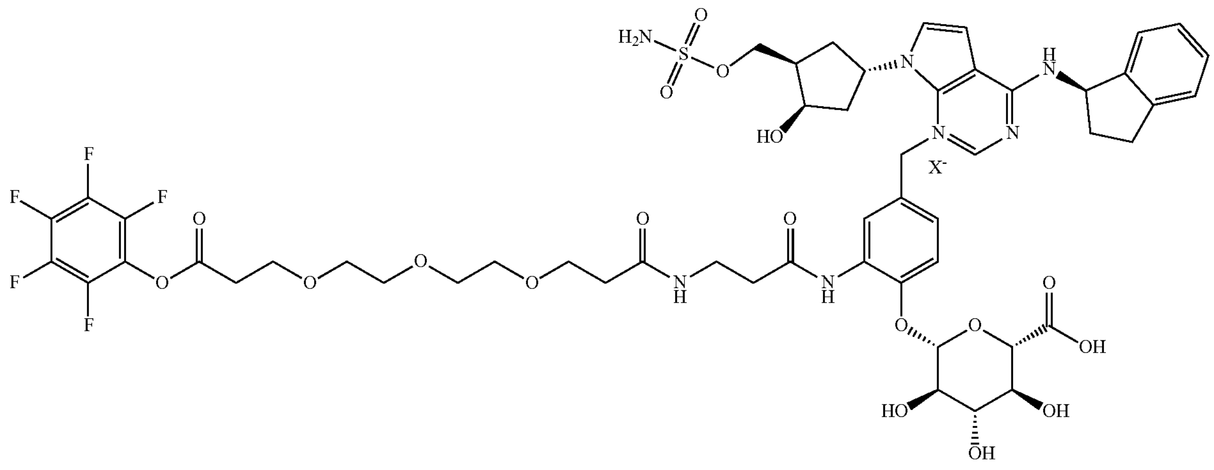 |

TABLE 3-continued
| Exemplary Compounds of Formula (I) | |
|---|---|
| Compound | Structure |
| A-92 | 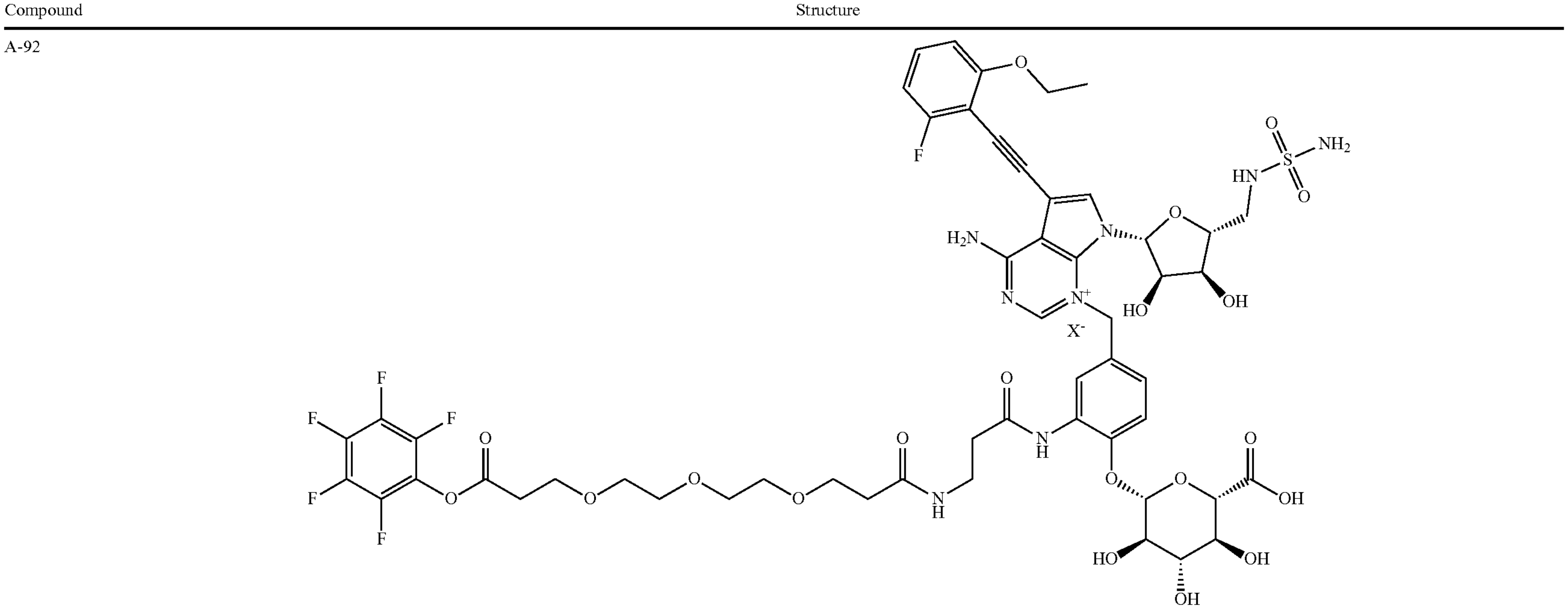 |

TABLE 3-continued
| Exemplary Compounds of Formula (I) | |
|---|---|
| Compound | Structure |
| A-93 | 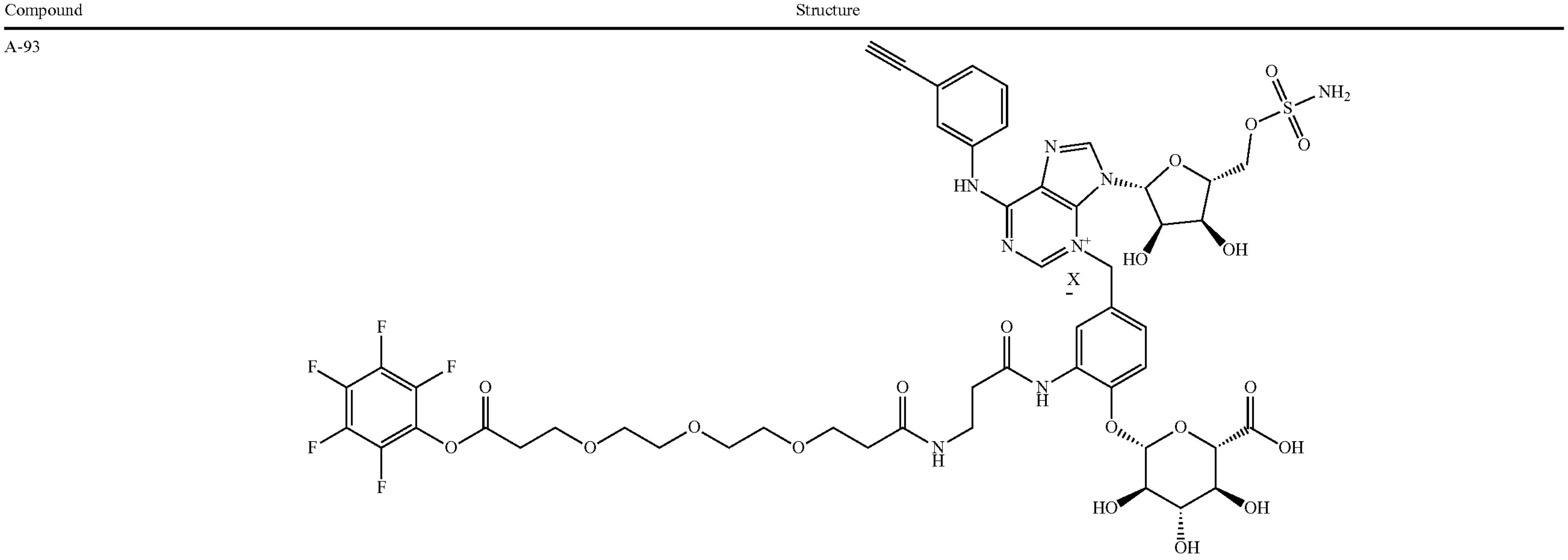 |

TABLE 3-continued
| Exemplary Compounds of Formula (I) | |
|---|---|
| Compound | Structure |
| A-94 | 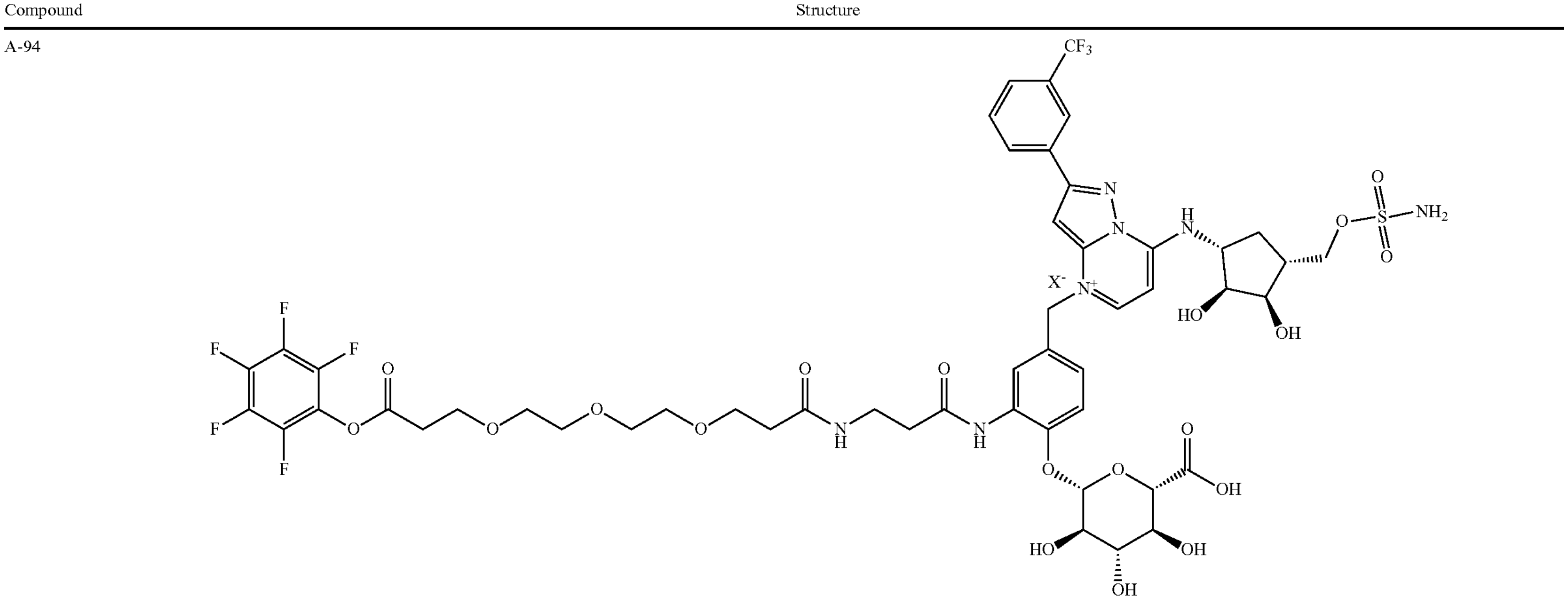 |

TABLE 3-continued
| Exemplary Compounds of Formula (I) | |
| --- | --- |
| Compound | Structure |
| A-95 | 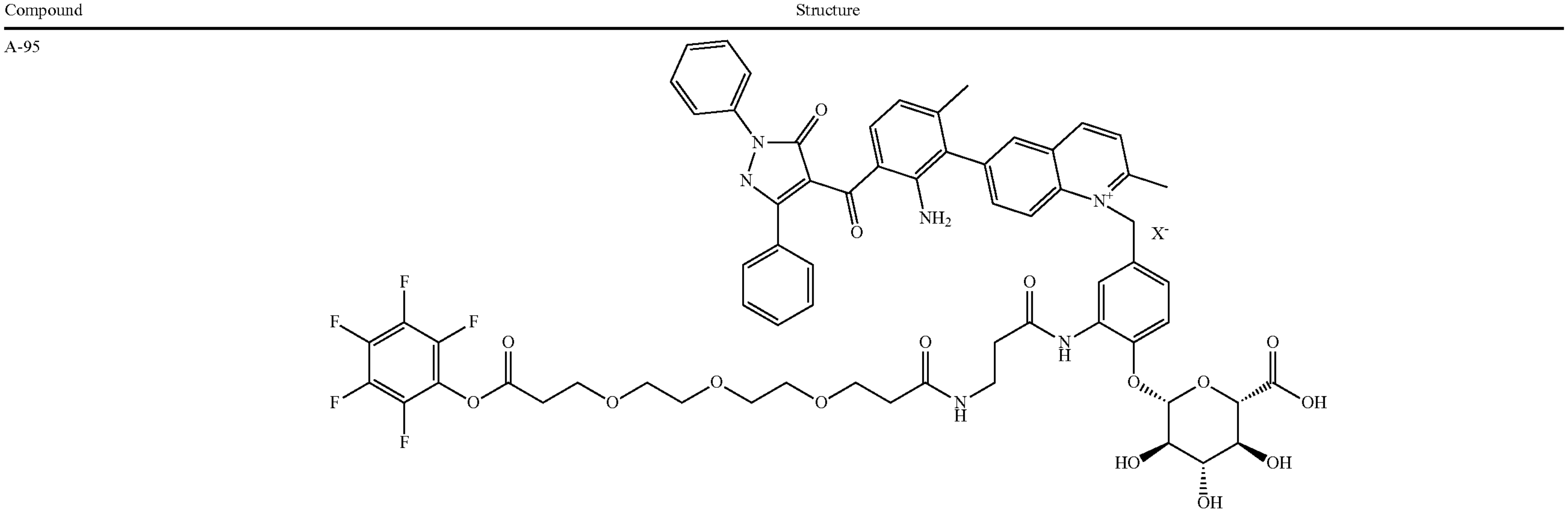 |
| A-96 | 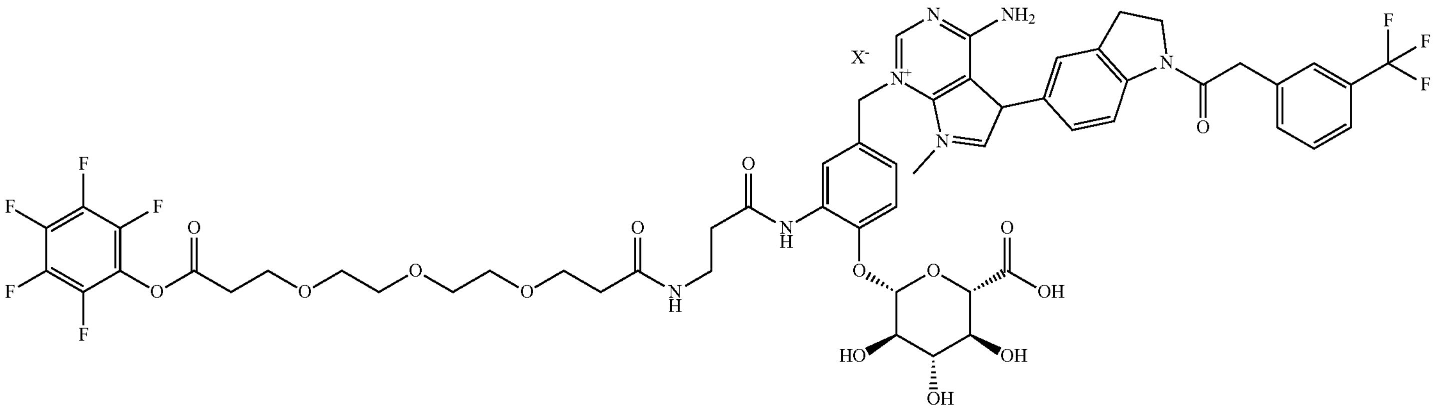 |

TABLE 3-continued
| Exemplary Compounds of Formula (I) | |
|---|---|
| Compound | Structure |
| A-97 | 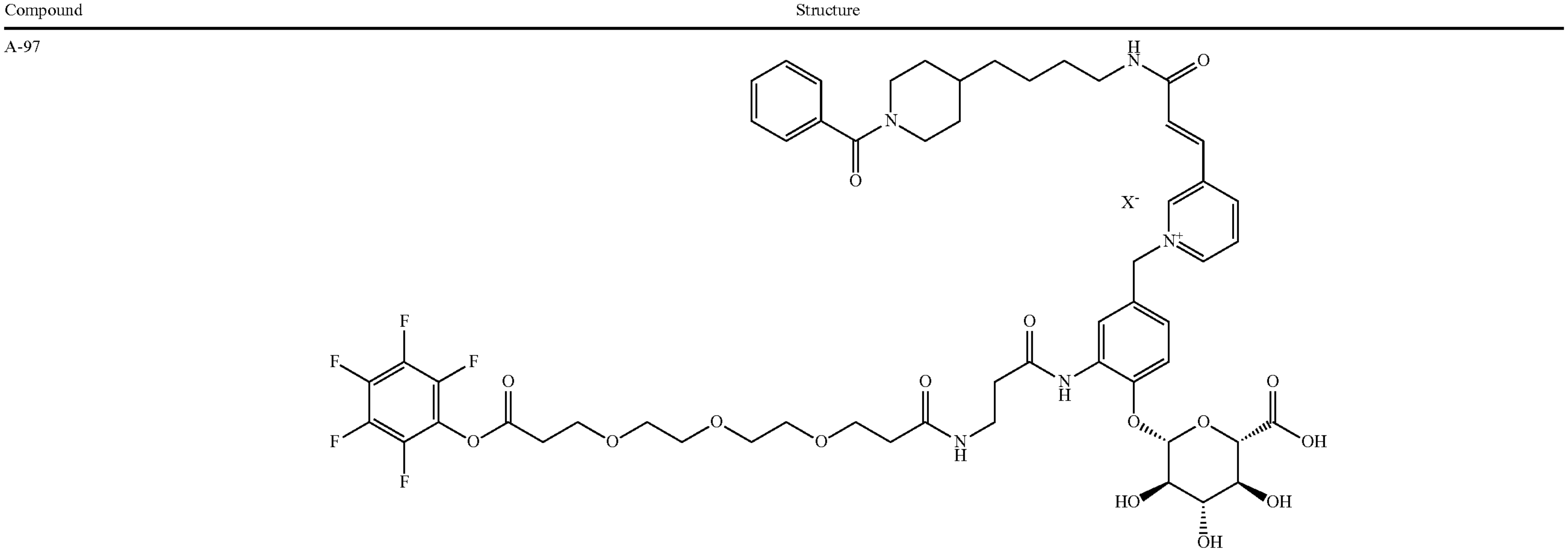 |

TABLE 3-continued
| Exemplary Compounds of Formula (I) | |
|---|---|
| Compound | Structure |
| A-98 | 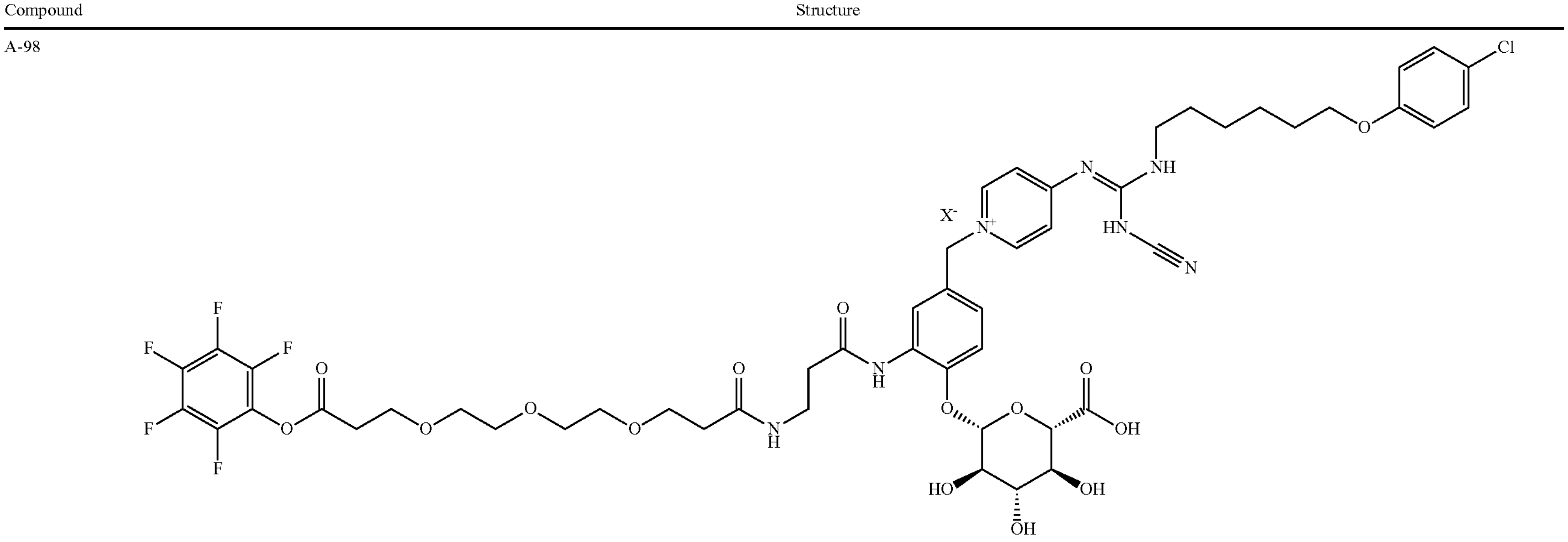 |
| A-99 | 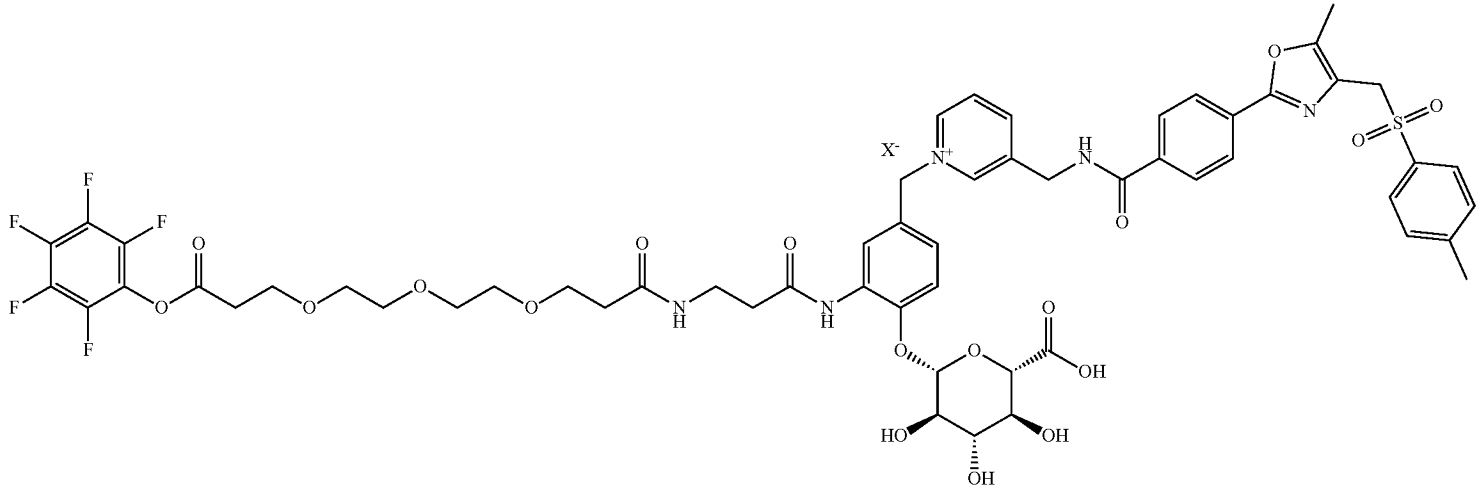 |

TABLE 3-continued
| Exemplary Compounds of Formula (I) | |
|---|---|
| Compound | Structure |
| A-100 | 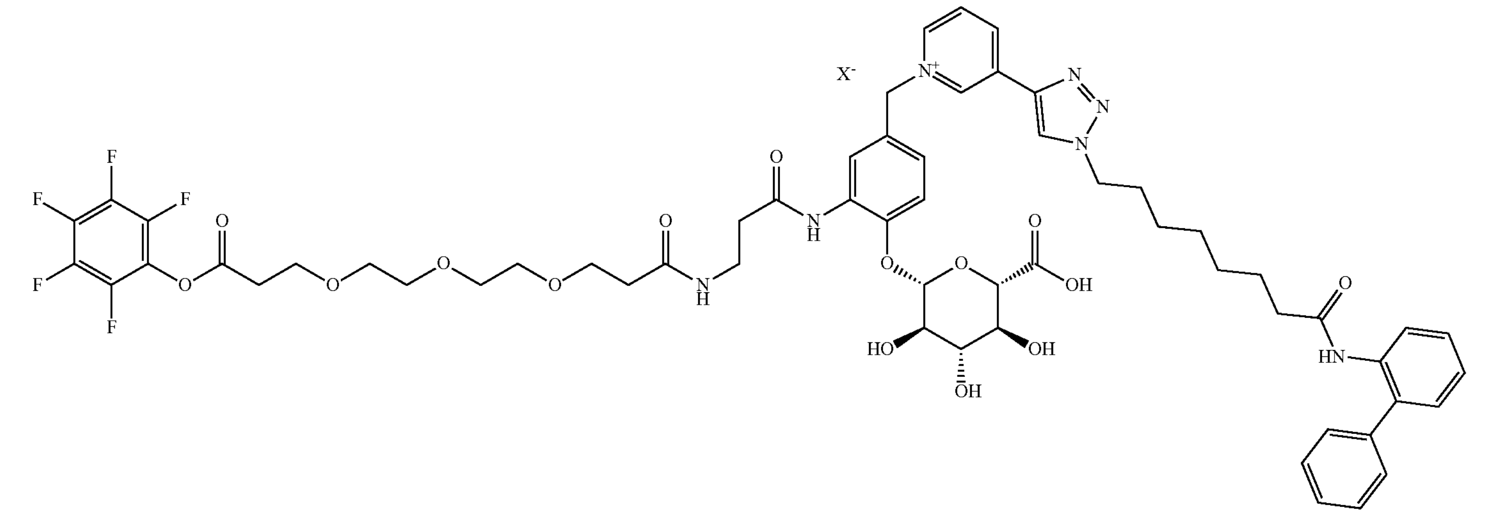 |
| A-101 | 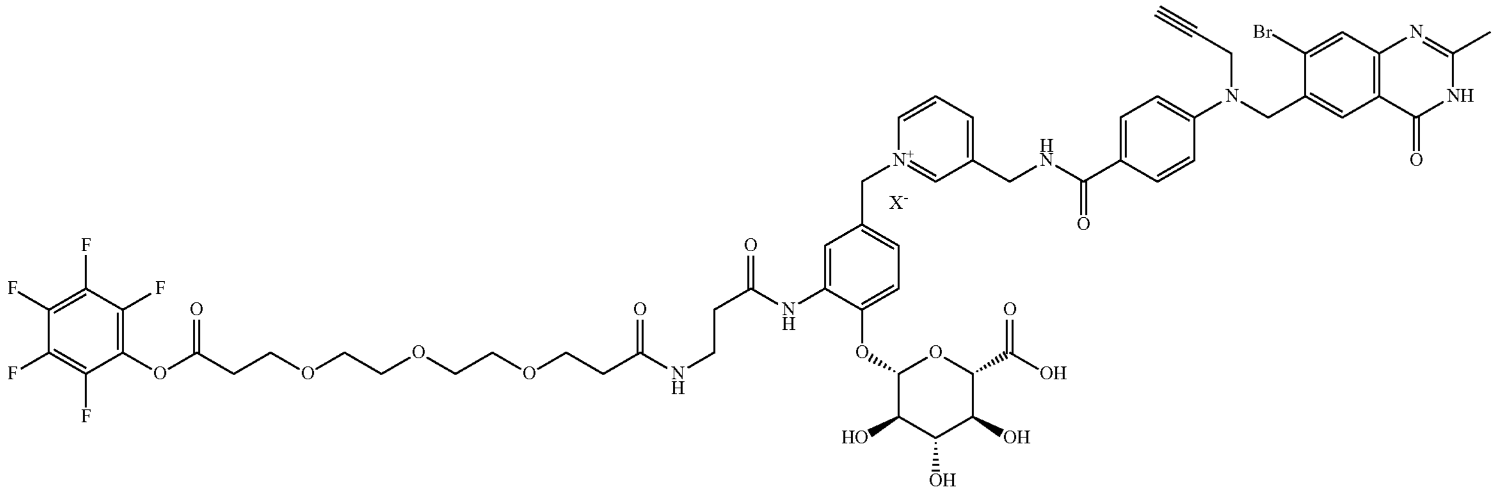 |

TABLE 3-continued
| Exemplary Compounds of Formula (I) | |
|---|---|
| Compound | Structure |
| A-102 | 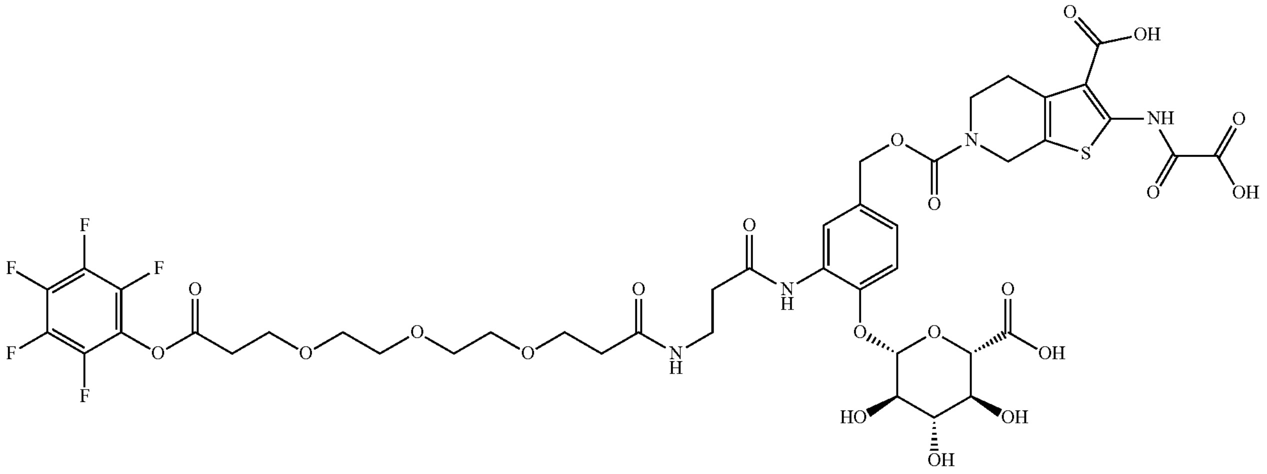 [SMILES: O=C(CCOCCOCCOCCC(=O)Oc1c(F)c(F)c(F)c(F)c1F)NCCC(=O)Nc1cc(COC(=O)N2CCc3c(sc(NC(=O)C(=O)O)c3C(=O)O)C2)ccc1O[C@@H]1O[C@H](C(=O)O)[C@@H](O)[C@H](O)[C@H]1O] |
| A-103 | 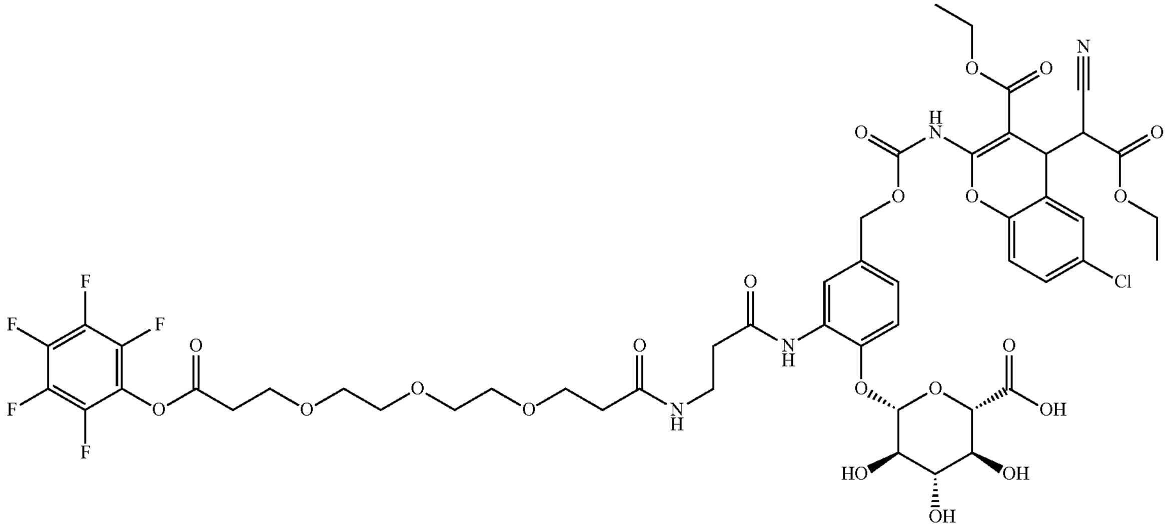 [SMILES: CCOC(=O)C1=C(NC(=O)OCc2ccc(O[C@@H]3O[C@H](C(=O)O)[C@@H](O)[C@H](O)[C@H]3O)c(NC(=O)CCNC(=O)CCOCCOCCOCCC(=O)Oc3c(F)c(F)c(F)c(F)c3F)c2)Oc2ccc(Cl)cc2C1C(C#N)C(=O)OCC] |

TABLE 3-continued
| Exemplary Compounds of Formula (I) | |
|---|---|
| Compound | Structure |
| A-104 | 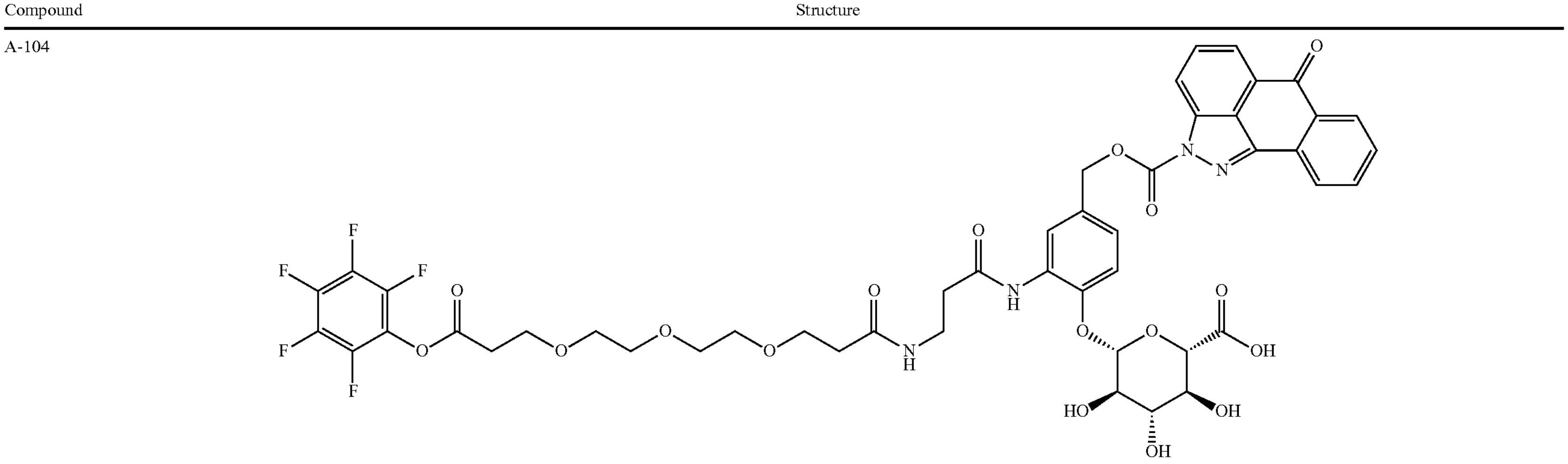 |
| A-105 | 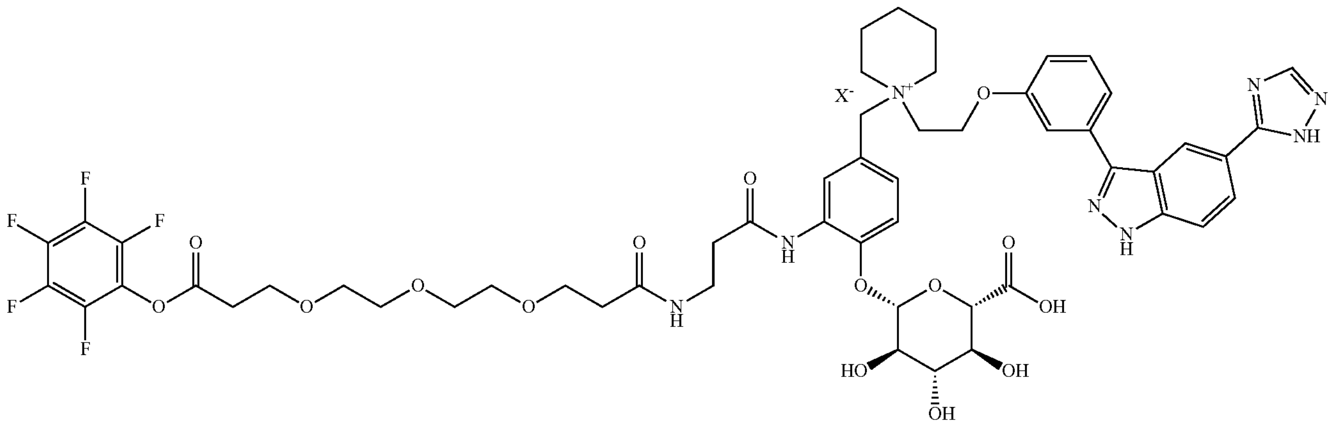 |

TABLE 3-continued
| Exemplary Compounds of Formula (I) | |
|---|---|
| Compound | Structure |
| A-106 | 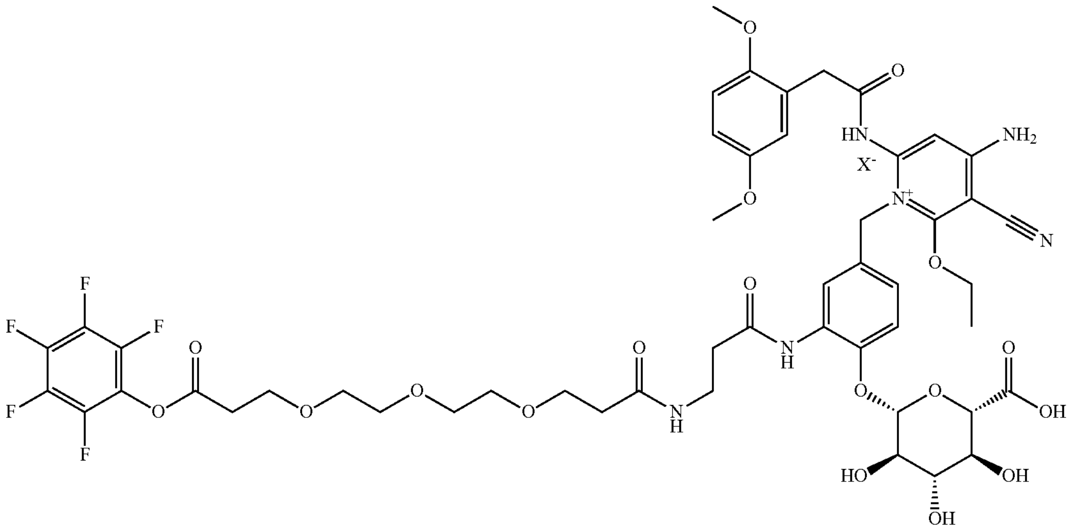 |
| A-107 | 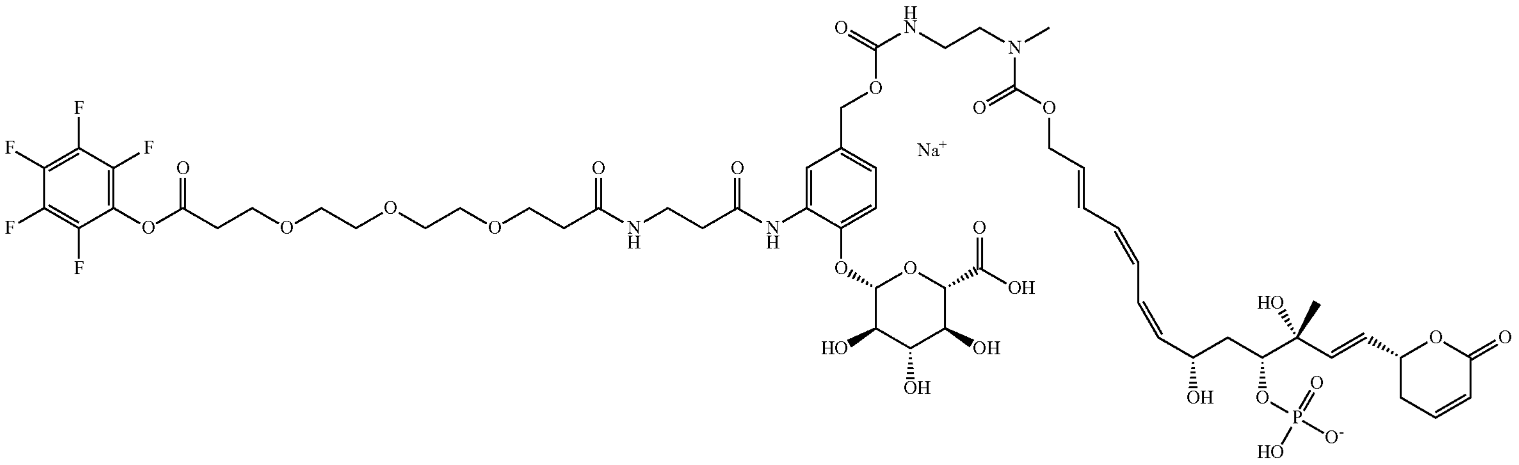 [SMILES: CN(CCNC(=O)OCc1ccc(O[C@@H]2O[C@H](C(=O)O)[C@@H](O)[C@H](O)[C@H]2O)c(NC(=O)CCNC(=O)CCOCCOCCOCCC(=O)Oc2c(F)c(F)c(F)c(F)c2F)c1)C(=O)OC/C=C/C=C\C=C/[C@@H](O)C[C@@H](OP(=O)([O-])O)[C@](C)(O)/C=C/[C@H]1CC=CC(=O)O1 ; [Na+]] |

TABLE 3-continued
| Exemplary Compounds of Formula (I) | |
|---|---|
| Compound | Structure |
| A-108 | 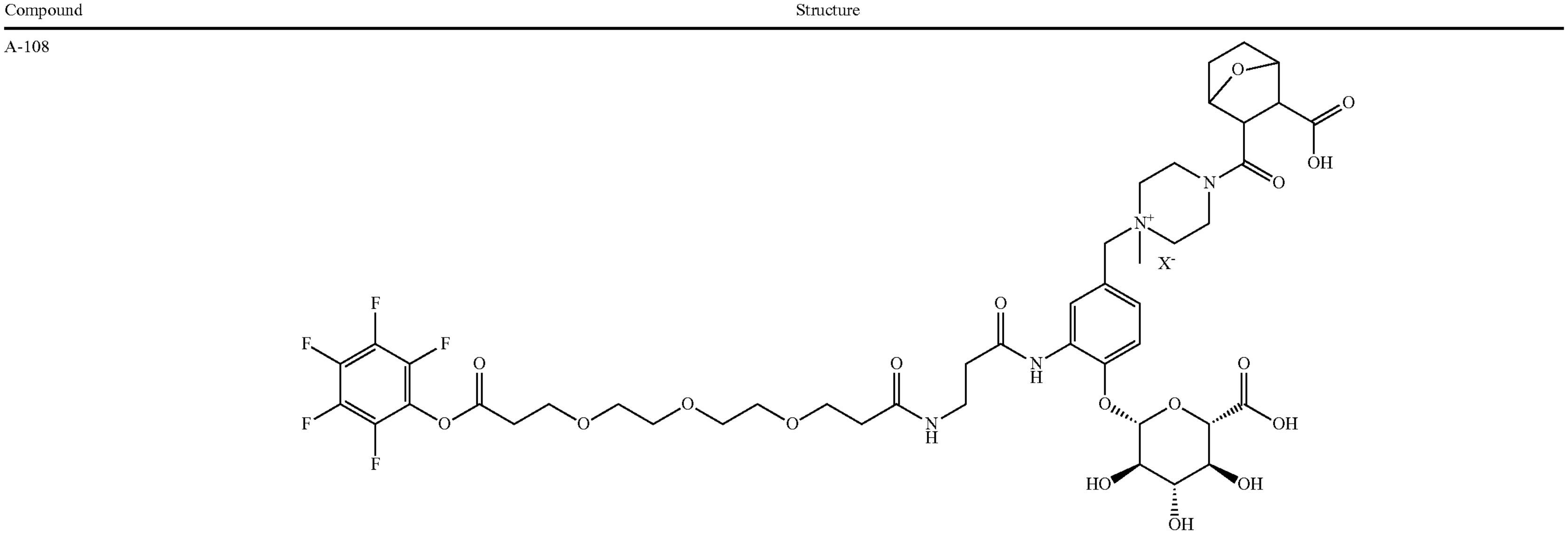 |

In some embodiments, the compound of Formula (I), or a pharmaceutically acceptable salt, solvate, hydrate, isomer, or tautomer thereof, is selected from the group consisting of A-1, A-2, A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-32, A-33, A-34, A-35, A-36, A-37, A-38, A-39, A-40, A-41, A-42, A-43, A-44, A-45, A-46, A-47, A-48, A-49, A-50, A-51, A-52, A-53, A-54, A-55, A-56, A-57, A-58, A-59, A-60, A-61, A-62, A-63, A-64, A-65, A-66, A-67, A-68, A-69, A-70, A-71, A-72, A-73, A-74, A-75, A-76, A-77, A-78, A-79, A-80, A-81, A-82, A-83, A-84, A-85, A-86, A-87, A-88, A-89, A-90, A-91, A-92, A-93, A-94, A-95, A-96, A-97, A-98, A-99, A-100, A-101, A-102, A-103, A-104, A-105, A-106, A-107 and A-108.

In some embodiments, the compound of Formula (I), or a pharmaceutically acceptable salt, solvate, hydrate, isomer, or tautomer thereof, is selected from the group consisting of A-1, A-2, A-3, A-4, A-5, A-6, A-7, A-8, A-9, A-10, A-11, A-15, A-16, A-18, A-19, A-20, A-21, A-22, A-23, A-24, A-25, A-26, A-27, A-28, A-29, A-33, A-34, A-36, A-37, A-38, A-39, A-40, A-41, A-42, A-43, A-44, A-45, A-46, A-47, A-51, A-52, A-54.

In some embodiments, the compound of Formula (I), or a pharmaceutically acceptable salt, solvate, hydrate, isomer, or tautomer thereof, selected from the group consisting of A-12, A-13, A-14, A-17, A-30, A-31, A-32, A-35, A-48, A-49, A-50, A-53.

In some embodiments, the compound of Formula (I), or a pharmaceutically acceptable salt, solvate, hydrate, isomer, or tautomer thereof, is selected from the group consisting of A-55, A-56, A-57, A-58, A-59, A-60, A-61, A-62, A-63, A-64, A-65, A-69, A-70, A-72, A-73, A-74, A-75, A-76, A-77, A-78, A-79, A-80, A-81, A-82, A-83, A-87, A-88, A-90, A-91, A-92, A-93, A-94, A-95, A-96, A-97, A-98, A-99, A-100, A-101, A-105, A-106, and A-108.

In some embodiments, the compound of Formula (I), or a pharmaceutically acceptable salt, solvate, hydrate, isomer, or tautomer thereof, is selected from the group consisting of A-66, A-67, A-68, A-71, A-84, A-85, A-86, A-89, A-102, A-103, A-104, A-107.

In an aspect, the present disclosure provides compounds having the structure of Formula (II):

$$X_1—[X_2—(X_3)_m]_n \qquad (II),$$

and pharmaceutically acceptable salts, solvates, hydrates, isomers, or tautomers thereof, wherein:

m is 1, 2, 3, 4, 5, 6, 7, 8, 9, or 10;

n is 1, 2, 3, 4, 5, 6, 7, 8, 9, 10, or 11;

$X_1$ is a biologically active polypeptide or hormone;

$X_2$ is a linker; and $X_3$ is a therapeutic compound.

In another aspect, the present disclosure provides compounds having the structure of Formula (III):

$$X_1—[X_2—(X_3)_m]_n \qquad (III),$$

and pharmaceutically acceptable salts, solvates, hydrates, isomers, or tautomers thereof, wherein:

m is 1, 2, 3, 4, 5, 6, 7, 8, 9, or 10;

n is 1, 2, 3, 4, 5, 6, 7, 8, 9, 10, or 11;

$X_1$ is an insulin, insulin-like proteins and homologs thereof;

$X_2$ is a linker; and $X_3$ is a therapeutic compound.

As shown in Formula (II) and Formula (III), multiple $X_3$ moieties, the number defined by m, may be attached to $X_2$, and multiple $X_2—(X_3)_m$ moieties, the number defined by n, may be attached to $X_1$. In other words, multiple therapeutic compounds may be linked to a single linker. And the therapeutic drug-linker compound may be attached to the polypeptide or hormone ($X_3$) at one or more positions on the polypeptide or hormone. In some embodiments of the compound of Formula (II) or Formula (III), $X_2$ is bound to $X_1$ at a Cys residue thereof. In some embodiments of the compound of Formula (II) or Formula (III), $X_2$ is bound to $X_1$ at a Lys residue thereof. In some embodiments of the compound of Formula (II) or Formula (III), $X_2$ is bound to $X_1$ at two different sites on $X_1$. In some embodiments of the compound of Formula (II) or Formula (III), $X_2$ is bound to $X_1$ at two different Cys residues on $X_1$. In some embodiments of the compound of Formula (II) or Formula (III), $X_2$ is bound to $X_1$ at two different Lys residues on $X_1$. In some embodiments of the compound of Formula (II) or Formula (III), $X_2$ is a mixture of $X_{2b}$ and $X_{2c}$, wherein $X_{2b}$ is a linker that is bound to one Cys residue on $X_1$ and $X_{2c}$ is a linker that is bound to two Cys residues on $X_1$, wherein n is a combination of n1 and n2, wherein n1 corresponds to the number of $X_{2b}$ moieties bound to $X_1$ and n2 corresponds to the number of $X_{2c}$ moieties bound to $X_1$, and wherein the sum of n1 and n2 is 2, 3, 4, 5, 6, 7, 8, 9, 10, or 11. By forming bonds with two Cys residues on the bioactive polypeptide, the two Cys residues may be rebridged into a disulfide bond, maintaining the structural integrity of the polypeptide and preserving receptor binding and function. The formula of the compound of Formula (II) or Formula (III), when $X_2$ is a mixture of $X_{2b}$ and $X_{2c}$, $X_{2b}$ is a linker that is bound to one Cys residue on $X_1$, $X_{2c}$ is a linker that is bound to two different Cys residues on $X_1$, n is a combination of n1 and n2, wherein n1 corresponds to the number of $X_{2b}$ moieties bound to $X_1$ and n2 corresponds to the number of $X_{2c}$ moieties bound to $X_1$, and wherein the sum of n1 and n2 is 2, 3, 4, 5, 6, 7, 8, 9, 10, or 11, may be illustrated by formula (IV):

$$[(X_3)_m—X_{2b}]_{n1}—X_1—[X_{2c}—(X_3)_m]_{n2} \qquad (IV),$$

and pharmaceutically acceptable salts, solvates, hydrates, isomers, or tautomers thereof.

The description of n as used in the disclosure is inclusive of n1, n2, and the combination of n1 and n2, with, the sum of n1 and n2 being between 2 and 11.

In some embodiments of the compound of Formula (II) or Formula (III), m is 1. In some embodiments of the compound of Formula (II) or Formula (III), m is 2, 3, 4, 5, 6, 7, or 8. In some embodiments of the compound of Formula (II) or Formula (III), m is 1, 2, or 3. In some embodiments of the compound of Formula (II) or Formula (III), m is 2, 3, 4, or 5. In some embodiments of the compound of Formula (II) or Formula (III), m is 2. In some embodiments of the compound of Formula (II) or Formula (III), m is 3. In some embodiments of the compound of Formula (II) or Formula (III), m is 4. In some embodiments of the compound of Formula (II) or Formula (III), m is 5. In some embodiments of the compound of Formula (II) or Formula (III), m is 6. In some embodiments of the compound of Formula (II) or Formula (III), m is 7. In some embodiments of the compound of Formula (II) or Formula (III), m is 8. In some embodiments of the compound of Formula (II) or Formula (III), m is 9. In some embodiments of the compound of Formula (II) or Formula (III), m is 10. In some embodiments, m is an integer between 1 and 10.

In some embodiments of the compound of Formula (II) or Formula (III), n is 2, 3, 4, 5, 6, 7, 8, or 9. In some embodiments of the compound of Formula (II) or Formula (III), n is 3, 4, 5, 6, 7, or 8. In some embodiments of the compound of Formula (II) or Formula (III), n is 4, 5, 6, or 7. In some embodiments of the compound of Formula (II) or Formula (III), n is 1, 2, 3, 4, 5, or 6. In some embodiments of the compound of Formula (II) or Formula (III), n is 1 or 2. In some embodiments of the compound of Formula (II) or Formula (III), n is 3 or 4. In some embodiments of the compound of Formula (II) or Formula (III), n is 5 or 6. In some embodiments of the compound of Formula (II) or Formula (III), n is 1. In some embodiments of the compound of Formula (II) or Formula (III), n is 2. In some embodiments of the compound of Formula (II) or Formula (III), n is 3. In some embodiments of the compound of Formula (II) or Formula (III), n is 4. In some embodiments of the compound of Formula (II) or Formula (III), n is 5. In some embodiments of the compound of Formula (II) or Formula (III), n is 6. In some embodiments of the compound of Formula (II) or Formula (III), n is 7. In some embodiments of the compound of Formula (II) or Formula (III), n is 8. In some embodiments of the compound of Formula (II) or Formula (III), n is 9. In some embodiments of the compound of Formula (II) or Formula (III), n is 10. In some embodiments of the compound of Formula (II) or Formula (III), n is 11. In some embodiments of the compound of Formula (II) or Formula (III), n is an integer between 2 and 9, an integer between 3 and 8, an integer between 4 and 7, or n can be 5 or 6. In some embodiments of the compound of Formula (II) or Formula (III), n is an integer between 1 and 11.

In some embodiments of the compound of Formula (II) or Formula (III), m=n. In some embodiments of the compound of Formula (II) or Formula (III), n is greater than m. In some embodiments of the compound of Formula (II) or Formula (III), m is 1 and n is 1, 2, 3, 4, 5, 6, 7, 8, 9, 10, or 11. In some embodiments of the compound of Formula (II) or Formula (III), m is 2 and n is 1, 2, 3, 4, 5, 6, 7, 8, 9, 10, or 11. In some embodiments of the compound of Formula (II) or Formula (III), m is 3 and n is 1, 2, 3, 4, 5, 6, 7, 8, 9, 10, or 11. In some embodiments of the compound of Formula (II) or Formula (III), m is 4 and n is 1, 2, 3, 4, 5, 6, 7, 8, 9, 10, or 11. In some embodiments of the compound of Formula (II) or Formula (III), m is 5 and n is 1, 2, 3, 4, 5, 6, 7, 8, 9, 10, or 11. In some embodiments of the compound of Formula (II) or Formula (III), m is 1 and n is 1. In some embodiments of the compound of Formula (II) or Formula (III), m is 1 and n is 2. In some embodiments of the compound of Formula (II) or Formula (III), m is 1 and n is 3. In some embodiments of the compound of Formula (II) or Formula (III), m is 1 and n is 4. In some embodiments of the compound of Formula (II) or Formula (III), m is 1 and n is 5. In some embodiments of the compound of Formula (II) or Formula (III), m is 1 and n is 6. In some embodiments of the compound of Formula (II) or Formula (III), m is 1 and n is 7. In some embodiments of the compound of Formula (II) or Formula (III), m is 1 and n is 8. In some embodiments of the compound of Formula (II) or Formula (III), m is 1 and n is 9. In some embodiments of the compound of Formula (II) or Formula (III), m is 1 and n is 10. In some embodiments of the compound of Formula (II) or Formula (III), m is 1 and n is 11. In some embodiments of the compound of Formula (II) or Formula (III), m is 2 and n is 1. In some embodiments of the compound of Formula (II) or Formula (III), m is 2 and n is 2. In some embodiments of the compound of Formula (II) or Formula (III), m is 2 and n is 3. In some embodiments of the compound of Formula (II) or Formula (III), m is 2 and n is 4. In some embodiments of the compound of Formula (II) or Formula (III), m is 2 and n is 5. In some embodiments of the compound of Formula (II) or Formula (III), m is 2 and n is 6. In some embodiments of the compound of Formula (II) or Formula (III), m is 2 and n is 7. In some embodiments of the compound of Formula (II) or Formula (III), m is 2 and n is 8. In some embodiments of the compound of Formula (II) or Formula (III), m is 2 and n is 9. In some embodiments of the compound of Formula (II) or Formula (III), m is 2 and n is 10. In some embodiments of the compound of Formula (II) or Formula (III), m is 2 and n is 11. In some embodiments of the compound of Formula (II) or Formula (III), m is 3 and n is 1. In some embodiments of the compound of Formula (II) or Formula (III), m is 3 and n is 2. In some embodiments of the compound of Formula (II) or Formula (III), m is 3 and n is 3. In some embodiments of the compound of Formula (II) or Formula (III), m is 3 and n is 4. In some embodiments of the compound of Formula (II) or Formula (III), m is 3 and n is 5. In some embodiments of the compound of Formula (II) or Formula (III), m is 3 and n is 6. In some embodiments of the compound of Formula (II) or Formula (III), m is 3 and n is 7. In some embodiments of the compound of Formula (II) or Formula (III), m is 3 and n is 8. In some embodiments of the compound of Formula (II) or Formula (III), m is 3 and n is 9. In some embodiments of the compound of Formula (II) or Formula (III), m is 3 and n is 10. In some embodiments of the compound of Formula (II) or Formula (III), m is 3 and n is 11. In some embodiments of the compound of Formula (II) or Formula (III), m is 4 and n is 1. In some embodiments of the compound of Formula (II) or Formula (III), m is 4 and n is 2. In some embodiments of the compound of Formula (II) or Formula (III), m is 4 and n is 3. In some embodiments of the compound of Formula (II) or Formula (III), m is 4 and n is 4. In some embodiments of the compound of Formula (II) or Formula (III), m is 4 and n is 5. In some embodiments of the compound of Formula (II) or Formula (III), m is 4 and n is 6. In some embodiments of the compound of Formula (II) or Formula (III), m is 4 and n is 7. In some embodiments of the compound of Formula (II) or Formula (III), m is 4 and n is 8. In some embodiments of the compound of Formula (II) or Formula (III), m is 4 and n is 9. In some embodiments of the compound of Formula (II) or Formula (III), m is 4 and n is 10. In some embodiments of the compound of Formula (II) or Formula (III), m is 4 and n is 11. In some embodiments of the compound of Formula (II) or Formula (III), m is 5 and n is 1. In some embodiments of the compound of Formula (II) or Formula (III), m is 5 and n is 2. In some embodiments of the compound of Formula (II) or Formula (III), m is 5 and n is 3. In some embodiments of the compound of Formula (II) or Formula (III), m is 5 and n is 4. In some embodiments of the compound of Formula (II) or Formula (III), m is 5 and n is 5. In some embodiments of the compound of Formula (II) or Formula (III), m is 5 and n is 6. In some embodiments of the compound of Formula (II) or Formula (III), m is 5 and n is 7. In some embodiments of the compound of Formula (II) or Formula (III), m is 5 and n is 8. In some embodiments of the compound of Formula (II) or Formula (III), m is 5 and n is 9. In some embodiments of the compound of Formula (II) or Formula (III), m is 5 and n is 10. In some embodiments of the compound of Formula (II) or Formula (III), m is 5 and n is 11. In some embodiments of the compound of Formula (II) or Formula (III), m is 6 and n is 1. In some embodiments of the compound of Formula (II) or Formula (III), m is 6 and n is 2. In some embodiments of the compound of Formula (II) or Formula (III), m is 6 and n is 3. In some embodiments of the compound of Formula (II) or Formula (III), m is 6 and n is 4. In some embodiments of the compound of Formula (II) or Formula (III), m is 6 and n is 5. In some embodiments of the compound of Formula (II) or Formula (III), m is 6 and n is 6. In some embodiments of the compound of Formula (II) or Formula (III), m is 6 and n is 7. In some embodiments of the compound of Formula (II) or Formula (III), m is 6 and n is 8. In some embodiments of the compound of Formula (II) or Formula (III), m is 6 and n is 9. In some embodiments of the compound of Formula (II) or Formula (III), m is 6 and n is 10. In some embodiments of the compound of Formula (II) or Formula (III), m is 6 and n is 11. In some embodiments of the compound of Formula (II) or Formula (III), m is 7 and n is 1. In some embodiments of the compound of Formula (II) or Formula (III), m is 7 and n is 2. In some embodiments of the compound of Formula (II) or Formula (III), m is 7 and n is 3. In some embodiments of the compound of Formula (II) or Formula (III), m is 7 and n is 4. In some embodiments of the compound of Formula (II) or Formula (III), m is 7 and n is 5. In some embodiments of the compound of Formula (II) or Formula (III), m is 7 and n is 6. In some embodiments of the compound of Formula (II) or Formula (III), m is 7 and n is 7. In some embodiments of the compound of Formula (II) or Formula (III), m is 7 and n is 8. In some embodiments of the compound of Formula (II) or Formula (III), m is 7 and n is 9. In some embodiments of the compound of Formula (II) or Formula (III), m is 7 and n is 10. In some embodiments of the compound of Formula (II) or Formula (III), m is 7 and n is 11. In some embodiments of the compound of Formula (II) or Formula (III), m is 8 and n is 1. In some embodiments of the compound of Formula (II) or Formula (III), m is 8 and n is 2. In some embodiments of the compound of Formula (II) or Formula (III), m is 8 and n is 3. In some embodiments of the compound of Formula (II) or Formula (III), m is 8 and n is 4. In some embodiments of the compound of Formula (II) or Formula (III), m is 8 and n is 5. In some embodiments of the compound of Formula (II) or Formula (III), m is 8 and n is 6. In some embodiments of the compound of Formula (II) or Formula (III), m is 8 and n is 7. In some embodiments of the compound of Formula (II) or Formula (III), m is 8 and n is 8. In some embodiments of the compound of Formula (II) or Formula (III), m is 8 and n is 9. In some embodiments of the compound of Formula (II) or Formula (III), m is 8 and n is 10. In some embodiments of the compound of Formula (II) or Formula (III), m is 8 and n is 11. In some embodiments of the compound of Formula (II) or Formula (III), m is 9 and n is 1. In some embodiments of the compound of Formula (II) or Formula (III), m is 9 and n is 2. In some embodiments of the compound of Formula (II) or Formula (III), m is 9 and n is 3. In some embodiments of the compound of Formula (II) or Formula (III), m is 9 and n is 4. In some embodiments of the compound of Formula (II) or Formula (III), m is 9 and n is 5. In some embodiments of the compound of Formula (II) or Formula (III), m is 9 and n is 6. In some embodiments of the compound of Formula (II) or Formula (III), m is 9 and n is 7. In some embodiments of the compound of Formula (II) or Formula (III), m is 9 and n is 8. In some embodiments of the compound of Formula (II) or Formula (III), m is 9 and n is 9. In some embodiments of the compound of Formula (II) or Formula (III), m is 9 and n is 10. In some embodiments of the compound of Formula (II) or Formula (III), m is 9 and n is 11. In some embodiments of the compound of Formula (II) or Formula (III), m is 10 and n is 1. In some embodiments of the compound of Formula (II) or Formula (III), m is 10 and n is 2. In some embodiments of the compound of Formula (II) or Formula (III), m is 10 and n is 3. In some embodiments of the compound of Formula (II) or Formula (III), m is 10 and n is 4. In some embodiments of the compound of Formula (II) or Formula (III), m is 10 and n is 5. In some embodiments of the compound of Formula (II) or Formula (III), m is 10 and n is 6. In some embodiments of the compound of Formula (II) or Formula (III), m is 10 and n is 7. In some embodiments of the compound of Formula (II) or Formula (III), m is 10 and n is 8. In some embodiments of the compound of Formula (II) or Formula (III), m is 10 and n is 9. In some embodiments of the compound of Formula (II) or Formula (III), m is 10 and n is 10. In some embodiments of the compound of Formula (II) or Formula (III), m is 10 and n is 11.

In some embodiments of the compound of Formula (II) or Formula (III), $X_2$ is a mixture of $X_{2b}$ and $X_{2c}$, wherein $X_{2b}$ is a linker that is bound to one Cys residue on $X_1$,$X_{2c}$ is a linker that is bound to two Cys residues on $X_1$, n is a combination of n1 and n2, wherein n1 corresponds to the number of $X_{2b}$ moieties bound to $X_1$ and n2 corresponds to the number of $X_{2c}$ moieties bound to $X_1$, and wherein the sum of n1 and n2 is 2, 3, 4, 5, 6, 7, 8, 9, 10, or 11. In some embodiments of the compound of Formula (II) or Formula (III), when $X_2$ is a mixture of $X_{2b}$ and $X_{2c}$ and n is a combination of n1 and n2, m is 1 and n is 2. In some embodiments of the compound of Formula (II) or Formula (III), when $X_2$ is a mixture of $X_{2b}$ and $X_{2c}$ and n is a combination of n1 and n2, m is 1 and n is 3. In some embodiments of the compound of Formula (II) or Formula (III), when $X_2$ is a mixture of $X_{2b}$ and $X_{2c}$ and n is a combination of n1 and n2, m is 1 and n is 4. In some embodiments of the compound of Formula (II) or Formula (III), when $X_2$ is a mixture of $X_{2b}$ and $X_{2c}$ and n is a mixture of n1 and n2, m is 1 and n is 5. In some embodiments of the compound of Formula (II) or Formula (III), wherein $X_2$ is a mixture of $X_{2b}$ and $X_{2c}$ and n is a mixture of n1 and n2, m is 1 and n is 6. In some embodiments of the compound of Formula (II) or Formula (III), wherein $X_2$ is a mixture of $X_{2b}$ and $X_{2c}$ and n is a mixture of n1 and n2, m is 1 and n is 7. In some embodiments of the compound of Formula (II) or Formula (III), wherein $X_2$ is a mixture of $X_{2b}$ and $X_{2c}$ and n is a mixture of n1 and n2, m is 1 and n is 8. In some embodiments of the compound of Formula (II) or Formula (III), wherein $X_2$ is a mixture of $X_{2b}$ and $X_{2c}$ and n is a mixture of n1 and n2, m is 1 and n is 9. In some embodiments of the compound of Formula (II) or Formula (III), wherein $X_2$ is a mixture of $X_{2b}$ and $X_{2c}$ and n is a mixture of n1 and n2, m is 1 and n is 10. In some embodiments of the compound of Formula (II) or Formula (III), wherein $X_2$ is a mixture of $X_{2b}$ and $X_{2c}$ and n is a mixture of n1 and n2, m is 1 and n is 11. In some embodiments of the compound of Formula (II) or Formula (III), wherein $X_2$ is a mixture of $X_{2b}$ and $X_{2c}$ and n is a mixture of n1 and n2, wherein $X_2$ is a mixture of $X_{2b}$ and $X_{2c}$ and n is a mixture of n1 and n2, m is 2 and n is 2. In some embodiments of the compound of Formula (II) or Formula (III), wherein $X_2$ is a mixture of $X_{2b}$ and $X_{2c}$ and n is a mixture of n1 and n2, m is 2 and n is 3. In some embodiments of the compound of Formula (II) or Formula (III), wherein $X_2$ is a mixture of $X_{2b}$ and $X_{2c}$ and n is a mixture of n1 and n2, m is 2 and n is 4. In some embodiments of the compound of Formula (II) or Formula (III), wherein $X_2$ is a mixture of $X_{2b}$ and $X_{2c}$ and n is a mixture of n1 and n2, m is 2 and n is 5. In some embodiments of the compound of Formula (II) or Formula (III), wherein $X_2$ is a mixture of $X_{2b}$ and $X_{2c}$ and n is a mixture of n1 and n2, m is 2 and n is 6. In some embodiments of the compound of Formula (II) or Formula (III), wherein $X_2$ is a mixture of $X_{2b}$ and $X_{2c}$ and n is a mixture of n1 and n2, m is 2 and n is 7. In some embodiments of the compound of Formula (II) or Formula (III), wherein $X_2$ is a mixture of $X_{2b}$ and $X_{2c}$ and n is a mixture of n1 and n2, m is 2 and n is 8. In some embodiments of the compound of Formula (II) or Formula (III), wherein $X_2$ is a mixture of $X_{2b}$ and $X_{2c}$ and n is a mixture of n1 and n2, m is 2 and n is 9. In some embodiments of the compound of Formula (II) or Formula (III), wherein $X_2$ is a mixture of $X_{2b}$ and $X_{2c}$ and n is a mixture of n1 and n2, m is 2 and n is 10. In some embodiments of the compound of Formula (II) or Formula (III), wherein $X_2$ is a mixture of $X_{2b}$ and $X_{2c}$ and n is a mixture of n1 and n2, m is 2 and n is 11. In some embodiments of the compound of Formula (II) or Formula (III), wherein $X_2$ is a mixture of $X_{2b}$ and $X_{2c}$ and n is a mixture of n1 and n2, m is 3 and n is 2. In some embodiments of the compound of Formula (II) or Formula (III), wherein $X_2$ is a mixture of $X_{2b}$ and $X_{2c}$ and n is a mixture of n1 and n2, m is 3 and n is 3. In some embodiments of the compound of Formula (II) or Formula (III), wherein $X_2$ is a mixture of $X_{2b}$ and $X_{2c}$ and n is a mixture of n1 and n2, m is 3 and n is 4. In some embodiments of the compound of Formula (II) or Formula (III), wherein $X_2$ is a mixture of $X_{2b}$ and $X_{2c}$ and n is a mixture of n1 and n2, m is 3 and n is 5. In some embodiments of the compound of Formula (II) or Formula (III), wherein $X_2$ is a mixture of $X_{2b}$ and $X_{2c}$ and n is a mixture of n1 and n2, m is 3 and n is 6. In some embodiments of the compound of Formula (II) or Formula (III), wherein $X_2$ is a mixture of $X_{2b}$ and $X_{2c}$ and n is a mixture of n1 and n2, m is 3 and n is 7. In some embodiments of the compound of Formula (II) or Formula (III), wherein $X_2$ is a mixture of $X_{2b}$ and $X_{2c}$ and n is a mixture of n1 and n2, m is 3 and n is 8. In some embodiments of the compound of Formula (II) or Formula (III), wherein $X_2$ is a mixture of $X_{2b}$ and $X_{2c}$ and n is a mixture of n1 and n2, m is 3 and n is 9. In some embodiments of the compound of Formula (II) or Formula (III), wherein $X_2$ is a mixture of $X_{2b}$ and $X_{2c}$ and n is a mixture of n1 and n2, m is 3 and n is 10. In some embodiments of the compound of Formula (II) or Formula (III), wherein $X_2$ is a mixture of $X_{2b}$ and $X_{2c}$ and n is a mixture of n1 and n2, m is 3 and n is 11. In some embodiments of the compound of Formula (II) or Formula (III), wherein $X_2$ is a mixture of $X_{2b}$ and $X_{2c}$ and n is a mixture of n1 and n2, m is 4 and n is 2. In some embodiments of the compound of Formula (II) or Formula (III), wherein $X_2$ is a mixture of $X_{2b}$ and $X_{2c}$ and n is a mixture of n1 and n2, m is 4 and n is 3. In some embodiments of the compound of Formula (II) or Formula (III), wherein $X_2$ is a mixture of $X_{2b}$ and $X_{2c}$ and n is a mixture of n1 and n2, m is 4 and n is 4. In some embodiments of the compound of Formula (II) or Formula (III), wherein $X_2$ is a mixture of $X_{2b}$ and $X_{2c}$ and n is a mixture of n1 and n2, m is 4 and n is 5. In some embodiments of the compound of Formula (II) or Formula (III), wherein $X_2$ is a mixture of $X_{2b}$ and $X_{2c}$ and n is a mixture of n1 and n2, m is 4 and n is 6. In some embodiments of the compound of Formula (II) or Formula (III), wherein $X_2$ is a mixture of $X_{2b}$ and $X_{2c}$ and n is a mixture of n1 and n2, m is 4 and n is 7. In some embodiments of the compound of Formula (II) or Formula (III), wherein $X_2$ is a mixture of $X_{2b}$ and $X_{2c}$ and n is a mixture of n1 and n2, m is 4 and n is 8. In some embodiments of the compound of Formula (II) or Formula (III), wherein $X_2$ is a mixture of $X_{2b}$ and $X_{2c}$ and n is a mixture of n1 and n2, m is 4 and n is 9. In some embodiments of the compound of Formula (II) or Formula (III), wherein $X_2$ is a mixture of $X_{2b}$ and $X_{2c}$ and n is a mixture of n1 and n2, m is 4 and n is 10. In some embodiments of the compound of Formula (II) or Formula (III), wherein $X_2$ is a mixture of $X_{2b}$ and $X_{2c}$ and n is a mixture of n1 and n2, m is 4 and n is 11. In some embodiments of the compound of Formula (II) or Formula (III), wherein $X_2$ is a mixture of $X_{2b}$ and $X_{2c}$ and n is a mixture of n1 and n2, m is 5 and n is 2. In some embodiments of the compound of Formula (II) or Formula (III), wherein $X_2$ is a mixture of $X_{2b}$ and $X_{2c}$ and n is a mixture of n1 and n2, m is 5 and n is 3. In some embodiments of the compound of Formula (II) or Formula (III), wherein $X_2$ is a mixture of $X_{2b}$ and $X_{2c}$ and n is a mixture of n1 and n2, m is 5 and n is 4. In some embodiments of the compound of Formula (II) or Formula (III), wherein $X_2$ is a mixture of $X_{2b}$ and $X_{2c}$ and n is a mixture of n1 and n2, m is 5 and n is 5. In some embodiments of the compound of Formula (II) or Formula (III), wherein $X_2$ is a mixture of $X_{2b}$ and $X_{2c}$ and n is a mixture of n1 and n2, m is 5 and n is 6. In some embodiments of the compound of Formula (II) or Formula (III), wherein $X_2$ is a mixture of $X_{2b}$ and $X_{2c}$ and n is a mixture of n1 and n2, m is 5 and n is 7. In some embodiments of the compound of Formula (II) or Formula (III), wherein $X_2$ is a mixture of $X_{2b}$ and $X_{2c}$ and n is a mixture of n1 and n2, m is 5 and n is 8. In some embodiments of the compound of Formula (II) or Formula (III), wherein $X_2$ is a mixture of $X_{2b}$ and $X_{2c}$ and n is a mixture of n1 and n2, m is 5 and n is 9. In some embodiments of the compound of Formula (II) or Formula (III), wherein $X_2$ is a mixture of $X_{2b}$ and $X_{2c}$ and n is a mixture of n1 and n2, m is 5 and n is 10. In some embodiments of the compound of Formula (II) or Formula (III), wherein $X_2$ is a mixture of $X_{2b}$ and $X_{2c}$ and n is a mixture of n1 and n2, m is 5 and n is 11. In some embodiments of the compound of Formula (II) or Formula (III), wherein $X_2$ is a mixture of $X_{2b}$ and $X_{2c}$ and n is a mixture of n1 and n2, m is 6 and n is 2. In some embodiments of the compound of Formula (II) or Formula (III), wherein $X_2$ is a mixture of $X_{2b}$ and $X_{2c}$ and n is a mixture of n1 and n2, m is 6 and n is 3. In some embodiments of the compound of Formula (II) or Formula (III), wherein $X_2$ is a mixture of $X_{2b}$ and $X_{2c}$ and n is a mixture of n1 and n2, m is 6 and n is 4. In some embodiments of the compound of Formula (II) or Formula (III), wherein $X_2$ is a mixture of $X_{2b}$ and $X_{2c}$ and n is a mixture of n1 and n2, m is 6 and n is 5. In some embodiments of the compound of Formula (II) or Formula (III), wherein $X_2$ is a mixture of $X_{2b}$ and $X_{2c}$ and n is a mixture of n1 and n2, m is 6 and n is 6. In some embodiments of the compound of Formula (II) or Formula (III), wherein $X_2$ is a mixture of $X_{2b}$ and $X_{2c}$ and n is a mixture of n1 and n2, m is 6 and n is 7. In some embodiments of the compound of Formula (II) or Formula (III), wherein $X_2$ is a mixture of $X_{2b}$ and $X_{2c}$ and n is a mixture of n1 and n2, m is 6 and n is 8. In some embodiments of the compound of Formula (II) or Formula (III), wherein $X_2$ is a mixture of $X_{2b}$ and $X_{2c}$ and n is a mixture of n1 and n2, m is 6 and n is 9. In some embodiments of the compound of Formula (II) or Formula (III), wherein $X_2$ is a mixture of $X_{2b}$ and $X_{2c}$ and n is a mixture of n1 and n2, m is 6 and n is 10. In some embodiments of the compound of Formula (II) or Formula (III), wherein $X_2$ is a mixture of $X_{2b}$ and $X_{2c}$ and n is a mixture of n1 and n2, m is 6 and n is 11. In some embodiments of the compound of Formula (II) or Formula (III), wherein $X_2$ is a mixture of $X_{2b}$ and $X_{2c}$ and n is a mixture of n1 and n2, m is 7 and n is 2. In some embodiments of the compound of Formula (II) or Formula (III), wherein $X_2$ is a mixture of $X_{2b}$ and $X_{2c}$ and n is a mixture of n1 and n2, m is 7 and n is 3. In some embodiments of the compound of Formula (II) or Formula (III), wherein $X_2$ is a mixture of $X_{2b}$ and $X_{2c}$ and n is a mixture of n1 and n2, m is 7 and n is 4. In some embodiments of the compound of Formula (II) or Formula (III), wherein $X_2$ is a mixture of $X_{2b}$ and $X_{2c}$ and n is a mixture of n1 and n2, m is 7 and n is 5. In some embodiments of the compound of Formula (II) or Formula (III), wherein $X_2$ is a mixture of $X_{2b}$ and $X_{2c}$ and n is a mixture of n1 and n2, m is 7 and n is 6. In some embodiments of the compound of Formula (II) or Formula (III), wherein $X_2$ is a mixture of $X_{2b}$ and $X_{2c}$ and n is a mixture of n1 and n2, m is 7 and n is 7. In some embodiments of the compound of Formula (II) or Formula (III), wherein $X_2$ is a mixture of $X_{2b}$ and $X_{2c}$ and n is a mixture of n1 and n2, m is 7 and n is 8. In some embodiments of the compound of Formula (II) or Formula (III), wherein $X_2$ is a mixture of $X_{2b}$ and $X_{2c}$ and n is a mixture of n1 and n2, m is 7 and n is 9. In some embodiments of the compound of Formula (II) or Formula (III), wherein $X_2$ is a mixture of $X_{2b}$ and $X_{2c}$ and n is a mixture of n1 and n2, m is 7 and n is 10. In some embodiments of the compound of Formula (II) or Formula (III), wherein $X_2$ is a mixture of $X_{2b}$ and $X_{2c}$ and n is a mixture of n1 and n2, m is 7 and n is 11. In some embodiments of the compound of Formula (II) or Formula (III), wherein $X_2$ is a mixture of $X_{2b}$ and $X_{2c}$ and n is a mixture of n1 and n2, m is 8 and n is 2. In some embodiments of the compound of Formula (II) or Formula (III), wherein $X_2$ is a mixture of $X_{2b}$ and $X_{2c}$ and n is a mixture of n1 and n2, m is 8 and n is 3. In some embodiments of the compound of Formula (II) or Formula (III), wherein $X_2$ is a mixture of $X_{2b}$ and $X_{2c}$ and n is a mixture of n1 and n2, m is 8 and n is 4. In some embodiments of the compound of Formula (II) or Formula (III), wherein $X_2$ is a mixture of $X_{2b}$ and $X_{2c}$ and n is a mixture of n1 and n2, m is 8 and n is 5. In some embodiments of the compound of Formula (II) or Formula (III), wherein $X_2$ is a mixture of $X_{2b}$ and $X_{2c}$ and n is a mixture of n1 and n2, m is 8 and n is 6. In some embodiments of the compound of Formula (II) or Formula (III), wherein $X_2$ is a mixture of $X_{2b}$ and $X_{2c}$ and n is a mixture of n1 and n2, m is 8 and n is 7. In some embodiments of the compound of Formula (II) or Formula (III), wherein $X_2$ is a mixture of $X_{2b}$ and $X_{2c}$ and n is a mixture of n1 and n2, m is 8 and n is 8. In some embodiments of the compound of Formula (II) or Formula (III), wherein $X_2$ is a mixture of $X_{2b}$ and $X_{2c}$ and n is a mixture of n1 and n2, m is 8 and n is 9. In some embodiments of the compound of Formula (II) or Formula (III), wherein $X_2$ is a mixture of $X_{2b}$ and $X_{2c}$ and n is a mixture of n1 and n2, m is 8 and n is 10. In some embodiments of the compound of Formula (II) or Formula (III), wherein $X_2$ is a mixture of $X_{2b}$ and $X_{2c}$ and n is a mixture of n1 and n2, m is 8 and n is 11. In some embodiments of the compound of Formula (II) or Formula (III), wherein $X_2$ is a mixture of $X_{2b}$ and $X_{2c}$ and n is a mixture of n1 and n2, m is 9 and n is 2. In some embodiments of the compound of Formula (II) or Formula (III), wherein $X_2$ is a mixture of $X_{2b}$ and $X_{2c}$ and n is a mixture of n1 and n2, m is 9 and n is 3. In some embodiments of the compound of Formula (II) or Formula (III), wherein $X_2$ is a mixture of $X_{2b}$ and $X_{2c}$ and n is a mixture of n1 and n2, m is 9 and n is 4. In some embodiments of the compound of Formula (II) or Formula (III), wherein $X_2$ is a mixture of $X_{2b}$ and $X_{2c}$ and n is a mixture of n1 and n2, m is 9 and n is 5. In some embodiments of the compound of Formula (II) or Formula (III), wherein $X_2$ is a mixture of $X_{2b}$ and $X_{2c}$ and n is a mixture of n1 and n2, m is 9 and n is 6. In some embodiments of the compound of Formula (II) or Formula (III), wherein $X_2$ is a mixture of $X_{2b}$ and $X_{2c}$ and n is a mixture of n1 and n2, m is 9 and n is 7. In some embodiments of the compound of Formula (II) or Formula (III), wherein $X_2$ is a mixture of $X_{2b}$ and $X_{2c}$ and n is a mixture of n1 and n2, m is 9 and n is 8. In some embodiments of the compound of Formula (II) or Formula (III), wherein $X_2$ is a mixture of $X_{2b}$ and $X_{2c}$ and n is a mixture of n1 and n2, m is 9 and n is 9. In some embodiments of the compound of Formula (II) or Formula (III), wherein $X_2$ is a mixture of $X_{2b}$ and $X_{2c}$ and n is a mixture of n1 and n2, m is 9 and n is 10.

In some embodiments of the compound of Formula (II) or Formula (III), wherein $X_2$ is a mixture of $X_{2b}$ and $X_{2c}$ and n is a mixture of n1 and n2, m is 9 and n is 11. In some embodiments of the compound of Formula (II) or Formula (III), wherein $X_2$ is a mixture of $X_{2b}$ and $X_{2c}$ and n is a mixture of n1 and n2, m is 10 and n is 2. In some embodiments of the compound of Formula (II) or Formula (III), wherein $X_2$ is a mixture of $X_{2b}$ and $X_{2c}$ and n is a mixture of n1 and n2, m is 10 and n is 3. In some embodiments of the compound of Formula (II) or Formula (III), wherein $X_2$ is a mixture of $X_{2b}$ and $X_{2c}$ and n is a mixture of n1 and n2, m is 10 and n is 4. In some embodiments of the compound of Formula (II) or Formula (III), wherein $X_2$ is a mixture of $X_{2b}$ and $X_{2c}$ and n is a mixture of n1 and n2, m is 10 and n is 5. In some embodiments of the compound of Formula (II) or Formula (III), wherein $X_2$ is a mixture of $X_{2b}$ and $X_{2c}$ and n is a mixture of n1 and n2, m is 10 and n is 6. In some embodiments of the compound of Formula (II) or Formula (III), wherein $X_2$ is a mixture of $X_{2b}$ and $X_{2c}$ and n is a mixture of n1 and n2, m is 10 and n is 7. In some embodiments of the compound of Formula (II) or Formula (III), wherein $X_2$ is a mixture of $X_{2b}$ and $X_{2c}$ and n is a mixture of n1 and n2, m is 10 and n is 8. In some embodiments of the compound of Formula (II) or Formula (III), wherein $X_2$ is a mixture of $X_{2b}$ and $X_{2c}$ and n is a mixture of n1 and n2, m is 10 and n is 9. In some embodiments of the compound of Formula (II) or Formula (III), wherein $X_2$ is a mixture of $X_{2b}$ and $X_{2c}$ and n is a mixture of n1 and n2, m is 10 and n is 10. In some embodiments of the compound of Formula (II) or Formula (III), wherein $X_2$ is a mixture of $X_{2b}$ and $X_{2c}$ and n is a mixture of n1 and n2, m is 10 and n is 11. In some embodiments of the compound of Formula (II) or Formula (III), wherein $X_2$ is a mixture of $X_{2b}$ and $X_{2c}$ and n is a mixture of n1 and n2, n1 is 2 or 3 and n2 is 1. In some embodiments of the compound of Formula (II) or Formula (III), wherein $X_2$ is a mixture of $X_{2b}$ and $X_{2c}$ and n is a mixture of n1 and n2, n1 is 2 and n2 is 1. In some embodiments of the compound of Formula (II) or Formula (III), wherein $X_2$ is a mixture of $X_{2b}$ and $X_{2c}$ and n is a mixture of n1 and n2, n1 is 3 and n2 is 1. In some embodiments of the compound of Formula (II) or Formula (III), wherein $X_2$ is a mixture of $X_{2b}$ and $X_{2c}$ and n is a mixture of n1 and n2, n1 is 1, 2, 3, 4, or 5 and n2 is 1, 2 or 3. In some embodiments of the compound of Formula (II) or Formula (III), wherein $X_2$ is a mixture of $X_{2b}$ and $X_{2c}$ and n is a mixture of n1 and n2, n1 is 1, 2, 3, 4, or 5 and n2 is 1. In some embodiments of the compound of Formula (II) or Formula (III), wherein $X_2$ is a mixture of $X_{2b}$ and $X_{2c}$ and n is a mixture of n1 and n2, n1 is 1, 2, 3, 4, or 5 and n2 is 2. In some embodiments of the compound of Formula (II) or Formula (III), wherein $X_2$ is a mixture of $X_{2b}$ and $X_{2c}$ and n is a mixture of n1 and n2, n1 is 1, 2, 3, 4, or 5 and n2 is 3. In some embodiments of the compound of Formula (II) or Formula (III), wherein $X_2$ is a mixture of $X_{2b}$ and $X_{2c}$ and n is a mixture of n1 and n2, n1 is 1 and n2 is 1, 2 or 3. In some embodiments of the compound of Formula (II) or Formula (III), wherein $X_2$ is a mixture of $X_{2b}$ and $X_{2c}$ and n is a mixture of n1 and n2, n1 is 2 and n2 is 1, 2 or 3. In some embodiments of the compound of Formula (II) or Formula (III), wherein $X_2$ is a mixture of $X_{2b}$ and $X_{2c}$ and n is a mixture of n1 and n2, n1 is 3 and n2 is 1, 2 or 3. In some embodiments of the compound of Formula (II) or Formula (III), wherein $X_2$ is a mixture of $X_{2b}$ and $X_{2c}$ and n is a mixture of n1 and n2, n1 is 4 and n2 is 1, 2 or 3. In some embodiments of the compound of Formula (II) or Formula (III), wherein $X_2$ is a mixture of $X_{2b}$ and $X_{2c}$ and n is a mixture of n1 and n2, n1 is 5 and n2 is 1, 2 or 3. In some embodiments of the compound of Formula (II) or Formula (III), wherein $X_2$ is a mixture of $X_{2b}$ and $X_{2c}$ and n is a mixture of n1 and n2, n1=n2. In some embodiments, each $X_2$ bound to $X_1$ is an $X_{2b}$ moiety. In some embodiments, each $X_2$ bound to $X_1$ is an $X_{2c}$ moiety.

In some embodiments of the compound of Formula (II) or Formula (III), the molar ratio of $X_3$ to $X_1$ is between 1:1 and 110:1. In some embodiments of the compound of Formula (II) or Formula (III), the molar ratio of $X_3$ to $X_1$ is between 1:1 and 50:1. In some embodiments of the compound of Formula (II) or Formula (III), the molar ratio of $X_3$ to $X_1$ is between 1:1 and 10:1. In some embodiments of the compound of Formula (II) or Formula (III), the molar ratio of $X_3$ to $X_1$ is between 1:1 and 5:1. In some embodiments of the compound of Formula (II) or Formula (III), the molar ratio of $X_3$ to $X_1$ is between 10:1 and 50:1. In some embodiments of the compound of Formula (II) or Formula (III), the molar ratio of $X_3$ to $X_1$ is between 50:1 and 110:1. In some embodiments of the compound of Formula (II) or Formula (III), the molar ratio of $X_3$ to $X_1$ is 1:1. In some embodiments of the compound of Formula (II) or Formula (III), the molar ratio of $X_3$ to $X_1$ is 2:1. In some embodiments of the compound of Formula (II) or Formula (III), the molar ratio of $X_3$ to $X_1$ is 3:1. In some embodiments of the compound of Formula (II) or Formula (III), the molar ratio of $X_3$ to $X_1$ is 4:1. In some embodiments of the compound of Formula (II) or Formula (III), the molar ratio of $X_3$ to $X_1$ is 5:1. In some embodiments of the compound of Formula (II) or Formula (III), the molar ratio of $X_3$ to $X_1$ is 6:1. In some embodiments of the compound of Formula (II) or Formula (III), the molar ratio of $X_3$ to $X_1$ is 7:1. In some embodiments of the compound of Formula (II) or Formula (III), the molar ratio of $X_3$ to $X_1$ is 8:1. In some embodiments of the compound of Formula (II) or Formula (III), the molar ratio of $X_3$ to $X_1$ is 9:1. In some embodiments of the compound of Formula (II) or Formula (III), the molar ratio of $X_3$ to $X_1$ is 10:1. In some embodiments of the compound of Formula (II) or Formula (III), the molar ratio of $X_3$ to $X_1$ is 11:1. In some embodiments of the compound of Formula (II) or Formula (III), the molar ratio of $X_3$ to $X_1$ is 12:1. In some embodiments of the compound of Formula (II) or Formula (III), the molar ratio of $X_3$ to $X_1$ is 13:1. In some embodiments of the compound of Formula (II) or Formula (III), the molar ratio of $X_3$ to $X_1$ is 14:1. In some embodiments of the compound of Formula (II) or Formula (III), the molar ratio of $X_3$ to $X_1$ is 15:1. In some embodiments of the compound of Formula (II) or Formula (III), the molar ratio of $X_3$ to $X_1$ is 16:1. In some embodiments of the compound of Formula (II) or Formula (III), the molar ratio of $X_3$ to $X_1$ is 17:1. In some embodiments of the compound of Formula (II) or Formula (III), the molar ratio of $X_3$ to $X_1$ is 18:1. In some embodiments of the compound of Formula (II) or Formula (III), the molar ratio of $X_3$ to $X_1$ is 19:1. In some embodiments of the compound of Formula (II) or Formula (III), the molar ratio of $X_3$ to $X_1$ is 20:1.

$X_1$ is a biologically active polypeptide, e.g., a polypeptide exerting its own biological effect on specified targets, or a hormone. Cytokines, growth factors (GF), and hormones are all chemical messengers that mediate intercellular communication. The regulation of cellular and nuclear functions by cytokines, growth factors, and hormones is initiated through the activation of cell surface receptors (Rc). All receptors generally have two main components: 1) a ligand-binding domain that ensures ligand specificity and 2) an effector domain that initiates the generation of the biological response upon ligand binding. The activated receptor may then interact with other cellular components to complete the signal transduction process. Among such proteins are insulin, insulin-like proteins and homologs.

Figure 2:
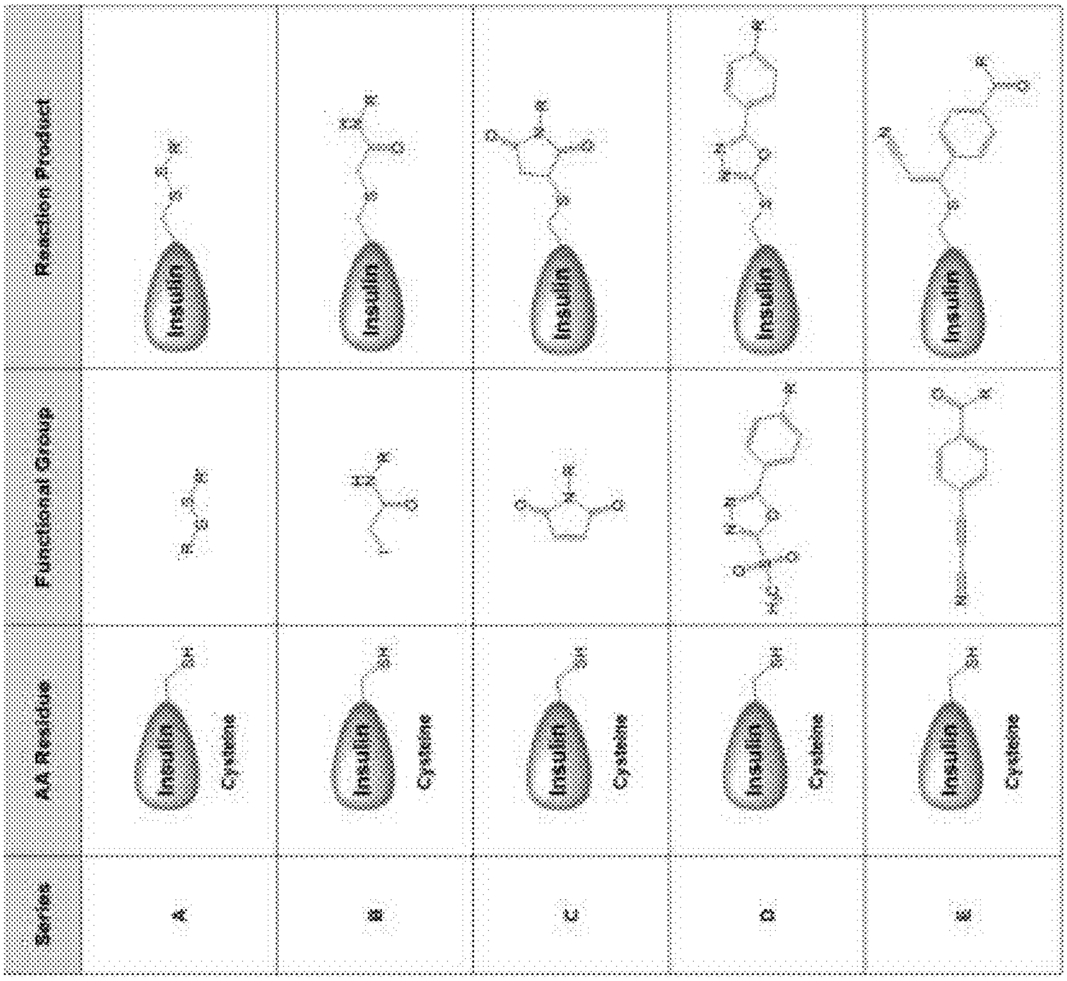
Figure 3:
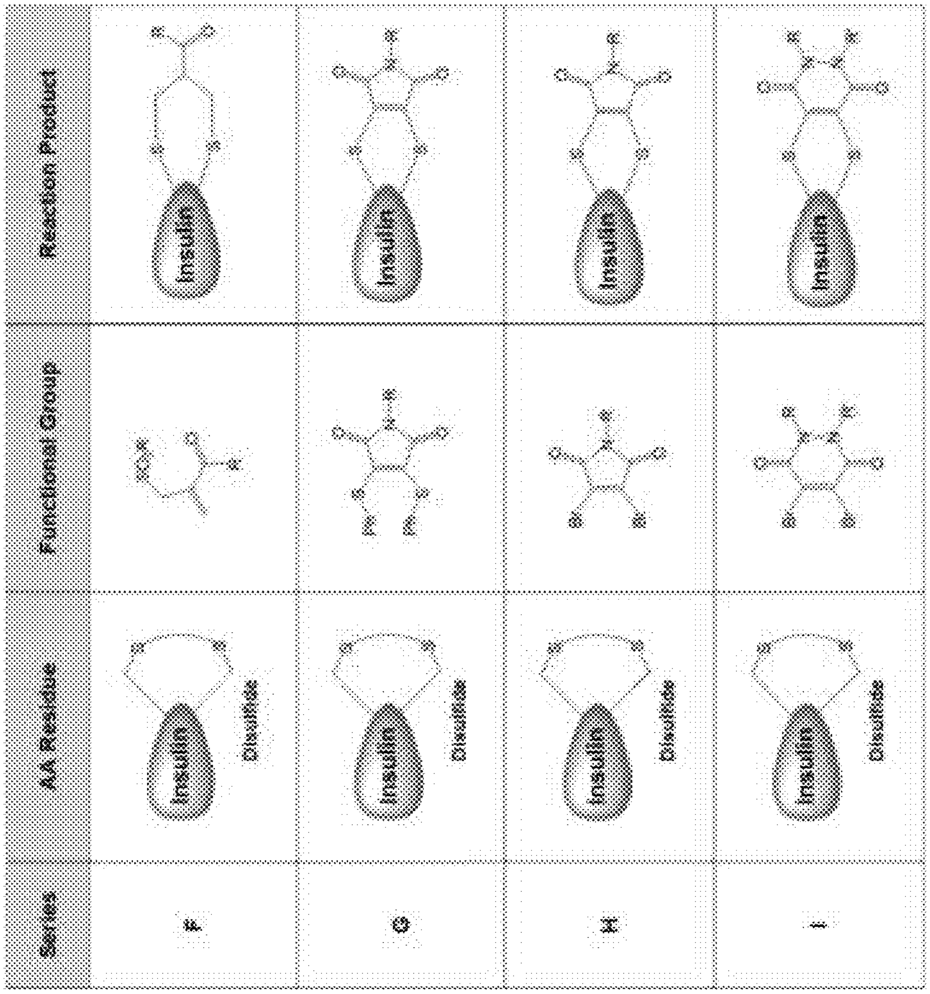
Figure 4:
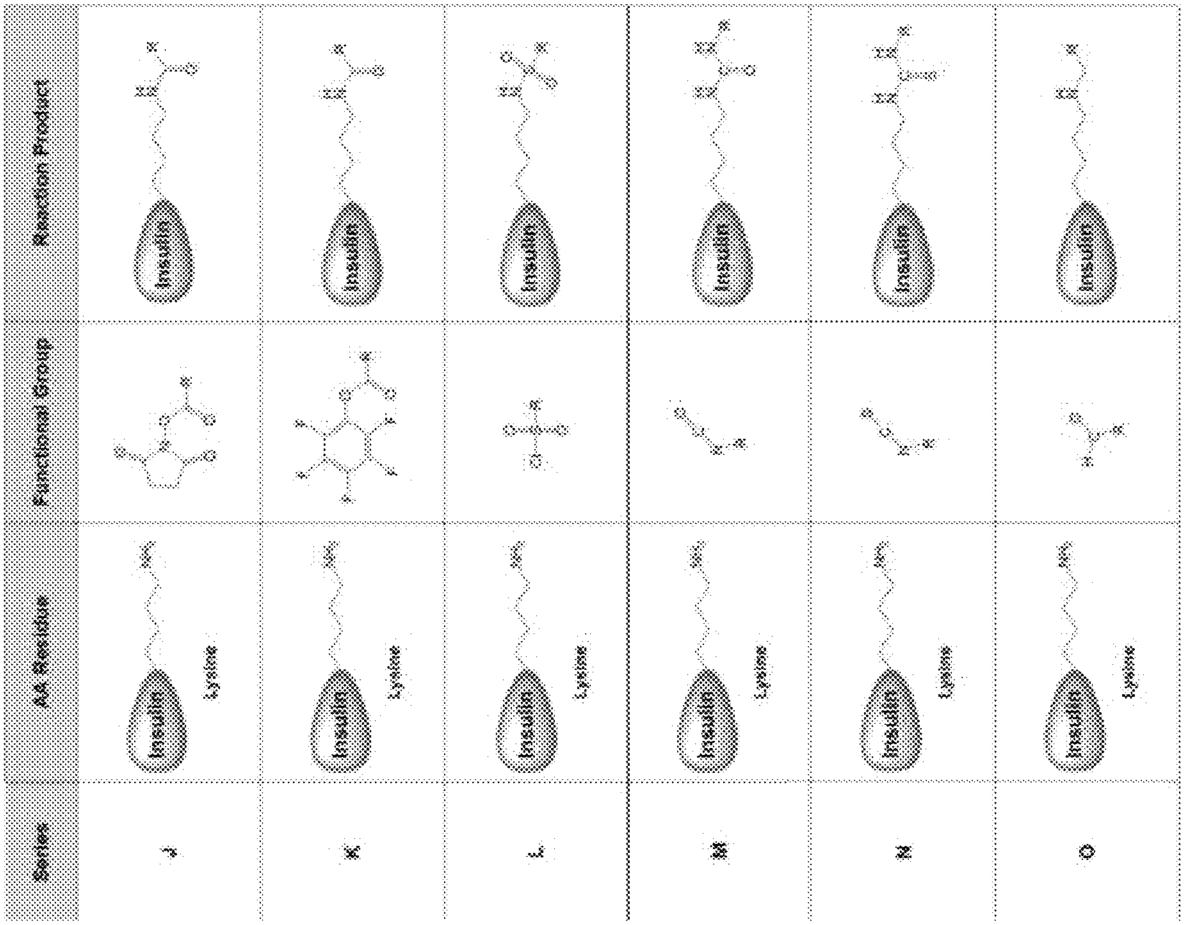

Many insulin, insulin-like proteins and homologs have been produced and clinically tested (see table I) and each allows for the conjugation of a linker to a distinct amino acid site available to attach the therapeutic compound payload. Cysteine residues or lysine residues in these proteins are chemically available for conjugation. There is only one Lys residue identified in the first amino acid chain which is available for conjugation (FIG. 1). There are 6 Cys residues present (through the formation of intra and inter-molecular disulfides) that are available for bioconjugation by re-bridging chemistry). Each of these distinct proteins can be conjugated using either the Cys or Lys amino acid residues through a series of different chemistries (FIGS. 2-4). [9,10, 11,12] _The Cys residue has been functionalized in the first 5 reactions shown (Series A through E). The resulting linkages are shown in FIG. 2 as reaction products. FIG. 3 (Series F through I) shows the re-bridging chemistry that can be utilized for the bioconjugation of disulfides and restore the structural integrity of the protein. The Lys residue can be functionalized through chemical reactions as shown in FIG. 4 (Series J through O). Other amino acid residues can be used to conjugate linkers and payloads for the formation of site-specific therapeutic compound conjugates. In some embodiments, the insulin protein of the compounds of the disclosure (e.g., compounds of Formula (II) or Formula (III), or pharmaceutically acceptable salts, solvates, hydrates, isomers, or tautomers thereof) is a wild-type human insulin protein or a known mutant or variant thereof.

Insulin, insulin-like proteins and homologs used in the disclosure are detailed in Table 4. The insulin and variants of Table 4 may exhibit increased half-life and solubility compared to wild-type human insulin. These proteins retain high affinity for the insulin receptor even after conjugation with a linker and a therapeutic compound.

TABLE 4

Insulin Polypeptides

| SEQ ID # | Name | Amino Acid Sequence |
|---|---|---|
| SEQ# 1 | Glargine | >A chain: GIVEQCCTSICSLYQLENYCG<br>>B chain: FVNQIILCGSHIL VEALYL VCGERGFFYTPKTRR |
| SEQ# 2 | Degludec | >A Chain: FVNQHILCGSIIL VEALYLVCGERGFFYTPK<br>>B Chain: GIVEQCCTSICSLYQLENYCN |
| SEQ# 3 | Aspart | >A chain: GIVEQCCTSICSI.YQLENYCN<br>>B chain: FVNQHLCGSHLVEALYLVCGERGFFYTDKT |
| SEQ# 4 | Lispro | >A chain: GIVEQCCTSICSLYQLENYCN<br>>B chain: FVNQHI.CGSHLVEALYLVCGERGFFYTKPT |

TABLE 4-continued

| Insulin Polypeptides | | |
|---|---|---|
| SEQ ID # | Name | Amino Acid Sequence |
| SEQ# 5 | Detemir | > A chain: GIVEQCCTSICSLYQLENYCN<br>i> B chain: FVNQHLCGSHLVEALYLVCGERGFFYTPK |
| SEQ# 6 | Glulisine | >A chain: GIVEQCCTSICSLYQLENYCN<br>>B chain: FVKQHLCGSHLVEALYLVCGERGFFYTPET |
| SEQ# 7 | WT Human Insulin | >A Chain: GIVEQCCTSICSLYQLENYCN<br>>B Chain: FVNQHLCGSHLVEALYLVCGERGFFYTPKT |
| SEQ# 8 | Human Thioredoxin C32S | MVKQIESKTAFQFALDAAGDKI,VVVDESATWSGPCKMIKPFFHS<br>LSEKYSNVIFLEVDVDDCQD<br>VASECEVKCMPTFQFFKKGQKVGEFSGANKEKLEATINELV |
| SEQ# 9 | Human Thioredoxin C35S | MVKQIESKTAFQEALDAAGDKLVVVDESATWCGPSKMIKPFFHS<br>LSEKYSNVIFLEVDVDDCQD<br>VASECEVKCMPTFQFFKKGQKVGEFSGANKEKLEATINELV |
| SEQ# 10 | Human Thioredoxin C32S C35S | MVKQIESKTAFQEALDAAGDKL.VVVDFSATWSGPSKMIKPFFHS<br>LSEKYSNVIFLEVDVDDCQD<br>VASECEVKCMPTFQFFKKGQKVGEFSGANKEKLEATINELV |
| SEQ# 11 | Human Thioredoxin WT | MVKQIESKTAFQEALDAAGDKL.VVVDFSATWCGPCKMIKPFFHS<br>LSEKYSNVIFLEVDVDDCQD<br>VASECEVKCMPTFQFFKKGQKVGEFSGANKEKLEATINELV |

General scheme for disulfides in all insulins

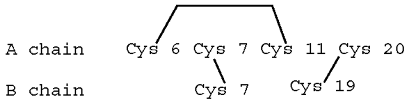

General scheme for disulfides in all insulins
A chain Cys 6 Cys 7 Cys 11 Cys 20
B chain
Cys 7
Cys'19
General Format of mature Insulin= B chain-A Chain
General format of insulin-Thioredoxin fusion proteins=
Thioredoxin (WT, C32S, C35S, C32S C35S)-B chain insulin-A chain insulin or
B chain insulin-A chain insulin- Thioredoxin (WT, C32S, C35S, C32S C35S)

In some embodiments, the Insulin polypeptides or bio-active homolog polypeptides of the disclosure have at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to an amino acid sequence of Table 4. In some embodiments, the Insulin polypeptides or bio-active homolog polypeptides of the disclosure have at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO: 2.

Hormones are any member of a class of signaling molecules produced by glands in, multicellular organisms that are transported by the circulatory system to target distant organs to regulate physiology and behavior. Hormones have diverse chemical structures, mainly of three classes: eicosanoids, steroids, and amino acid/protein derivatives (amines, peptides, and proteins). The glands that secrete hormones comprise the endocrine signaling system. The term hormone is sometimes extended to include chemicals produced by cells that affect the same cell (autocrine or intracrine signaling) or nearby cells (paracrine signaling).

Hormones are used to communicate between organs and tissues for physiological regulation and behavioral activities, such as digestion, metabolism, respiration, tissue function, sensory perception, sleep, excretion, lactation, stress, growth and development, movement, reproduction, and mood. Hormones affect distant cells by binding to specific receptor proteins in the target cell resulting in a change in cell function. When a hormone binds to the receptor, it results in the activation of a signal transduction pathway that typically activates gene transcription resulting in increased expression of target proteins; non-genomic effects are more rapid and can be synergistic with genomic effects. Amino acid-based hormones (amines and peptide or protein hormones) are water-soluble and act on the surface of target cells via second messengers; steroid hormones, being lipid-soluble, move through the plasma membranes of target cells (both cytoplasmic and nuclear) to act within their nuclei.

In some embodiments of the compound of Formula (II) or Formula (III), $X_2$ is a linker, which can take many forms as shown herein. In some embodiments of the compound of Formula (II) or Formula (III), $X_2$ is a cleavable linker. In some embodiments of the compound of Formula (II) or Formula (III), $X_2$ is a non-cleavable linker. In some embodiments of the compound of Formula (II) or Formula (III), $X_2$ is a mixture of $X_{2b}$ and $X_{2c}$, wherein $X_{2b}$ is a linker that is bound to one Cys residue on $X_1$ and $X_{2c}$ is a linker that is bound to two Cys residues on $X_1$, wherein n is a combination of n1 and n2, wherein n1 corresponds to the number of $X_{2b}$ moieties bound to $X_1$ and n2 corresponds to the number of $X_{2c}$ moieties bound to $X_1$, and wherein the sum of n1 and n2 is 2, 3, 4, 5, 6, 7, 8, 9, 10, or 11. In some embodiments, each $X_2$ bound to $X_1$ is an $X_{2b}$ moiety. In some embodiments, each $X_2$ bound to $X_1$ is an $X_{2c}$ moiety. In some embodiments of the compound of Formula (II) or Formula (III), $X_2$ is a linker listed in Table 5, wherein the left side of $X_2$, as drawn, is bound to $X_1$, and the right side of $X_2$, as drawn, is bound to $X_3$. In Table 5, R=H, alkyl, aryl, arylalkyl, glycol ether, or an additional glycol linker attaching to the therapeutic compound.

TABLE 5
| Exemplary $X_2$ Linkers | |
|---|---|
| Linker | Structure |
| K-1 Cleavable Linker | 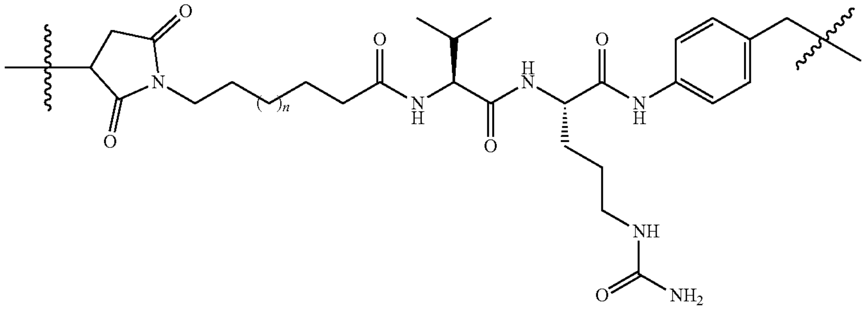 |
| K-2 Cleavable Linker | 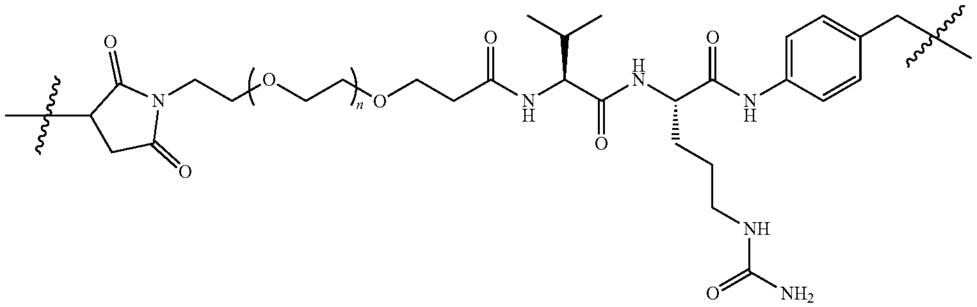 |
| K-3 Cleavable Linker | 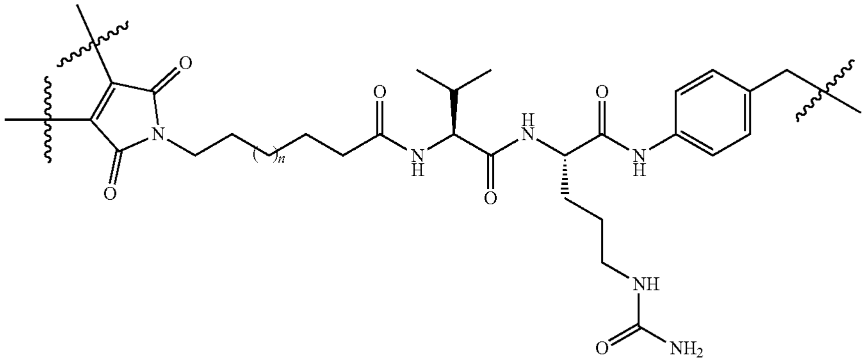 |
| K-4 Cleavable Linker | 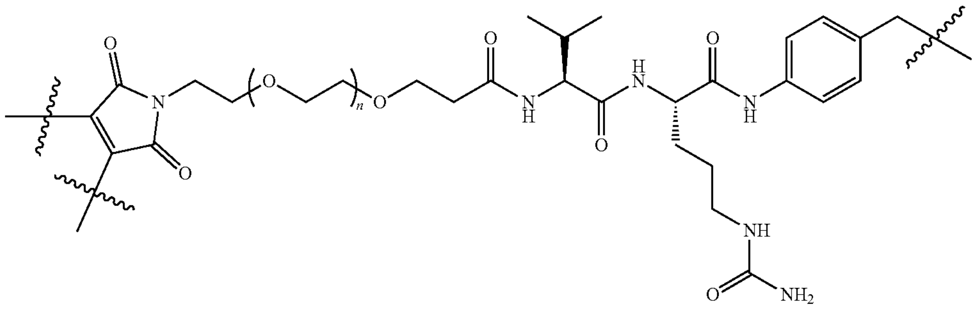 |

TABLE 5-continued
| Exemplary $X_2$ Linkers | |
|---|---|
| Linker | Structure |
| K-5 Cleavable Linker | 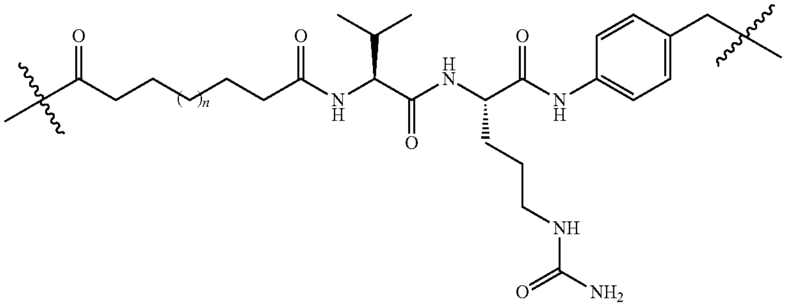 |
| K-6 Cleavable Linker | 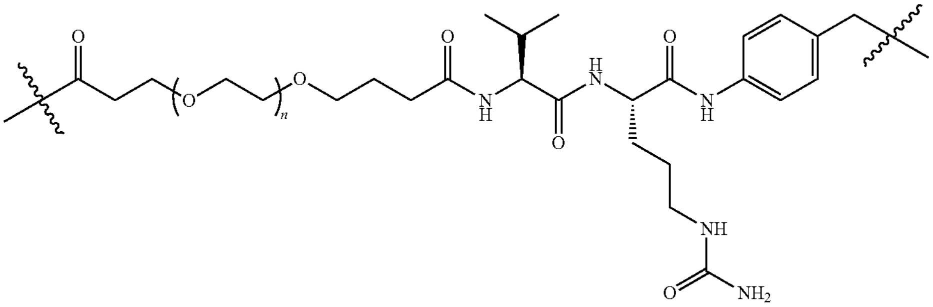 |
| K-7 Cleavable Linker | 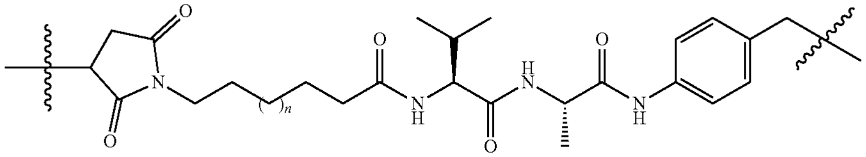 |
| K-8 Cleavable Linker | 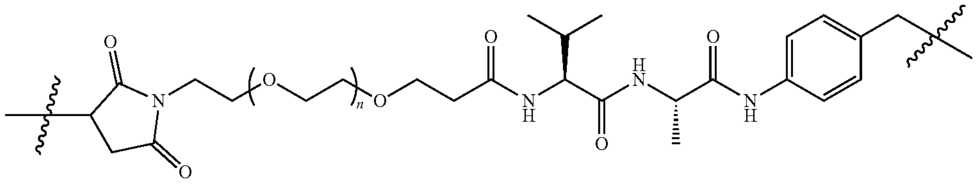 |
| K-9 Cleavable Linker | 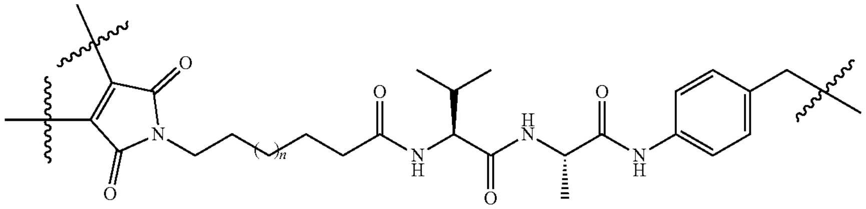 |
| K-10 Cleavable Linker | 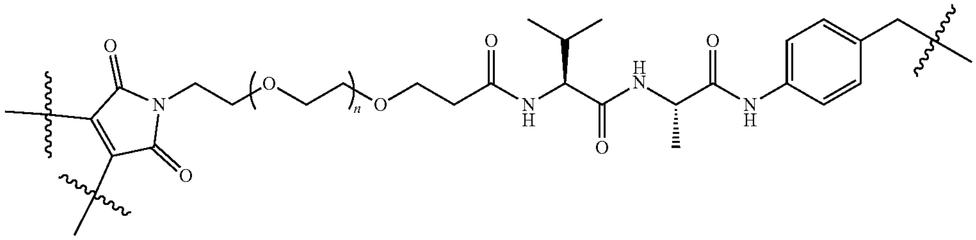 |

TABLE 5-continued
| Exemplary $X_2$ Linkers | |
|---|---|
| Linker | Structure |
| K-11 Cleavable Linker | 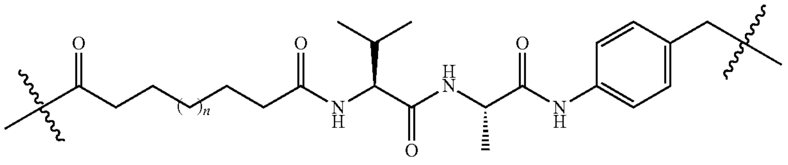 |
| K-12 Cleavable Linker | 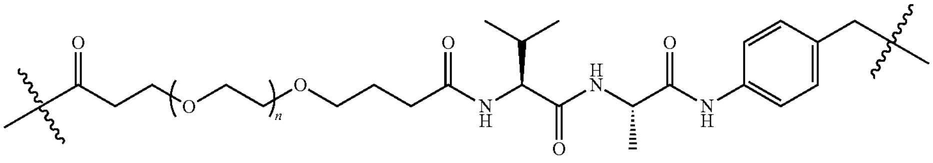 |
| K-13 Cleavable Linker | 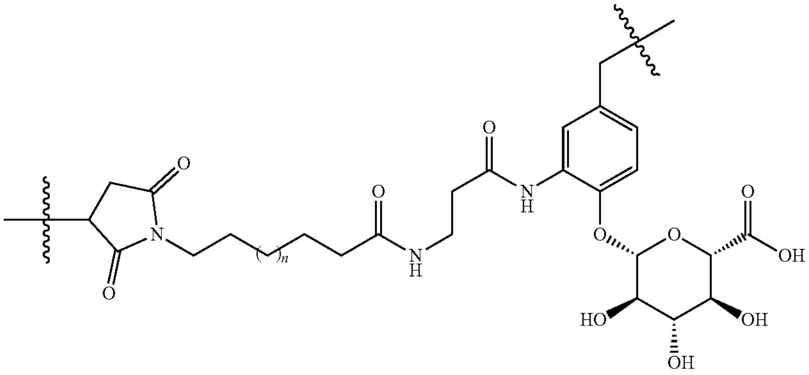 |
| K-14 Cleavable Linker | 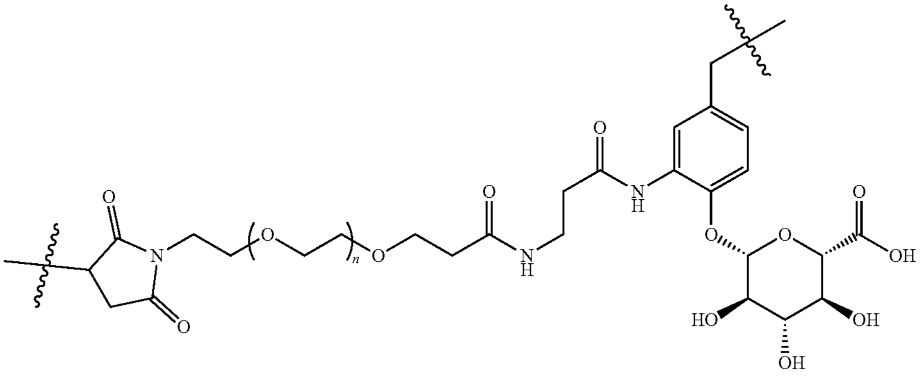 |
| K-15 Cleavable Linker | 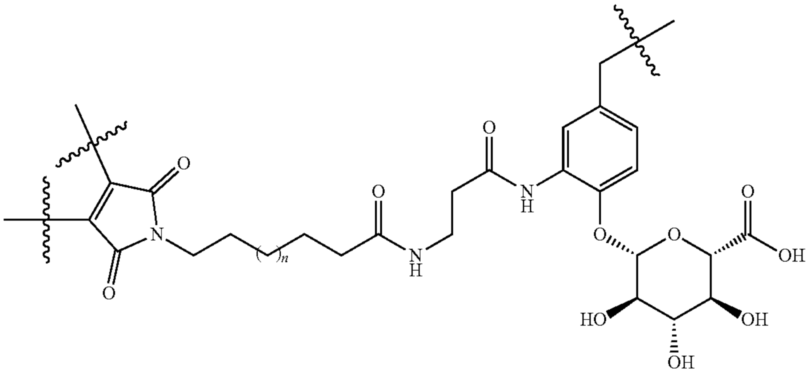 |

TABLE 5-continued
| Exemplary $X_2$ Linkers | |
|---|---|
| Linker | Structure |
| K-16 Cleavable Linker | 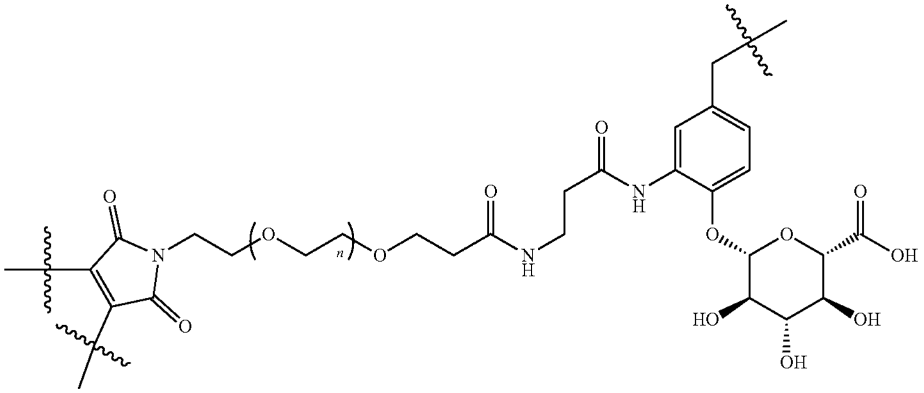 |
| K-17 Cleavable Linker | 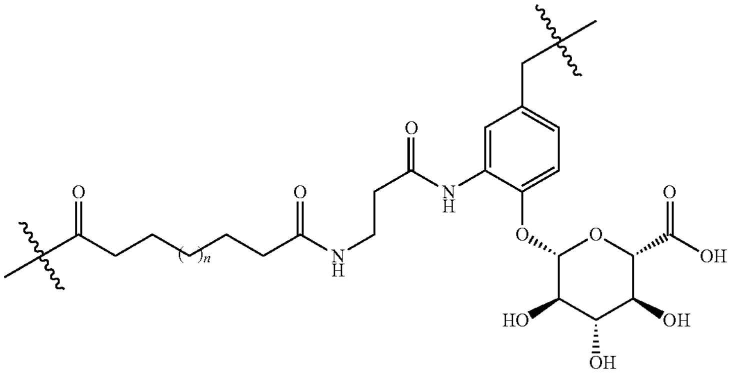 |
| K-18 Cleavable Linker | 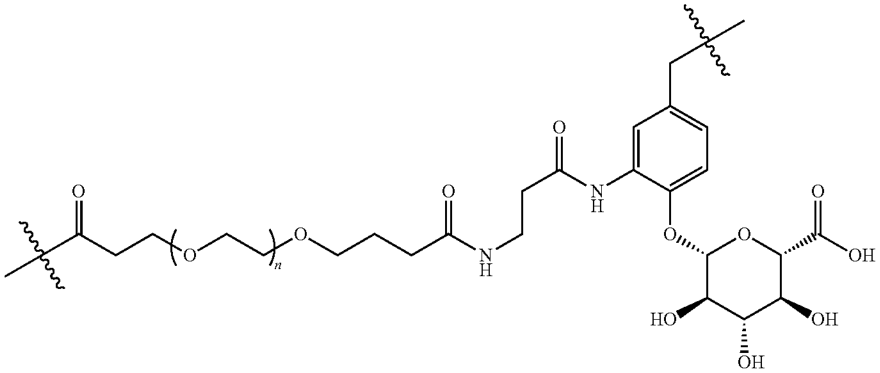 |
| K-19 Non-Cleavable Linker | 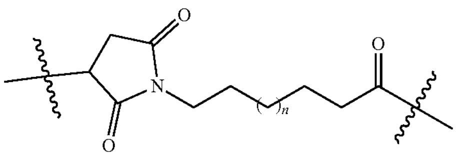 |
| K-20 Non-Cleavable Linker | 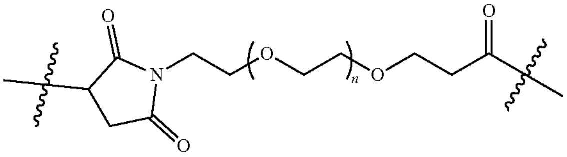 |

TABLE 5-continued

Exemplary $X_2$ Linkers

| Linker | Structure |
|---|---|
| K-21 Non-Cleavable Linker | 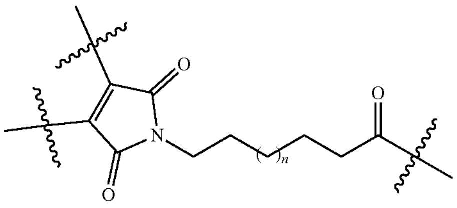 |
| K-22 Non-Cleavable Linker | 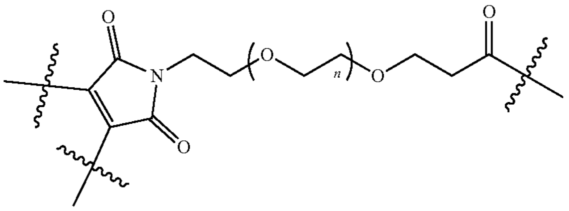 |
| K-23 Non-Cleavable Linker | 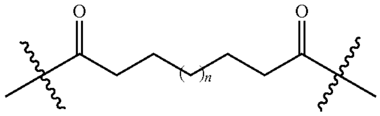 |
| K-24 Non-Cleavable Linker | 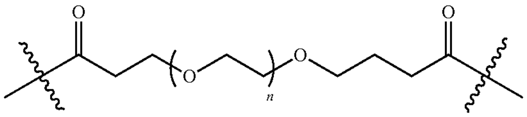 |

In some embodiments of the compound of Formula (II) or Formula (III), $X_2$ is a cleavable or non-cleavable linker selected from the group consisting of K-1, K-2, K-3, K-4, K-5, K-6, K-7, K-8, K-9, K-10, K-11, K-12, K-13, K-14, K-15, K-16, K-17, K-18, K-19, K-20, K-21, K-22, K-23 and K-24.

In some embodiments of the compound of Formula (II) or Formula (III), $X_2$ is a cleavable linker and is selected from the group consisting of K-1, K-2, K-3, K-4, K-5, K-6, K-7, K-8, K-9, K-10, K-11, K-12, K-13, K-14, K-15, K-16, K-17 and K-18.

In some embodiments of the compound of Formula (II) or Formula (III), $X_2$ is a non-cleavable linker selected from the group consisting of K-19, K-20, K-21, K-22, K-23 and K-24.

In some embodiments of the compound of Formula (II) or Formula (III), $X_2$ is a mixture of $X_{2b}$ and $X_{2c}$, wherein $X_{2b}$ is a linker that is bound to one Cys residue on $X_1$ and $X_{2c}$ is a linker that is bound to two Cys residues on $X_1$, n is a combination of n1 and n2, wherein n1 corresponds to the number of $X_{2b}$ moieties bound to $X_1$ and n2 corresponds to the number of $X_{2c}$ moieties bound to $X_1$, and wherein the sum of n1 and n2 is 2, 3, 4, 5, 6, 7, 8, 9, 10, or 11. In certain such embodiments, $X_{2b}$ is K-1 and $X_{2c}$ is K-19. In some embodiments of the compound of Formula (II) or Formula (III), wherein $X_2$ is a mixture of $X_{2b}$ and $X_{2c}$, $X_{2b}$ is selected from the group consisting of K-1, K-2, K-4, K-6, K-8, K-11, K-13, K-15, K-17, and K-18 and $X_{2c}$ is K-19. In some embodiments, each $X_2$ bound to $X_1$ is an $X_{2b}$ moiety. In some embodiments, each $X_2$ bound to $X_1$ is an $X_{2c}$ moiety.

In some embodiments of the compound of Formula (II) or Formula (III), $X_3$ is a therapeutic compound as detailed herein.

In some embodiments, the compound of Formula (II) or Formula (III) is a compound listed in Tables 6, or a pharmaceutically acceptable salt, solvate, hydrate, isomer, or tautomer thereof, wherein $X_1$ is a biologically active polypeptide or hormone or if the compound is of Formula (III), an Insulin polypeptide or a bio-active homolog polypeptide thereof, and n is 1, 2, 3, 4, 5, 6, 7, 8, 9, 10 or 11. In Table 6, R=H, alkyl, aryl, arylalkyl, glycol ether, or an additional glycol linker attaching to the therapeutic compound; q is 1, 2, 3, or 4; n1 is 1, 2, 3, 4, 5, 6, 7, 8, 9, or 10; and n2 is 1, 2, 3, 4, 5, 6, 7, 8, 9, or 10, wherein the sum of n1 and n2 is 2, 3, 4, 5, 6, 7, 8, 9, 10, or 11.

TABLE 6
| Exemplary Compounds of Formula (II) or Formula (III) for Treating Insulin Resistance, Type 2 Diabetes and Metabolic Syndrome | |
|---|---|
| Compound | Structure |
| B1 | 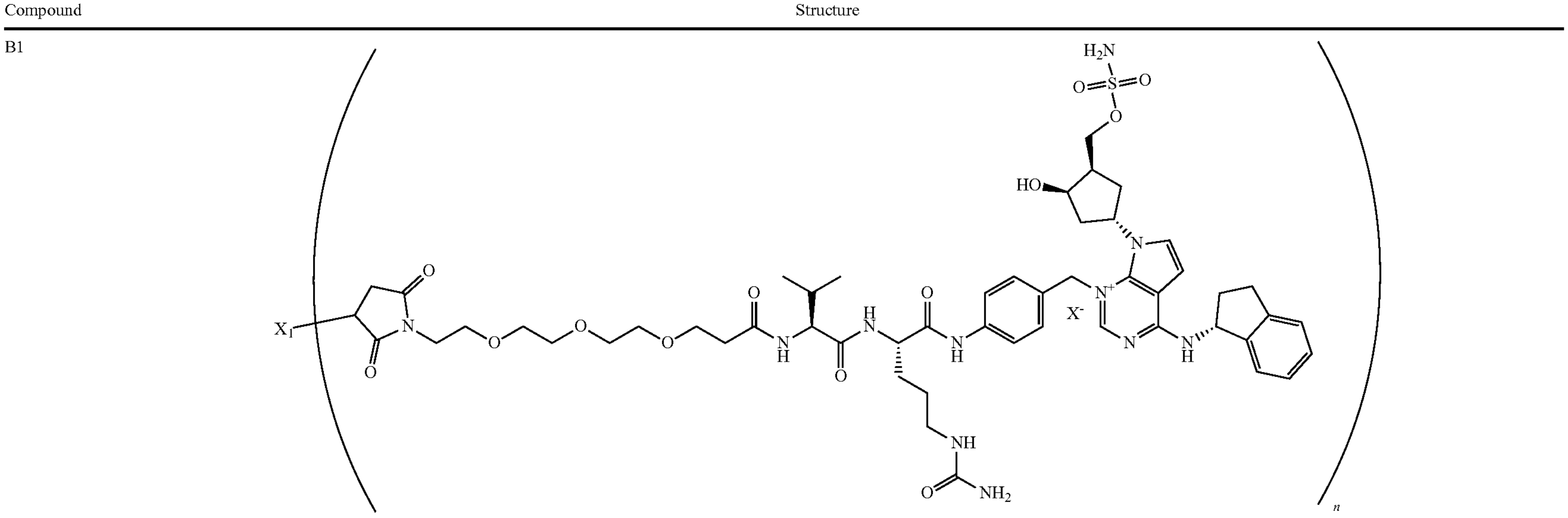 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B2 | 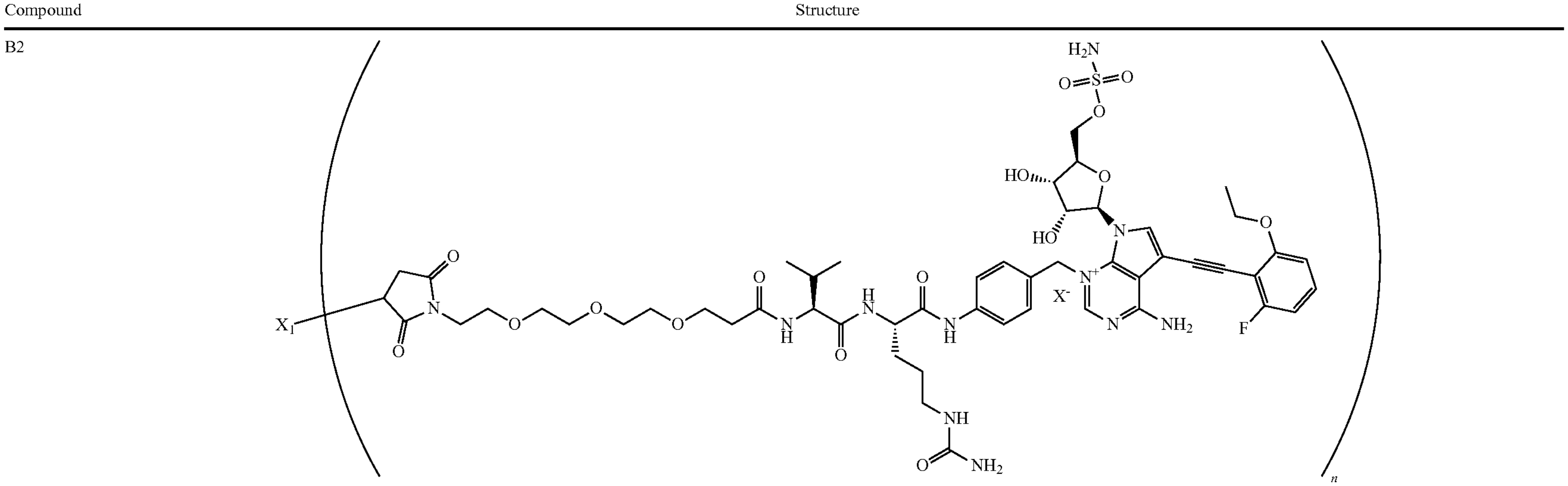 |
| B3 | 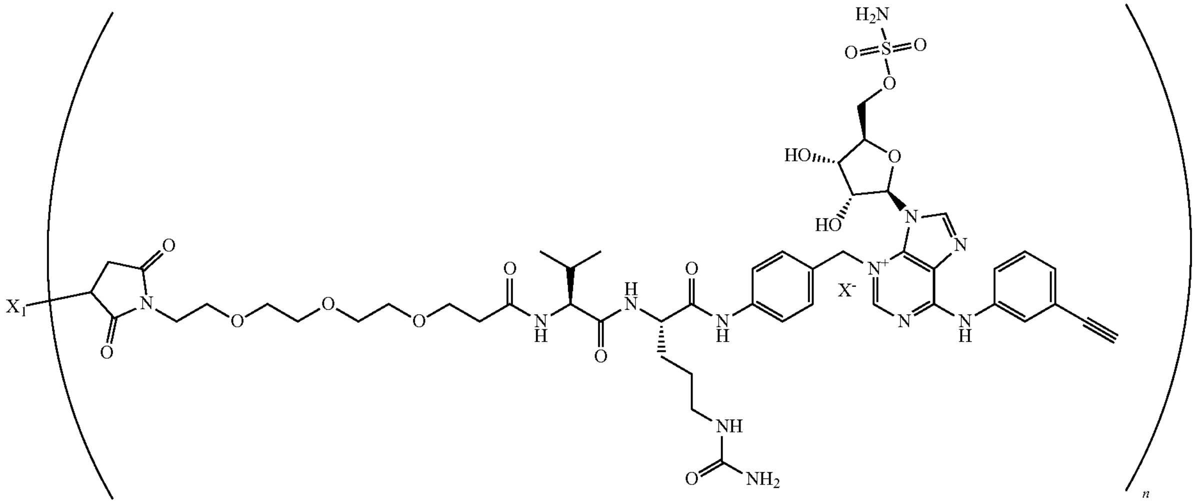 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B4 | 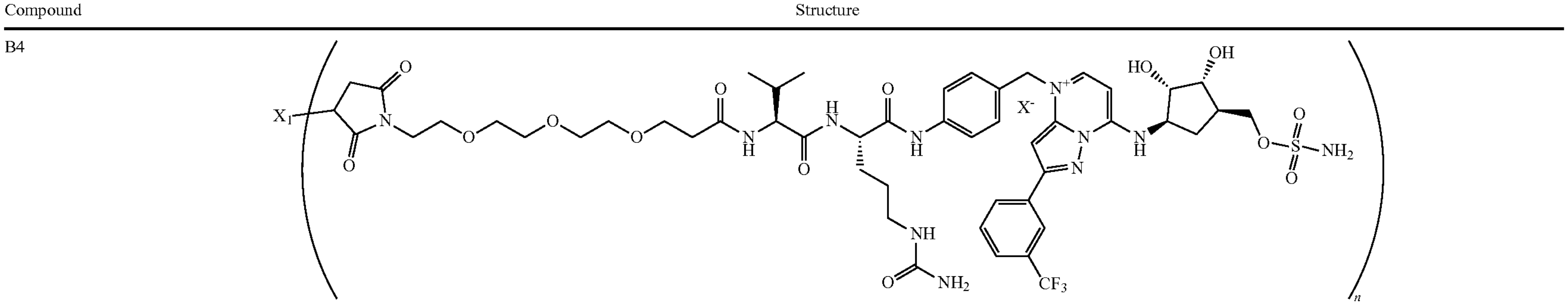 |
| B5 | 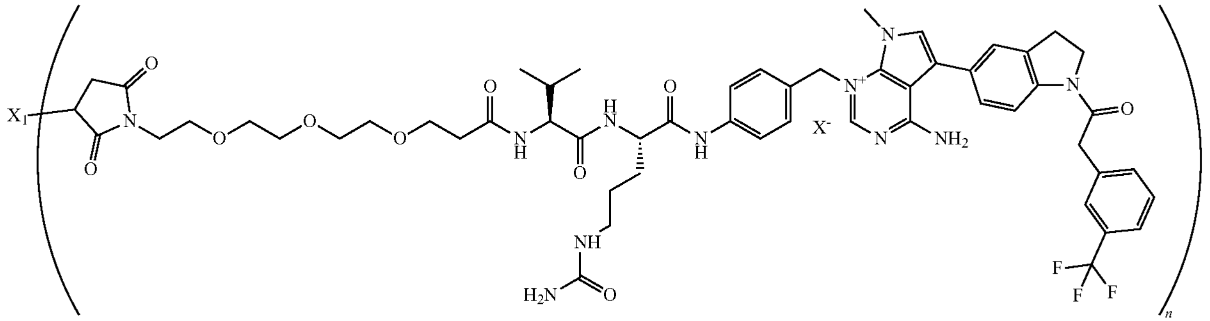 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B6 | 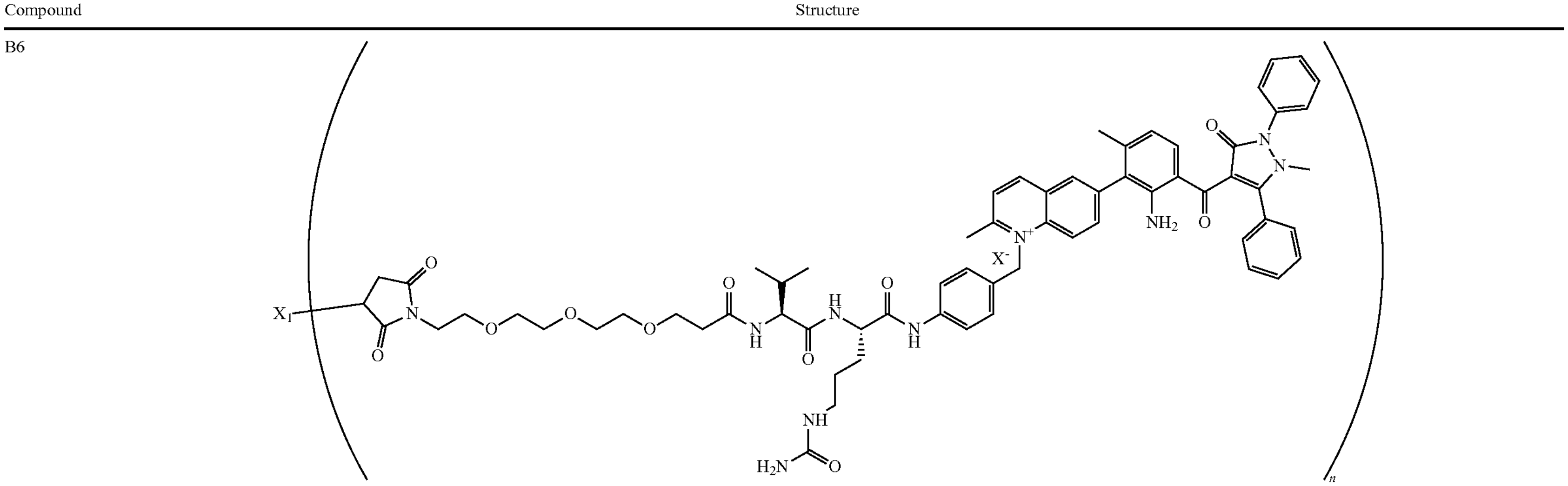 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B7 | 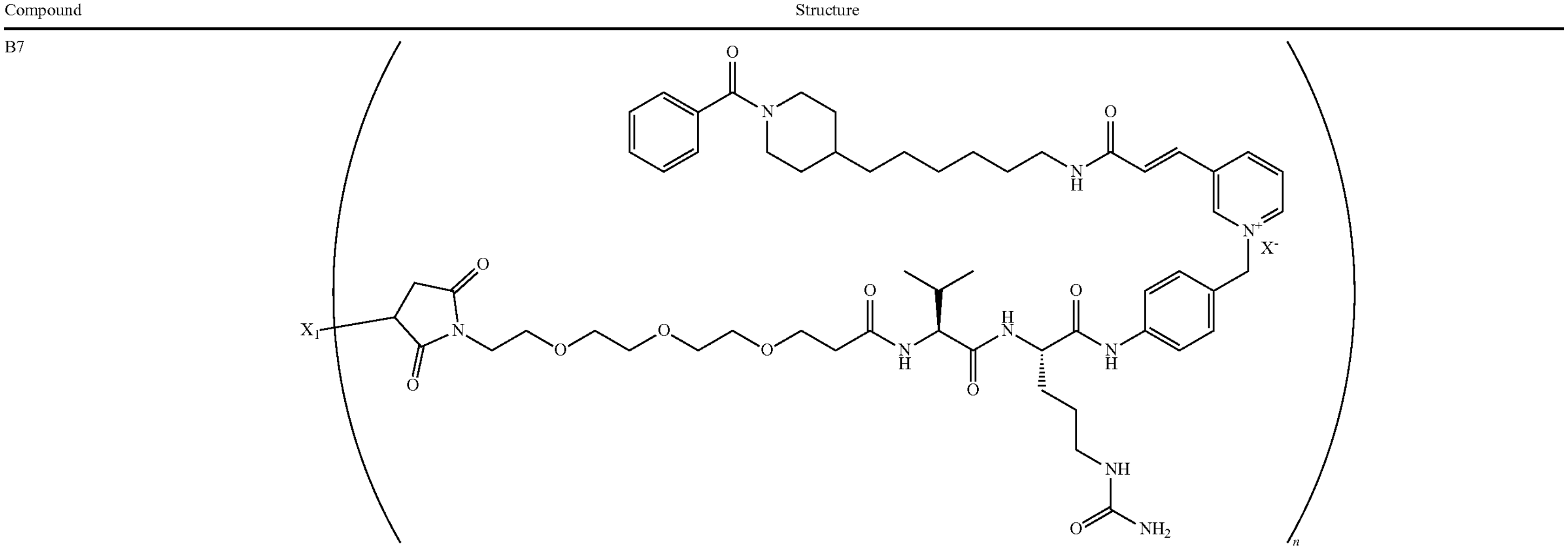 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B8 | 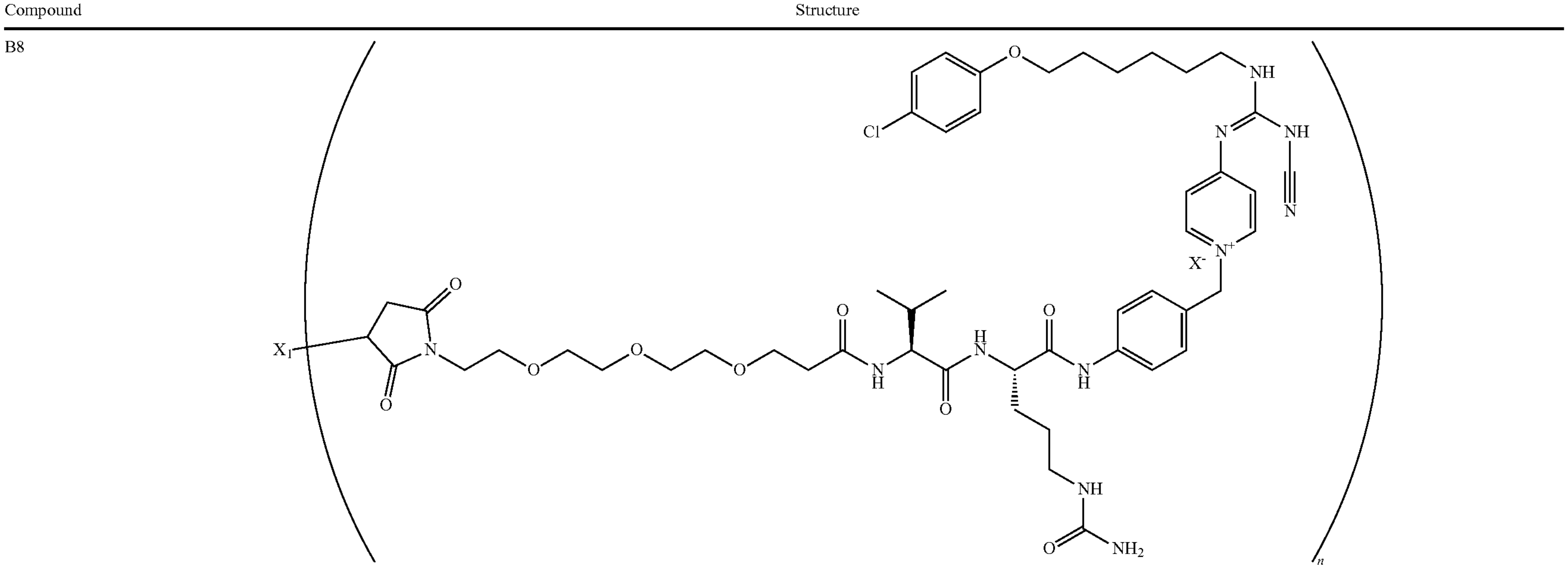 |
| B9 | 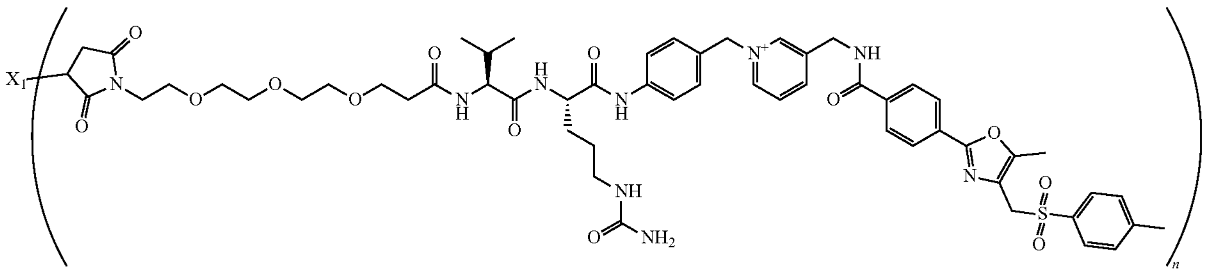 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B10 | 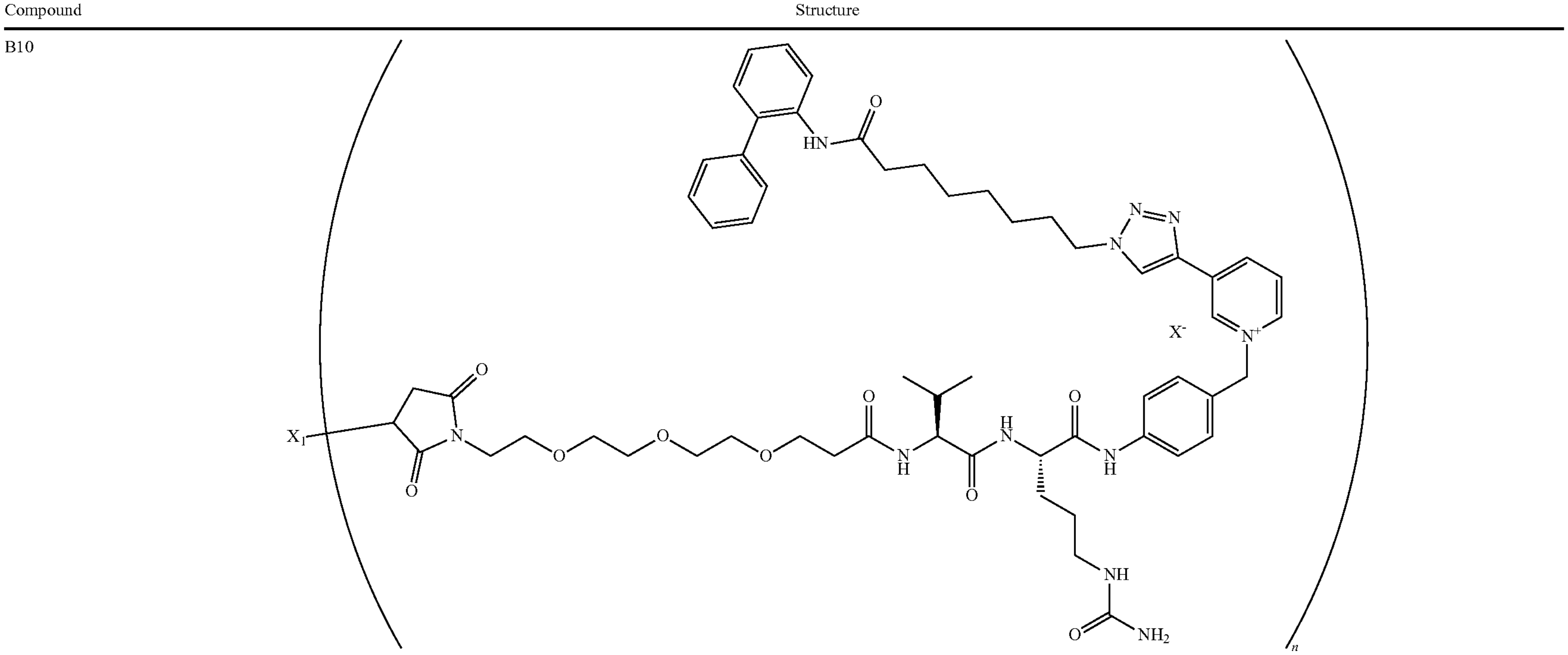 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B11 | 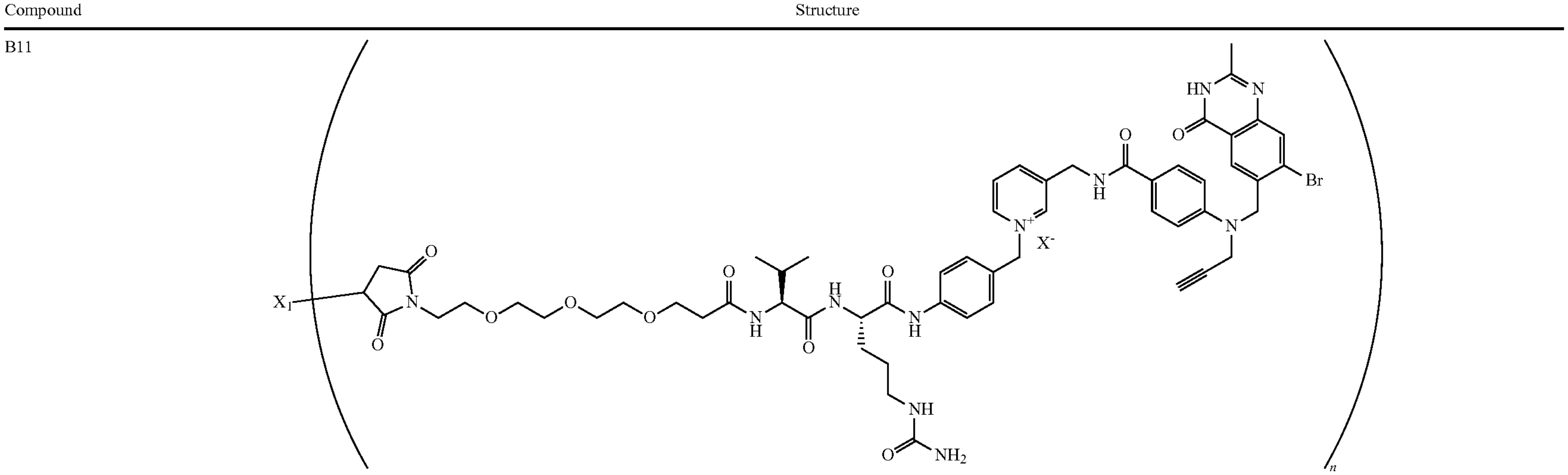 |
| B12 | 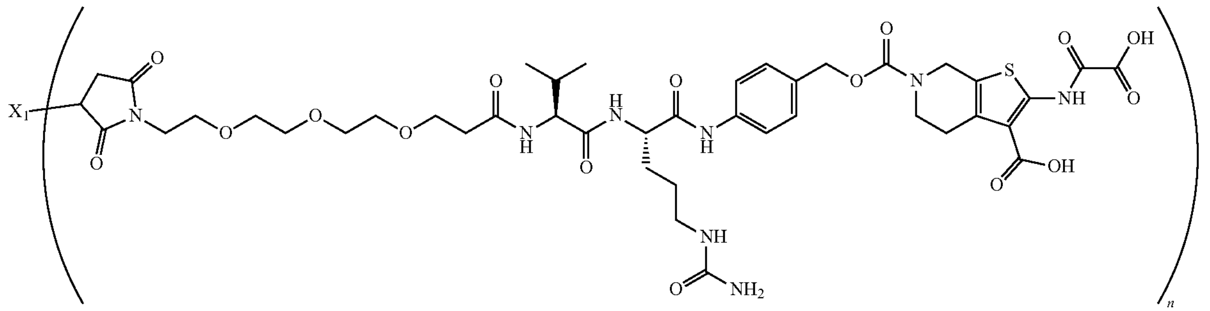 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B13 | 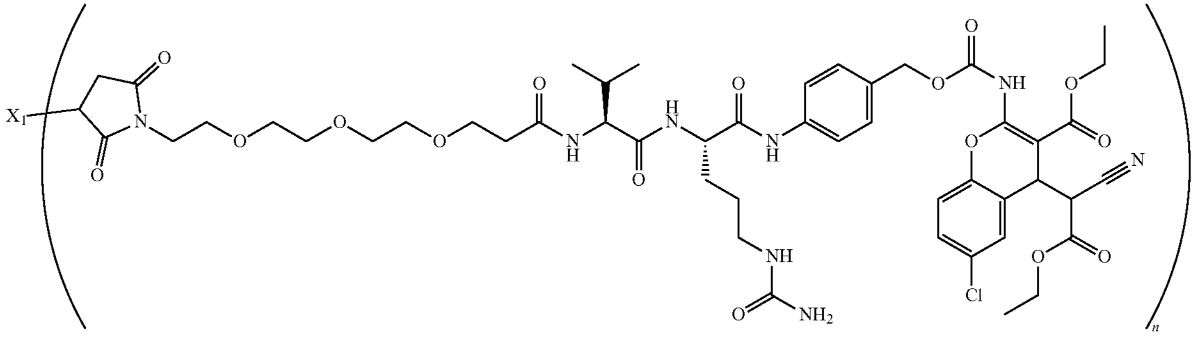 |
| B14 | 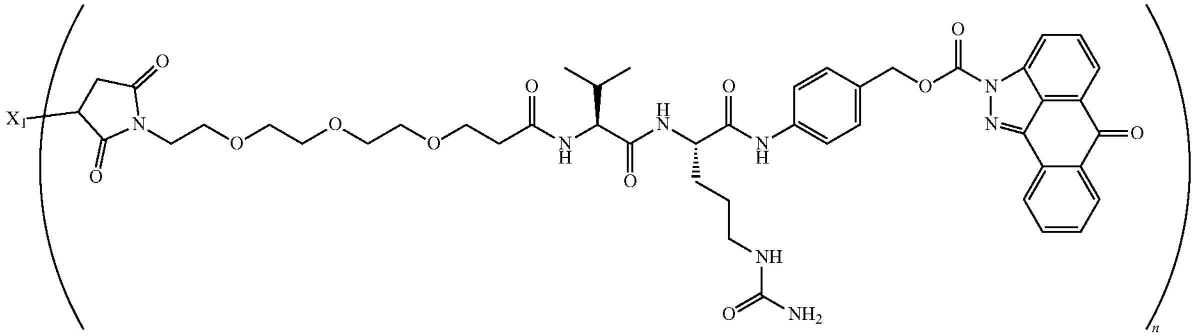 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B15 | 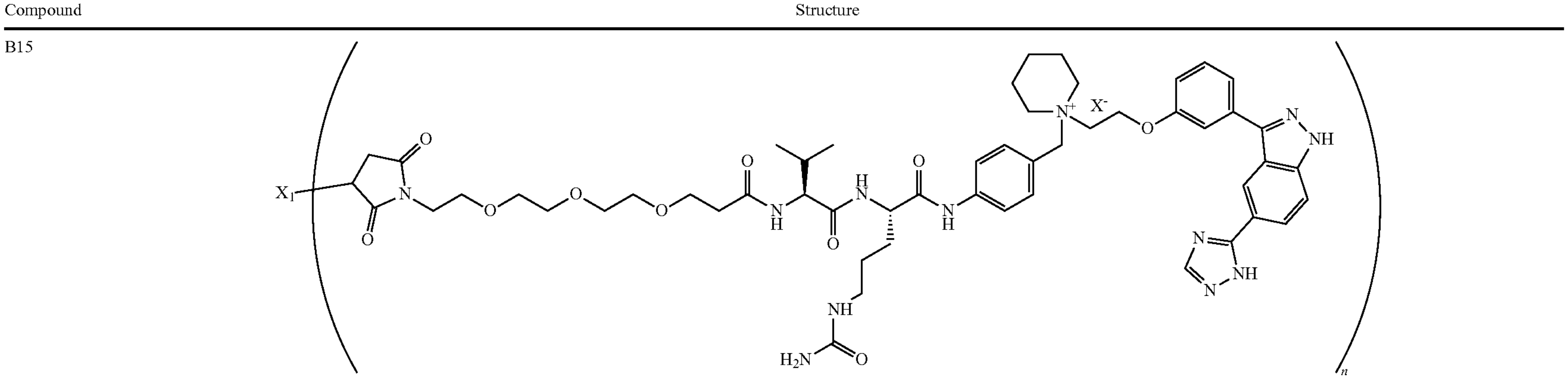 |
| B16 | 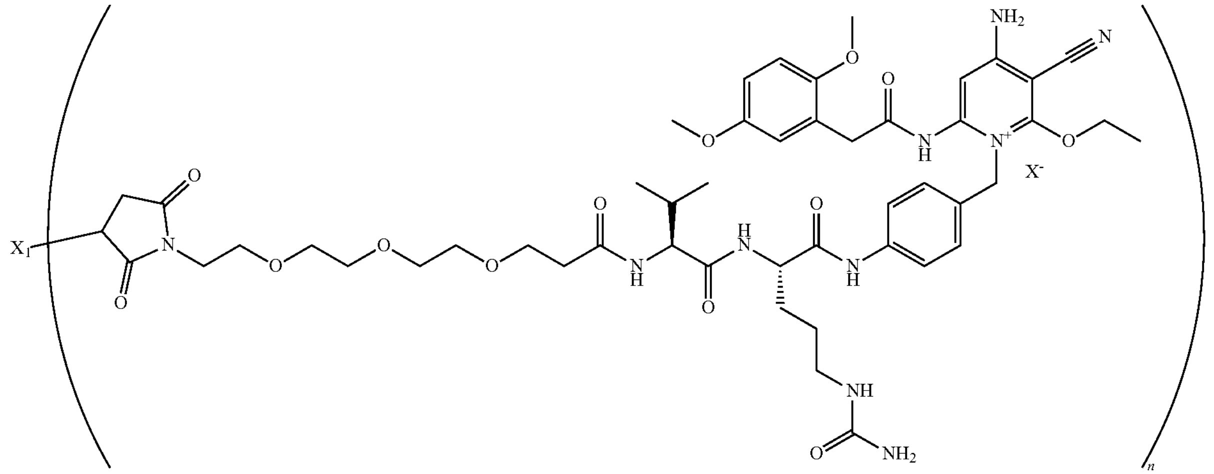 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B17 | 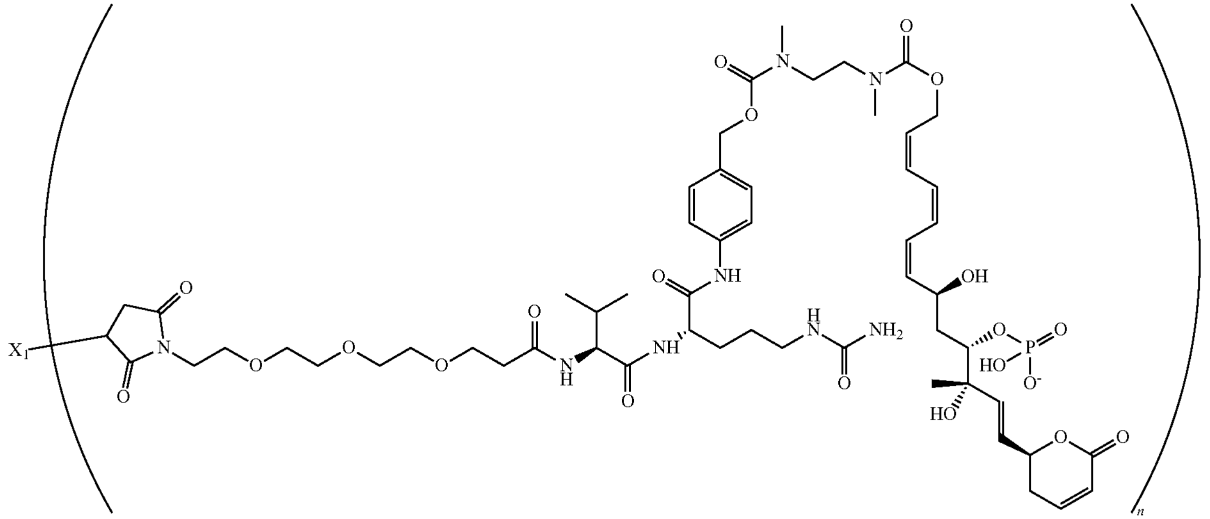 |
| B18 | 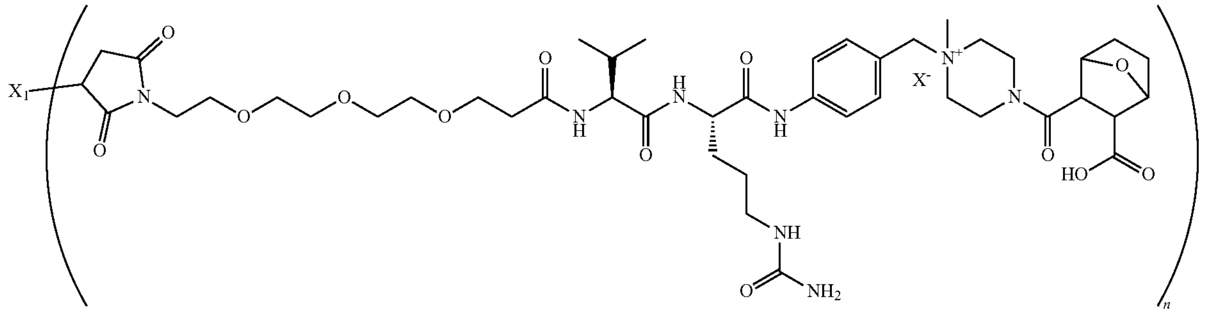 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B19 | 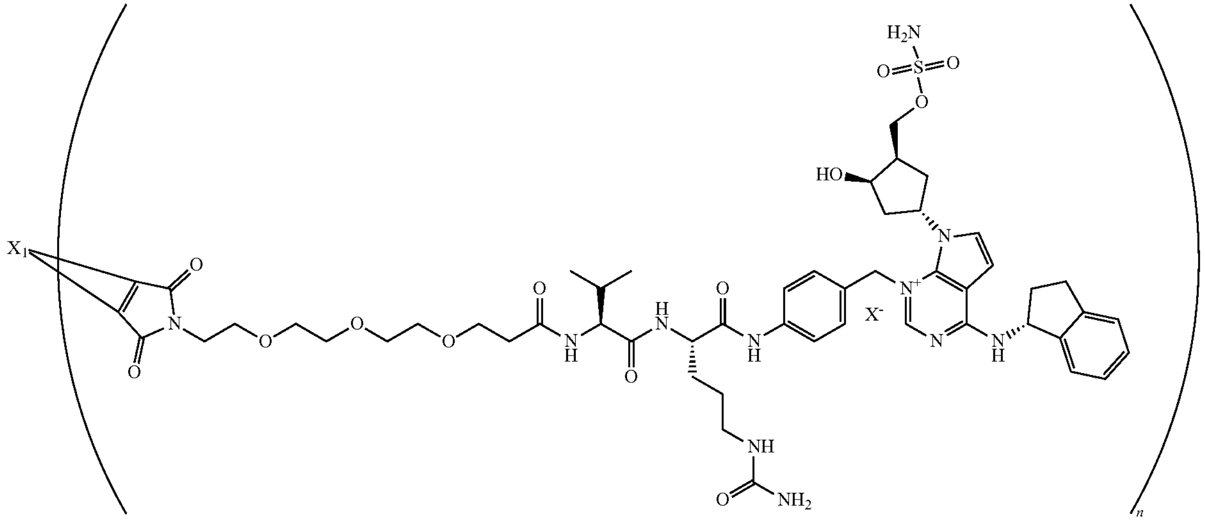 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B20 | 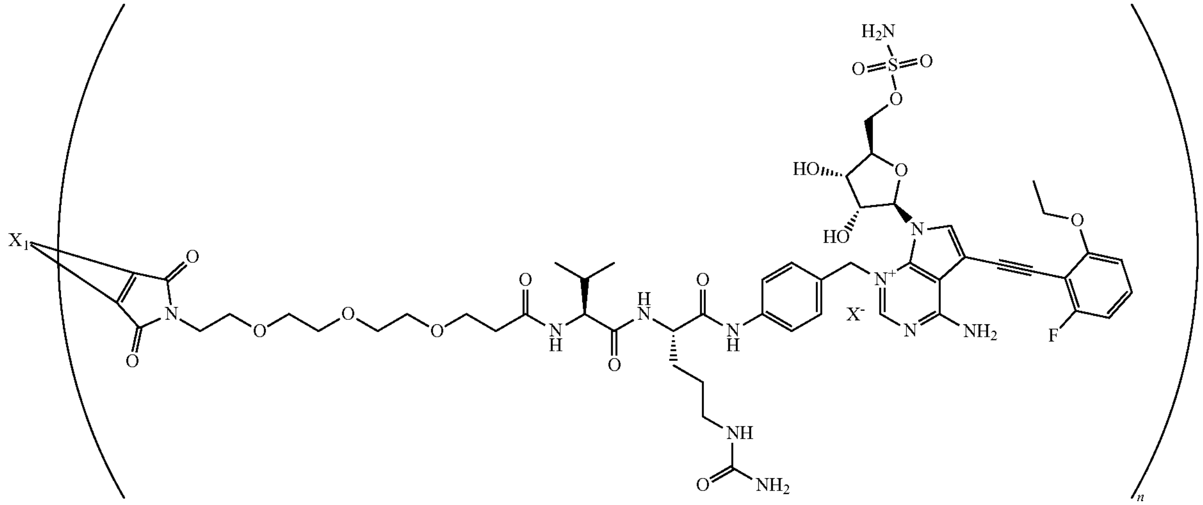 |
| B21 | 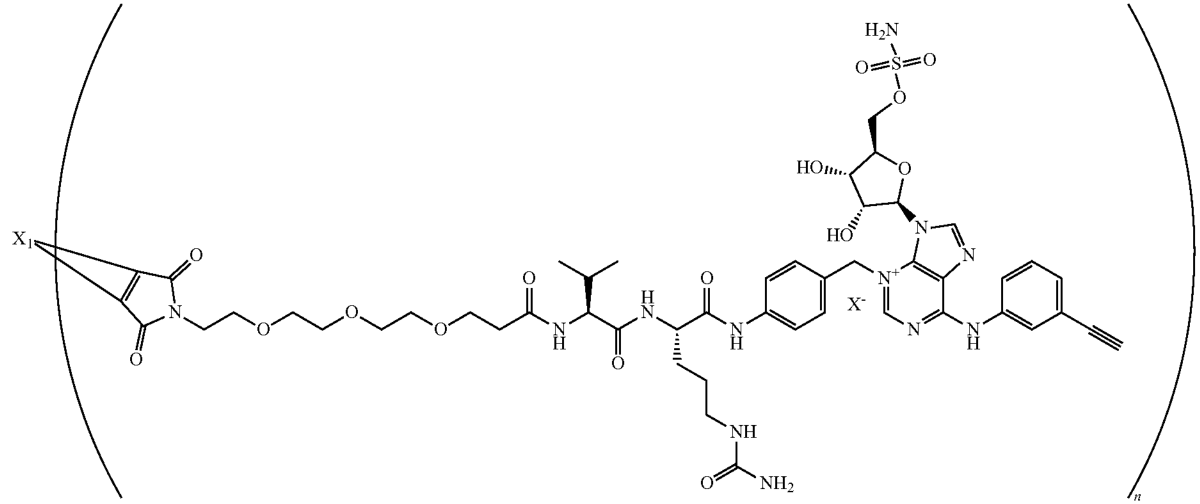 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B22 | 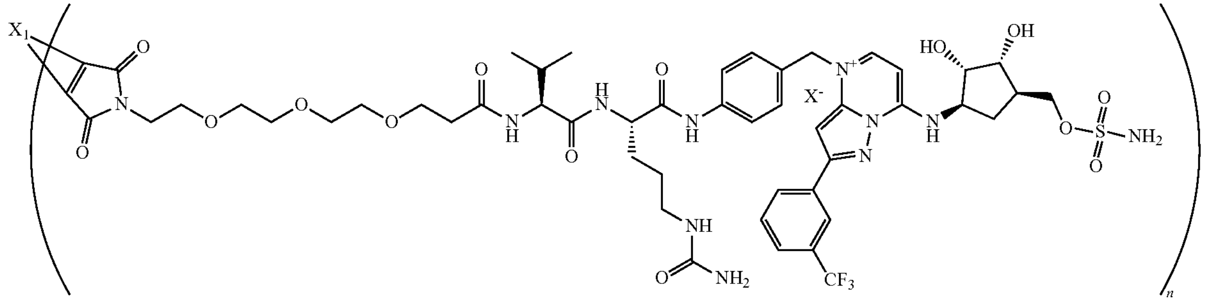 |
| B23 | 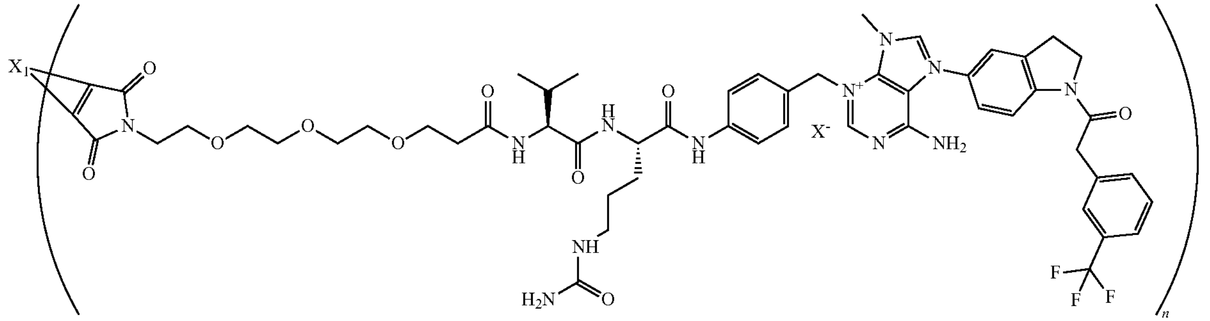 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B24 | 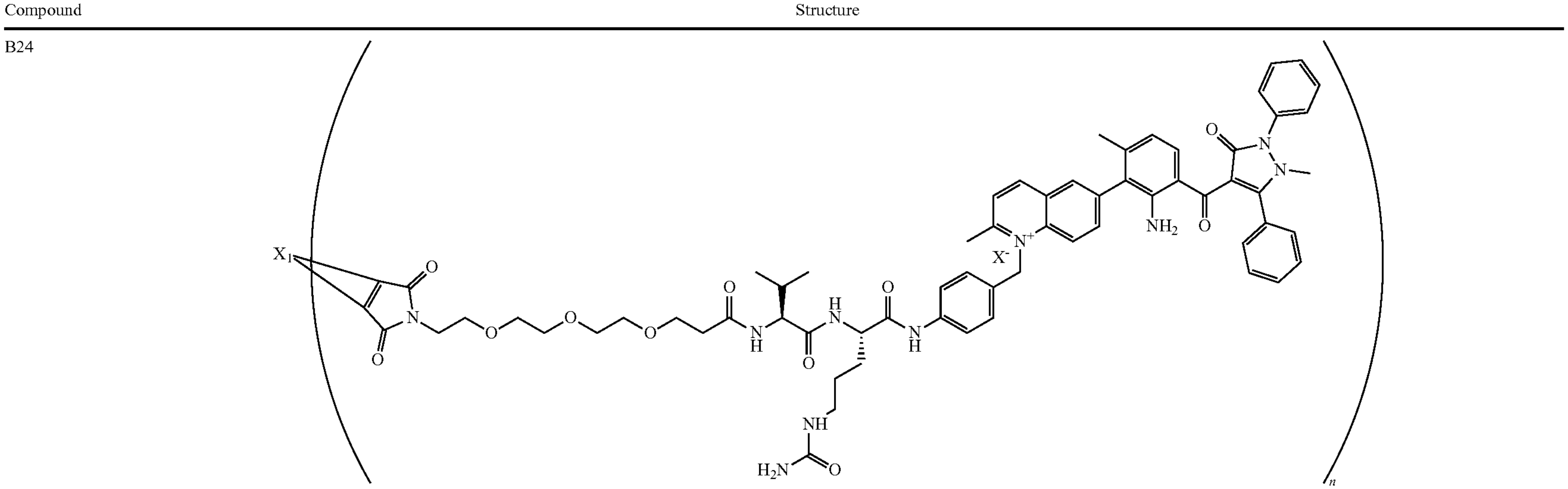 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B25 | 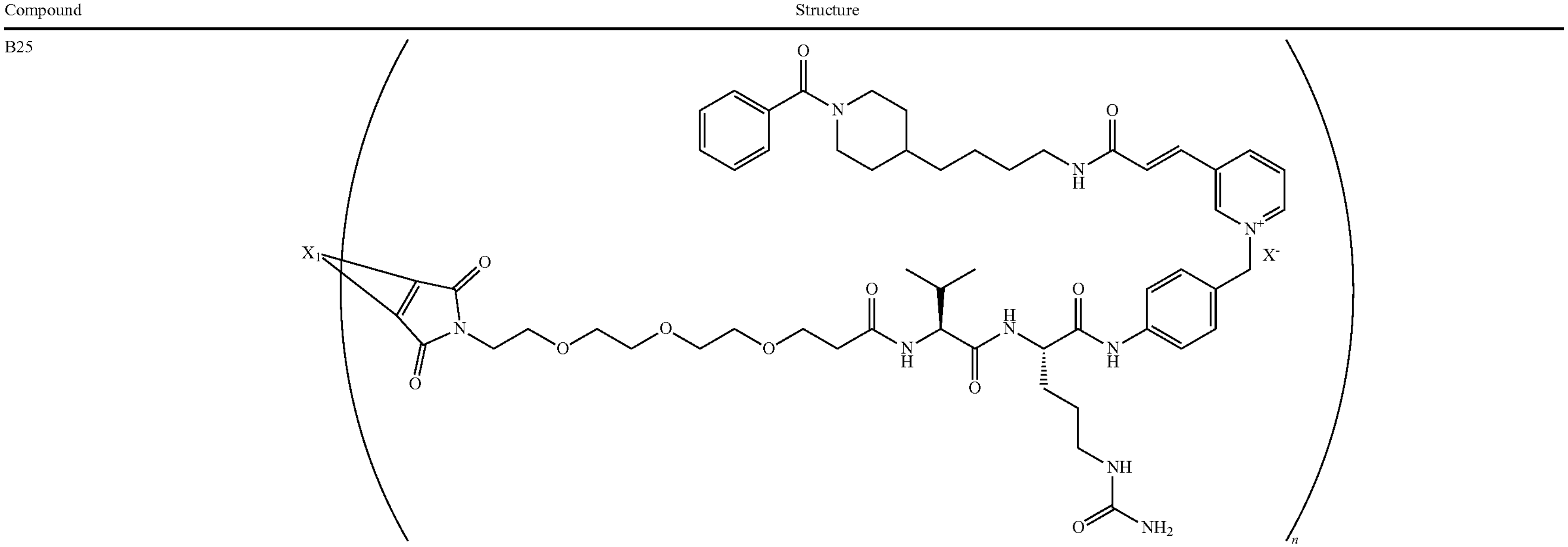 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B26 | 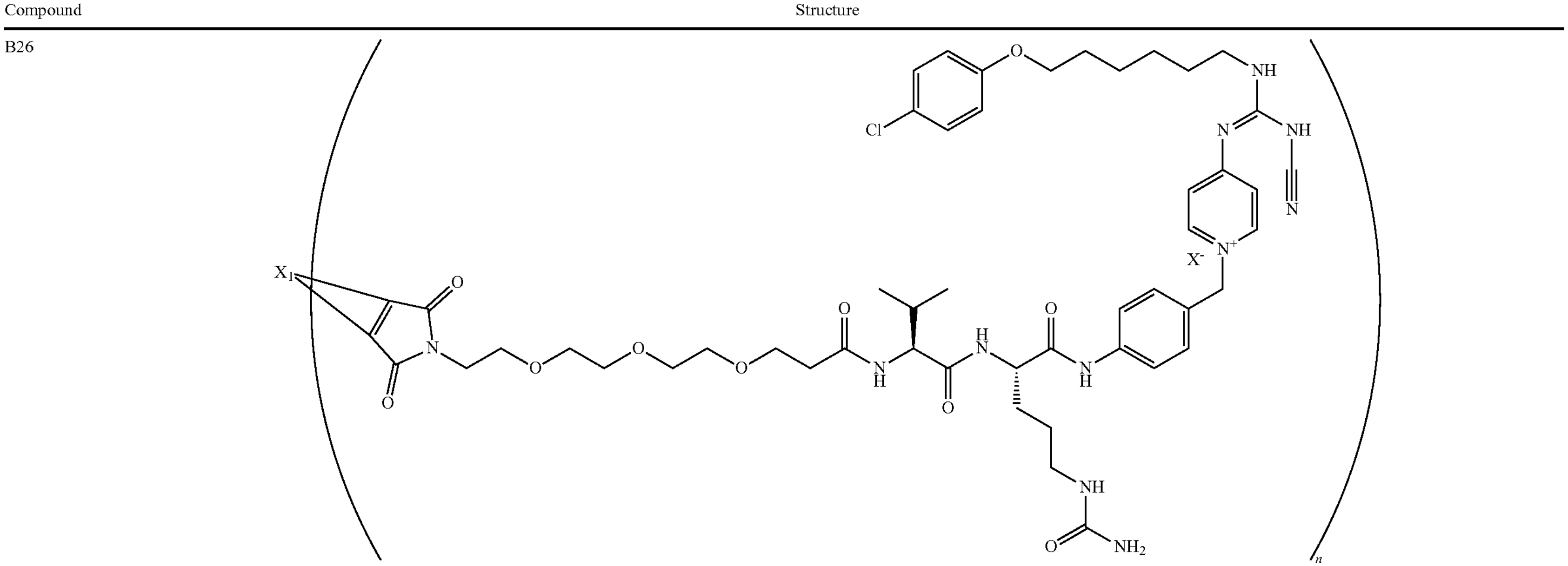 |
| B27 | 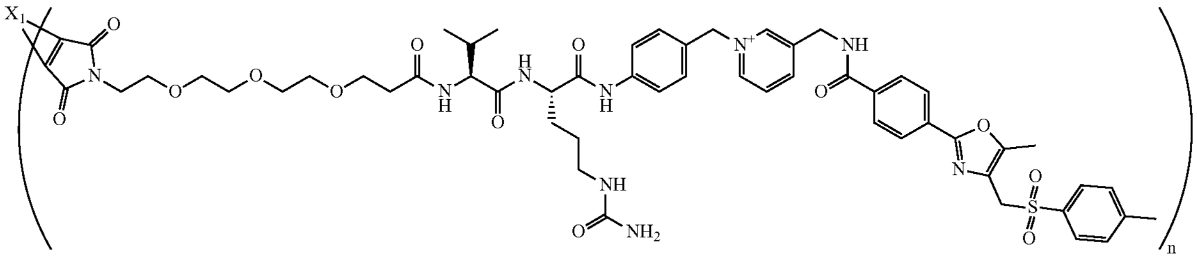 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B28 | 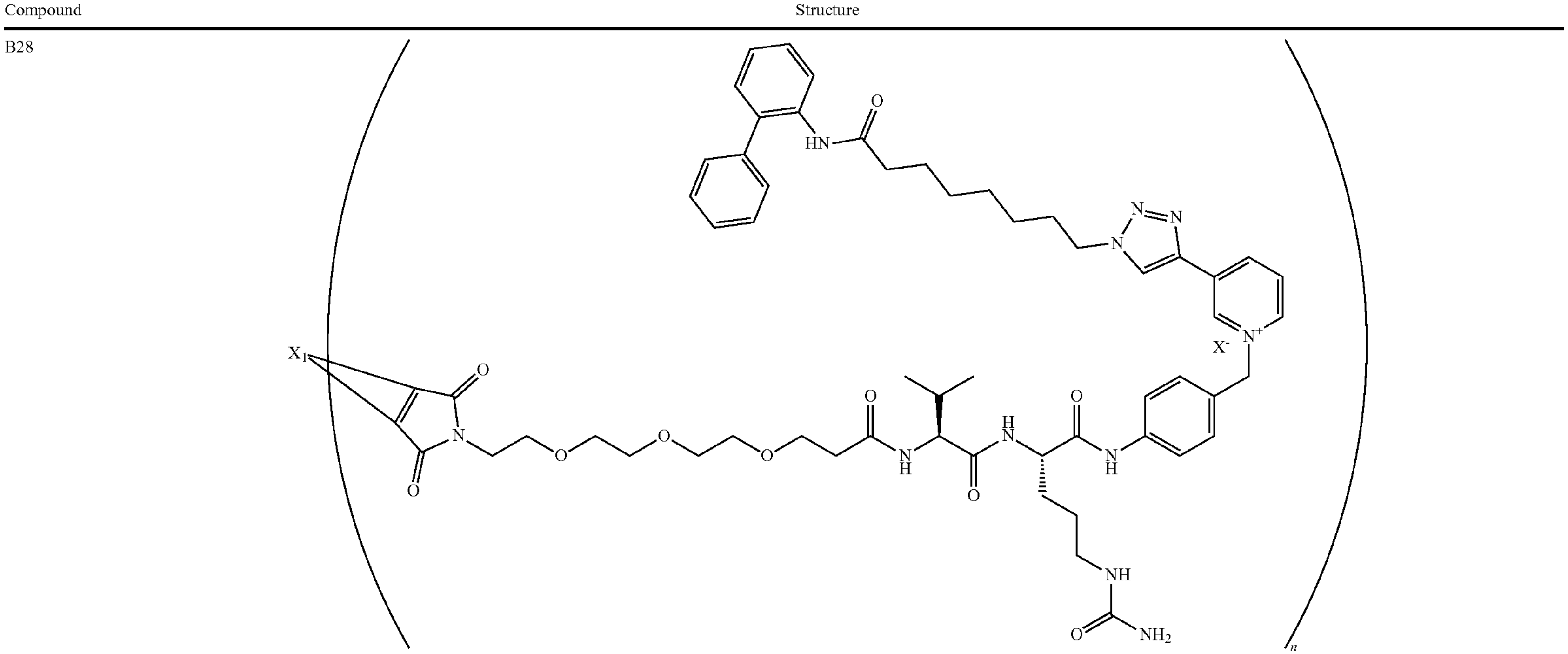 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B29 | 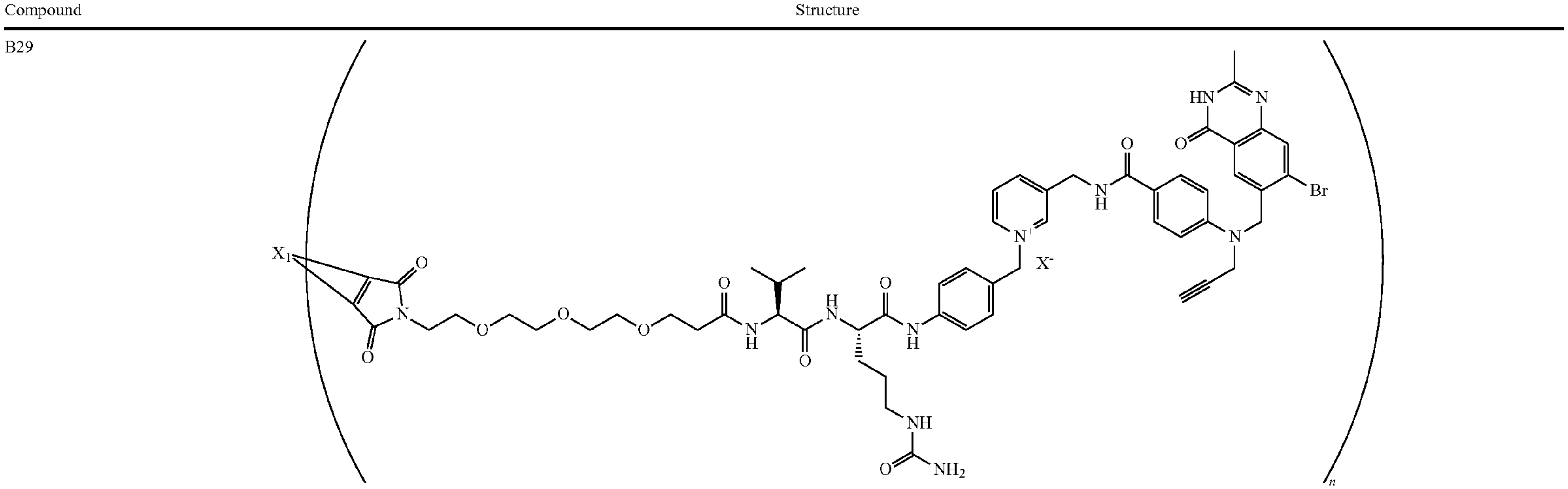 |
| B30 | 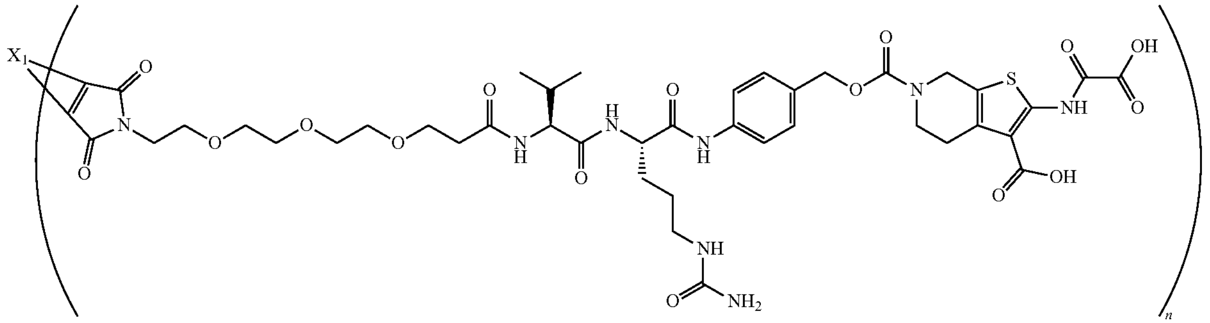 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B31 | 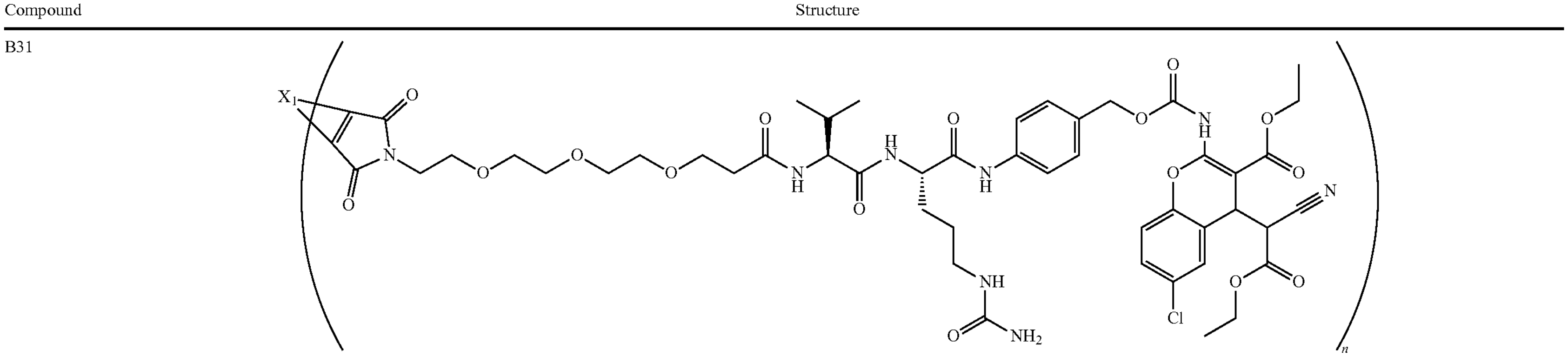 |
| B32 | 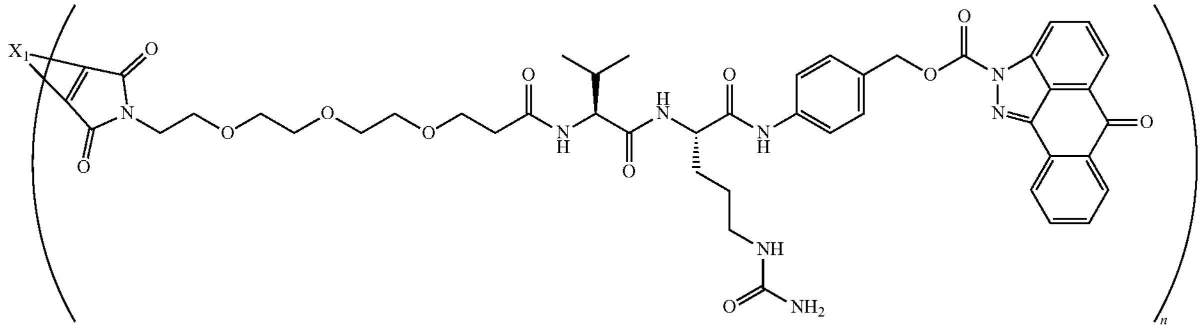 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B33 | 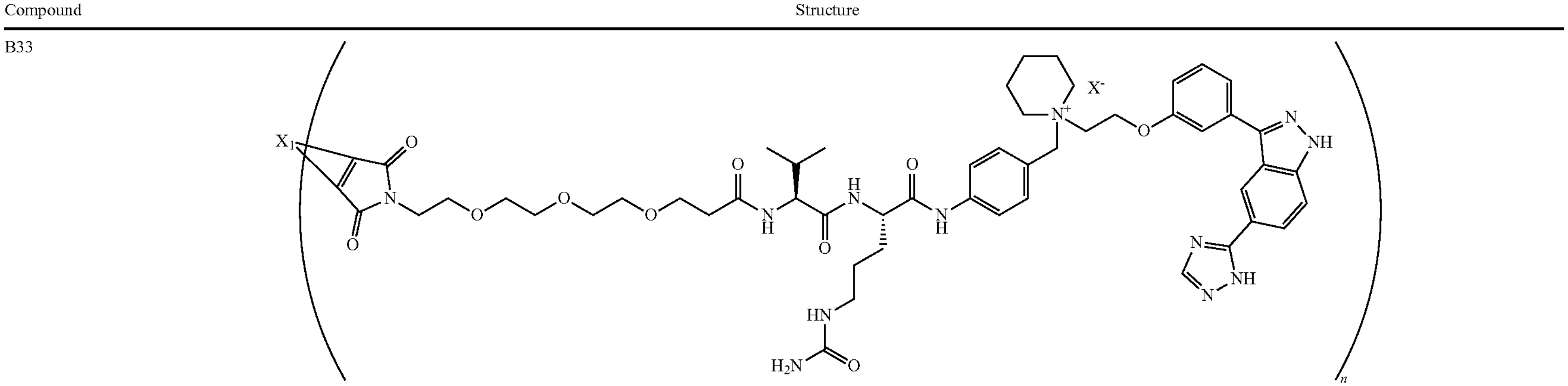 |
| B34 | 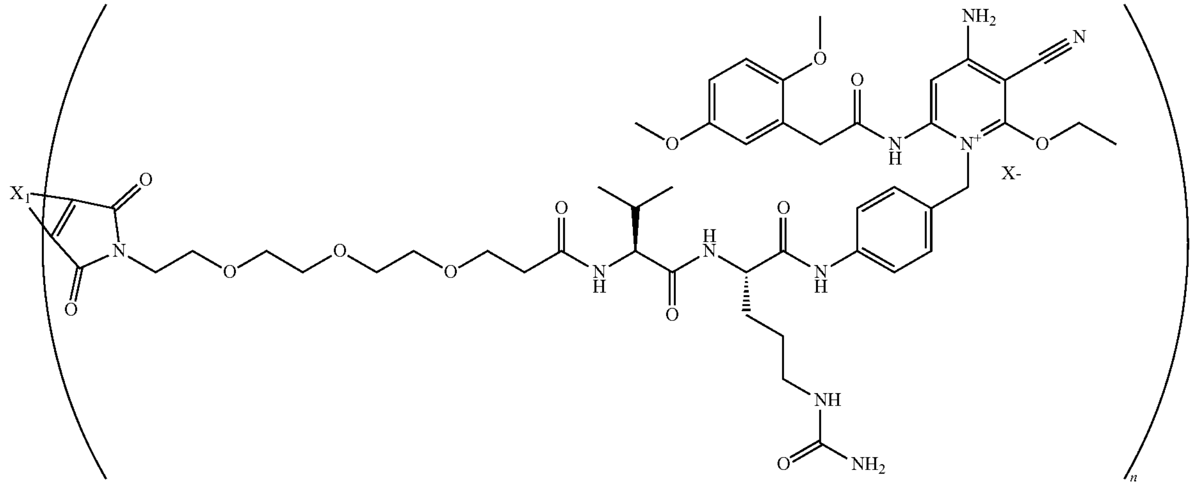 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B35 | 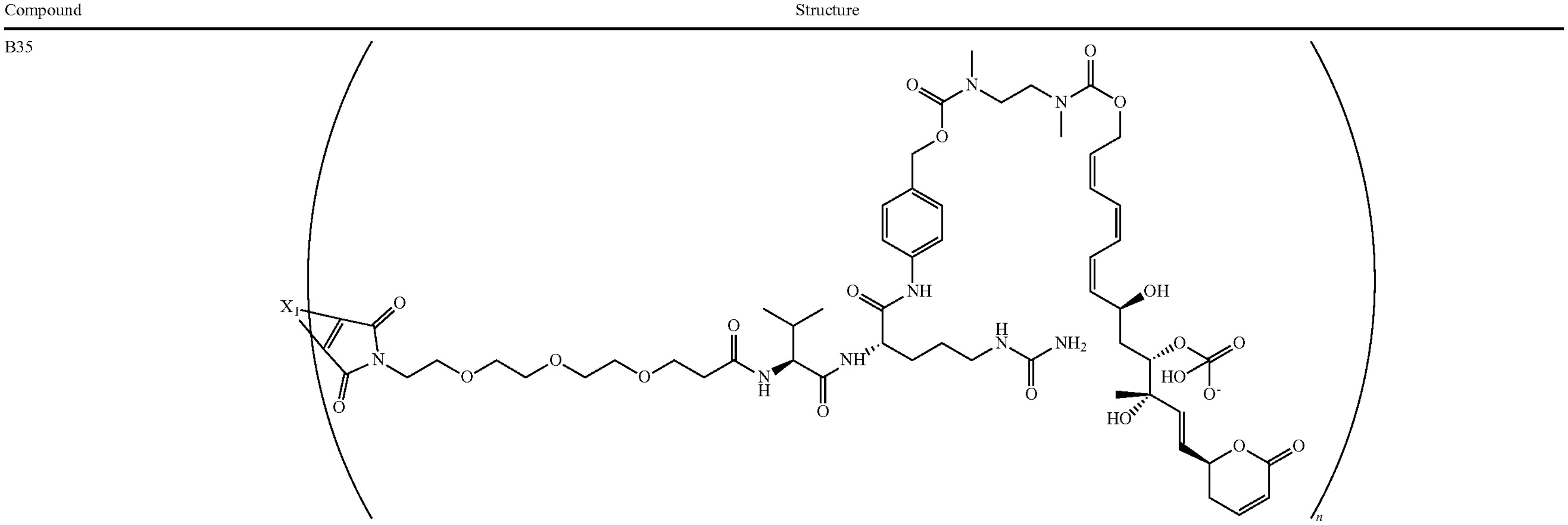 |
| B36 | 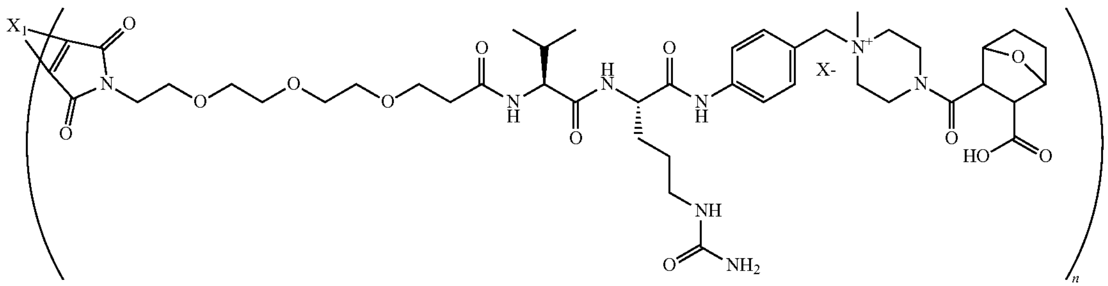 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B37 | 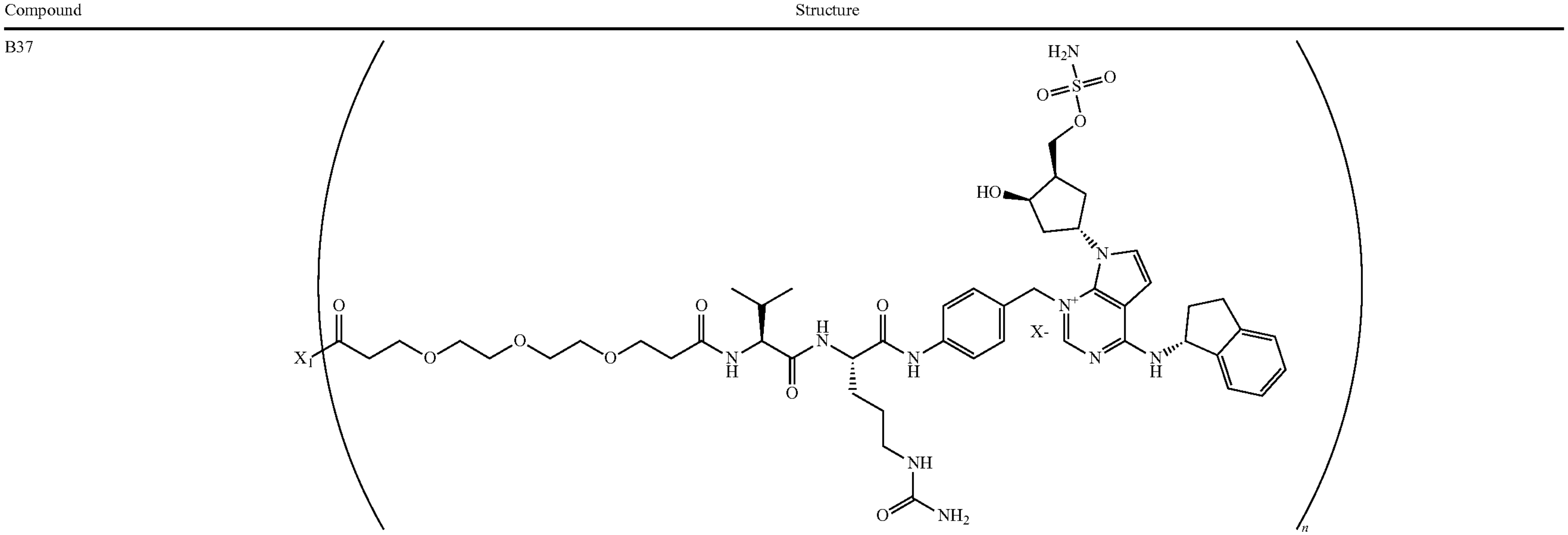 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B38 | 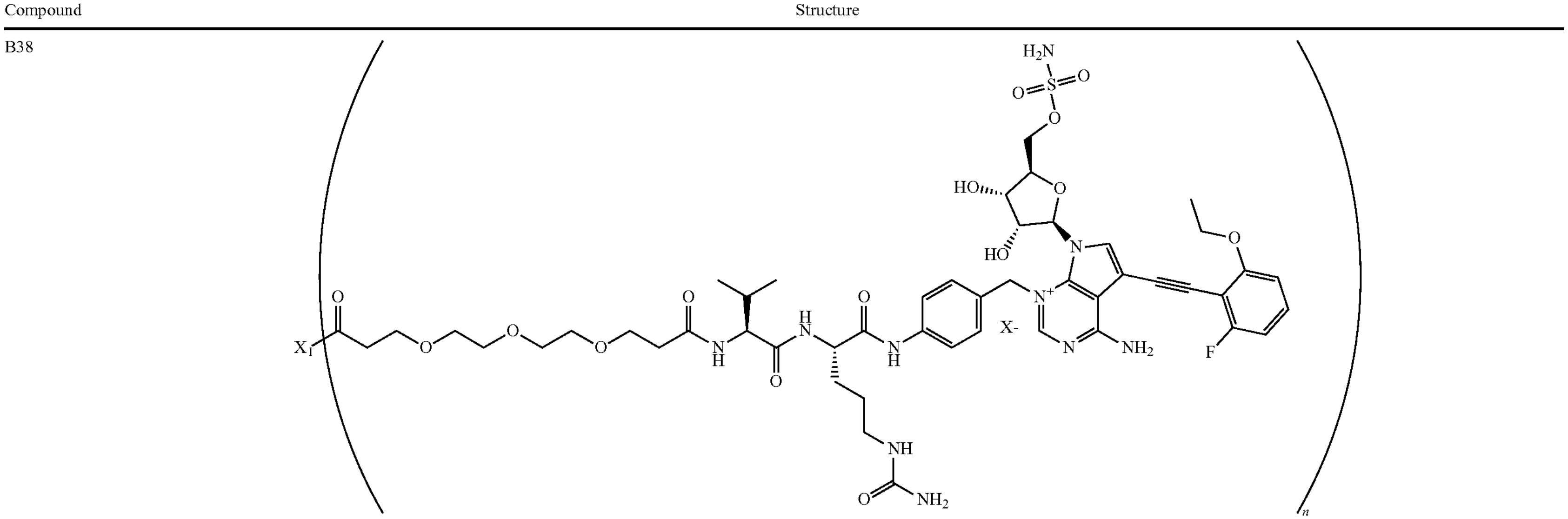 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B39 | 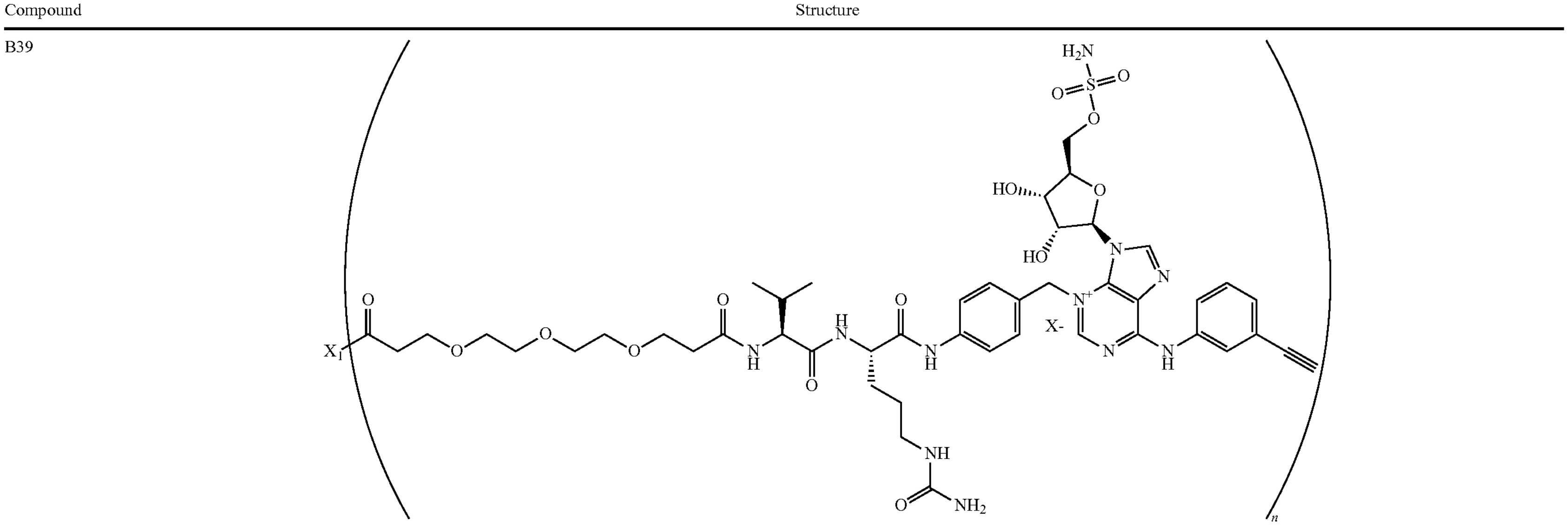 |
| B40 | 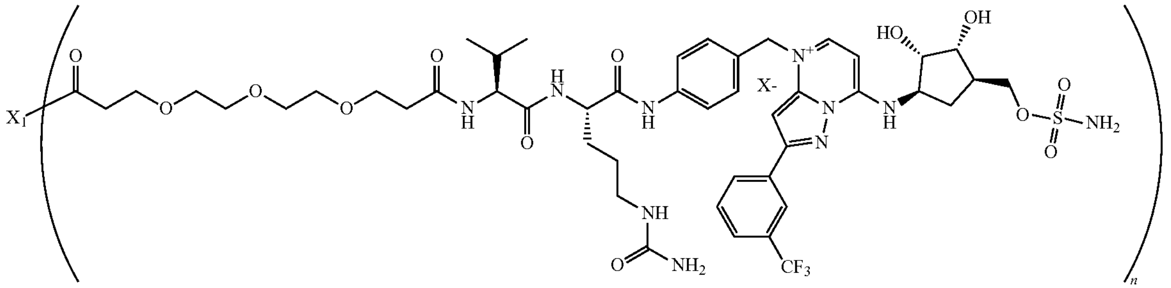 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B41 | 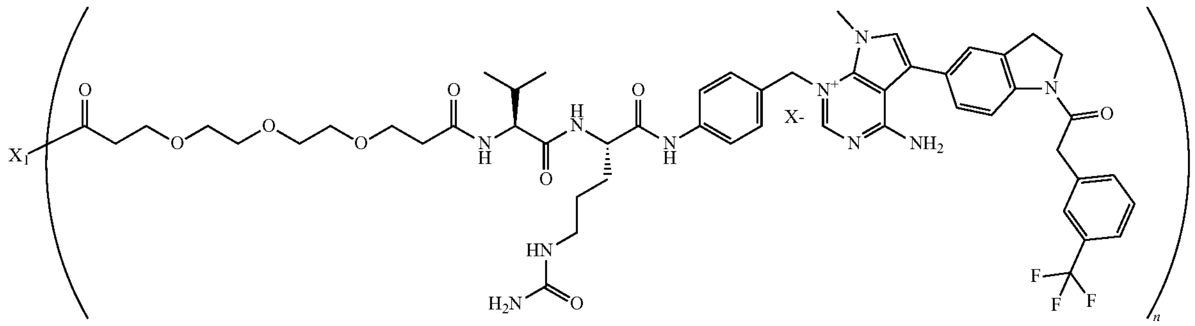 |
| B42 | 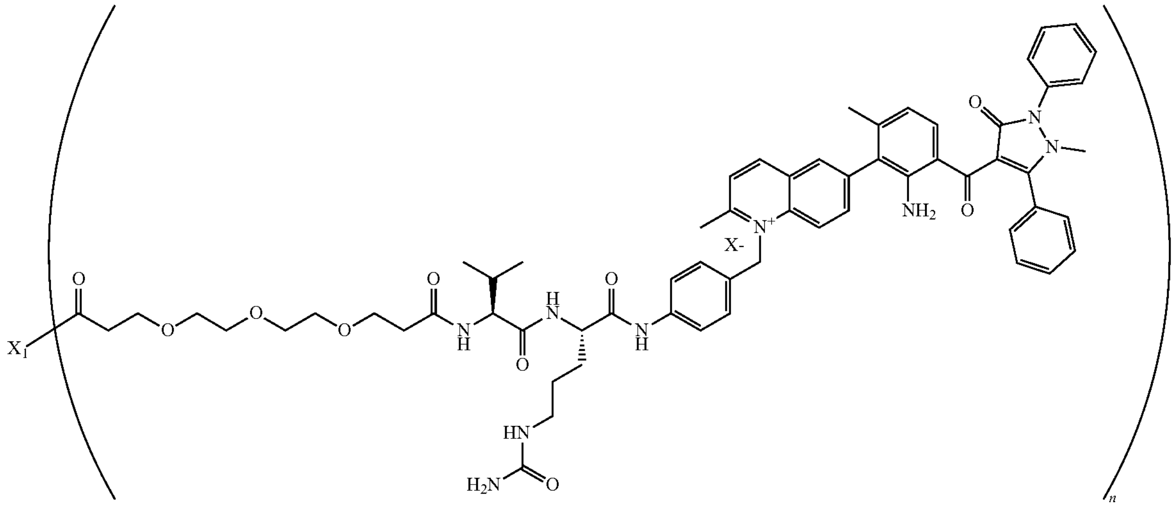 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B43 | 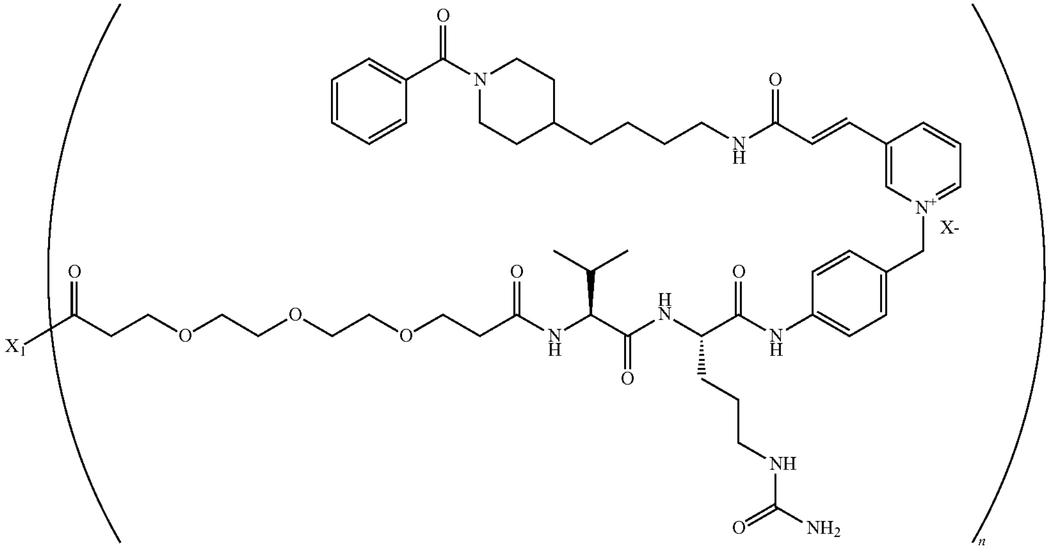 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B44 | 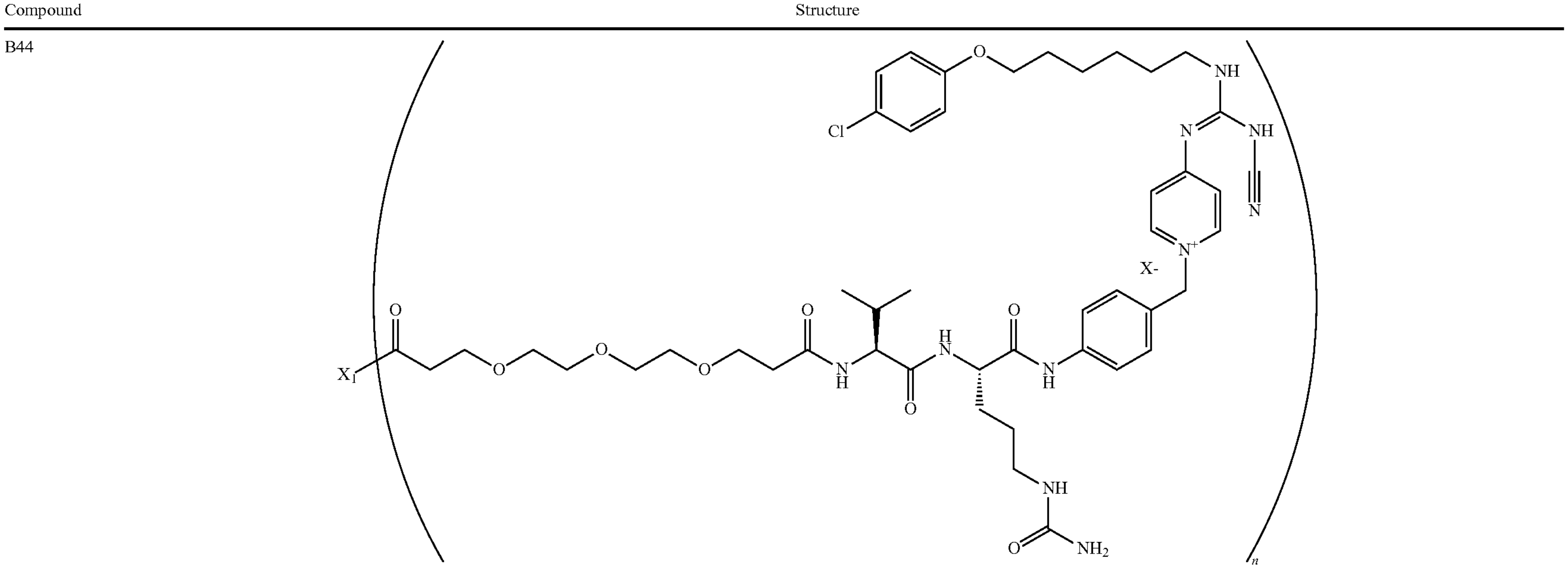 |
| B45 | 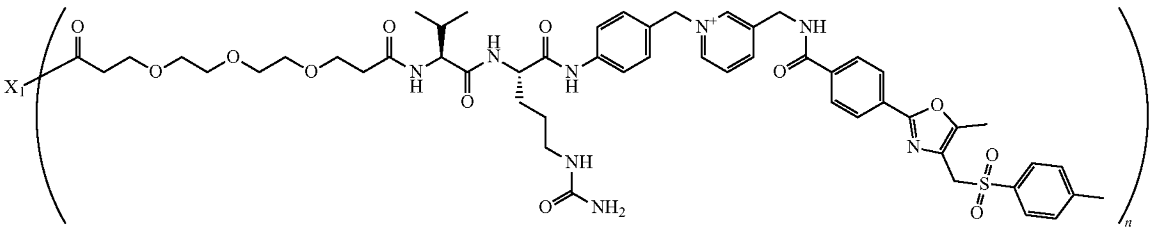 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B46 | 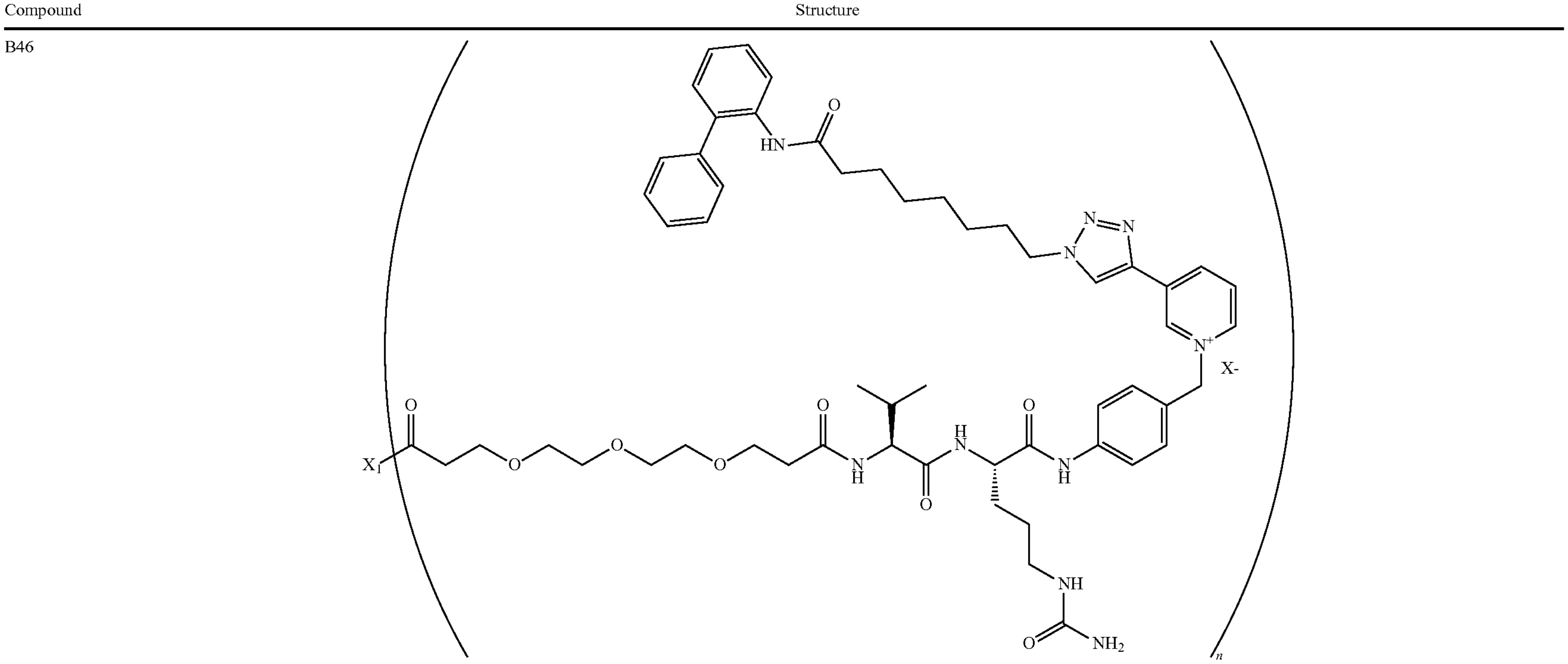 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B47 | 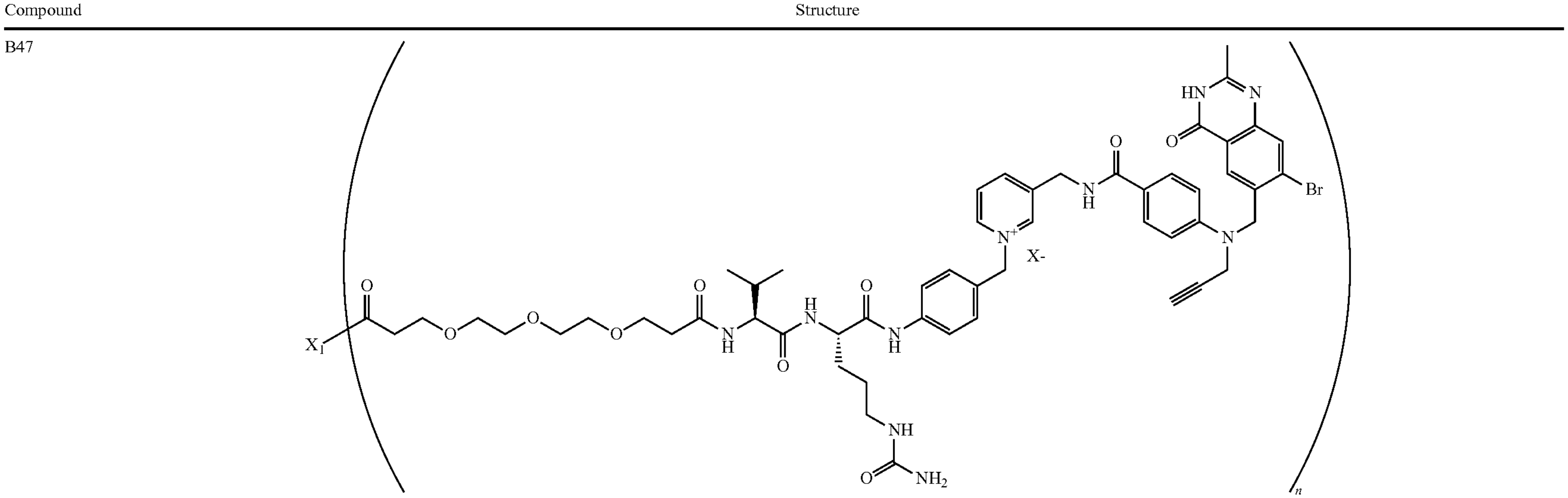 |
| B48 | 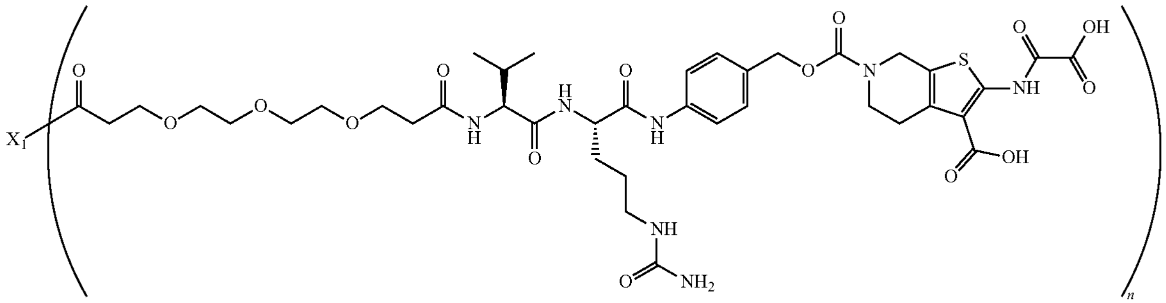 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B49 | 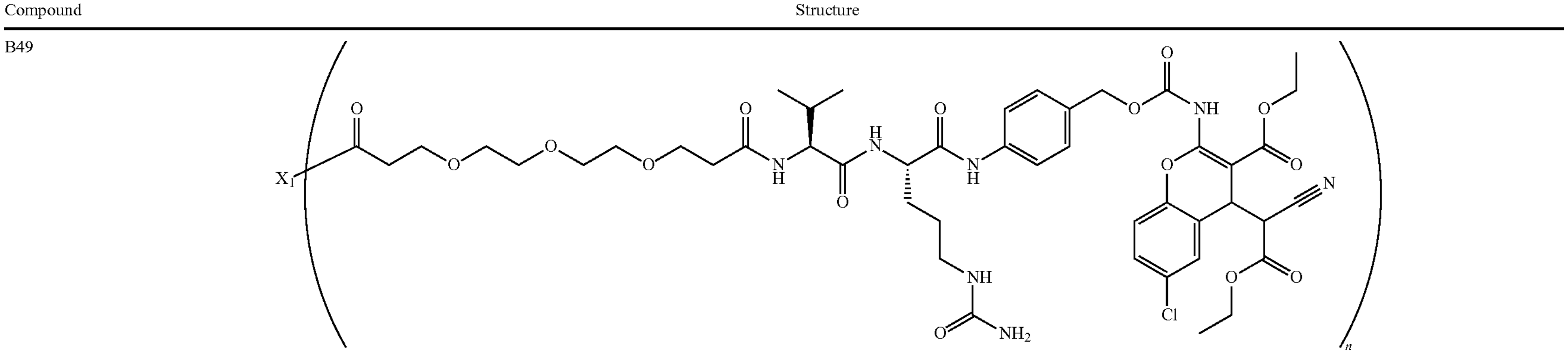 |
| B50 | 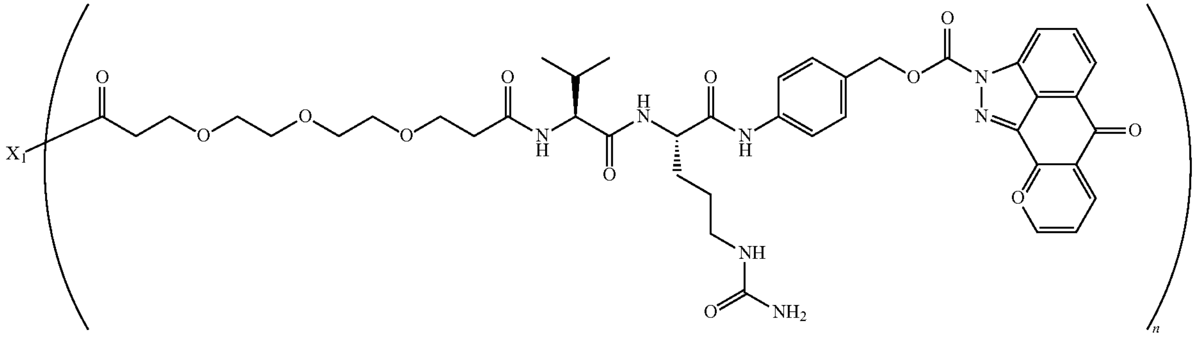 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B51 | 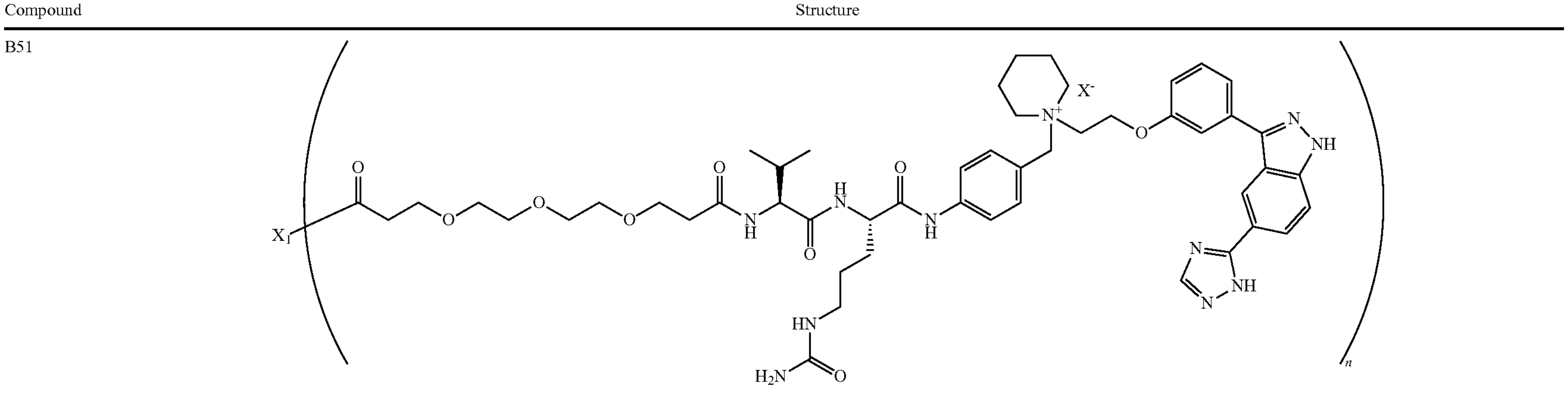 |
| B52 | 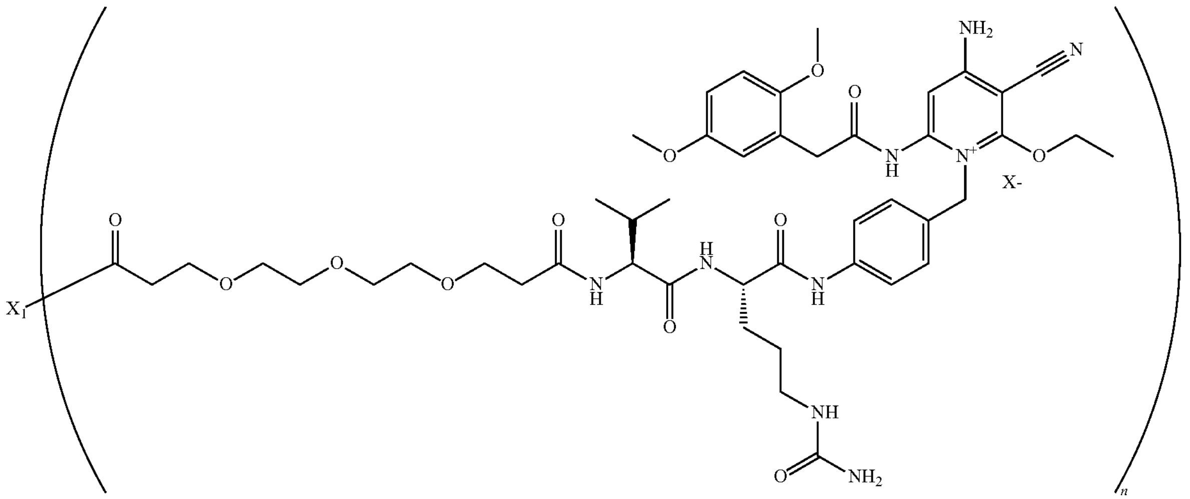 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B53 | 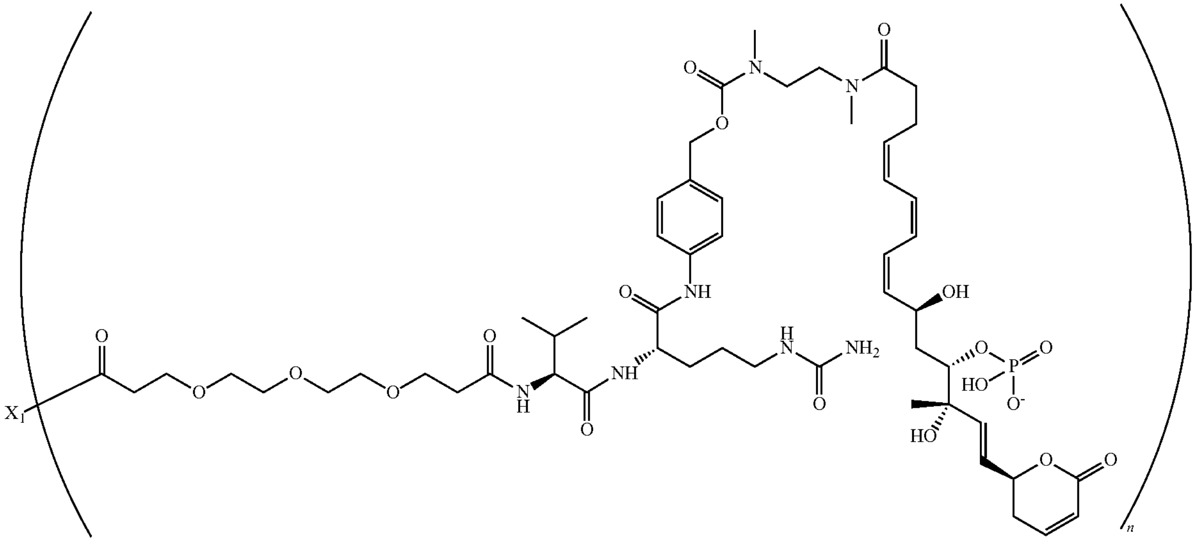 |
| B54 | 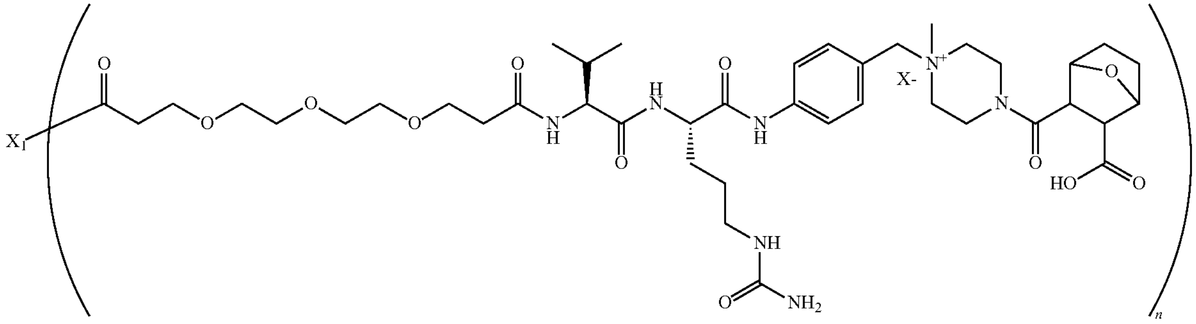 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B55 | 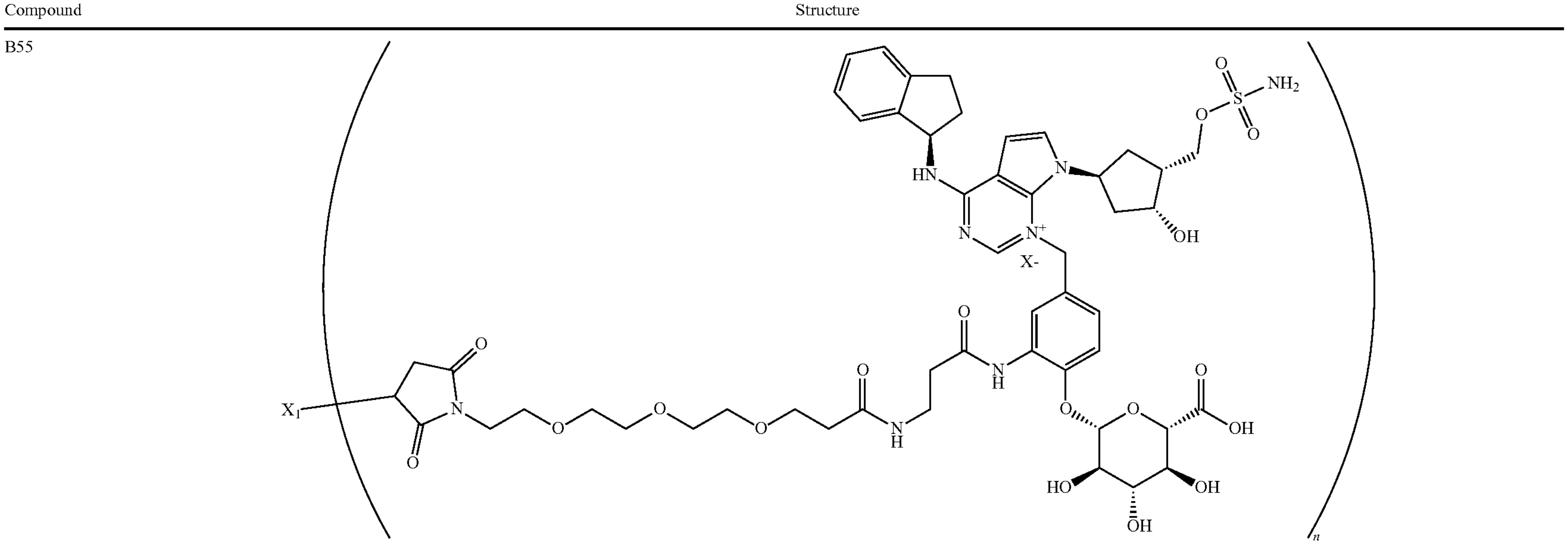 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B56 | 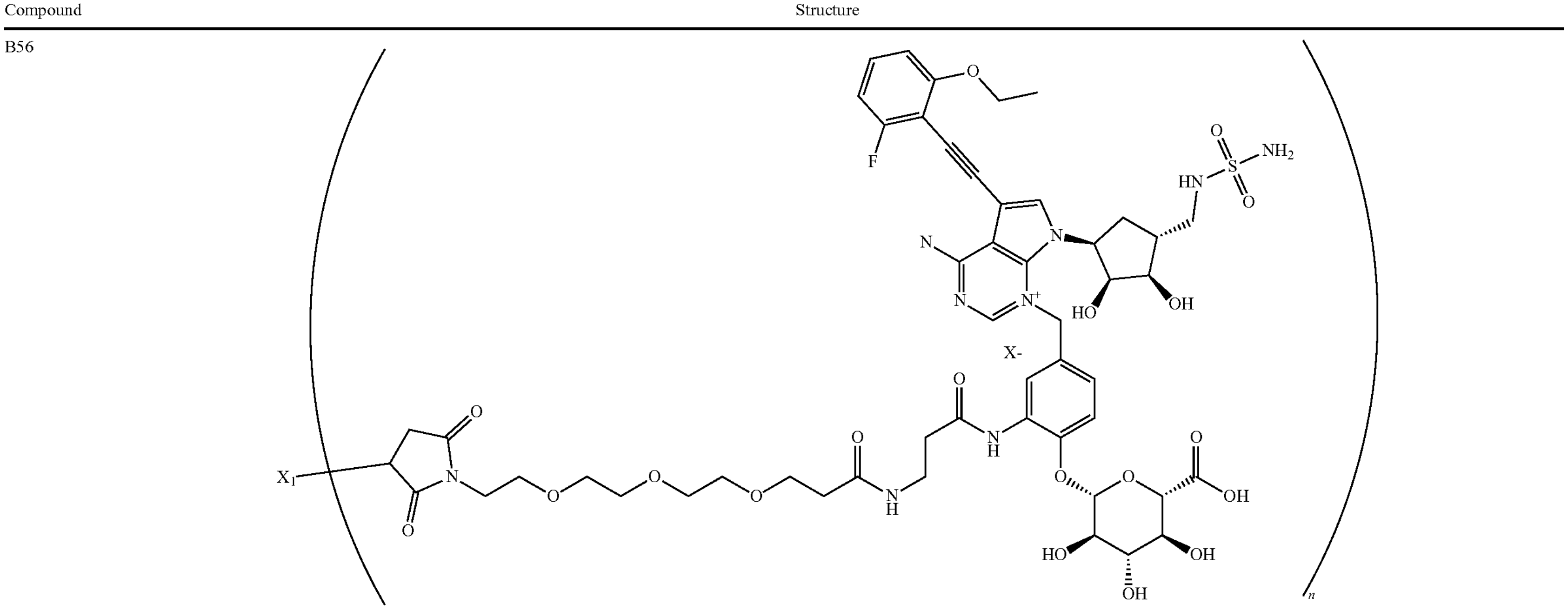 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B57 | 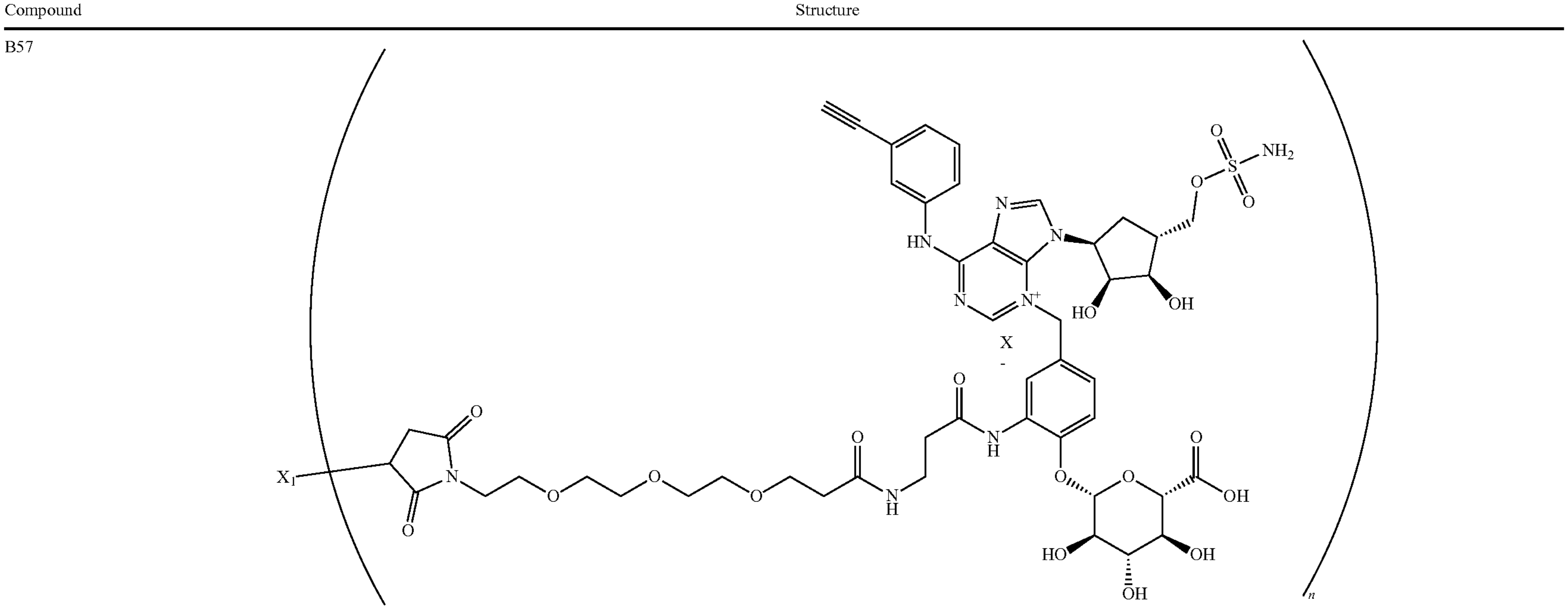 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B58 | 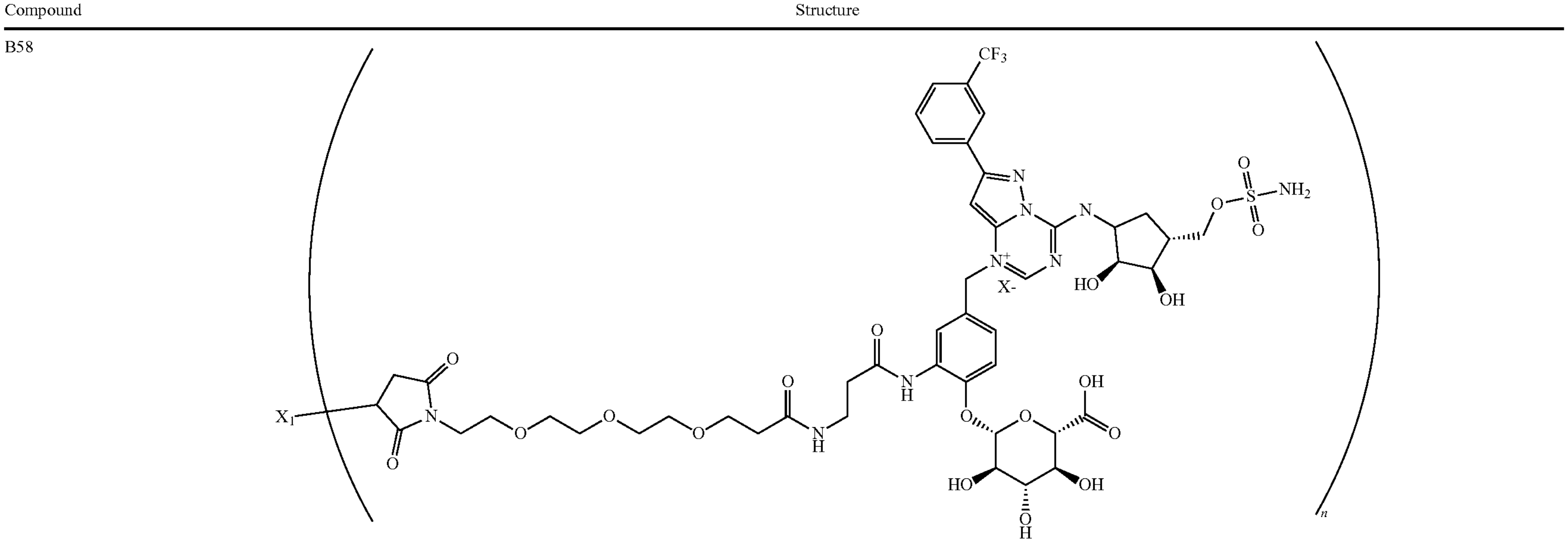 |
| B59 | 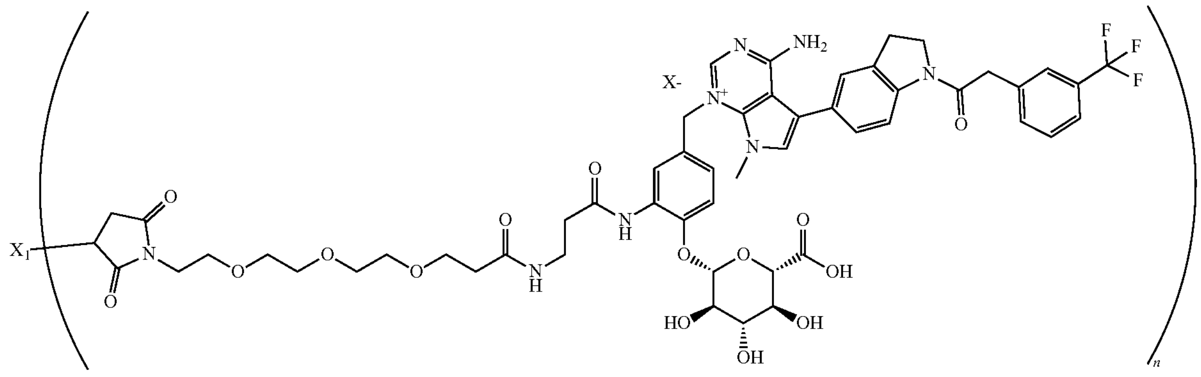 |

TABLE 6-continued
Exemplary Compounds of Formula (II) or Formula (III) for Treating Insulin Resistance, Type 2 Diabetes and Metabolic Syndrome
| Compound | Structure |
| --- | --- |
| B60 | 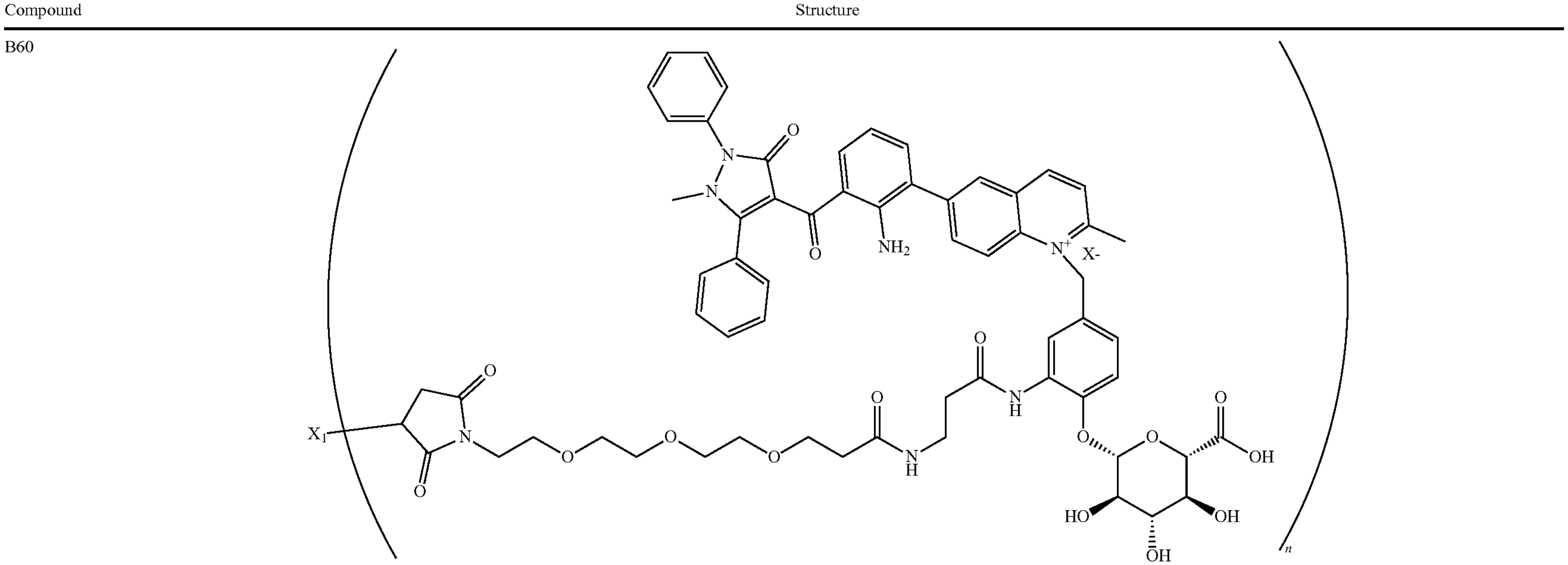 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B61 | 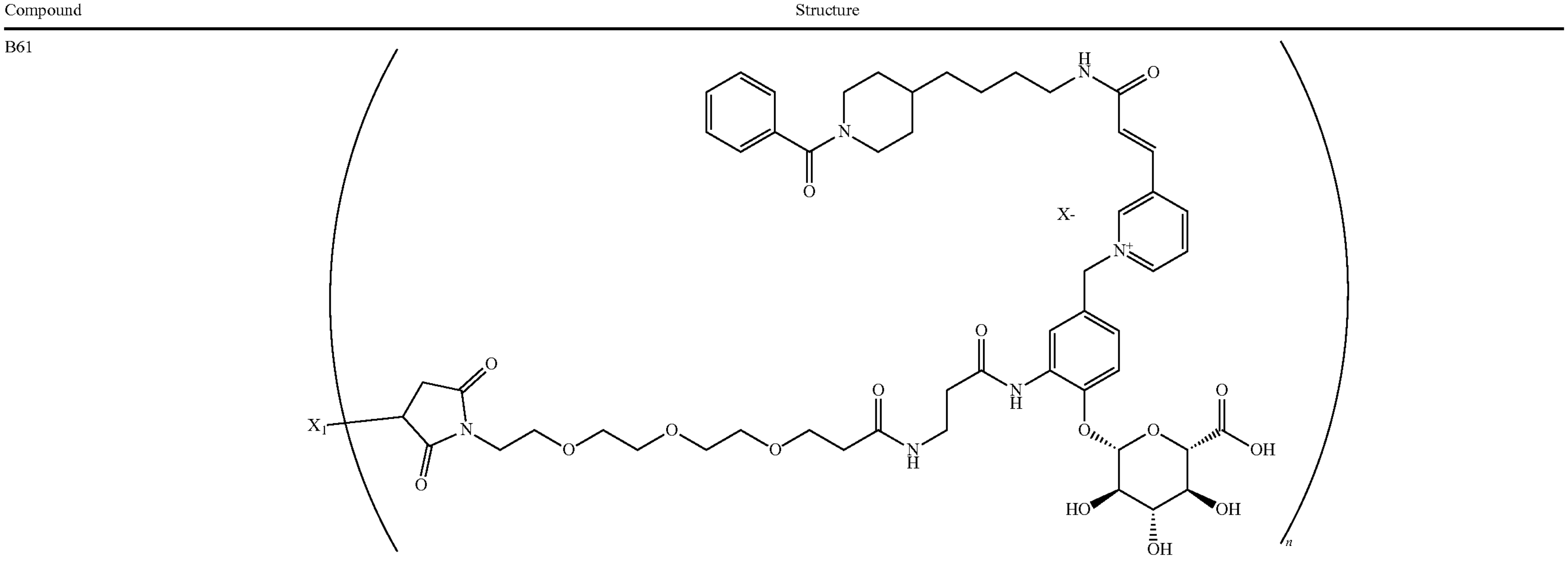 |
| B62 | 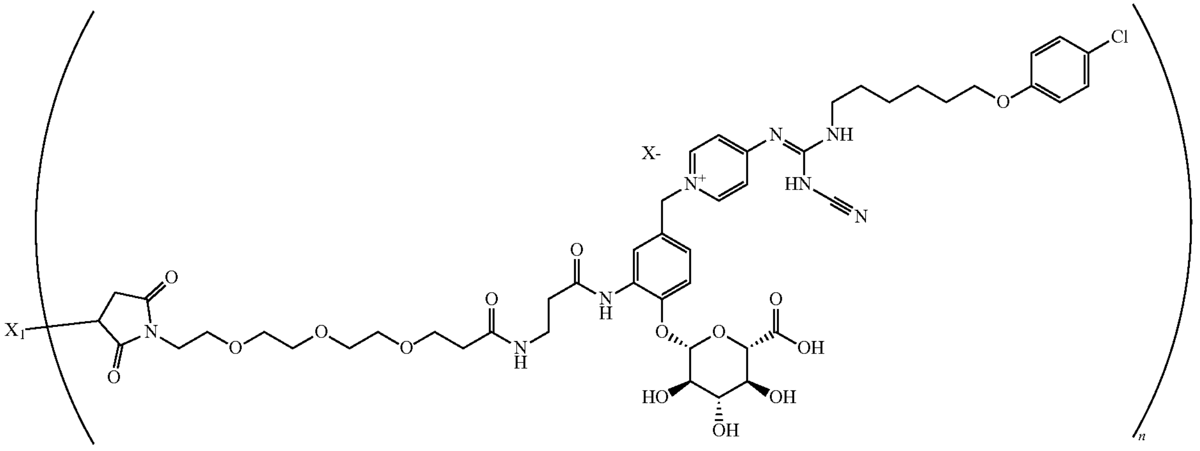 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B63 | 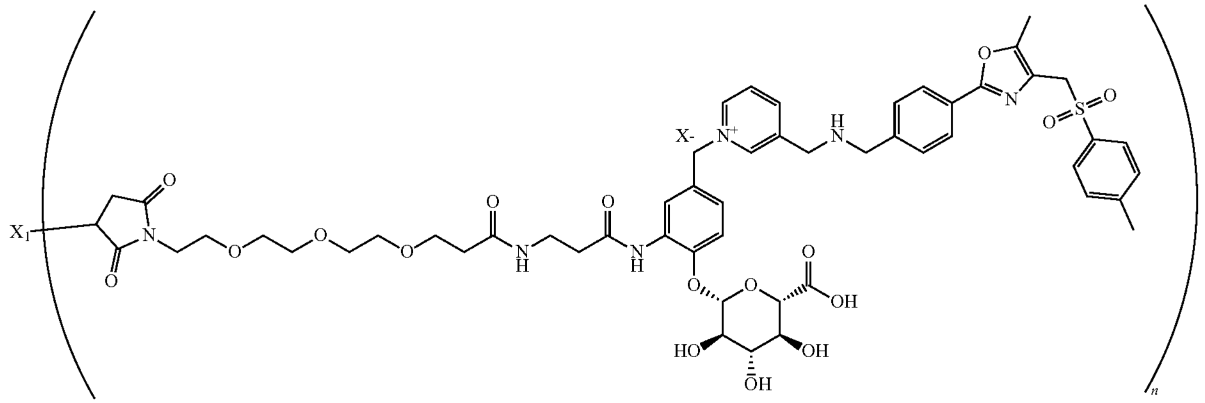 |
| B64 | 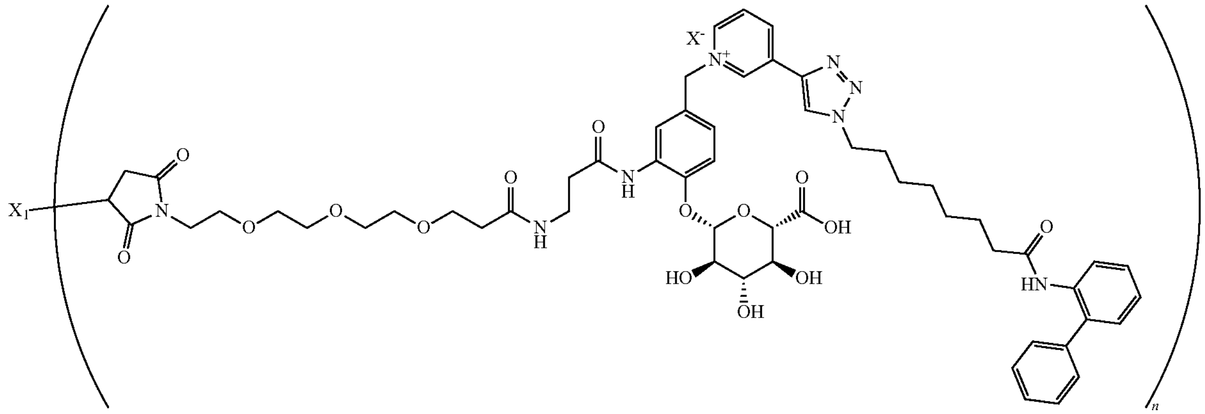 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B65 | 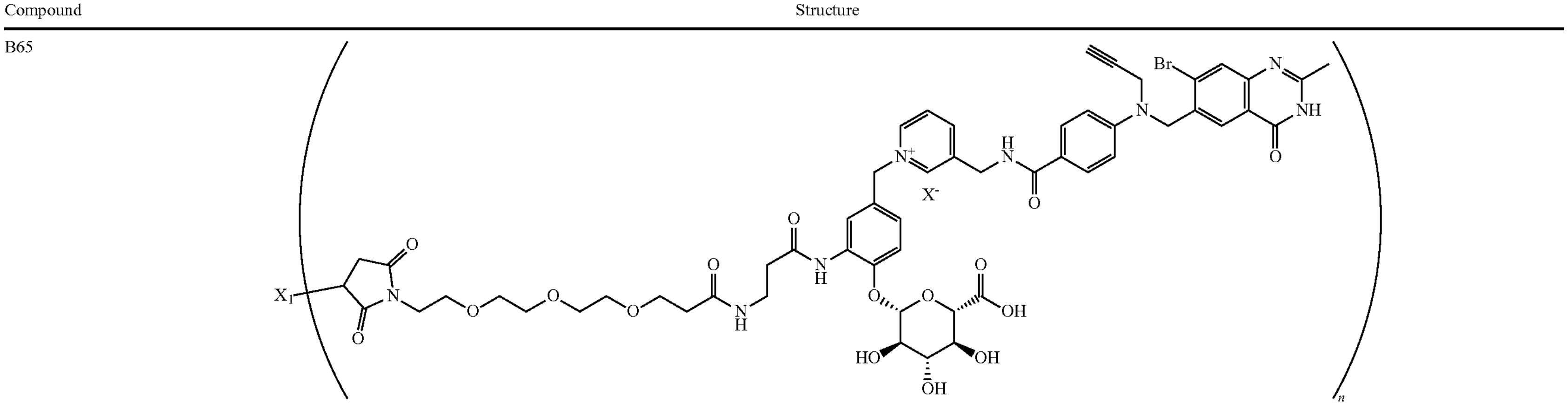 |
| B66 | 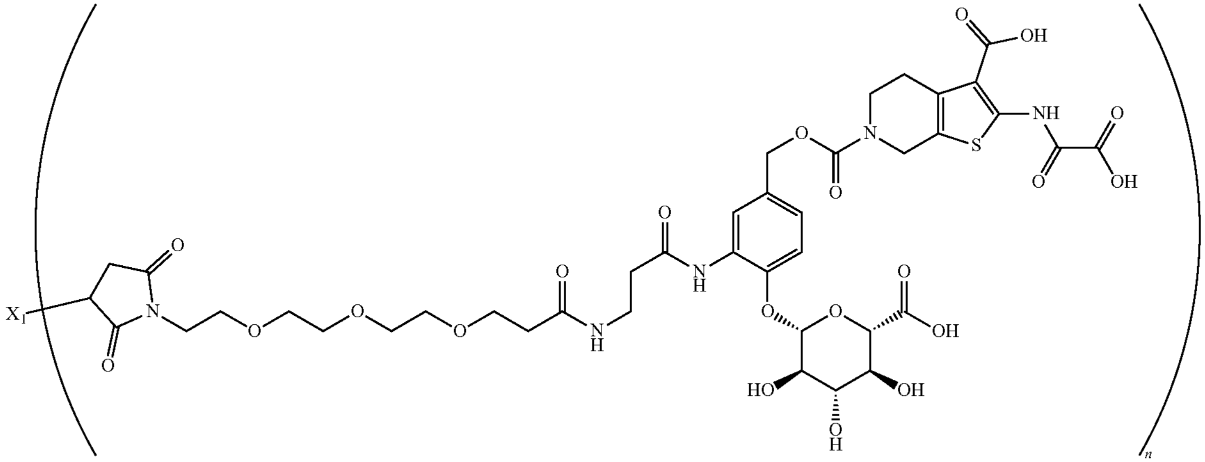 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B67 | 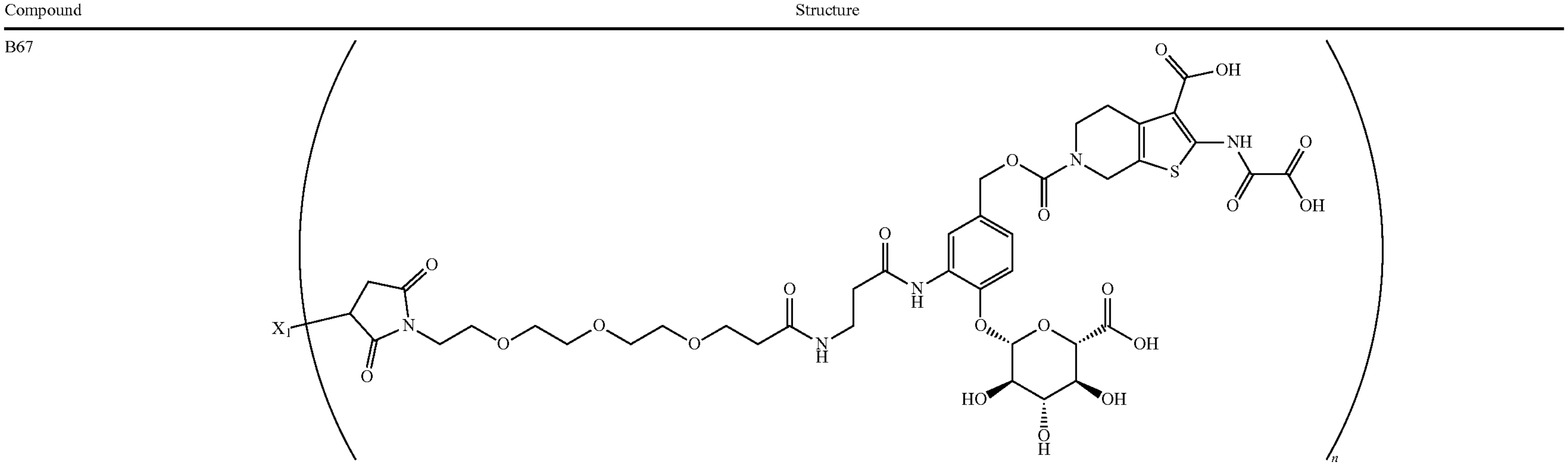 |
| B68 | 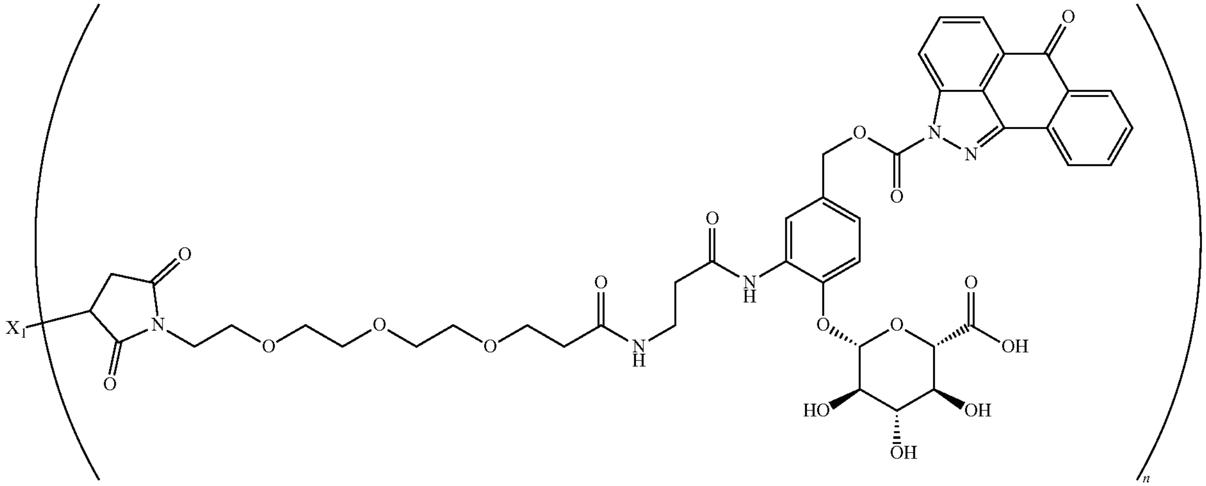 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B69 | 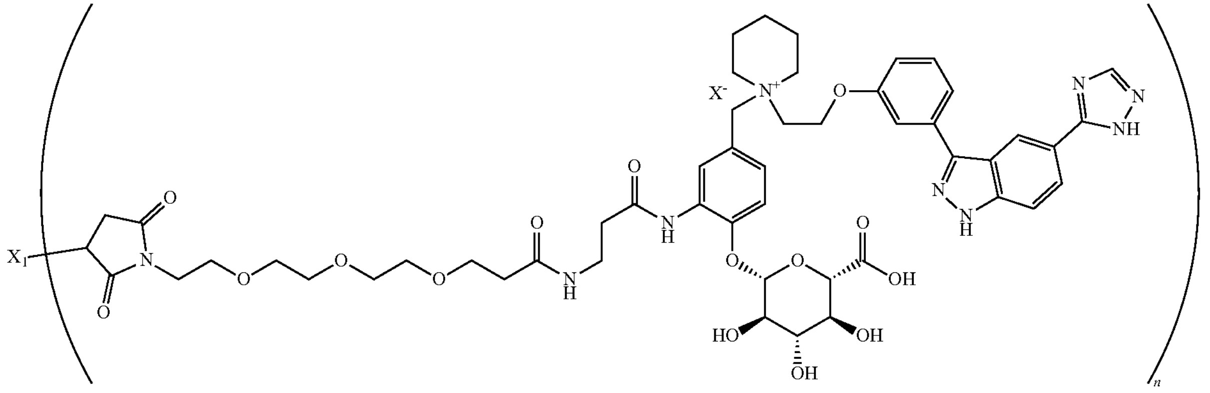 |
| B70 | 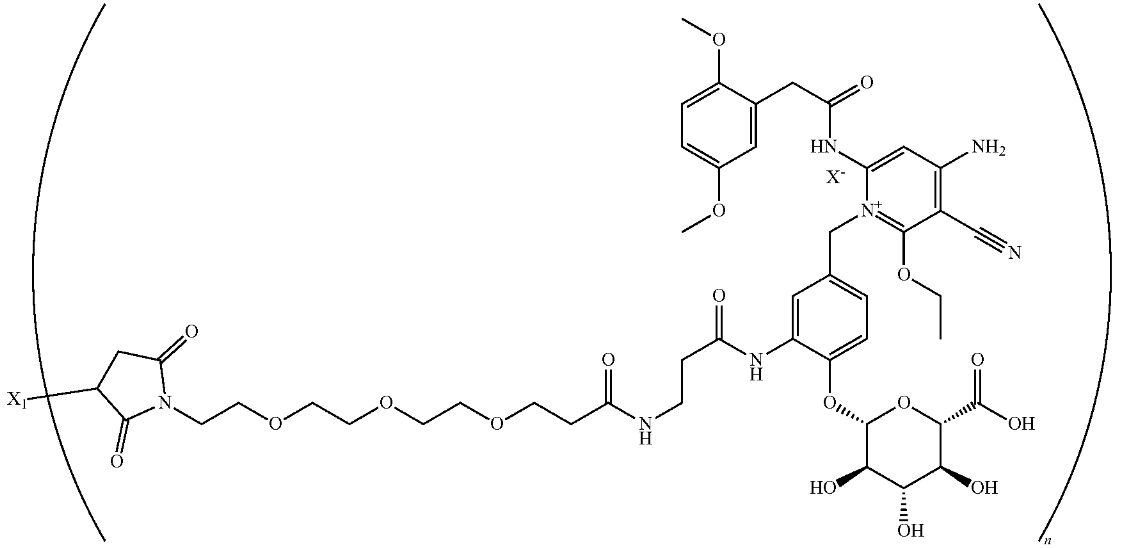 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B71 | 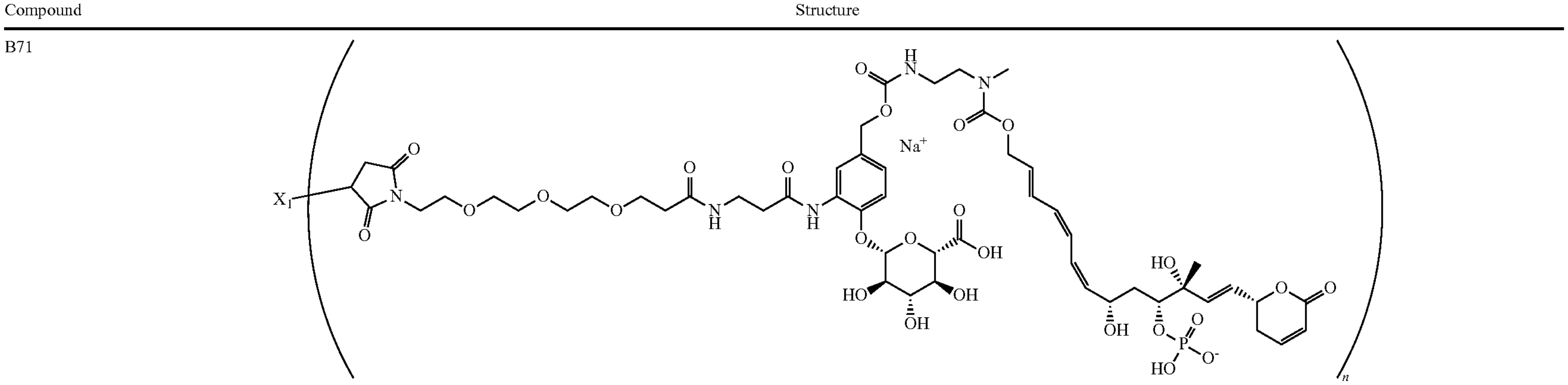 |
| B72 | 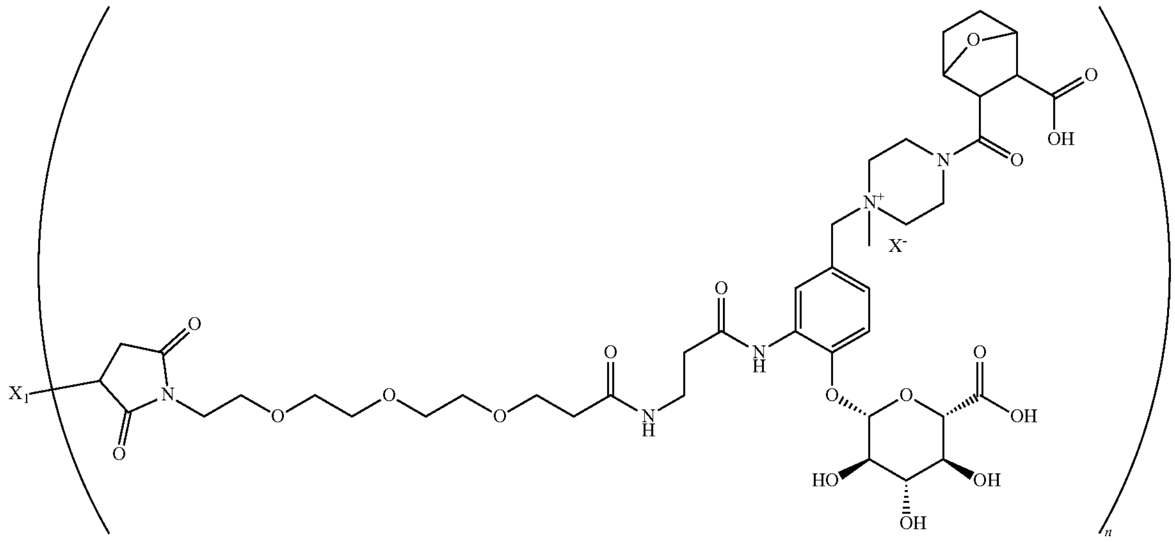 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B73 | 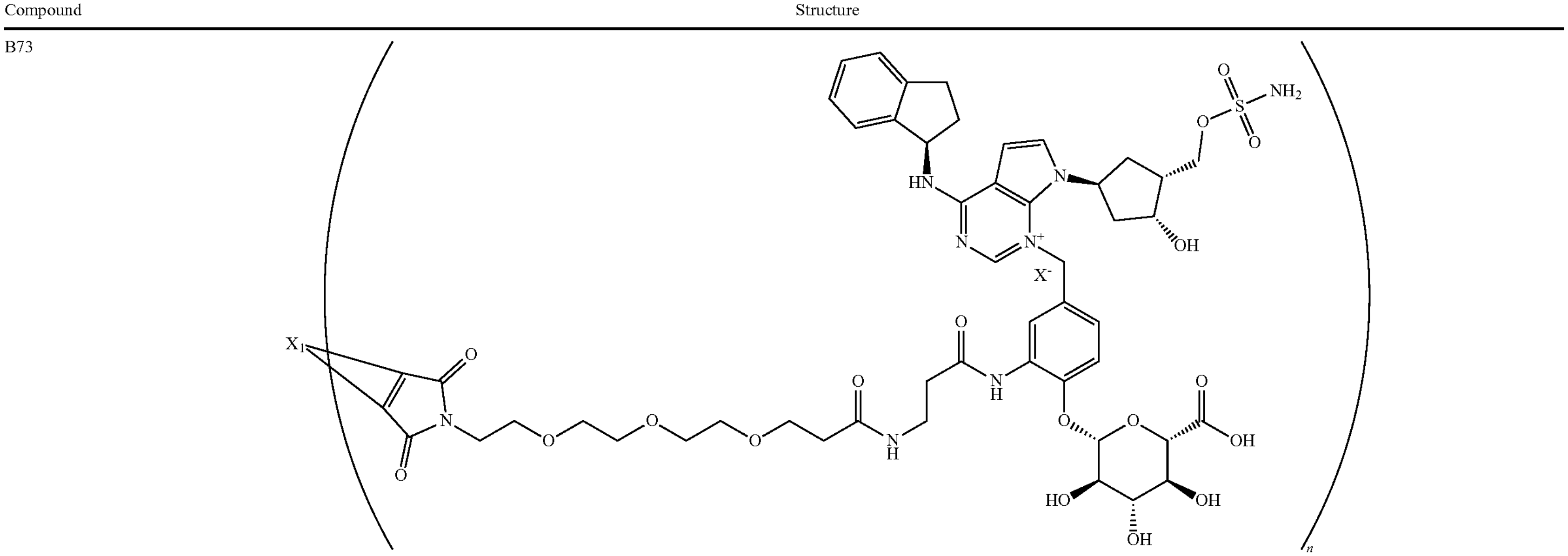 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B74 | 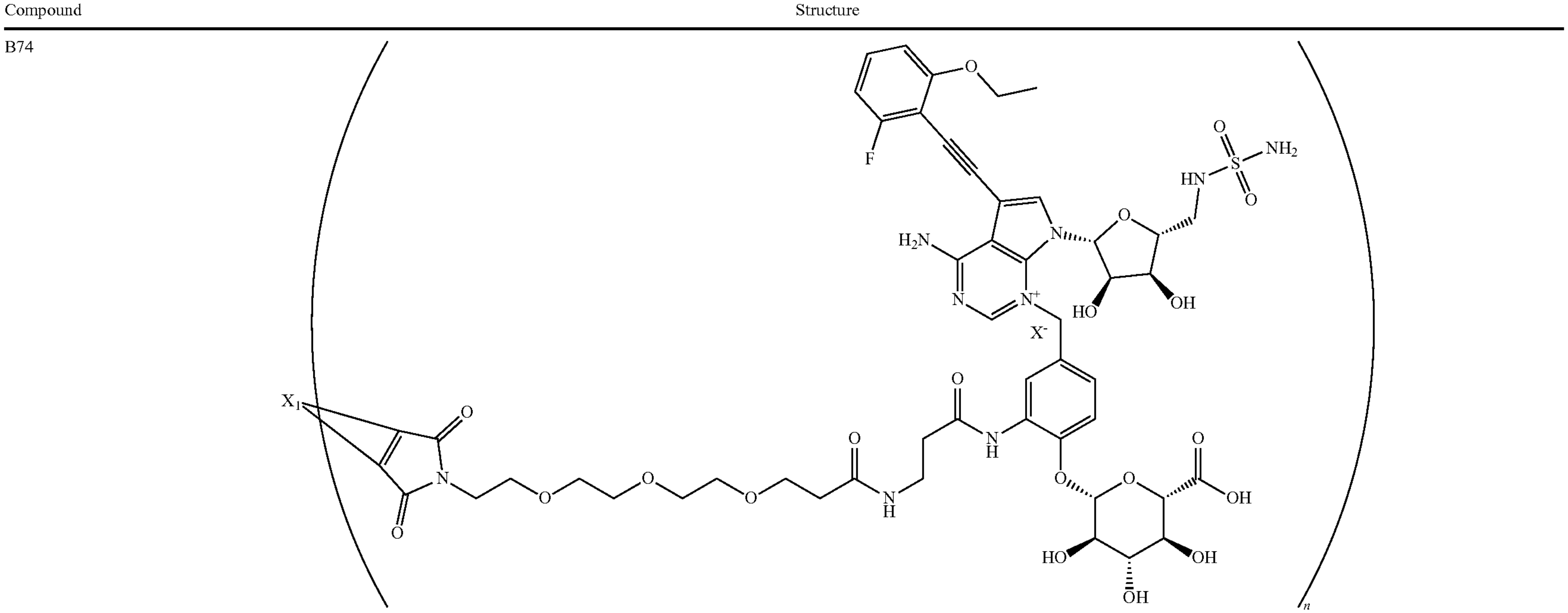 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B75 | 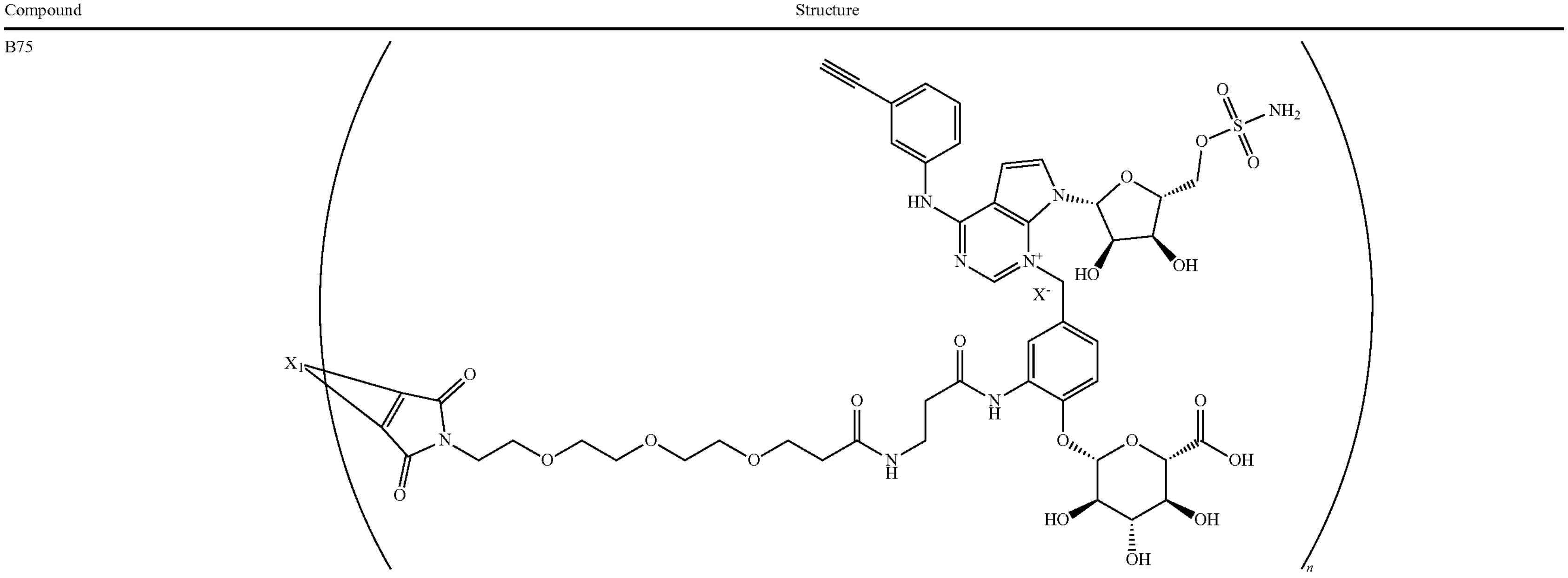 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B76 | 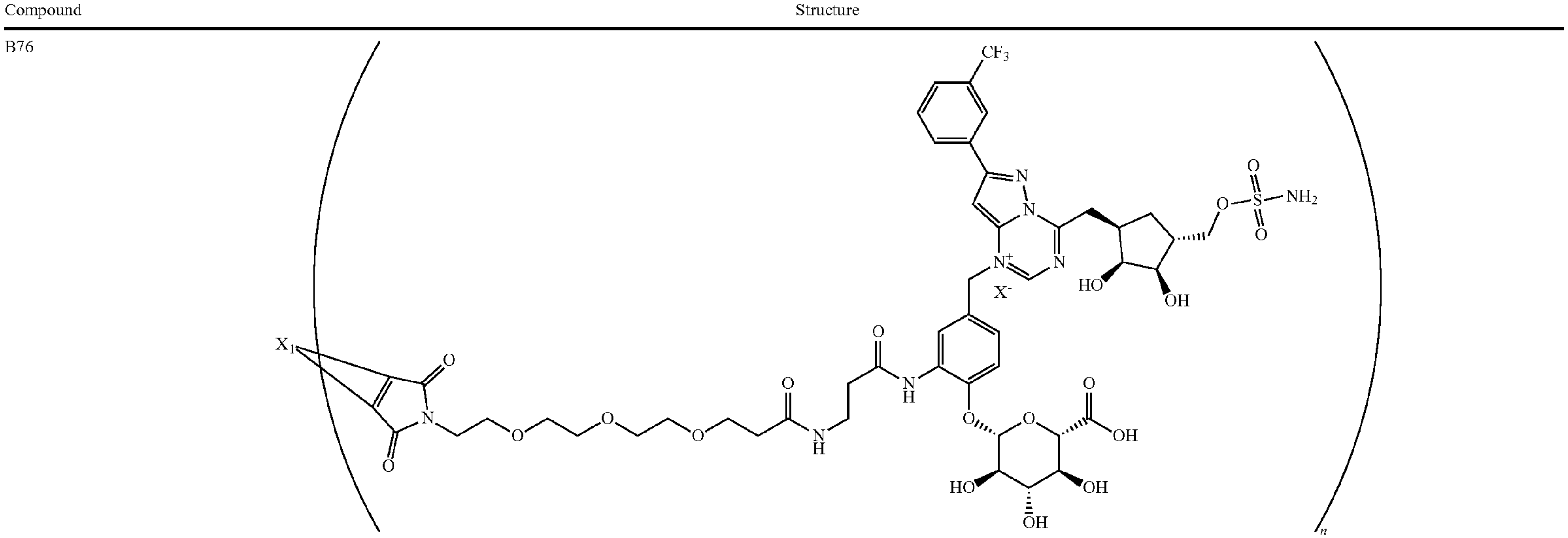 |
| B77 | 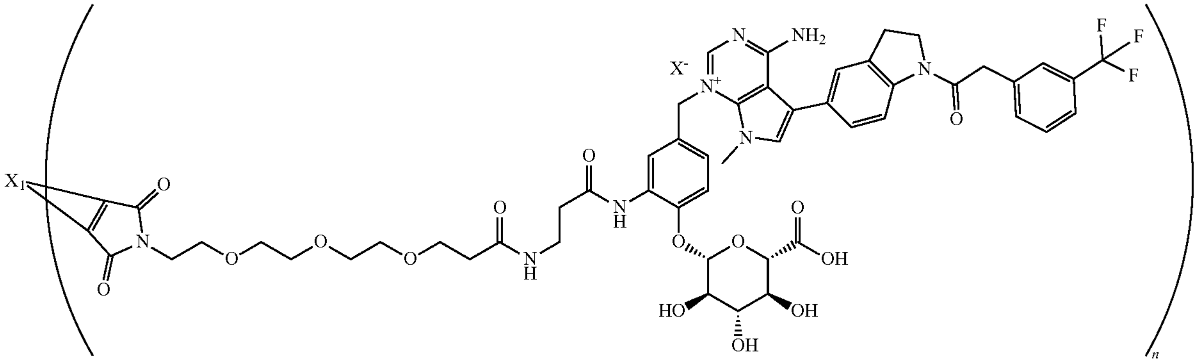 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B78 | 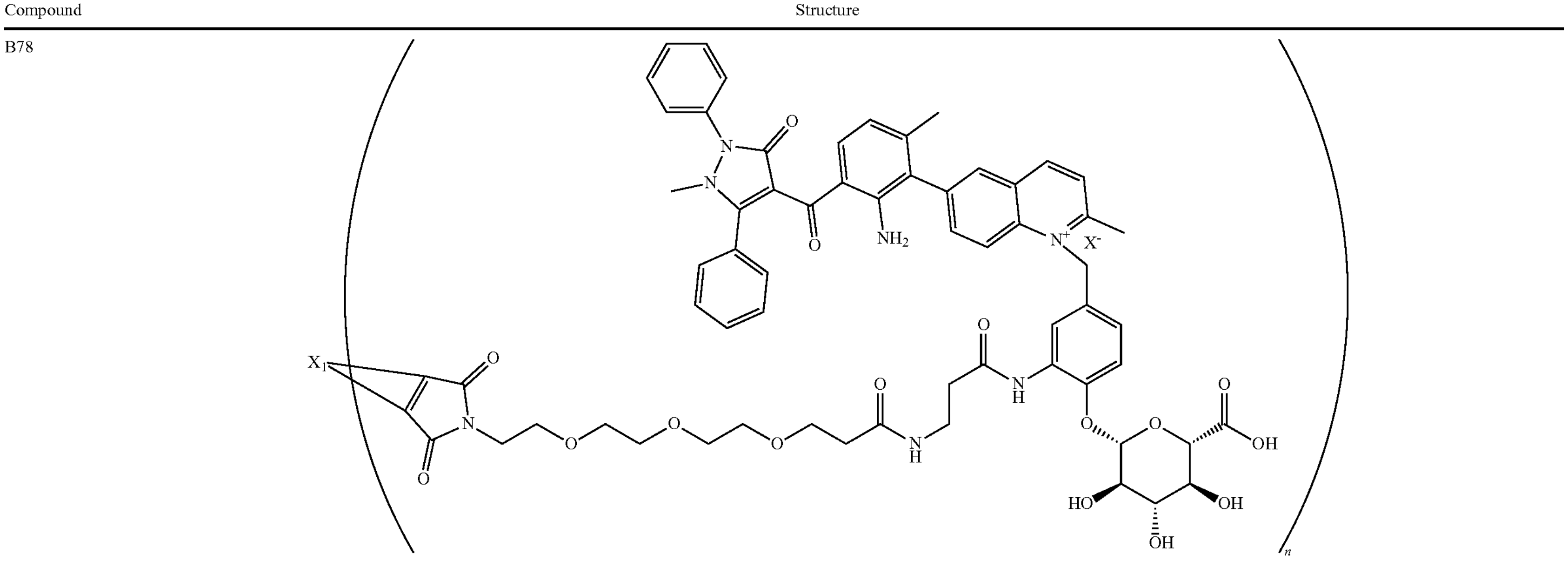 |

TABLE 6-continued
| Compound | Structure |
| --- | --- |
| | Exemplary Compounds of Formula (II) or Formula (III) for Treating Insulin Resistance, Type 2 Diabetes and Metabolic Syndrome |
| B79 | 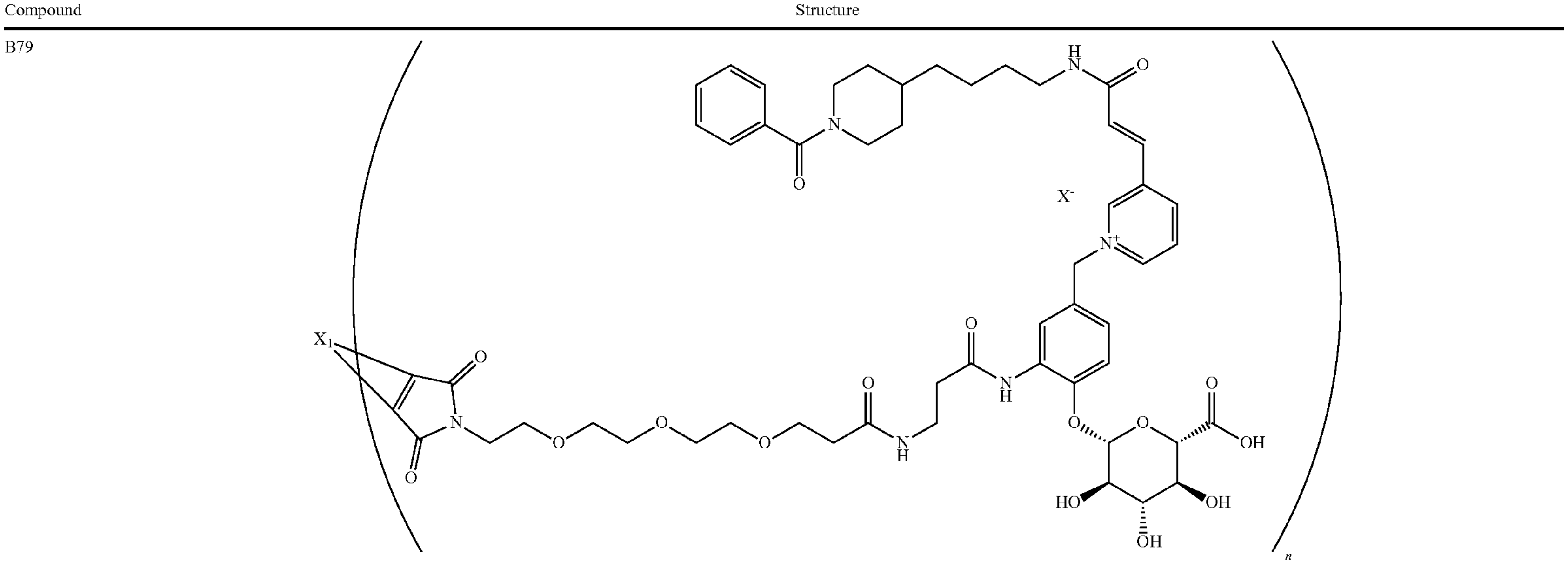 |
| B80 | 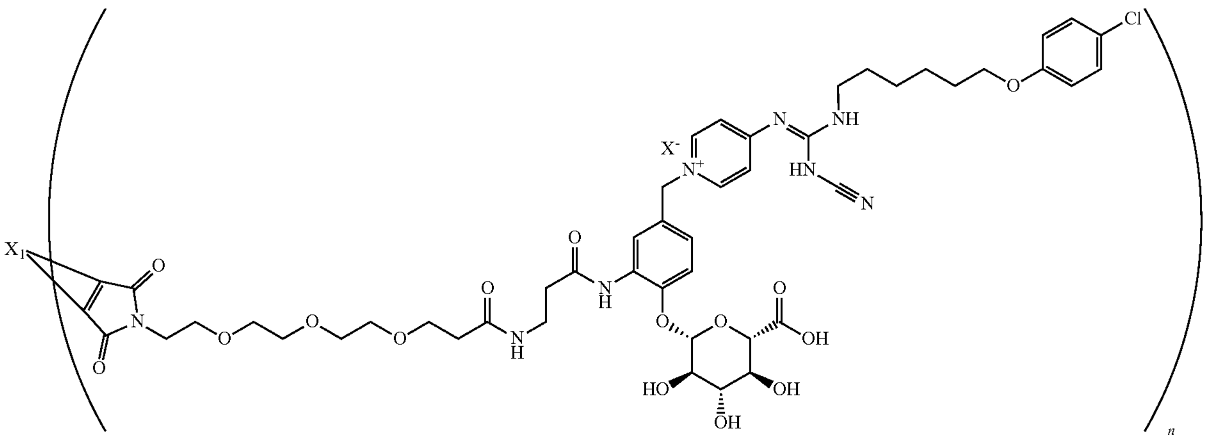 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B81 | 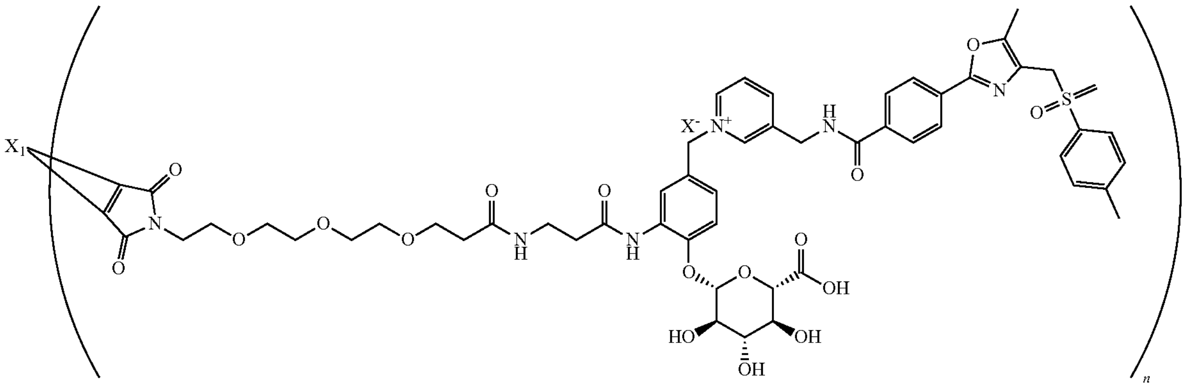 |
| B82 | 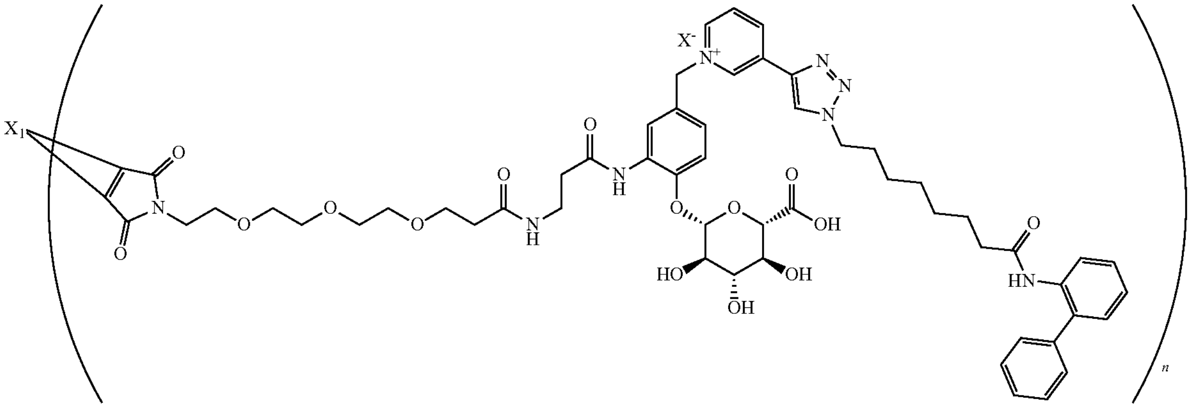 |

TABLE 6-continued
Exemplary Compounds of Formula (II) or Formula (III) for Treating Insulin Resistance, Type 2 Diabetes and Metabolic Syndrome
| Compound | Structure |
|---|---|
| B83 | 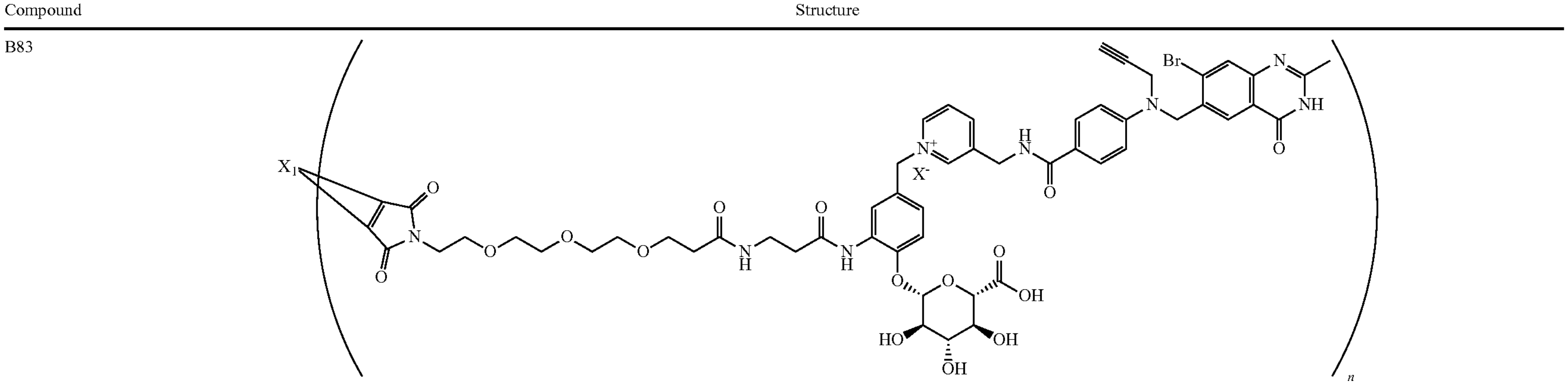 |
| B84 | 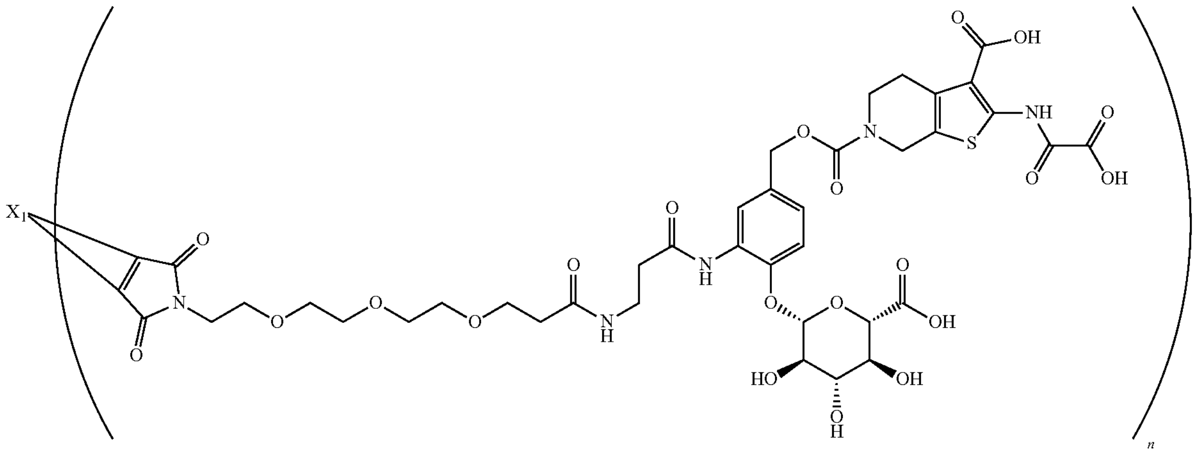 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B85 | 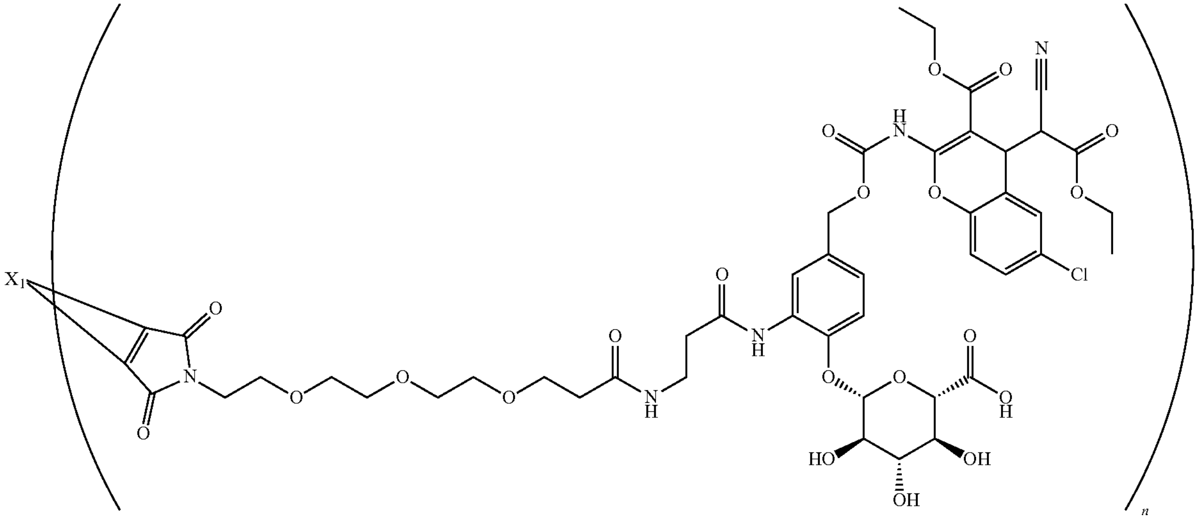 |
| B86 | 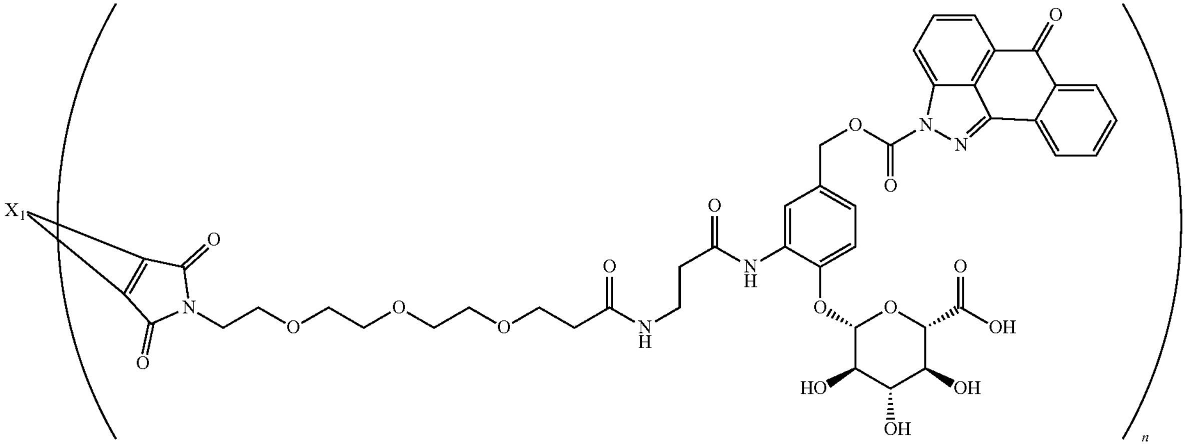 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B87 | 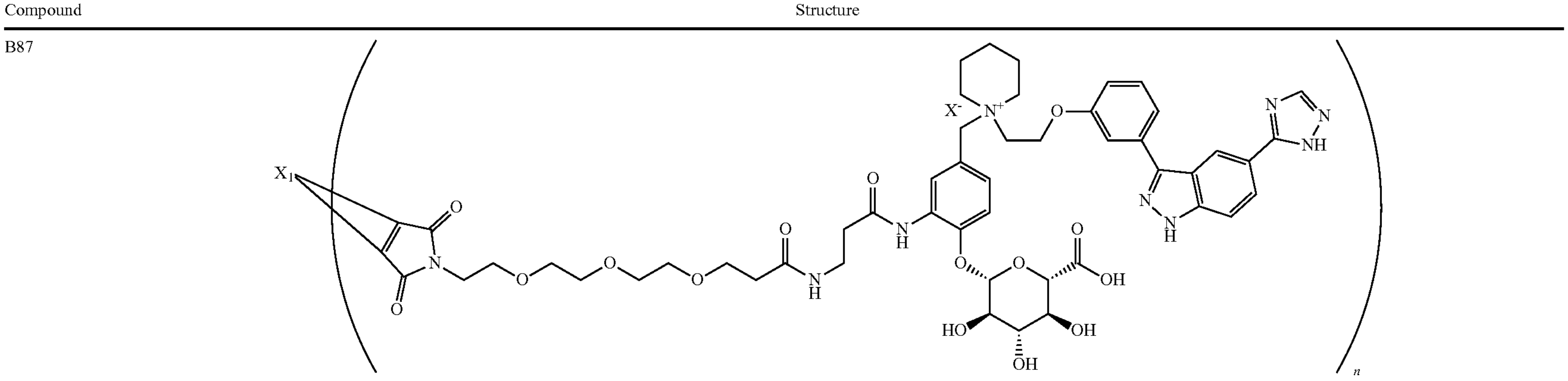 |
| B88 | 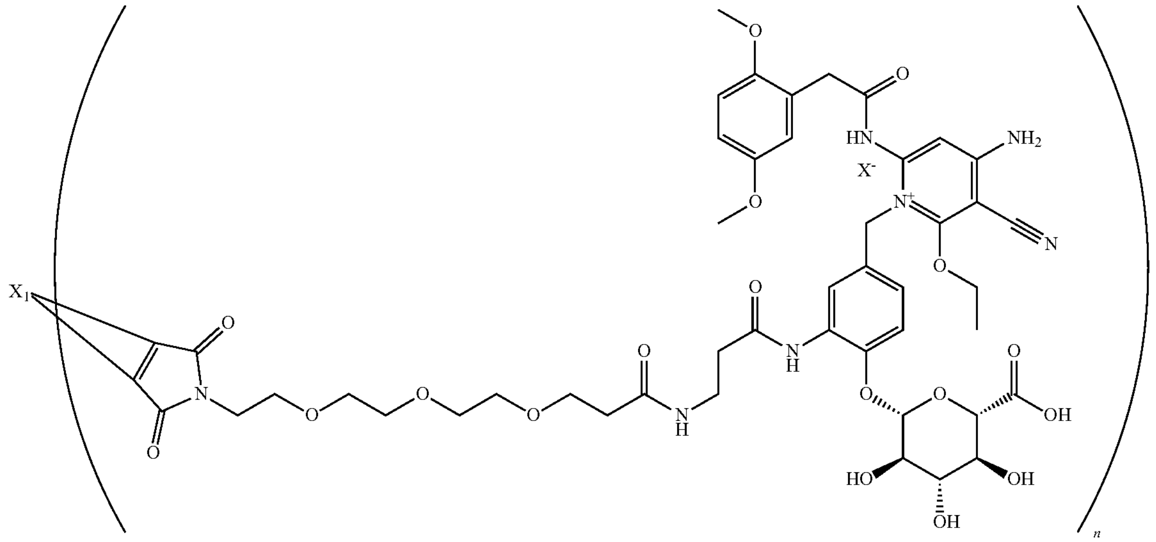 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B89 | 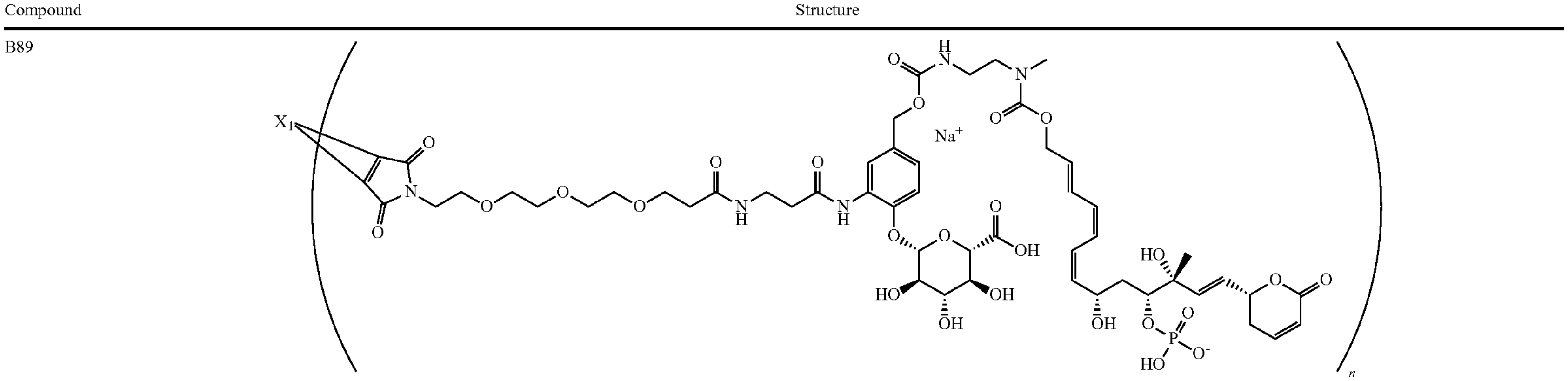 |
| B90 | 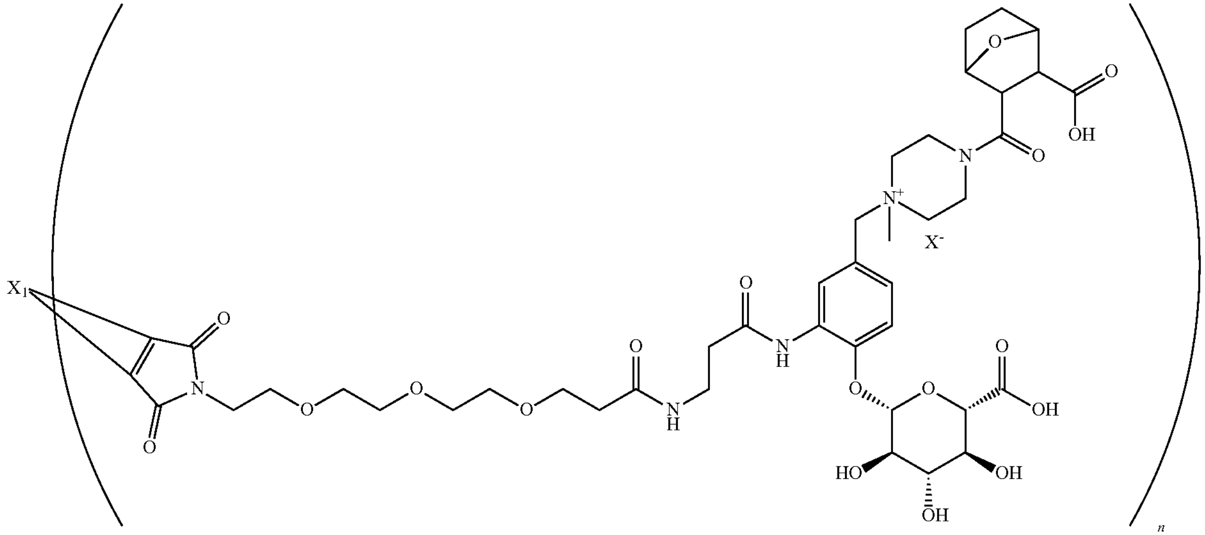 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B91 | 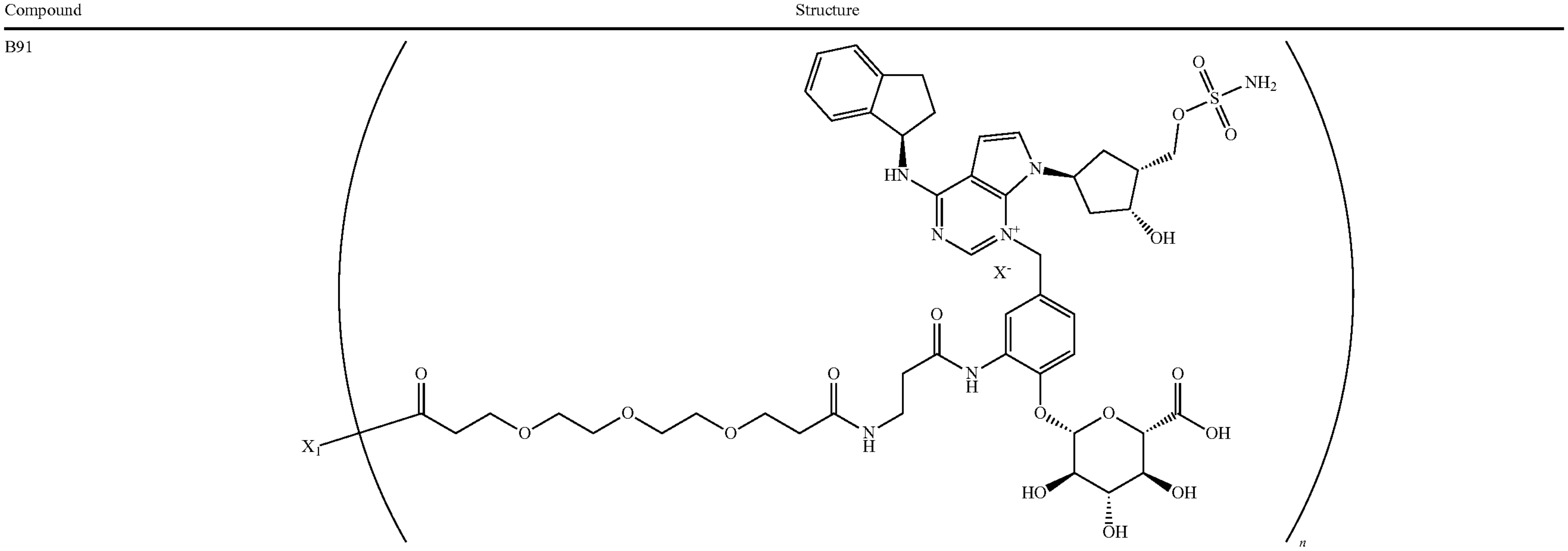 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B92 | 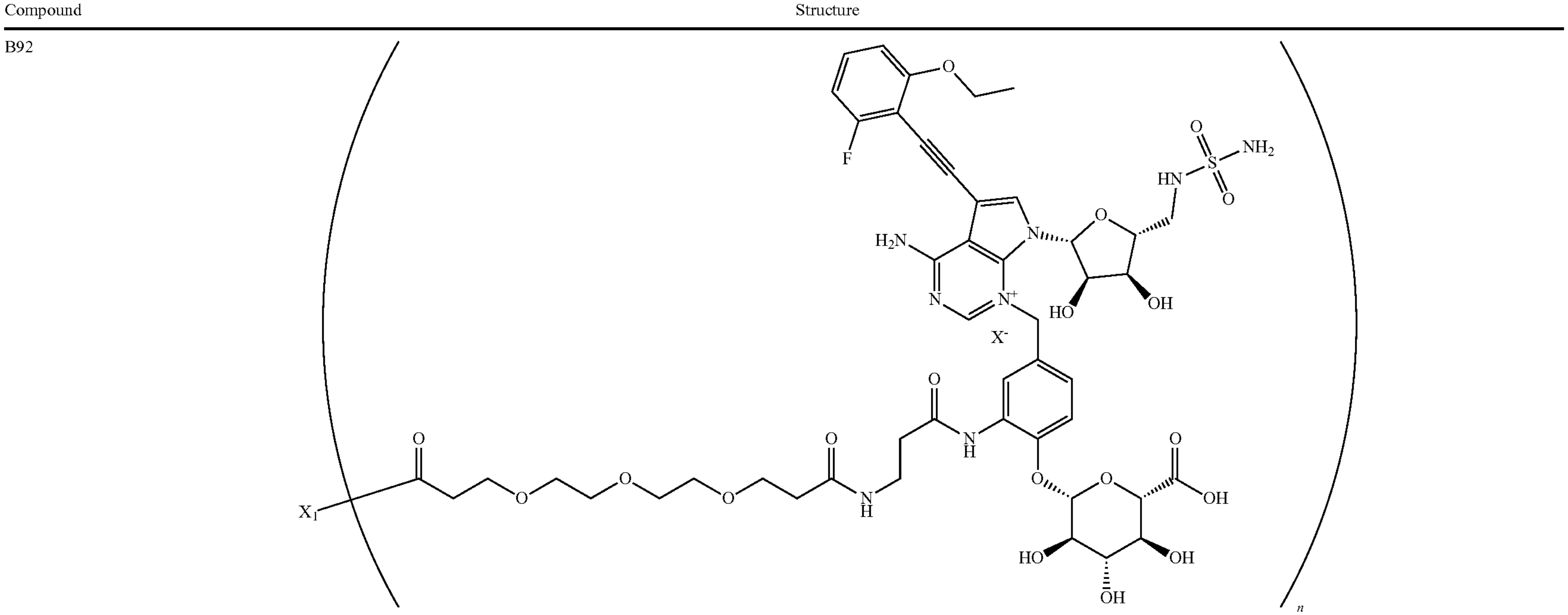 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B93 | 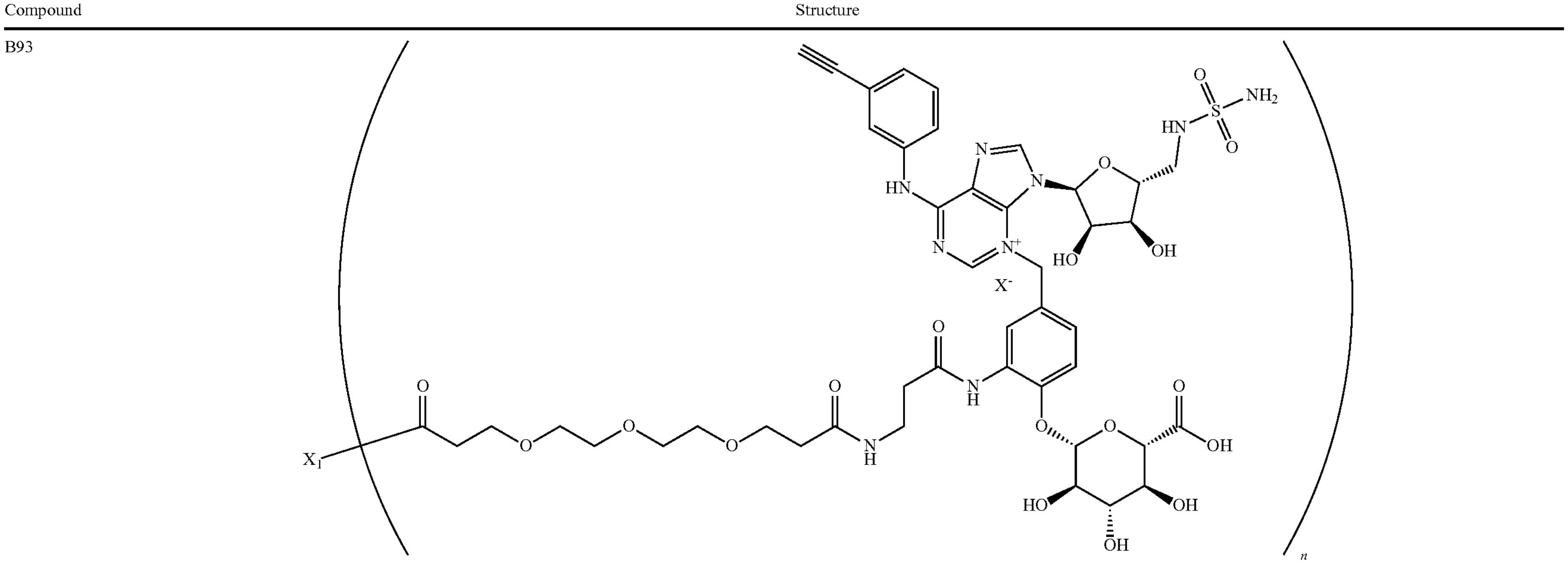 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B94 | 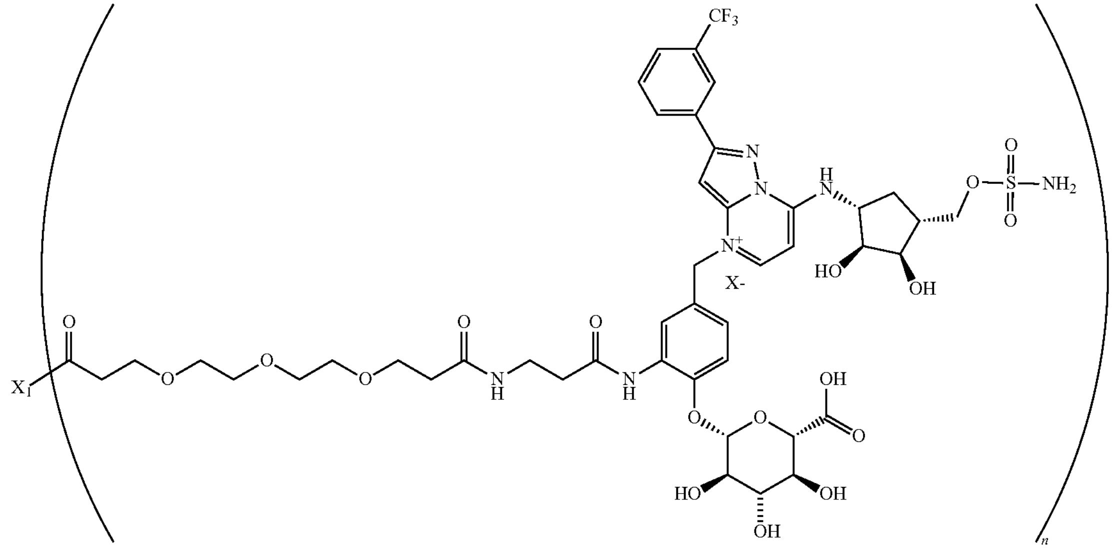 |
| B95 | 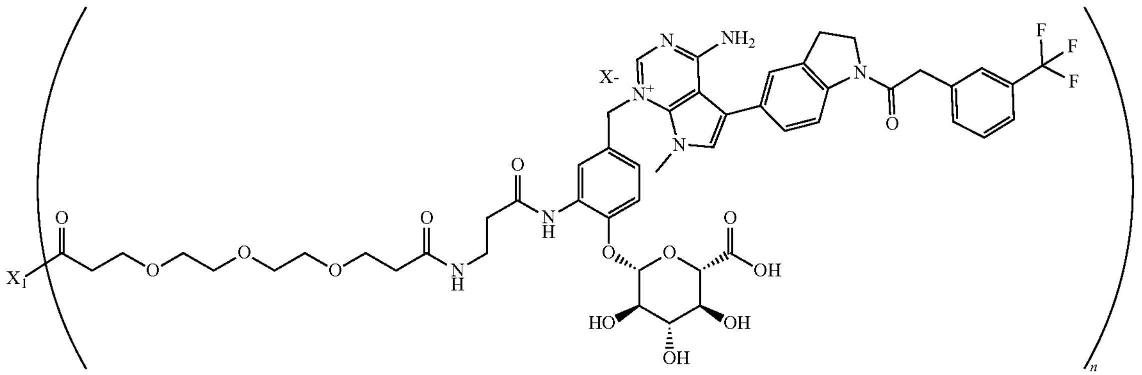 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B96 | 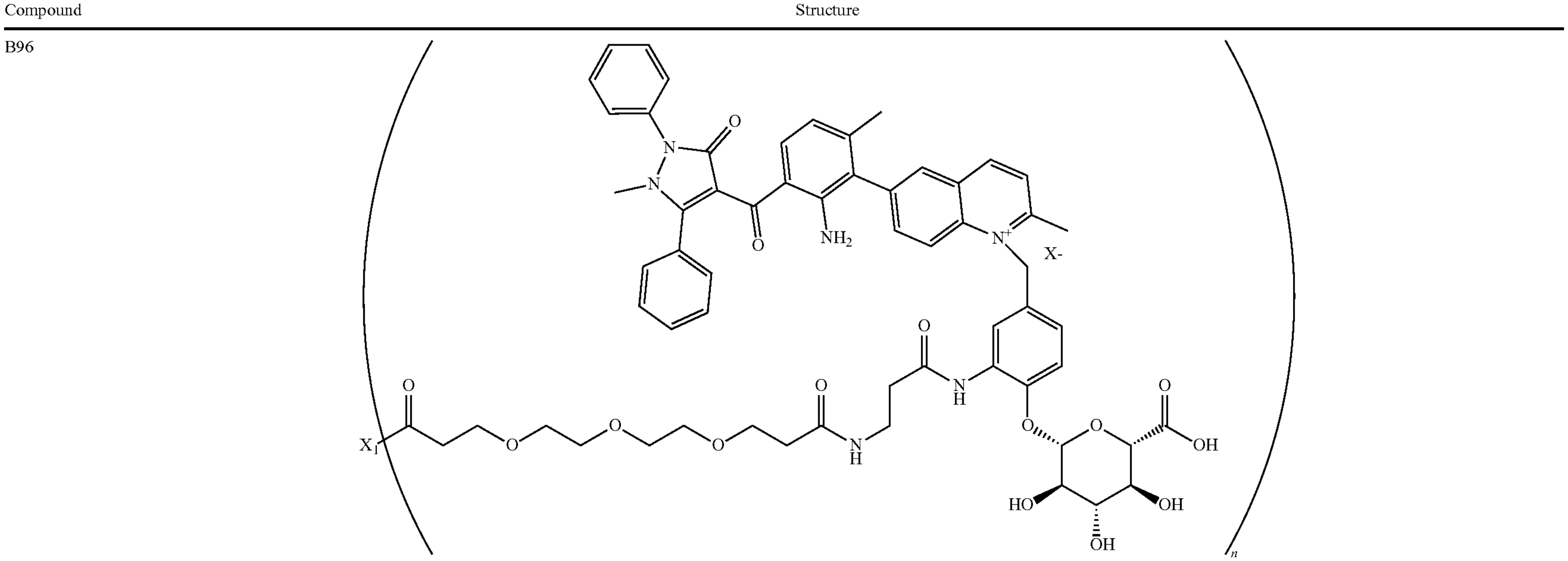 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B97 | 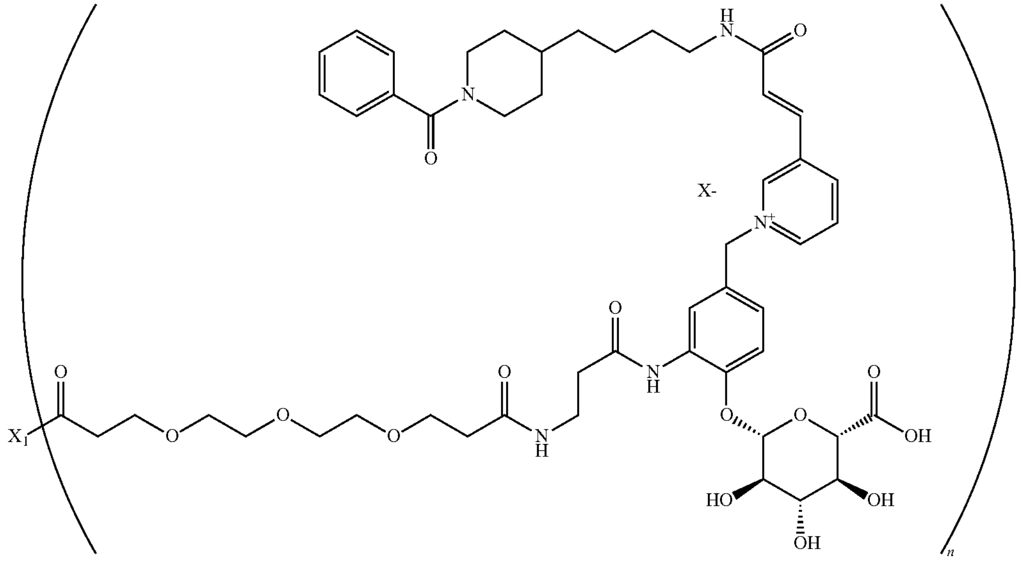 |

TABLE 6-continued
| Compound | Structure |
|---|---|
| | Exemplary Compounds of Formula (II) or Formula (III) for Treating Insulin Resistance, Type 2 Diabetes and Metabolic Syndrome |
| B98 | 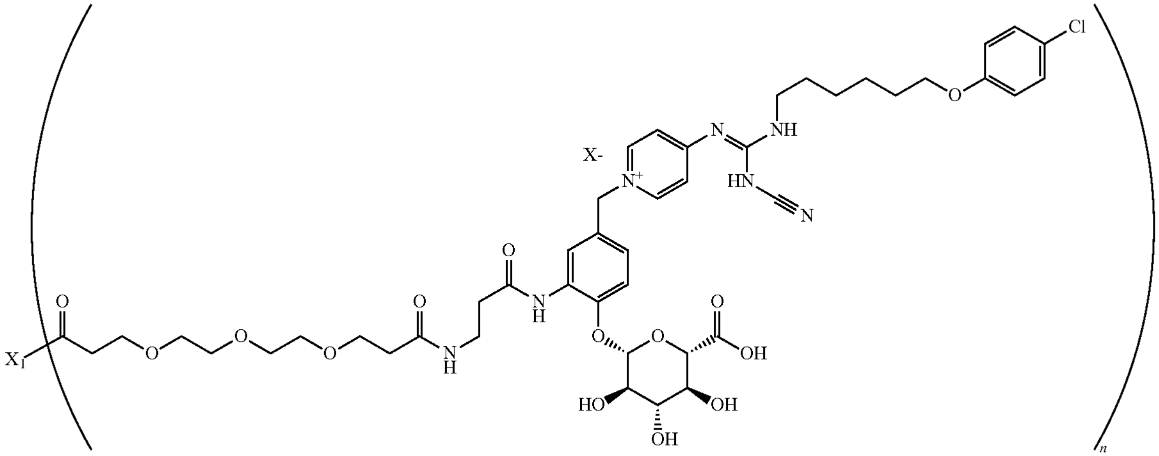 |
| B99 | 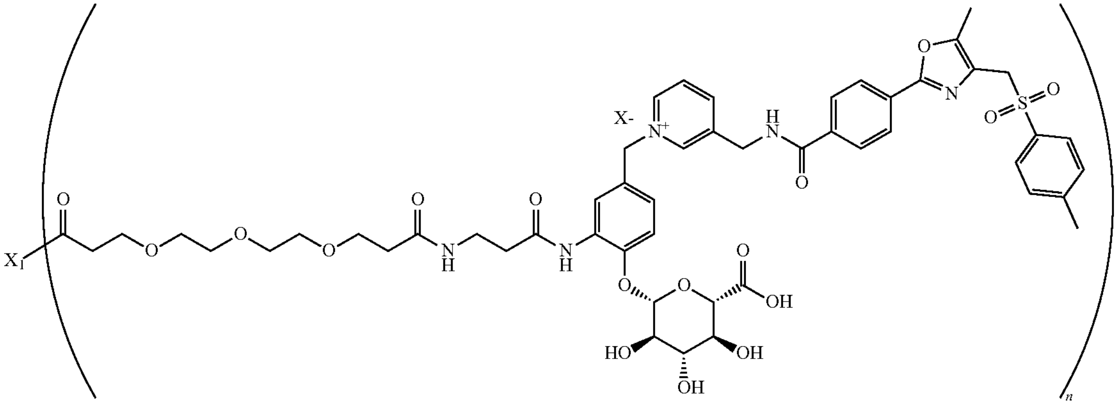 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B100 | 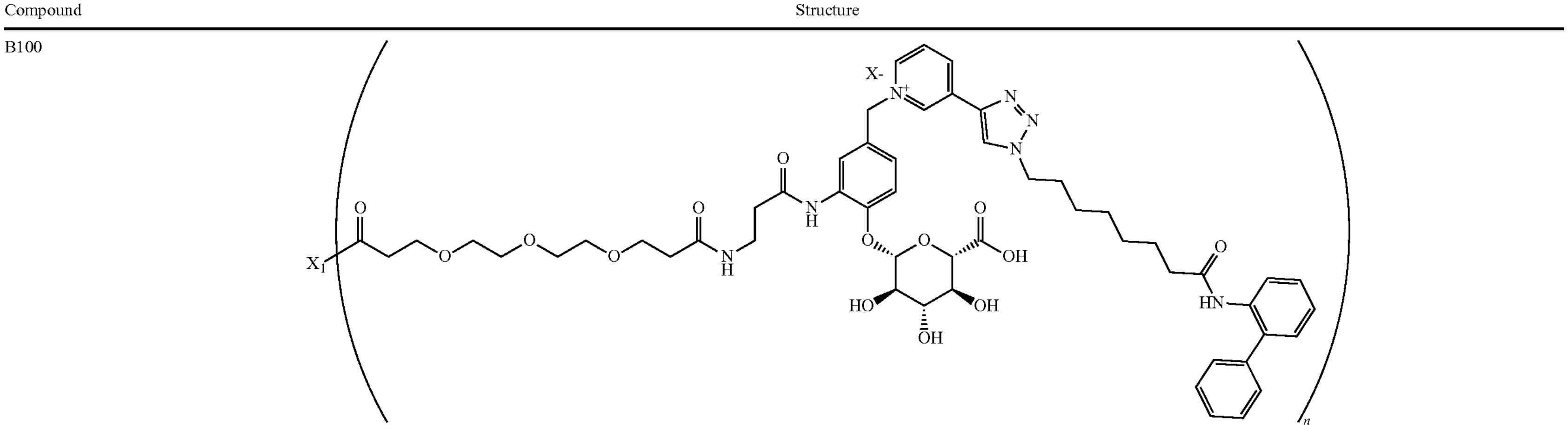 |
| B101 | 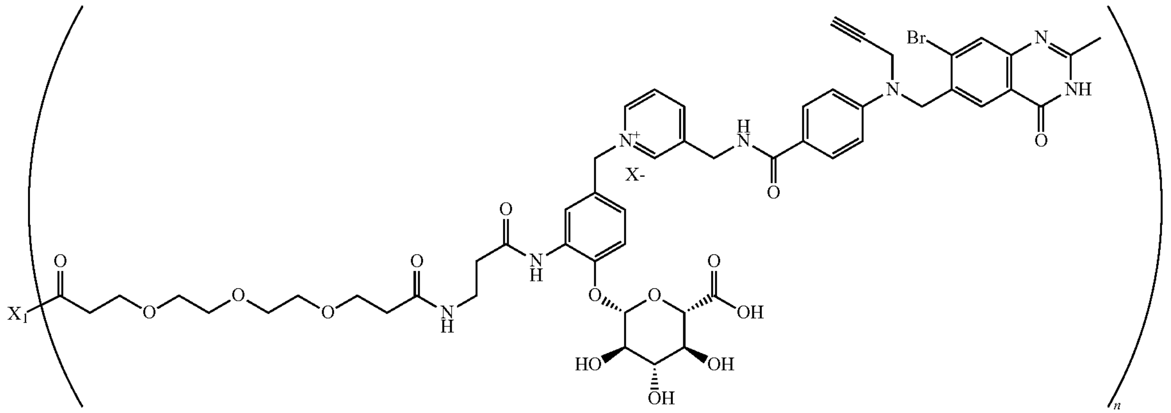 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B102 | 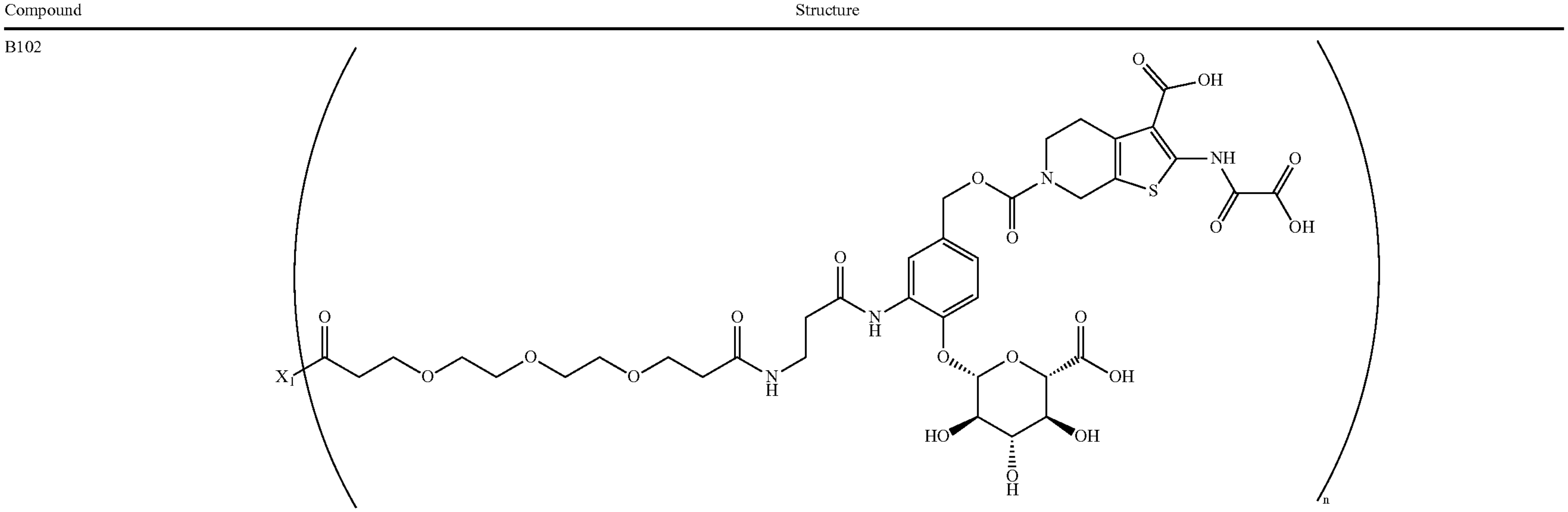 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B103 | 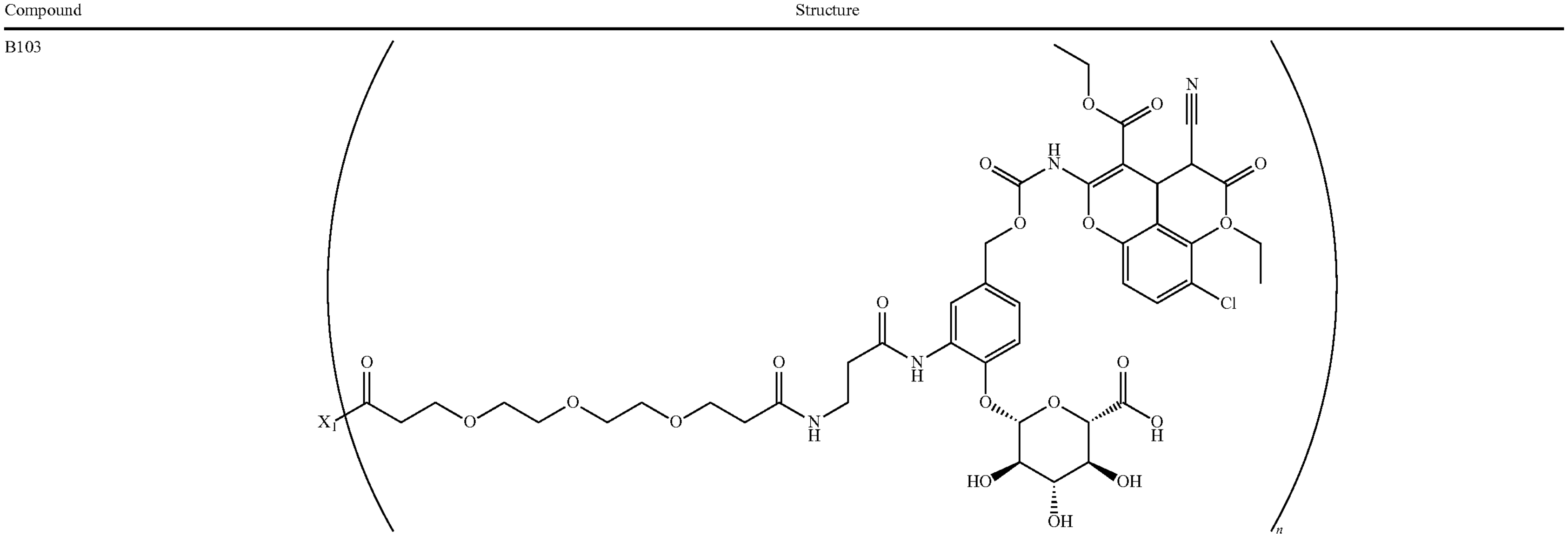 |
| B104 | 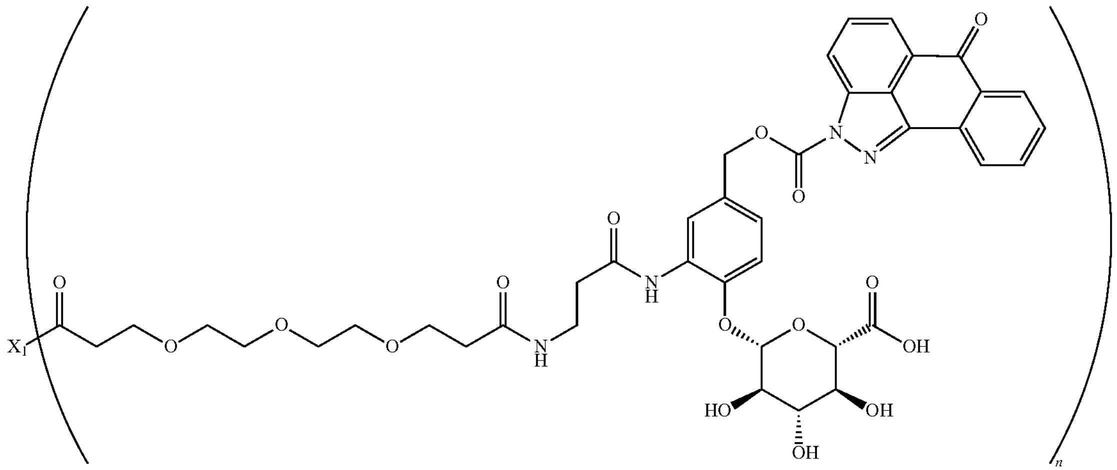 |

TABLE 6-continued
Exemplary Compounds of Formula (II) or Formula (III) for Treating Insulin Resistance, Type 2 Diabetes and Metabolic Syndrome
| Compound | Structure |
|---|---|
| B105 | 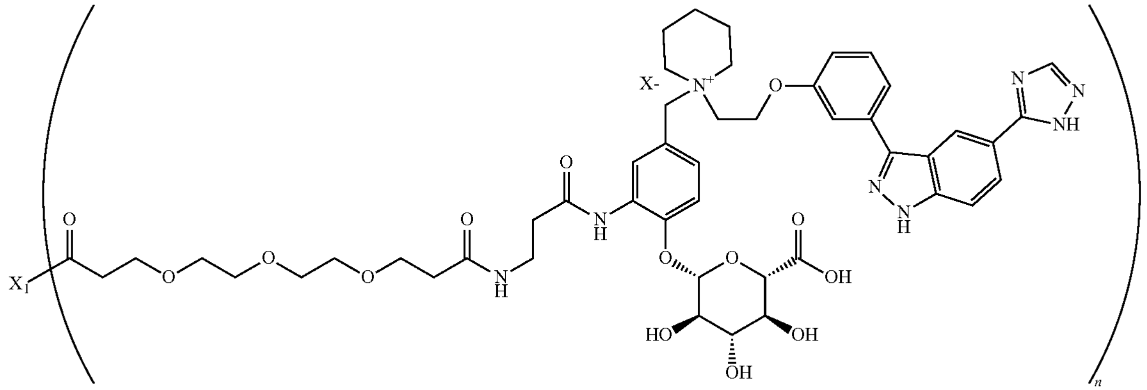 |
| B106 | 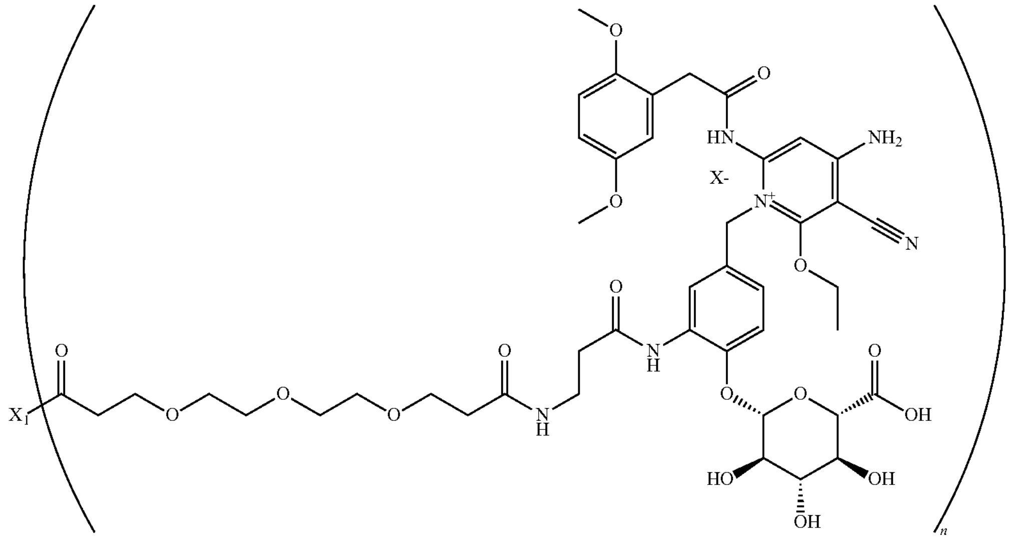 |

TABLE 6-continued
| Exemplary Compounds of Formula (II) or Formula (III) for Treating Insulin Resistance, Type 2 Diabetes and Metabolic Syndrome | |
|---|---|
| Compound | Structure |
| B107 | 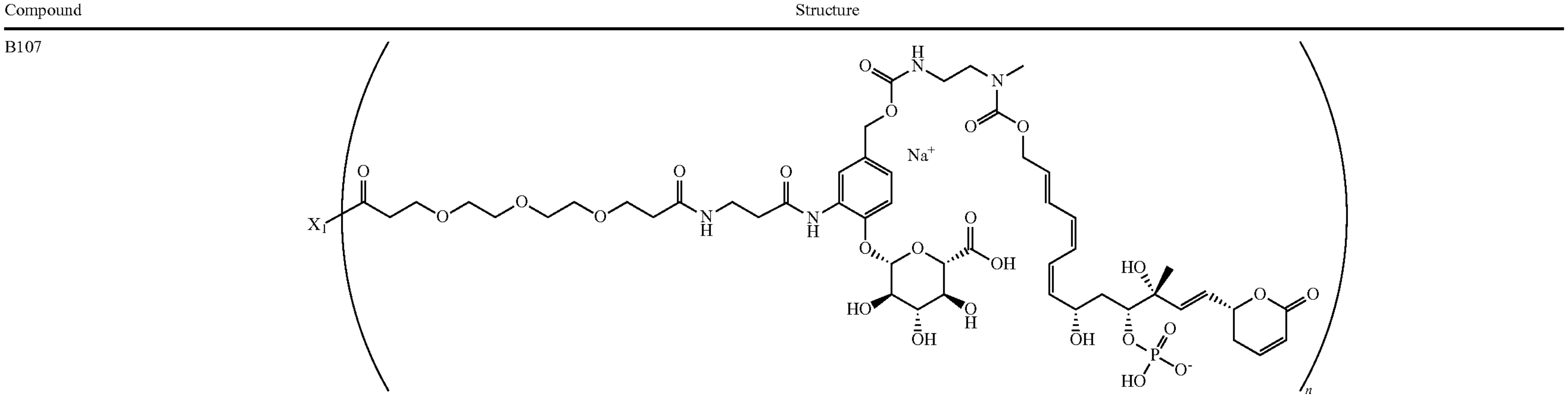 |
| B108 | 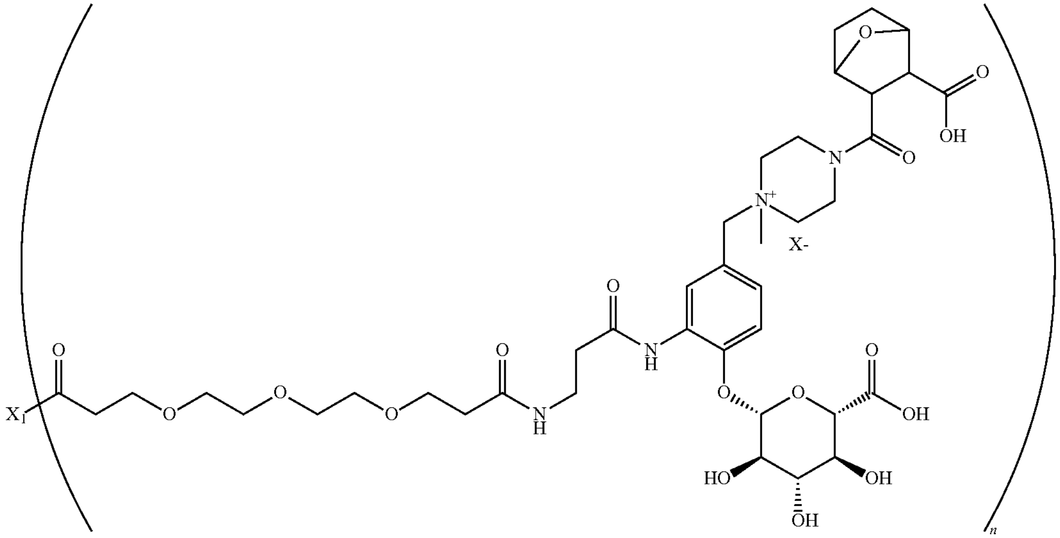 |

In some embodiments, the compound of Formula (II) or Formula (III), or a pharmaceutically acceptable salt, solvate, hydrate, isomer, or tautomer thereof, is selected from the group consisting of B-1, B-2, B-3, B-4, B-19, B-20, B-21, B-22, B-37, B-38, B-39, B-40, B-55, B-56, B-57, B-58, B-73, B-74, B-75, B-76, B-91, B-92, B-93 and B-94.

In some embodiments, the compound of Formula (II) or Formula (III), or a pharmaceutically acceptable salt, solvate, hydrate, isomer, or tautomer thereof, is selected from the group consisting of B-13, B-31, B-49, B-67, B-67, B-85 and B-103.

In some embodiments, the compound of Formula (II) or Formula (III), or a pharmaceutically acceptable salt, solvate, hydrate, isomer, or tautomer thereof, is selected from the group consisting of B-5, B-6, B-23, B-24, B-41, B-42, B-59, B-60, B-77, B-78, B-095 and B-95.

In some embodiments, the compound of Formula (II) or Formula (III), or a pharmaceutically acceptable salt, solvate, hydrate, isomer, or tautomer thereof, is selected from the group consisting of B-14, B-15, B-16, B-32, B-33, B-34, B-50, B-51, B-52, B-68, B-69, B-70, B-86, B-87, B-88, B-104, B- 105 and B-106.

In some embodiments, the compound of Formula (II) or Formula (III), or a pharmaceutically acceptable salt, solvate, hydrate, isomer, or tautomer thereof, is selected from the group consisting of B-12, B-30, B-48, B-66, B-84 and B-102.

In some embodiments, the compound of Formula (II) or Formula (III), or a pharmaceutically acceptable salt, solvate, hydrate, isomer, or tautomer thereof, is selected from the group consisting of B-7, B-8, B-9, B-10, B-11, B-25, B-26, B-27, B-28, B-29, B-43, B-44, B-45, B-46, B-47, B-61, B-62, B-63, B-64, B-65, B-79, B-80, B-81, B-82, B-83, B-97, B-98, B-99, B-100 and B-101.

In some embodiments, the compound of Formula (II) or Formula (III), or a pharmaceutically acceptable salt, solvate, hydrate, isomer, or tautomer thereof, is selected from the group consisting of B-17, B-18, B-35, B-36, B-53, B-54, B-71, B-72, B-89, B-90, B-107 and B-108.

In some embodiments, the compound of Formula (II) or Formula (III), or a pharmaceutically acceptable salt, solvate, hydrate, isomer, or tautomer thereof, is selected from the group consisting of B-1, B-2, B-3, B-4, B-19, B-20, B-21, B-22, B-37, B-38, B-39, B-40, B-55, B-56, B-57, B-58, B-73, B-74, B-75, B-76, B-91, B-92, B-93 and B-94, wherein n is 1, 2, 3, 4, 5, or 6, and wherein $X_1$ is an Insulin polypeptide or a bio-active homolog polypeptide thereof comprising an amino acid sequence set forth in SEQ ID NO:1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-13, B-31, B-49, B-67, B-67, B-85 and B-103, wherein n is 1, 2, 3, 4, 5, or 6, and wherein $X_1$ is an Insulin polypeptide or a bio-active homolog polypeptide thereof comprising an amino acid sequence set forth in SEQ ID NO:1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-5, B-6, B-23, B-24, B-41, B-42, B-59, B-60, B-77, B-78, B-095 and B-95, wherein n is 1, 2, 3, 4, 5, or 6, and wherein $X_1$ is an Insulin polypeptide or a bio-active homolog polypeptide thereof comprising an amino acid sequence set forth in SEQ ID NO:1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-14, B-15, B-16, B-32, B-33, B-34, B-50, B-51, B-52, B-68, B-69, B-70, B-86, B-87, B-88, B-104, B- 105 and B-106, wherein n is 1, 2, 3, 4, 5, or 6, and wherein $X_1$ is an Insulin polypeptide or a bio-active homolog polypeptide thereof comprising an amino acid sequence set forth in SEQ ID NO: 1 or SEQ ID NO: 2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-12, B-30, B-48, B-66, B-84 and B-102, wherein n is 1, 2, 3, 4, 5, or 6, and wherein $X_1$ is an Insulin polypeptide or a bio-active homolog polypeptide thereof comprising an amino acid sequence set forth in SEQ ID NO:1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-7, B-8, B-9, B-10, B-11, B-25, B-26, B-27, B-28, B-29, B-43, B-44, B-45, B-46, B-47, B-61, B-62, B-63, B-64, B-65, B-79, B-80, B-81, B-82, B-83, B-97, B-98, B-99, B-100 and B-101, wherein n is 1, 2, 3, 4, 5, or 6, and wherein $X_1$ is an Insulin polypeptide or a bio-active homolog polypeptide thereof comprising an amino acid sequence set forth in SEQ ID NO:1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO: 1.

In some embodiments, the compound of Formula (II) or Formula (III), or a pharmaceutically acceptable salt, solvate, hydrate, isomer, or tautomer thereof, is selected from the group consisting of B-17, B-18, B-35, B-36, B-53, B-54, B-71, B-72, B-89, B-90, B-107 and B-108, wherein n is 1, 2, 3, 4, 5, or 6, and wherein $X_1$ is an Insulin polypeptide or a bio-active homolog polypeptide thereof comprising an amino acid sequence set forth in SEQ ID NO:1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-1, B-2, B-3, B-4, B-19, B-20, B-21, B-22, B-37, B-38, B-39, B-40, B-55, B-56, B-57, B-58, B-73, B-74, B-75, B-76, B-91, B-92, B-93 and B-94, wherein n is 1, 2, 3, 4, 5, or 6, and wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO: 1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-13, B-31, B-49, B-67, B-67, B-85 and B-103, wherein n is 1, 2, 3, 4, 5, or 6, and wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO: 1.

In some embodiments, the compound of Formula (II) or Formula (III), or a pharmaceutically acceptable salt, solvate, hydrate, isomer, or tautomer thereof, is selected from the group consisting of B-5, B-6, B-23, B-24, B-41, B-42, B-59, B-60, B-77, B-78, B-095 and B-95, wherein n is 1, 2, 3, 4, 5, or 6, and wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO: 2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-14, B-15, B-16, B-32, B-33, B-34, B-50, B-51, B-52, B-68, B-69, B-70, B-86, B-87, B-88, B-104, B- 105 and B-106, wherein n is 1, 2, 3, 4, 5, or 6, and wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-12, B-30, B-48, B-66, B-84 and B-102, wherein n is 1, 2, 3, 4, 5, or 6, and wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-7, B-8, B-9, B-10, B-11, B-25, B-26, B-27, B-28, B-29, B-43, B-44, B-45, B-46, B-47, B-61, B-62, B-63, B-64, B-65, B-79, B-80, B-81, B-82, B-83, B-97, B-98, B-99, B-100 and B-101, wherein n is 1, 2, 3, 4, 5, or 6, and wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-17, B-18, B-35, B-36, B-53, B-54, B-71, B-72, B-89, B-90, B-107 and B-108, wherein n is 1, 2, 3, 4, 5, or 6, and wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO: 2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-1, B-2, B-3, B-4, B-19, B-20, B-21, B-22, B-37, B-38, B-39, B-40, B-55, B-56, B-57, B-58, B-73, B-74, B-75, B-76, B-91, B-92, B-93 and B-94, wherein n is 1 or 2, and wherein $X_1$ is an Insulin polypeptide or a bio-active homolog polypeptide thereof comprising an amino acid sequence set forth in SEQ ID NO: 1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-13, B-31, B-49, B-67, B-67, B-85 and B-103, wherein n is 1 or 2, and wherein $X_1$ is an Insulin polypeptide or a bio-active homolog polypeptide thereof comprising an amino acid sequence set forth in SEQ ID NO:1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-5, B-6, B-23, B-24, B-41, B-42, B-59, B-60, B-77, B-78, B-095 and B-95, wherein n is 1 or 2, and wherein $X_1$ is an Insulin polypeptide or a bio-active homolog polypeptide thereof comprising an amino acid sequence set forth in SEQ ID NO:1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-14, B-15, B-16, B-32, B-33, B-34, B-50, B-51, B-52, B-68, B-69, B-70, B-86, B-87, B-88, B-104, B- 105 and B-106, wherein n is 1 or 2, and wherein $X_1$ is an Insulin polypeptide or a bio-active homolog polypeptide thereof comprising an amino acid sequence set forth in SEQ ID NO: 1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-12, B-30, B-48, B-66, B-84 and B-102, wherein n is 1 or 2, and wherein $X_1$ is an Insulin polypeptide or a bio-active homolog polypeptide thereof comprising an amino acid sequence set forth in SEQ ID NO: 1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-7, B-8, B-9, B-10, B-11, B-25, B-26, B-27, B-28, B-29, B-43, B-44, B-45, B-46, B-47, B-61, B-62, B-63, B-64, B-65, B-79, B-80, B-81, B-82, B-83, B-97, B-98, B-99, B-100 and B-101, wherein n is 1 or 2, and wherein $X_1$ is an Insulin polypeptide or a bio-active homolog polypeptide thereof comprising an amino acid sequence set forth in SEQ ID NO:1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-17, B-18, B-35, B-36, B-53, B-54, B-71, B-72, B-89, B-90, B-107 and B-108, wherein n is 1 or 2, and wherein $X_1$ is an Insulin polypeptide or a bio-active homolog polypeptide thereof comprising an amino acid sequence set forth in SEQ ID NO:1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-1, B-2, B-3, B-4, B-19, B-20, B-21, B-22, B-37, B-38, B-39, B-40, B-55, B-56, B-57, B-58, B-73, B-74, B-75, B-76, B-91, B-92, B-93 and B-94, wherein n is 1 or 2, and wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-13, B-31, B-49, B-67, B-67, B-85 and B-103, wherein n is 1 or 2, and wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO: 1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-5, B-6, B-23, B-24, B-41, B-42, B-59, B-60, B-77, B-78, B-095 and B-95, wherein n is 1 or 2, and wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-14, B-15, B-16, B-32, B-33, B-34, B-50, B-51, B-52, B-68, B-69, B-70, B-86, B-87, B-88, B-104, B- 105 and B-106, wherein n is 1 or 2, and wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-12, B-30, B-48, B-66, B-84 and B-102, wherein n is 1 or 2, and wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-7, B-8, B-9, B-10, B-11, B-25, B-26, B-27, B-28, B-29, B-43, B-44, B-45, B-46, B-47, B-61, B-62, B-63, B-64, B-65, B-79, B-80, B-81, B-82, B-83, B-97, B-98, B-99, B-100 and B-101, wherein n is 1 or 2, and wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO: 1 or SEQ ID NO: 2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-17, B-18, B-35, B-36, B-53, B-54, B-71, B-72, B-89, B-90, B-107 and B-108, wherein n is 1 or 2, and wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-1, B-2, B-3, B-4, B-19, B-20, B-21, B-22, B-37, B-38, B-39, B-40, B-55, B-56, B-57, B-58, B-73, B-74, B-75, B-76, B-91, B-92, B-93 and B-94, wherein n is 3 or 4, and wherein $X_1$ is an Insulin polypeptide or a bio-active homolog polypeptide thereof comprising an amino acid sequence set forth in SEQ ID NO: 1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-13, B-31, B-49, B-67, B-67, B-85 and B-103, wherein n is 3 or 4, and wherein $X_1$ is an Insulin polypeptide or a bio-active homolog polypeptide thereof comprising an amino acid sequence set forth in SEQ ID NO:1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-5, B-6, B-23, B-24, B-41, B-42, B-59, B-60, B-77, B-78, B-095 and B-95, wherein n is 3 or 4, and wherein $X_1$ is an Insulin polypeptide or a bio-active homolog polypeptide thereof comprising an amino acid sequence set forth in SEQ ID NO:1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-14, B-15, B-16, B-32, B-33, B-34, B-50, B-51, B-52, B-68, B-69, B-70, B-86, B-87, B-88, B-104, B- 105 and B-106, wherein n is 3 or 4, and wherein $X_1$ is an Insulin polypeptide or a bio-active homolog polypeptide thereof comprising an amino acid sequence set forth in SEQ ID NO:1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-12, B-30, B-48, B-66, B-84 and B-102, wherein n is 3 or 4, and wherein $X_1$ is an Insulin polypeptide or a bio-active homolog polypeptide thereof comprising an amino acid sequence set forth in SEQ ID NO: 1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-7, B-8, B-9, B-10, B-11, B-25, B-26, B-27, B-28, B-29, B-43, B-44, B-45, B-46, B-47, B-61, B-62, B-63, B-64, B-65, B-79, B-80, B-81, B-82, B-83, B-97, B-98, B-99, B-100 and B-101, wherein n is 3 or 4, and wherein $X_1$ is an Insulin polypeptide or a bio-active homolog polypeptide thereof comprising an amino acid sequence set forth in SEQ ID NO:1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-17, B-18, B-35, B-36, B-53, B-54, B-71, B-72, B-89, B-90, B-107 and B-108, wherein n is 3 or 4, and wherein $X_1$ is an Insulin polypeptide or a bio-active homolog polypeptide thereof comprising an amino acid sequence set forth in SEQ ID NO:1 or SEQ ID NO:2. In certain such embodiments, the Insulin polypeptide or the bio-active homolog polypeptide thereof comprises the amino acid sequence set forth in SEQ ID NO:2. In certain such embodiments, the Insulin polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-1, B-2, B-3, B-4, B-19, B-20, B-21, B-22, B-37, B-38, B-39, B-40, B-55, B-56, B-57, B-58, B-73, B-74, B-75, B-76, B-91, B-92, B-93 and B-94, wherein n is 3 or 4, and wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO:2. In certain such embodiments, the Insulin polypeptide or the bio-active homolog polypeptide thereof comprises the amino acid sequence set forth in SEQ ID NO:2.

In some embodiments, the compound of Formula (II) or Formula (III), or a pharmaceutically acceptable salt, solvate, hydrate, isomer, or tautomer thereof, is selected from the group consisting of B-13, B-31, B-49, B-67, B-67, B-85 and B-103, wherein n is 3 or 4, and wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO:2. In certain such embodiments, the Insulin polypeptide or the bio-active homolog polypeptide thereof comprises the amino acid sequence set forth in SEQ ID NO:2.

In some embodiments, the compound of Formula (II) or Formula (III), or a pharmaceutically acceptable salt, solvate, hydrate, isomer, or tautomer thereof, is selected from the group consisting of B-5, B-6, B-23, B-24, B-41, B-42, B-59, B-60, B-77, B-78, B-095 and B-95, wherein n is 3 or 4, and wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO:2. In certain such embodiments, the Insulin polypeptide or the bio-active homolog polypeptide thereof comprises the amino acid sequence set forth in SEQ ID NO:2.

In some embodiments, the compound of Formula (II) or Formula (III), or a pharmaceutically acceptable salt, solvate, hydrate, isomer, or tautomer thereof, is selected from the group consisting of B-14, B-15, B-16, B-32, B-33, B-34, B-50, B-51, B-52, B-68, B-69, B-70, B-86, B-87, B-88, B-104, B- 105 and B-106, wherein n is 3 or 4, and wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO: 1 or SEQ ID NO:2. In certain such embodiments, the Insulin polypeptide or the bio-active homolog polypeptide thereof comprises the amino acid sequence set forth in SEQ ID NO:2.

In some embodiments, the compound of Formula (II) or Formula (III), or a pharmaceutically acceptable salt, solvate, hydrate, isomer, or tautomer thereof, is selected from the group consisting of B-12, B-30, B-48, B-66, B-84 and B-102, wherein n is 3 or 4, and wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO:2. In certain such embodiments, the Insulin polypeptide or the bio-active homolog polypeptide thereof comprises the amino acid sequence set forth in SEQ ID NO:2.

In some embodiments, the compound of Formula (II) or Formula (III), or a pharmaceutically acceptable salt, solvate, hydrate, isomer, or tautomer thereof, is selected from the group consisting of B-7, B-8, B-9, B-10, B-11, B-25, B-26, B-27, B-28, B-29, B-43, B-44, B-45, B-46, B-47, B-61, B-62, B-63, B-64, B-65, B-79, B-80, B-81, B-82, B-83, B-97, B-98, B-99, B-100 and B-101, wherein n is 3 or 4, and wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO: 2. In certain such embodiments, the Insulin polypeptide or the bio-active homolog polypeptide thereof comprises the amino acid sequence set forth in SEQ ID NO:2.

In some embodiments, the compound of Formula (II) or Formula (III), or a pharmaceutically acceptable salt, solvate, hydrate, isomer, or tautomer thereof, is selected from the group consisting of B-17, B-18, B-35, B-36, B-53, B-54, B-71, B-72, B-89, B-90, B-107 and B-108, wherein n is 3 or 4, and wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO:2. In certain such embodiments, the Insulin polypeptide or the bio-active homolog polypeptide thereof comprises the amino acid sequence set forth in SEQ ID NO:2.

In some embodiments, the compound of Formula (II) or Formula (III), or a pharmaceutically acceptable salt, solvate, hydrate, isomer, or tautomer thereof, is selected from the group consisting of B-1, B-2, B-3, B-4, B-19, B-20, B-21, B-22, B-37, B-38, B-39, B-40, B-55, B-56, B-57, B-58, B-73, B-74, B-75, B-76, B-91, B-92, B-93 and B-94, wherein n is 5 or 6, and wherein $X_1$ is an Insulin polypeptide or a bio-active homolog polypeptide thereof comprising an amino acid sequence set forth in SEQ ID NO: 1 or SEQ ID NO:2. In certain such embodiments, the Insulin polypeptide or the bio-active homolog polypeptide thereof comprises the amino acid sequence set forth in SEQ ID NO:2.

In some embodiments, the compound of Formula (II) or Formula (III), or a pharmaceutically acceptable salt, solvate, hydrate, isomer, or tautomer thereof, is selected from the group consisting of B-13, B-31, B-49, B-67, B-67, B-85 and B-103, wherein n is 5 or 6, and wherein $X_1$ is an Insulin polypeptide or a bio-active homolog polypeptide thereof comprising an amino acid sequence set forth in SEQ ID NO:1 or SEQ ID NO:2. In certain such embodiments, the Insulin polypeptide or the bio-active homolog polypeptide thereof comprises the amino acid sequence set forth in SEQ ID NO:2.

In some embodiments, the compound of Formula (II) or Formula (III), or a pharmaceutically acceptable salt, solvate, hydrate, isomer, or tautomer thereof, is selected from the group consisting of B-5, B-6, B-23, B-24, B-41, B-42, B-59, B-60, B-77, B-78, B-095 and B-95, wherein n is 5 or 6, and wherein $X_1$ is an Insulin polypeptide or a bio-active homolog polypeptide thereof comprising an amino acid sequence set forth in SEQ ID NO:1 or SEQ ID NO:2. In certain such embodiments, the Insulin polypeptide or the bio-active homolog polypeptide thereof comprises the amino acid sequence set forth in SEQ ID NO:2.

In some embodiments, the compound of Formula (II) or Formula (III), or a pharmaceutically acceptable salt, solvate, hydrate, isomer, or tautomer thereof, is selected from the group consisting of B-14, B-15, B-16, B-32, B-33, B-34, B-50, B-51, B-52, B-68, B-69, B-70, B-86, B-87, B-88, B-104, B- 105 and B-106, wherein n is 5 or 6, and wherein $X_1$ is an Insulin polypeptide or a bio-active homolog polypeptide thereof comprising an amino acid sequence set forth in SEQ ID NO: 1 or SEQ ID NO:2. In certain such embodiments, the Insulin polypeptide or the bio-active homolog polypeptide thereof comprises the amino acid sequence set forth in SEQ ID NO:2.

In some embodiments, the compound of Formula (II) or Formula (III), or a pharmaceutically acceptable salt, solvate, hydrate, isomer, or tautomer thereof, is selected from the group consisting of B-12, B-30, B-48, B-66, B-84 and B-102, wherein n is 5 or 6, and wherein $X_1$ is an Insulin polypeptide or a bio-active homolog polypeptide thereof comprising an amino acid sequence set forth in SEQ ID NO: 1 or SEQ ID NO:2. In certain such embodiments, the Insulin polypeptide or the bio-active homolog polypeptide thereof comprises the amino acid sequence set forth in SEQ ID NO:2.

In some embodiments, the compound of Formula (II) or Formula (III), or a pharmaceutically acceptable salt, solvate, hydrate, isomer, or tautomer thereof, is selected from the group consisting of B-7, B-8, B-9, B-10, B-11, B-25, B-26, B-27, B-28, B-29, B-43, B-44, B-45, B-46, B-47, B-61, B-62, B-63, B-64, B-65, B-79, B-80, B-81, B-82, B-83, B-97, B-98, B-99, B-100 and B-101, wherein n is 5 or 6, and wherein $X_1$ is an Insulin polypeptide or a bio-active homolog polypeptide thereof comprising an amino acid sequence set forth in SEQ ID NO:1 or SEQ ID NO:2. In certain such embodiments, the Insulin polypeptide or the bio-active homolog polypeptide thereof comprises the amino acid sequence set forth in SEQ ID NO:2.

In some embodiments, the compound of Formula (II) or Formula (III), or a pharmaceutically acceptable salt, solvate, hydrate, isomer, or tautomer thereof, is selected from the group consisting of B-17, B-18, B-35, B-36, B-53, B-54, B-71, B-72, B-89, B-90, B-107 and B-108, wherein n is 5 or 6, and wherein $X_1$ is an Insulin polypeptide or a bio-active homolog polypeptide thereof comprising an amino acid sequence set forth in SEQ ID NO:1 or SEQ ID NO:2. In certain such embodiments, the Insulin polypeptide or the bio-active homolog polypeptide thereof comprises the amino acid sequence set forth in SEQ ID NO:2.

In some embodiments, the compound of Formula (II) or Formula (III), or a pharmaceutically acceptable salt, solvate, hydrate, isomer, or tautomer thereof, is selected from the group consisting of B-1, B-2, B-3, B-4, B-19, B-20, B-21, B-22, B-37, B-38, B-39, B-40, B-55, B-56, B-57, B-58, B-73, B-74, B-75, B-76, B-91, B-92, B-93 and B-94, wherein n is 5 or 6, and wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO:2. In certain such embodiments, the Insulin polypeptide or the bio-active homolog polypeptide thereof comprises the amino acid sequence set forth in SEQ ID NO:2.

In some embodiments, the compound of Formula (II) or Formula (III), or a pharmaceutically acceptable salt, solvate, hydrate, isomer, or tautomer thereof, is selected from the group consisting of B-13, B-31, B-49, B-67, B-67, B-85 and B-103, wherein n is 5 or 6, and wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO: 1 or SEQ ID NO:2. In certain such embodiments, the Insulin polypeptide or the bio-active homolog polypeptide thereof comprises the amino acid sequence set forth in SEQ ID NO:2.

In some embodiments, the compound of Formula (II) or Formula (III), or a pharmaceutically acceptable salt, solvate, hydrate, isomer, or tautomer thereof, is selected from the group consisting of B-5, B-6, B-23, B-24, B-41, B-42, B-59, B-60, B-77, B-78, B-095 and B-95, wherein n is 5 or 6, and wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO:2. In certain such embodiments, the Insulin polypeptide or the bio-active homolog polypeptide thereof comprises the amino acid sequence set forth in SEQ ID NO:2.

In some embodiments, the compound of Formula (II) or Formula (III), or a pharmaceutically acceptable salt, solvate, hydrate, isomer, or tautomer thereof, is selected from the group consisting of B-14, B-15, B-16, B-32, B-33, B-34, B-50, B-51, B-52, B-68, B-69, B-70, B-86, B-87, B-88, B-104, B- 105 and B-106, wherein n is 5 or 6, and wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO:2. In certain such embodiments, the Insulin polypeptide or the bio-active homolog polypeptide thereof comprises the amino acid sequence set forth in SEQ ID NO:2.

In some embodiments, the compound of Formula (II) or Formula (III), or a pharmaceutically acceptable salt, solvate, hydrate, isomer, or tautomer thereof, is selected from the group consisting of B-12, B-30, B-48, B-66, B-84 and B-102, wherein n is 5 or 6, and wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO:2. In certain such embodiments, the Insulin polypeptide or the bio-active homolog polypeptide thereof comprises the amino acid sequence set forth in SEQ ID NO:2.

In some embodiments, the compound of Formula (II) or Formula (III), or a pharmaceutically acceptable salt, solvate, hydrate, isomer, or tautomer thereof, is selected from the group consisting of B-7, B-8, B-9, B-10, B-11, B-25, B-26, B-27, B-28, B-29, B-43, B-44, B-45, B-46, B-47, B-61, B-62, B-63, B-64, B-65, B-79, B-80, B-81, B-82, B-83, B-97, B-98, B-99, B-100 and B-101, wherein n is 5 or 6, and wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO: 2. In certain such embodiments, the Insulin polypeptide or the bio-active homolog polypeptide thereof comprises the amino acid sequence set forth in SEQ ID NO:2.

In some embodiments, the compound of Formula (II) or Formula (III), or a pharmaceutically acceptable salt, solvate, hydrate, isomer, or tautomer thereof, is selected from the group consisting of B-17, B-18, B-35, B-36, B-53, B-54, B-71, B-72, B-89, B-90, B-107 and B-108, wherein n is 5 or 6, and wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO: 1 or SEQ ID NO:2. In certain such embodiments, the Insulin polypeptide or the bio-active homolog polypeptide thereof comprises the amino acid sequence set forth in SEQ ID NO:2.

In some embodiments, the compound of Formula (II) or Formula (III), or a pharmaceutically acceptable salt, solvate, hydrate, isomer, or tautomer thereof, $X_2$ is a mixture of $X_{2b}$ and $X_{2c}$, wherein $X_{2b}$ is a linker that is bound to one Cys residue on $X_1$,$X_{2c}$ is a linker that is bound to two Cys residues on $X_1$, n is a combination of n1 and n2, wherein n is 1, 2, 3, 4, 5, or 6, and $X_1$ is an Insulin polypeptide or a bio-active homolog polypeptide thereof comprising an amino acid sequence set forth in SEQ ID NO: 1 or SEQ ID NO:2. In certain such embodiments, the compound of Formula (II) or Formula (III), or a pharmaceutically acceptable salt, solvate, hydrate, isomer, or tautomer thereof, is B-49. In certain such embodiments, n1 is 2 or 3 and n2 is 1. In certain such embodiments, n1 is 2 and n2 is 1. In some embodiments, n1 is 3 and n2 is 1. In some embodiments, the compound of Formula (II) or Formula (III), or a pharmaceutically acceptable salt, solvate, hydrate, isomer, or tautomer thereof, is B-49, wherein $X_1$ is an Insulin polypeptide or a bio-active homolog polypeptide thereof comprising an amino acid sequence set forth in SEQ ID NO: 1 or SEQ ID NO:2, and n1 is 2 or 3 and n2 is 1. In some embodiments, the compound of Formula (II) or Formula (III), or a pharmaceutically acceptable salt, solvate, hydrate, isomer, or tautomer thereof, is B-49, wherein $X_1$ is an Insulin polypeptide or a bio-active homolog polypeptide thereof comprising an amino acid sequence set forth in SEQ ID NO:2, and n1 is 2 or 3 and n2 is 1.

In some embodiments, the compound of Formula (II) or Formula (III), or a pharmaceutically acceptable salt, solvate, hydrate, isomer, or tautomer thereof, $X_2$ is a mixture of $X_{2b}$ and $X_{2c}$, wherein $X_{2b}$ is a linker that is bound to one Cys residue on $X_1$,$X_2$e is a linker that is bound to two Cys residues on $X_1$, n is a combination of n1 and n2, wherein n is 1, 2, 3, 4, 5, or 6, and $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO:2. In certain such embodiments, the compound of Formula (II) or Formula (III), or a pharmaceutically acceptable salt, solvate, hydrate, isomer, or tautomer thereof, is B-49. In certain such embodiments, n1 is 2 or 3 and n2 is 1. In certain such embodiments, n1 is 2 and n2 is 1. In some embodiments, n1 is 3 and n2 is 1. In some embodiments, the compound of Formula (II) or Formula (III), or a pharmaceutically acceptable salt, solvate, hydrate, isomer, or tautomer thereof, is B-49, wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO:2, and n1 is 2 or 3 and n2 is 1. In some embodiments, the compound of Formula (II) or Formula (III), or a pharmaceutically acceptable salt, solvate, hydrate, isomer, or tautomer thereof, is B-49, wherein $X_1$ is an Insulin polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:2, and n1 is 2 or 3 and n2 is 1.

The disclosure is directed to compounds as described herein and pharmaceutically acceptable salts, solvates, hydrates, isomers, or tautomers thereof. The use of the terms "salt," "hydrate," "solvate," and the like, is intended to equally apply to the salt, hydrate, or solvate of isomers, tautomers, or racemates of the disclosed compounds.

It should be understood that all isomeric forms are included within the present disclosure, including mixtures thereof. The term "isomer" may refer to compounds that have the same composition and molecular weight but differ in physical and/or chemical properties. The structural difference may be in constitution (geometric or positional isomers) or in the ability to rotate the plane of polarized light (stereoisomers). With regard to stereoisomers, the compounds of the disclosure may have one or more asymmetric carbon atom and may occur as racemates, racemic mixtures and as individual enantiomers or diastereomers. Individual isomers of the compounds of the disclosure may, for example, be substantially free of other isomers, or may be admixed, for example, as racemates or with all other, or other selected, isomers. If the compound contains a double bond, the substituent may be in the E or Z configuration or cis or trans configuration or mixtures of any of the foregoing. Disclosed assay results may reflect the data collected for the racemic form, the enantiomerically pure form, or any other form in terms of stereochemistry or constitution (e.g., geometric or positional isomers).

The compounds of the disclosure may contain asymmetric or chiral centers, and, therefore, exist in different stereoisomeric forms. The term "stereoisomers" may refer to the set of compounds which have the same number and type of atoms and share the same bond connectivity between those atoms, but differ in three dimensional structure. The term "stereoisomer" may refer to any member of this set of compounds. For instance, a stereoisomer may be an enantiomer or a diastereomer. It is intended that all stereoisomeric forms of the compounds of the disclosure as well as mixtures thereof, including racemic mixtures, form part of the present disclosure.

The term "enantiomers" may refer to a pair of stereoisomers which are non-superimposable mirror images of one another. The term "enantiomer" may refer to a single member of this pair of stereoisomers. The term "racemic" may refer to a 1:1 mixture of a pair of enantiomers. Each compound herein disclosed may include all the enantiomers (which may exist even in the absence of asymmetric carbons) that conform to the general structure of the compound, unless the stereochemistry is specifically indicated. The compounds may be in a racemic or enantiomerically pure form, or any other form in terms of stereochemistry. The chiral centers of the present disclosure may have the S or R configuration as defined by the IUPAC 1974 Recommendations. In some examples presented, the synthetic route may produce a single enantiomer or a mixture of enantiomers. In some embodiments of the disclosure, the compounds of the disclosure are enantiomers. In some embodiments, the compounds of the disclosure are the(S)-enantiomer. In other embodiments, the compounds of the disclosure are the (R)-enantiomer. In yet other embodiments, the compounds of the disclosure may be (+) or (−) enantiomers.

The term "diastereomers" may refer to the set of stereoisomers which cannot be made superimposable by rotation around single bonds. For example, cis- and trans-double bonds, endo- and exo-substitution on bicyclic ring systems, and compounds containing multiple stereogenic centers with different relative configurations may be considered to be diastereomers. The term "diastereomer" may refer to any member of this set of compounds. In some examples presented, the synthetic route may produce a single diastereomer or a mixture of diastereomers. The disclosure may include diastereomers of the compounds described herein.

In some embodiments, pharmaceutical compositions of the disclosure may be enriched to provide predominantly one enantiomer of a compound described herein. An enantiomerically enriched mixture may comprise, for example, at least 60 mol percent of one enantiomer, or more preferably at least 75, at least 80, at least 85, at least 90, at least 95, at least 96, at least 97, at least 98, at least 99, at least 99.5 or even 100 mol percent. In some embodiments, the compound described herein enriched in one enantiomer may be substantially free of the other enantiomer, wherein substantially free may mean that the substance in question makes up less than 10%, or less than 5%, or less than 4%, or less than 3%, or less than 2%, or less than 1% as compared to the amount of the other enantiomer, e.g., in the pharmaceutical composition or compound mixture. For example, if a pharmaceutical composition or compound mixture contains 98 grams of a first enantiomer and 2 grams of a second enantiomer, it would be said to contain 98 mol percent of the first enantiomer and only 2 mol percent of the second enantiomer.

In some embodiments, the pharmaceutical compositions of the disclosure may be enriched to provide predominantly one diastereomer of a compound disclosed herein. A diastereomerically enriched mixture may comprise, for example, at least 60 mol percent of one diastereomer, or more preferably at least 75, at least 80, at least 85, at least 90, at least 95, at least 96, at least 97, at least 98, at least 99, at least 99.5, or even 100 mol percent. In some embodiments, the compound described herein enriched in one diastereomer may be substantially free of other diastereomers, wherein substantially free may mean that the substance in question makes up less than 10%, or less than 5%, or less than 4%, or less than 3%, or less than 2%, or less than 1% as compared to the amount of other disastereomers, e.g., in the pharmaceutical composition or compound mixture.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by use of a chiral HPLC column. Also, some of the compounds of the disclosure may be atropisomers or rotameric forms and are considered as part of this disclosure.

Compounds of the disclosure may exist in their tautomeric form (for example, as an amide or imino ether). All such tautomeric forms are contemplated herein as part of the present disclosure.

In some embodiments, the present disclosure provides compounds of Formula (I), (II), or (III), or pharmaceutically acceptable salts, solvates, hydrates, or tautomers thereof, or pharmaceutical compositions comprising the compounds, or pharmaceutically acceptable salts, solvates, hydrates, or tautomers thereof, wherein the isomeric form and/or stereochemistry is not determined. All isomers, including stereoisomers, of Formula (I), (II), or (III), or pharmaceutically acceptable salts, solvates, hydrates, or tautomers thereof, are hereby included in the disclosure.

The disclosure may include pharmaceutically acceptable salts of the compounds disclosed herein. A "pharmaceutically acceptable salt" may be acceptable for use in humans or domestic animals and may refer to those salts that retain the biological effectiveness and properties of the free forms, which are not biologically or otherwise undesirable. Representative "pharmaceutically acceptable salts" may include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, sethionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate, 1,1-methene-bis-2-hydroxy-3-naphthoate, einbonate, pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

Pharmaceutically acceptable salts may also include both acid and base addition salts. "Pharmaceutically acceptable acid addition salt" may refer to those salts which retain the biological effectiveness and properties of the free bases, which are not biologically or otherwise undesirable, and which may be formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" may refer to those salts that retain the biological effectiveness and properties of the free acids, which are not biologically or otherwise undesirable. These salts may be prepared from addition of an inorganic base or an organic base to the free acid. Salts derived from inorganic bases may include, but are not limited to, the sodium, potassium, lithium, ammonium, calcium, magnesium, iron, zinc, copper, manganese, aluminum salts and the like. For example, inorganic salts may include, but are not limited to, ammonium, sodium, potassium, calcium, and magnesium salts. Salts derived from organic bases may include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like.

Compounds of the disclosure may exist as solvates. The term "solvate" may refer to a complex of variable stoichiometry formed by a solute and solvent. Such solvents for the purpose of the disclosure may not interfere with the biological activity of the solute. Examples of suitable solvents include, but are not limited to, water, MeOH, EtOH, and AcOH. Solvates wherein water is the solvent molecule are typically referred to as hydrates. Hydrates may include compositions containing stoichiometric amounts of water, as well as compositions containing variable amounts of water.

The compounds described herein further include all pharmaceutically acceptable isotopically labeled compounds. An "isotopically" or "radio-labeled" compound may be a compound where one or more atoms are replaced or substituted by an atom having an atomic mass or mass number different from the atomic mass or mass number typically found in nature (i.e., naturally occurring). For example, in some embodiments, in the compounds described herein hydrogen atoms are replaced or substituted by one or more deuterium or tritium. Certain isotopically labeled compounds of this disclosure, for example, those incorporating a radioactive isotope, may be useful in drug and/or substrate tissue distribution studies. The radioactive isotopes tritium, i.e., $^{3}H$, and carbon 14, i.e., $^{14}C$, may be particularly useful for this purpose in view of their ease of incorporation and ready means of detection. Substitution with heavier isotopes such as deuterium, i.e., 2H, may afford certain therapeutic advantages resulting from greater metabolic stability, for example, increased in vivo half-life or reduced dosage requirements, and hence may be preferred in some circumstances. Suitable isotopes that may be incorporated in compounds described herein include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$, and $^{131}I$. Substitution with positron emitting isotopes, such as $^{11}C$, $^{18}F$, $^{15}O$, and $^{13}N$, can be useful in Positron Emission Topography (PET) studies.

Methods of Synthesizing the Compounds

The compounds of the present disclosure (e.g., a compound of Formula (I), (II), or (III)), or pharmaceutically acceptable salts, hydrates, solvates, isomers, or tautomers thereof, may be made by a variety of methods, including standard chemistry. Suitable synthetic routes are depicted in the schemes given herein.

The compounds disclosed herein (e.g., a compound of Formula (I), (II), or (III)), or pharmaceutically acceptable salts, hydrates, solvates, isomers, or tautomers thereof, may be prepared by methods known in the art of organic synthesis as set forth in part by the following synthetic schemes. In the schemes described herein, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis," Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of disclosed herein (e.g., a compound of Formula (I), (II), or (III)), or pharmaceutically acceptable salts, hydrates, solvates, isomers, or tautomers thereof.

Those skilled in the art will recognize if a stereocenter exists in the compounds disclosed herein (e.g., a compound of Formula (I), (II), or (III)), or pharmaceutically acceptable salts, hydrates, solvates, isomers, or tautomers thereof. Compounds disclosed herein can exist as enantiomeric or diastereomeric stereoisomers. Accordingly, the present disclosure includes all possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. For example, enantiomerically pure compounds of the disclosure can be prepared using enantiomerically pure chiral building blocks. Alternatively, racemic mixtures of the final compounds or a racemic mixture of an advanced intermediate can be subjected to chiral purification as described herein to deliver the desired enantiomerically pure intermediates or final compounds. In the instances where an advanced intermediate is purified into its individual enantiomers, each individual enantiomer can be carried on separately to deliver the final enantiomerically pure compounds of the disclosure. Resolution of the final product, an intermediate, or a starting material may be affected by any suitable method known in the art. See, for example, "Stereochemistry of Organic Compounds," by E. L. Eliel, S. H. Wilen, and L. N. Mander (Wiley-Interscience, 1994).

The compounds described herein (e.g., a compound of Formula (I), (II), or (III)), or pharmaceutically acceptable salts, hydrates, solvates, isomers, or tautomers thereof, may be made from commercially available starting materials or synthesized using known organic, inorganic, and/or enzymatic processes.

In certain aspects, such as for the production of bioactive polypeptides or hormones utilized in the disclosure or for evaluating the biological activities of the compounds of the disclosure (e.g., a compound of Formula (I), (II), or (III)), or pharmaceutically acceptable salts, hydrates, solvates, isomers, or tautomers thereof, the practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature: "*Molecular Cloning: A Laboratory Manual*," second edition (Sambrook et al., 1989); "*Oligonucleotide Synthesis*" (M. J. Gait, ed., 1984); "*Animal Cell Culture*" (R. I. Freshney, ed., 1987); "*Methods in Enzymology*" (Academic Press, Inc.); "*Current Protocols in Molecular Biology*" (F. M. Ausubel et al., eds., 1987, and periodic updates); "*PCR: The Polymerase Chain Reaction*," (Mullis et al., eds., 1994). Singleton et al., *Dictionary of Microbiology and Molecular Biology* 2nd ed., J. Wiley & Sons (New York, N.Y. 1994), and March, *Advanced Organic Chemistry Reactions, Mechanisms and Structure* 4th ed., John Wiley & Sons (New York, N.Y. 1992), provide one skilled in the art with a general guide to many of the terms used in the present application.

Dipeptide Linkers

In some cases, the dipeptide based linkers described herein have been utilized as cleavable groups for the delivery of therapeutic compound payloads in other constructs to cells or tissue of interest. Several combinations of dipeptides have been utilized, with the valine-citrulline (Val-Cit) and valine-alanine (Val-Ala) as the most successful combinations. [13,14,15,16,17] The synthetic pathway leading to the synthesis of Val-Cit and Val-Ala dipeptides are very similar and shown in the Scheme 1 herein. The amino group of Valine is initially protected with a Fluorenylmethyloxycarbonyl (Fmoc) group, followed by the activation of the carboxylic acid group with N-Hydroxysuccinimide (NHS) to form compound 3. Compound 3 can then be reacted with either citrulline or alanine in an aqueous solution of $NaHCO_3$ with DMF and THE present to ensure proper solubility. The resulting compound 4 can be coupled to para-aminobenzylalcohol group (PABOH) using N-ethoxycarbonyl-2-ethoxy-1,2-dihydroquinoline ("EEDQ"), which leads to the formation of compound 5. [18] Removal of the Fmoc group may be carried out with diethyl amine in DMF at room temperature to give amino-alcohol 6.

Scheme 1

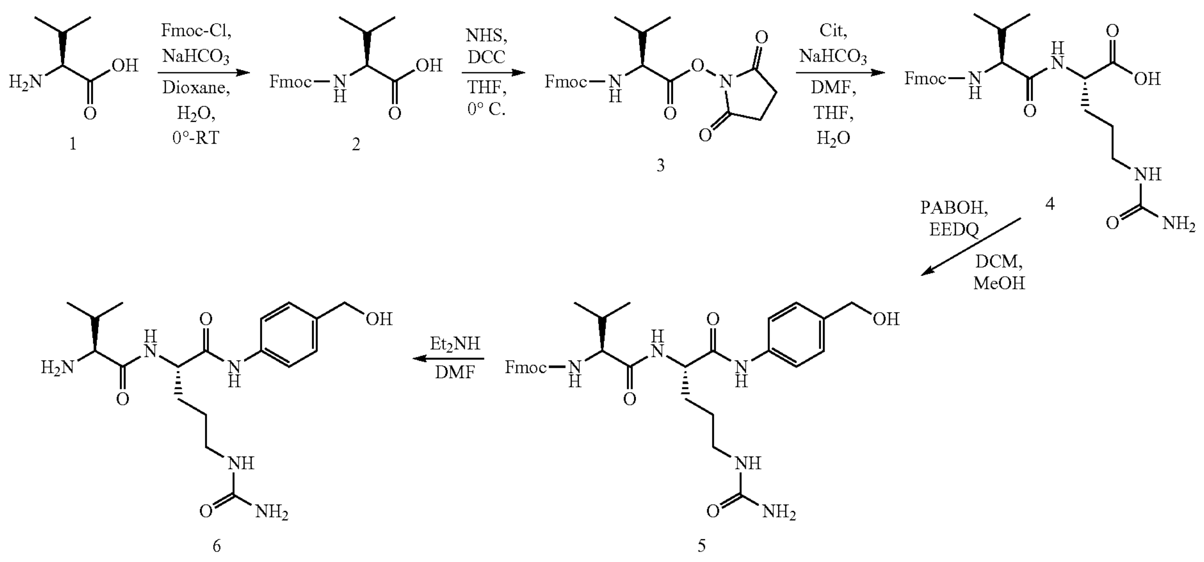

1 2 3 4 5 6

As shown in Scheme 2, glycols of various lengths may be reacted with a catalytic amount of sodium metal under anhydrous condition to promote the addition to tert-butyl acrylate for the Michael Addition product 9.[19] Next, maleimide can be reacted with glycol under Mitsunobu conditions to produce compound 10 in good yields.[20] Deprotection of the tert-butyl ester with trifluoroacetic acid with perfluorophenyl 2,2,2-trifluoroacetate (PPTA) in the presence of pyridine in DMF.[22] The conditions are very mild and produce very good yields of the pentafluoroester. NHS has also been frequently been used to form the activated ester. These methods allow for the introduction of halogenated maleimides as well as the thiophenol derivatives.

Scheme 2

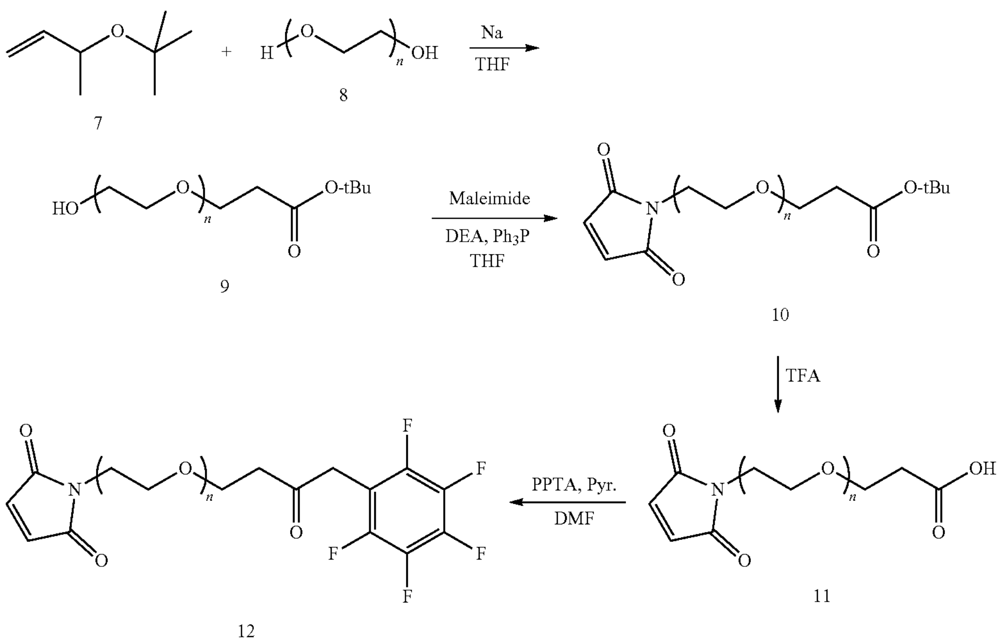

7 8 9 10 11 12 may be followed by the esterification under Steglich conditions with DIC and pentafluorophenol to give compound 12.[21] An alternative approach to the formation of the pentafluorophenol ester is the reaction of the carboxylic acid Scheme 3 shows the synthesis of a non-cleavable linker using the maleiminde as the key group to attach to a cysteine residue. With the incorporation of halogens on the maleimide, multiple cysteine residues or sulfides resulting from the cleavage of a disulfide bond can react at both halogenated positions. The synthesis of this versatile linker begins with the condensation of maleic anhydride (with or without halogens) with 3-(2-(2-(2-aminoethoxy)ethoxy)ethoxy)propanoic acid in refluxing acid to give a near quantitative yield of compound 15. Carboxylic acid 15 can be converted to the pentafluoro ester through either a DCC coupling in ethyl acetate or using perfluorophenyl 2,2,2-trifluoroacetate (PPTA) in the presence of pyridine in DMF to give compound 16 [22]. The pentafluoro ester 16 is very amenable to displacement by amines under mild conditions to give a non-cleavable drug conjugate, where the maleimide moiety reacts under mild conditions with available cysteine residues and n is 1, 2, 3, 4, 5, 6, 7, 8, 9, or 10.

Scheme 3

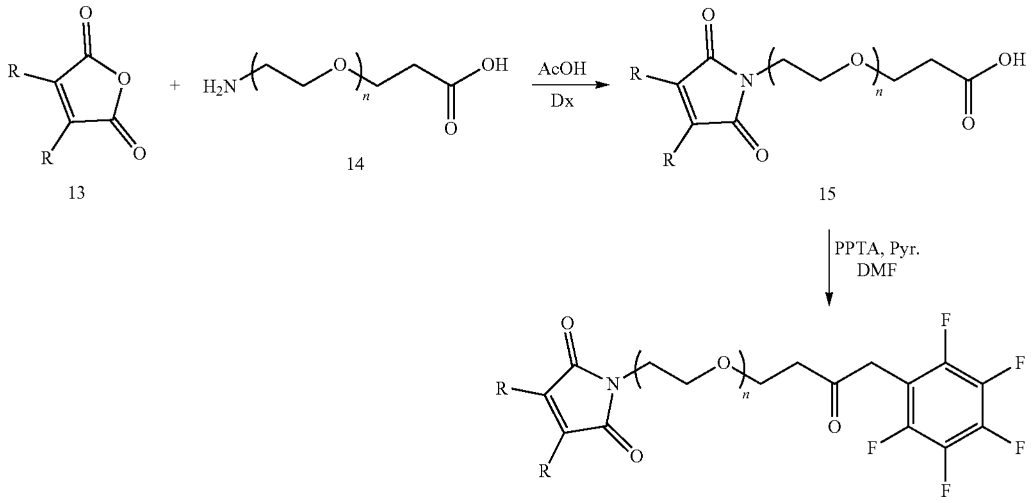

13 14 15

16

R = H, Cl, Br, I

Key Structures and Abbreviations

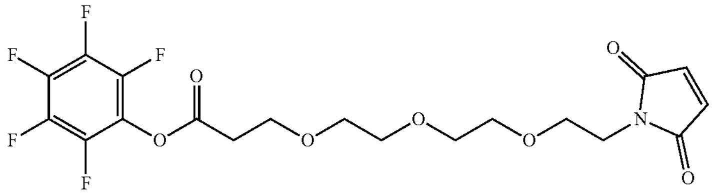

Mal-PEG$_3$-PFP
perfluorophenyl 3-(2-(2-(2-(2,5-dioxo-2,5-dihydro-1H-pyrrol-1-yl)ethoxy)ethoxy)ethoxy)propanoate

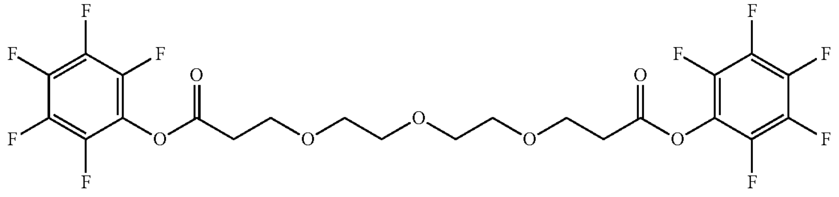

Bis-PEG3-PFP ester
bis(perfluorophenyl) 3,3'-((oxybis(ethane-2,1-diyl))bis(oxy))dipropionate -continued

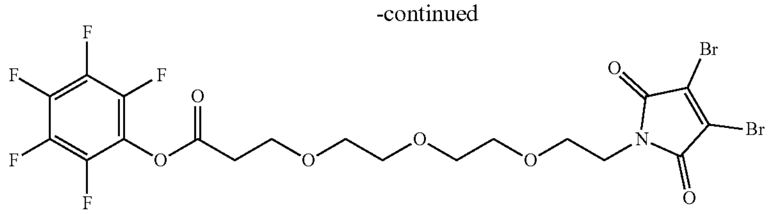

DBMal-PEG$_3$-PFP
perfluorophenyl 3-(2-(2-(2-(3,4-dibromo-2,5-dioxo-2,5-dihydro-1H-pyrrol-1-yl)ethoxy)ethoxy)ethoxy)propanoate

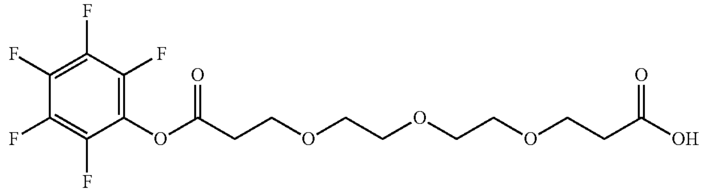

Acid-PEG3-PFP ester
3-(2-(2-(3-oxo-3-(perfluorophenoxy)propoxy) ethoxy)ethoxy)propanoic acid To improve the stability of the heterobifunctional cross-linking reagent, 6-maleimidohexanoic acid pentafluorophenyl ester (Mal-PEGn-PFP, where n is defined below) may be prepared as a substitute for the more popular 6-maleimidohexanoic acid N-hydroxysuccinimide ester (MHSu). [24] Mal-PEGn-PFP is prepared in two steps in very good yields to give compounds 12 and 16 as shown herein in Schemes 2 and 3. [14 and 15] Subsequent reaction of compound 6 with Mal-PEG3-PFP and DBMal-PEG$_3$-PFP in DMF provided very good yields of compounds 17 and 18 shown in Scheme 4.

Scheme 4

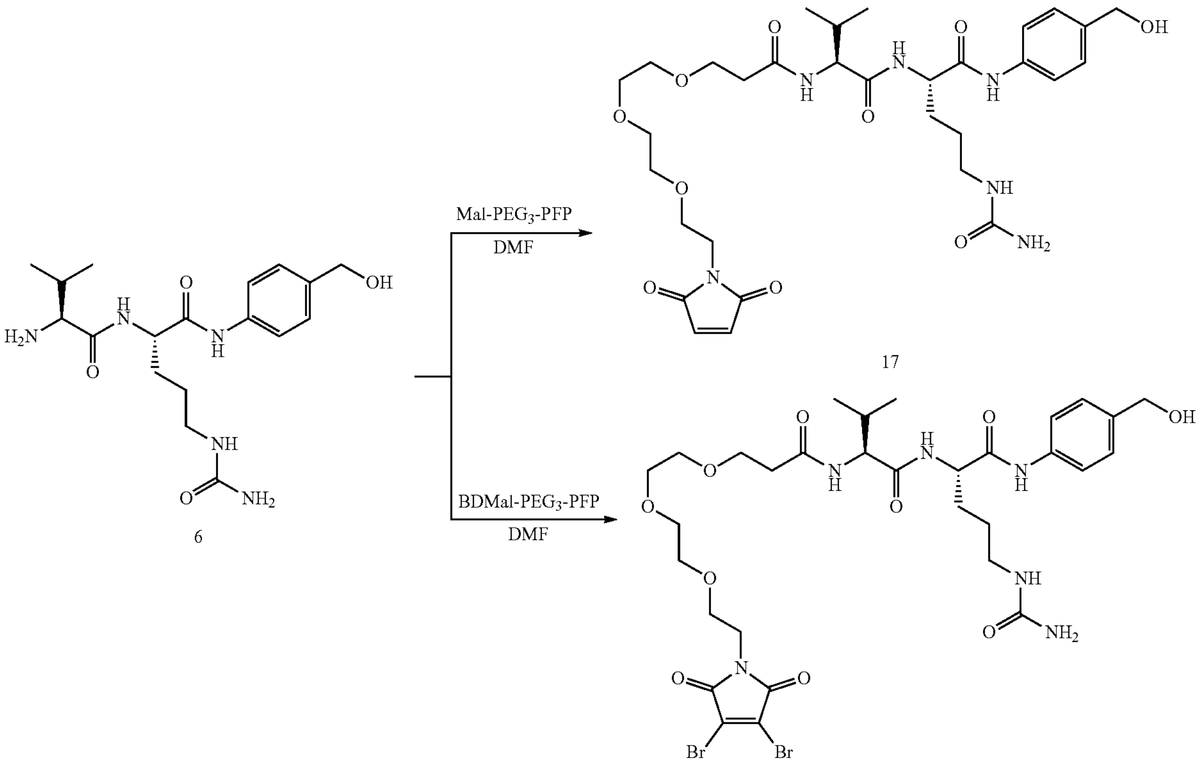

6

17

18

As shown in Scheme 5, compound 17 can be activated using two different methods to facilitate the attachment of various therapeutic compound as payloads before bio-conjugation to either Cys or Lys residues of biologically active polypeptides, such as Insulin polypeptides. Initially, Bis(4-nitrophenyl) carbonate was reacted with compound 7 in the presence of N,N-Diisopropylethylamine and DMF to give carbonate 12.[24] Alternatively, N,N-disuccinimidyl carbonate can be used in a similar fashion under the same conditions. Both the p-Nitrophenol and the N-Hydroxysuccinimde function as leaving groups in the subsequent reaction. In a similar fashion, the mesylate 20 can be generated from the benzyl alcohol using $Ms_2O$ in dichloromethane.

1

Scheme 5

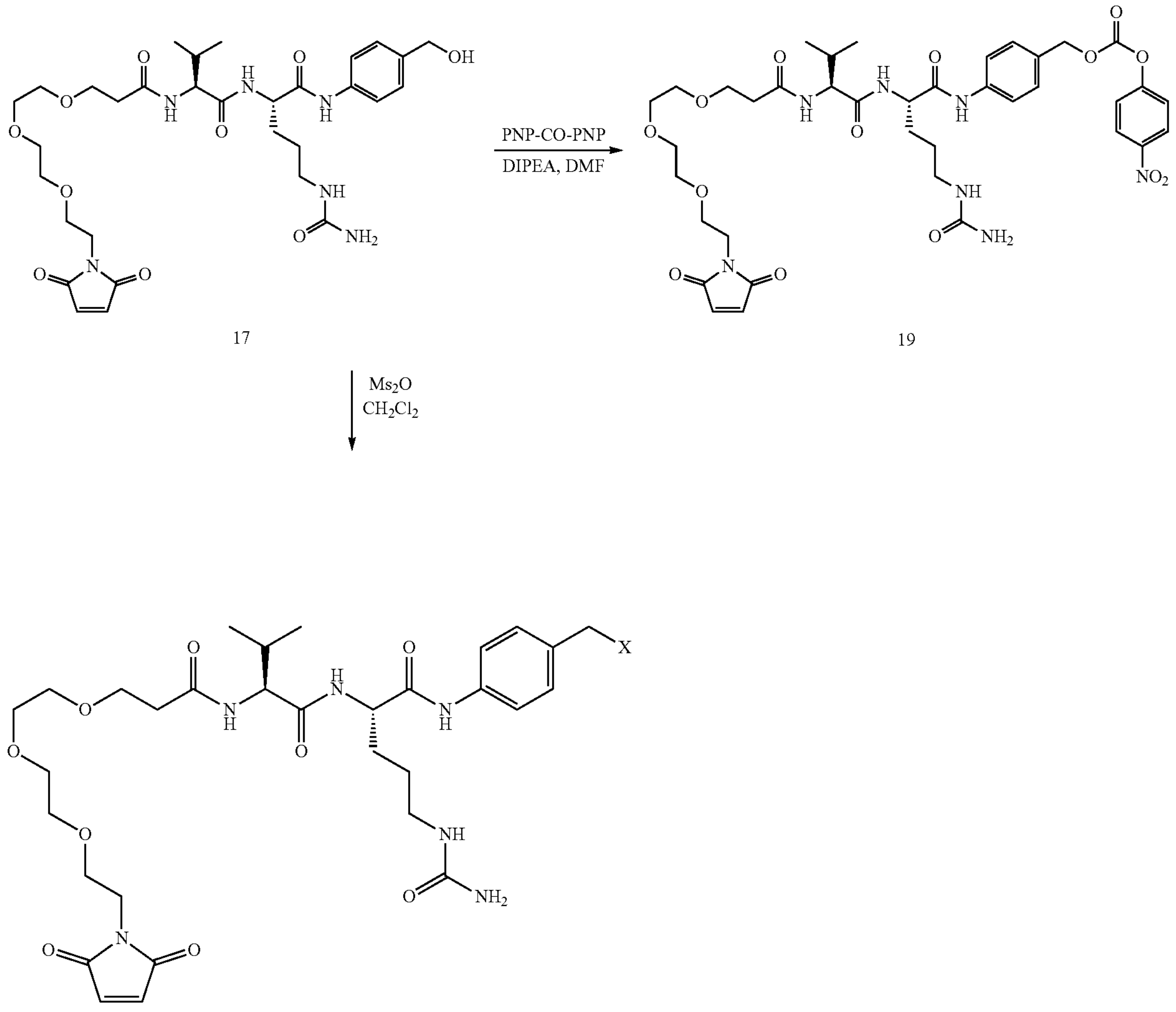

17

19

20

X = Ms, Tf, Ts, Cl, Br, I

Nitro-carbonate 19 can react with the therapeutic compound to form carbonyl compound 21 which can take the form of a carbamate or a carbonate, depending on whether the reactive site on the therapeutic compound is an amine or an alcohol. When the therapeutic compound possesses a tertiary or heteroaryl amine, it can be reacted with compound 20 to generate a quaternary amine attachment to deliver the payload.

Scheme 6
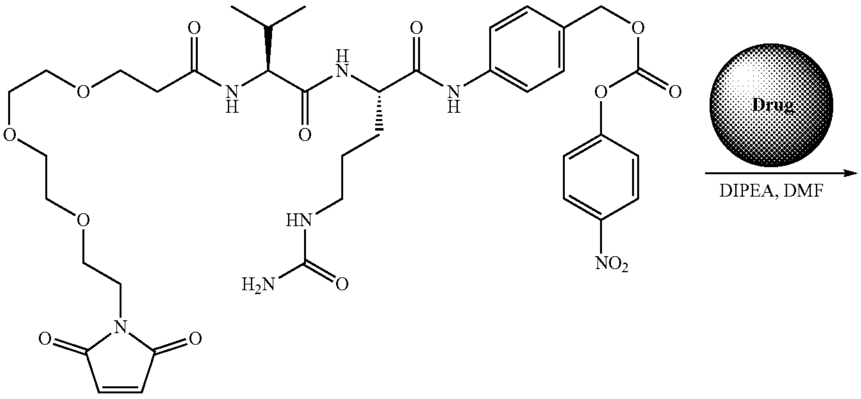
19
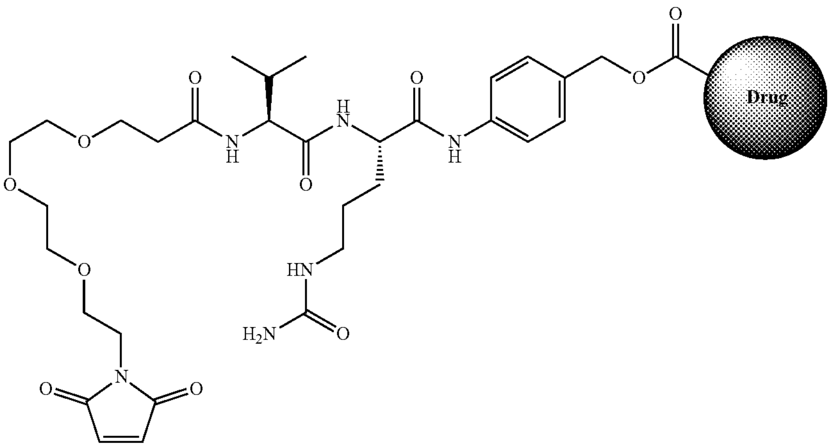
21
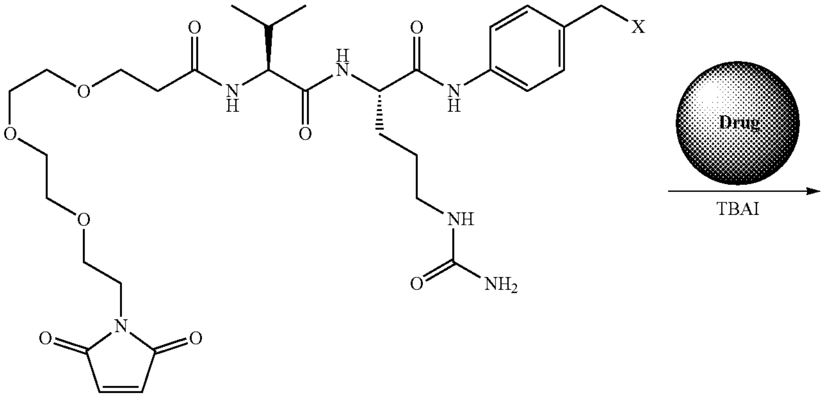
20
X = OMs, OTf, OTs, Cl, Br, I -continued

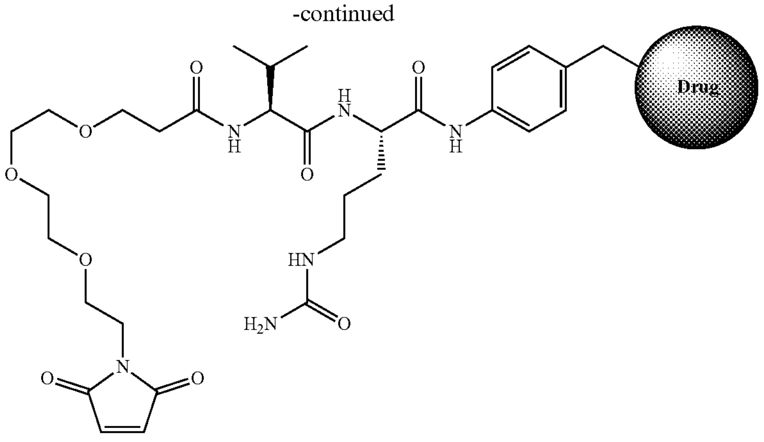

22

Below in Scheme 7, benzyl alcohol 5 was converted to a Mesylate (or similar leaving group) and subsequently replaced by the drug to form a quaternary ammonium bond with the linker. The mesylate (and potentially the triflate) offer an improvement in reactivity over the Iodo or Bromo substituted benzyl group. To finish functionalizing the PDC, the Fmoc group was deprotected and attach to a linker capable of reacting with Lysine residues on the protein as shown in Scheme 8.

Scheme 7

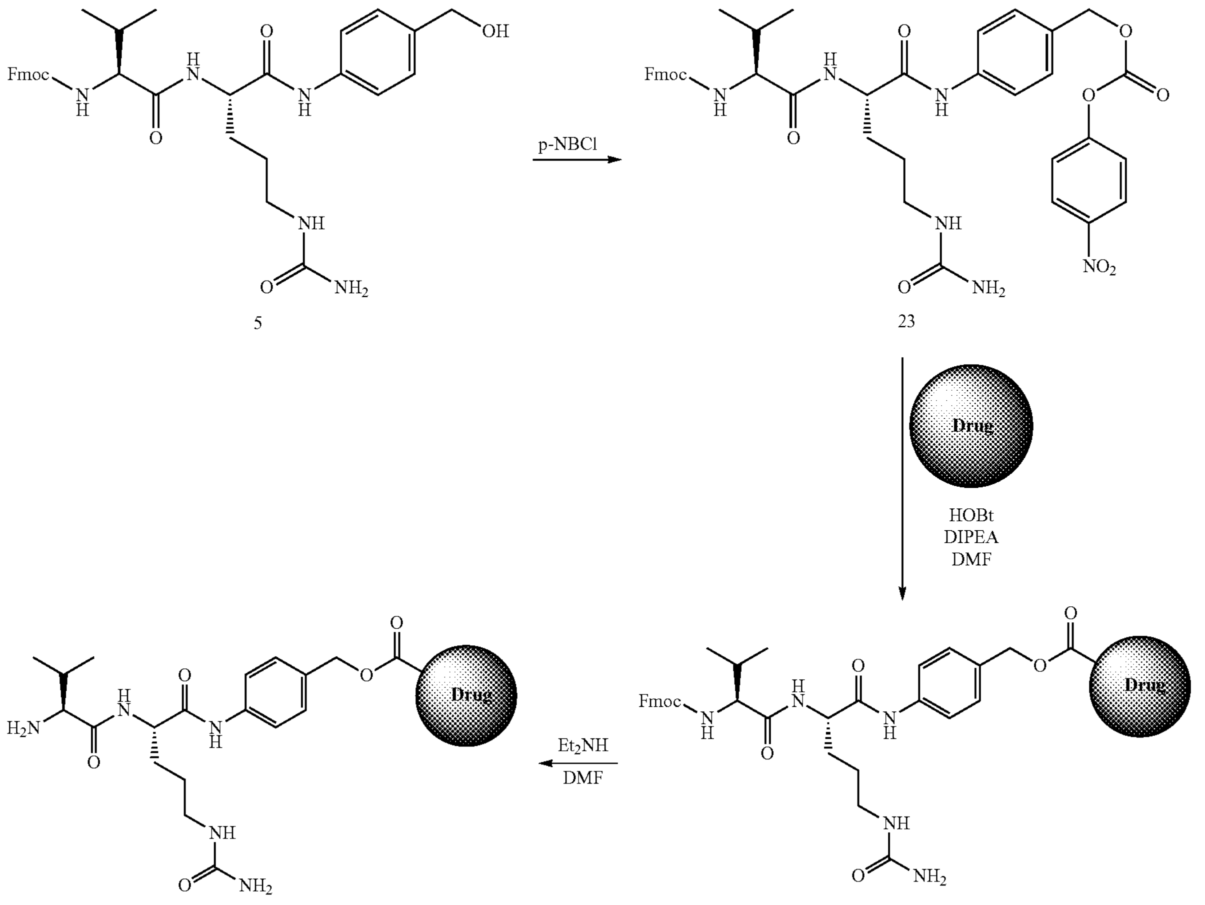

Scheme 8 shows the final deprotection of the Fmoc group of Valine, making the primary amine available for reaction with the Bis-PEG3-PFP ester to generate compound 27. The alternative to this one step conversion is reacting compound 25 with Acid-PEG3-PFP-Ester to generate the carboxylic acid 26. The carboxylic acid can then be converted to the PFP ester using PPTA in DMF with pyridine as a solvent.

Scheme 8
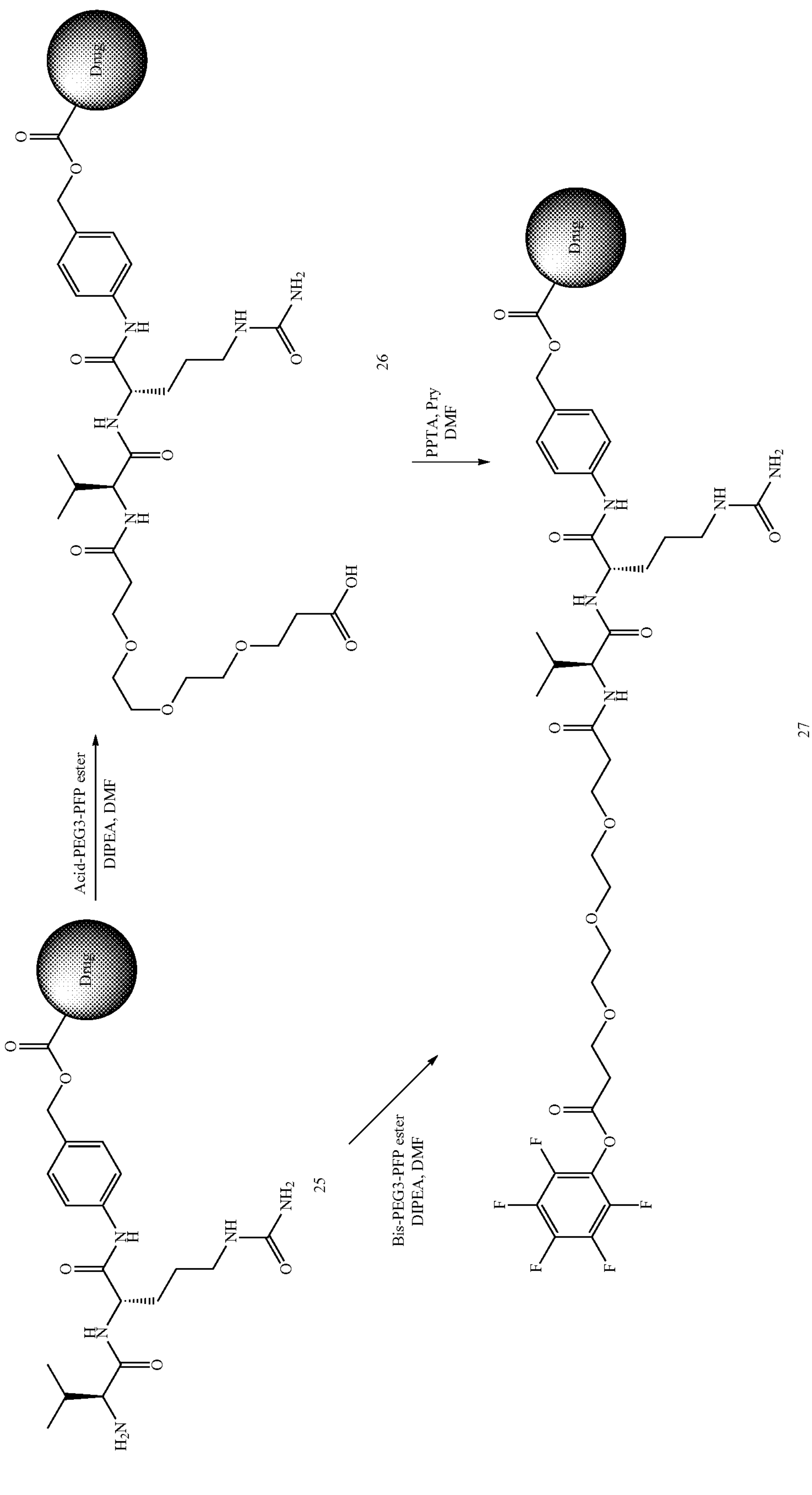
25
26
27

Glucuronide-Based Linkers

The Glucuronide scaffold has been utilized in assisting the transport of active biological agents and therapeutic compound payloads to a specific location.[26,27,28,29,30] As shown in Scheme 1, the synthesis of the transport molecule may be initiated with the commercially available (2S,3R,4S,5S,6S)-6-(methoxycarbonyl)tetrahydro-2H-pyran-2,3,4,5-tetrayl tetraacetate) undergoing a mild bromide substitution of the acetate group through the reaction of compound 28 with HBr in acetic acid to form compound 29. The bromide may be replaced by reacting 4-hydroxy-3-nitrobenzaldehyde with silver oxide in acetonitrile resulting in the formation of compound 30. Reduction of the formal group with sodium borohydride in methanol to give compound 31, may be followed by the reduction of the nitro group by palladium hydroxide to give the amino alcohol 32.

Scheme 9

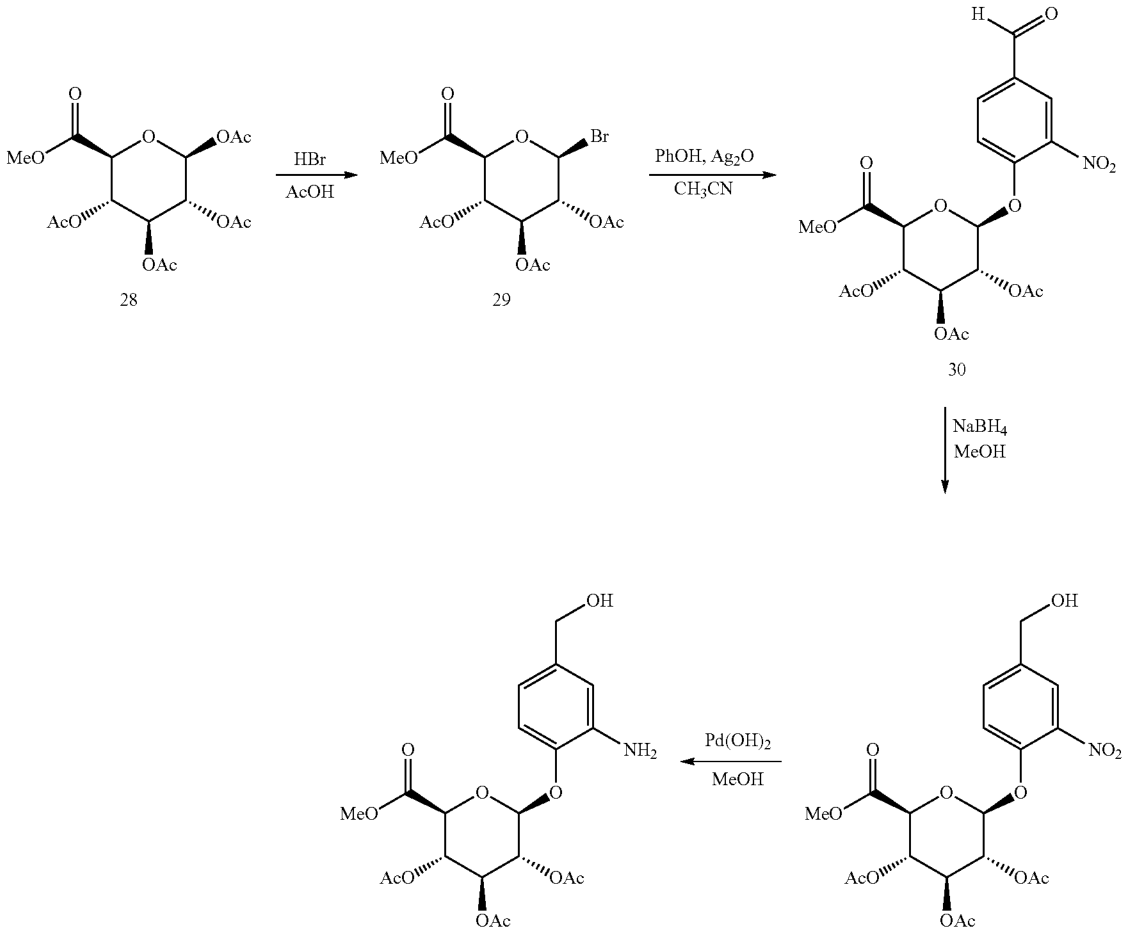

28 29 30 32 31

Commercially available Fmoc-B-Alanine was sonicated with thionyl chloride in dichloromethane at room temperature to form the resulting (9H-fluoren-9-yl)methyl (3-chloro-3-oxopropyl)carbamate or compound 34.

Scheme 10

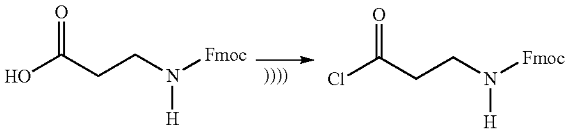

33 34

As shown in Scheme 11, the amino group of compound 32 can be selectively reacted with (9H-fluoren-9-yl)methyl (3-chloro-3-oxopropyl)carbamate followed by the formation of mesylate intermediate 35. Mesylate 35 can be reacted with the tertiary amine of the therapeutic compound to form a stable bio-reversible quaternary ammonium linkage of compound 36. Deprotection of the acetate groups with LiOH, which also lead to the removal of the Fmoc group gives compound 37.

Scheme 11

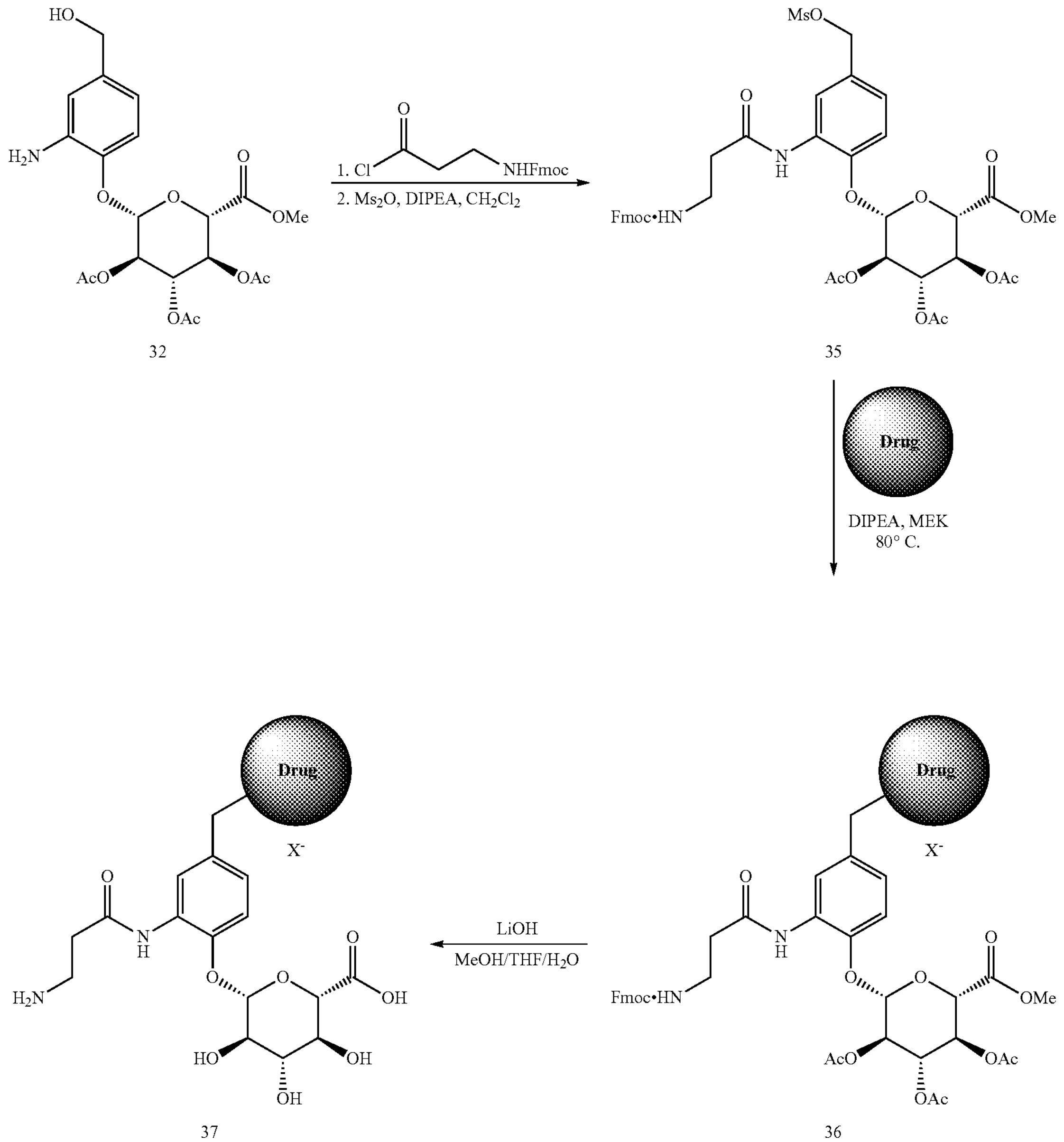

32

35

37

36

As shown in Schemes 12 and 13, compound 37 can be functionalized to react with either the Cys or Lys residues on biologically active polypeptides, such as Insulin polypeptides. For a bioconjugation to the Cys residue, the free amine on compound 37 can be reacted with the heterobifunctional cross-linking reagent Mal-$PEG_3$-PFP to react with a single Cysteine of the protein or reacted with DBMal-$PEG_3$-PFP to re-bridge the reduced disulfide to maintain the structural integrity of the protein. For the bioconjugation to the Insulin Lys residue, the free amine 37 can be reacted with Acid-$PEG_3$-PFP ester to give the acid 40, followed by the conversion to the PFP ester 41 using PPTA with pyridine in a solution of DMF. Alternatively, the PFP ester 41 can be formed directly from compound 36 through a reaction with Bis-PEG3-PFP ester shown in Scheme 7.

Scheme 12
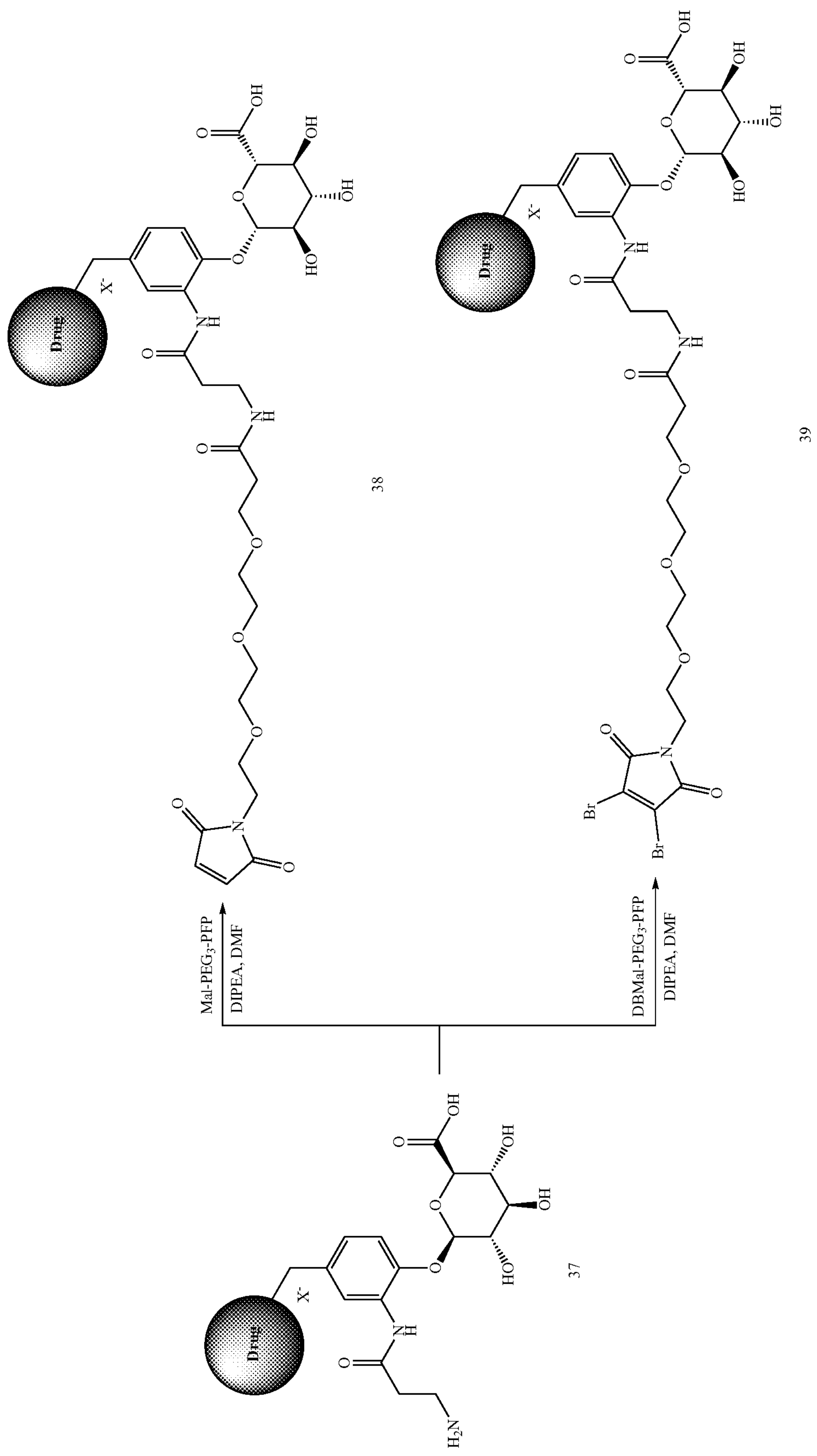
37
38
39

-continued
Scheme 13
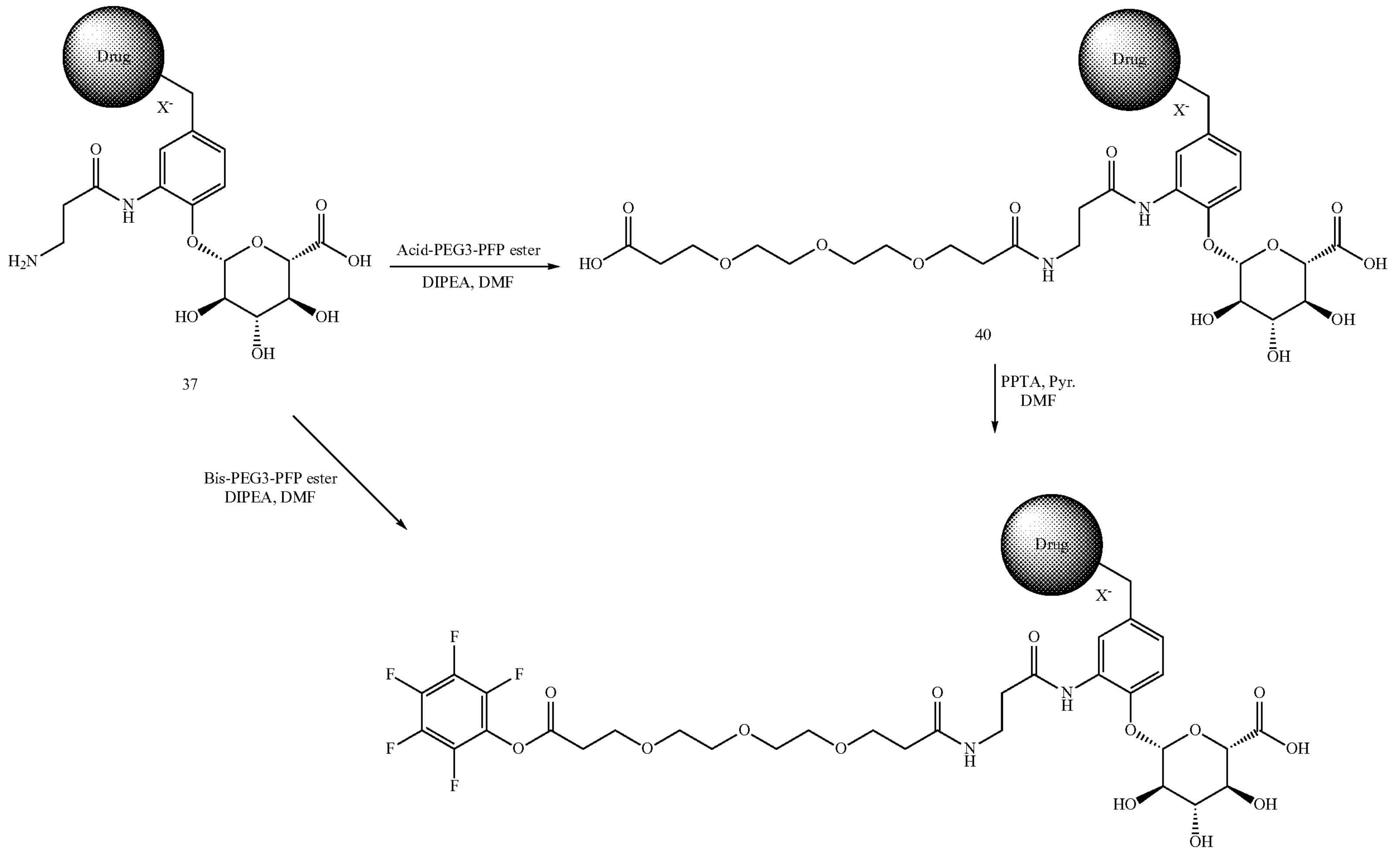
37
40
41

Additional Linkers

Attachment of the payload to the drug conjugate often requires a functional linker with very good solubility properties as well as serum stability. Glycols may be used in this capacity. Below in schemes 14, 15, and 16, there are several approaches for the synthesis of glycol side chains that allow for easy attachment of both the payload as well as the conjugate linkers. In Scheme 5, an ethylene glycol may be reacted with Tosyl chloride to produce the Bis-Tosylate. The Bis-Tosylate may then be reacted with the Bis-tert-butyl carbamate to form compound 44. Subsequent reaction with LiBr results in the bromide substitution of the Tosylate to give compound 45.[31] In Schemes 14, 15, and 16, n is 1, 2, 3, 4, 5, 6, 7, 8, 9, or 10.

Scheme 14

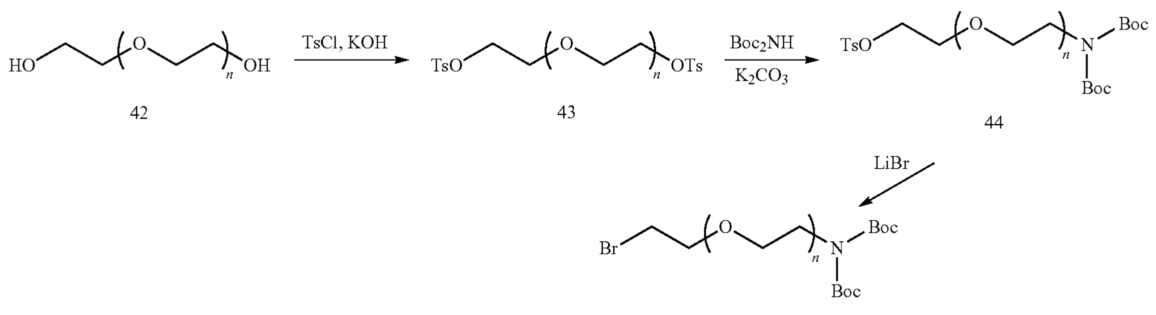

42 43 44 45

Glycol 46 in Scheme 15 has a terminal chloride, which is available for substitution. Sodium azide may be used to displace the chloride atom and the azide was then reduced with triphenylphosphine followed by protection of the amine with Boc anhydride to give compound 48. The hydroxyl group may then finally be converted to a bromide using triphenylphosphine and carbon tetrabromide to give compound 49.[32]

Scheme 15

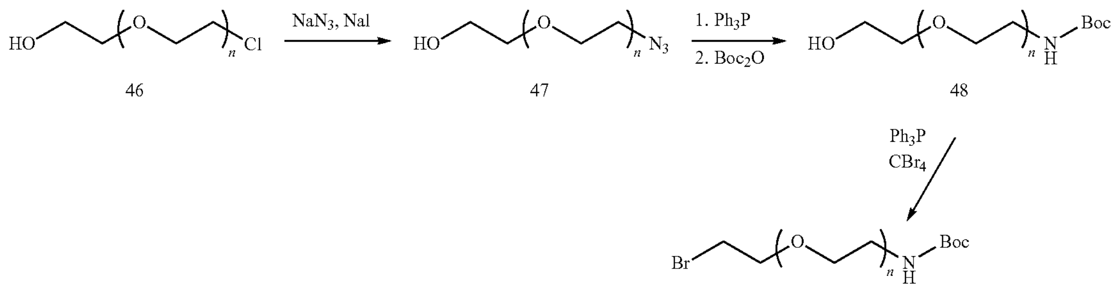

46 47 48 49

In Scheme 16, the di-iodinated glycol is reacted with the Bis-Boc-carbamate to produce the Bis-Boc protected amino-iodo-glycol 51.

Scheme 16

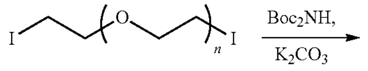

50

-continued

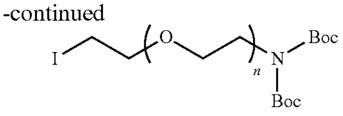
51

Example

Hypothetical examples are disclosed below to illustrate the invention. Persons skilled in the art will recognize many different variations of these hypotheticals based on the disclosure in this document and known prior art. All variations are intended to be within the scope of this invention. Therefore, the examples disclosed are not intended to limit the scope of the claims. Animal Distribution into Treatment Groups: Mice were distributed into treatment groups by body weight so that there is no significant difference between the means across groups.

Intraperitoneal (IP) Dosing: A 27 g ½" gauge needle is used for injection. Injection volume for the study is 5 ml/kg per injection. Restrain the mouse and identify the injection location which is above or equal to the top of the hips and below the middle of the abdomen, generally just to the right of the midline.

Glucose Tolerance Test (ipGTT): Mice are weighed and transferred to individual clean cages that provide water and bedding only (no food pellets) for a fast of 6 hours.

A dextrose (glucose) solution is prepared aseptically for injection by diluting sterile 50% dextrose with sterile 0.9% saline for a 20% working stock. The working concentration is 0.2 g/mL (20%) and the dose is 2 g/kg body weight. The volume of the dextrose solution needed for each individual mouse is calculated and individually labeled insulin syringes (27-31G, 5/16" length) are filled with the appropriate volume of solution for each mouse. The mouse is restrained by hand and the tip of the tail is cut using sterile surgical scissors. A drop of blood (~5 μL) from the tail is placed on the glucose test strip and the baseline blood glucose level is measured and recorded using a handheld blood glucose meter that has been calibrated prior to experimental testing.

Dextrose is administered by means of an intra-peritoneal injection immediately after the baseline measurement is taken. Additional glucose measurements are repeated at 15, 30, 60, 90 and 120 minutes following the IP dextrose injection.

Mice were divided into four groups at ten mice each and each mouse was dosed daily for five days with Compound B-55.

Group 1 received Vehicle Control. Group 2 received the positive control, Pioglitazone at 30 mg/Kg. Group 3 received Compound B-55 at 0.3 IU/Kg. Group 4 received Compound B-55 at 0.6 IU/Kg.

The results of this test can be found in table 7 Below:

TABLE 7

| | Time (min) | | | | |
|---|---|---|---|---|---|
| | 15 | 30 | 60 | 90 | 120 |
| | Avg Glucose (ug/dL) | | | | |
| Vehicle Control | 698 | 755 | 814 | 665 | 609 |
| Positive Control-Pioglitazone | 605 | 613 | 367 | 250 | 213 |
| Compound B-55 0.03 IU/kg | 665 | 693 | 638 | 502 | 424 |
| Compound B-55 0.06 IU/kg | 628 | 684 | 642 | 531 | 427 |

As shown is in table 7 above, A highly significant difference in glucose tolerance was observed between treatment groups: vehicle <Compound B-55<Pioglitazone.

SEQUENCE LISTING

Below is a sequence listing of the nucleotide and/or amino acid sequences and associated information. This sequence listing is also being submitted as ASCII text file. The ASCII Text file is named "Insulin Sequences Doc v5 20230830_ST25" and was created on Aug. 30, 2023 and has a file size of 9 KB and is hereby incorporated by reference.

```
<110> Hurt, Clarence
Soares, Luis

<120> COMPOUNDS, COMPOSITIONS, METHODS, AND USES FOR TREATING INSULIN
RESISTANCE, TYPE 2 DIABETES AND METABOLIC SYNDROME

<130> 62915680

<150> 17073138

<151> 2020-10-16

<160> 18

<170> PatentIn version 3.5

<210> 1

<211> 21

<212> PRT

<213> Homo sapien

<400> 1

Gly Ile Val Glu Gln Cys Cys Thr Ser Ile Cys Ser Leu Tyr Gln Leu
1               5                   10                  15

Glu Asn Tyr Cys Gly
            20

<210> 2

<211> 32

<212> PRT
```

-continued

<213> Homo sapien

<400> 2

Phe Val Asn Gln His Leu Cys Gly Ser His Leu Val Glu Ala Leu Tyr
1 5 10 15

Leu Val Cys Gly Glu Arg Gly Phe Phe Tyr Thr Pro Lys Thr Arg Arg
20 25 30

<210> 3

<211> 29

<212> PRT

<213> Homo sapien

<400> 3

Phe Val Asn Gln His Leu Cys Gly Ser His Leu Val Glu Ala Leu Tyr
1 5 10 15

Leu Val Cys Gly Glu Arg Gly Phe Phe Tyr Thr Pro Lys
20 25

<210> 4

<211> 21

<212> PRT

<213> Homo sapien

<400> 4

Gly Ile Val Glu Gln Cys Cys Thr Ser Ile Cys Ser Leu Tyr Gin Leu
1 5 10 15

Glu Asn Tyr Cys Asn
20

<210> 5

<211> 21

<212> PRT

<213> Homo sapien

<400> 5

Gly Ile Val Glu Gln Cys Cys Thr Ser Ile Cys Ser Leu Tyr Gln Leu
1 5 10 15

Glu Asn Tyr Cys Asn
20

<210> 6

<211> 30

<212> PRT

<213> Homo sapien

<400> 6

Phe Val Asn Gln His Leu Cys Gly Ser His Leu Val Glu Ala Leu Tyr
1 5 10 15

Leu Val Cys Gly Glu Arg Gly Phe Phe Tyr Thr Asp Lys Thr
20 25 30

<210> 7

<211> 21

<212> PRT

-continued

<213> Homo sapien

<400> 7

Gly Ile Val Glu Gin Cys Cys Thr Ser Ile Cys Ser Leu Tyr Gln Leu
1 5 10 15

Glu Asn Tyr Cys Asn
20

<210> 8

<211> 30

<212> PRT

<213> Homo sapien

<400> 8

Phe Val Asn Gln His Leu Cys Gly Ser His Leu Val Glu Ala Leu Tyr
1 5 10 15

Leu Val Cys Gly Glu Arg Gly Phe Phe Tyr Thr Lys Pro Thr
20 25 30

<210> 9

<211> 21

<212> PRT

<213> Homo sapien

<400> 9

Gly Ile Val Glu Gln Cys Cys Thr Ser Ile Cys Ser Leu Tyr Gln Leu
1 5 10 15

Glu Asn Tyr Cys Asn
20

<210> 10

<211> 29

<212> PRT

<213> Homo sapien

<400> 10

Phe Val Asn Gln His Leu Cys Gly Ser His Leu Val Glu Ala Leu Tyr
1 5 10 15

Leu Val Cys Gly Glu Arg Gly Phe Phe Tyr Thr Pro Lys
20 25

<210> 11

<211> 21

<212> PRT

<213> Homo sapien

<400> 11

Gly Ile Val Glu Gln Cys Cys Thr Ser Ile Cys Ser Leu Tyr Gln Leu
1 5 10 15

Glu Asn Tyr Cys Asn
20

<210> 12

<211> 30

<212> PRT

<213> Homo sapien

-continued

<400> 12

Phe Val Lys Gln His Leu Cys Gly Ser His Leu Val Glu Ala Leu Tyr
1 5 10 15

Leu Val Cys Gly Glu Arg Gly Phe Phe Tyr Thr Pro Glu Thr
20 25 30

<210> 13

<211> 21

<212> PRT

<213> Homo sapien

<400> 13

Gly Ile Val Glu Gin Cys Cys Thr Ser Ile Cys Ser Leu Tyr Gln Leu
1 5 10 15

Glu Asn Tyr Cys Asn
20

<210> 14

<211> 3

<212> PRT

<213> Homo sapien

<400> 14

Phe Val Asn Gln His Leu Cys Gly Ser His Leu Val Glu Ala Leu Tyr
1 5 10 15

Leu Val Cys Gly Glu Arg Gly Phe Phe Tyr Thr Pro Lys Thr
20 25 30

<210> 15

<211> 105

<212> PRT

<213> Homo sapien

<400> 15

Met Val Lys Gln Ile Glu Ser Lys Thr Ala Phe Gln Glu Ala Leu Asp
1 5 10 15

Ala Ala Gly Asp Lys Leu Val Val Val Asp Phe Ser Ala Thr Trp Ser
20 25 30

Gly Pro Cys Lys Met Ile Lys Pro Phe Phe His Ser Leu Ser Glu Lys
35 40 45

Tyr Ser Asn Val Ile Phe Leu Glu Val Asp Val Asp Asp Cys Gln Asp
50 55 60

Val Ala Ser Glu Cys Glu Val Lys Cys Met Pro Thr Phe Gln Phe Phe
65 70 75 80

Lys Lys Gly Gln Lys Val Gly Glu Phe Ser Gly Ala Asn Lys Glu Lys
85 90 95

Leu Glu Ala Thr Ile Asn Glu Leu Val
100 105

<210> 16

<211> 105

-continued

<212> PRT

<213> Homo sapien

<400> 16

Met Val Lys Gln Ile Glu Ser Lys Thr Ala Phe Gln Glu Ala Leu Asp
1 5 10 15

Ala Ala Gly Asp Lys Leu Val Val Val Asp Phe Ser Ala Thr Trp Cys
20 25 30

Gly Pro Ser Lys Met Ile Lys Pro Phe Phe His Ser Leu Ser Glu Lys
35 40 45

Tyr Ser Asn Val Ile Phe Leu Glu Val Asp Val Asp Asp Cys Gln Asp
50 55 60

Val Ala Ser Glu Cys Glu Val Lys Cys Met Pro Thr Phe Gln Phe Phe
65 70 75 80

Lys Lys Gly Gln Lys Val Gly Glu Phe Ser Gly Ala Asn Lys Glu Lys
85 90 95

Leu Glu Ala Thr Ile Asn Glu Leu Val
100 105

<210> 17

<211> 105

<212> PRT

<213> Homo sapien

<400> 17

Met Val Lys Gln Ile Glu Ser Lys Thr Ala Phe Gln Glu Ala Leu Asp
1 5 10 15

Ala Ala Gly Asp Lys Leu Val Val Val Asp Phe Ser Ala Thr Trp Ser
20 25 30

Gly Pro Ser Lys Met Ile Lys Pro Phe Phe His Ser Leu Ser Glu Lys
35 40 45

Tyr Ser Asn Val Ile Phe Leu Glu Val Asp Val Asp Asp Cys Gin Asp
50 55 60

Val Ala Ser Glu Cys Glu Val Lys Cys Met Pro Thr Phe Gln Phe Phe
65 70 75 80

Lys Lys Gly Gln Lys Val Gly Glu Phe Ser Gly Ala Asn Lys Glu Lys
85 90 95

Leu Glu Ala Thr Ile Asn Glu Leu Val
100 105

<210> 18

<211> 105

<212> PRT

<213> Homo sapien

<400> 18

Met Val Lys Gln Ile Glu Ser Lys Thr Ala Phe Gln Glu Ala Leu Asp
1 5 10 15

Ala Ala Gly Asp Lys Leu Val Val Val Asp Phe Ser Ala Thr Trp Cys
20 25 30

Gly Pro Cys Lys Met Ile Lys Pro Phe Phe His Ser Leu Ser Glu Lys
35 40 45

Tyr Ser Asn Val Ile Phe Leu Glu Val Asp Val Asp Asp Cys Gln Asp
50 55 60

-continued

```
Val Ala Ser Glu Cys Glu Val Lys Cys Met Pro Thr Phe Gln Phe Phe
65              70              75              80

Lys Lys Gly Gln Lys Val Gly Glu Phe Ser Gly Ala Asn Lys Glu Lys
          85              90              95

Leu Glu Ala Thr Ile Asn Glu Leu Val
        100             105
```

SEQUENCE LISTING

```
<160> NUMBER OF SEQ ID NOS: 18

<210> SEQ ID NO 1
<211> LENGTH: 21
<212> TYPE: PRT
<213> ORGANISM: Homo sapien

<400> SEQUENCE: 1

Gly Ile Val Glu Gln Cys Cys Thr Ser Ile Cys Ser Leu Tyr Gln Leu
1               5                   10                  15

Glu Asn Tyr Cys Gly
            20


<210> SEQ ID NO 2
<211> LENGTH: 32
<212> TYPE: PRT
<213> ORGANISM: Homo sapien

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30


<210> SEQ ID NO 3
<211> LENGTH: 29
<212> TYPE: PRT
<213> ORGANISM: Homo sapien

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25


<210> SEQ ID NO 4
<211> LENGTH: 21
<212> TYPE: PRT
<213> ORGANISM: Homo sapien

<400> SEQUENCE: 4

Gly Ile Val Glu Gln Cys Cys Thr Ser Ile Cys Ser Leu Tyr Gln Leu
1               5                   10                  15

Glu Asn Tyr Cys Asn
            20


<210> SEQ ID NO 5
<211> LENGTH: 21
<212> TYPE: PRT
<213> ORGANISM: Homo sapien

<400> SEQUENCE: 5

Gly Ile Val Glu Gln Cys Cys Thr Ser Ile Cys Ser Leu Tyr Gln Leu
```

1 5 10 15

Glu Asn Tyr Cys Asn
20

<210> SEQ ID NO 6
<211> LENGTH: 30
<212> TYPE: PRT
<213> ORGANISM: Homo sapien

<400> SEQUENCE: 6

Phe Val Asn Gln His Leu Cys Gly Ser His Leu Val Glu Ala Leu Tyr
1 5 10 15

Leu Val Cys Gly Glu Arg Gly Phe Phe Tyr Thr Asp Lys Thr
20 25 30

<210> SEQ ID NO 7
<211> LENGTH: 21
<212> TYPE: PRT
<213> ORGANISM: Homo sapien

<400> SEQUENCE: 7

Gly Ile Val Glu Gln Cys Cys Thr Ser Ile Cys Ser Leu Tyr Gln Leu
1 5 10 15

Glu Asn Tyr Cys Asn
20

<210> SEQ ID NO 8
<211> LENGTH: 30
<212> TYPE: PRT
<213> ORGANISM: Homo sapien

<400> SEQUENCE: 8

Phe Val Asn Gln His Leu Cys Gly Ser His Leu Val Glu Ala Leu Tyr
1 5 10 15

Leu Val Cys Gly Glu Arg Gly Phe Phe Tyr Thr Lys Pro Thr
20 25 30

<210> SEQ ID NO 9
<211> LENGTH: 21
<212> TYPE: PRT
<213> ORGANISM: Homo sapien

<400> SEQUENCE: 9

Gly Ile Val Glu Gln Cys Cys Thr Ser Ile Cys Ser Leu Tyr Gln Leu
1 5 10 15

Glu Asn Tyr Cys Asn
20

<210> SEQ ID NO 10
<211> LENGTH: 29
<212> TYPE: PRT
<213> ORGANISM: Homo sapien

<400> SEQUENCE: 10

Phe Val Asn Gln His Leu Cys Gly Ser His Leu Val Glu Ala Leu Tyr
1 5 10 15

Leu Val Cys Gly Glu Arg Gly Phe Phe Tyr Thr Pro Lys
20 25

<210> SEQ ID NO 11
<211> LENGTH: 21
<212> TYPE: PRT

<213> ORGANISM: Homo sapien

<400> SEQUENCE: 11

Gly Ile Val Glu Gln Cys Cys Thr Ser Ile Cys Ser Leu Tyr Gln Leu
1 5 10 15

Glu Asn Tyr Cys Asn
20

<210> SEQ ID NO 12
<211> LENGTH: 30
<212> TYPE: PRT
<213> ORGANISM: Homo sapien

<400> SEQUENCE: 12

Phe Val Lys Gln His Leu Cys Gly Ser His Leu Val Glu Ala Leu Tyr
1 5 10 15

Leu Val Cys Gly Glu Arg Gly Phe Phe Tyr Thr Pro Glu Thr
20 25 30

<210> SEQ ID NO 13
<211> LENGTH: 21
<212> TYPE: PRT
<213> ORGANISM: Homo sapien

<400> SEQUENCE: 13

Gly Ile Val Glu Gln Cys Cys Thr Ser Ile Cys Ser Leu Tyr Gln Leu
1 5 10 15

Glu Asn Tyr Cys Asn
20

<210> SEQ ID NO 14
<211> LENGTH: 30
<212> TYPE: PRT
<213> ORGANISM: Homo sapien

<400> SEQUENCE: 14

Phe Val Asn Gln His Leu Cys Gly Ser His Leu Val Glu Ala Leu Tyr
1 5 10 15

Leu Val Cys Gly Glu Arg Gly Phe Phe Tyr Thr Pro Lys Thr
20 25 30

<210> SEQ ID NO 15
<211> LENGTH: 105
<212> TYPE: PRT
<213> ORGANISM: Homo sapien

<400> SEQUENCE: 15

Met Val Lys Gln Ile Glu Ser Lys Thr Ala Phe Gln Glu Ala Leu Asp
1 5 10 15

Ala Ala Gly Asp Lys Leu Val Val Val Asp Phe Ser Ala Thr Trp Ser
20 25 30

Gly Pro Cys Lys Met Ile Lys Pro Phe Phe His Ser Leu Ser Glu Lys
35 40 45

Tyr Ser Asn Val Ile Phe Leu Glu Val Asp Val Asp Asp Cys Gln Asp
50 55 60

Val Ala Ser Glu Cys Glu Val Lys Cys Met Pro Thr Phe Gln Phe Phe
65 70 75 80

Lys Lys Gly Gln Lys Val Gly Glu Phe Ser Gly Ala Asn Lys Glu Lys
85 90 95

Leu Glu Ala Thr Ile Asn Glu Leu Val 100 105

<210> SEQ ID NO 16
<211> LENGTH: 105
<212> TYPE: PRT
<213> ORGANISM: Homo sapien

<400> SEQUENCE: 16

Met Val Lys Gln Ile Glu Ser Lys Thr Ala Phe Gln Glu Ala Leu Asp
1 5 10 15

Ala Ala Gly Asp Lys Leu Val Val Val Asp Phe Ser Ala Thr Trp Cys
20 25 30

Gly Pro Ser Lys Met Ile Lys Pro Phe Phe His Ser Leu Ser Glu Lys
35 40 45

Tyr Ser Asn Val Ile Phe Leu Glu Val Asp Val Asp Asp Cys Gln Asp
50 55 60

Val Ala Ser Glu Cys Glu Val Lys Cys Met Pro Thr Phe Gln Phe Phe
65 70 75 80

Lys Lys Gly Gln Lys Val Gly Glu Phe Ser Gly Ala Asn Lys Glu Lys
85 90 95

Leu Glu Ala Thr Ile Asn Glu Leu Val
100 105

<210> SEQ ID NO 17
<211> LENGTH: 105
<212> TYPE: PRT
<213> ORGANISM: Homo sapien

<400> SEQUENCE: 17

Met Val Lys Gln Ile Glu Ser Lys Thr Ala Phe Gln Glu Ala Leu Asp
1 5 10 15

Ala Ala Gly Asp Lys Leu Val Val Val Asp Phe Ser Ala Thr Trp Ser
20 25 30

Gly Pro Ser Lys Met Ile Lys Pro Phe Phe His Ser Leu Ser Glu Lys
35 40 45

Tyr Ser Asn Val Ile Phe Leu Glu Val Asp Val Asp Asp Cys Gln Asp
50 55 60

Val Ala Ser Glu Cys Glu Val Lys Cys Met Pro Thr Phe Gln Phe Phe
65 70 75 80

Lys Lys Gly Gln Lys Val Gly Glu Phe Ser Gly Ala Asn Lys Glu Lys
85 90 95

Leu Glu Ala Thr Ile Asn Glu Leu Val
100 105

<210> SEQ ID NO 18
<211> LENGTH: 105
<212> TYPE: PRT
<213> ORGANISM: Homo sapien

<400> SEQUENCE: 18

Met Val Lys Gln Ile Glu Ser Lys Thr Ala Phe Gln Glu Ala Leu Asp
1 5 10 15

Ala Ala Gly Asp Lys Leu Val Val Val Asp Phe Ser Ala Thr Trp Cys
20 25 30

Gly Pro Cys Lys Met Ile Lys Pro Phe Phe His Ser Leu Ser Glu Lys
35 40 45

Tyr Ser Asn Val Ile Phe Leu Glu Val Asp Val Asp Asp Cys Gln Asp
50 55 60

-continued

```
Val Ala Ser Glu Cys Glu Val Lys Cys Met Pro Thr Phe Gln Phe Phe
65                  70                  75                  80

Lys Lys Gly Gln Lys Val Gly Glu Phe Ser Gly Ala Asn Lys Glu Lys
                85                  90                  95

Leu Glu Ala Thr Ile Asn Glu Leu Val
            100                 105
```

What is claimed is:

1. A compound having a structure of Formula (I):

X1-[X2-(X3)*m*]*n* (I)

or a pharmaceutically acceptable salt, solvate, hydrate, isomer, or tautomer thereof: wherein:

m is 1, 2, or 3;

n is 1, 2, or 3;

X1 is a wild type human insulin;

X2 is a glucuronide or dipeptide cleavable linker; and

X3 is Pevonedistat.

2. The compound, or a pharmaceutically acceptable salt, solvate, hydrate, isomer, or tautomer thereof: of claim 1, wherein n is 2 or 3.

3. The compound, or a pharmaceutically acceptable salt, solvate, hydrate, isomer, and tautomer thereof, of claim 1, wherein X2 is selected from the group consisting of:

| Linker | Structure |
|---|---|
| K-1 Cleavable Linker | 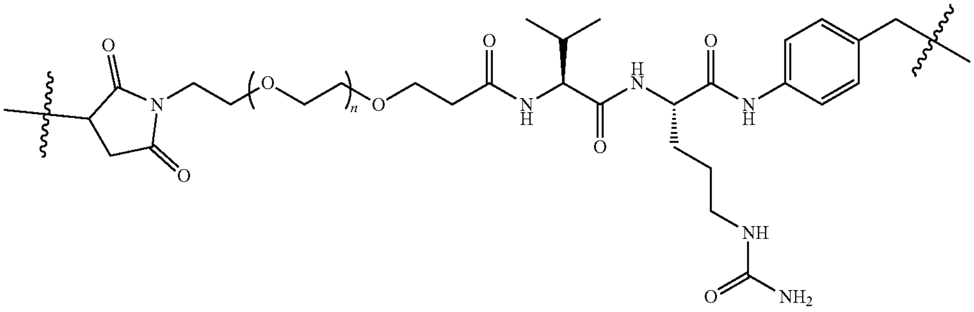 |
| K-2 Cleavable Linker | 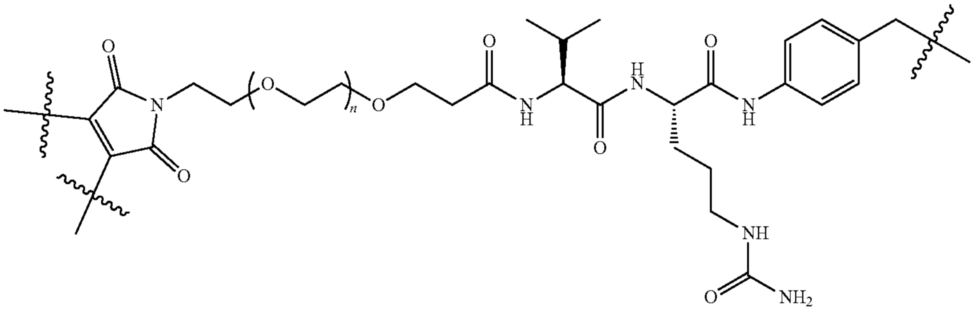 |
| K-3 Cleavable Linker | 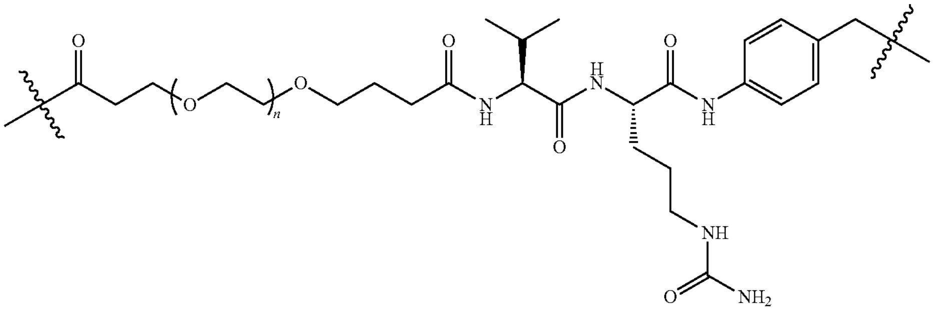 |

-continued
| Linker | Structure |
|---|---|
| K-4<br>Cleavable Linker | 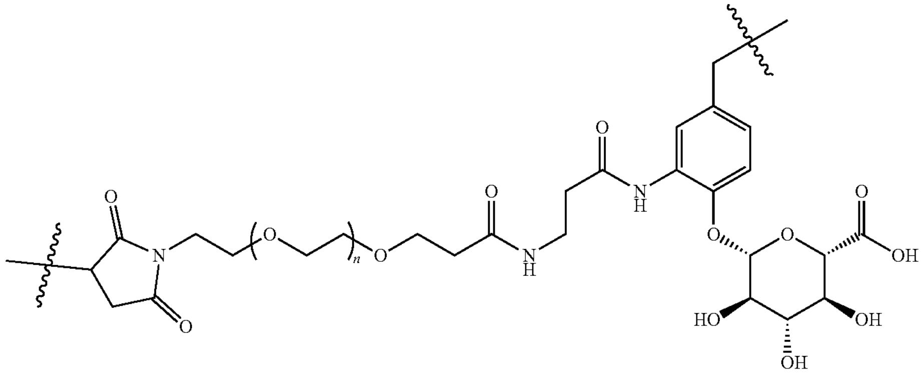 |
| K-5<br>Cleavable Linker | 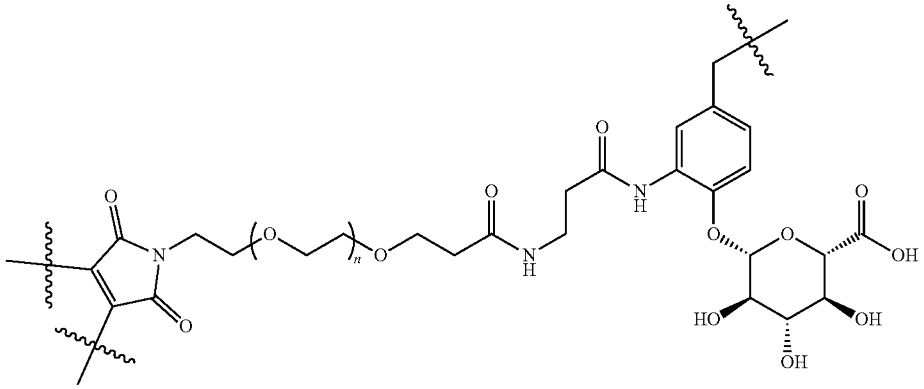 |
| K-6<br>Cleavable Linker<br>and | 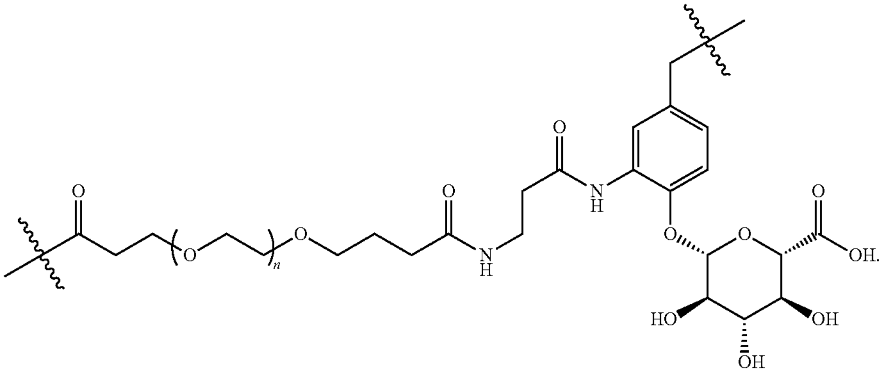 |

4. The compound, or a pharmaceutically acceptable salt, solvate, hydrate, isomer, or tautomer thereof, of claim 1, wherein X2 is bound to X1 at a Cys residue or a Lys residue thereof.
5. The compound, or a pharmaceutically acceptable salt, solvate, hydrate, isomer, or tautomer thereof, of claim 1, wherein the compound of Formula (I) is selected from the group consisting of:
B1
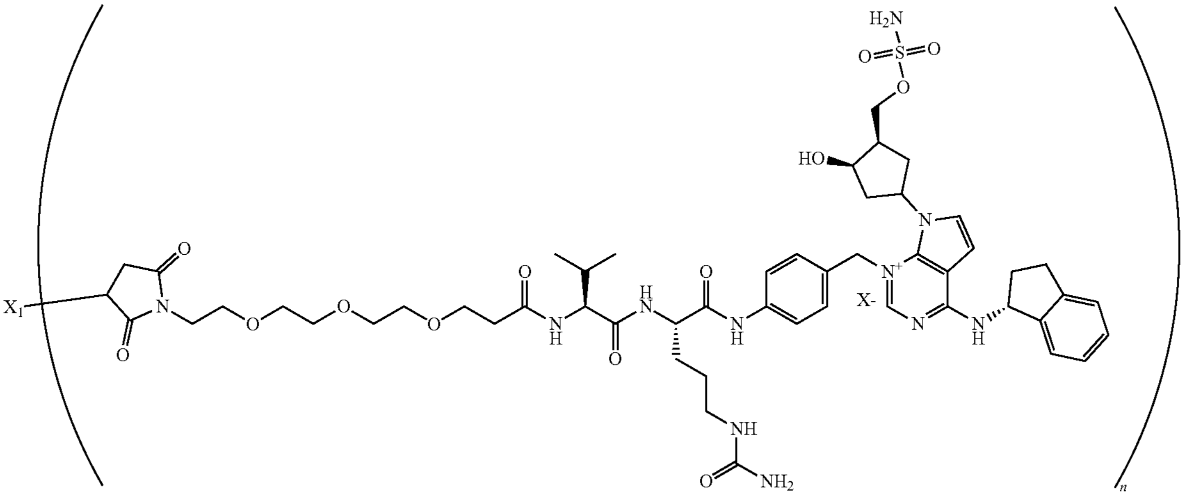
,
B13
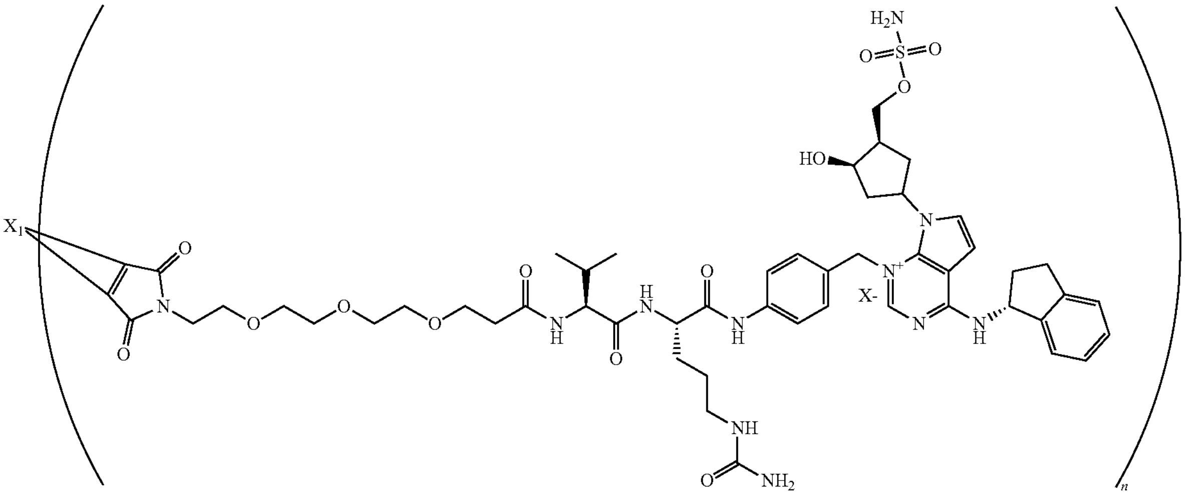
, -continued
B25
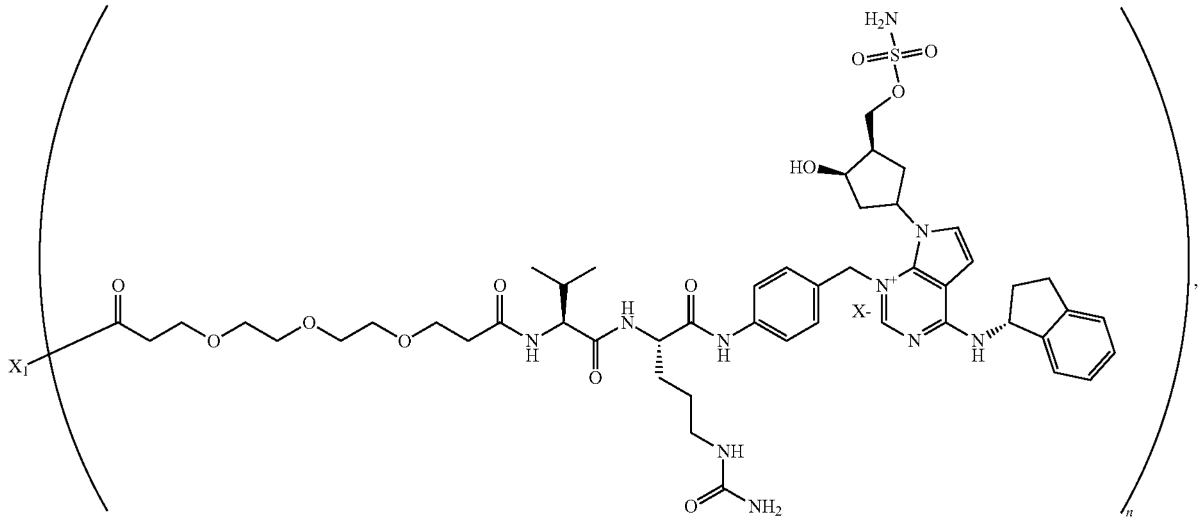
,
B37
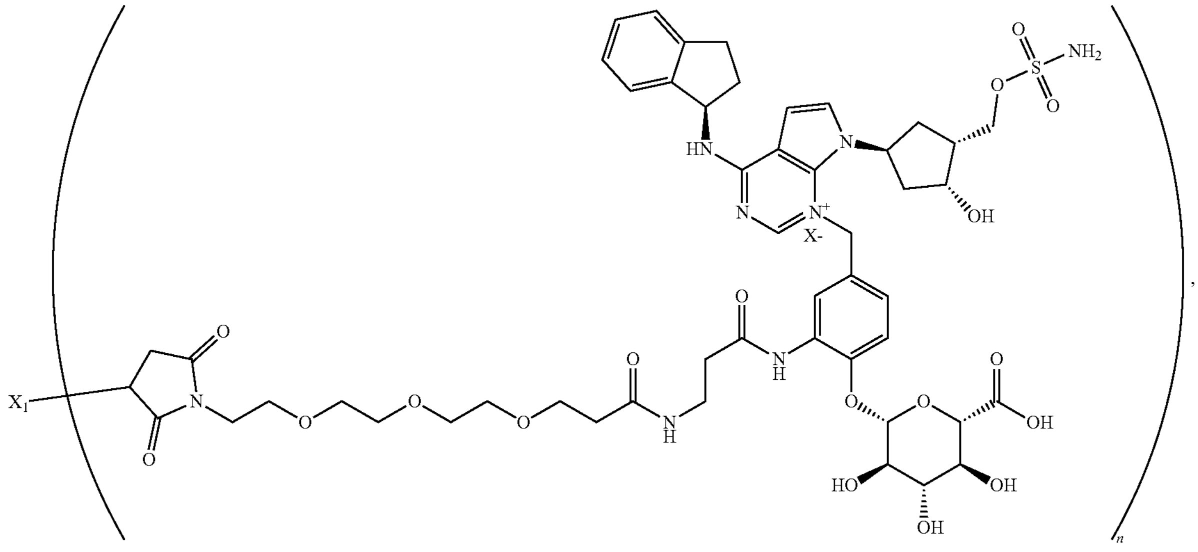
, -continued

B49

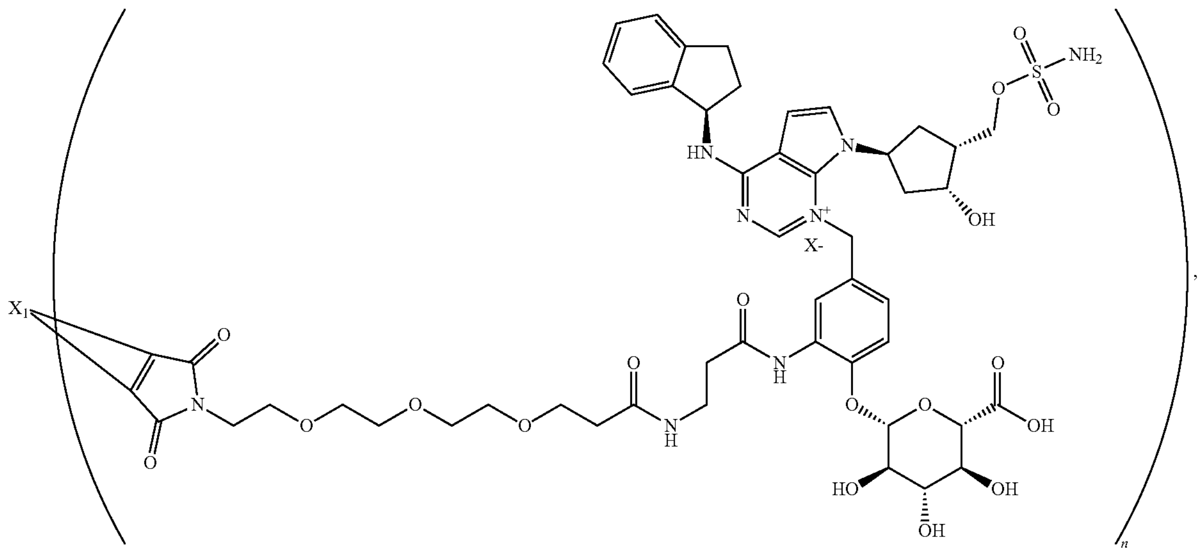

and

B61

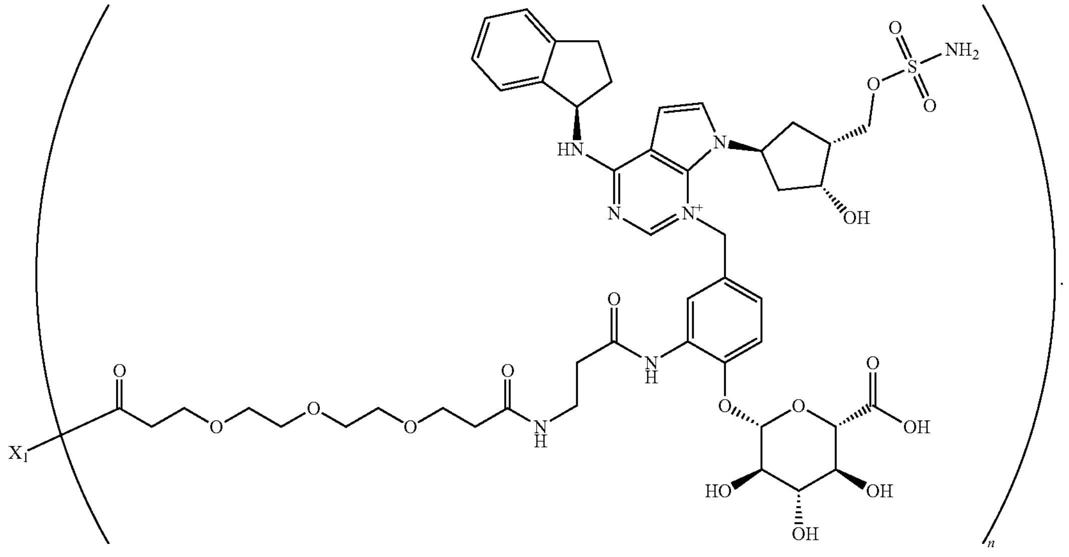

6. The compound, or a pharmaceutically acceptable salt, solvate, hydrate, isomer, or tautomer thereof, of claim 1, wherein the compound of Formula (I) is selected from the group consisting of B-37 and B-49.

7. The compound, or a pharmaceutically acceptable salt, solvate, hydrate, isomer, or tautomer thereof, of claim 1, wherein X2 is bound to X1 at two different sites on X1.

8. The compound, or a pharmaceutically acceptable salt, solvate, hydrate, isomer, or tautomer thereof, of claim 1, wherein X2 is bound to X1 at two different Cys residues on X1.

9. The compound, or a pharmaceutically acceptable salt, solvate, hydrate, isomer, or tautomer thereof, of claim 1, wherein X2 is bound to X1 at two different Lys residues on X1.

* * * * *